US012478068B2

(12) United States Patent
Rezaei et al.

(10) Patent No.: US 12,478,068 B2
(45) Date of Patent: Nov. 25, 2025

(54) STABLE LIQUID FORMULATIONS FOR NITROGEN-FIXING MICROORGANISMS

(71) Applicant: Pivot Bio, Inc., Berkeley, CA (US)

(72) Inventors: Farzaneh Rezaei, Berkeley, CA (US); Mahsa Mohiti-Asli, Berkeley, CA (US); Naomi Kreamer, Berkeley, CA (US); Allison Nicole Johnson, Berkeley, CA (US); Tabitha Amendolara, Berkeley, CA (US)

(73) Assignee: Pivot Bio, Inc., Berkeley, CA (US)

( * ) Notice: Subject to any disclaimer, the term of this patent is extended or adjusted under 35 U.S.C. 154(b) by 524 days.

(21) Appl. No.: 18/050,698

(22) Filed: Oct. 28, 2022

(65) Prior Publication Data

US 2023/0148607 A1 May 18, 2023

Related U.S. Application Data

(63) Continuation of application No. PCT/US2021/029993, filed on Apr. 29, 2021.

(60) Provisional application No. 63/019,096, filed on May 1, 2020.

(51) Int. Cl.

| | |
|---|---|
| ***A01N 63/20*** | (2020.01) |
| ***C05F 11/08*** | (2006.01) |
| ***C12N 1/04*** | (2006.01) |
| ***C12N 1/20*** | (2006.01) |

(52) U.S. Cl.

CPC .............. *A01N 63/20* (2020.01); *C05F 11/08* (2013.01); *C12N 1/04* (2013.01); *C12N 1/20* (2013.01)

(58) Field of Classification Search

None

See application file for complete search history.

(56) References Cited

U.S. PATENT DOCUMENTS

| | | | |
|---|---|---|---|
| 1,520,545 | A | 12/1924 | Murphy |
| 4,782,022 | A | 11/1988 | Puhler et al. |
| 4,832,728 | A | 5/1989 | Allan et al. |
| 4,970,147 | A | 11/1990 | Huala et al. |
| 5,071,743 | A | 12/1991 | Slilaty et al. |
| 5,116,506 | A | 5/1992 | Williamson et al. |
| 5,229,291 | A | 7/1993 | Nielsen et al. |
| 5,300,127 | A | 4/1994 | Williams |
| 5,354,670 | A | 10/1994 | Nickoloff et al. |
| 5,427,785 | A | 6/1995 | Ronson et al. |
| 5,780,270 | A | 7/1998 | Lesley |
| 5,789,166 | A | 8/1998 | Bauer et al. |
| 5,916,029 | A | 6/1999 | Smith et al. |
| 6,033,861 | A | 3/2000 | Schafer et al. |
| 6,114,148 | A | 9/2000 | Seed et al. |
| 6,391,548 | B1 | 5/2002 | Bauer et al. |
| 6,484,879 | B2 | 11/2002 | Desmarais et al. |
| 6,548,289 | B1 | 4/2003 | Beynon et al. |
| 6,596,509 | B1 | 7/2003 | Bauer et al. |
| 6,673,610 | B2 | 1/2004 | Miyawaki et al. |
| 6,713,285 | B2 | 3/2004 | Bauer et al. |
| 6,773,900 | B2 | 8/2004 | Short et al. |
| 6,821,590 | B2 | 11/2004 | Verrall et al. |
| 6,841,358 | B1 | 1/2005 | Locht et al. |
| 7,005,168 | B2 | 2/2006 | Verrall et al. |
| 7,084,331 | B2 | 8/2006 | Isawa et al. |
| 7,132,265 | B2 | 11/2006 | Bauer et al. |
| 7,357,891 | B2 | 4/2008 | Yang et al. |
| 7,470,427 | B2 | 12/2008 | Cocking |
| 7,485,451 | B2 | 2/2009 | Vandergheynst et al. |
| 7,642,226 | B2 | 1/2010 | Verrall et al. |
| 7,803,872 | B2 | 9/2010 | Verrall et al. |
| 7,824,588 | B2 | 11/2010 | Yang et al. |
| 7,897,080 | B2 | 3/2011 | Yang et al. |
| 8,029,593 | B2 | 10/2011 | Amy |
| 8,076,142 | B2 | 12/2011 | Huang et al. |
| 8,137,665 | B2 | 3/2012 | Cocking |
| 8,268,584 | B1 | 9/2012 | Harwood et al. |
| 8,268,914 | B2 | 9/2012 | Verrall et al. |
| 8,377,671 | B2 | 2/2013 | Cournac et al. |
| 8,481,026 | B1 | 7/2013 | Woodruff et al. |
| 8,617,589 | B2 | 12/2013 | Fuisz et al. |
| 8,728,449 | B2 | 5/2014 | Verrall et al. |
| 8,795,965 | B2 | 8/2014 | Zhang |
| 9,073,294 | B2 | 7/2015 | Kumar et al. |
| 9,150,782 | B2 | 10/2015 | Lee et al. |
| 9,150,851 | B2 | 10/2015 | Wigley et al. |
| 9,321,697 | B2 | 4/2016 | Das et al. |
| 9,394,092 | B2 | 7/2016 | Lee et al. |
| 9,487,451 | B2 | 11/2016 | Doty et al. |
| 9,512,431 | B2 | 12/2016 | Mirsky et al. |

(Continued)

FOREIGN PATENT DOCUMENTS

| | | | |
|---|---|---|---|
| AU | 2018314720 | A1 | 5/2019 |
| CA | 2051071 | A1 | 3/1993 |

(Continued)

OTHER PUBLICATIONS

Non-Final Office Action for U.S. Appl. No. 17/287,377 dated May 20, 2025, 32 pages.

(Continued)

*Primary Examiner* — Alton N Pryor

(74) *Attorney, Agent, or Firm* — COOLEY LLP

(57) ABSTRACT

The present disclosure provides agronomically stable liquid agricultural compositions, methods of formulation thereof, and methods of application thereof. The agricultural compositions comprise nitrogen-fixing microorganisms and one or more of a buffering agent, a microbial stabilizer, and a physical stabilizer. The disclosed liquid agricultural compositions have a longer shelf life and greater ease of application than other existing dry and liquid formulations. The disclosed liquid agricultural compositions are stable for a period of thirty days or longer with low toxin accumulation and high microbial stability. The compositions are suitable for use on agricultural plant tissues or the environs thereof for providing a source of fixed atmospheric nitrogen to the agricultural plant. The compositions are used to increase crop yield and decrease yield variance.

23 Claims, 11 Drawing Sheets

Specification includes a Sequence Listing.

(56) References Cited

U.S. PATENT DOCUMENTS

| | | | |
|---|---|---|---|
| 9,546,352 | B2 | 1/2017 | Mazeaud et al. |
| 9,657,298 | B2 | 5/2017 | Soto, Sr. et al. |
| 9,670,437 | B2 | 6/2017 | Kumar et al. |
| 9,670,440 | B2 | 6/2017 | Bullock et al. |
| 9,700,519 | B2 | 7/2017 | Zicari et al. |
| 9,796,833 | B2 | 10/2017 | Verrall et al. |
| 9,828,154 | B2 | 11/2017 | Edwards |
| 9,834,354 | B2 | 12/2017 | Kumar et al. |
| 9,873,558 | B2 | 1/2018 | Edwards |
| 9,908,675 | B2 | 3/2018 | Lee et al. |
| 9,957,509 | B2 | 5/2018 | Mirsky et al. |
| 9,975,817 | B2 | 5/2018 | Temme et al. |
| 10,087,401 | B2 | 10/2018 | Lee et al. |
| 10,183,794 | B2 | 1/2019 | Souter et al. |
| 10,202,227 | B2 | 2/2019 | Nii et al. |
| 10,208,422 | B2 | 2/2019 | Edwards et al. |
| 10,384,983 | B2 | 8/2019 | Temme et al. |
| 10,428,297 | B2 | 10/2019 | Souter et al. |
| 10,443,024 | B2 | 10/2019 | Souter et al. |
| 10,513,588 | B2 | 12/2019 | Friedrich et al. |
| 10,526,479 | B2 | 1/2020 | Friedrich et al. |
| 10,556,839 | B2 | 2/2020 | Temme et al. |
| 10,562,701 | B2 | 2/2020 | Lee et al. |
| 10,604,318 | B2 | 3/2020 | Kumar et al. |
| 10,611,555 | B2 | 4/2020 | Edwards |
| 10,662,432 | B2 | 5/2020 | Mirsky et al. |
| 10,696,460 | B2 | 6/2020 | Lee et al. |
| 10,808,210 | B2 | 10/2020 | Lee et al. |
| 10,815,346 | B2 | 10/2020 | Nii et al. |
| 10,829,621 | B2 | 11/2020 | Lee et al. |
| 10,844,183 | B2 | 11/2020 | Friedrich et al. |
| 10,899,518 | B2 | 1/2021 | Keuleers et al. |
| 10,907,117 | B2 | 2/2021 | Souter et al. |
| 10,913,832 | B2 | 2/2021 | Friedrich et al. |
| 10,919,814 | B2 | 2/2021 | Temme et al. |
| 10,934,226 | B2 | 3/2021 | Temme et al. |
| 10,968,446 | B2 | 4/2021 | Zhao et al. |
| 11,028,352 | B2 | 6/2021 | Simonsen et al. |
| 11,104,497 | B2 | 8/2021 | Lee et al. |
| 11,168,289 | B2 | 11/2021 | Friedrich et al. |
| 11,193,092 | B2 | 12/2021 | Goetz et al. |
| 11,352,468 | B2 | 6/2022 | Lee et al. |
| 11,407,866 | B2 | 8/2022 | Childers et al. |
| 11,453,754 | B2 | 9/2022 | Childers et al. |
| 11,459,433 | B2 | 10/2022 | Nii et al. |
| 11,473,039 | B2 | 10/2022 | Souter et al. |
| 11,473,040 | B2 | 10/2022 | Courchay et al. |
| 11,479,516 | B2 | 10/2022 | Voigt et al. |
| 11,492,190 | B2 | 11/2022 | Nakano |
| 11,565,979 | B2 | 1/2023 | Temme et al. |
| 11,678,667 | B2 | 6/2023 | Reisinger et al. |
| 11,678,668 | B2 | 6/2023 | Reisinger et al. |
| 11,739,032 | B2 | 8/2023 | Temme et al. |
| 11,946,162 | B2 | 4/2024 | Zhao et al. |
| 11,963,530 | B2 | 4/2024 | Reisinger et al. |
| 11,993,778 | B2 | 5/2024 | Tamsir et al. |
| 12,151,988 | B2 | 11/2024 | Tamsir et al. |
| 12,209,245 | B2 | 1/2025 | Mirsky et al. |
| 12,268,212 | B2 | 4/2025 | Reisinger et al. |
| 12,281,299 | B2 | 4/2025 | Voigt et al. |
| 12,281,980 | B2 | 4/2025 | Wood et al. |
| 12,290,074 | B2 | 5/2025 | Reisinger et al. |
| 2001/0033883 | A1 | 10/2001 | Boody |
| 2004/0235663 | A1 | 11/2004 | Cocking |
| 2004/0241847 | A1 | 12/2004 | Okuyama et al. |
| 2005/0081262 | A1 | 4/2005 | Cook et al. |
| 2005/0266541 | A1 | 12/2005 | Dillon |
| 2006/0096918 | A1 | 5/2006 | Semmens |
| 2006/0127988 | A1 | 6/2006 | Wood et al. |
| 2006/0243011 | A1 | 11/2006 | Someus |
| 2007/0068072 | A1 | 3/2007 | Xavier et al. |
| 2008/0311632 | A1 | 12/2008 | Figge et al. |
| 2009/0105076 | A1 | 4/2009 | Stewart et al. |
| 2009/0137390 | A1 | 5/2009 | Triplett |
| 2009/0152195 | A1 | 6/2009 | Rodgers et al. |
| 2009/0162477 | A1 | 6/2009 | Nadel et al. |
| 2009/0258404 | A1 | 10/2009 | Mikkelsen et al. |
| 2009/0308121 | A1 | 12/2009 | Reddy et al. |
| 2010/0028870 | A1 | 2/2010 | Welch et al. |
| 2010/0267147 | A1 | 10/2010 | Qiao |
| 2011/0104690 | A1 | 5/2011 | Yu et al. |
| 2012/0015806 | A1 | 1/2012 | Paikray et al. |
| 2012/0107889 | A1 | 5/2012 | Doty et al. |
| 2012/0192605 | A1 | 8/2012 | McSpadden Gardener et al. |
| 2012/0266332 | A1 | 10/2012 | Kuykendall |
| 2012/0284813 | A1 | 11/2012 | Olivier et al. |
| 2013/0126428 | A1 | 5/2013 | Jones et al. |
| 2014/0011261 | A1 | 1/2014 | Wang et al. |
| 2014/0155283 | A1 | 6/2014 | Venkateswaran et al. |
| 2014/0230504 | A1 | 8/2014 | Finlayson et al. |
| 2014/0273226 | A1 | 9/2014 | Wu |
| 2014/0301990 | A1 | 10/2014 | Gregory et al. |
| 2014/0329326 | A1 | 11/2014 | Mirsky et al. |
| 2014/0336050 | A1 | 11/2014 | Soto, Sr. et al. |
| 2015/0080261 | A1 | 3/2015 | Wigley et al. |
| 2015/0101373 | A1 | 4/2015 | Munusamy et al. |
| 2015/0128670 | A1 | 5/2015 | Das |
| 2015/0237807 | A1 | 8/2015 | Valiquette |
| 2015/0239789 | A1 | 8/2015 | Kang et al. |
| 2015/0315570 | A1 | 11/2015 | Zhao et al. |
| 2016/0174570 | A1 | 6/2016 | Vujanovic et al. |
| 2016/0264929 | A1 | 9/2016 | Barney et al. |
| 2016/0292355 | A1 | 10/2016 | Lou et al. |
| 2016/0295868 | A1 | 10/2016 | Jones et al. |
| 2017/0119690 | A1 | 5/2017 | Hansen et al. |
| 2017/0135378 | A1 | 5/2017 | Tse et al. |
| 2017/0143006 | A1 | 5/2017 | Awati et al. |
| 2017/0152519 | A1 | 6/2017 | Mirsky et al. |
| 2017/0367349 | A1 | 12/2017 | Gruver et al. |
| 2018/0002243 | A1 | 1/2018 | Temme et al. |
| 2018/0020671 | A1 | 1/2018 | Wigley et al. |
| 2018/0065896 | A1 | 3/2018 | Van Iersel et al. |
| 2018/0073028 | A1 | 3/2018 | Mirsky et al. |
| 2018/0078586 | A1 | 3/2018 | Jones et al. |
| 2018/0153174 | A1 | 6/2018 | Riley et al. |
| 2018/0290942 | A1 | 10/2018 | Voigt et al. |
| 2019/0039964 | A1 | 2/2019 | Temme et al. |
| 2019/0144352 | A1 | 5/2019 | Temme et al. |
| 2019/0307131 | A1 | 10/2019 | Yoon et al. |
| 2019/0339964 | A1 | 11/2019 | Young et al. |
| 2019/0348154 | A1 | 11/2019 | Fröse et al. |
| 2020/0008431 | A1 | 1/2020 | Mitter et al. |
| 2020/0085065 | A1 | 3/2020 | Kellar et al. |
| 2020/0115715 | A1 | 4/2020 | Mirsky et al. |
| 2020/0163343 | A1 | 5/2020 | Verstraete et al. |
| 2020/0299637 | A1 | 9/2020 | Voigt et al. |
| 2020/0308594 | A1 | 10/2020 | Tamsir et al. |
| 2020/0331820 | A1 | 10/2020 | Tamsir et al. |
| 2021/0009483 | A1 | 1/2021 | Temme et al. |
| 2021/0163374 | A1 | 6/2021 | Bloch et al. |
| 2021/0214282 | A1 | 7/2021 | Temme et al. |
| 2021/0284995 | A1 | 9/2021 | Zhao et al. |
| 2021/0315212 | A1 | 10/2021 | Rezaei et al. |
| 2021/0345618 | A1 | 11/2021 | Bloch et al. |
| 2022/0017911 | A1 | 1/2022 | Temme et al. |
| 2022/0079163 | A1 | 3/2022 | Reisinger et al. |
| 2022/0090095 | A1 | 3/2022 | Higgins et al. |
| 2022/0106238 | A1 | 4/2022 | Rezaei et al. |
| 2022/0127627 | A1 | 4/2022 | Bloch et al. |
| 2022/0162544 | A1 | 5/2022 | Voigt et al. |
| 2022/0211048 | A1 | 7/2022 | Temme et al. |
| 2022/0282340 | A1 | 9/2022 | Ryu et al. |
| 2022/0396530 | A1 | 12/2022 | Tamsir et al. |
| 2022/0411344 | A1 | 12/2022 | Voigt et al. |
| 2023/0019267 | A1 | 1/2023 | Hapes et al. |
| 2023/0033451 | A1 | 2/2023 | Reisinger et al. |
| 2023/0062568 | A1 | 3/2023 | Temme et al. |
| 2023/0175959 | A1 | 6/2023 | Wood et al. |
| 2023/0257317 | A1 | 8/2023 | Temme et al. |
| 2023/0276807 | A1 | 9/2023 | Reisinger et al. |
| 2023/0295559 | A1 | 9/2023 | Ozaydin Eskiyenenturk et al. |
| 2024/0010576 | A1 | 1/2024 | Temme et al. |
| 2024/0196903 | A1 | 6/2024 | Reisinger et al. |
| 2024/0294953 | A1 | 9/2024 | Eskiyenenturk et al. |

(56) References Cited

U.S. PATENT DOCUMENTS

| | | | |
|---|---|---|---|
| 2024/0298647 | A1 | 9/2024 | Reisinger et al. |
| 2024/0327851 | A1 | 10/2024 | Tamsir et al. |
| 2024/0397955 | A1 | 12/2024 | Belcher et al. |
| 2025/0027228 | A1 | 1/2025 | Zhao et al. |
| 2025/0075222 | A1 | 3/2025 | Bloch et al. |
| 2025/0145544 | A1 | 5/2025 | Strobel et al. |
| 2025/0185667 | A1 | 6/2025 | Reisinger et al. |

FOREIGN PATENT DOCUMENTS

| | | | |
|---|---|---|---|
| CN | 102031231 | A * | 4/2011 |
| CN | 102093995 | A | 6/2011 |
| CN | 102595938 | A | 7/2012 |
| CN | 104204211 | A | 12/2014 |
| CN | 104244985 | A | 12/2014 |
| CN | 105039300 | A | 11/2015 |
| CN | 107494518 | A | 12/2017 |
| CN | 113662009 | A | 11/2021 |
| EP | 1072258 | A1 | 1/2001 |
| EP | 1375637 | A1 | 1/2004 |
| EP | 1394065 | A1 | 3/2004 |
| EP | 2186890 | A1 | 5/2010 |
| EP | 2978300 | B1 | 12/2020 |
| EP | 3131866 | B1 | 7/2022 |
| FR | 2494297 | | 5/1982 |
| JP | 2018528760 | A | 10/2018 |
| RU | 2567668 | C2 | 11/2015 |
| WO | WO-8704182 | A1 | 7/1987 |
| WO | WO-9305154 | A1 | 3/1993 |
| WO | WO-9801088 | A1 | 1/1998 |
| WO | WO-9909834 | A2 | 3/1999 |
| WO | WO-0057183 | A1 | 9/2000 |
| WO | WO-0107567 | A1 | 2/2001 |
| WO | WO-03089640 | A2 | 10/2003 |
| WO | WO-2006005100 | A1 | 1/2006 |
| WO | WO-2009060012 | A2 | 5/2009 |
| WO | WO-2009091557 | A1 | 7/2009 |
| WO | WO-2010088112 | A1 | 8/2010 |
| WO | WO-2011004375 | A1 | 1/2011 |
| WO | WO-2011099019 | A1 | 8/2011 |
| WO | WO-2011099024 | A1 | 8/2011 |
| WO | WO-2011154960 | A1 | 12/2011 |
| WO | WO-2012174271 | A2 | 12/2012 |
| WO | WO-2013076687 | A2 | 5/2013 |
| WO | WO-2013132518 | A1 | 9/2013 |
| WO | WO-2013142792 | A1 | 9/2013 |
| WO | WO-2014042517 | A2 | 3/2014 |
| WO | WO-2014071182 | A1 | 5/2014 |
| WO | WO-2014201044 | A2 | 12/2014 |
| WO | WO-2014202412 | A1 | 12/2014 |
| WO | WO-2016016629 | A1 | 2/2016 |
| WO | WO-2016016630 | A1 | 2/2016 |
| WO | WO-2016100727 | A1 | 6/2016 |
| WO | WO-2016146955 | A1 | 9/2016 |
| WO | WO-2016178580 | A2 | 11/2016 |
| WO | WO-2016179046 | A1 | 11/2016 |
| WO | WO-2016181228 | A2 | 11/2016 |
| WO | WO-2016191828 | A1 | 12/2016 |
| WO | WO-2017011602 | A1 | 1/2017 |
| WO | WO-2017042833 | A1 | 3/2017 |
| WO | WO-2017062412 | A1 | 4/2017 |
| WO | WO-2017069717 | A1 | 4/2017 |
| WO | WO-2017203440 | A1 | 11/2017 |
| WO | WO-2017208237 | A1 | 12/2017 |
| WO | WO-2018045051 | A1 | 3/2018 |
| WO | WO-2018132774 | A1 | 7/2018 |
| WO | WO-2019032926 | A1 | 2/2019 |
| WO | WO-2019084059 | A2 | 5/2019 |
| WO | WO-2019084342 | A1 | 5/2019 |
| WO | WO-2019140125 | A1 | 7/2019 |
| WO | WO-2020006064 | A2 | 1/2020 |
| WO | WO-2020006246 | A1 | 1/2020 |
| WO | WO-2020014498 | A1 | 1/2020 |
| WO | WO-2020061363 | A1 | 3/2020 |
| WO | WO-2020092940 | A1 | 5/2020 |
| WO | WO-2020118111 | A1 | 6/2020 |
| WO | WO-2020121219 | A1 | 6/2020 |
| WO | WO-2020132632 | A2 | 6/2020 |
| WO | WO-2020146372 | A1 | 7/2020 |
| WO | WO-2020163251 | A1 | 8/2020 |
| WO | WO-2020190363 | A1 | 9/2020 |
| WO | WO-2020191201 | A1 | 9/2020 |
| WO | WO-2020219893 | A2 | 10/2020 |
| WO | WO-2020219932 | A1 | 10/2020 |
| WO | WO-2020245841 | A1 | 12/2020 |
| WO | WO-2021113352 | A1 | 6/2021 |
| WO | WO-2021146209 | A1 | 7/2021 |
| WO | WO-2021221689 | A1 | 11/2021 |
| WO | WO-2021221690 | A1 | 11/2021 |
| WO | WO-2021222567 | A2 | 11/2021 |
| WO | WO-2021222643 | A1 | 11/2021 |
| WO | WO-2021231449 | A2 | 11/2021 |
| WO | WO-2022029661 | A1 | 2/2022 |
| WO | WO-2022140656 | A1 | 6/2022 |
| WO | WO-2022260676 | A1 | 12/2022 |
| WO | WO-2022261433 | A1 | 12/2022 |
| WO | WO-2023278804 | A1 | 1/2023 |
| WO | WO-2023147050 | A1 | 8/2023 |
| WO | WO-2023154805 | A2 | 8/2023 |
| WO | WO-2024006524 | A1 | 1/2024 |
| WO | WO-2024015230 | A1 | 1/2024 |
| WO | WO-2024137259 | A1 | 6/2024 |
| WO | WO-2025024750 | A2 | 1/2025 |

OTHER PUBLICATIONS

Abd-Elhafeez, E., et al., "Isolation and Characterization of Enterobacter Strains Causing Potato Soft Rot Disease in Egypt," Minia Science Bulletin, Botany Section, Mar. 2018, 29(1), pp. 1-13.

An, Q., et al. "Constitutive expression of the nifA gene activates associative nitrogen fixation of Enterobacter gergoviae 57-7, an opportunistic endophytic diazotroph". Journal of Applied Microbiology, Sep. 2007, vol. 103, No. 3, pp. 613-620, doi: 10.1111/j.1365-2672.2007.03289.

Arriel-Elias, M.T., et al., "Shelf life enhancement of plant growth promoting rhizobacteria using a simple formulation screening method," African Journal of Microbiology Research, Feb. 7, 2018, vol. 12(5), pp. 115-126, DOI: 10.5897/AJMR2017.8787.

Bali, A et al., "Excretion of ammonium by a nifL mutant of Azotobacter vinelandii fixing nitrogen," Appl Environ Microbiol, May 1992, vol. 58, No. 5, pp. 1711-1718.

Bashan, Y., et al., "Advances in plant growth-promoting bacterial inoculant technology: formulations and practical perspectives (1998-2013)", Plant Soil 2014, 378:1-33, DOI: 10.1007/s11104-013-1956-x.

Bashan, Y., et al., "Alginate microbeads as inoculant carriers for plant growth-promoting bacteria", Biology and Fertility of Soils, vol. 35, No. 5, Jun. 2002, pp. 359-368, DOI: 10.1007/s0037 4-002-0481-5.

Batista et al. "Manipulating nitrogen regulation in diazotrophic bacteria for agronomic benefit," Biochemical Society Transactions 2019, vol. 47, pp. 603-614, doi: 10.1042/BST20180342.

Baum, et al. "Control of coleopteran insect pests through RNA interference." Nat Biotechnol. Nov. 2007;25(11):1322-6. doi: 10.1038/nbtl359.

Berninger et al., "Maintenance and Assessment of Cell Viability in Formulation of Non-Sporulating Bacterial Inoculants," Microbial Biotechnology, Mar. 2018, 11(2): 277-301.

Blanco, G. et al., "Sequence and molecular analysis of the nifL gene of Azotobacter vinelandii," Mol Microbiol, 9(4):869-879 (1993). doi: 10.1111/j.1365-2958.1993.tb01745.x.

Bloch, S. E., et al., Biological nitrogen fixation in maize: optimizing nitrogenase expression in a root-associated diazotroph, Journal of Experimental Botany 2020, vol. 71, No. 15, pp. 4591-4603, doi: 10.1093/jxb/eraa176.

Bosmans, et al. "Sea anemone venom as a source of insecticidal peptides acting on voltage-gated Na+ channels." Toxicon. Mar. 15, 2007;49(4):550-60. doi: 10.1016/j.toxicon.2006.11.029.

(56) References Cited

OTHER PUBLICATIONS

Buckley Lab NifH database, retrieved from URL web.archive.org/web/20180110043803/https:/ /blogs.cornell .edu/buckley/nifh-sequence-database/, available on or before Jan. 10, 2018, 2 pages.
Butzen, S., "Corn Seeding Rate Considerations," Mar. 2019, 4 pages; www.pioneer.com/home/site/us/agronomy/library/corn-seeding-rate-considerations/.
CERA GM Crop Database Center for Environmental Risk Assessment (CERA), ILSI Research Foundation, Washington, DC, 2010, Web Page, 1 page; http://cera-gmc.org/index.ph/? action=gm_crop_database.
Chakroun, et al. "Bacterial Vegetative Insecticidal Proteins (Vip) from Entomopathogenic Bacteria." Microbial Mal Biol Rev. Mar. 2, 2016;80(2):329-50. doi: 10.I 128/MMBR.00060-15.
Chen M., et al., "Complete genome sequence of Kosakonia sacchari type strain SP1T," Standards in Genomic Sciences 2014, 9:1311-1318, DOI: 10.4056/sigs.5779977.
Chiang, et al. "Mutagenic oligonucleotide-directed PCR amplification (Mod-PCR): an efficient method for generating random base substitution mutations in a DNA sequence element." PCR Methods Annl. Feb. 1993;2(3):210-7. doi: 10.1101/gr.2.3.210.
Clancy, P., et al., "The domains carrying the opposing activities in adenylyl transferase are separated by a central regulatory domain," FEBS Journal (2007), 274:2865-2877.
Colby, S. R., et al., "Calculating synergistic and antagonistic responses of herbicide combinations," Weeds (1967), 15(1): 20-22.
Common Buffers and Stock Solutions, Current Protocols in Nucleic Acid Chemistry, A.2A.1-A.2A.14, Sep. 2011, DOI: 10.1002/0471142700.nca02as46.
Costerton, J. W., et al., "Microbial Biofilms," Annu. Rev. Microbiol. 1995, 49:711-745.
Crickmore, et al. "Revision of the nomenclature for the Bacillus thuringiensis pesticidal crystal proteins." Microbial Mal Biol Rev. Sep. 1998;62(3):807-13.
Da Silva, M. F., et al., "Survival of endophytic bacteria in polymer-based inoculants and efficiency of their application to sugarcane," Plant and Soil 356, pp. 231-243 (2012), https://doi.org/10.1007/s11104-012-1242-3.
Davin-Regli et al. "Enterobacter aerogenes and Enterobacter cloacae; versatile bacterial pathogens confronting antibiotic treatment," Front Microbiol, May 2015, vol. 6, 392:1-10.
Deaker et al., "Desiccation tolerance of rhizobia when protected by synthetic polymers", Soil Biology and Biochemistry, vol. 39, No. 2, Nov. 29, 2006, pp. 573-580, DOI: 10.1016/j.soilbio.2006.09.005.
Dixon, R. et al. "Genetic regulation of biological nitrogen fixation," Nature Reviews Microbiology, Aug. 2004, vol. 2, pp. 621-631.
European Search Report and Search Opinion, dated Oct. 19, 2022, for European Patent Application No. 19880057.5 (14 total pages).
Examination Report and Search Report, dated May 29, 2023, for Russian Patent Application No. 2021119675 (22 pages).
Examination Report, dated Apr. 30, 2022, for Pakistan Patent Application No. 335/2021 (2 pages).
Examination Report, dated Jun. 9, 2023, for Canadian Patent Application No. 3,120,608 (4 pages).
Extended European Search Report and Search Opinion, dated Oct. 11, 2022, for European Application No. 19892518.2 (8 total pages).
Eyraud, et al. "Expression and biological activity of the cystine knot bioinsecticide PAlb (Pea Albumin 1 Subunit b)." PLoS One. Dec. 11, 2013;8(12):e81619, 9 pages, doi: 10.1371/journal.pone.0081619.
Flores-Núñez, V. M., et al., "Functional Signatures of the Epiphytic Prokaryotic Microbiome of Agaves and Cacti," Frontiers in Microbiology, Jan. 2020, vol. 10, Art. 3044, 13 pages, doi: 10.3389/fmicb.2019.03044.
Gaby, et al. "A comprehensive aligned nifH gene database: a multipurpose tool for studies of nitrogen-fixing bacteria." Database (Oxford). Feb. 5, 2014; 2014:bau001, 8 pages, doi: 10.1093/database/bau001.
Giri, K., "The First Report of Indigenous Free-Living Diazotroph Kosakonia sacchari Isolated from Himalayan Alder-Based Shifting Cultivation System in Nagaland, India," Journal of Soil Science and Plant Nutrition 2019, 19, pp. 574-579, https://doi.org/10.1007/s42729-019-00056-5.
Gu, C. T., et al., "*Enterobacter xiangfangensis* sp. nov., isolated from Chinese traditional sourdough, and reclassification of *Enterobacter sacchari* Zhu et al. 2013 as *Kosakonia sacchari* comb. nov.," International Journal of Systematic and Evolutionary Microbiology (2014), 64, 2650-2656, DOI: 10.1099/js.0.064709-0.
Hay, I. D., et al., "Microbial alginate production, modification and its applications," Microbial Biotechnology (2013), vol. 6, No. 6, pp. 637-650, doi: 10.1111/1751-7915.12076.
He, L., et al., "NtrC Is Required for Control of Klebsiella pneumoniae NifL Activity," Journal of Bacteriology, Dec. 1997, vol. 179, No. 23, pp. 7446-7455.
Hidaka, M. et al., "Promotion of the Growth of Rice by Inoculation of Nitrogen-Fixing-Activity-Enhanced Bacteria to the Rhizosphere," Nitrogen Fixation: From Molecules to Crop Productivity, p. 445 (Jan. 1, 2002).
Higdon, S. M., et al., "Genomic characterization of a diazotrophic microbiota associated with maize aerial root mucilage," PLoS One, 15(9): e0239677, Sep. 2020, 26 pages, https://doi.org/10.1371/journal.pone.0239677.
Hoeschle-Zeledon, I et al., "Regulatory challenges for biological control," The CGIAR Systemwide Program on Integrated Pest Management, Jan. 2013, SP-IPM Secretariat, International Institute of Tropical Agriculture (IITA), Ibadan, Nigeria, 53 pages.
Hosseini-Abari, A., et al., "LC/MS detection of oligogalacturonic acids obtained from tragacanth degradation by pectinase producing bacteria," Journal of Basic Microbiology, 2019, 59:249-255, DOI: 10.1002/jobm.201800332.
Hu, L., et al., "Application of bryophyte rhizoid-associated bacteria increases silicon accumulation and growth in maize (*Zea mays* L.) seedlings," App. Ecol. Env. Res., 2019, 17(6):13423-13433, DOI: http://dx.doi.org/10.15666/aeer/1706_1342313433.
International Preliminary Report on Patentability for International Application No. PCT/US2021/029993 dated Nov. 10, 2022, 08 pages.
International Preliminary Report on Patentability for International Application No. PCT/US2022/033002 dated Dec. 21, 2023, 10 pages.
International Preliminary Report on Patentability, mailed Dec. 21, 2023, for International Application No. PCT/US2021/036863, 9 pages.
International Preliminary Report on Patentability, mailed Jun. 17, 2021, for International Application No. PCT/US2019/064782 (9 pages).
International Preliminary Report on Patentability, mailed May 14, 2021, for International Application No. PCT/US2019/059450 (16 pages).
International Search Report and Written Opinion for International Application No. PCT/US2023/062299 dated Aug. 7, 2023, 21 pages.
International Search Report and Written Opinion mailed Apr. 16, 2020 for International Application No. PCT/US2019/064782, 13 pages.
International Search Report and Written Opinion, mailed Mar. 10, 2020, for International Appl. No. PCT/US2019/059450, 20 pages.
International Search Report and Written Opinion, mailed Mar. 9, 2022, for International Application No. PCT/US2021/036863, 13 pages.
International Search Report and Written Opinion, mailed Nov. 3, 2022, for International Application No. PCT/US2022/033002, 14 pages.
International Search Report and Written Opinion, mailed Sep. 15, 2021, for International Application No. PCT/US2021/029993, 11 pages.
Invitation to Pay Additional Fees and, Where Applicable, Protest Fee, mailed Jan. 17, 2020, for International Application No. PCT/US2019/059450, 2 pages.
Invitation to Pay Fees for International Application No. PCT/US2023/062299 dated Jun. 16, 2023, 13 pages.

(56) References Cited

OTHER PUBLICATIONS

Jahn, A. & Nielsen, P. H., "Extraction of Extracellular Polymeric Substances (EPS) from Biofilms Using a Cation Exchange Resin," Wat. Sci. Tech., 32(8):157-164 (1995).
Kabaluk, J. Todd, et al., ed. 2010, The use and regulation of microbial pesticides in representative jurisdictions worldwide. International Organization for Biological Control of Noxious Animals and Plants (IOBC), 99 pp. (108 total pages).
Kant, et al. "Understanding plant response to nitrogen limitation for the improvement of crop nitrogen use efficiency." J Exp Bot. Feb. 2011;62(4):1499-509. doi: 10.1093/jxb/erq297.
Khandeparker, R. D. S., et al., "Extracellular polymeric substances of the marine fouling diatom amphora rostrata Wm.Sm," Biofouling (2001), 17(2):117-127, DOI: 10.1080/08927010109378471.
Kim, Y. et al., "Constitutive expression of nitrogenase system in Klebsiella oxytoca by gene targeting mutation to the chromosomal nifLA operon," Journal of Biotechnology, 10(3-4):293-301 (1989).
King, et al. "Spider-venom peptides: structure, pharmacology, and potential for control of insect pests." Annu Rev Entomol. 2013;58:475-96. doi: 10.1146/ammrev-ento-120811-153650.
Kiss, S., et al., "Effect of Urease Inhibitors on Other Enzyme Activities, Microbial Counts and Biomass as well as on Respiration and Other Microbial Processes in Soils," Chapter 8, Improving Efficiency of Urea Fertilizers by Inhibition of Soil Urease Activity, pp. 321-342 (2002).
Kloepper, J. W., "Development of a Powder Formulation of Rhizobacteria for Inoculation of Potato Seed Pieces", Phytopathology, vol. 71, No. 6, Jan. 1981, pp. 590-592.
Klose, K., et al., "Glutamate at the Site of Phosphorylation of Nitrogen-regulatory Protein NTRC Mimics Aspartyl-Phosphate and Activates the Protein," Journal of Molecular Biology (1993), vol. 232, pp. 67-78.
Leo Daniel, Amalraj E et al., "Effect of Polymeric Additives, Adjuvants, Surfactants on Survival, Stability and Plant Growth Promoting Ability of Liquid Bioinoculants," J Plant Physiol Pathol 2013, 1:2, 5 pages; http://dx.doi.org/10.4172/jppp.1000105.
Lin, et al. "PC, a Novel Oral Insecticidal Toxin from Bacillus bombysepticus Involved in Host Lethality via APN and BtR-175." Sci Rep. Jun. 9, 2015; 5:11101, 14 pages, doi: 10.1038/srep11101.
Liu, J., et al., "Enhancing viability of two biocontrol yeasts in liquid formulation by applying sugar protectant combined with antioxidant," BioControl 2009, 54:817-824, DOI 10.1007/s10526-009-9229-6.
Madhaiyan, M., et al., "Complete Genome Sequence of *Enterobacter* sp. Strain R4-368, an Endophytic N-Fixing Gammaproteobacterium Isolated from Surface-Sterilized Roots of *Jatropha curcas* L.," Genome Announcements, Jul./Aug. 2013, vol. 1, Issue 4, e00544-13, 2 pages.
Mann, E. E., et al., "Pseudomonas biofilm matrix composition and niche biology," FEMS Microbiology Reviews, Jul. 2012, vol. 36, No. 4, pp. 893-916, 41 pages, doi: 10.1111/j.1574-6976.2011.00322.x.
Mao, et al. "Silencing a cotton bollworm P450 monooxygenase gene by plant-mediated RNAi impairs larval tolerance of gossypol," Nature Biotechnology (2007); 25(11): 1307-1313. Epub Nov. 4, 2007.
Martinelli, et al. "Structure-function studies on jaburetox, a recombinant insecticidal peptide derived from jack bean (*Canavalia ensiformis*) urease." Biochim Biophys Acta. Mar. 2014;1840(3):935-44. doi: 10.1016/j.bbagen.2013.11.010.
Marx, C. J., et al., "Broad-Host-Range cre-lox System for Antibiotic Marker Recycling in Gram-Negative Bacteria," Biotechniques, 33:1062-1067 (Nov. 2002).
Mengel, D., "Roots, Growth and Nutrient Uptake," Dept. of Agronomy publication #AGRY-95-08 (Rev. May-95), 8 pages.
Mosquito, S., et al., "In Planta Colonization and Role of T6SS in Two Rice Kosakonia Endophytes," MPMI 2020, vol. 33, No. 2, pp. 349-363, https://doi.org/10.1094/MPMI-09-19-0256-R.
Mus, F., et al. Symbiotic Nitrogen Fixation and the Challenges to Its Extension to Nonlegumes. Appl. Environ. Microbiol., Jul. 2016, 82(13):3698-3710.
Nagy, Zs. K., et al., "Nanofibrous solid dosage form of living bacteria prepared by electrospinning," eXPRESS Polymer Letters, (2014), vol. 8, No. 5, pp. 352-361, DOI: 10.3144/expresspolymlett.2014.39.
Naimov, et al. "Solubilization, activation, and insecticidal activity of Bacillus thuringiensis serovar thompsoni HD542 crystal proteins." Appl Environ Microbiol. Dec. 2008;74(23):7145-51. doi: 10.1128/AEM.00752-08.
NCBI GenBank Accession No. JQ001784.1, Enterobacter sacchari strain SP1 16S ribosomal RNA gene, partial sequence, Jul. 23, 2013, 2 pages.
NCBI GenBank Accession No. KY235364.1, Kosakonia sacchari strain 312 16S ribosomal RNA gene, partial sequence, Oct. 31, 2017, 1 page.
NCBI GenBank Accession No. MG196044.1, Kosakonia sacchari strain KhAn 16S ribosomal RNA gene, partial sequence, Feb. 7, 2018, 2 pages.
Nestmann, et al. "Mutagenesis by nitrosoguanidine, ethyl methanesulfonate, and mutator gene mutH in continuous cultures of *Escherichia coli*." Mutat Res. Jun. 1975;28(3):323-30. doi: 10.1016/00275107(75)90226-2.
Nielsen, H., et al., "Extraction of EPS," Wingender et al. (eds.), Microbial Extracellular Polymeric Substances, 1999, Chapter 3, 24 pages.
Nielsen, P. H. et al., "Conceptual model for production and composition of exopolymers in biofilms," Wat. Sci. Tech., vol. 36, No. 1, pp. 11-19 (1997).
Nita, P. et al., "Liquid formulations of Acetobacter diazotrophicus L1 and Herbaspirillum seropedicae J24 and their field trials on wheat," International Journal of Environmental Science, 2012, 3(3):1116-1129, DOI: 10.6088/ijes.2012030133019.
Nopcharoenkul, W., et al., "The development of a liquid formulation of *Pseudoxanthomonas* sp. RN402 and its application in the treatment of pyrene-contaminated soil," Journal of Applied Microbiology 2011, 111, pp. 36-47, doi:10.1111/j.1365-2672.2011.05037.x.
Notice of Allowance and Search Report, dated Oct. 20, 2023, for Chinese Patent Application No. 201980091416.X, 8 pages.
Office Action, dated Feb. 13, 2023, for Thailand Patent Application No. 2101002976, 6 pages.
Office Action, dated Jan. 26, 2023, for Indonesia Patent Application No. P00202104394, 6 pages.
Office Action, dated Mar. 25, 2023, for Chinese Patent Application No. 201980091416.X (14 pages).
Office Action, dated Oct. 11, 2023, for Japanese Patent Application No. 2021-531992, 11 pages.
Office Action, dated Oct. 14, 2022, for Chinese Patent Application No. 201980091416.X (13 total pages).
Office Action for Canadian Patent Application No. 3172321, dated Nov. 27, 2023, 5 pages.
Office Action for Chinese Application No. 201980091416, mailed on Mar. 3, 2022, 18 pages.
Office Action with Search Report for Brazilian Patent Application No. BR112021010947-1 dated Aug. 14, 2023, 8 pages.
Ow, D. W., et al., "Promoters regulated by the glnG (ntrC) and nifA gene products share a heptameric consensus sequence in the -15 region," Proc. Natl. Acad. Sci. USA, May 1983, vol. 80, pp. 2524-2528.
Parker and Feil. "Pore-forming protein toxins: from structure to function." Prog Biophys Mol Biol. May 2005;88(1):91-142. doi: 10.1016/j.pbiomolbio.2004.01.009.
Partial European Search Report and Search Opinion, dated Jul. 15, 2022, for European Application No. 19880057.5 (17 total pages).
Pelton, J G, et al., "Solution structure of the DNA-binding domain of NtrC with three alanine substitutions," J. Mol. Biol. 1999, 292, pp. 1095-1110.
Purcell, et al. "Cholesterol oxidase: a potent insecticidal protein active against boll weevil larvae." Biochem Biophys Res Commun. Nov. 15, 1993;196(3):1406-13. doi: 10.1006/bbrc.1993.2409.

(56) References Cited

OTHER PUBLICATIONS

Qaim and Zilberman. "Yield effects of genetically modified crops in developing countries." Science. Feb. 7, 2003;299(5608):900-2. doi: 10.1126/science.1080609.
Qiu, D.-Y. & Shen, B.-F., "Construction of Genetically Engineered Strains of Enterobacter Cloacae (nifL-Ac)," Acta Phytophysiologica Sinica, 25(3):269-273 (1999). English translation.
Quick, D., "Bacteria-laden silk coating makes seeds suitable for salty soil," New Atlas, Nov. 25, 2019, 3 pages.
Restriction Requirement, dated Nov. 16, 2023, for U.S. Appl. No. 17/287,377, 8 pages.
Rivarez, M. P. S., et al., "Defense Biopriming and Antimicrobial Activity of Endophytic Bacteria and Associated *Bacillus* Species Contribute to Bacterial Crown Rot Tolerance in Papaya," bioRxiv 2019, 24 pages, doi: https://doi.org/10.1101/2019.12.22.886341.
Rocha, I., et al., "Seed Coating: A Tool for Delivering Beneficial Microbes to Agricultural Crops," Frontiers in Plant Science, Nov. 2019, vol. 10, Article 1357, 16 pages, doi: 10.3389/fpls.2019.01357.
Rojas-Tapias, D. et al., "Preservation of Azotobacter chroococcum vegetative cells in dry polymers," Univ. Sci. 2015, vol. 20(2): 201-207, doi: 10.11144/Javeriana.SC20-2.pacv.
Salas-Jara, M., et al., "Biofilm Forming Lactobacillus: New Challenges for the Development of Probiotics," Microorganisms 2016, 4, 35, 14 pages, doi: 10.3390/microorganisms4030035.
Sanahuja, et al. "Bacillus thuringiensis: a century of research, development and commercial applications." Plant Biotechnol J. Apr. 2011;9(3):283-300. doi: 10.1111/j.1467-7652.2011.00595.x.
Schmitz, R. A., et al., "Regulation of Nitrogen Fixation in Klebsiella pneumoniae and Azotobacter vinelandii: NifL, Transducing Two Environmental Signals to the nif Transcriptional Activator NifA," J. Mol. Microbiol. Biotechnol. 2002, 4(3): 235-242.
Schoebitz, M., et al., "Bioencapsulation of microbial inoculants for better soil-plant fertilization. A review", Agronomy for Sustainable Development, vol. 33, No. 4, Mar. 27, 2013, pp. 751-765, DOI: 10.1007/S13593-013-0142-0.
Schoug, A., et al., "Differential effects of polymers PVP90 and Ficoll400 on storage stability and viability of Lactobacillus coryniformis Si3 freeze-dried in sucrose," J Appl Microbial., Mar. 2010, 108(3):1032-1040, doi: 10.1111/j.1365-2672.2009.04506.x.
Schuler, et al., "Insect-resistant transgenic plants," Trends Biotechnol., Apr. 1998, vol. 16, pp. 168-175.
Shahid, M., et al., "Colonization of Vigna radiata by a halotolerant bacterium Kosakonia sacchari improves the ionic balance, stressor metabolites, antioxidant status and yield under NaCl stress," Applied Soil Ecology 2021, vol. 158, 103809, 14 pages, https://doi.org/10.1016/j.apsoil.2020.103809.
Shamseldin, A., "The Role of Different Genes Involved in Symbiotic Nitrogen Fixation—Review," Global Journal of Biotechnology & Biochemistry, 8(4):84-94 (2013).
Shinjo, R., et al., "Complete Genome Sequence of Kosakonia sacchari Strain BO-1, an Endophytic Diazotroph Isolated from a Sweet Potato, " Genome Announcements, Sep./Oct. 2016, vol. 4, Issue 5, e00868-16, 2 pages.
Stemmer, "DNA shuffling by random fragmentation and reassembly: in vitro recombination for molecular evolution." Proc Natl Acad Sci U S A. Oct. 25, 1994;91(22):10747-51. doi: 10.1073/pnas.91.22.10747.
Stemple, "Tilling—a high-throughput harvest for functional genomics." Nat Rev Genet. Feb. 2004;5(2):145-50. doi: 10.1038/nrg1273.
Strobel, et al., "Industrially-Scalable Microencapsulation of Plant Beneficial Bacterial in Dry Cross-Linked Alginate Matrix," Industrial Biotechnology, vol. 14, No. 3, Jun. 2018, pp. 138-148, DOI: 10.1089/ind.2017.0032.
Temme et al., "Refactoring the nitrogen fixation gene cluster from Klebsiella oxytoca," Proc. Natl. Acad. Sci. USA, May 2012, 109(18):7085-7090.
Tian, H., et al., "Six New Families of Aerobic Arsenate Reducing Bacteria: Leclercia, Raoultella, Kosakonia, Lelliottia, Yokenella, and Kluyvera," Geomicrobiology Journal 2019, vol. 36, No. 4, 339-347, https://doi.org/10.1080/01490451.2018.1554726.
Tijssen, P., "Hybridization with Nucelic Acid Probes," Laboratory Techniques in Biochemistry and Molecular Biology. Department for Physiological Chemistry, University of Utrecht, Utrecht, The Netherlands, vol. 24 (1993) 65 pages.
Tu, L., et al., "Preparation and characterization of alginate-gelatin microencapusulated Bacillus subtilis SL-13 by emulsification/internal gelatin," Journal of Biomaterials Science, vol. 26, No. 12, Jul. 10, 2015, pp. 735-749, doi: 10.1080/09205063.2015.1056075.
Volova, T. G., et al., "Microbial Degradation of Polyhydroxyalkanoates with Different Chemical Compositions and Their Biodegradability," Microbial Ecology 2017, vol. 73, pp. 353-367, doi: 10.1007/S00248-016-0852-3.
Vroman, I., et al., "Biodegradable Polymers," Materials 2009, 2, 307-344, doi:10.3390/ma2020307.
Wang, C., et al., "*Kosakonia quasisacchari* sp. nov. recovered from human wound secretion in China," International Journal of Systemic and Evolutionary Microbiology, 2019, 69:3155-3160, DOI 10.1099/ijsem.0.003606.
Wang, D. et al., "Biofilm formation enables free-living nitrogen-fixing rhizobacteria to fix nitrogen under aerobic conditions," The ISME Journal 2017, vol. 11, No. 7, pp. 1602-1613, published online Mar. 24, 2017, doi: 10.1038/ismej.2017.30.
Wang, W. et al., "Screening, Identification and Growth Promotion Ability of Phosphate Solubilizing Bacteria from Soybean Rhizosphere under Maize-Soybean Intercropping Systems," bioRxiv 2020, 25 pages, doi: https://doi.org/10.1101/2020.12.15.422997.
Wang, X., et al., "Emergence of a novel mobile colistin resistance gene, mcr-8, in NDM-producing Klebsiella pneumoniae," Emerging Microbes & Infections 2018, 7:122, 10 pages, DOI 10.1038/s41426-018-0124-z.
Watson, C. J., "Urease Activity and Inhibition—Principles and Practice," Proceedings, No. 454, pp. 1-40, presented to The International Fertiliser Society, London, Nov. 28, 2000.
Wimpenny, J. et al., "An overview of biofilms as functional communities," Community structure and co-operation in biofilms, 59th Symposium of the Society for General Microbiology, D.G. Allison, P. Gilbert, H.M. Lappin-Scott and M. Wilson, Eds., 2000, 28 pages.
Witkowski, A. et al., "Conversion of a β-Ketoacyl Synthase to a Malonyl Decarboxylase by Replacement of the Active-Site Cysteine with Glutamine," Biochemistry 1999, 38, pp. 11643-11650.
Wu, et al., "Effects of different amendments on contents of phenolic acids and specific microbes in rhizo-sphere of Pseudostellaria heterophylla," Chinese Journal of Applied Ecology, Nov. 2016, 27(11): 3623-3630, DOI: 10.13287/j.1001-9332.201611.004 (English abstract only).
Wu, et al., "Mixed Phenolic Acids Mediated Proliferation of Pathogens Talaromyces helicus and Kosakonia sacchari in Continuously Monocultured Radix pseudostellariae Rhizosphere Soil," Frontiers in Microbiology, Mar. 2016, vol. 7, Article 335, 14 pages, doi: 10.3389/fmicb.2016.00335.
Wu, H., et al., "Insights into the Mechanism of Proliferation on the Special Microbes Mediated by Phenolic Acids in the Radix pseudostellariae Rhizosphere under Continuous Monoculture Regimes," Frontiers in Plant Science, May 2017, vol. 8, Article 659, 15 pages, DOI: 10.3389/fpls.2017.00659.
Wu, H., et al., "The role of organic acids on microbial deterioration in the Radix pseudostellariae rhizosphere under continuous monoculture regimes," Scientific Reports, 7:3497, 13 pages, published online Jun. 14, 2017, doi: 10.1038/s41598-017-03793-8.
Yarza, et al. "Uniting the classification of cultured and uncultured bacteria and archaea using 16S rRNA gene sequences." Nat Rev Microbiol. Sep. 2014; 12(9):635-45. doi: 10.1038/nrmicro3330.
Zehr lab NifH database, https://wwwzehr.pmc.ucsc.edu/nifH_Database_Public/nifH.Database.Archives/, Apr. 4, 2014, 8 total pages.
Zhang et al., "Mutagenesis and functional characterization of the four domains of GlnD, a bifunctional nitrogen sensor protein," Journal of Bacteriology, Jun. 2010, 192(11):2711-2721.
Zhu, B., et al., "*Enterobacter sacchari* sp. nov., a nitrogen-fixing bacterium associated with sugar cane (*Saccharum officinarum* L.)," International Journal of Systemic and Evolutionary Microbiology (2013), 63, 2577-2582, DOI 10.1099/ijs.0.045500-0.

(56) References Cited

OTHER PUBLICATIONS

Zhu, B., et al., "Genome Sequence of *Enterobacter* sp. Strain SP1, an Endophytic Nitrogen-Fixing Bacterium Isolated from Sugarcane," J. Bacterial., Dec. 2012, vol. 194, No. 24, pp. 6963-6964, doi:10.1128/JB.01933-12.
Amiet-Charpentier, C., et al., "Rhizobacteria microencapsulation: properties of microparticles obtained by spray-drying," Journal of Microencapsulation 1999, vol. 16, No. 2, pp. 215-229, https://doi.org/10.1080/026520499289194.
Bageshwar, U. K., "Studies on Some Nitrogen Fixing Genes of Azotobacter Vinelandii," Thesis submitted to the Jamia Millia Isamia for the awad of Degree of Doctor of Philosophy, Department of Biosciences, Faculty of Natural Sciences, Jamia Millia Islamia, New Delhi, Aug. 1994, 254 pages.
Balasundararajan, V., et al., "Occurrence of diversified N-acyl homoserine lactone mediated biofilm-forming bacteria in rice rhizoplane," Journal of Basic Microbiology, 2019, vol. 59, pp. 1031-1039, DOI: 10.1002/jobm.201900202.
Berninger, T., et al., "Zeolite-based, dry formulations for conservation and practical application of Paraburkholderia phytofirmans PsJN," Journal of Applied Microbiology 2017, 122: 974-986.
Bisutti I. L., et al., "Influence of different growth conditions on the survival and the efficacy of freeze-dried Pseudomonas fluorescens strain Pf153," Biocontrol Science and Technology 2015, vol. 25, No. 11, pp. 1269-1284, http://dx.doi.org/10.1080/09583157.2015.1044498.
Bonaterra, A., et al., "Increasing survival and efficacy of a bacterial biocontrol agent of fire blight of rosaceous plants by means of osmoadaptation," FEMS Microbiol Ecol 2007, 61: 185-195, DOI: 10.1111/j.1574-6941.2007.00313.x.
Cabrefiga, J., et al., "Improvement of fitness and efficacy of a fire blight biocontrol agent via nutritional enhancement combined with osmoadaptation," Applied and Environmental Microbiology, May 2011, vol. 77, No. 10, pp. 3174-3181, doi: 10.1128/AEM.02760-10.
Chaurasia, A. K., et al., "Improved Eco-Friendly Recombinant *Anabaena* sp. Strain PCC7120 with Enhanced Nitrogen Biofertilizer Portential," Applied and Environmental Microbiology, Jan. 2011, vol. 77, No. 2, pp. 395-399, doi: 10.1128/AEM.01714-10.
Costa, E., et al., "Effect of package and storage conditions on viability and efficacy-of the freeze-dried biocontrol agent Pantoea agglomerans strain CPA-2," Journal of Applied Microbiology 2002, 92, pp. 873-878.
Costa E, et al., "Effect of protective agents, rehydration media and initial cell concentration on viability of Pantoea agglomerans strain CPA-2 subjected to freeze-drying," Journal of Applied Microbiology 2000, 89, 793-800.
Costa, E., et al., "Survival of Pantoea agglomerans strain CPA-2 in a spray-drying process," Journal of Food Protection 2002, vol. 65, No. 1, pp. 185-191.
Dandurand, L. M., et al., "Survival of *Pseudomonas* spp. in air-dried mineral powders," Soil Biol Biochem 1994 , vol. 26, No. 10, pp. 1423-1430.
Examination Report, dated Oct. 4, 2024, for Australian Patent Application No. 2019394973, 4 pages.
Examination report for Canadian Patent Application No. 3,172,321 dated May 1, 2025, 5 pages.
Feoktistova, M., et al., "Crystal Violet Assay for Determining Viability of Cultured Cells," Cold Spring Harbor Protocols, 2016, 2016(4), pp. 343-346, doi: 10.1101/pdb.prot087379.
Final Office Action, dated Oct. 24, 2024, for U.S. Appl. No. 17/287,377, 53 pages.
Furtado, G.Q., et al., "First Report of Enterobacter cowanii Causing Bacterial Spot on *Mabea fistulifera*, a Native Forest Species in Brazil," Plant Disease, published online Sep. 5, 2012, 2 pages, https://doi.org/10.1094/PDIS-02-12-0160-PDN.
Han, Y. et al., "Kosakonia cowanii, a new bacterial pathogen affecting foxtail millet (*Setaria italica*[L.]*P. Beauv.*) in China," Microbial Pathogenesis, vol. 181, Aug. 2023, 106201, 8 pages, https://doi.org/10.1016/j.micpath.2023.106201.
International Preliminary Report on Patentability, mailed Aug. 22, 2024, for International Application No. PCT/US2023/062299, 14 pages.
Jean-Noel, M. K., et al., "Accelerated storage testing of freeze-dried Pseudomonas fluorescens BTP1, BB2 and PI9 strains," African Journal of Biotechnology, Nov. 27, 2012, vol. 11(95),p p. 16187-16191, DOI: 10.5897/AJB12.2370.
Joe, M. M., et al., "Survival of Azospirillum brasilense flocculated cells in alginate and its inoculation effect on growth and yield of maize under water deficit conditions," European Journal of Soil Biology 2012, 50: 198-206, doi:10.1016/j.ejsobi.2012.03.002.
Krawczyk, K. and Borodynko-Filas, N., "Kosakonia cowanii as the New Bacterial Pathogen Affecting Soybean (Glycine max Willd.).," Eur J Plant Pathol 2020, 157: 173-183, published online May 5, 2020, https://doi.org/10.1007/s10658-020-01998-8.
Ikuma, K., et al., 2013, The Extracellular Bastions of Bacteria—A Biofilm Way of Life, Nature Education Knowledge 4(2):2, 6 pages, retrieved from https://www.nature.com/scitable/knowledge/library/the-extracellular-bastions-of-bacteria-nbsp-a-100450088/ on Oct. 16, 2024.
Martínez-Romero, E., et al., "Draft genome sequences of Klebsiella variicola plant isolates", Genome Announc., vol. 3, No. 5: 01015-15, Sep. 10, 2015.
Meriam-Webster, "Prevent", Merriam Webster Dictionary, available online at https://www.merriam-webster.com/dictionary/preventing?utm_campaign=sd&utm_medium=serp&utm_source=jsonld, 10 pages (accessed on Oct. 15, 24) at p. 1. (Year: 2024).
Moenne-Loccoz, Y., et al., "Effect of inoculum preparation and formulation on survival and biocontrol efficacy of Pseudomonas fluorescens F113," Journal of Applied Microbiology 1999, 86, pp. 108-116.
Non-Final Office Action, dated Apr. 10, 2024, for U.S. Appl. No. 17/287,377, 30 pages.
Non-Final Office Action, dated Jan. 13, 2025, for U.S. Appl. No. 17/299,871, 9 pages.
Notice of Allowance, dated Jun. 21, 2024, for Japanese Patent Application No. 2021-531992, 7 pages.
Office Action, dated Apr. 16, 2025, for Australian Patent Application No. 2019394973, 5 pages.
Office Action, dated Nov. 22, 2024, for Canadian Patent Application No. 3,120,608, 8 pages.
Peralta, H., et al., "Engineering the nifH Promoter Region and Abolishing Poly-β-Hydroxybutyrate Accumulation in Rhizobium etli Enhance Nitrogen Fixation in Symbiosis with Phaseolus vulgaris," Applied and Environmental Microbiology, Jun. 2004, vol. 70, No. 6, pp. 3272-3281.
Restriction Requirement, dated Aug. 15, 2024, for U.S. Appl. No. 17/299,871, 7 pages.
Rosenblueth, Monica, et al. "*Klebsiella variicola*a novel species with clinical and plant-associated isolates." Systematic and applied microbiology 27(1):27-35 (2004).
Schisler, D. A., et al., "Appraisal of selected osmoprotectants and carriers for formulating Gram-negative biocontrol agents active against Fusarium dry rot on potatoes in storage," Biological Control 2016, 98, 1-10, http://dx.doi.org/10.1016/j.biocontrol.2016.03.009.
Schoebitz, M., et al., "Starch filler and osmoprotectants improve the survival of rhizobacteria in dried alginate beads," Journal of Microencapsulation 2012, 29(6): 532-538, DOI: 10.3109/02652048.2012.665090.
Segarra, G., et al., "Stepwise flow diagram for the development of formulations of non spore-forming bacteria against foliar pathogens: The case of Lysobacter capsici AZ78," Journal of Biotechnology 2015, 216: 56-64, dx.doi.org/10.1016/j.jbiotec.2015.10.004.
Simon, H. M., et al., "Importance of cis Determinants and Nitrogenase Activity in Regulated Stability of the Klebsiella pneumoniae Nitrogenase Structural Gene mRNA," Journal of Bacteriology, Jun. 1999, vol. 181, No. 12, pp. 3751-3760.
Slininger, P.J., and Schisler, D.A., "High-throughput assay for optimising microbial biological control agent production and delivery," Biocontrol Science and Technology 2013, vol. 23, No. 8, 920-943, http://dx.doi.org/10.1080/09583157.2013.808739.
Slininger, P.J., et al., "Multi-strain co-cultures surpass blends for broad spectrum biological control of maladies of potatoes in stor-

(56) References Cited

OTHER PUBLICATIONS age," Biocontrol Science and Technology 2010, vol. 20, No. 8, pp. 763-786, DOI: 10.1080/09583151003717201.
Slininger, P.J., et al., "Polysaccharide production benefits dry storage survival of the biocontrol agent Pseudomonas fluorescens S11:P:12 effective against several maladies of stored potatoes," Biocontrol Science and Technology 2010, vol. 20, No. 3, pp. 227-244, DOI: 10.1080/09583150903469525.
Streeter, J. G., "Effect of trehalose on survival of Bradyrhizobium japonicum during desiccation," Journal of Applied Microbiology 2003, 95, pp. 484-491, doi:10.1046/j.1365-2672.2003.02017.x.
Swarnalakshmi, K., et al., "Evaluating the influence of novel cyanobacterial biofilmed biofertilizers on soil fertility and plant nutrition in wheat," European Journal of Soil Biology, 55 (2013), pp. 107-116.

* cited by examiner

SEQUENCE LISTING

```
Sequence total quantity: 223
SEQ ID NO: 1          moltype = DNA  length = 1270
FEATURE               Location/Qualifiers
gene                  1..1270
                      note = 16S
variation             186
                      note = n is a, c, t, g, unknown or other
variation             458
                      note = n is a, c, t, g, unknown or other
variation             1041
                      note = n is a, c, t, g, unknown or other
variation             1131..1132
                      note = n is a, c, t, g, unknown or other
variation             1135
                      note = n is a, c, t, g, unknown or other
variation             1139..1140
                      note = n is a, c, t, g, unknown or other
source                1..1270
                      mol_type = genomic DNA
                      organism = Rahnella aquatilis
SEQUENCE: 1
attgaagagt ttgatcatgg ctcagattga acgctggcgg caggcctaac acatgcaagt  60
cgagcggcag cgggaagtag cttgctactt tgccggcgag cggcggacgg gtgagtaatg  120
tctgggaaac tgcctgatgg agggggataa ctactggaaa cggtagctaa taccgcatga  180
cctcgnaaga gcaaagtggg ggatcttcgg acctcacgcc atcggatgtg cccagatggg  240
attagctagt aggtgaggta atggctcacc taggcgacga tccctagctg gtctgagagg  300
atgaccagcc acactggaac tgagacacgg tccagactcc tacgggaggc agcagtgggg  360
aatattgcac aatgggcgca agcctgatgc agccatgccg cgtgtgtgaa gaaggcctta  420
gggttgtaaa gcactttcag cgaggaggaa ggcatcanac ttaatacgtg tggtgattga  480
cgttactcgc agaagaagca ccggctaact ccgtgccagc agccgcggta atacggaggg  540
tgcaagcgtt aatcggaatt actgggcgta aagcgcacgc aggcggtttg ttaagtcaga  600
tgtgaaatcc ccgcgcttaa cgtgggaact gcatttgaaa ctggcaagct agagtcttgt  660
agaggggggt agaattccag gtgtagcggt gaaatgcgta gagatctgga ggaataccgg  720
tggcgaaggc ggccccctgg acaaagactg acgctcaggt gcgaaagcgt ggggagcaaa  780
caggattaga taccctggta gtccacgctg taaacgatgt cgacttggag gttgtgccct  840
tgaggcgtgg cttccggagc taacgcgtta agtcgaccgc ctggggagta cggccgcaag  900
gttaaaactc aaatgaattg acgggggccc gcacaagcgg tggagcatgt ggtttaattc  960
gatgcaacgc gaagaacctt acctactctt gacatccacg gaattcgcca gagatggctt  1020
agtgccttcg ggaaccgtga nacaggtgct gcatggctgt cgtcagctcg tgttgtgaaa  1080
tgttgggtta agtcccgcaa cgagcgcaac ccttatcctt tgttgccagc nngtnatgnn  1140
gggaactcaa aggagactgc cggtgataaa ccggaggaag gtggggatga cgtcaagtca  1200
tcatggccct tacgagtagg gctacacacg tgctacaatg gcatatacaa agagaagcga  1260
actcgcgagg                                                        1270

SEQ ID NO: 2          moltype = DNA  length = 876
FEATURE               Location/Qualifiers
gene                  1..876
                      note = nifH
source                1..876
                      mol_type = genomic DNA
                      organism = Rahnella aquatilis
SEQUENCE: 2
atggcaatgc gtcaatgcgc aatctacggg aaagggggta ttgggaaatc caccactacc  60
caaaaccttg tagcggctct ggccgaaatg aataagaagg tcatgatcgt cggctgtgac  120
cctaaggctg attcaacccg cctcattctg catgcgaaag cacagaacac catcatggaa  180
atggccgctg aagtgggctc cgtggaagat ctggagctgg aagatgtgat gcaaatcggc  240
```

```
tatggcggcg tgcgctgtgc ggaatcaggc ggccctgagc ctggtgtggg ttgtgccgga  300
cgcggggtga tcaccgccat caacttcctc gaagaagaag gcgcgtatgt gccggatctg  360
gattttgtgt tttacgacgt attgggcgat gtggtctgtg gcggtttcgc gatgccaatt  420
cgcgaaaaca aagcgcagga aatctacatc gtgtgctccg gtgaaatgat ggcgatgtat  480
gccgccaaca acatttccaa aggcatcgtg aaatacgcga aatcgggcaa agttcgcctg  540
gccgggctga tctgtaactc ccgccagacg gatcgcgaag atgaactgat catcgcgctg  600
gctgaaaaac ttggcacgca aatgatccac ttcgtgccgc gtgacaacat tgtgcaacgc  660
gctgaaatcc gccgcatgac ggtcatcgaa tacgacccga cttgtgcgca ggcagatcag  720
tatcgtgcac tggcgaacaa aatcgtcaac aacaccaaaa tggtggtgcc gacaccggtc  780
accatggatg agctggaagc cctgttaatg gaatttggca ttatggaaga agaagacctg  840
gccatcgtcg gtcgtaccgc cgccgaagag gcgtga                            876

SEQ ID NO: 3            moltype = DNA  length = 1374
FEATURE                 Location/Qualifiers
gene                    1..1374
                        note = nifD1
source                  1..1374
                        mol_type = genomic DNA
                        organism = Rahnella aquatilis
SEQUENCE: 3
atgaaggcaa aagagattct ggcgctgatt gatgagccag cctgtgagca taaccacaag  60
cagaagtcgg gttgcagcct gccgaaaccg ggcgcgacgg caggcggttg tgcgtttgat  120
ggcgcgcaga ttgcgctgct gccggtcgcg gacgtcgcgc atctggtgca cggccccgatt  180
ggctgtaccg gcagttcatg ggacaaccgt ggcagccgca gttccgggcc ttccatcaac  240
cgcatgggct tcaccaccga catgagcgag caggatgtga ttatggggcg cggcgagcga  300
cgcttatttc acgccgtgca gcacatcgtc agccattacc atccggtggc ggtctttatt  360
tacaacacct gcgtacccgc gatggaaggg gatgacgttg aagccgtgtg tcgcgccgca  420
tcggccgctg ccggtgtgcc ggttatttca gtcgatgccg ccggtttcta cggcagcaaa  480
aatctcggta accgcattgc cggggacgtg atggtcaaaa aggtgatcgg ccagcgcgaa  540
cccgcgccgt ggccggaaaa ctcaccgatc cccgccggac accgccacag catcagcctg  600
attggcgaat tcaatattgc cggcgagttc tggcacgttc tgccgctgct cgatgagctc  660
gggatccgcg tgctgtgcag cctttccggg gattcccgtt ttgctgaaat ccagactatg  720
caccgtggcg aagccaacat gctggtgtgc tcgcgggcgc tgatcaacgt cgcccgaaaa  780
atggaagagc gttaccagat cccatggttt gaaggcagtt tttatggcct gcgttccatg  840
gctgattccc tgcgcacgat cgccgtgctg ctcaaagacc cggatttaca ggcgcgcaca  900
gaacgtctga ttgagcgcga ggaggcggcg acacatcttg cgcttgcgcc ttaccgtgcg  960
cggctcagcg ggcgcaaggc gctgctgtat accggtggcg tgaaatcctg gtcggtggtc  1020
tcggcgttac aggatttagg catcacggtg gtggcgaccg gcacccgaaa atcaaccgaa  1080
gaagacaagc agcgtattcg cgaactgatg ggtgaagacg tgctgatgct cgacgaaggc  1140
aatgccagaa ccttgctcga caccctctat cgtttcggcg gcgacatcat gatcgccggg  1200
ggccgcaaca tgtataccgc gtacaaagcc cgcctgccgt tcctggatat caatcaggag  1260
cgcgagcatg cgtttgccgg atatcacggg ctggtaaatc tggccgaaca gttgtgtatc  1320
accctggaaa gcccggtctg ggcgcaggtc aaccgtctgg cgccgtggcg ctaa        1374

SEQ ID NO: 4            moltype = DNA  length = 1449
FEATURE                 Location/Qualifiers
gene                    1..1449
                        note = nifD2
source                  1..1449
                        mol_type = genomic DNA
                        organism = Rahnella aquatilis
SEQUENCE: 4
atgaccagtg aaacacgcga acgtaacgag gcattgatcc aggaagtgct ggagatcttc  60
cccgagaagg cgcttaaaga tcgtaagaaa cacatgatga ccaccgaccc ggcgatggaa  120
tctgtcggca agtgtattgt ctcaaaccgc aaatcacagc cgggcgtgat gaccgtgcga  180
ggctgcgctt acgccggttc caaaggcgtg gtctttggcc cgatcaaaga catggcgcat  240
atctcccacg gcccggttgg ttgcggccag tattcccgtg ccggacgccg taactattac  300
accggctgga gcggcgtgaa cagctttggc accctcaact tcaccagtga ttttcaggaa  360
cgggacatcg tatttggcgg cgataaaaag ctcgacaaat tgatcgatga actggagatg  420
ttgttcccgc tgagcaaagg catttcggtg cagtcggaat gtccggtcgg tctgatcggc  480
gatgacattt ctgccgtcgc caaagccagc agcgccaaaa tcggtaagcc ggtcgtgccg  540
gtacgctgcg aggggttccg cggtgtgtcg caatcgctcg gccatcacat tgctaacgat  600
gtcatccgcg actgggtgct ggataaccgc gaaggcaatg aatttgaaac cacgccttac  660
gacgtggcga ttatcggcga ctacaacatc ggcggtgacg cctgggcctc acgtattctg  720
ctcgaagaaa tggggctgcg cgtggtggcg cagtggtccg gcgacggcac gctggtggag  780
atggaaaaca ccccgaaagt cgcgctcaat ctggtgcact gctaccgctc gatgaactac  840
atctcccgtc atatggaaga aaaacacggc attccgtgga tggaatacaa cttctttggc  900
ccgaccaaaa ttgcggaatc tctgcgcgaa atcgcggcgc gttttgacga taccatccgg  960
aaaaacgccg aagcggtgat tgaaaaatat caggcgcaaa cgcaggcggt gatcgacaaa  1020
taccgtccgc gtctggaagg caaaaaggtg ctgttgtatc tcggcggttt acgtccgcgc  1080
cacatcatcg gggcgtatga agatctggga atggaaatca tcggtaccgg ctatgaattc  1140
ggtcataacg atgattacga ccgcacctta ccgatgctca aagaaggcac gttgctgttc  1200
gatgacctga gcagttatga gctggaagcg ttcgttaaag cgctgaaacc ggatcttgtc  1260
gggtcaggta tcaaagaaaa atacattttc cagaaaatgg gcgtgccgtt ccgccagatg  1320
cactcctggg attattccgg cccttatcac ggctacgacg gtttcggcat ttttgcccgt  1380
gacatggaca tgacgctgaa caatccgggc tggagtcagc tgaccgcccc ctggttgaaa  1440
acggcctga                                                          1449

SEQ ID NO: 5            moltype = DNA  length = 1386
```

```
FEATURE                 Location/Qualifiers
gene                    1..1386
                        note = nifK1
source                  1..1386
                        mol_type = genomic DNA
                        organism = Rahnella aquatilis
SEQUENCE: 5
atggctcaaa ttctgcgtaa tgccaagccg cttgccacca cgcctgtcaa aagcgggcaa  60
ccgctcgggg cgatcctggc cagtcagggg ctggaaaatt gcatcccgct ggttcacggc  120
gcgcaaggtt gtagcgcgtt cgccaaagtt ttcttcatcc agcattttca cgatccgatc  180
ccgttgcagt ccacggcgat ggaatcgacc acgactatca tgggctcgga tggcaacgtc  240
agtactgcgt tgaccacgtt gtgtcagcgc agtaatccaa aagccattgt gattttgagc  300
accggactgt cagaagcgca gggcagtgat ttgtcgatgg cgctgcgtga gtttcgcgac  360
aaagaaccgc gctttaatgc catcgctatt ctgaccgtta acacgccgga tttttacggc  420
tcgctggaaa acggctacag cgcgctgatg gaaagcgtga tcactcagtg ggtgccggaa  480
aagccgccga ccggcatgcg taacaagcgc gtgaacctgc tggtgagcca tctgctgacg  540
ccgggggatc tggaattact gcgcagctat gtcgaagcct ttggcctgca accggtgatc  600
ctgccggatt tatcacagtc gctggacgga catctggcga atggcgattt caatccggtc  660
acgcagggcg gcacgtcgca acgccagatt gaacaaatgg ggcagagcct gaccaccatt  720
accattggca gttcgctcaa ctgcgccgcc agtctgatgg cgatgcgcag ccgtggcatg  780
gcgctgaacc tgccgcacct gatgacgctg gaaaacatgg acagtctgat ccgccatctg  840
catcaggtgt caggccgcga ggtaccggca tggattgagc gccagcgcgg gcaactgctg  900
gacgccatga tcgactgcca tacctggctg cagtcacagc gtattgcgct ggcggcagaa  960
gcggatttgc tggtggcgtg gtgcgatttc gctcagagcc agggaatgcg cgtcgggccg  1020
gtgattgcgc cggttaatca gcagtcactg gccgggctgc cggtcgaaca ggtggtgatc  1080
ggcgatctgg aagatttaca aacccggctc gacagctacc cggtttcact gctggtggcg  1140
aactcccacg ctgcaccact ggcggaaaaa aacggtatcg cgctggtacg tgccggtttc  1200
ccgctttacg accgtctcgg ggaatttcgc cgcgtgcggc agggctatgc gggtattcgc  1260
gacaccttgt tcgaactcgc gaacctgatg caggcgcgcc atcacatgct gacggcgtat  1320
cactcaccgc ttaggcaggt gttcggcctg agcccggtac cggaggccag tcatgaggcg  1380
cgctaa                                                             1386

SEQ ID NO: 6            moltype = DNA  length = 1569
FEATURE                 Location/Qualifiers
gene                    1..1569
                        note = nifK2
source                  1..1569
                        mol_type = genomic DNA
                        organism = Rahnella aquatilis
SEQUENCE: 6
atgagtcaag atcttggcac cccaaaatcc tgtttcccgc tgttcgagca ggatgaatac  60
cagaatatgt ttacccacaa acgcgcgctg gaagaagcac acggcgaggc gaaagtgcgg  120
gaagtgtttg aatggaccac cacgcaggaa tatcaggatc tgaacttctc gcgtgaagcg  180
ctgaccgtcg acccggcgaa agcctgccag ccgttaggcg cggtactttg cgcgctgggt  240
tttaccaaca cgttgccgta tgtccatggt tcacaaggct gtgtggcgta tttccgtacc  300
tattttaatc gtcatttcaa agagccggtg gcctgtgttt ccgactcaat gaccgaagat  360
gccgccgttt ttggcggaaa taacaacatg aatgtcggtc tggaaaacgc cagcgcgctg  420
tacaagccgg aaattattgc ggtctccacc acctgtatgg cggaagtgat cggtgatgac  480
ctgcaggctt ttatcgccaa cgccaaaaaa gacggatttg tggatgccgg tatgccaatc  540
ccgtatgccc atacaccgag ttttctgggc agtcatgtca ccggctggga caacatgttt  600
gaaggcttcg cccgtacctt taccaccgac gccacgcggg aatatcagcc gggcaaactt  660
gccaaactga acgtggtgac cggttttgaa acttatctcg gcaactaccg ggttattcac  720
cgcatgatga gccagatggg ggtcgaatgc agcgtcttgt ccgatccgtc tgaagtgctc  780
gacacccccgg ctgacggcca ataccgcatg tatgccggcg gcaccacgca aaccgaaatg  840
cgtgatgcac cggatgccat cgacaccttg ctgctgcaac cgtggcaatt acagaaaacc  900
aaaaaggtgg tgcagggcga ctggaatcag ccgggcaccg aagtcagtgt accgattggc  960
ctggcggcga ccgatgcctt gctgatgacg gtaagcgaac tgaccggcaa accgatagct  1020
gacgcgctgg cgactgaacg tggccgtctg gtggacatga tgctcgattc tcacacctgg  1080
ctgcacggca agcgtttcgg tctctacggt gacccggatt ttgtgatggg catgaccgca  1140
ttcctgctgg aactgggctg tgaaccgacc accattctca gccataacgg caacaaacgc  1200
tggcagaaag ccatgaagaa aatgctggct gattcgcctt acggacagga cagcgaagtg  1260
tatgtgaact gcgatctgtg gcatttccgc tcgctgatgt ttacccgtaa accggacttt  1320
atgatcggca actcttacgg aaaattcatt cagcgtgaca cgctggccaa aggcgaacag  1380
ttcgaagtgc cgctgatccg tatcggattc ccgatttttg accggcacca tttgcaccgt  1440
cagaccacct ggggatacga gggcgcgatg agcatcctga cgcaactggt gaatgcggtg  1500
ctcgaacagc tggatcgcga aaccatgaag ctcggcaaaa ccgactacaa cttcgatctg  1560
atccgctaa                                                          1569

SEQ ID NO: 7            moltype = DNA  length = 1488
FEATURE                 Location/Qualifiers
gene                    1..1488
                        note = nifL
source                  1..1488
                        mol_type = genomic DNA
                        organism = Rahnella aquatilis
SEQUENCE: 7
atgagcatca cggcgttatc agcatcattt cctgagggga atatcgccag ccgcttgtcg  60
ctgcaacatc cttcactgtt ttataccgtg gttgaacaat catcggtggc gatttcgctg  120
accgatccgc aggcgcgcat ttgttatgcc aatccggcat tctgccgcca gacgggtttt  180
```

```
gcacttgaga cacttttggg cgagaaccac cgtctgctgg ccagccagca gacgccgaaa  240
catatctatg acgaaatgtg gcgcactttg ttgcagggca aatcctggaa cggccaactg  300
atcaaccggc gtaataaccg ttcgctttat ctggcggatg tcactatcac gcctgtttta  360
ggcgcggacg ggcaggtgga gcattacctc ggcatgcaca aagatatcag cgagaaatac  420
gcgctggagc agcggttgcg caaccacatc accttgttca cggaggtgct gaacaatatt  480
cccgccgccg tggtggtggt ggatgagcag gacaatgtgg tgatggacaa tctggcctac  540
aaaaccctgt gcgctgactg cggcggaaaa gagctgttgg ccgaaatggg ctatccgcaa  600
ctcaaagaga tgctcaacag tggcgaaccg gtgccggttt ccatgcgcgg caacgtacgc  660
tggttttctt tcggtcagtg gtcattgcag ggcgttaatg aagaggccag ccgctttttt  720
accggcatta ccgcgccggg aaaactgatt gttctcaccg actgcaccga tcagcatcac  780
cggcagcagc agggttatct tgaccggctc aagcaaaaac ttaccaacgg caaattgctg  840
gcagccatcc gcgagtcgct tgatgccgcg ctgattcagc tcaacgggcc aattaatatg  900
ctggcggctg cgcgtcgtct taacggcgaa gaaggcaaca acatggcgct ggaattcgcc  960
tggcgcgaag gcgagcaggc ggtgagtcgc ttacaggcct gccgtccgtc gctggatttt  1020
gagccgcagg cagaatggcc ggtcagtgaa ttcttcgacg atctgagcgc gctgtacgac  1080
agccattttc tcagtgacgg tgaattgcgt tacgtggtca tgccatctga tctgcacgct  1140
gtcgggcaac gaacgcaaat ccttaccgcg ctgagcttat ggattgatca cacgctgtca  1200
caggcgcagg ccatgccgtc tctgaagctc tcggtgaaca ttgttgcgaa gcaggatgcg  1260
agctggttgt gttttgacat taccgataat gtgccgcgtg aacgggtgcg ttatgcccgc  1320
ccggaagcgg cgttttcccg tccggggaat ggcatggagc tgcgccttat ccagacgctg  1380
atcgcccatc atcgcggttc tttagatctc tcggtccgcc ctgatggcgg caccttgctg  1440
acgttacgcc tgccggtaca gcaggttatc accggaggct taaaatga              1488

SEQ ID NO: 8           moltype = DNA  length = 1557
FEATURE                Location/Qualifiers
gene                   1..1557
                       note = nifA
source                 1..1557
                       mol_type = genomic DNA
                       organism = Rahnella aquatilis
SEQUENCE: 8
atgacccagt tacctaccgc gggcccggtt atccggcgct ttgatatgtc tgcccagttt  60
acggcgcttt atcgcatcag cgtggcgctg agtcaggaaa gcaataccgc gcgcgcactg  120
gcggcgatcc tcgaagtgct tcacgatcat gcatttatgc aatacggcat ggtgtgtctg  180
ttcgataaag aacgcaatgc actgtttgtg gaatccctgc atggcatcga cggcgaaagg  240
aaaaaagaga cccgccatgt ccgttaccgc atgggggaag gcgtgatcgg cgcggtgatg  300
agccagcgtc aggcgctggt gttaccgcgc atttcagacg atcagcgttt tctcgaccgc  360
ctgaatattt acgattacag cctgccgctg attggtgtgc cgatccccgg tgcggataat  420
cagcctgcgg gtgtgctggt ggcacagccg atggcgttgc acgaagaccg gctggctgcc  480
agtacgcggt ttttagaaat ggtcgccaat ctcatcagcc agccactgcg ttctgccacg  540
cccccggaat cattgcctgc tcaaacgccg gtccggtgca gtgttccgcg ccagtttggt  600
tttgagcaga tggtcgggaa aagtcaggcg atgcgccaga cgatggacat tttacggcag  660
gtttccaaat gggataccac ggttctggtg cgtggtgaaa gcggcaccgg caaggaactt  720
atcgccaatg ccattcatta caactcaccc cgtgcggccg cgccatttgt gaaattcaac  780
tgcgccgcgc tgccggataa cctgctggaa agcgaactgt tcggtcatga aaaaggggcc  840
ttcaccggcg ctatacgcac ccgaaaaggc cgctttgaac tggcggacgg gggcacgtta  900
ttcctcgatg aaatcggcga atcgagcgcg tcgtttcagg ccaaattgct gcgcattttg  960
caggaaggtg aaatggaacg ggtcggcggc gataccacgc tgaaagttga tgtgcgcatt  1020
attgctgcca ccaaccgtaa tcttgaggag gaagtgcgtg ccgggaattt tcgcgaagac  1080
ctgtattatc gcctgaacgt gatgccggtt tcgctgcctg cactgcgtga aaggctggat  1140
gatatcgccg atctggcgcc gtttctggtc aaaaagattg cgctgcgtca ggggcgggaa  1200
ctgcgcatca gtgatggtgc ggtgcgtctg ctgatgacct acagctggcc aggcaacgtg  1260
cgtgaactgg aaaactgcct cgaacgggcg tcggtaatga ccgatgaagg gctgatcgac  1320
cgcgacgtga tcctgttcaa tcaccatgag tccccggcgc tgtccgtcaa acccggtctg  1380
ccgctggcga cagatgaaag ctggctggat caggaactcg acgaacgcca gcgggtgatt  1440
gctgcactgg agaaaaccgg ctgggtgcag gccaaagcgg cccgactgct gggcatgaca  1500
ccgcgccaga ttgcctaccg tatccagatt atggacatca acatgcaccg tatctga     1557

SEQ ID NO: 9           moltype = DNA  length = 2838
FEATURE                Location/Qualifiers
gene                   1..2838
                       note = glnE
source                 1..2838
                       mol_type = genomic DNA
                       organism = Rahnella aquatilis
SEQUENCE: 9
atgttgccac tttcttctgt tttgcaaagc cacgcgcaga gtttgcctga acgctggcat  60
gaacatcctg aaaacctgcc cctccccgat gatgaacagc tggctgtgct gagcagcagt  120
gaattcatga cggacagttt gctggctttt ccgcagtggt ggcatgaaat tgtccaaaat  180
ccccctcagg cgcaggagtg gcaactttac cgtcagtggc tggatgaatc gctgacgcag  240
gtgactgacg aagccgggtt aatgaaagct ttgcgtctgt tccgccgccg tattctgacc  300
cgcattgcgt ggtcacagtc cgcgcaaacc agcgaagcaa aagatacgct tcaccagctg  360
agtgaactgg cggaattatt gattgtcagc gcccgtgact ggctgtatgc cgcttgctgt  420
cgcgagttcg gtacgccggt caatgccgca ggggaaccgc agagaatgct gatcctcggg  480
atgggcaaac tcggcggtgg cgagctgaat ttctcatcgg acatcgacct gatttttgct  540
tatccggaaa atggccagac acgcggcggt cggcgtgaac tggataacgc acaatttttc  600
acccggctcg gccagcgtct gatcaaagcg ctggatcagc ccactatcga cggttttgtc  660
tatcgcgtgg acatgcgttt gcgtccgttc ggcgacagtg gcccgctggt gatgagcttc  720
ccggcactgg aagattatta tcaggaacag gggcgcgact gggaacgcta cgcaatggtg  780
```

```
aaagcgcgtc tgatgggcgg cgcggaggac atcagcagtc aggaattgcg taaaatgctg  840
atgccttttg tcttccgccg ttatatcgat ttcagtgtga tccagtccct gcgtaacatg  900
aaaggcatga tcgcccgcga agtacgccgc cgtggtctga aagacaacat caaactcggc  960
gcaggcggta ttcgtgaaat tgaatttatc gtgcaggtat ttcagctgat ccgtggcggt  1020
cgtgaaccgg cattgcagca gcgtgcgttg ttgccaacgc ttcaggcgct ggaaaatctg  1080
gggctgctgc cggtagagca ggtgttgcag ttgcgtaaca gctatctgtt cctgcgacgt  1140
ctggaaaacc tgttgcaggc cattgctgac gagcaaacgc aaaccttacc gtccgatgag  1200
ctgaatcagg cgcgtctggc gtgggggatg aattacgctg gctggccgca gcttctggat  1260
gcagtgaatg ctcacatgca ggccgtacgc gcggtattta acgatctgat tggcgatgac  1320
acgccagatg ccgaagatga cgtgcaactc tcccggttca gcagtttatg gattgatacg  1380
cttgagcctg acgagctggc tccgctggtg ccgcaacttg acgaaaatgc gcaacggcat  1440
gttttacatc agattgctga ttttcgccgt gacgtggata aacgcacgat agggccacgt  1500
gggcgtgatc agttggattt gctgatgccg cgtttactgg cccaggtctg cacctataaa  1560
aatgcggatg tgacgttaca gcgcctgatg cagttgctgc tcaatatcgt cacgcgcacg  1620
acgtatatcg agctgctggt ggaatatccc ggtgcgctca aacagttaat acgtctgtgc  1680
gctgcctcgc cgatggtggc gacgcaactt gcgcgtcatc ctttattgct cgacgaactg  1740
ctcgacccgc gcacgcttta ccagccgatt gagccgggcg cgtaccgtga tgaactgcgg  1800
caatatctga tgcgggtgcc aaccgaagac gaagaacaac agcttgaagc cgtgcgccag  1860
ttcaaacagg cacagcattt acgtattgcg gccggggata tttccggtgc gttgccggtg  1920
atgaaagtca gtgaccattt aacctacctt gcggaggcca ttctcgacgt tgtggtgcaa  1980
caggcgtggg aacaaatggt cgtaaaatac ggtcagccaa cccatcttca gcaccgtaaa  2040
gggcgcggtt ttgccgtggt gggttacgga aaactcggtg gctgggagct gggttacagc  2100
tcggatctgg atctggtctt cctgctcgat tgcgcgccgg aagtcatgac cgacggcgaa  2160
cgcagcattg acgggcgtca gttttatctg cggctggcgc agcgcatcat gcatttattc  2220
agcacccgta cgtcgtcagg cattctttat gaggttgacc cgcgtctgcg gccttccggt  2280
gcttccggca tgctggtcag caccatcgaa gcttttgcgg attatcaggc caacgaagcc  2340
tggacatggg agcatcaggc gctggttcgc gcgcgtgtgg tttatggtga tccgcaactg  2400
acgcagcaat ttaatgccac gcgtcgcgac attctttgcc gccagcgcga tgccgacggc  2460
ttgcgtaagg aagtccgtga aatgcgcgag aaaatgtatg cccatctggg cagcaaaaga  2520
gccgacgagt ttgatctgaa agccgatccg ggtggcataa cggatattga attcatcgca  2580
caatatctgg ttctgcgttt cgcgcatgat gagccgaagc tgacccgctg gtctgataac  2640
gtgcggattt tcgaactgat ggcgcgacat gacatcatgc cggaagagga agcacgccat  2700
ctgacgcagg cttacgtgac attgcgcgat gaaattcatc atctggcgtt gcaggaacac  2760
agcgggaaag tggccgcaga cagctttgcc actgagcgcg cgcaaatccg cgccagctgg  2820
gcaaactggc ttggctga                                                2838
```

```
SEQ ID NO: 10          moltype = DNA  length = 1290
FEATURE                Location/Qualifiers
gene                   1..1290
                       note = amtB
source                 1..1290
                       mol_type = genomic DNA
                       organism = Rahnella aquatilis
SEQUENCE: 10
atgaaaaaac ttttatccat gatggggctt ggtgcagtgg ctttgctacc ttcgcttgcc  60
atggcagcag caccagcagc ggcaaacggt gctgataacg cctttatgat gatttgtacc  120
gcgctggtat tgttcatgac cgtacccggt gtggcgttgt tctacggcgg cttactgcgt  180
tctaaaaacg ttttgtccat gctgactcag gttattgtta cctttgctct ggtctgcgtc  240
ctgtggatcc tctacggtta cagccttgcc ttcagtgaag gtaacgcgtt cttcggtggt  300
ttcagcaacg taatgatgaa aggcattggc ctggattctg tgactggcac cttctcgcag  360
atgatccacg ttgcattcca gtgttcattt gcctgcatca ctgtagcgct gatcgtaggt  420
ggtattgctg aacgtgtgcg tttctcagca gttctgattt tcactgtgat ctggctgact  480
ttctcttata ttccgatggc tcacatggta tgggcaggcg gtttcctggc tgctgacggt  540
gcgctggact ttgccggtgg taccgttgtt catatcaatg ccgcaattgc tggcctggta  600
ggggcttatc tgctgggtaa acgcgccggt tttggcaaag aagctttcaa accacacaac  660
ctgccaatgg tcttcactgg cgcctcaatc ctgtatgtgg gctggttcgg cttcaatgcg  720
ggttcagcaa gtgccgcaag ctctgttgcc gcgctggctt tcctgaacac tgtcattgct  780
actgctggcg caatcctgtc ctggacgctg gttgagtgga tggtgcgcgg taagccctca  840
ctgctgggcg caagctccgg tgctatcgca ggtctggtgg ctatcacgcc tgcatgtggt  900
acggtcggcg taggtggtgc tctgattatc ggtctggtag gcggtatcac tggtctgtgg  960
ggggttgtta ccctgaaaaa atggctgcgt gttgatgaca cctgtgatgt gttcggtgtt  1020
catggcgtgt gcggtatcgt aggttgtctg ctgacgggtg tattcacgtc cagttcactt  1080
ggcggcgtgg gctacgcaga aggcgtgacc atgggccatc aggtttgggt gcagttcttc  1140
agcgtgtgcg taacattggt ctggtcaggc gttgttgcct tcatcggtta caaagtggct  1200
gacatgatcg taggtctgcg tgttcctgaa gaacaagaac gcgaaggtct ggacgttaac  1260
agccacggcg aaaacgctta caaccaataa                                  1290
```

```
SEQ ID NO: 11          moltype = DNA  length = 500
FEATURE                Location/Qualifiers
gene                   1..500
                       note = PinfC
source                 1..500
                       mol_type = genomic DNA
                       organism = Rahnella aquatilis
SEQUENCE: 11
tgaatatcac tgactcacaa gctacctatg tcgaagaatt aactaaaaaa ctgcaagatg  60
caggcattcg cgttaaagcc gacttgagaa atgagaagat tggctttaaa attcgcgaac  120
acacgctacg ccgtgttcct tatatgttag tttgtggcga taaagaggtc gaagcaggca  180
aagttgctgt tcgtactcgt cgcggcaaag acttaggaag catggatgtt agcgaagtcg  240
```

```
ttgacaaact gctggcggaa atccgcagca gaagtcatca tcaactggag gaataaagta  300
ttaaaggcgg aaaacgagtt caaccggcgc gtcctaatcg cattaacaaa gagattcgcg  360
cgcaagaagt tcgcctcacc ggcgtcgatg gcgagcagat tggtattgtc agtctgaatg  420
aagctcttga aaaagctgag gaagcgggcg tcgatttagt agaaatcagt ccgaatgccg  480
agccgccagt ttgtcgaatc                                              500

SEQ ID NO: 12           moltype = DNA  length = 1085
FEATURE                 Location/Qualifiers
gene                    1..1085
                        note = 16S
source                  1..1085
                        mol_type = genomic DNA
                        organism = Klebsiella variicola
SEQUENCE: 12
attgaagagt ttgatcatgg ctcagattga acgctggcgg caggcctaac acatgcaagt  60
cgagcggtag cacagagagc ttgctctcgg gtgacgagcg gcggacgggt gagtaatgtc  120
tgggaaactg cctgatggag ggggataact actggaaacg gtagctaata ccgcataacg  180
tcgcaagacc aaagtggggg accttcgggc ctcatgccat cagatgtgcc cagatgggat  240
tagctagtag gtggggtaac ggctcaccta ggcgacgatc cctagctggt ctgagaggat  300
gaccagccac actggaactg agacacggtc cagactccta cgggaggcag cagtggggaa  360
tattgcacaa tgggcgcaag cctgatgcag ccatgccgcg tgtgtgaaga aggccttcgg  420
gttgtaaagc actttcagcg gggaggaagg cggtgaggtt aataacctca ccgattgacg  480
ttacccgcag aagaagcacc ggctaactcc gtgccagcag ccgcggtaat acggagggtg  540
caagcgttaa tcggaattac tgggcgtaaa gcgcacgcag gcggtctgtc aagtcggatg  600
tgaaatcccc gggctcaacc tgggaactgc attcgaaact ggcaggctag agtcttgtag  660
aggggggtag aattccaggt gtagcggtga aatgcgtaga gatctggagg aataccggtg  720
gcgaaggcgg cccccctggac aaagactgac gctcaggtgc gaaagcgtgg ggagcaaaca  780
ggattagata ccctggtagt ccacgctgta aacgatgtcg atttggaggt tgtgcccttg  840
aggcgtggct tccggagcta acgcgttaaa tcgaccgcct ggggagtacg gccgcaaggt  900
taaaactcaa atgaattgac gggggcccgc acaagcggtg gagcatgtgg tttaattcga  960
tgcaacgcga agaaccttac ctggtcttga catccacaga actttccaga gatggattgg  1020
tgccttcggg aactgtgaga caggtgctgc atggctgtcg tcagctcgtg ttgtgaaatg  1080
ttggg                                                              1085

SEQ ID NO: 13           moltype = DNA  length = 882
FEATURE                 Location/Qualifiers
gene                    1..882
                        note = nifH1
source                  1..882
                        mol_type = genomic DNA
                        organism = Klebsiella variicola
SEQUENCE: 13
atgaccatgc gtcaatgcgc tatctacggt aaaggcggta tcggtaaatc caccaccacc  60
cagaatctcg tcgcggccct cgccgagatg ggtaagaaag tgatgatcgt cggctgcgat  120
ccgaaagcgg attccacccg tctgatcctc cacgctaaag cccagaacac catcatggag  180
atggcggcgg aagtgggctc ggtcgaggat ctggagctcg aagacgttct gcaaatcggc  240
tatggcgatg tccgttgcgc cgaatccggc ggcccggagc caggcgtcgg ctgcgccgga  300
cgcggggtga tcaccgccat caacttcctc gaggaagaag gcgcctatga agaagatttg  360
gatttcgtct tctatgacgt cctcggcgac gtggtctgcg gcggcttcgc tatgccgatc  420
cgcgaaaaca aagcccagga gatctacatc gtctgctccg gcgagatgat ggcgatgtat  480
gccgccaaca atatctccaa agggatcgtg aagtacgcca aatccggcaa ggtgcgcctc  540
ggcggcctga tctgtaactc gcgcaaaacc gaccgggaag acgaactgat catcgccctg  600
gcggagaagc ttggcacgca gatgatccac ttcgttcccc gcgacaacat tgtgcagcgc  660
gcggagatcc gccggatgac ggtgatcgag tacgacccga cctgtcagca ggcgaatgaa  720
tatcgtcaac tggcgcagaa gatcgtcaat aacaccaaaa aagtggtgcc gacgccgtgc  780
accatggacg agctggaatc gctgctgatg gagttcggca tcatggaaga agaagacacc  840
agcatcattg gtaaaaccgc cgctgaagaa aacgcggcct ga                     882

SEQ ID NO: 14           moltype = DNA  length = 1113
FEATURE                 Location/Qualifiers
gene                    1..1113
                        note = nifH2
source                  1..1113
                        mol_type = genomic DNA
                        organism = Klebsiella variicola
SEQUENCE: 14
atggttagga aaagtagaag taaaaataca aatatagaac taactgaaca tgaccattta  60
ttaataagtc aaataaaaaa gcttaaaaca caaaccactt gctttttaa taataaagga  120
ggggttggga agactacatt agtagcaaat ttaggagcag agctatcaat aaactttagt  180
gcaaaagttc ttattgtgga tgccgaccct caatgtaatc tcacgcagta tgtattaagt  240
gatgaagaaa ctcaggactt atatgggcaa gaaaatccag atagtattta tacagtaata  300
agaccactat cctttggtaa aggatatgaa agtgacctcc ctataaggca tgtagagaat  360
ttcggttttg acataattgt cggtgaccct agacttgctt tacaggaaga cctttagct  420
ggagactggc gagatgccaa aggcggtggg atgcgaggaa ttaggacaac ttttgtattt  480
gcagagttaa ttaagaaagc tcgtgagcta aattatgatt ttgttttctt tgacatggga  540
ccatcattag gcgcaatcaa cagggcagta ttactggcaa tggaattctt tgtcgtccca  600
atgtcaatcg atgtattttc actatgggct attaaaaata ttggctccac ggtttcaata  660
tggaaaaaag aattagacac agggattcgg ctctcagagg aacctagcga attatcacaa  720
ttatcacctc aaggaaaact aaagtttctc ggttacgtca cccaacaaca taaagaacgc  780
```

```
tctggatacg atacaattca gcttgagaat actgaggaag aaataaaatc gaaacgtcgg  840
gtaaaggcgt atgaagacat tggagaggtg tttccttcta aaattactga gcatctttct  900
aaactttatg catcaaaaga tatgaaccca caccttggag atatacgtca tttaggtagt  960
ttagctccga aatcacaatc acaacacgtt ccgatgatat cagtgtctgg tacaggaaat  1020
tacaccagac ttagaaaaag cgcgcgtgaa ctttatcgag atattgcaag aagatactta  1080
gagaacattc agactgctaa tggcgagaaa tag                             1113

SEQ ID NO: 15          moltype = DNA  length = 1374
FEATURE                Location/Qualifiers
gene                   1..1374
                       note = nifD1
source                 1..1374
                       mol_type = genomic DNA
                       organism = Klebsiella variicola
SEQUENCE: 15
atgaagggaa aggaaattct ggcgctgctg gacgaacccg cctgcgagca caaccagaag  60
caaaaatccg gctgcagcgc ccctaagccc ggcgctaccg ccggcggttg cgccttcgac  120
ggcgcgcaga taacgctcct gcccatcgcc gacgtcgcgc acctggtgca cggccccatc  180
ggctgcgcgg gcagctcgtg ggataaccgc ggcagcgtca gcgccggccc ggccctcaac  240
cggctcggct ttaccaccga tcttaacgaa caggatgtga ttatgggccg cggcgaacgc  300
cgcctgttcc acgccgtgcg tcacatcgtc gaccgctatc atccggcggc ggtctttatc  360
tacaacacct gcgtaccggc gatggagggc gatgacatcg aggcggtctg ccaggccgca  420
cagaccgcca ccggcgtccc ggtcatcgct attgacgccg ccggtttcta cggcagtaaa  480
aatcttggca accgaatggc gggcgacgtg atgctcaggc aggtgattgg ccagcgcgaa  540
ccggccccgt ggccagacaa cacgcccttt gccccggccc agcgccacga tatcggcctg  600
attggcgaat tcaatatcgc cggcgagttc tggcaggtcc agccgctgct cgacgagctg  660
gggatccgcg tcctcggcag cctctccggc gacggccgct ttgccgagat ccagaccctg  720
caccgggcgc aggccaatat gctggtgtgc tcgcgcgcgc tgatcaacgt cgcccggggg  780
ctggagctgc gctacggcac gccgtggttt gaaggcagct tctacgggat ccgcgccacc  840
tccgacgcct tgcgccagct ggcgacgctg ctgggggatg acgacctgcg ccgccgcacc  900
gaggcgctga tcgcccgcga agagcaggcg gcggagcagg ctcttgcgcc gtggcgtgag  960
cagctccgcg ggcgcaaagt gctgctctat accggcggcg tgaaatcctg gtcggtggta  1020
tcggccctgc aggatctcgg catgaccgtg gtggccaccg gcacgcgcaa atccaccgag  1080
gaggacaaac agcggatccg tgagctgatg ggcgacgagg cggtgatgct tgaggagggc  1140
aatgcccgca ccctgctcga cgtggtgtac cgctatcagg ccgacctgat gatcgccggc  1200
ggacgcaata tgtacaccgc ctggaaagcc cggctgccgt ttctcgatat caatcaggag  1260
cgcgagcacg cctacgccgg ctatcagggc atcatcaccc tcgcccgcca gctctgtctg  1320
accctcgcca gccccgtctg gccgcaaacg catacccgcg ccccgtggcg ctag       1374

SEQ ID NO: 16          moltype = DNA  length = 1449
FEATURE                Location/Qualifiers
gene                   1..1449
                       note = nifD2
source                 1..1449
                       mol_type = genomic DNA
                       organism = Klebsiella variicola
SEQUENCE: 16
atgaccaacg caacaggcga acgtaacctt gcgctcatcc aggaagtcct ggaggtgttt  60
cccgaaaccg cgcgcaaaga gcgcagaaag cacatgatga tcagcgatcc gcagatggag  120
agcgtcggca agtgcattat ctcgaaccgt aaatcgcagc ccggggtgat gaccgtgcgc  180
ggctgcgcct atgcgggctc gaaaggggtg gtgtttgggc caatcaaaga catggcccat  240
atctcgcacg gccccatcgg ctgcggccag tattcccgcg ccggacggcg caactactat  300
accggcgtca gcggtgtcga cagcttcggc accctgaact tcacctctga ttttcaggag  360
cgcgatattg ttttcggcgg cgataaaaag ctgaccaaac tgatcgaaga gatggagctg  420
ctgttcccgc tgaccaaagg gatcaccatc cagtcggagt gcccggtggg cctgatcggc  480
gatgacatca gcgccgtagc caacgccagc agcaaggcgc tggataaacc ggtgatcccg  540
gtgcgctgcg aaggctttcg cggcgtatcg caatcgctgg gccaccatat cgccaacgac  600
gtggtgcgcg actgggtgct gaacaatcgc gaagggcagc cgtttgccag caccccgtac  660
gatgttgcca tcattggcga ttacaacatc ggcggcgacg cctgggcctc gcgcattctg  720
ctggaagaga tggggctgcg cgtagtggcg cagtggtccg gcgacggcac cctggtggag  780
atggagaaca ccccattcgt taagcttaac ctcgtccact gctaccgttc gatgaactat  840
atcgcccgcc atatggagga gaaacatcag atcccatgga tggaatataa cttcttcggc  900
ccgaccaaaa tcgccgaatc gctgcgcaag atcgccgatc aatttgatga caccattcgc  960
gccaatgcgg aagcggtgat cgccaaatat gaggggcaga tggcggccat catcgccaaa  1020
tatcgcccgc ggctggaggg gcgcaaagtg ctgctgtaca tggggggggct gcggccgcgc  1080
cacgtcatcg gcgcctatga ggatctcggg atggagatca tcgccgccgg ctacgagttt  1140
gcccataacg atgattacga ccgcaccctg ccggacctga aagagggcac cctgctgttt  1200
gacgatgcca gcagctatga gctggaggcc ttcgtcaaag cgctgaaacc tgacctcatc  1260
ggctccggga tcaaagagaa atatatcttc cagaaaatgg gggtgccgtt ccgccagatg  1320
cactcctggg actattccgg cccctatcac ggctatgacg gcttcgccat ctttgcccgc  1380
gatatggata tgaccctgaa caatccggcg tggaacgaac tgactgcccc gtggctgaag  1440
tctgcgtga                                                         1449

SEQ ID NO: 17          moltype = DNA  length = 1386
FEATURE                Location/Qualifiers
gene                   1..1386
                       note = nifK1
source                 1..1386
                       mol_type = genomic DNA
```

```
                        organism = Klebsiella variicola
SEQUENCE: 17
atggcagata ttatccgcag tgaaaaaccg ctggcggtga gcccgattaa aaccgggcaa  60
ccgctcgggg cgatcctcgc cagcctcggg ctggcccagg ccatcccgct ggtccacggc  120
gcccagggct gcagcgcctt cgccaaagtt ttctttattc agcatttcca tgacccggtg  180
ccgctgcagt cgacggccat ggatccgacc gccacgatca tgggggccga cggcaatatc  240
ttcaccgcgc tcgacaccct ctgccagcgc cacagcccgc aggccatcgt gctgctcagc  300
accggtctgg cggaagcgca gggcagcgat atcgcccggg tggtgcgcca gtttcgcgag  360
gcgcatccgc gccataacgg cgtggcgatc ctcaccgtca ataccccgga tttttttggc  420
tctatggaaa acggctacag cgcggtgatc gagagcgtga tcgagcagtg ggtcgcgccg  480
acgccgcgtc cggggcagcg gccccggcgg gtcaacctgc tggtcagcca cctctgttcg  540
ccaggggata tcgaatggct gggccgctgc gtggaggcct ttggcctgca gccggtgatc  600
ctgccggacc tctcgcagtc aatggatggc cacctcggtg aaggggattt tacgcccctg  660
acccagggcg gcgcctcgct gcgccagatt gcccagatgg gccagagtct gggcagcttc  720
gccattggcg tgtcgctcca gcgggcggca tcgctcctga cccaacgcag ccgcggcgac  780
gtgatcgccc tgccgcatct gatgaccctc gaccattgcg atacctttat ccatcagctg  840
gcgaagatgt ccggacgccg cgtaccggcc tggattgagc gccagcgtgg ccagctgcag  900
gatgcgatga tcgactgcca tatgtggctt cagggccagc gcatggcgat ggcggcggag  960
ggcgacctgc tggcggcgtg gtgtgatttc gcccgcagcc aggggatgca gcccggcccg  1020
ctggtcgccc ccaccagcca ccccagcctg cgccagctgc cggtcgagca agtcgtgccg  1080
ggggatcttg aggatctgca gcagctgctg agccaccaac ccgccgatct gctggtggct  1140
aactctcacg cccgcgatct ggcggagcag tttgccctgc cgctgatccg cgtcggtttt  1200
cccctcttcg accggctcgg tgagtttcgt cgcgtccgcc aggggtacgc cggtatgcga  1260
gatacgctgt ttgaactggc caatctgctg cgcgaccgcc atcaccacac cgccctctac  1320
cgctcgccgc ttcgccaggg cgccgacccc cagccggctt caggagacgc ttatgccgcc  1380
cattaa                                                             1386

SEQ ID NO: 18           moltype = DNA  length = 1563
FEATURE                 Location/Qualifiers
gene                    1..1563
                        note = nifK2
source                  1..1563
                        mol_type = genomic DNA
                        organism = Klebsiella variicola
SEQUENCE: 18
atgagccaaa cgatcgataa aattcacagc tgttatccgc tgtttgaaca ggatgaatac  60
cagaccctgt tccagaataa aaagaccctt gaagaggcgc acgacgcgca gcgtgtgcag  120
gaggtttttg cctggaccac caccgccgag tatgaagcgc tgaacttcca gcgcgaggcg  180
ctgaccgtcg acccggccaa agcctgccag ccgctcggcg ccgtactctg cgcgctgggg  240
ttcgccggca ccctgcccta cgtgcacggc tcccagggct gcgtcgccta ttttcgcacc  300
tactttaacc gccattttaa agagccggtc gcctgcgtct ccgactccat gaccgaggac  360
gcggcggtgt tcggcggcaa caacaacatg aatctgggcc tgcagaatgc cagcgcgctg  420
tataaacccg agattatcgc cgtctccacc acctgtatgg ccgaggtgat cggcgacgat  480
ctgcaggcgt ttatcgccaa cgccaaaaaa gagggatttg ttgacgaccg catcgccatt  540
ccttacgccc atacccccag ctttatcggc agccatgtca ccggctggga caatatgttc  600
gaagggttcg cgaagacctt taccgctgac tacgccgggc agccgggcaa acagcaaaag  660
ctcaatctgg tgaccggatt tgagacctat ctcggcaact tccgcgtgct gaagcggatg  720
atggcgcaga tggatgtccc gtgcagcctg ctctccgacc catcagaggt gctcgacacc  780
cccgccgacg gccattaccg gatgtacgcc ggcggcacca gccagcagga gatcaaaacc  840
gcgccggacg ccattgacac cctgctgctg cagccgtggc agctggtgaa aagcaaaaag  900
gtggttcagg agatgtggaa ccagcccgcc accgaggtgg ccgttccgct gggcctggcc  960
gccaccgacg cgctgctgat gaccgtcagt cagctgaccg gcaaaccgat cgccgacgct  1020
ctgaccctgg agcgcggccg gctggtcgac atgatgctgg attcccacac ctggctgcat  1080
ggcaaaaaat tcggcctcta cggcgatccg gatttcgtga tggggctgac gcgcttcctg  1140
ctggagctgg gctgcgagcc gacggtgatc ctcagtcata acgccaataa acgctggcaa  1200
aaagcgatga agaaaatgct cgatgcctcg ccgtacggtc aggaaagcga agtgttcatc  1260
aactgcgacc tgtggcactt ccggtcgctg atgttcaccc gtcagccgga ctttatgatc  1320
ggtaactcct acggcaagtt tatccagcgc gataccctgg caaagggcaa agccttcgaa  1380
gtgccgctga tccgtctggg ctttccgctg ttcgaccgcc atcatctgca ccgccagacc  1440
acctggggct atgaaggcgc aatgaacatc gtcacgacgc tggtgaacgc cgtgctggaa  1500
aaactggacc acgacaccag ccagttgggc aaaaccgatt acagcttcga cctcgttcgt  1560
taa                                                                1563

SEQ ID NO: 19           moltype = DNA  length = 1485
FEATURE                 Location/Qualifiers
gene                    1..1485
                        note = nifL
source                  1..1485
                        mol_type = genomic DNA
                        organism = Klebsiella variicola
SEQUENCE: 19
atgaccctga atatgatgct cgataacgcc gcgccggagg ccatcgccgg cgcgctgact  60
caacaacatc cggggctgtt ttttaccatg gtggaacagg cctcggtggc catctccctc  120
accgatgcca gcgccaggat catttacgcc aacccggcgt tttgccgcca gaccggctat  180
tcgctggcgc aattgttaaa ccagaacccg cgcctgctgg ccagcagcca gacgccgcgc  240
gagatctatc aggagatgtg gcataccctg ctccagcgtc agccctggcg cggtcagctg  300
attaatcagc gtcgggacgg cggcctgtac ctggtggaga ttgacatcac cccggtgctt  360
agcccgcaag ggaactggaa gcattatctg gcgatgcagc gggatatcag cgtcagctac  420
accctcgaac agcggctgcg caaccatatg accctgatgg aggcggtgct gaataatatc  480
```

```
cccgccgccg tggtagtggt ggacgagcag gatcgggtgg tgatggacaa cctcgcctac  540
aaaaccttct gcgctgactg cggcggccgg gagctgctca ccgagctgca ggtctcccct  600
ggccggatga cgcccggcgt ggaggcgatc ctgccggtgg cgctgcgcgg ggccgcgcgc  660
tggctgtcgg taacctgctg gccgttgccc ggcgtcagtg aagaggccag ccgctacttt  720
atcgacagcg cgctggcgcg gaccctggtg gtgatcgccg actgtaccca gcagcgtcag  780
cagcaggagc aagggcgcct tgaccggctg aagcagcaaa tgaccgccgg caagctgctg  840
gcggcgatcc gcgagtcgct ggacgccgcg ctgatccagc tgaactgccc gattaatatg  900
ctggcggcag cccgtcggct gaacggcgag ggaagcggga atgtggcgct ggaggccgcc  960
tggcgtgaag gggaagaggc gatggcgcgg ctccagcgct gtcgcccatc gctggaactc  1020
gaaaaccccg ccgtctggcc gctgcagccc tttttcgacg atctgtgcgc cctctaccgt  1080
acacgcttcg atcccgacgg gctgcaggtc gacatggcct caccgcatct gatcggcttt  1140
ggccagcgca ccccactgct ggcgtgctta agcctgtggc tcgatcgcac cctggccctc  1200
gccgccgaac tcccctccgt gccgctggcg atgcagctct acgccgagga gaacgacggc  1260
tggctgtcgc tgtatctgac tgacaacgta ccgctgctgc aggtgcgcta cgctcactcc  1320
cccgacgcgc tgaactcgcc gggcaaaggc atggagctgc ggctgatcca gaccctggtg  1380
gcgcaccatc gcggggccat tgagctggct tcccgaccgc agggcggcac ctgcctgacc  1440
ctgcgtttcc cgctgtttaa caccctgacc ggaggtgaag catga                 1485
```

```
SEQ ID NO: 20          moltype = DNA  length = 1575
FEATURE                Location/Qualifiers
gene                   1..1575
                       note = nifA
source                 1..1575
                       mol_type = genomic DNA
                       organism = Klebsiella variicola
SEQUENCE: 20
atgatccctg aatccgaccc ggacaccacc gtcagacgct tcgacctctc tcagcagttc  60
accgccatgc agcggataag cgtggtgctg agccgggcca ccgaggccag caaaacgctg  120
caggaggtgc tcagcgtatt acacaacgat gcctttatgc agcacgggat gatctgcctg  180
tacgacagcg agcaggagat cctcagtatc gaagcgctgc agcaaaccgg ccagcagccc  240
ctccccggca gcacgcagat ccgctatcgc cccggcgagg gactggtggg gaccgtgctg  300
gcccaggggc agtcgctggt gctgccccgg gtcgccgacg atcagcgttt tctcgaccgc  360
ctgagcctct acgattacga tctgccgttt atcgccgtac cgttgatggg gcccaacgcc  420
cggccaatag gggtgctggc ggcccagccg atggcgcgcc aggaagagcg gctgccggcc  480
tgcacccgtt ttctcgaaac cgtcgccaac ctcgtcgccc agaccatccg gctgatgatc  540
cttccggcct cacccgccct gtcgagccgc cagccgccga aggtggaacg gccgccggcc  600
tgctcgtcgt cgcgcggcgt gggccttgac aatatggtcg gcaagagccc ggcgatgcgc  660
cagatcgtgg aggtgatccg tcaggtttcg cgctgggaca ccaccgtgct ggtacgcggc  720
gaaagcggca ccgggaaaga gctgatcgcc aacgccatcc atcaccattc gccacgggct  780
ggcgccgcct tcgtcaaatt taactgcgcg gcgctgccgg acaccctgct ggaaagcgaa  840
ctgttcggcc atgagaaagg cgcctttacc ggggcggtgc gtcagcgtaa aggacgtttt  900
gagctggcgg atggcggcac cctgttcctc gatgagattg gtgaaagcag cgcctcgttc  960
caggccaagc tgctgcgtat cctccaggag ggggagatgg agcgggtcgg cggcgatgag  1020
accctgcggg tgaatgtccg catcatcgcc gccaccaacc gtcacctgga ggaggaggtc  1080
cggctgggcc atttccgcga ggatctctac tatcgtctga acgtgatgcc catcgccctg  1140
cccccgctgc gcgagcgtca ggaggacatc gccgagctgg cgcacttcct ggtgcgcaaa  1200
atcggccagc atcaggggcg cacgctgcgg atcagcgagg gcgcgatccg cctgctgatg  1260
gagtacagct ggccgggtaa cgttcgcgaa ctggagaact gcctcgaacg atcggcggtg  1320
atgtcggaga gtggcctgat cgatcgcgac gtgatcctct tcactcacca ggatcgtccc  1380
gccaaagccc tgcctgccag cgggccagcg gaagacagct ggctggacaa cagcctggac  1440
gaacgtcagc gactgatcgc cgcgctggaa aaagccggct gggtgcaggc caaggcggca  1500
cggctgctgg ggatgacgcc gcgccaggtc gcttatcgga tccagatcat ggatatcacc  1560
ctgccgcgtc tgtag                                                  1575
```

```
SEQ ID NO: 21          moltype = DNA  length = 2838
FEATURE                Location/Qualifiers
gene                   1..2838
                       note = glnE
source                 1..2838
                       mol_type = genomic DNA
                       organism = Klebsiella variicola
SEQUENCE: 21
atgatgccgc tttctccgca attacagcag cactggcaga cggtcgctga ccgtctgcca  60
gcggattttc ccattgccga actgagccca caggccaggt cggtcatggc gttcagcgat  120
tttgtcgaac agagtgtgat cgcccagccg ggctggctga atgagcttgc ggactcctcg  180
ccggaggcgg aagagtggcg gcattacgag gcctggctgc aggatcgcct gcaggccgtc  240
actgacgaag cggggttgat gcgagagctg cgtctcttcc gccgccagat gatggtccgc  300
atcgcctggg cgcaggcgct gtcgctggtg agcgaagaag agactctgca gcagctgagc  360
gtcctggcgg agaccctgat tgtcgccgcc cgcgactggc tgtacgccgc ctgctgtaag  420
gagtggggaa cgccatgcaa tgccgagggc cagccgcagc cgctgctgat cctcgggatg  480
ggaaagctgg gcggcggcga gctgaacttc tcttccgata tcgatctgat ctttgcctgg  540
cctgagcatg gcgccacccg cggcggccgc cgcgagctgg ataacgccca gttctttacc  600
cgtctggggc agcggctgat caaggccctt gaccagccga cgcaggacgg ctttgtctat  660
cgggttgaca tgcgcctgcg gccgtttggc gacagtgggc cgctggtact cagttttgcg  720
gcgctggaag attattacca ggagcagggt cgggactggg aacgctatgc gatggtgaaa  780
gcgcggatca tgggcgataa cgacggcgtg tacgccagcg agttgcgcgc gatgctccgt  840
cctttcgtct tccgccgtta tatcgacttc agcgtgatcc agtcgctgcg taacatgaaa  900
ggcatgatcg cccgcgaagt gcggcgtcgc gggctgaaag acaacatcaa gctcggcgcc  960
ggcgggatcc gtgaaattga gtttatcgtt caggtctttc aactgatccg cggtggtcgc  1020
```

```
gaacctgcac tgcagcagcg cgccctgctg ccgacgctgg cggcgattga tgagctacat  1080
ctgctgccgg aaggcgacgc ggcgctgctg cgcgaggcct atctgttcct gcgccggctg  1140
gaaaacctgc tgcaaagcat caacgatgag cagacccaga ccctgccgca ggatgaactt  1200
aaccgcgcca ggctggcgtg gggatgcat accgaagact gggagacgct gagcgcgcag  1260
ctggcgagcc agatggccaa cgtgcggcga gtgtttaatg aactgatcgg cgatgatgag  1320
gatcagtccc cggatgagca actggccgag tactggcgcg agctgtggca ggatgcgctg  1380
gaagaagatg acgccagccc ggcgctggcg catttaaacg ataccgaccg ccgtagcgtg  1440
ctggcgctga ttgccgattt tcgtaaagag ctggatcggc gcaccatcgg cccgcgcggc  1500
cgccaggtgc tggatcagct gatgccgcat ctgctgagcg aaatctgctc gcgcgccgat  1560
gcgccgctgc ctctggcgcg gatcacgccg ctgttgaccg ggatcgtcac ccgtaccacc  1620
tatcttgagc tgctgagcga attccccggc gcgctgaagc acctgatcac gctctgcgcg  1680
gcgtcgccga tggtcgccag ccagctggcg cgccacccgc tgctgctgga tgagctgctg  1740
gatcccaaca ccctctatca gccgacggcg accgatgcct atcgcgacga gctgcgccag  1800
tacctgctgc gcgtgccgga agaggatgaa gagcagcagc tggaggcgtt gcgccagttt  1860
aagcaggcgc agcagctgca tatcgcggcg gcggatatcg ctggtaccct gccggtgatg  1920
aaggtcagcg atcacttaac ctggcttgcc gaagcgatcc tcgacgcggt ggtgcagcag  1980
gcatgggggc agatggtcgc tcgctacggc cagccgaccc acctgcacga tcgccagggt  2040
cgcggcttcg ccgtcgtcgg ctacggtaag cttggcggct gggagctggg ctacagctcc  2100
gatctcgatc tggtgttcct ccatgactgc ccggcggagg tgatgaccga cggcgagcgg  2160
gagattgacg gccgtcagtt ctacctgcgg ctggcccagc ggatcatgca cctgttcagc  2220
acccgcacct cgtccggtat tctctacgaa gtggacgccc ggctgcgtcc ttctggcgcg  2280
gcggggatgc tggtcaccac cgccgacgcg tttgctgact atcagcagaa cgaagcctgg  2340
acgtgggaac atcaggcgct ggtgcgcgcc cgcgtggtct atggcgaccc ggcgctgcag  2400
gcgcgctttg acgccattcg tcgcgatatc ctgaccaccc cgcgggaggg gatgaccctg  2460
cagaccgagg ttcgcgagat gcgcgagaag atgcgcgccc accttggcaa caaacatccc  2520
gatcgttttg atatcaaagc cgatgccggc gggatcaccg atattgaatt tattactcag  2580
tatctggtcc tacgctatgc cagtgacaag ccgaagctga cccgctggtc tgacaacgtg  2640
cgtattcttg agctgctggc gcagaacgac atcatggacg aggaggaggc gcgcgcctta  2700
acgcatgcgt acaccacctt gcgtgatgcg ctccatcacc tggccctgca ggagcagccg  2760
ggacacgtgg cgccagaggc cttcagccgg gagcgtcagc aggtcagcgc cagctggcag  2820
aagtggctga tggcttaa                                                2838
```

```
SEQ ID NO: 22          moltype = DNA  length = 500
FEATURE                Location/Qualifiers
gene                   1..500
                       note = PinfC
source                 1..500
                       mol_type = genomic DNA
                       organism = Klebsiella variicola
SEQUENCE: 22
agcgtcaggt accggtcatg attcaccgtg cgattctcgg ttccctggag cgcttcattg  60
gcatcctgac cgaagagttc gctggcttct tcccaacctg gattgcacca gtgcaggtag  120
tggtcatgaa tattaccgat tctcaggctg aatacgttaa cgaattgacg cgtaaactac  180
aaaatgcggg cattcgtgta aaagcagact tgagaaatga gaagattggc tttaaaatcc  240
gcgagcacac tttacgtcgt gtcccgtata tgttggtctg tggcgacaaa gaagtcgaag  300
ccggcaaagt ggccgtgcgc acccgtcgcg ggaaagacct cggcagcatg gacgtaagtg  360
aagtgattga gaagctgcaa caagagattc gcagccgcag tcttcaacaa ctggaggaat  420
aaggtattaa aggcggaaaa cgagttcaaa cggcacgtcc gaatcgtatc aatggcgaga  480
ttcgcgccct ggaagttcgc                                              500
```

```
SEQ ID NO: 23          moltype = DNA  length = 1287
FEATURE                Location/Qualifiers
gene                   1..1287
                       note = amtB
source                 1..1287
                       mol_type = genomic DNA
                       organism = Klebsiella variicola
SEQUENCE: 23
atgaaaatgg caacaatgaa atcgggtctg ggggcattag cccttcttcc gggactggca  60
atggccgcgc ccgcagtggc ggacaaagcc gataacgcgt ttatgatgat ttgcaccgcg  120
ctggttctgt ttatgaccat cccggggatc gcgctgtttt acggcggcct gatccgcggc  180
aaaaacgtcc tttccatgct gactcaggtg attgtgacct ttggcctggt ctgcgtactg  240
tgggtgattt atggctatac cctggccttc ggcaccggcg gcagcttctt cggtagtttt  300
gactgggtga tgctgaaaaa tattgaactg aaagcgctga tgggcacctt ctatcagtac  360
atccacgtgg ccttccaggg ctcgttcgcc tgtatcaccg tcgggctgat cgtgggggcg  420
ctggctgagc gtattcgttt ctccgccgtg ctgatttttg tggtggtgtg gatgacgctc  480
tcttatgttc cgattgcgca catggtctgg ggcggcggtc tgctggcgac ccacggcgcg  540
ctggacttcg cgggcggcac cgttgtacac atcaacgccg cggttgccgg gctggtgggt  600
gcgtacatga tgggcaaacg tgtgggcttc ggcaaagaag cgttcaaacc gcacaatctg  660
ccgatggtgt tcaccggaac cgccatcctc tacgtgggct ggttcggctt caacgccggc  720
tccgccagcg cagcgaacga aattgccgca ttggctttcg tcaacaccgt cgtcgccaca  780
gcggctgcca tcctggcgtg gacctttggc gaatgggccc tgcgcggtaa accttcactg  840
ctgggcgcct gctccggggc gattgccggt ctggttggcg tcacaccagc ctgtgggtat  900
atcggtgtcg gtggggcgtt gattgtgggt atcgcatctg gtctggcggg catctggggc  960
gtaacggcgc tgaaacgctg gctgcgggtt gatgaccctt gcgacgtctt cggcgtccac  1020
ggcgtctgcg gcatcgtcgg ctgtatcctg accggtatct tcgcggccac ctctctgggc  1080
ggcgtgggtt atgcagaagg cgtcaccatg ggccatcagc tgctggtgca actcgagagt  1140
atcgcgatta ccatcgtctg gtcgggcgtt gtcgctttca ttggctacaa agtggcggac  1200
atgaccgtgg ggctgcgcgt accagaagag caggagcgcg aaggactgga cgtcaacagc  1260
```

```
catggcgaaa acgcctacaa cgcctga                                   1287

SEQ ID NO: 24          moltype = DNA  length = 299
FEATURE                Location/Qualifiers
gene                   1..299
                       note = Prm8.2
source                 1..299
                       mol_type = genomic DNA
                       organism = Klebsiella variicola
SEQUENCE: 24
cgccgtcctc gcagtaccat tgcaaccgac tttacagcaa gaagtgattc tggcacgcat  60
ggaacaaatt cttgccagtc gggctttatc cgatgacgaa cgcgcacagc ttttatatga  120
gcgcggagtg ttgtatgata gtctcggtct gagggcatta gcgcgaaatg atttttcaca  180
agcgctggca atccgacccg atatgcctga agtattcaat tacttaggca tttacttaac  240
gcaggcaggc aattttgatg ctgcctatga agcgtttgat tctgtacttg agcttgatc   299

SEQ ID NO: 25          moltype = DNA  length = 300
FEATURE                Location/Qualifiers
gene                   1..300
                       note = Prm6.2
source                 1..300
                       mol_type = genomic DNA
                       organism = Klebsiella variicola
SEQUENCE: 25
gctaaagttc tcggctaatc gctgataaca tttgacgcaa tgcgcaataa aagggcatca  60
tttgatgccc tttttgcacg ctttcatacc agaacctggc tcatcagtga ttttttttgt  120
cataatcatt gctgagacag gctctgaaga gggcgtttat acaccaaacc attcgagcgg  180
tagcgcgacg gcaagtcagc gttctccttt gcaatagcag ggaagaggcg ccagaaccgc  240
cagcgttgaa gcagtttgaa cgcgttcagt gtataatccg aaacttaatt tcggtttgga  300

SEQ ID NO: 26          moltype = DNA  length = 400
FEATURE                Location/Qualifiers
gene                   1..400
                       note = Prm1.2
source                 1..400
                       mol_type = genomic DNA
                       organism = Klebsiella variicola
SEQUENCE: 26
gcccgctgac cgaccagaac ttccaccttg gactcggcta tacccttggc gtgacggcgc  60
gcgataactg ggactacatc cccattccgg tgatcttacc attggcgtca ataggttacg  120
gtccggcgac tttccagatg acctatattc ccggcaccta caataacggt aacgtttact  180
tcgcctgggc tcgtatacag ttttaattcg ctaagtctta gcaataaatg agataagcgg  240
tgtgtcttgt ggaaaaacaa ggactaaagc gttacccact aaaaaagata gcgactttta  300
tcactttta gcaaagttgc actggacaaa aggtaccaca attggtgtac tgatactcga  360
cacagcatta gtgtcgattt ttcatataaa ggtaattttg                    400

SEQ ID NO: 27          moltype = DNA  length = 1536
FEATURE                Location/Qualifiers
gene                   1..1536
                       note = 16S
variation              245
                       note = n is a, c, t, g, unknown or other
variation              452
                       note = n is a, c, t, g, unknown or other
variation              454
                       note = n is a, c, t, g, unknown or other
variation              1131..1132
                       note = n is a, c, t, g, unknown or other
source                 1..1536
                       mol_type = genomic DNA
                       organism = Klebsiella variicola
SEQUENCE: 27
ttgaagagtt tgatcatggc tcagattgaa cgctggcggc aggcctaaca catgcaagtc  60
gagcggtagc acagagagct tgctctcggg tgacgagcgg cggacgggtg agtaatgtct  120
gggaaactgc ctgatggagg gggataacta ctggaaacgg tagctaatac cgcataacgt  180
cgcaagacca aagtgggggga ccttcgggcc tcatgccatc agatgtgccc agatgggatt  240
agctngtagg tggggtaacg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtgtgaagaa ggccttcggg  420
ttgtaaagca ctttcagcgg ggaggaaggc gntnaggtta ataaccttgt cgattgacgt  480
tacccgcaga agaagcaccg gctaactccg tgccagcagc cgcggtaata cggagggtgc  540
aagcgttaat cggaattact gggcgtaaag cgcacgcagg cggtctgtca agtcggatgt  600
gaaatccccg ggctcaacct gggaactgca ttcgaaactg gcaggctaga gtcttgtaga  660
ggggggtaga attccaggtg tagcggtgaa atgcgtagag atctggagga ataccggtgg  720
cgaaggcggc cccctggaca aagactgacg ctcaggtgcg aaagcgtggg gagcaaacag  780
gattagatac cctggtagtc cacgctgtaa acgatgtcga tttggaggtt gtgcccttga  840
ggcgtggctt ccggagctaa cgcgttaaat cgaccgcctg ggagtacggc ccgcaaggtt  900
aaaactcaaa tgaattgacg ggggcccgca caagcggtgg agcatgtggt ttaattcgat  960
gcaacgcgaa gaaccttacc tggtcttgac atccacagaa ctttccagag atggattggt  1020
```

```
gccttcggga actgtgagac aggtgctgca tggctgtcgt cagctcgtgt tgtgaaatgt  1080
tgggttaagt cccgcaacga gcgcaaccct tatcctttgt tgccagcggt nnggccggga  1140
actcaaagga gactgccagt gataaactgg aggaaggtgg ggatgacgtc aagtcatcat  1200
ggcccttacg accagggcta cacacgtgct acaatggcat atacaaagag aagcgacctc  1260
gcgagagcaa gcggacctca taaagtatgt cgtagtccgg attggagtct gcaactcgac  1320
tccatgaagt cggaatcgct agtaatcgta gatcagaatg ctacggtgaa tacgttcccg  1380
ggccttgtac acaccgcccg tcacaccatg ggagtgggtt gcaaaagaag taggtagctt  1440
aaccttcggg agggcgctta ccactttgtg attcatgact ggggtgaagt cgtaacaagg  1500
taaccgtagg ggaacctgcg gttggatcac ctcctt                            1536

SEQ ID NO: 28          moltype = DNA  length = 882
FEATURE                Location/Qualifiers
gene                   1..882
                       note = nifH
source                 1..882
                       mol_type = genomic DNA
                       organism = Klebsiella variicola
SEQUENCE: 28
atgaccatgc gtcaatgcgc tatctacggt aaaggcggta tcggtaaatc caccaccacc  60
cagaatctcg tcgcggccct cgccgagatg ggtaagaaag tgatgatcgt cggctgcgat  120
ccgaaagcgg actccacccg tctgatcctt cacgctaaag cccagaacac catcatggag  180
atggcggcgg aagtgggctc ggtcgaggat ctggagctcg aagacgttct gcaaatcggc  240
tatggcgatg tccgttgcgc cgaatccggc ggcccggagc caggcgtcgg ctgcgccgga  300
cgcggggtga tcaccgccat caacttcctc gaggaagaag gcgcctatga ggaagatttg  360
gatttcgtct tctatgacgt cctcggcgac gtagtctgcg gcggcttcgc catgccgatc  420
cgcgaaaaca aagcccagga gatctacatc gtctgctccg gcgagatgat ggcgatgtat  480
gccgccaaca atatctccaa ggggatcgtg aagtacgcga aatctggcaa ggtgcgcctc  540
ggcggcctga tctgtaactc gcgcaaaacc gaccgggaag acgaactgat catcgccctg  600
gcggagaagc ttggcacgca gatgatccac ttcgttcccc gcgacaacat tgtgcagcgc  660
gcggagatcc gccggatgac ggtgatcgag tacgacccga cctgtcagca ggcgaatgaa  720
tatcgtcaac tggcgcagaa gatcgtcaat aacaccaaaa aagtggtgcc aacgccgtgc  780
accatggacg agctggaatc gctgctgatg gagttcggca tcatggaaga agaagacacc  840
agcatcattg gtaaaaccgc cgctgaagaa aacgcggcct ga                     882

SEQ ID NO: 29          moltype = DNA  length = 1449
FEATURE                Location/Qualifiers
gene                   1..1449
                       note = nifD1
source                 1..1449
                       mol_type = genomic DNA
                       organism = Klebsiella variicola
SEQUENCE: 29
atgaccaacg caacaggcga acgtaacctt gcgctcatcc aggaagtcct ggaggtgttt  60
cccgaaaccg cgcgcaaaga gcgcagaaag cacatgatga tcagcgatcc gcagatggag  120
agcgtcggca agtgcattat ctcgaaccgt aaatcgcagc ccggggtgat gaccgtgcgt  180
ggctgcgcct atgcgggctc gaaaggggtg gtgtttgggc caatcaaaga catggcccat  240
atctcgcacg gccccatcgg ctgcggccag tactcgcgcg ccggacggcg caactactat  300
accggcgtca gcggtgtcga cagcttcggc accctgaact tcacctctga ttttcaggag  360
cgcgatattg ttttcggcgg cgataaaaag ctgaccaaac tgatcgaaga gatggagctg  420
ctgttcccgc tgaccaaagg gatcaccatc cagtcggagt gcccggtggg cctgatcggc  480
gatgacatca gcgccgtggc caacgccagc agcaaggcgc tggataaacc ggtgatcccg  540
gtgcgctgcg aaggctttcg cggcgtatcg caatcgctgg gccaccatat cgccaacgac  600
gtggtgcgcg actgggtgct gaacaatcgc gaagggcagc cgtttgccag caccccgtat  660
gatgttgcca tcattggcga ttacaacatc ggcggcgacg cctgggcctc gcgcattctg  720
ctggaagaga tggggctgcg cgtagtggcg cagtggtccg gcgacggcac cctggtggag  780
atggagaaca ccccattcgt taagcttaac ctcgtccact gctaccgttc gatgaactat  840
atcgcccgcc atatggagga gaaacatcag atcccgtgga tggaatataa cttcttcggc  900
ccgaccaaaa tcgccgaatc gctgcgcaag atcgccgatc aatttgatga caccattcgc  960
gccaatgcgg aagcggtgat cgccaaatat gaggggcaga tggcggccat catcgccaaa  1020
tatcgcccgc ggctggaggg gcgcaaagtg ctgctgtaca tggggggggct gcggccgcgc  1080
cacgtcatcg gcgcctatga ggatctcggg atggagatca tcgccgccgg ctacgagttt  1140
gcccataacg atgattacga ccgcaccctg ccggacctga aagagggcac cctgctgttt  1200
gacgatgcca gcagctatga gctggaggcc ttcgtcaaag cgctgaaacc tgacctcatc  1260
ggctccggga tcaaagagaa atatatcttc cagaaaatgg gggtgccgtt ccgccagatg  1320
cactcctggg actattccgg cccctatcac ggctatgacg gcttcgccat ctttgcccgc  1380
gatatggata tgaccctgaa caatccggcg tggaacgaac tgactgcccc gtggctgaag  1440
tctgcgtga                                                          1449

SEQ ID NO: 30          moltype = DNA  length = 1374
FEATURE                Location/Qualifiers
gene                   1..1374
                       note = nifD2
source                 1..1374
                       mol_type = genomic DNA
                       organism = Klebsiella variicola
SEQUENCE: 30
atgaagggaa aggaaattct ggcgctgctg gacgaacccg cctgcgagca caaccagaag  60
caaaaatccg gctgcagcgc tcctaagccc ggcgcaaccg ccggcggctg cgccttcgac  120
ggcgcgcaga taacgctcct gcccatcgcc gacgtcgcgc acctggtgca cggccccatc  180
```

```
ggctgcgcgg gcagctcgtg ggataaccgc ggcagcgtca gcgccggccc ggccctcaac  240
cggctcggct ttaccaccga tcttaacgaa caggatgtga ttatgggccg cggcgaacgc  300
cgcctgttcc acgccgtccg tcacatcgtc gaccgctatc atccggcggc ggtctttatc  360
tacaacacct gcgtaccggc gatggagggg gatgacctgg aggccgtctg ccaggccgca  420
cagaccgcca ccggcgtccc ggtcatcgcc attgacgccg ccggtttcta cggcagtaaa  480
aatcttggca accgaatggc gggcgacgtg atgctcaggc aggtgattgg ccagcgcgaa  540
ccggcccccgt ggccagacaa cacgcccttt gccccggccc agcgccacga tatcggcctg  600
attggcgaat tcaatatcgc cggcgagttc tggcaggtcc agccgctgct cgacgagctg  660
gggatccgcg tcctcggcag cctctccggc gacggccgct ttgccgagat ccagaccctg  720
caccgggcgc aggccaatat gctggtgtgc tcgcgcgcgc tgatcaacgt cgcccggggg  780
ctggagctgc gctacggcac gccgtggttt gaaggcagct tctacgggat ccgcgccacc  840
tccgacgcct tgcgccagct ggcggcgctg ctgggggatg acgacctgtg ccgccgcacc  900
gaggcgctga tcgcccgcga agagcaggcg gcggagcagg cgctggcgcc gtggcgcgag  960
cagctccgtg ggcgcaaagt gttgctctac accggcggcg tgaaatcctg gtcggtggta  1020
tcagccctgc aggatctcgg catgaccgtg gtggccaccg gcacgcggaa atccaccgag  1080
gaggacaaac agcggatccg tgagctgatg ggcgacgagg cggtgatgct tgaggagggc  1140
aatgcccgca ccctgctcga cgtggtgtac cgctatcagg ccgacctgat gatcgccggc  1200
ggacgcaata tgtacaccgc ctggaaagcc cggctgccgt ttctcgatat caatcaggag  1260
cgcgagcacg cctacgccgg ctatcagggc atcatcaccc tcgcccgcca gctctgtctg  1320
accctcgcca gtcccgtctg gccgcaaacg catacccgcg ccccgtggcg ctag        1374

SEQ ID NO: 31          moltype = DNA  length = 1386
FEATURE                Location/Qualifiers
gene                   1..1386
                       note = nifK1
source                 1..1386
                       mol_type = genomic DNA
                       organism = Klebsiella variicola
SEQUENCE: 31
atggcagaca ttatccgcag tgaaaaaccg ctggcggtga gcccgattaa aaccgggcaa  60
ccgctcgggg cgatcctcgc cagcctcggg ctggcccagg ccatcccgct ggtccacggc  120
gcccagggct gcagcgcctt cgccaaagtt ttctttattc agcatttcca tgacccggtg  180
ccgctgcagt cgacggccat ggatccgacc gccacgatca tgggggcgga cggcaatatc  240
ttcaccgcgc tcgacaccct ctgccagcgc cacagcccgc aggccatcgt gctgctcagc  300
accggtctgg cggaagcgca gggcagcgat atcgcccggg tggtgcgcca gtttcgtgag  360
gcgcatccgc gccataacgg cgtggcgatc ctcaccgtca ataccccgga ttttttggc  420
tcgatggaaa acggctacag cgcggtgatc gagagcgtga tcgagcagtg ggtcgcgccg  480
acgccgcgtc cggggcagcg gccccggcgg gtcaacctgc tggtcagcca cctctgttcg  540
ccaggggata tcgaatggct gggccgctgc gtggaggcct ttggcctgca gccggtgatc  600
ctgccggacc tctcgcagtc aatggatggc cacctcggtg aaggggattt tacgcccctg  660
acccagggcg gcgcctcgct gcgccagatt gcccagatgg gccagagtct gggcagcttc  720
gccattggcg tgtcgctcca gcgggcggca tcgctcctga cccaacgcag ccgcggcgac  780
gtgatcgccc tgccgcatct gatgaccctc gaccattgcg ataccttat ccatcagctg  840
gcgaagatgt ccggacgccg cgtaccggcc tggattgagc gccagcgcgg ccagctgcag  900
gatgcgatga tcgactgcca tatgtggctt cagggccagc gcatggcgat ggcggcggag  960
ggcgacctgc tggcggcgtg gtgtgatttc gcccgcagcc aggggatgca gcccggcccg  1020
ctggtcgccc ccaccagcca ccccagcctg cgccagctgc cggtcgatca ggtcgtgccg  1080
ggggatcttg aggatctgca gcagctgctg agccaccaac ccgccgatct gctggtggct  1140
aactctcacg cccgcgatct ggcggagcag tttgccctgc cgctgatccg cgtcggtttt  1200
cccctcttcg accggctcgg tgagtttcgt cgcgtccgcc aggggtacgc cggtatgcga  1260
gatacgctgt ttgagctggc caatctgctg cgcgaccgcc atcaccacac cgccctctac  1320
cgctcgccgc ttcgccaggg cgccgacccc ctgccggctt caggagacgc ttatgccgcc  1380
cattaa                                                             1386

SEQ ID NO: 32          moltype = DNA  length = 183
FEATURE                Location/Qualifiers
gene                   1..183
                       note = nifK2
source                 1..183
                       mol_type = genomic DNA
                       organism = Klebsiella variicola
SEQUENCE: 32
gtgccgctga tccgtctggg ctttccgctg ttcgaccgcc atcatctgca ccgccagacc  60
acctggggct atgaaggcgc aatgaacatc gtcacgacgc tggtgaacgc cgtgctggaa  120
aaactggacc acgacaccag ccagttgggc aaaaccgatt acagcttcga cctcgttcgt  180
taa                                                                183

SEQ ID NO: 33          moltype = DNA  length = 1485
FEATURE                Location/Qualifiers
gene                   1..1485
                       note = nifL
source                 1..1485
                       mol_type = genomic DNA
                       organism = Klebsiella variicola
SEQUENCE: 33
atgaccctga atatgatgct cgataacgcc gcaccggagg ccatcgccgg cgcgctgact  60
caacaacatc cggggctgtt ttttaccatg gtggaacagg cctcggtggc catatccctc  120
accgatgcca gcgccaggat catttacgcc aacccagcgt tttgccgcca gaccggctat  180
tcgctggcgc aattgttaaa ccagaacccg cgcctgctgg ccagcagcca gacgccgcgc  240
```

```
gcgatctatc aggagatgtg gcataccctg ctccagcgtc agccctggcg cggtcagctg  300
attaatcagc gtcgggacgg cggcctgtgc ctggtggaga ttgacatcac cccggtgctt  360
agcccgcaag gggaactgga gcattatctg gcgatgcagc gggatatcag cgtcagctac  420
accctcgaac aacggctgcg caaccatatg accctgatgg aggcggtgct gaataatatc  480
cccgccgccg tggtggtggt ggacgagcag gatcgggtgg tgatggacaa cctcgcctac  540
aaaaccttct gcgctgactg cggcggccgg gagctgctca ccgagctgca ggtctcccct  600
ggccggatga cgcccggcgt ggaggcgatc ctgccggtag cgctgcgcgg ggccgcgcgc  660
tggctgtcgg taacctgctg gccgttgccc ggcgtcagtg aagaggccag ccgctacttt  720
atcgacagcg cgctggcgcg gaccctggtg gtgatcgccg actgtaccca gcagcgtcag  780
cagcaggagc aaggacgcct tgaccggctg aagcagcaaa tgaccgccgg caagctgctg  840
gcggcgatcc gcgagtcgct ggacgccgcg ctgatccagc tgaactgccc gattaatatg  900
ctggcggcag cccgtcggct gaacggcgag ggaagcggga atgtggcgct ggaggccgcc  960
tggcgtgaag gggaagaggc gatggcgcgg ctccagcgct gtcgcccatc gctggaactc  1020
gaaaaccccg ccgtctggcc gctgcagccc tttttcgacg atctgtgcgc cctctaccgt  1080
acccgcttcg atcccgacgg gctgcaggtc gacatggcct caccgcatct gatcggcttt  1140
ggccagcgca ccccgctgct ggcgtgctta agcctgtggc tcgaccgcac cctggccctc  1200
gccgccgaat tgccctccgt gccgctggcg atgcagctct atgccgagga gaacgacggc  1260
tggctgtcgc tgtacctgac tgataacgta ccgctgttgc aggtgcgcta cgcccactcc  1320
cccgacgcgc tgaactcgcc gggtaaaggc atggagctgc ggctgatcca gaccctggtg  1380
gcgcaccatc gcggggccat tgagctggct tcccgaccgc agggcggcac ctgcctgacc  1440
ctgcgtttcc cgctgtttaa caccctgacc ggaggtgaag catga                  1485
```

```
SEQ ID NO: 34          moltype = DNA  length = 1575
FEATURE                Location/Qualifiers
gene                   1..1575
                       note = nifA
source                 1..1575
                       mol_type = genomic DNA
                       organism = Klebsiella variicola
SEQUENCE: 34
atgatccctg aatccgaccc ggacaccacc gtcagacgct tcgacctctc tcagcagttc  60
accgccatgc agcggataag cgtggtgctg agccgggcca ccgaggccag caaaacgctg  120
caggaggtac tcactgtatt gcacaacgat gcctttatgc agcacgggat gatctgcctg  180
tacgacagcg agcaggagat cctcagtatc gaagcgctgc agcaaaccgg ccagcagccc  240
ctccccggca gcacgcagat ccgctatcgc cccggcgagg gactggtggg gaccgtgctg  300
gcccaggggc agtcgctggt gctgccccgg gtcgccgacg atcagcgttt tctcgaccgc  360
ctgagcctct acgattacga tctgccgttt atcgccgtac cgttgatggg gcccaacgcc  420
cggccaatag gggtgctggc ggcccagccg atggcgcgcc aggaagagcg gctgccggcc  480
tgcacccgtt ttctcgaaac cgtcgccaac ctcgtcgccc agaccatccg gctgatgatc  540
cttccggcct caccgccct gtcgagccgc cagccgccga aggtggaacg gccgccggcc  600
tgctcgtcgt cgcgcggcgt gggccttgac aatatggtcg gcaagagccc ggcgatgcgc  660
cagatcgtgg aggtgatccg tcaggtttcg cgctgggaca ccaccgtgct ggtgcgcggt  720
gaaagcggca ccgggaaaga gctgatcgcc aacgccatcc atcaccattc gccacgggct  780
ggcgccgcct tcgtcaaatt taactgcgcg gcgctgccgg acaccctgct ggaaagcgaa  840
ctgttcggcc atgagaaagg cgcctttacc ggggcggtgc gtcagcgtaa aggacgtttt  900
gagctggcgg atggcggcac cctgttcctc gatgagattg gtgaaagcag cgcctcgttc  960
caggccaagc tgctgcgtat cctccaggag ggggagatgg agcgggtcgg cggcgatgag  1020
accctgcggg tgaatgtccg catcatcgcc gccaccaacc gtcacctgga ggaggaggtc  1080
cggctgggcc atttccgcga ggatctctat tatcgtctga acgtgatgcc catcgccctg  1140
cccccgctgc gcgagcgtca ggaggacatc gccgagctgg cgcacttcct ggtgcgcaaa  1200
atcggccagc atcaggggcg cacgctgcgg atcagcgagg gcgcgatccg cctgctgatg  1260
gagtacagct ggccgggtaa cgttcgcgaa ctggagaact gcctcgaacg atcggcggtg  1320
atgtcggaga gtggcctgat cgatcgcgac gtgatcctct tcactcacca ggatcgtccc  1380
gccaaagccc tgcctgccag cgggccagcg gaagacagct ggctggacaa cagcctggac  1440
gaacgtcagc gactgatcgc cgcgctggaa aaagccggct gggtgcaggc caaggcggca  1500
cggctgctgg ggatgacgcc gcgccaggtc gcttaccgga tccagatcat ggatatcacc  1560
ctgccgcgtc tgtag                                                  1575
```

```
SEQ ID NO: 35          moltype = DNA  length = 2838
FEATURE                Location/Qualifiers
gene                   1..2838
                       note = glnE
source                 1..2838
                       mol_type = genomic DNA
                       organism = Klebsiella variicola
SEQUENCE: 35
atgatgccgc tttctccgca attacagcag cactggcaga cggtcgctga ccgtctgcca  60
gcggattttc ccattgcaga actgagccca caggccaggt cggtcatggc gttcagcgat  120
tttgtcgaac agagtgtgat cgcccagccg ggctggctga atgagcttgc ggactcctcg  180
ccggaggcgg aagagtggcg gcattacgag gcctggctgc aggatcgcct gcaggccgtc  240
actgacgaag cggggttgat gcgagagctg cgtctcttcc gccgccagat gatggtccgc  300
atcgcctggg cgcaggcgct gtcgctggtg agcgaagaag agaccctgca gcagctgagc  360
gccctggcgg agaccctgat tgtcgccgcc cgcgactggc tctacgccgc ctgctgtaag  420
gagtggggaa cgccatgcaa tgccgagggc cagccgcagc cgctgctgat cctcgggatg  480
ggaaagctgg gcggcggcga gctgaacttc tcttccgata tcgatctgat ctttgcctgg  540
cctgagcatg gcgccacccg cggcggccgc cgcgagctgg ataacgccca gttctttacc  600
cgtctggggc agcggctgat caaggccctt gaccagccga cgcaggacgg ctttgtctat  660
cgggttgaca tgcgcctgcg gccgtttggc gacagtgggc cgctggtact cagctttgcg  720
gcactggaag attattacca ggagcagggt cgggactggg aacgctatgc gatggtgaaa  780
```

```
gcgcggatca tgggcgataa cgacggcgtg tacgccagcg agttgcgcgc gatgctccgt  840
cctttcgtct tccgccgtta tatcgacttc agcgtgatcc agtcgctgcg taacatgaaa  900
ggcatgatcg cccgcgaagt gcggcgtcgc gggctgaaag acaacatcaa gctcggcgcc  960
ggcgggatcc gtgaaattga gtttatcgtt caggtctttc agctgatccg cggtggtcgc  1020
gaacctgcac tgcagcagcg cgccctgctg ccgacgctgg cggcgattga tgagctacat  1080
ctgctgccgg aaggcgacgc ggcgctgctg cgcgaggcct atctgttcct gcgccggctg  1140
gaaaacctgc tgcaaagcat caacgatgaa cagacccaga ccctgccgca ggatgaactt  1200
aaccgcgcca ggctggcgtg ggggatgcat accgaagact gggagacgct gagcgcgcag  1260
ctggcgagcc agatggccaa cgtgcggcga gtgtttaatg aactgatcgg cgatgatgag  1320
gatcagtccc cggatgagca actggccgag tactggcgcg agctgtggca ggatgcgctg  1380
gaagaagatg acgccagccc ggcgctggcg catttaaacg ataccgaccg ccgtagcgtg  1440
ctggcgctga ttgccgattt tcgtaaagag ctggatcggc gcaccatcgg cccgcgcggc  1500
cgccaggtgc tggatcagct gatgccgcat ctgctgagcg aaatctgctc gcgtgccgat  1560
gcgccgctgc ctctggcgcg gatcacgccg ctgttgaccg ggatcgtcac ccgtaccacc  1620
tatcttgagc tgctgagcga attccccggc gcgctgaagc acctgatcac gctctgcgcg  1680
gcgtcgccga tggtcgccag ccagctggcg cgccacccgc tgctgctgga tgagctgctg  1740
gatcccaaca ccctctatca gccgacggcg accgatgcct atcgcgacga gctgcgccag  1800
tacctgctgc gcgtgccgga agaggatgaa gagcagcagc tggaggcgtt gcgccagttt  1860
aagcaggcgc agcagctgca tatcgcggcg gcggatatcg ctggtaccct gccggtgatg  1920
aaggtcagcg atcacttaac ctggcttgcc gaagcgatcc tcgacgcggt ggtgcagcag  1980
gcatgggggc agatggtcgc tcgctacggt cagccgaccc acctgcacga tcgccagggt  2040
cgcggcttcg ccgttgtcgg ctacggtaag ctcggcggct gggagctggg ctacagctcc  2100
gatctcgatc tggtgttcct ccatgactgc ccggcggagg tgatgaccga cggcgagcgg  2160
gagattgacg gccgtcagtt ctacctgcgg ctggcccagc ggatcatgca cctgttcagc  2220
acccgcacct cgtccggtat tctctacgaa gtggacgccc ggctgcgtcc ttctggcgcg  2280
gcggggatgc tggtcaccac cgccgacgcg tttgctgact atcagcagaa cgaagcctgg  2340
acgtgggaac atcaggcgct ggtgcgcgcc cgcgtggtct atggcgaccc ggcgctgcag  2400
gcgcgctttg acgccattcg tcgcgatatc ctgaccaccc cgcgggaggg gacgaccctg  2460
cagaccgagg ttcgcgagat gcgcgagaag atgcgcgccc accttggcaa caaacatccc  2520
gatcgttttg atatcaaagc cgatgccggc gggatcaccg atattgaatt tattactcag  2580
tatctggtcc tacgctatgc cagtgacaag ccgaagctga cccgctggtc tgacaacgtg  2640
cgtattcttg agctgctggc gcagaacgac atcatggacg aggaggaggc gcgcgcctta  2700
acgcatgcat acaccacctt gcgtgatgcg ctccatcacc tggccctgca ggagcagccg  2760
ggacacgtgg cgccagaggc cttcagccgg gagcgtcagc aggtcagcgc cagctggcag  2820
aagtggctga tggcttaa                                                2838
```

```
SEQ ID NO: 36          moltype = DNA  length = 1287
FEATURE                Location/Qualifiers
gene                   1..1287
                       note = amtB
source                 1..1287
                       mol_type = genomic DNA
                       organism = Klebsiella variicola
SEQUENCE: 36
atgaaaatgg caacaatgaa atcgggtctg gggcattag ccccttcttcc gggactggca  60
atggccgcgc ccgcagtggc ggacaaagcc gataacgcgt ttatgatgat ttgcaccgcg  120
ctggttctgt ttatgaccat cccggggatc gcgctgtttt acggcggcct gatccgcggc  180
aaaaacgtcc tttccatgct gactcaggtg attgtgacct ttggcctggt ctgcgtactg  240
tgggtgattt atggctatac cctggccttc ggcaccggcg gcagcttctt cggtagcttt  300
gactgggtga tgctgaaaaa tattgaactg aaagcgctga tgggcacctt ctatcagtac  360
atccacgtgg ccttccaggg ctcgttcgcc tgtatcaccg tcgggctgat cgtgggggcg  420
ctggctgagc gtattcgttt ctccgccgtg ctgattttcg tggtggtgtg gatgacgctc  480
tcttatgttc cgattgcgca catggtctgg ggcggcggtc tgctggcgac ccacggcgcg  540
ctggacttcg cgggcggcac cgttgtacac atcaacgccg cggttgccgg gctggtgggt  600
gcgtatatga tgggcaaacg tgtgggcttc ggcaaagaag cgttcaaacc gcacaatctg  660
ccgatggtgt tcaccggaac cgccatcctc tacgtgggct ggttcggctt caacgccggc  720
tccgccagcg cagcgaacga aattgccgca ctggctttcg tcaacaccgt cgtcgccaca  780
gcggcagcca tcctggcctg gacctttggc gaatgggctc tgcgcggcaa accttcactg  840
ctgggcgcct gctccggggc gattgccggt ctggttggcg tcacaccagc ctgtgggtat  900
atcggtgtcg gtggggcgtt gattgtgggt atcgcatctg gtctggcggg catctggggc  960
gtaacggcgc tgaaacgctg gctgcgggtt gatgaccctt gcgacgtctt cggcgtccac  1020
ggcgtctgcg gcatcgtcgg ctgtatcctg accggtatct tcgcggccac ctctctgggc  1080
ggcgtgggtt atgcagaagg cgtcaccatg ggccatcagc tgctggtgca actcgagagt  1140
atcgcgatta ccatcgtctg gtcgggcgtt gtcgctttca ttggctacaa agtggcggac  1200
atgaccgtgg ggctgcgcgt accagaagag caggagcgcg aaggactgga cgtcaacagc  1260
catggcgaaa acgcctacaa cgcctga                                      1287
```

```
SEQ ID NO: 37          moltype = DNA  length = 1435
FEATURE                Location/Qualifiers
gene                   1..1435
                       note = 16S
variation              255
                       note = n is a, c, t, g, unknown or other
variation              454
                       note = n is a, c, t, g, unknown or other
source                 1..1435
                       mol_type = genomic DNA
                       organism = Achromobacter spiritinus
SEQUENCE: 37
```

```
ctgaagagtt tgatcctggc tcagattgaa cgctagcggg atgccttaca catgcaagtc  60
gaacggcagc acggacttcg gtctggtggc gagtggcgaa cgggtgagta atgtatcgga  120
acgtgcctag tagcggggga taactacgcg aaagcgtagc taataccgca tacgccctac  180
gggggaaagc aggggatcgc aagaccttgc actattagag cggccgatat cggattagct  240
agttggtggg gtaanggctc accaaggcga cgatccgtag ctggtttgag aggacgacca  300
gccacactgg gactgagaca cggcccagac tcctacggga ggcagcagtg gggaattttg  360
gacaatgggg gaaaccctga tccagccatc ccgcgtgtgc gatgaaggcc ttcgggttgt  420
aaagcacttt tggcaggaaa gaaacgtcat gggntaatac cccgtgaaac tgacggtacc  480
tgcagaataa gcaccggcta actacgtgcc agcagccgcg gtaatacgta gggtgcaagc  540
gttaatcgga attactgggc gtaaagcgtg cgcaggcggt tcggaaagaa agatgtgaaa  600
tcccagagct taactttgga actgcatttt taactaccgg gctagagtgt gtcagaggga  660
ggtggaattc cgcgtgtagc agtgaaatgc gtagatatgc ggaggaacac cgatggcgaa  720
ggcagcctcc tgggataaca ctgacgctca tgcacgaaag cgtggggagc aaacaggatt  780
agataccctg gtagtccacg ccctaaacga tgtcaactag ctgttggggc cttcgggcct  840
tagtagcgca gctaacgcgt gaagttgacc gcctggggag tacggtcgca agattaaaac  900
tcaaaggaat tgacggggac ccgcacaagc ggtggatgat gtggattaat tcgatgcaac  960
gcgaaaaacc ttacctaccc ttgacatgtc tggaattctg aagagattcg gaagtgctcg  1020
caagagaacc ggaacacagg tgctgcatgg ctgtcgtcag ctcgtgtcgt gagatgttgg  1080
gttaagtccc gcaacgagcg caacccttgt cattagttgc tacgaaaggg cactctaatg  1140
agactgccgg tgacaaaccg gaggaaggtg gggatgacgt caagtcctca tggcccttat  1200
gggtagggct tcacacgtca tacaatggtc gggacagagg gtcgccaacc cgcgaggggg  1260
agccaatccc agaaacccga tcgtagtccg gatcgcagtc tgcaactcga ctgcgtgaag  1320
tcggaatcgc tagtaatcgc ggatcagcat gtcgcggtga atacgttccc gggtcttgta  1380
cacaccgccc gtcacaccat gggagtgggt tttaccagaa gtagttagcc taacc       1435

SEQ ID NO: 38          moltype = DNA  length = 1528
FEATURE                Location/Qualifiers
gene                   1..1528
                       note = 16S
variation              255
                       note = n is a, c, t, g, unknown or other
variation              999
                       note = n is a, c, t, g, unknown or other
variation              1009
                       note = n is a, c, t, g, unknown or other
variation              1437
                       note = n is a, c, t, g, unknown or other
source                 1..1528
                       mol_type = genomic DNA
                       organism = Achromobacter marplatensis
SEQUENCE: 38
ctgaagagtt tgatcctggc tcagattgaa cgctagcggg atgccttaca catgcaagtc  60
gaacggcagc acggacttcg gtctggtggc gagtggcgaa cgggtgagta atgtatcgga  120
acgtgcctag tagcggggga taactacgcg aaagcgtagc taataccgca tacgccctac  180
gggggaaagc aggggatcgc aagaccttgc actattagag cggccgatat cggattagct  240
agttggtggg gtaanggctc accaaggcga cgatccgtag ctggtttgag aggacgacca  300
gccacactgg gactgagaca cggcccagac tcctacggga ggcagcagtg gggaattttg  360
gacaatgggg gaaaccctga tccagccatc ccgcgtgtgc gatgaaggcc ttcgggttgt  420
aaagcacttt tggcaggaaa gaaacgtcat gggttaatac cccgtgaaac tgacggtacc  480
tgcagaataa gcaccggcta actacgtgcc agcagccgcg gtaatacgta gggtgcaagc  540
gttaatcgga attactgggc gtaaagcgtg cgcaggcggt tcggaaagaa agatgtgaaa  600
tcccagagct taactttgga actgcatttt taactaccgg gctagagtgt gtcagaggga  660
ggtggaattc cgcgtgtagc agtgaaatgc gtagatatgc ggaggaacac cgatggcgaa  720
ggcagcctcc tgggataaca ctgacgctca tgcacgaaag cgtggggagc aaacaggatt  780
agataccctg gtagtccacg ccctaaacga tgtcaactag ctgttggggc cttcgggcct  840
tagtagcgca gctaacgcgt gaagttgacc gcctggggag tacggtcgca agattaaaac  900
tcaaaggaat tgacggggac ccgcacaagc ggtggatgat gtggattaat tcgatgcaac  960
gcgaaaaacc ttacctaccc ttgacatgtc tggaattcng aagagattng gaagtgctcg  1020
caagagaacc ggaacacagg tgctgcatgg ctgtcgtcag ctcgtgtcgt gagatgttgg  1080
gttaagtccc gcaacgagcg caacccttgt cattagttgc tacgaaaggg cactctaatg  1140
agactgccgg tgacaaaccg gaggaaggtg gggatgacgt caagtcctca tggcccttat  1200
gggtagggct tcacacgtca tacaatggtc gggacagagg gtcgccaacc cgcgaggggg  1260
agccaatccc agaaacccga tcgtagtccg gatcgcagtc tgcaactcga ctgcgtgaag  1320
tcggaatcgc tagtaatcgc ggatcagcat gtcgcggtga atacgttccc gggtcttgta  1380
cacaccgccc gtcacaccat gggagtgggt tttaccagaa gtagttagcc taaccgnaag  1440
gggggcgatt accacggtag gattcatgac tggggtgaag tcgtaacaag gtagccgtat  1500
cggaaggtgc ggctggatca cctccttt                                     1528

SEQ ID NO: 39          moltype = DNA  length = 1522
FEATURE                Location/Qualifiers
gene                   1..1522
                       note = 16S
source                 1..1522
                       mol_type = genomic DNA
                       organism = Microbacterium murale
SEQUENCE: 39
tacggagagt ttgatcctgg ctcaggatga acgctggcgg cgtgcttaac acatgcaagt  60
cgaacggtga acacggagct tgctctgtgg gatcagtggc gaacgggtga gtaacacgtg  120
agcaacctgc ccctgactct gggataagcg ctggaaacgg cgtctaatac tggatatgtg  180
```

```
acgtggccgc atggtctgcg tctggaaaga atttcggttg gggatgggct cgcggcctat  240
cagcttgttg gtgaggtaat ggctcaccaa ggcgtcgacg ggtagccggc ctgagagggt  300
gaccggccac actgggactg agacacggcc cagactccta cgggaggcag cagtggggaa  360
tattgcacaa tgggcgcaag cctgatgcag caacgccgcg tgagggatga cggccttcgg  420
gttgtaaacc tcttttagca gggaagaagc gaaagtgacg gtacctgcag aaaaagcgcc  480
ggctaactac gtgccagcag ccgcggtaat acgtagggcg caagcgttat ccggaattat  540
tgggcgtaaa gagctcgtag gcggtttgtc gcgtctgctg tgaaatccgg aggctcaacc  600
tccggcctgc agtgggtacg ggcagactag agtgcggtag gggagattgg aattcctggt  660
gtagcggtgg aatgcgcaga tatcaggagg aacaccgatg gcgaaggcag atctctgggc  720
cgtaactgac gctgaggagc gaaagggtgg ggagcaaaca ggcttagata ccctggtagt  780
ccaccccgta aacgttggga actagttgtg gggtccattc cacggattcc gtgacgcagc  840
taacgcatta agttccccgc ctggggagta cggccgcaag gctaaaactc aaaggaattg  900
acggggaccc gcacaagcgg cggagcatgc ggattaattc gatgcaacgc gaagaacctt  960
accaaggctt gacatatacg agaacgggcc agaaatggtc aactctttgg acactcgtaa  1020
acaggtggtg catggttgtc gtcagctcgt gtcgtgagat gttgggttaa gtcccgcaac  1080
gagcgcaacc ctcgttctat gttgccagca cgtaatggtg ggaactcatg ggatactgcc  1140
ggggtcaact cggaggaagg tggggatgac gtcaaatcat catgcccctt atgtcttggg  1200
cttcacgcat gctacaatgg ccggtacaaa gggctgcaat accgcgaggt ggagcgaatc  1260
ccaaaaagcc ggtcccagtt cggattgagg tctgcaactc gacctcatga agtcggagtc  1320
gctagtaatc gcagatcagc aacgctgcgg tgaatacgtt cccgggtctt gtacacaccg  1380
cccgtcaagt catgaaagtc ggtaacacct gaagccggtg gcctaaccct tgtggaggga  1440
gccgtcgaag gtgggatcgg taattaggac taagtcgtaa caaggtagcc gtaccggaag  1500
gtgcggctgg atcacctcct tt                                           1522
```

```
SEQ ID NO: 40          moltype = DNA  length = 1537
FEATURE                Location/Qualifiers
gene                   1..1537
                       note = 16S
variation              455
                       note = n is a, c, t, g, unknown or other
variation              1004
                       note = n is a, c, t, g, unknown or other
source                 1..1537
                       mol_type = genomic DNA
                       organism = Kluyvera intermedia
SEQUENCE: 40
attgaagagt ttgatcatgg ctcagattga acgctggcgg caggcctaac acatgcaagt  60
cgaacggtag cacagagagc ttgctctcgg gtgacgagtg gcggacgggt gagtaatgtc  120
tgggaaactg cccgatggag ggggataact actggaaacg gtagctaata ccgcataatg  180
tcgcaagacc aaagaggggg accttcgggc ctcttgccat cggatgtgcc cagatgggat  240
tagcttgttg gtgaggtaat ggctcaccaa ggcgacgatc cctagctggt ctgagaggat  300
gaccagccac actggaactg agacacggtc cagactccta cgggaggcag cagtggggaa  360
tattgcacaa tgggcgcaag cctgatgcag ccatgccgcg tgtgtgaaga aggccttcgg  420
gttgtaaagc actttcagcg gggaggaagg cgatncggtt aataaccgtg ttgattgacg  480
ttacccgcag aagaagcacc ggctaactcc gtgccagcag ccgcggtaat acggagggtg  540
caagcgttaa tcggaattac tgggcgtaaa gcgcacgcag gcggtctgtc aagtcggatg  600
tgaaatcccc gggctcaacc tgggaactgc attcgaaact ggcaggcttg agtcttgtag  660
aggggggtag aattccaggt gtagcggtga aatgcgtaga gatctggagg aataccggtg  720
gcgaaggcgg ccccctggac aaagactgac gctcaggtgc gaaagcgtgg ggagcaaaca  780
ggattagata ccctggtagt ccacgccgta aacgatgtcg acttggaggt tgtgcccttg  840
aggcgtggct tccggagcta acgcgttaag tcgaccgcct ggggagtacg gccgcaaggt  900
taaaactcaa atgaattgac gggggcccgc acaagcggtg gagcatgtgg tttaattcga  960
tgcaacgcga agaaccttac ctggtcttga catccacgga attnggcaga gatgccttag  1020
tgccttcggg aaccgtgaga caggtgctgc atggctgtcg tcagctcgtg ttgtgaaatg  1080
ttgggttaag tcccgcaacg agcgcaaccc ttatcctttg ttgccagcgg tccggccggg  1140
aactcaaagg agactgccag tgataaactg gaggaaggtg gggatgacgt caagtcatca  1200
tggcccttac gaccagggct acacacgtgc tacaatggca tatacaaaga gaagcgacct  1260
cgcgagagca agcggacctc ataaagtatg tcgtagtccg gattggagtc tgcaactcga  1320
ctccatgaag tcggaatcgc tagtaatcgt ggatcagaat gccacggtga atacgttccc  1380
gggccttgta cacaccgccc gtcacaccat gggagtgggt tgcaaaagaa gtaggtagct  1440
taaccttcgg gagggcgctt accactttgt gattcatgac tggggtgaag tcgtaacaag  1500
gtaaccgtag gggaacctgc ggttggatca cctcctt                           1537
```

```
SEQ ID NO: 41          moltype = DNA  length = 882
FEATURE                Location/Qualifiers
gene                   1..882
                       note = nifH
source                 1..882
                       mol_type = genomic DNA
                       organism = Kluyvera intermedia
SEQUENCE: 41
atgaccatgc gtcaatgcgc catttatggc aaaggtggga tcggcaaatc caccaccacg  60
caaaacctcg tcgccgctct cgcggaaatg ggtaaaaaag tgatgatcgt cggctgcgac  120
ccgaaagcgg actccacccg tctgatcctg catgcgaaag cacagaacac cattatggag  180
atggccgccg aagtgggttc agtggaagac cttgaactgg aagatgtgct gcaaatcggt  240
tacggcggcg tgcgttgtgc agaatccggc ggcccggagc caggcgtggg ttgtgcaggc  300
cgcggcgtta ttaccgccat taacttcctt gaagaagaag gcgcctatgt cagcgacctc  360
gactttgtct tctatgacgt cctcggtgac gtggtctgcg gcgggttcgc catgccgatt  420
cgtgaaaaca aagcgcaaga gatctatatc gtctgctccg ggaaatgat ggcgatgtat  480
```

```
gccgctaaca acatctccaa aggcatcgtg aaatacgcta aatccggcaa ggtgcgcctg  540
ggcgggctga tttgtaactc ccgtcagacc gaccgcgaag atgaactgat catcgcgctg  600
gcagaaaaac tgggcaccca gatgattcac tttgtgccac gcgacaacat cgtccagcgc  660
gcggaaattc gccgtatgac ggttatcgaa tatgacccga aatgcaacca ggccgacgaa  720
taccgcgcgc tggcgaacaa gatcgtcaac aacaccctga tggtcgtccc gaccccttgc  780
accatggatg aactggaaga gctgctgatg gaattcggca ttatggatgt ggaagacgcc  840
agcatcatcg gtaaaaccgc cgccgaagaa aacgcggcct ga                     882

SEQ ID NO: 42          moltype = DNA  length = 660
FEATURE                Location/Qualifiers
misc_feature           1..660
                       note = Dinitrogenase iron-molybdenum cofactor coding
                        sequence
source                 1..660
                       mol_type = genomic DNA
                       organism = Kluyvera intermedia
SEQUENCE: 42
atgaacgata acgatgtcct tttctggcgc atgctggcgc tatttcagtg tctgccggaa  60
ctgcaacccg cgcagatcct ggcctggctg acaggagaac gcgacgacgc cttaaccccg  120
gcgtacctcg ataagcttaa cgtccgcgaa ctggaagcga ccttcccgtc tgaaacggcg  180
atgatgtcgc ccgcacgctg gagccgcgtt aacgcgtgcc ttcacggtac gctgcccgca  240
cacctgcagg taaaaagcac cactcgtcag gggcaattac gggtagcctt ttgttcacag  300
gatggattgc tgatcaatgg tcattttggt caggggcggc tgttttttat ctacgccttt  360
gatgaacagg gcggatggct acacgcgtta cgccgtcttc cctcggcccc gcaaacccag  420
gagccgaatg aagttcgcgc gcagctcctg agtgattgcc acctgctgtt ttgtgaagcc  480
attggcggcc ctgcggcggc ccggctgatt cgtcacaata tccacccgat gaaagtgtcg  540
ccagggatgt ccattgccgc ccagtgtgat gccattaccg cactgctgag cggacgtctg  600
ccaccgtggc tggcaaaacg tcttgagaaa gccaacccgc tggaagagcg ggtgttttaa  660

SEQ ID NO: 43          moltype = DNA  length = 1374
FEATURE                Location/Qualifiers
gene                   1..1374
                       note = nifD1
source                 1..1374
                       mol_type = genomic DNA
                       organism = Kluyvera intermedia
SEQUENCE: 43
atgaagggaa atgacattct cgcgctgctg gatgaacccg cctgcgaaca caatcacaaa  60
cagaaatccg gctgtagcgc ccctaaaccc ggtgccacgg cgggcggttg cgcgttcgac  120
ggcgcgcaaa tcaccctgtt gccgctgtcg gatgtggcgc acctggtcca cggaccgatt  180
ggctgcacgg gaagctcctg ggataaccgg ggcagtatga gctccggccc cagtctcaac  240
cggctcggct ttaccaccga cctgaacgag caggatgtca ttatggggcg cggcgaacgg  300
cggcttttcc acgcggtgcg tcatatcgtc aaccgttatc accctgccgc cgtgtttatc  360
tataacacct gcgttccggc gatggagggt gatgatattg acgccgtctg tcaggcggcg  420
gaaaccgcca ccggcgtgcc agtgattgcc gttgatgccg ccgggttcta tggcagcaaa  480
aaccttggca accgtctcgc gggtgaagtg atggttaaca aggtcattgg acggcgcccg  540
cccgcccccct ggccggacga taccccttc gcgccggaac accgccacga tatcggcctg  600
attggcgaat ttaatatcgc cggggagttc tggcacgttc agccgctgct cgatgagctg  660
ggtattcgcg tgctgggcag cctttccggg gatggccgtt ttagtgaaat ccagaccctg  720
caccacgcgc aggtcaatat gctggtctgc tcaagagcgc tgatcaatgt tgcccgcacc  780
ctggaacagc gctatggcac cccctggttt gagggcagtt tttacggcgt gcgcgctacc  840
tccgatgccc tgcgtcaact ggcatccctg cttggcgaca gcgatctgat tgcccgcacc  900
gaagccgtta ttgcccgcga agaagccacg gcaaatcagg cgctcgcccc gtggcgcgaa  960
cggctacagg gtcgcaaagt gctgctctat accggtgggg tgaaatcctg gtcggtggtc  1020
tccgcattgc aggatttagg gatgaccgtc gtggcgactg gcacccgcaa atctaccgaa  1080
gaagataagc agcgtattcg cgaattaatg ggcgatgacg cgctaatgct ggaagaaggc  1140
aacgcccgca ccctgctgga tgtggtgtac cgctatcagg cggatttgat gatcgctggg  1200
gggcgtaaca tgtataccgc gtacaaagcg cggctgccgt ttctggatat caaccaggag  1260
cgtgaacacg cctttgcggg ttatcgcggc atcgtcaccc tcgcccaaca gctttgccag  1320
actattgaaa gccccgtctg gccgcaaaca cacgcccgcg cgccgtggca ataa        1374

SEQ ID NO: 44          moltype = DNA  length = 1449
FEATURE                Location/Qualifiers
gene                   1..1449
                       note = nifD2
source                 1..1449
                       mol_type = genomic DNA
                       organism = Kluyvera intermedia
SEQUENCE: 44
atgagcaatg caacaggcga acgtaatctg gaaattatcc aggaagtgct ggagatcttt  60
cccgaaaaaa cgcgcaaaga acgcagaaag cacatgatgg tgaccgaccc ggagatggaa  120
agcgtcggga aatgcatcat ctctaaccgc aaatcgcagc cgggtgtgat gactgtccgc  180
ggctgctcct acgccgggtc gaaaggcgtg gtttttgggc cgattaaaga tatggcccac  240
atctcccacg gcccgatcgg ctgtgggcag tactcccgtg ccgggcggcg caactactac  300
accggggtca gcggcgttga ttccttcggg acgctgaact ttacctctga ttttcaggag  360
cgcgatatcg tcttcggcgg cgataaaaag ctcaccaaac tgattgagga gatggaggaa  420
ctgttcccgc tgaccaaagg catctccatt cagtcggagt gcccggtagg tttaatcggt  480
gacgatatcg aagcggtggc gaatgccagt aaaaaagcgc tcaacaagcc ggtgatcccg  540
gtgcgttgcg aaggctttcg cggcgtgtcg cagtcgctcg gtcaccatat cgccaacgac  600
```

-continued

```
gttatccgcg actgggtgct ggataaccgc gaagggaagc ccttcgaatc taccccctat  660
gacgtggcca tcatcggcga ttacaacatc gggggggatg cctgggcgtc gcgcattctg  720
cttgaagaga tggggttacg cgtggtggcg cagtggtccg gtgacggcac gctggtagag  780
atggaaaaca ccccgttcgt caagctgaac ctggtgcact gctaccgctc tatgaactac  840
atctctcgcc atatggaaga gaaacacggt atcccgtgga tggagtacaa cttcttcggc  900
ccgaccaaaa tcgccgaatc gctgcgtaag atcgccgatc aatttgacga caccatccgc  960
gccaatgcgg aagcggtgat cgccaaatat caggcgcaaa acgatgcgat tatcgccaaa  1020
taccgcccgc gtctcgaagg ccgcaaggtg ctgctctata tgggtggcct gcgtcctcgc  1080
cacgtgattg gcgcgtatga ggatttgggc atggagattg tcgccgccgg gtatgaattt  1140
gcccataacg acgattacga ccgcaccctg ccggacctca aagagggcac gctgttgttc  1200
gacgatgcca gcagttatga actggaagcc ttcgtgaagg cgattaagcc ggacctcatt  1260
ggctcaggca tcaaggaaaa atacattttc cagaaaatgg gggtaccgtt tcgccagatg  1320
cactcctggg attactccgg cccgtatcac ggctatgacg gctttgccat ctttgcccgc  1380
gatatggaca tgacgctcaa caatcccgcc tggggcgagt tgaccgcacc ctggctgaaa  1440
tcagcctga                                                         1449

SEQ ID NO: 45          moltype = DNA  length = 1383
FEATURE                Location/Qualifiers
gene                   1..1383
                       note = nifK1
source                 1..1383
                       mol_type = genomic DNA
                       organism = Kluyvera intermedia
SEQUENCE: 45
atggcagata tcatccgtaa tcagaaaccg ctggcggtaa gcccggtaaa aagcggccag  60
ccgttaggcg ccattctggc gagcctcggc tttgagcaca gtattccact ggtgcacggt  120
gcgcagggat gcagcgcgtt cgccaaagtg ttttttatcc aacattttca tgaccctatt  180
ccgctgcaat ccacggcgat ggaccccacc tcaacggtca tgggggcgga cggcaatatc  240
cttgccgcgc tcaatacgct gtgccagcgc aacaccccga aagctatcgt cctgttgagt  300
accggcctgt ctgaggcgca gggcagcgat atcagccgcg tggtacgtca gtttcgtgag  360
gattttcccc gccacaaaaa tatcgccctc ctgacggtca acaccccgga tttttacggc  420
acgctggaga acggctttag tgcggtggtg gaaagcgtca tcgaacagtg ggtgccggaa  480
aagcctcagc atggcctgcg taaccggcgg gtcaacttgt tgttaagtca cctgctgacg  540
cccggtgatg ttgagttgct gcgcagctac gtggaggctt ttggcctgca accggtgatc  600
gtgccggatc tttcacagtc gctggatggt cacctggcaa gcggtgattt ttcgccggtc  660
actcaggggg gaacgcccct gcgcattatc gaacagatgg gacagagcct gtgcacgttt  720
gctattggcg tgtcgctgtc ccgtgcggca tcgctgctgg cacagcgtag ccgtggcgag  780
gtgatcgtgc ttccccatct gatgaccatg gaacattgcg accgttttat tcatcaactg  840
aagatcattt ccgggcgcga ggttcccgcc tggattgagc gccagcgcgg acaattgcag  900
gatgcgatga tcgattgtca tatgtggttg caggataccc ggctcgcgct ggccgccgag  960
ggcgatctgc tggcgggctg gtgtgatttc gcccgtagcc agggcatgct ccccggcccc  1020
gttgtggcgc cggtcagcca gccgggcctg caacagcttc ccgtggagaa agtggtcatt  1080
ggcgatctgg aagatatgca ggatttactc tgcgctatgc ctgctgacct gctggtcgcc  1140
aactcccatg ccgcagacct ggccgaacaa ttctccatcc cgctgatccg cgccgggttc  1200
cctatcttcg acaggcttgg cgaatttcgt cgcgtgcgtc agggataccc cggcattcgc  1260
gacacgctgt ttgagctggc gaacctgatg cgcgaacgtc atcaccacct gcccgtctac  1320
cgctcccccc tgcgccagca atttgcccag gacgctgacg gaggccgcta tgcaacatgt  1380
taa                                                               1383

SEQ ID NO: 46          moltype = DNA  length = 1563
FEATURE                Location/Qualifiers
gene                   1..1563
                       note = nifK2
source                 1..1563
                       mol_type = genomic DNA
                       organism = Kluyvera intermedia
SEQUENCE: 46
atgagccaaa ctgctgagaa aattgtcacc tgtcatccgc tgtttgaaca ggacgaatac  60
cagacgctgt ttcgcaataa gcgcggtctg gaagaggcgc acgacccgca gcgcgtgcaa  120
gaggtttttg aatggaccac cacggcggag tatgaagcgc tgaactttaa gcgtgaagcg  180
ttaaccgtcg atccggcaaa ggcctgccag cctttaggat cggtactctg ctcgctgggt  240
tttgccaata cgctgcctta tgtgcacggt tcccagggct gtgtggccta tttccgcacc  300
tattttaacc gtcatttcaa agagccgatc gcttgcgttt ccgactctat gacagaggat  360
gcggcggtct tcggcggcaa caacaacctt aacaccgggt tgcaaaatgc cagcgccctg  420
tacaaaccgg aaattgtcgc tgtctccact acctgtatgg cggaggtcat cggcgatgac  480
ctgcaggcct ttatcgccaa cgccaaaaag gacgggttta ttgatgccgc cattccggtg  540
ccctacgccc atacgccaag ttttatcggt agccacatca ccggctggga caacatgttt  600
gaaggtttcg cccgggcatt taccgccgat cacgtggcgc aaccgggcaa actggcgaag  660
ctaaacctgg tgaccggttt tgaaacctat cttggcaatt accgcgtgct caaacgcatg  720
atggcccaga tggaggtgcc ctgtagcctg ctgtctgacc cgtctgaggt gttagatacg  780
ccagccgacg gccactatcg catgtatgcg ggcggcacaa cgcaacaaga gatgcgcgac  840
gcccccgatg ctatcgacac cctgctgctg caaccctggc atctggtgaa gagtaaaaaa  900
gtggtgcagg agtcctgggg ccagcccgcc acagaagtgt ccatcccaat gggactgacc  960
gggaccgacg aactgctgat ggcagtcagt cagttaaccg gcaaaccggt ggccgatgaa  1020
ctgacgctgg agcgtgggcg cctggtggat atgattctcg attcacacac ctggctgcac  1080
ggtaagaaat tcggtctcta cggcgatccg gattttgtga tggggctgac gcgtttcctg  1140
ctggaactgg gctgcgagcc gacggttatc ctctgtcata acggtagcaa gcgctggcag  1200
aaagcgatga agaaaatgct tgaggcatcg ccctacggtc aggagagcga agtgttcatc  1260
aactgcgatc tgtggcattt ccgctcgctg atgtttaccc gcaaaccgga ctttatgatc  1320
```

-continued

```
ggcaactcgt acgccaaatt catccagcgt gacacgctgg cgaaaggcga acagtttgaa  1380
gttccgctga tccgtcttgg cttcccgttg ttcgaccgcc accacctgca tcgccagacc  1440
acatggggtt atgaaggggc gatgaatatc gtcaccaccc tggtcaacgc cgtgctggaa  1500
aaagtcgacc gcgataccat caaactgggc aaaacggact acagcttcga ccttgtccgc  1560
taa                                                                1563

SEQ ID NO: 47          moltype = DNA  length = 1488
FEATURE                Location/Qualifiers
gene                   1..1488
                       note = nifL
source                 1..1488
                       mol_type = genomic DNA
                       organism = Kluyvera intermedia
SEQUENCE: 47
atgaccttta atatgatgct ggagaccagc gcaccgcagc acattgcggg caacctctca  60
cttcaacatc ccggactgtt ttccacgatg gttgaacagg ctccgatcgc gatttcgctg  120
accgacccgg acgcgaggat tctgtacgct aatccggcct tttgtcgcca gaccggttat  180
agcctggaag agctgctcaa ccagaaccat cgcatactgg caagccaaca gacgccgcgc  240
agcatttatc aggaactgtg gcaaacgctg ctgcaacaga tgccctggcg cggtcagctc  300
atcaatcgcc gtcgggatgg cagcctttat ctggctgagg tcgatatcac cccggtcgtc  360
aacaaacagg gcgaactgga acactacctc gccatgcaac gtgatatcag cgccagctat  420
gcgctcgaac agcgattgcg caatcacacc accatgagcg aggcggtgct gaacaacatt  480
cctgccgccg tggtggtggt caacgagcag gaccaggtag tcatggacaa cctcgcctac  540
aaaaccttct gtgccgactg cggtggcaag gagctgctca ccgaactgga tttctcccgg  600
cgcaaaagcg atctctatgc cgggcaaata ctgcctgtgg tgctgcgcgg cgccgtgcgc  660
tggctctctg tcacctgctg gaccttgccg ggggtgagcg aagaagccag ccgctacttt  720
attgataccg cgctgccccg caccctggtg gtgatcaccg actgcaccca gcaacaacaa  780
caggccgaac agggccgtct cgatcgtctc aaacaggaga tgaccaccgg gaagctgctg  840
gccgcgatcc gtgaatcgtt ggatgccgcg ctggttcagc taaactgccc catcaatatg  900
ctggcggcgg cgcgacgtct caacggtgaa gataaccata acgtggcgct ggatgccgcg  960
tggcgcgagg gggaagaggc gctggcccgc ctgcaacgct gccgcccttc tctcgatctg  1020
gaagagagcg cgctgtggcc tctgcaaccg ctgtttgacg acctgcgcgc cctttaccat  1080
acccgctata acaatggcga aatctgcac gttgaaatgg cctctccgca tctggcgggg  1140
tttggtcagc gcacgcagat ccttgcctgt ctcagtttgt ggctcgaccg tacgctggcc  1200
ctcgccgccg cgctaccgga cagaacgctg catacccagc tttacgcccg tgaagaagat  1260
ggctggctgt ccatttggct gacagataat gtgccgctca tccatgtgcg atacgcccac  1320
tcccccgatg ccctgaacgc ccccggcaaa gggatggagc tgcgattgat tcaaaccctg  1380
gttgcccatc atcgcggcgc aatagaacta actacccgcc ctgaaggcgg tacctgcctg  1440
accctgcgat tcccgttatt tcattcactg accggaggcc cacgatga               1488

SEQ ID NO: 48          moltype = DNA  length = 1572
FEATURE                Location/Qualifiers
gene                   1..1572
                       note = nifA
source                 1..1572
                       mol_type = genomic DNA
                       organism = Kluyvera intermedia
SEQUENCE: 48
atgacccagc gacccgagtc gggcaccacc gtctggcgtt ttgatctctc acagcaattt  60
accgccatgc agcgcatcag cgtggtgttg agtcgcgcaa ccgagataag ccagacgctg  120
caggaggtgc tgtgtgttct gcataatgac gcatttatgc aacacggcat gctgtgtctg  180
tatgacaacc agcaggaaat tctgagtatt gaagccttgc aggaggcaga ccaacatctg  240
atccccggca gctcgcaaat tcgctatcgc cctggcgaag ggctggtagg agccgtactg  300
tcccagggac aatctcttgt gctgccgcgt gtcgccgacg atcaacgctt tctcgacagg  360
cttggcatct atgattacaa cctgccgttt atcgccgtcc ccttaatggg gccaggcgcg  420
cagacgattg gcgtgctcgc cgcgcagccg atggcgcgtc tggaggagcg gcttccttcc  480
tgtacgcgct ttctggaaac cgtcgccaat ctggtcgcac agacagtccg gctgatgacc  540
ccgcctgccg ccgccacacc gcgcgccgcg attgcccaga ccgaacgcca gcgcaactgt  600
ggcactcctc gcccccttcgg ctttgagaat atggtgggca aaagcccggc catgcagcag  660
acaatggaca ttatccgcca ggtttcgcgc tgggatacca cggtactggt gcgcggcgaa  720
agcggcaccg gtaaagaact tatcgccaat gctattcatc acaactcccc tcgcgccgcc  780
gcgccctttg tgaaatttaa ctgcgcggcg ctaccggata cgctactgga gagcgaattg  840
ttcggccatg aaaaaggggc gttcaccggc gcggttcgcc agcgtaaagg acgttttgaa  900
ctggccgatg gcggcacact gtttcttgat gaaattggcg aaagcagcgc ctcgttccag  960
gccaaactgc tgcgtatttt gcaggagggt gaaatggagc gcgttggcgg cgacgaaacc  1020
ctgcgcgtca atgtgcgtat catcgccgcc accaaccgga atctggaaga agaggtgcgg  1080
atgggcaatt tccgcgagga tctctattat cgcctcaacg taatgcccat ctccctgccc  1140
ccgctgcgtg aacgtcagga ggacattgcc gagctggcgc actttctggt gcgcaaaatc  1200
gcccataacc aggggcgtac gctgcgcatc agtgatggcg ccatccgtct gctgatgggt  1260
tacaactggc ccggtaacgt gcgtgagctg gaaaattgcc tggaacgttc ggcagtgatg  1320
tcagaaaacg gcctgatcga ccgcgatgtg gtgctcttta accaccgtga gaacacgcca  1380
aaactcgcta tcgccgccgc gccaaaagag gatagctggc ttgatcaaac gctggatgaa  1440
cgtcaacggc tgattgccgc gctggaaaaa gccgggtggg tgcaggccaa agcggcgcgt  1500
ctgctgggta tgacgccccg tcaggtcgcc tatcggatac aaattatgga tatcagcatg  1560
cccaggatgt ga                                                      1572

SEQ ID NO: 49          moltype = DNA  length = 2853
FEATURE                Location/Qualifiers
gene                   1..2853
```

```
                         note = glnE
source                   1..2853
                         mol_type = genomic DNA
                         organism = Kluyvera intermedia
SEQUENCE: 49
atgatgccgc actctccaca gctacagcag cactggcaaa ctgtactggc ccgcttgcct  60
gagtcattca gtgaaacacc gcttagtgaa caagcgcagt tagtgcttac tttcagtgat  120
tttgtgcagg atagccttgc cgcgcatcct gactggctgg ctgagctgga aagcgcaccg  180
ccacaggcgg acgagtggaa gcagtatgcg caaacccttc gcgaatcgct ggaaggtgtg  240
ggagatgagg catcattaat gcgtgcgctg cgcctgttcc gtcgccatat gatggtgcgc  300
attgcctggg cgcagtcgct ggcgctggtg gcagaagatg agacgttgca gcagttgagc  360
gtactggcgg agaccctgat cgtcgctgca cgcgactggc tttacgatgc ctgctgtcgc  420
gagtggggaa cgccgtgcaa tcagcagggg gaaccgcagc cgttgctgat cctgggcatg  480
ggcaagctgg gtggcgggga gcttaacttt tcgtccgata tcgatctgat ttttgcctgg  540
ccggaaaacg gttcaacgcg cggtgggcga cgcgaacttg ataacgccca gttttttact  600
cgcttgggac agcgcctgat caaagtgctc gaccagccga cgcaggatgg ctttgtctat  660
cgcgtggata tgcggctgcg cccgtttggc gacagcggtc cgctggtgct gagttttgcc  720
gcgctggaag attattatca ggagcagggg cgcgactggg aacgttatgc gatggtgaaa  780
gcccgcatta tgggcgataa ggacgatgtt tacgctggcg aattacgggc catgctgcgg  840
ccgttcgtct tccgtcgcta tatcgatttc agcgttattc agtctctgcg taacatgaaa  900
gggatgattg cccgcgaagt gcgccgccgt ggtctgaaag ataacattaa gctgggcgcg  960
ggcggcatcc gtgagattga gtttatcgtt caggtgttcc agttgatacg cggtgggcgc  1020
gagccgtcgt tgcagtcccg ttcactgtta ccgacgctgg acgctatcga taagctgggt  1080
ttgctgccgc ctggcgatgc accggcgtta cgccaggcct atttgtatct gcgccgtctg  1140
gaaaacctgc tgcaaagcat taacgacgaa caaacgcaga cgctgccgac agatgaactc  1200
aatcgcgcgc gtctggcctg gggatgcgg  gtcgcagact gggaaaccct gaccgctgag  1260
cttgaaaagc agatgtctgc cgtacgaggg atattcaaca ccctgattgg cgatgacgaa  1320
gccgaagagc agggggatgc gctctgcggg caatggagtg agttgtggca ggatgcgttt  1380
caggaagatg acagcacgcc tgtgctggcg cacctttctg acgatgatcg ccgccgcgtg  1440
gtcgcgatga ttgctgattt tcgcaaagag ctggataaac gcaccattgg cccacgcggc  1500
cgccaggtgc tcgaccatct gatgccgcat ctgttgagtg atgtctgctc ccgtgaggat  1560
gcccctgtac cgttgtctcg cgtgacgccg ctgttaacgg gaattgtcac gcgtacgacg  1620
tatcttgagc tgctcagcga gtttcctggt gcgcgtaagc atctgatttc actctgtgcc  1680
gcctcgccga tggtggccag taagctggcg cgctatccgt tattgctgga tgagttgctc  1740
gatccgaata ccctttatca gcccacggcg atgaatgcct accgggatga gctacgtcag  1800
tatctgctgc gtgtgccgga tgacgatgaa gagcagcaac tggaggcgtt acgccagttt  1860
aaacaggctc aattgttgcg tgtggcggca gcagatctgg caggcacact ccccgtgatg  1920
aaagtgagcg atcacttaac atggcttgcc gaagccatca ttgaagccgt ggtacaacag  1980
gcgtggagcc tgatggtatc gcgttatggg cagccgaaac acttacgcga ccgtgaaggc  2040
cgtgggtttg cagtggtcgg ttacggcaaa ctgggcggtt gggagctggg ctatagttcc  2100
gatctggatt tgattttcct tcatgactgt ccggtggacg tgatgactga cggcgagcgg  2160
gaaatcgatg gccgccaatt ttatctgcgc cttgcccagc gcgtgatgca cctgttcagt  2220
acgcgcacct catccgggat cctgtatgag gtagacgcgc gcttgcgccc gtccggtgcg  2280
gcgggaatgc tggtgacctc aaccgaatcc tttgccgact accagcgcac cgaagcctgg  2340
acctgggaac atcaggcgct ggttcgcgcc cgcgttgtct atggcgatcc acaattaaac  2400
gcgcaatttg atgccatccg ccgcgatatc accatgaccg tgcgtaatgg tgcaacgtta  2460
caaaccgagg tgcgcgagat gcgcgaaaaa atgcgcgccc acttgagcaa taagcacaag  2520
gatcgctttg atattaaagc cgatgagggt ggaattaccg atatcgaatt tatcacccag  2580
tatctggtgc tgcgttatgc ccatgccaaa ccgaaactga cgcgctggtc ggacaatgtc  2640
cgcattctgg aagggctggc gcaaaacggc attatggaag agcaggaagc gcaggcactt  2700
accaccgcct atacaacgtt gcgtgatgag ctgcatcacc tggcgctaca ggagctgcca  2760
ggacatgttc cggaggcatg ttttgtcgct gaacgcgcga tggtgcgagc ctgctggaac  2820
aagtggttgg tggagccgtg cgaggacgcg taa                                2853

SEQ ID NO: 50            moltype = DNA  length = 1290
FEATURE                  Location/Qualifiers
gene                     1..1290
                         note = amtB
source                   1..1290
                         mol_type = genomic DNA
                         organism = Kluyvera intermedia
SEQUENCE: 50
atgaagaaag cactattaaa agcgggtctg gcctcgctgg cattactgcc gtgtctggct  60
atggcagccg atccggttgt cgtcgataaa gccgacaatg cctttatgat gatttgcacc  120
gcgctggtgc tgtttatgtc aattccgggc atcgccctgt tctatggtgg tttaatccgc  180
ggtaaaaacg tcctttctat gctgacacag gttgcggtta cgttcgcact ggtgtgcgtg  240
ctgtgggtgg tttacggcta ctctctggcc tttggcactg gcggcagctt cttcggtagc  300
ttcgactggg tgatgctgaa aaatattgag ctgaaagcgc tgatgggcac catctatcag  360
tacattcacg ttgcgttcca gggctcgttt gcctgtatta ccgtcggcct gattgtcggt  420
gcgctggcag aacgtatccg tttctccgca gtactgattt tcgtcgtggt atggctgacg  480
ctgtcctacg tgccgatcgc acacatggtc tggggcggcg gtctgctggc aacccatggc  540
gccatggatt ttgcgggcgg tacagtcgtt cacatcaacg cagccgttgc aggcctggtg  600
ggtgcttacc tgattggcaa acgtgtcggt ttcggtaaag aagcgtttaa accgcacaac  660
ctgccgatgg tgtttaccgg tacggcaatc ctctactttg gctggttcgg attcaacgcg  720
ggttctgcaa gcgcggcgaa cgaaattgcg ggtctggctt ttgttaacac cgtcgtggca  780
acagcgggtg caatcctctc ctgggtcttc ggtgagtggg cgctgcgcgg caaaccgtct  840
ctgttgggtg cctgttctgg tgcgattgct ggcctcgtgg gtatcacccc ggcgtgtggt  900
tacgttggtg tgggtggcgc gctgatcgtg ggcatcgttg caggcctggc gggtctgtgg  960
ggcgttaccg cgctgaaacg ctggctgcgt gttgacgacc cgtgtgatgt cttcggtgtt  1020
```

```
cacggcgtgt gcggtatcgt aggttgtatc atgacaggta tcttcgcagc cacttcactg  1080
ggcggcgtgg gttatgccga aggcgtgacc atgggccatc aggttctggt acaactggaa  1140
agtatcgcca ttactatcgt atggtctggt atcgtcgcct ttatcggtta caaactggct  1200
gatatgacag tgggtctgcg tgttccggaa gatcaggaac gcgaagggct ggacgtcaac  1260
agccacggcg agaacgccta caacgcctga                                   1290

SEQ ID NO: 51          moltype = DNA  length = 498
FEATURE                Location/Qualifiers
gene                   1..498
                       note = PinfC
source                 1..498
                       mol_type = genomic DNA
                       organism = Kluyvera intermedia
SEQUENCE: 51
ctggggtcac tggagcgctt tatcggcatc ctgaccgaag aatttgccgg tttcttcccg  60
acctggctgg cccctgttca ggttgtggtg atgaatatca ctgattctca agctgaatat  120
gtcaacgaat tgacccgtaa attgcaaaat gcgggcattc gtgtaaaagc ggacttgaga  180
aacgagaaga ttggctttaa aatccgcgag cacactttac gtcgtgtccc ttatatgttg  240
gtctgtggtg ataaagaggt ggaagcaggc aaagtggccg ttcgcacccg ccgcggtaaa  300
gacctgggca gcctggacgt aagtgaagtg attgagaagc tgcaacaaga gattcgcagc  360
cgcagtcttc aacaactgga ggaataaggt attaaaggcg gaaaacgagt tcaaacggca  420
cgtccgaatc gtatcaatgg cgagattcgc gcccaggaag ttcgcttaac tggtctggaa  480
ggtgagcagc tgggtatt                                                498

SEQ ID NO: 52          moltype = DNA  length = 1537
FEATURE                Location/Qualifiers
gene                   1..1537
                       note = 16S
variation              454
                       note = n is a, c, t, g, unknown or other
source                 1..1537
                       mol_type = genomic DNA
                       organism = Kosakonia pseudosacchari
SEQUENCE: 52
attgaagagt ttgatcatgg ctcagattga acgctggcgg caggcctaac acatgcaagt  60
cgaacggtag cacagagagc ttgctctcgg gtgacgagtg gcggacgggt gagtaatgtc  120
tgggaaactg cctgatggag ggggataact actggaaacg gtagctaata ccgcataacg  180
tcgcaagacc aaagaggggg accttcgggc ctcttgccat cagatgtgcc cagatgggat  240
tagctagtag gtggggtaac ggctcaccta ggcgacgatc cctagctggt ctgagaggat  300
gaccagccac actggaactg agacacggtc cagactccta cgggaggcag cagtggggaa  360
tattgcacaa tgggcgcaag cctgatgcag ccatgccgcg tgtatgaaga aggccttcgg  420
gttgtaaagt actttcagcg gggaggaagg cganacggtt aataaccgtg ttgattgacg  480
ttacccgcag aagaagcacc ggctaactcc gtgccagcag ccgcggtaat acggagggtg  540
caagcgttaa tcggaattac tgggcgtaaa gcgcacgcag gcggtctgtc aagtcggatg  600
tgaaatcccc gggctcaacc tgggaactgc atccgaaact ggcaggcttg agtctcgtag  660
agggaggtag aattccaggt gtagcggtga aatgcgtaga gatctggagg aataccggtg  720
gcgaaggcgg cctcctggac gaagactgac gctcaggtgc gaaagcgtgg ggagcaaaca  780
ggattagata ccctggtagt ccacgccgta aacgatgtct atttggaggt tgtgcccttg  840
aggcgtggct tccggagcta acgcgttaaa tagaccgcct ggggagtacg gccgcaaggt  900
taaaactcaa atgaattgac gggggcccgc acaagcggtg gagcatgtgg tttaattcga  960
tgcaacgcga agaaccttac ctggtcttga catccacaga acttgccaga gatggcttgg  1020
tgccttcggg aactgtgaga caggtgctgc atggctgtcg tcagctcgtg ttgtgaaatg  1080
ttgggttaag tcccgcaacg agcgcaaccc ttatcctttg ttgccagcgg tccggccggg  1140
aactcaaagg agactgccag tgataaactg gaggaaggtg gggatgacgt caagtcatca  1200
tggcccttac gaccagggct acacacgtgc tacaatggcg catacaaaga gaagcgacct  1260
cgcgagagca agcggacctc ataaagtgcg tcgtagtccg gattggagtc tgcaactcga  1320
ctccatgaag tcggaatcgc tagtaatcgt ggatcagaat gccacggtga atacgttccc  1380
gggccttgta cacaccgccc gtcacaccat gggagtgggt tgcaaaagaa gtaggtagct  1440
taaccttcgg gagggcgctt accactttgt gattcatgac tggggtgaag tcgtaacaag  1500
gtaaccgtag gggaacctgc ggttggatca cctcctt                           1537

SEQ ID NO: 53          moltype = DNA  length = 882
FEATURE                Location/Qualifiers
gene                   1..882
                       note = nifH
source                 1..882
                       mol_type = genomic DNA
                       organism = Kosakonia pseudosacchari
SEQUENCE: 53
atgaccatgc gtcaatgcgc catttacggc aaaggtggga tcggtaaatc gaccaccaca  60
cagaacctgg tcgccgcgct ggcggagatg ggtaagaaag tcatgatcgt cggctgcgat  120
ccgaaagccg actccacgcg tttgatcctg catgcgaaag cgcagaacac cattatggag  180
atggccgccg aagtcggctc cgtcgaagac ctggaattag aagacgtgct gcaaatcggt  240
tacggcggcg tgcgctgcgc ggaatccggt ggcccggagc caggtgtggg ttgtgccggt  300
cgtggcgtga tcaccgcgat taacttcctc gaagaagaag gcgcttacgt gccggatctg  360
gattttgttt tctacgacgt gctgggcgac gtggtatgcg gtggtttcgc catgccgatt  420
cgtgaaaaca aagcgcagga gatctacatc gtttgctctg gcgaaatgat ggcgatgtac  480
gccgccaata acatctccaa aggcatcgtg aaatatgcca aatccggtaa agtgcgcctc  540
ggcgggctga tttgtaactc gcgccagacc gaccgcgaag atgaactcat cattgcgctg  600
```

```
gcggaaaaac tcggcacgca aatgatccac tttgttcccc gcgacaacat tgtgcagcgt  660
gcggaaatcc gccgtatgac ggttatcgaa tatgacccga cctgcaatca ggccaacgaa  720
tatcgcagcc ttgccagcaa aatcgtcaac aacaccaaaa tggtggtacc aaccccctgc  780
accatggatg aactggaaga actgctgatg gagttcggca ttatggatgt ggaagacgcc  840
agcatcattg gtaaaaccgc cgccgaagaa aacgccgtct ga                     882

SEQ ID NO: 54          moltype = DNA  length = 1449
FEATURE                Location/Qualifiers
gene                   1..1449
                       note = nifD1
source                 1..1449
                       mol_type = genomic DNA
                       organism = Kosakonia pseudosacchari
SEQUENCE: 54
atgagcaatg caacaggcga acgtaacctg gaaatcatcg agcaggtgct ggaggttttc  60
ccggaaaaga cgcgcaaaga gcgcagaaaa cacatgatgg tgacggaccc ggagcaggag  120
agcgtcggca agtgcatcat ctctaaccgc aaatcgcagc cgggcgtgat gaccgtgcgt  180
ggctgctcgt atgccggatc aaaaggggtg gtatttgggc caatcaaaga tatggcgcat  240
atctcccacg gcccgatcgg ctgcgggcag tactcccgcg ccgggcggcg taactactat  300
accggcgtca gcggcgtgga cagtttcggc acgctcaact tcacctccga tttccaggag  360
cgcgacatcg tgtttggcgg cgacaaaaag ctcgccaaac tgattgaaga gctggaagaa  420
ctgtttccgc tgaccaaagg catttcgatt cagtcggaat gcccggtcgg cctgattggc  480
gatgatattg aagccgtggc gaacgccagc cgcaaagcga tcaacaaacc ggttattccg  540
gtgcgttgcg aaggctttcg cggcgtgtcg caatccctcg gtcaccatat tgccaacgat  600
gtgatccgcg actgggtact ggataaccgc gaaggcaaac cgtttgaatc caccccttac  660
gatgtggcga tcatcggcga ttacaacatc ggtggcgacg cctgggcctc gcgcattttg  720
ctcgaagaga tggggttgcg ggtggtcgcg cagtggtccg gcgacggtac gctggtggag  780
atggaaaaca cgccgttcgt caaactgaac ctggtgcact gctaccgctc gatgaactac  840
atctcgcgcc atatggagga gaagcacggt attccgtgga tggaatacaa cttctttggc  900
ccgacgaaaa tcgcggaatc gctgcgcaaa atcgccgacc tgttcgacga caccattcgc  960
gccaacgccg aagcggtgat cgcccgatac caggcgcaga acgacgccat tatcgccaaa  1020
tatcgcccac gtctggaggg tcgcaaagtg ttgctctata tgggcgggct gcgtccgcgc  1080
catgtgattg gcgcctatga agatctggga atggagatca tcgccgccgg ttatgagttt  1140
ggtcataacg acgattacga ccgcaccctg ccggatctga aagagggcac gctgctgttt  1200
gatgacgcca gcagctatga gctggaggcg tttgtcaacg cgctgaaacc ggatctcatc  1260
ggttccggca tcaaagagaa gtacatcttt cagaaaatgg gcgtgccgtt tcgccagatg  1320
cactcctggg attactccgg cccgtaccac ggctatgacg gcttcgccat cttcgcccgc  1380
gatatggata tgacgctcaa caaccccgcc tggggtcagt tgaccgcgcc gtggcttaaa  1440
tccgcctga                                                          1449

SEQ ID NO: 55          moltype = DNA  length = 1374
FEATURE                Location/Qualifiers
gene                   1..1374
                       note = nifD2
source                 1..1374
                       mol_type = genomic DNA
                       organism = Kosakonia pseudosacchari
SEQUENCE: 55
atgaagggga acgacatcct ggctctgctc gatgaaccag cctgcgagca taaccataaa  60
cagaaaaccg gctgtagcgc gccaaaaccc ggcgccaccg ccggaggctg cgccttcgac  120
ggcgcacaga tcaccctgct gccactttcc gatgtggcgc atctggtaca tggcccgatt  180
ggctgcgccg gcagctcatg ggataaccgt ggcagcctga gttctggccc gctgattaac  240
cgactcggat tcaccactga tttgaacgaa caggatgtca tcatggggcg cggcgagcgg  300
cggttgtttc acgcggtgcg ccatattgtc gagcgctatc acccggcggc ggtatttatt  360
tacaacacct gcgttccggc tatggaaggc gatgacattg acgcggtctg ccaggccgcc  420
gcgaccgcca ccggtgtgcc cgtgattgcc gtagatgtgg ccggttttta cggtagcaaa  480
aacctgggta accgcctcgc gggcgaggtg atggtgaaaa aagttatcgg cgggcgcgaa  540
cccgcgccgt ggccggacaa tacacctttt gccccggcgc accgccatga cataggcctg  600
attggcgaat ttaacatcgc cggcgagttc tggcatatcc agccgctgct tgatgagctg  660
ggtattcgcg tccttggctc cctttccggc gacgggcgct ttgccgagat ccagacgttg  720
caccgcgcgc aggtcaatat gctggtgtgc tccagggcgc tgattaatgt cgccagatcg  780
cttgaacaac gttatggcac accctggttt gaaggcagtt tttatggcgt tcgcgccacc  840
tccgatgccc tgcgccagct ggcaacactc accggcgata gcgatttaat ggcgcgaacc  900
gaacggctga tcgcacgtga agagcaagcc acagaacagg cgctagcacc gctgcgtgaa  960
cggttacacg gccggaaagt gctgctctat accggtggcg tgaaatcctg gtcggtggtt  1020
tcggcgctgc aggatctcgg catgacggtc gttgctaccg gaacgcgcaa atccaccgaa  1080
gaggataaac aacgcatccg tgaactgatg ggcgatgacg ccatcatgct ggatgaaggc  1140
aatgcccgcg ccttgctgga tgtggtctat cgctacaaag ccgacatgat gatcgcgggc  1200
gggcgcaaca tgtacaccgc ctataaagcg cgtctgccct ttctggatat caaccaggag  1260
cgtgaacacg cgtttgccgg ttatcgcggc atcatcacgc ttgccgaaca actttgtcag  1320
acgctggaaa gcccggtctg gccgcaaaca catgcccgcg ccccgtggca ataa        1374

SEQ ID NO: 56          moltype = DNA  length = 1563
FEATURE                Location/Qualifiers
gene                   1..1563
                       note = nifK1
source                 1..1563
                       mol_type = genomic DNA
                       organism = Kosakonia pseudosacchari
```

```
SEQUENCE: 56
atgagccaga ctgctgagaa aatacagaat tgccatcccc tgtttgaaca ggacgcctac  60
cagacactat ttgccggtaa acgggcactc gaagaggctc actcgccgga gcgggtgcag  120
gaagtgtttc aatggaccac caccccggaa tacgaagcgc tgaacttcaa acgcgaagcg  180
ctgactatcg acccggcaaa agcctgccag ccgctggggg cggtgctctg ttcgctgggg  240
tttgccaaca ccctgccgta tgtgcacggt tcacagggtt gtgtggccta tttccgtacg  300
tactttaacc gccacttcaa agaaccggtg gcctgcgtgt cggattcgat gacggaagac  360
gcggccgtgt tcggcgggaa taacaacctc aacaccgggt tacaaaacgc cagcgcactg  420
tataaaccgg agattatcgc cgtctctacc acctgtatgg cggaagtgat cggtgatgat  480
ttacaggcgt ttatcgccaa cgccaaaaaa gatggttttc tcgatgccgc catccccgtg  540
ccctacgccc acacccccag ttttatcggt agccatatca ccggctggga caacatgttt  600
gaaggttttg cccgtacctt taccgcaaac catcagccac agcccggtaa actttcacgc  660
ctgaacctgg tgaccgggtt tgaaacctat ctcggcaatt tccgcgtgct gaaacgcatg  720
atggaacaaa tggaggtgca ggcgagtgtg ctctccgatc cgtcggaggt gctggacacc  780
cccgccaatg gccattacca gatgtacgcg ggcggtacga cgcagcaaga gatgcgcgag  840
gcaccggatg ccatcgacac cctgctgctg caaccgtggc agctggtgaa aagcaaaaaa  900
gtggtgcagg agatgtggaa tcagcccgcc accgaggttg ccattcccgt cgggctggca  960
ggcacagacg aactgttgat ggcgattagc cagttaaccg gcaaagccat tcccgattcg  1020
ctggcgctgg agcgcgggcg gctggtcgat atgatgctcg actcccacac ctggttacac  1080
ggtaaaaaat tcggtctgtt tggcgatccg gattttgtca tgggattgac ccgcttcctg  1140
ctggaactgg gctgtgaacc tgccgtcatc ctctgccata acggtaacaa acgctggcaa  1200
aaagcgatga agaaaatgct cgatgcttca ccgtacggcc aggagagcga agtgtttatc  1260
aactgcgact tgtggcattt ccgctcgctg atgttcaccc gccagccgga ttttatgatt  1320
ggcaactcgt acgccaagtt tattcagcgc gacaccttag ccaagggcga acagtttgaa  1380
gtcccgctga tccgcctcgg ttttccgctg ttcgaccgtc accatctgca ccgccagacc  1440
acctggggct acgagggcgc gatgagcatt ctcacgacgc tggtgaatgc ggtactggag  1500
aaagtggaca aagagaccat caagctcggc aaaaccgact acagcttcga tcttatccgt  1560
taa                                                                1563

SEQ ID NO: 57          moltype = DNA  length = 1386
FEATURE                Location/Qualifiers
gene                   1..1386
                       note = nifK2
source                 1..1386
                       mol_type = genomic DNA
                       organism = Kosakonia pseudosacchari
SEQUENCE: 57
atggctgata ttgttcgtag taaaaaaccg ctggcggtga gcccgataaa aagcggccag  60
ccgctggggg cgatcctggc aagcctgggt ttcgaacagt gcataccgct ggtacacggc  120
gctcaggggt gcagcgcgtt cgcgaaagtg ttctttattc aacattttca cgacccgatc  180
ccgctgcaat cgacggcgat ggacccgact tccaccatta tgggcgccga tgaaaacatt  240
tttaccgcgc tcaatgttct ctgccagcgc aacgccgcga aagccatcgt gctgctcagc  300
accgggctgt cagaagccca gggcagcgat atttcacgag tggtgcgcca gtttcgtgat  360
gactttccgc ggcataaaaa cgtggcgctg ctcaccgtca acaccccgga tttctacggc  420
tcgctggaaa acggctacag cgccgtgctg gaaagcatga ttgaacagtg ggtgcccgcg  480
cagcccgccg ccagcctgcg caaccgtcgc gtcaacctgc tggtcagcca tttactgacg  540
ccgggcgata tcgaactgtt acgcagttat gtggaagcat tcggtctgca accggtgatt  600
gtgccggatc tatcgcagtc gctggacgga catctggcca acggtgattt ttcgcccgtc  660
acccaggggg gaacaccgct gcgcatgatt gaacagatgg ggcaaaacct ggccactttt  720
gtgattggcc actcgctggg gcgggcggcg gcgttactgg cgcagcgcag ccgtggcgag  780
gtgatcgccc tgccgcatct gatgacgctt gatgcgtgcg acacctttat ccatcgcctg  840
aaaaccctct ccgggcgcga cgtgcccgcg tggattgagc gccagcgcgg gcaagtgcag  900
gatgcgatga tcgattgcca tatgtggttg cagggcgcgg ctatcgccat ggccgcagaa  960
ggcgatcacc tggcggcatg gtgcgatttc gcccgcagcc agggcatgat ccccggcccg  1020
gttgtcgcgc cggtcagcca gccggggttg caaaatctgc cggttgaaat ggtggtcatc  1080
ggcgatctgg aagatatgca ggatcggctt tgcgcgacgc ccgccgcgtt actggtggcc  1140
aattctcatg ccgccgatct cgccacgcag tttgatatgt cgcttatccg cgccgggttt  1200
ccggtgtatg accggctggg ggaatttcgt cggctgcgcc aggggtatag cggcattcgt  1260
gacacgctgt ttgagctggc gaatgtgatg cgcgaacgcc attgcccgct tgcaacctac  1320
cgctcgccgc tgcgtcagcg cttcggcgac aacgttacgc caggagatcg gtatgccgca  1380
tgttaa                                                             1386

SEQ ID NO: 58          moltype = DNA  length = 1488
FEATURE                Location/Qualifiers
gene                   1..1488
                       note = nifL
source                 1..1488
                       mol_type = genomic DNA
                       organism = Kosakonia pseudosacchari
SEQUENCE: 58
atgaccctga atatgatgat ggatgccagc gcgcccgagg ccatcgccgg tgcgctttcg  60
caacaacatc ctgggctgtt ttttaccatc gttgaagaag cccccgtcgc tatttcacta  120
accgatgccg aggcacgtat tgtctatgcc aacccggcat tctgccgcca gaccggctat  180
gagcttgagg agttgttgca gcaaaatccc cgcctgcttg ccagtcagca gaccccacgg  240
gaaatctacc aggatatgtg gcacaccctg ttacaacgtc gaccatggcg cgggcaattg  300
atcaaccgcc accgtgacgg cagccttttt ctggttgaga tcgatatcac cccggtgatt  360
aacccgtttg gcgaactgga acactacctg gccatgcagc gcgatatcag cgccggttat  420
gcgctggagc agcggttgcg taatcacatg gcgctgaccg aagcggtgct gaataacatt  480
ccggcggcgg tggtcgtggt cgatgaacgc gatcgtgtgg ttatggataa cctcgcctat  540
```

```
aaaactttct gtgctgattg cggcggaaaa gagctactga gcgaactcca tttttcagcc  600
cgtaaagcgg agctggcaaa cggccaggtc ttaccggtgg tgctgcgcgg cgcggtgcgc  660
tggttgtcgg tcacctgctg ggcgctgcca ggcgtcagcg aagaagccag tcgctacttt  720
attgataata ccttgacgcg cacgctggtg gtcatcaccg acgacaccca gcagcgccag  780
cagcaagagc aaggacggct tgaccgcctt aaacagcaga tgaccagcgg caaactgctg  840
gcggcgatcc gcgaagcgct tgacgccgcg ctgatccagc ttaactgccc catcaatatg  900
ctggcggcgg cgcggcgttt aaacggcagt gataacagca acgtagcgct ggacgccgcg  960
tggcgcgaag gtgaagaagc gatggcgcgg ctgaaacggt gccgcccgtc gctggagctg  1020
gaaagtgccg ccgtctggcc gctgcaaccc ttttttgacg acttgcgcgc gctttatcac  1080
acccgctacg agcagggtaa aaatttgcag gtcacgctgg attcgacgca tctggtggga  1140
tttggtcagc gaacccaact gctggcctgc ctgagtctgt ggctcgatcg cacgctggat  1200
attgccgtcg ggctgcgtga tttcaccgcc caaacgcaga tttacgcccg ggaagaagcg  1260
ggctggctct cgttgtatat cactgacaat gtgccgttga ttccgctgcg ccatacccat  1320
tcgccggatg cgcttaacgc accgggaaaa ggtatggagt tgcggctgat ccagacgctg  1380
gtagcgcatc acaacggcgc gatagaactc acttcacgcc ccgaaggggg aagctgcctg  1440
accctacgat tcccgctatt tcattcactg accggaggtt caaaatga             1488
```

```
SEQ ID NO: 59          moltype = DNA  length = 1575
FEATURE                Location/Qualifiers
gene                   1..1575
                       note = nifA
source                 1..1575
                       mol_type = genomic DNA
                       organism = Kosakonia pseudosacchari
SEQUENCE: 59
atgacccagc gaaccgagtc gggtaatacc gtctggcgct tcgatttatc ccagcagttc  60
accgcgatgc agcggataag cgtggttctc agccgggcga ccgaggttga acagacactc  120
cagcaggtgc tgtgcgtatt gcacaatgac gccttttttgc agcacggcat gatctgtctg  180
tacgacagcc agcaggcgat tttgactatt gaagcgttgc aggaagccga tcagcagttg  240
atccccggca gctcgcaaat tcgctaccgt ccgggtgaag ggctggtcgg gacggtgctt  300
tcgcaggggc aatcgttagt gctggcgcgt gtggctgacg atcagcgctt tcttgaccgc  360
ctgggactgt atgattacaa cctgccgttt atcgccgtgc cgctgatagg gccggatgcg  420
cagacttttg gcgtgctgac ggcgcaaccg atggcgcgtt acgaagagcg gttacccgcc  480
tgcacccgct ttctggaaac ggtcgcgaat ctggtggcgc agaccgtgcg tttgatgacg  540
ccgccggctg cacgcccttc cccacgcgct gccatcacgc caaccgccag cccgaaatcg  600
tgcagtactt cacgcgcgtt cggcttcgaa aatatggtcg gcaacagccc ggcaatgcgc  660
cagaccatgg agattatccg tcaggtttcg cgctgggata ccaccgttct ggtgcgcggc  720
gagagcggca ccggcaagga actgattgcc aacgccatcc atcacaattc gccgcgcgcc  780
agtgcgccat ttgtgaaatt caactgtgcg gcgctgccgg acacattgct tgaaagcgaa  840
ttatttggtc atgaaaaagg cgcctttacc ggcgcggtac gccagcgtaa aggccgtttt  900
gagctggccg atggcggcac gctgtttctt gacgaaattg gggaaagcag cgcctcgttt  960
caggctaagc tgctgcgtat tttgcaggag ggcgaaatgg aacgcgtcgg tggtgacgag  1020
acattgcaag tgaatgtgcg catcattgcc gcgacgaacc gcaaccttga agatgaagta  1080
cgcctgggac attttcgcga agatctctat taccgcctga atgtgatgcc catcgccctg  1140
ccgccgctgc gcgaacgcca ggacgacatc gccgaactgg cacattttct ggtgcgtaaa  1200
atcgcccaca accagaaccg cacgctgcgc attagcgagg gcgctatccg cctgctgatg  1260
agctacagct ggcccggcaa tgtgcgcgaa ctggaaaact gccttgagcg ctctgcggtg  1320
atgtcggaaa acggtctgat cgatcgggac gtgattttat ttaatcatcg cgaccagcca  1380
gccaaaccgc cggttatcag cgtcacgccc gacgataact ggctcgataa cacccttgac  1440
gagcgccagc ggctgattgc cgcgctggaa aaagcgggat gggtacaagc caaagccgcc  1500
cgcttgctgg ggatgacgcc gcgccaggtc gcttatcgta ttcagaccat ggatatcacc  1560
ctgccaaggc tataa                                                  1575
```

```
SEQ ID NO: 60          moltype = DNA  length = 2850
FEATURE                Location/Qualifiers
gene                   1..2850
                       note = glnE
source                 1..2850
                       mol_type = genomic DNA
                       organism = Kosakonia pseudosacchari
SEQUENCE: 60
atgccgcacc acgcaggatt gtcgcagcac tggcaaacgg tttttctcg tctgccggaa  60
gcgctcaccg cgcaaccatt gagcgcgcag gcgcagtcag tgctcacttt tagtgatttt  120
gttcaggaca gcatcatcgt gcatcctgag tggctggcag agcttgaaag cgcaccgccg  180
ccagcgaacg agtggcaaca ctacgcgcaa tggctgcaag cggcgctgga gggcgtcacc  240
gatgaaacct cgctgatgcg cacgctgcgg ctgtttcgcc gtcgcattat ggtgcgcatc  300
gcctggagtc aggcgctaca gttggtggcg gaagaggata tcctgcaaca gctcagcgtg  360
ctggcggaaa ctctgatcgt cgccgcgcgc gactggctct atgacgcctg ctgccgtgag  420
tggggaacgc cgtgcaatcc gcaaggcgtc gcgcagccga tgctggtgct cggcatgggc  480
aaacttggcg gcggcgaact caatttctca tccgatatcg atttgatttt tgcctggccg  540
gaaaatggca ccacgcgcgg cggacgccgt gaactggata acgcgcagtt ttttacccgc  600
cttggtcaac ggctaattaa agtcctcgac cagcccacgc aggatggctt tgtctaccgc  660
gtcgatatgc gcttgcgtcc ctttggcgac agcggcccgc tggtgctgag ttttgccgcg  720
ctggaagatt actaccagga gcaggggcgc gactgggaac gatacgcgat ggtgaaagcg  780
cgcattatgg gggacaacga cggcgaccat gcgcgagagt tgcgcgccat gctgcgcccg  840
ttcgttttcc gccgctatat cgacttcagc gtgatccagt ctctgcgcaa catgaaaggc  900
atgattgccc gcgaagtgcg gcgtcgcggc ctgaaggaca acataaaact cggcgcgggc  960
ggtattcgcg aaatagagtt tatcgtgcag gttttccagt tgattcgcgg cggtcgcgag  1020
cctgcgctgc aatcgcgttc gctgttgccg acgcttgctg ccattgatca actacatctg  1080
```

```
ctgccggatg gtgatgcacc ccggctgcgc gaggcgtatt tgtggctgcg acggctggaa  1140
aacttgctgc aaagcattaa tgacgaacag acacagacgc tgccggccga tgatttgaat  1200
cgcgcgcgcc tcgcctgggg aatgggcaaa gagagctggg aagcgctctg cgaaacgctg  1260
gaagcgcata tgtcggcggt gcggcagatt ttcaacgatc tgattggcga tgatgaaacg  1320
gattcgccgg aagatgcgct ttctgagggc tggcgcgaat tgtggcagga tgcgttgcag  1380
gaagaggact ctacgcccgt gctggcgcat ctttccgagg acgatcgccg ccgcgtggtg  1440
gcgctgattg ctgattttcg caaagagctg gataaacgca ccattggccc gcgcgggcga  1500
caggtactcg atcacttaat gccgcatctg ctcagcgatg tatgctcgcg tgacgatgcg  1560
ccagtgccgc tgtcgcgtct gacgccgctg ctcaccggta ttattacgcg caccacttac  1620
cttgagctgc tgagtgaatt ccccggtgcg ctgaaacacc tcatttccct gtgcgccgcg  1680
tcgccgatgg tggccagcca actggcgcgc tacccgatcc tgctcgatga actgctcgac  1740
ccgaacacgc tctatcaacc gacggcgatg aacgcctatc gcgatgaact gcgacaatac  1800
ctgttgcgcg tgccggaaga ggatgaagag cagcaactgg aggcgctacg gcagtttaag  1860
caggcgcagt tgttgcgcgt agcggcggcg gatatcgccg gtacgttacc cgtcatgaaa  1920
gtgagcgatc acttaacctg gctggcggaa gcgattatcg atgcggtggt gcagcaagcc  1980
tggaaccaga tggtggcgcg ttacggccag ccgacgcatc tgcacgatcg cgaagggcgc  2040
ggtttcgccg tggtcggtta cggcaaactt ggcggctggg aattaggtta cagctccgat  2100
ctggatctgg tgttcctgca cgactgcccc atggatgtga tgaccgatgg cgagcgtgaa  2160
atcgatggcc gccagttcta tttgcgcctc gcgcagcgcg tgatgcacct gttcagcacg  2220
cgcacgtcgt ccggcattct ttatgaagtc gatgcgcgtt tgcgcccgtc cggcgcggcc  2280
ggaatgctgg tgaccactgc ggaagcgttc gccgattatc aaaaaaatga agcctggaca  2340
tgggagcatc aggcgctggc gcgtgcgcgc gtggtgtacg gcgatccgca actgaccgcc  2400
gaatttgacg ccattcgccg cgatatcctg atgacctccc gcgatgccgc taccctgcaa  2460
accgaagtgc gggaaatgcg tgagaaaatg cgcgcccatc ttggtaacaa gcacaaagac  2520
cgtttcgatc tgaaagccga tgaaggcggt atcaccgata ttgagtttat cgctcagtat  2580
ctggtgctgc gctttgccca tgagaagccg aaactgacgc gctggtcgga taatgtgcgc  2640
atcctcgaag ggctggcgca aaacggcatc atggatgagc aggaagcgca ggcattgacg  2700
ctggcgtaca ccacgttgcg tgatgagctg caccacctgg cgctgcaaga gctgccagga  2760
catgtggcgc tctcctgttt tgtcgccgag cgtgcgctta tcaaaaccag ctgggacaag  2820
tggctggtgg aaccgtgcgc cccggcgtaa                                   2850
```

```
SEQ ID NO: 61          moltype = DNA  length = 1287
FEATURE                Location/Qualifiers
gene                   1..1287
                       note = amtB
source                 1..1287
                       mol_type = genomic DNA
                       organism = Kosakonia pseudosacchari
SEQUENCE: 61
atgaaaaaca caacattaaa aacggctctt gcttcgctgg cgttgctgcc aggcctggcg  60
atggcggctc ccgctgtggc ggataaagcc gacaacggct ttatgatgat ttgcaccgcg  120
ctggtgctgt ttatgaccat tccgggcatt gcgctgttct acggcggttt gatccgcggt  180
aaaaacgtgc tgtcgatgct gacgcaggtt gccgtcacct tcgctctggt gtgcatcctg  240
tgggtggttt acggctactc tctggcattt ggcgagggca acagcttctt cggcagtttc  300
aactgggcga tgttgaaaaa catcgaattg aaagccgtga tgggcagcat ttatcagtac  360
atccacgtgg cgttccaggg ctcctttgct tgtatcaccg ttggcctgat tgtcggtgcg  420
ctggctgagc gtattcgctt ctctgcggtg ctgatttttg tggtggtatg gctgacgctt  480
tcttatgtgc cgattgcgca catggtctgg ggtggcggtc tgctggcaac ccacggcgcg  540
ctggatttcg cgggcggtac ggttgttcac atcaacgccg cgatcgcagg tctggtgggg  600
gcttacctga ttggcaaacg cgtgggcttt ggcaaagaag cgttcaaacc gcataacctg  660
ccgatggtct tcaccggcac cgcgatcctc tatgttggct ggtttggctt caacgccggc  720
tctgcaagct cggcgaacga aatcgctgcg ctggctttcg tgaacacggt tgttgccact  780
gcggccgcta ttctggcgtg ggtatttggc gagtgggcaa tgcgcggtaa gccgtctctg  840
ctcggtgcct gttctggtgc catcgcgggt ctggttggta tcaccccggc gtgcggttat  900
gtgggtgtcg gcggcgcgct gattgtgggt ctgattgccg gtctggcagg gctgtggggc  960
gttactgcac tgaaacgtat gttgcgtgtt gatgacccat gcgatgtctt cggtgtgcac  1020
ggcgtgtgcg gcatcgtggg ttgtatcctg accggtatct tcgcgtctac gtcgctgggc  1080
ggtgtcggtt tcgctgaagg ggtgaccatg ggccatcagg tactggtaca gctggaaagc  1140
gttgccatca ctatcgtgtg gtctggcgtg gtggccttta tcggttacaa actggcggat  1200
atgacggtag gcctgcgcgt accggaagag caagagcgtg aagggctgga tgtgaacagc  1260
cacggcgaaa atgcgtataa cgcctga                                     1287
```

```
SEQ ID NO: 62          moltype = DNA  length = 500
FEATURE                Location/Qualifiers
gene                   1..500
                       note = PinfC
source                 1..500
                       mol_type = genomic DNA
                       organism = Kosakonia pseudosacchari
SEQUENCE: 62
ttcttggttc tctggagcgc tttatcggca tcctgactga agaatttgca ggcttcttcc  60
caacctggct tgcacccgtg caggtagttg tgatgaacat cactgattcg caggctgaat  120
acgttaacga attgacccgt aaactgcaaa atgcgggcat tcgtgtaaaa gcagacttga  180
gaaacgagaa gattggcttt aaaatccgcg agcacacttt acgtcgtgtc ccttatatgc  240
tggtttgtgg tgacaaagag gtcgaagccg gcaaagttgc tgtgcgtacc cgtcgcggta  300
aagacctggg tagcctggac gtaaatgatg ttatcgagaa gctgcaacaa gagattcgca  360
gccgcagtct tcaacaactg gaggaataag gtattaaagg cggaaaacga gttcaaacgg  420
cgcgtcccaa tcgtattaat ggcgagattc gcgccacgga agttcgctta acaggtctgg  480
aaggcgagca gcttggtatt                                              500
```

```
SEQ ID NO: 63          moltype = DNA  length = 348
FEATURE                Location/Qualifiers
gene                   1..348
                       note = Prm1
source                 1..348
                       mol_type = genomic DNA
                       organism = Kosakonia pseudosacchari
SEQUENCE: 63
cgttctgtaa taataaccgg acaattcgga ctgattaaaa aagcgccctc gcggcgcttt  60
ttttatattc tcgactccat ttaaaataaa aaatccaatc ggatttcact atttaaactg  120
gccattatct aagatgaatc cgatggaagc tcgctgtttt aacacgcgtt ttttaacctt  180
ttattgaaag tcggtgcttc tttgagcgaa cgatcaaatt taagtggatt cccatcaaaa  240
aaatattctc aacctaaaaa agtttgtgta atacttgtaa cgctacatgg agattaactc  300
aatctagagg gtattaataa tgaatcgtac taaactggta ctgggcgc              348

SEQ ID NO: 64          moltype = DNA  length = 339
FEATURE                Location/Qualifiers
gene                   1..339
                       note = Prm7
source                 1..339
                       mol_type = genomic DNA
                       organism = Kosakonia pseudosacchari
SEQUENCE: 64
cgcgtcaggt tgaacgtaaa aaagtcggtc tgcgcaaagc acgtcgtcgt ccgcagttct  60
ccaaacgtta attggtttct gcttcggcag aacgattggc gaaaaaaccc ggtgcgaacc  120
gggttttttt atggataaag atcgtgttat ccacagcaat ccattgatta tctcttcttt  180
ttcagcattt ccagaatccc ctcaccacaa agcccgcaaa atctggtaaa ctatcatcca  240
atttctgcc caaatggctg ggattgttca ttttttgttt gccttacaac gagagtgaca  300
gtacgcgcgg gtagttaact caacatctga ccggtcgat                       339

SEQ ID NO: 65          moltype = DNA  length = 1538
FEATURE                Location/Qualifiers
gene                   1..1538
                       note = 16S
variation              62
                       note = n is a, c, t, g, unknown or other
variation              265
                       note = n is a, c, t, g, unknown or other
variation              457
                       note = n is a, c, t, g, unknown or other
variation              469
                       note = n is a, c, t, g, unknown or other
variation              539
                       note = n is a, c, t, g, unknown or other
variation              551..552
                       note = n is a, c, t, g, unknown or other
variation              559
                       note = n is a, c, t, g, unknown or other
variation              561
                       note = n is a, c, t, g, unknown or other
variation              576
                       note = n is a, c, t, g, unknown or other
variation              587
                       note = n is a, c, t, g, unknown or other
variation              591
                       note = n is a, c, t, g, unknown or other
variation              655..657
                       note = n is a, c, t, g, unknown or other
variation              665
                       note = n is a, c, t, g, unknown or other
variation              678
                       note = n is a, c, t, g, unknown or other
variation              706
                       note = n is a, c, t, g, unknown or other
variation              710
                       note = n is a, c, t, g, unknown or other
misc_feature           714
                       note = n is a, c, t, g, unknown or other
variation              718
                       note = n is a, c, t, g, unknown or other
variation              735
                       note = n is a, c, t, g, unknown or other
variation              755
                       note = n is a, c, t, g, unknown or other
variation              759
                       note = n is a, c, t, g, unknown or other
variation              796
                       note = n is a, c, t, g, unknown or other
```

```
variation              1006..1007
                       note = n is a, c, t, g, unknown or other
variation              1016..1017
                       note = n is a, c, t, g, unknown or other
variation              1133
                       note = n is a, c, t, g, unknown or other
source                 1..1538
                       mol_type = genomic DNA
                       organism = Enterobacter sp.
SEQUENCE: 65
ttgaagagtt tgatcatggc tcagattgaa cgctggcggc aggcctaaca catgcaagtc  60
gngcggaagc acaggagagc ttgctctctg ggtgacgagc ggcggacggg tgagtaatgt  120
ctgggaaact gcctgatgga gggggataac tactggaaac ggtagctaat accgcataac  180
gtcgcaagac caaagagggg gaccttcggg cctcttgcca tcagatgtgc ccagatggga  240
ttagctagta ggtggggtaa cggcncacct aggcgacgat ccctagctgg tctgagagga  300
tgaccagcca cactggaact gagacacggt ccagactcct acgggaggca gcagtgggga  360
atattgcaca atgggcgcaa gcctgatgca gccatgccgc gtgtatgaag aaggccttcg  420
ggttgtaaag tactttcagc ggggaggaag gtgttgnggt taataaccnc agcaattgac  480
gttacccgca gaagaagcac cggctaactc cgtgccagca gccgcggtaa tacggaggnt  540
gcaagcgtta nncggaatna ntgggcgtaa agcgtncgca ggcggtntgt naagtcggat  600
gtgaaatccc cgggctcaac ctgggaactg cattcgaaac tggcaggcta gagtnnngta  660
gaggnggggta gaattccngg tgtagcggtg aaatgcgtag agatcnggan gaanaccngt  720
ggcgaaggcg gcccnctgga caaagactga cgctnaggng cgaaagcgtg gggagcaaac  780
aggattagat accctngtag tccacgccgt aaacgatgtc gacttggagg ttgtgccctt  840
gaggcgtggc ttccggagct aacgcgttaa gtcgaccgcc tggggagtac ggccgcaagg  900
ttaaaactca aatgaattga cgggggcccg cacaagcggt ggagcatgtg gtttaattcg  960
atgcaacgcg aagaacctta cctactcttg acatccagag aacttnncag agatgnnttg  1020
gtgccttcgg gaactctgag acaggtgctg catggctgtc gtcagctcgt gttgtgaaat  1080
gttgggttaa gtcccgcaac gagcgcaacc cttatccttt gttgccagcg gtncggccgg  1140
gaactcaaag gagactgcca gtgataaact ggaggaaggt ggggatgacg tcaagtcatc  1200
atggccctta cgagtagggc tacacacgtg ctacaatggc gcatacaaag agaagcgacc  1260
tcgcgagagc aagcggacct cataaagtgc gtcgtagtcc ggattggagt ctgcaactcg  1320
actccatgaa gtcggaatcg ctagtaatcg tagatcagaa tgctacggtg aatacgttcc  1380
cgggccttgt acacaccgcc cgtcacacca tgggagtggg ttgcaaaaga agtaggtagc  1440
ttaaccttcg ggagggcgct taccactttg tgattcatga ctggggtgaa gtcgtaacaa  1500
ggtaaccgta ggggaacctg cggttggatc acctcctt                          1538

SEQ ID NO: 66          moltype = DNA  length = 882
FEATURE                Location/Qualifiers
gene                   1..882
                       note = nifH
source                 1..882
                       mol_type = genomic DNA
                       organism = Enterobacter sp.
SEQUENCE: 66
atgaccatgc gtcaatgtgc catttacggc aaaggtggta tcggtaaatc cactaccacg  60
caaaacctgg tcgccgcgct ggcggagatg ggcaagaaag taatgatcgt cggctgcgac  120
ccgaaagcag actccactcg tctgatcctg catgcgaaag cgcagaacac cattatggag  180
atggcggctg aagtcggctc cgtggaagac cttgaactgg aagatgtgct gcaaatcggt  240
tacggcgacg tacgctgcgc agaatccggc ggcccggaac caggcgttgg ctgtgctggt  300
cgcggggtaa ttaccgccat caacttcctg gaagaagaag gcgcctatgt tcccgacctc  360
gatttcgtct tttacgacgt gttgggcgac gtggtgtgcg gggggttcgc catgccgatt  420
cgcgaaaaca aagcgcagga gatctacatc gtctgctccg gcgaaatgat ggcgatgtac  480
gccgccaaca acatctctaa aggcatcgtg aaatacgcca aatccggcaa agtgcgcctt  540
ggcgggctga tctgtaactc ccgtcagacc gaccgcgaag atgagctgat catagcgctg  600
gcggaaaaac tcggcaccca gatgatccac ttcgtgccgc gcgacaacat cgtgcaacgc  660
gctgaaatcc gccgtatgac ggtgattgag tacgatccga aatgcaacca ggccaatgaa  720
taccgcacgc tggcgaacaa gatcgtcaac aacaccaaaa tggtcgtgcc aacgcccatc  780
accatggacg aactggaaga gctgttgatg gaattcggca ttatggatgt ggaagacacc  840
agcattatcg gtaaaaccgc cgcagaagaa aacgcggttt ga                    882

SEQ ID NO: 67          moltype = DNA  length = 1449
FEATURE                Location/Qualifiers
gene                   1..1449
                       note = nifD1
source                 1..1449
                       mol_type = genomic DNA
                       organism = Enterobacter sp.
SEQUENCE: 67
atgagcaatg caacaggcga acgtaatctg gagatcatcc aggaagtgct ggagatcttt  60
ccggaaaaaa cgcgcaaaga acgcagaaag cacatgatgg tgagcgaccc ggagatggaa  120
agcgtcggga aatgcatcat ctccaaccgt aagtcgcagc ccggcgtaat gaccgtgcgc  180
ggttgctctt acgccggttc taaaggggtg gtattcgggc cgatcaaaga tatggcccat  240
atttcccacg gcccggtcgg ctgcggtcag tactcccgcg ccgggcggcg taactactac  300
accggcgtca gcggtgtgga tagcttcggt acgctcaact ttacctccga ttttcaggag  360
cgcgatatcg tgtttggcgg cgataaaaag ctgaccaaac tgattgaaga gatggagacg  420
ctgttcccgc tgaccaaagg gatctccatt cagtccgaat gcccggtcgg cctgattggc  480
gacgacattg aagccgttgc caacgccagc cgcaaagcca tcaataaacc ggtcattccg  540
gtgcgctgcg aaggttttcg cggcgtttcc cagtcactcg gtcaccacat tgccaacgac  600
```

```
gtgatccgcg actgggtact ggataaccgc gaaggcaagc cgtttgaggc cggtccttat  660
gacgtggcga tcatcggcga ttacaacatc ggcggcgatg cctgggcgtc gcgcattttg  720
ctcgaagaga tgggcctgcg cgtggtggcg cagtggtccg gcgacggcac gctggttgag  780
atggagaaca cgccgttcgt caaactcaac cttgtgcact gctaccgctc aatgaactat  840
atctcccgcc atatggagga gaaacacggt attccgtgga tggagtacaa cttcttcggt  900
ccgaccaaag tcgccgaatc gttgcgcaaa atcgccgata tgtttgatga caccattcgc  960
gccaacgccg aagcggtgat cgccaaatat caggcgcaga acgacgccat catcgccaaa  1020
taccgtccgc gtctggaagg ccgcaaagtg ctgctgtata tgggcggttt acgtcctcgc  1080
catgtgattg gcgcttatga agatctgggg atggaaatta tcgctgcggg ttatgaattc  1140
gcccacaacg atgactacga ccgcaccctg ccggatctga aagaaggcac cttgctgttc  1200
gacgatgcca gcagttatga actggaagcc tttgtcaaag cgctgaagcc ggatctgatc  1260
ggctccggca ttaaagagaa gtacatcttc cagaaaatgg gcgtgccgtt tcgccagatg  1320
cactcctggg attactccgg cccctatcac ggttatgacg gctttgccat cttcgcccgc  1380
gatatggata tgacgatcaa caaccccgcg tggggccagt tgaccgcgcc gtggctgaaa  1440
tccgcctga                                                          1449
```

```
SEQ ID NO: 68          moltype = DNA  length = 1092
FEATURE                Location/Qualifiers
gene                   1..1092
                       note = nifD2
variation              709
                       note = n is a, c, t, g, unknown or other
source                 1..1092
                       mol_type = genomic DNA
                       organism = Enterobacter sp.
SEQUENCE: 68
atgggacgcg gcgagcgccg cctgttccat gccgtgcgcc acatcgtcaa ccgctaccac  60
ccggccgccg tctttatcta taacacctgc gttcccgcga tggagggcga cgatatcgaa  120
gccgtctgcc aggcggcaga aaccgccatc ggcgtaccgg tgattgccgt tgatgtcgcc  180
gggttttacg gcagcaaaaa tctcggcaac cggttggccg gtgaagtgat ggtgaaaaag  240
gtgattggcg ggcgtgaacc cgcgccgtgg ccggaagata ccccttttgc cccggcgcac  300
cgccacgata tcgggctgat tggcgaattc aatattgccg gagagttctg gcatattcag  360
ccgctgctcg atgagctggg tattcgcgtg ctcggcagcc tctccggcga cgggcgcttc  420
agtgaaatcc agacgctgca ccgggcgcag gtcaatatgc tggtctgctc cagggcgctg  480
atcaacgtcg cccgctcgct ggagcagcgc tacggcacgc cgtggtttga aggcagtttt  540
tatggtgttc gcgccacctc tgacgccctg cgccaactgg cggcgctgac cggagaccgc  600
gatctgatgc agcgcaccga acagctcatt gcccgcgaag agcagcaaac agagcaggcg  660
ctggccccgc tgcgcgagcg cctgcgcggg cgcaaagcgc tgctctatnc cggcggcgtg  720
aaatcctggt cggtggtttc ggcgcttcag gatctgggca tggaagtggt ggcgaccggc  780
acgcgcaaat ccaccgaaga ggataaacag cgcatccgcg aactgatggg cgccgacgcg  840
ctgatgcttg atgaaggtaa cgcccgctcg ctgctggacg tggtttaccg ctacaaggcg  900
gacatgatga tcgccggggg acgcaatatg tacaccgcct acaaagcgcg gctgccgttc  960
ctcgatatca atcaggagcg cgagcacgcc tttgccggct accgcggcat tgtcaccctg  1020
gccgaacagc tctgcctgac catggaaagc ccggtctggc cgcaaaccca ttcccgcgca  1080
ccgtggcaat aa                                                      1092
```

```
SEQ ID NO: 69          moltype = DNA  length = 846
FEATURE                Location/Qualifiers
gene                   1..846
                       note = nifK
source                 1..846
                       mol_type = genomic DNA
                       organism = Enterobacter sp.
SEQUENCE: 69
atgatggagc aaatggacgt gccgtgcagc ctgctttccg atccctccga agtgctggat  60
accccggctg acgggcatta ccacatgtat gcgggcggta cgacccagca ggagatgcgc  120
gaagcgcctg acgctatcga caccctgctg ctgcaaccct ggcaactggt gaaaaccaaa  180
aaagtggtgc aggaaagctg gaaccagccc gctaccgagg tgcaaatccc aatggggctg  240
gccggaaccg acgagctgct gatgacggta agccagttaa ccggcaaagc cattccggat  300
agcttagcgc tggaacgcgg tcggctggtg gatatgatgc tcgactccca cacctggctg  360
cacggcaaga aattcggcct gttcggtgac ccggattttg tcatggggct gacccgcttc  420
ctgctggaac tgggctgcga accgacggtg attctgtgcc ataacggcag caagcgctgg  480
cagaaagcga tgaagaaaat gcttgaagcc tcgccgtacg ggaaagagag cgaagtcttt  540
atcaactgcg atttgtggca tttccgctcg ctgatgttta cccgtcagcc ggactttatg  600
atcggcaact cctacgccaa gtttatccag cgcgatacgc tggcgaaggg tgagcagttt  660
gaagtgccgc tgatccgcct ggggttcccg ctgttcgatc gccaccatct gcaccgccag  720
accacctggg gttacgaagg ggccatgagt atcctcacca cgctggttaa tgcggtgctg  780
gagaaagtcg acagagagac catcaagctc ggcaaaaccg actacagctt cgatcttatc  840
cgttaa                                                             846
```

```
SEQ ID NO: 70          moltype = DNA  length = 1095
FEATURE                Location/Qualifiers
gene                   1..1095
                       note = nifL
variation              942
                       note = n is a, c, t, g, unknown or other
source                 1..1095
                       mol_type = genomic DNA
                       organism = Enterobacter sp.
```

```
SEQUENCE: 70
atgcagcgcg acatcagcac cagctacgcg ctggaacaac ggctgcgcaa tcatatgacg  60
ctgaccgaag ccgtcttgaa taacattccg gcggcggttg tagtggtgga tgaacgcgat  120
cgggtggtga tggataacct cgcctacaaa accttttgcg ccgattgcgg cggtaaagaa  180
ctactcaccg aaatcaactt ttccgcccat aaggcggagc tggcgcaggg cctggtactg  240
ccggtagtgc tgcgcggcac cgtgcgctgg ttgtccgtta cctgttgggc gctgccgggc  300
gtcagcgaag aagcaggccg ctactttatt gatagcgccg tgccgcgcac gctggtggtg  360
atcaccgata atactcagca gcagcaacaa caggagcagg ggcgtcttga tcgtctgaag  420
cagcagataa ccagcggtaa attgctggcg gcgatccgcg aatcgctgga cgccgcgctg  480
gtacaactca attgcccaat taatatgctg gccgccgcac gccgcttaaa tggcgacgag  540
catagcaatc tggcgctgga tgccgcatgg cgtgaaggcg aagaagcgat ggcgcggttg  600
cagcgctgcc gcccgtcgct ggaactggaa agcccggcag tctggccgct ccagccgttc  660
cttgacgatc tgcgtgccct gtatcacacc cgatataacc agggcgaaaa cctgcaaatt  720
gagctggaat cccccgacct ggtgggcttt ggccagcgaa cacaactgct tgcctgcctg  780
agcctgtggc tcgacagaac cctggatatt gccgcggagc tacgtgattt cacggtacag  840
actcaacttt acgcccgcga agagagcggc tggctgtcgt tctatttaaa cgacaatgtg  900
ccgctgattc aggtgcgcta cacccattca cccgatgcac tnaatgcgcc cggtaaaggc  960
atggagctgc ggctgatcca gacgctggtc gcccaccatc gaggcgcaat agaactgacc  1020
tcacgccctc agggaggcac ctgtctgatc ctgcgtttcc cattatttta ctcgctgaca  1080
ggaggctcac tatga                                                   1095

SEQ ID NO: 71          moltype = DNA  length = 219
FEATURE                Location/Qualifiers
gene                   1..219
                       note = nifA partial gene
source                 1..219
                       mol_type = genomic DNA
                       organism = Enterobacter sp.
SEQUENCE: 71
atgactcagc gaaccgagtc gggtacaacc gtctggcgct ttgacctctc ccaacagttt  60
acagccatgc agcgtatcag tgtggtgtta agccgcgcga cggagatcgg gcagacgcta  120
caggaagtgc tgtgcgtgct gcacaacgat gcctttatgc agcacgggat gatctgtccg  180
tacgcgcggg tgcgcgtctt cgcgagcgta tggctttga                         219

SEQ ID NO: 72          moltype = DNA  length = 1635
FEATURE                Location/Qualifiers
gene                   1..1635
                       note = glnE
variation              234
                       note = n is a, c, t, g, unknown or other
variation              274
                       note = n is a, c, t, g, unknown or other
variation              1535
                       note = n is a, c, t, g, unknown or other
source                 1..1635
                       mol_type = genomic DNA
                       organism = Enterobacter sp.
SEQUENCE: 72
atgcgcgtgg aagactggtc aacgctgacc gaacggctcg atgcccatat ggcaggcgtg  60
cgcccgaatct ttaacgaact gatcggtgat gacgaaagtg agtcgcagga cgatgcgctc  120
tccgagcact ggcgcgagct gtggcaggac gcgcttcagg aagatgacac cacgccggtg  180
ctgacgcact taaccgacga cgcgcgccat cgcgtggtgg cgctgatcgc tganttccgt  240
cttgagctga acaaacgcgc catcggcccg cgtngtcgcc aggtgctgga tcacctgatg  300
ccgcacctgc tgagcgaagt ctgctcgcgt gccgatgcgc cggtgccgct gtcgcggatg  360
atgcccctgc tgagcgggat tatcacccgt actacctacc ttgaactcct gagcgagttc  420
cctggcgcgc ttaagcacct gatttcactc tgcgccgcgt cgccgatggt ggccaacaag  480
ctggcgcgtt acccgctgct gctggatgag ctgctcgatc cgaataccct ttatcaaccg  540
acggcgaccg acgcctaccg ggacgaactg cgtcagtatc tgctgcgcgt gccggaagaa  600
gacgaagagc aacagctgga ggcgctgcgt cagtttaagc aggcccagat gctgcgcgtg  660
gcggccgcag atattgccgg aacgctgccg gtgatgaaag tgagcgatca cttaacctgg  720
cttgcggaag cgattatcga cgcggtggtg catcaggcct gggtgcagat ggtggcgcgc  780
tatggccagc cgaaacatct ggctgaccgt gatggtcgcg gcttcgcggt ggtgggttac  840
ggtaagctcg gcggttggga gctgggctat agctccgatc tggatttaat cttcctccac  900
gactgccccgg ttgatgtgat gaccgacggc gagcgcgaga ttgacgggcg tcagttctac  960
ctgcgcctgg cgcagcgcat catgcacctg ttcagcaccc gcacctcgtc gggcattttg  1020
tatgaagtgg atgcccgtct gcgcccgtcc ggcgcggcgg gcatgctggt cacctcgacg  1080
gagtccttcg ctgattacca gaagaatgaa gcctggacgt gggagcatca ggcgctggtg  1140
cgcgcccgtg tggtgtatgg cgatccgctg ctgaaaacgc agtttgacgt gattcgtaag  1200
gaagtcatga ccaccgtgcg cgatggcagc acgctgcaaa cggaagtgcg cgaaatgcgc  1260
gagaaaatgc gcgcgcactt aggcaataaa catcgcgatc gctttgatat taaagccgat  1320
gagggcggta ttaccgatat tgagtttatt acccagtatc tggtgttgct gcacgcgcat  1380
gacaagccga agctgacgcg ctggtcggat aacgtgcgca ttctggaact gctggcgcaa  1440
aacgacatta tggacgagca ggaggcgcag gccttaaccc gtgcctatac aacgcttcgc  1500
gatgagctcc atcatctggc gttgcaggag cagcngggac acgtggcgct ggactgtttc  1560
accgctgaac gcgctcaggt aacggccagc tggcagaagt ggctggtgga accgtgcgta  1620
acaaatcaag tgtga                                                   1635

SEQ ID NO: 73          moltype = DNA  length = 1316
FEATURE                Location/Qualifiers
```

```
gene                    1..1316
                        note = 16S
variation               43
                        note = n is a, c, t, g, unknown or other
variation               247
                        note = n is a, c, t, g, unknown or other
variation               784..785
                        note = n is a, c, t, g, unknown or other
variation               794..795
                        note = n is a, c, t, g, unknown or other
source                  1..1316
                        mol_type = genomic DNA
                        organism = Enterobacter sp.
SEQUENCE: 73
agatgtgccc agatgggatt agctagtagg tggggtaacg gcncacctag gcgacgatcc  60
ctagctggtc tgagaggatg accagccaca ctggaactga gacacggtcc agactcctac  120
gggaggcagc agtggggaat attgcacaat gggcgcaagc ctgatgcagc catgccgcgt  180
gtatgaagaa ggccttcggg ttgtaaagta ctttcagcgg ggaggaaggt gttgtggtta  240
ataaccncag caattgacgt tacccgcaga agaagcaccg gctaactccg tgccagcagc  300
cgcggtaata cggagggtgc aagcgttaat cggaattact gggcgtaaag cgcacgcagg  360
cggtctgtca agtcggatgt gaaatccccg ggctcaacct gggaactgca ttcgaaactg  420
gcaggctaga gtcttgtaga ggggggtaga attccaggtg tagcggtgaa atgcgtagag  480
atctggagga ataccggtgg cgaaggcggc cccctggaca aagactgacg ctcaggtgcg  540
aaagcgtggg gagcaaacag gattagatac cctggtagtc cacgccgtaa acgatgtcga  600
cttggaggtt gtgcccttga ggcgtggctt ccggagctaa cgcgttaagt cgaccgcctg  660
gggagtacgg ccgcaaggtt aaaactcaaa tgaattgacg gggcccgca caagcggtgg  720
agcatgtggt ttaattcgat gcaacgcgaa gaaccttacc tactcttgac atccagagaa  780
cttnncagag atgnnttggt gccttcggga actctgagac aggtgctgca tggctgtcgt  840
cagctcgtgt tgtgaaatgt tgggttaagt cccgcaacga gcgcaaccct tatcctttgt  900
tgccagcggt ccggccggga actcaaagga gactgccagt gataaactgg aggaaggtgg  960
ggatgacgtc aagtcatcat ggcccttacg agtagggcta cacacgtgct acaatggcgc  1020
atacaaagag aagcgacctc gcgagagcaa gcggacctca taaagtgcgt cgtagtccgg  1080
attggagtct gcaactcgac tccatgaagt cggaatcgct agtaatcgta gatcagaatg  1140
ctacggtgaa tacgttcccg ggccttgtac acaccgcccg tcacaccatg ggagtgggtt  1200
gcaaaagaag taggtagctt aaccttcggg agggcgctta ccactttgtg attcatgact  1260
ggggtgaagt cgtaacaagg taaccgtagg ggaacctgcg gttggatcac ctcctt      1316

SEQ ID NO: 74           moltype = DNA  length = 882
FEATURE                 Location/Qualifiers
gene                    1..882
                        note = nifH
source                  1..882
                        mol_type = genomic DNA
                        organism = Enterobacter sp.
SEQUENCE: 74
atgaccatgc gtcaatgtgc catttacggc aaaggtggta tcggtaaatc cactaccacg  60
caaaacctgg tcgccgcgct ggcggagatg ggcaagaaag taatgatcgt cggctgcgac  120
ccgaaagcag actccactcg tctgatcctg catgcgaaag cgcagaacac cattatggag  180
atggcggctg aagtcggctc cgtggaagac cttgaactgg aagatgtgct gcaaatcggt  240
tacggcgacg tacgctgcgc agaatccggc ggcccggaac caggcgttgg ctgtgctggt  300
cgcggggtaa ttaccgccat caacttcctg gaagaagaag gcgcctatgt tcccgacctc  360
gatttcgtct tttacgacgt gttgggcgac gtggtgtgcg gggggttcgc catgccgatt  420
cgcgaaaaca aagcgcagga gatctacatc gtctgctccg gcgaaatgat ggcgatgtac  480
gccgccaaca acatctctaa aggcatcgtg aaatacgcca aatccggcaa agtgcgcctt  540
ggcgggctga tctgtaactc ccgtcagacc gaccgcgaag atgagctgat catagcgctg  600
gcggaaaaac tcggcaccca gatgatccac ttcgtgccgc gcgacaacat cgtgcaacgc  660
gctgaaatcc gccgtatgac ggtgattgag tacgatccga aatgcaacca ggccaatgaa  720
taccgcacgc tggcgaacaa gatcgtcaac aacaccaaaa tggtcgtgcc aacgcccatc  780
accatggacg aactggaaga gctgttgatg gaattcggca ttatggatgt ggaagacacc  840
agcattatcg gtaaaaccgc cgcagaagaa aacgcggttt ga                     882

SEQ ID NO: 75           moltype = DNA  length = 1449
FEATURE                 Location/Qualifiers
gene                    1..1449
                        note = nifD1
source                  1..1449
                        mol_type = genomic DNA
                        organism = Enterobacter sp.
SEQUENCE: 75
atgagcaatg caacaggcga acgtaatctg gagatcatcc aggaagtgct ggagatcttt  60
ccggaaaaaa cgcgcaaaga acgcagaaag cacatgatgg tgagcgaccc ggagatggaa  120
agcgtcggga aatgcatcat ctccaaccgt aagtcgcagc ccggcgtaat gaccgtgcgc  180
ggttgctctt acgccggttc taaaggggtg gtattcgggc cgatcaaaga tatggcccat  240
atttcccacg gcccggtcgg ctgcggtcag tactcccgcg ccgggcggcg taactactac  300
accggcgtca gcggtgtgga tagcttcggt acgctcaact ttacctccga ttttcaggag  360
cgcgatatcg tgtttggcgg cgataaaaag ctgaccaaac tgattgaaga gatggagacg  420
ctgttcccgc tgaccaaagg gatctccatt cagtccgaat gcccggtcgg cctgattggc  480
gacgacattg aagccgttgc caacgccagc cgcaaagcca tcaataaacc ggtcattccg  540
gtgcgctgcg aaggttttcg cggcgtttcc cagtcactcg gtcaccacat tgccaacgac  600
```

```
gtgatccgcg actgggtact ggataaccgc gaaggcaagc cgtttgaggc cggtccttat  660
gacgtggcga tcatcggcga ttacaacatc ggcggcgatg cctgggcgtc gcgcattttg  720
ctcgaagaga tgggcctgcg cgtggtggcg cagtggtccg gcgacggcac gctggttgag  780
atggagaaca cgccgttcgt caaactcaac cttgtgcact gctaccgctc aatgaactat  840
atctcccgcc atatggagga gaaacacggt attccgtgga tggagtacaa cttcttcggt  900
ccgaccaaag tcgccgaatc gttgcgcaaa atcgccgata tgtttgatga caccattcgc  960
gccaacgccg aagcggtgat cgccaaatat caggcgcaga acgacgccat catcgccaaa  1020
taccgtccgc gtctggaagg ccgcaaagtg ctgctgtata tgggcggttt acgtcctcgc  1080
catgtgattg gcgcttatga agatctgggg atggaaatta tcgctgcggg ttatgaattc  1140
gcccacaacg atgactacga ccgcaccctg ccggatctga aagaaggcac cttgctgttc  1200
gacgatgcca gcagttatga actggaagcc tttgtcaaag cgctgaagcc ggatctgatc  1260
ggctccggca ttaaagagaa gtacatcttc cagaaaatgg gcgtgccgtt tcgccagatg  1320
cactcctggg attactccgg cccctatcac ggttatgacg gctttgccat cttcgcccgc  1380
gatatggata tgacgatcaa caaccccgcg tggggccagt tgaccgcgcc gtggctgaaa  1440
tccgcctga                                                          1449

SEQ ID NO: 76          moltype = DNA  length = 1374
FEATURE                Location/Qualifiers
gene                   1..1374
                       note = nifD2
source                 1..1374
                       mol_type = genomic DNA
                       organism = Enterobacter sp.
SEQUENCE: 76
atgaagggga acgagatcct ggctttgctc gatgaacctg cctgcgagca caaccataaa  60
cagaaatccg gctgcagcgc gccgaaaccc ggcgcgacag cgggcggctg cgcctttgac  120
ggtgcgcaga tcaccctgct gccactctcc gatgttgccc acctggtaca cggccccatt  180
ggttgtaccg gtagctcatg ggataaccgt ggcagcttca gttccggccc gacgatcaac  240
cggctgggtt ttaccaccga tctgagcgaa caggatgtga tcatgggacg cggcgagcgc  300
cgcctgttcc atgccgtgcg ccacatcgtc aaccgctacc acccggccgc cgtctttatc  360
tataacacct gcgttcccgc gatggagggc gacgatatcg aagccgtctg ccaggcggca  420
gaaaccgcca tcggcgtacc ggtgattgcc gttgatgtcg ccgggtttta cggcagcaaa  480
aatctcggca accggttggc cggtgaagtg atggtgaaaa aggtgattgg cgggcgtgaa  540
cccgcgccgt ggccggaaga taccccttttt gccccggcgc accgccacga tatcgggctg  600
attggcgaat tcaatattgc cggagagttc tggcatattc agccgctgct cgatgagctg  660
ggtattcgcg tgctcggcag cctctccggc gacgggcgct tcagtgaaat ccagacgctg  720
caccgggcgc aggtcaatat gctggtctgc tccagggcgc tgatcaacgt cgcccgctcg  780
ctggagcagc gctacggcac gccgtggttt gaaggcagtt tttatggtgt tcgcgccacc  840
tctgacgccc tgcgccaact ggcggcgctg accggagacc gcgatctgat gcagcgcacc  900
gaacagctca ttgcccgcga agagcagcaa acagagcagg cgctggcccc gctgcgcgag  960
cgcctgcgcg ggcgcaaagc gctgctctat accggcggcg tgaaatcctg gtcggtggtt  1020
tcggcgcttc aggatctggg catggaagtg gtggcgaccg gcacgcgcaa atccaccgaa  1080
gaggataaac agcgcatccg cgaactgatg ggcgccgacg cgctgatgct tgatgaaggt  1140
aacgccccgct cgctgctgga cgtggtttac cgctacaagg cggacatgat gatcgccggg  1200
ggacgcaata tgtacaccgc ctacaaagcg cggctgccgt tcctcgatat caatcaggag  1260
cgcgagcacg cctttgccgg ctaccgcggc attgtcaccc tggccgaaca gctctgcctg  1320
accatggaaa gcccggtctg gccgcaaacc cattcccgcg caccgtggca ataa        1374

SEQ ID NO: 77          moltype = DNA  length = 1563
FEATURE                Location/Qualifiers
gene                   1..1563
                       note = nifK1
source                 1..1563
                       mol_type = genomic DNA
                       organism = Enterobacter sp.
SEQUENCE: 77
atgagccaaa gtgctgagaa aattcaaaac tgtcatccgc tgtttgaaca ggatgcgtac  60
cagatgctgt ttaaagataa acggcaactg gaagaggccc acgatccggc gcgcgtgcag  120
gaggtctttc aatggaccac caccgccgag tatgaagcgc ttaactttca acgcgaagcg  180
ctgactatcg atccggccaa agcctgccag ccgctgggtg cggtactgtg ctcgctgggc  240
tttgccaata ccctgcccta tgttcacggc tcccaggggt gcgtggccta tttccgcacc  300
tattttaacc gtcactttaa agagccgatt gcctgtgttt ctgactcgat gacggaagat  360
gcggcagtat tcggcggcaa caacaacctg aacaccgggt tgcagaacgc cagcgccctc  420
tacaagccgg aaatcattgc cgtctccacc acctgtatgg cggaggtcat cggcgacgac  480
ctgcaggcgt ttattgctaa cgccaaaaaa gacggcttta tcgacgcggc gatcccggtg  540
ccttacgcgc acacgccaag ctttatcggc agccatatca ccggctggga caatatgttt  600
gagggcttcg cccgtacctt taccgccgat tacagcggac aaccgggcaa attaccgcgt  660
atcaatctgg tcagcggatt tgaaacctat ctcggtaatt tccgcgtgct gaaacgcatg  720
atggagcaaa tggacgtgcc gtgcagcctg ctttccgatc cctccgaagt gctggatacc  780
ccggctgacg ggcattacca catgtatgcg ggcggtacga cccagcagga gatgcgcgaa  840
gcgcctgacg ctatcgacac cctgctgctg caaccctggc aactggtgaa aaccaaaaaa  900
gtggtgcagg aaagctggaa ccagcccgct accgaggtgc aaatcccaat ggggctggcc  960
ggaaccgacg agctgctgat gacggtaagc cagttaaccg gcaaagccat tccggatagc  1020
ttagcgctgg aacgcggtcg gctggtggat atgatgctcg actcccacac ctggctgcac  1080
ggcaagaaat tcggcctgtt cggtgacccg gattttgtca tggggctgac ccgcttcctg  1140
ctggaactgg gctgcgaacc gacggtgatt ctgtgccata acggcagcaa gcgctggcag  1200
aaagcgatga agaaaatgct tgaagcctcg ccgtacggga aagagagcga agtctttatc  1260
aactgcgatt tgtggcattt ccgctcgctg atgtttaccc gtcagccgga ctttatgatc  1320
ggcaactcct acgccaagtt tatccagcgc gatacgctgg cgaagggtga gcagtttgaa  1380
```

```
gtgccgctga tccgcctggg gttcccgctg ttcgatcgcc accatctgca ccgccagacc  1440
acctggggtt acgaaggggc catgagtatc ctcaccacgc tggttaatgc ggtgctggag  1500
aaagtcgaca gagagaccat caagctcggc aaaaccgact acagcttcga tcttatccgt  1560
taa                                                                1563

SEQ ID NO: 78          moltype = DNA  length = 1386
FEATURE                Location/Qualifiers
gene                   1..1386
                       note = nifK2
source                 1..1386
                       mol_type = genomic DNA
                       organism = Enterobacter sp.
SEQUENCE: 78
atggcagaaa ttatccgtag taaaaagccg ctggccgtca gcccggtaaa aagtggccag  60
ccgctgggcg cgattctggc gagcatgggc tttgaacaga gcattccgct ggttcatggc  120
gctcaggggt gcagcgcctt cgcgaaggtc ttttttatcc agcattttca cgatccgatc  180
ccgctgcaat cgacggcaat ggacccgaca tcgaccatta tgggtgccga tgagaacatc  240
tttaccgcgc tgaatgtgct gtgttcacgc aacaacccga aagcgattgt tctgctgagc  300
actggccttt ccgaggcgca gggcagcgat atttcgcgcg tggtgcgcca gttccgcgat  360
gaatatccgc gccataaagg ggtggcgctg ctgaccgtca acacgccgga tttttacggc  420
agcctggaaa acggctacag cgcggtgctg gagagcatgg ttgaacagtg ggtgccggaa  480
aaaccgcagc cgggcgtgcg caatcgccgc gtgaacctgc tgctcagcca tttgcttacg  540
ccgggcgaca ttgagctgct gcgaagttat gtcgaggcat ttggcctgca gccggtgatg  600
gtgccggatc tttcccagtc gctggatggc catctcgcca gcggggattt ctcgccaatt  660
acccagggcg gcagcagcct gcggctgatt gaacagatgg gacagagtct tggcacgttc  720
gccattggcg tatccctctc ccgcgccgcg caattgctgg cgcagcgcag ccatgcggaa  780
gtggtcaccc tgccgcatct gatgaccatg agccagtgcg atacgtttat tcatcaactg  840
aagcgcctct ccgggcgcga tgttccggcg tggatcgaac gccagcgcgg gcaactgcag  900
gatgcgatga tcgattgtca tatgtggttg cagggcgcgc ctgtcgcgct ggccgccgag  960
ggcgatctgc tcgccgcctg gtgcgatttc gcctgcgata tgggcatggt gcccggcccg  1020
gtggtggcgc cggtgagcca gaaagggttg caggatctgc cggtcgaaaa agtcattatc  1080
ggcgatctgg aggatatgca ggatctgttg tgtgaaacgc ctgcatcgct gctcgtctct  1140
aattctcacg ccgctgattt ggccgggcag ttcgacattc cgctggtgcg cgccggtttc  1200
cccctgttcg accgtctggg cgagtttcgc cgcgtgcgcc agggttacgc cgggatgcgc  1260
gacaccttgt ttgagctggc gaatgcgctg cgcgatcgcc atcatcatct tgccgcttat  1320
cactcgccgc tgcgccagcg tttttacgaa cccgcatctt cgggaggtga ctatgcaaca  1380
tgttaa                                                             1386

SEQ ID NO: 79          moltype = DNA  length = 1488
FEATURE                Location/Qualifiers
gene                   1..1488
                       note = nifL
source                 1..1488
                       mol_type = genomic DNA
                       organism = Enterobacter sp.
SEQUENCE: 79
atgaccctga atatgatgat ggacgccacc gcgcccgccg agatcgccgg agcgctctca  60
caacagcatc ccgggttgtt tttcaccatg gttgaacagg cgcccgtcgc gatttcactg  120
accgatgccg atgcccacat tctctacgcc aaccccgcgt tttgtcgcca gtcggggtat  180
gaactggaag agttgttgca gcaaaacccg cgcctgcttg ccagtaagca gacgccgcgt  240
gaaatctacc aggaaatgtg gcacaccctg ctgcaacacc gtccgtggcg cggacaactg  300
atcaaccgtc gccgcgacgg cagcctgttt ctggtggaaa tcgacatcac cccactgttt  360
gatgcgttcg gcaaactcga acattacctg gccatgcagc gcgacatcag caccagctac  420
gcgctggaac aacggctgcg caatcatatg acgctgaccg aagccgtctt gaataacatt  480
ccggcggcgg ttgtagtggt ggatgaacgc gatcgggtgg tgatggataa cctcgcctac  540
aaaacctttt gcgccgattg cggcggtaaa gaactactca ccgaaatcaa cttttccgcc  600
cataaggcgg agctggcgca gggcctggta ctgccggtag tgctgcgcgg caccgtgcgc  660
tggttgtccg ttacctgttg ggcgctgccg ggcgtcagcg aagaagcagg ccgctacttt  720
attgatagcg ccgtgccgcg cacgctggtg gtgatcaccg ataatactca gcagcagcaa  780
caacaggagc aggggcgtct tgatcgtctg aagcagcaga taaccagcgg taaattgctg  840
gcggcgatcc gcgaatcgct ggacgccgcg ctggtacaac tcaattgccc aattaatatg  900
ctggccgccg cacgccgctt aaatggcgac gagcatagca atctggcgct ggatgccgca  960
tggcgtgaag gcgaagaagc gatggcgcgg ttgcagcgct gccgcccgtc gctggaactg  1020
gaaagcccgg cagtctggcc gctccagccg ttccttgacg atctgcgtgc cctgtatcac  1080
acccgatata accagggcga aaacctgcaa attgagctgg aatcccccga cctggtgggc  1140
tttggccagc gaacacaact gcttgcctgc ctgagcctgt ggctcgacag aaccctggat  1200
attgccgcgg agctacgtga tttcacggta cagactcaac tttacgcccg cgaagagagc  1260
ggctggctgt cgttctattt aaacgacaat gtgccgctga ttcaggtgcg ctacacccat  1320
tcacccgatg cactcaatgc gcccggtaaa ggcatggagc tgcggctgat ccagacgctg  1380
gtcgcccacc atcgaggcgc aatagaactg acctcacgcc ctcagggagg cacctgtctg  1440
atcctgcgtt tcccattatt ttactcgctg acaggaggct cactatga               1488

SEQ ID NO: 80          moltype = DNA  length = 1575
FEATURE                Location/Qualifiers
gene                   1..1575
                       note = nifA
source                 1..1575
                       mol_type = genomic DNA
                       organism = Enterobacter sp.
```

```
SEQUENCE: 80
atgactcagc gaaccgagtc gggtacaacc gtctggcgct ttgacctctc ccaacagttt  60
acagccatgc agcgtatcag tgtggtgtta agccgcgcga cggagatcgg gcagacgcta  120
caggaagtgc tgtgcgtgct gcacaacgat gcctttatgc agcacgggat gatctgtctg  180
tacgacagta agcaagcgat cctttccatt gaagccttgc atgaggccga tcagcagtta  240
attcccggca gttcacagat tcgctaccgt ccgggcgaag ggctggtagg cacggtgctt  300
tcacagggac agtcgctggt actgccctgt gtctccgacg atcggcgttt tctcgatcgc  360
ctgggattgt atgattacag cttgccgttt atcgccgtgc cgctgatggg gccaaactcg  420
cagcctatcg gcgtgctggc cgcccagcct atggcgcgtt acgaggagcg gctgcccgcc  480
tgcacgcgtt ttcttgaaac cgtcgccaat ctggtggcgc aaaccgttcg cctgatgaca  540
ccgcccagcg tcgcgtctcc accccgtgct gctgccgcgc agattgccag ccagcgcggg  600
tgcgcgtctt cgcgagcgta tggctttgaa aacatggtcg gtaaaagcgc ggctatgcgt  660
cagacgctgg aaattattcg ccaggtatca cgctgggaca ccaccgtgct ggtgcgtggc  720
gaaagcggaa ccggtaaaga gttgatagcc aacgctatcc accacaattc accgcgcgcc  780
gccgcgccgt ttgtcaaatt caactgcgcg gcgctgcccg atacgctgct ggagagtgaa  840
ctcttcggtc atgaaaaagg cgcgtttacc ggcgcggtgc gccagcgcaa aggccgtttc  900
gaactggcgg atggcggtac gctgtttctt gatgagatcg gcgaaagtag cgcctcgttt  960
caggcgaaat tgctgcgtat cttgcaggaa ggcgaaatgg aacgcgtcgg cggcgacgaa  1020
acgctgcggg tgaatgtacg gatcattgcc gccaccaacc gcaatctgga agaggaagtg  1080
cggctgggta attttcgcga agatctctac tatcgcctta atgtgatgcc gatctccctg  1140
cccccgctcc gcgagcgtca ggaggacatc gtcgagctgg cgcattttct ggtgcgcaaa  1200
atcgcgcaaa accagaaccg cacgctgcgc atcagcgatg gcgcgatccg tttgttgatg  1260
agctatagct ggcctggaaa cgtgcgtgag ctggaaaact gccttgagcg atcggcggtg  1320
atgtcggaaa acgggctgat cgatcgcgac gtgattttgt ttcaccacag ggaaaatctg  1380
ccaaaaacgc cacagaccag tgcgccgcgc gaagagagct ggctcgatca gaacctcgat  1440
gagcgacaaa gattgatcgc cgcgctggag aaagccggtt gggtacaggc aaaagccgcg  1500
cgcctgctgg gaatgacccc gcgccaggtg gcctatcgta ttcagacgat ggacattgcc  1560
atgccgagat tgtag                                                  1575

SEQ ID NO: 81          moltype = DNA  length = 2856
FEATURE                Location/Qualifiers
gene                   1..2856
                       note = glnE
source                 1..2856
                       mol_type = genomic DNA
                       organism = Enterobacter sp.
SEQUENCE: 81
atgccgcttt cttcgcagtt acagcagcag tggcagaccg tttgcgaacg tctgcctgag  60
tcattaccgg cgtcatcgtt aagcgagcag gcaaagagcg tgctcgtctt cagtgatttt  120
gtgcaggaaa gtatcaccgc caacccgaac tggctggcgg aacttgagaa cgcaccaccg  180
caggcagaag agtggcggca ctatgctggc tggctgcaaa ctgtactcga agacgttacg  240
gatgaggcca cgctgatgcg cgtcctgcgc cagttccgtc gtcgggtgat ggtgcgcatt  300
gcctgggctc aggcgctgga actggtgagc gaagagagta cgctgcagca gttaagcgag  360
ctggcgcaaa cgttgattgt cgccgcgcga gactggctct atgccgcctg ctgtaaagag  420
tggggcacgc cgtgcagcga tgaaggggtt cctcagccgc tgttgattct ggggatggga  480
aagctgggcg gctgcgagct gaacttctcc tctgatatcg acctgatttt tgcctggccg  540
gagaacggct ccacgcgcgg aggccgccgc gagctggaca acgcgcagtt ctttacccgt  600
ctcggccagc gcctgattaa agcgctggat cagcccacgc aggacggttt tgtttaccgc  660
gtggacatgc gcctgcgtcc gtttggcgac agcgggccgc tggtgctgag ctttgcggcg  720
ctggaagatt attaccagga gcaaggtcgc gactgggagc gttacgcgat ggtcaaagcg  780
cggatcatgg gcgacagcga cgacgcttat gccaacgagc tgcgcgccat gctgcgtccg  840
ttcgtgttcc gtcgctatat cgacttcagc gtcatccagt ccctgcgaaa tatgaaaggg  900
atgattgccc gcgaggtgcg ccgccgtggg ctgaaagaca atatcaagct cggtgcgggc  960
ggcatccgcg aaatcgaatt tatcgtccag gtcttccagc ttattcgcgg cggacgcgag  1020
ccgtcgctgc agtcccgttc cttattaccg acgctgagcg ccattgcgca gctgcatctc  1080
ctgccggacg gcgacgcgca aaccctgcgc gaggcctatc ttttcctgcg tcgtctggaa  1140
aacctgctgc aaagcattaa tgacgaacag acccaaaccc tgccgggcga cgaccttaac  1200
cgggcgcgtc tggcctgggg aatgcgcgtg gaagactggt caacgctgac cgaacggctc  1260
gatgcccata tggcaggcgt gcgccgaatc tttaacgaac tgatcggtga tgacgaaagt  1320
gagtcgcagg acgatgcgct ctccgagcac tggcgcgagc tgtggcagga cgcgcttcag  1380
gaagatgaca ccacgccggt gctgacgcac ttaaccgacg acgcgcgcca tcgcgtggtg  1440
gcgctgatcg ctgatttccg tcttgagctg aacaaacgcg ccatcggccc gcgtggtcgc  1500
caggtgctgg atcacctgat gccgcacctg ctgagcgaag tctgctcgcg tgccgatgcg  1560
ccggtgccgc tgtcgcggat gatgcccctg ctgagcggga ttatcacccg tactacctac  1620
cttgaactcc tgagcgagtt ccctggcgcg cttaagcacc tgatttcact ctgcgccgcg  1680
tcgccgatgg tggccaacaa gctggcgcgt tacccgctgc tgctggatga gctgctcgat  1740
ccgaataccc tttatcaacc gacggcgacc gacgcctacc gggacgaact gcgtcagtat  1800
ctgctgcgcg tgccggaaga agacgaagag caacagctgg aggcgctgcg tcagtttaag  1860
caggcccaga tgctgcgcgt ggcggccgca gatattgccg gaacgctgcc ggtgatgaaa  1920
gtgagcgatc acttaacctg gcttgcggaa gcgattatcg acgcggtggt gcatcaggcc  1980
tgggtgcaga tggtggcgcg ctatggccag ccgaaacatc tggctgaccg tgatggtcgc  2040
ggcttcgcgg tggtgggtta cggtaagctc ggcggttggg agctgggcta tagctccgat  2100
ctggatttaa tcttcctcca cgactgcccg gttgatgtga tgaccgacgg cgagcgcgag  2160
attgacgggc gtcagttcta cctgcgcctg gcgcagcgca tcatgcacct gttcagcacc  2220
cgcacctcgt cgggcatttt gtatgaagtg gatgcccgtc tgcgcccgtc cggcgcggcg  2280
ggcatgctgg tcacctcgac ggagtccttc gctgattacc agaagaatga agcctggacg  2340
tgggagcatc aggcgctggt gcgcgcccgt gtggtgtatg gcgatccgct gctgaaaacg  2400
cagtttgacg tgattcgtaa ggaagtcatg accaccgtgc gcgatggcag cacgctgcaa  2460
acggaagtgc gcgaaatgcg cgagaaaatg cgcgcgcact taggcaataa acatcgcgat  2520
```

```
cgctttgata ttaaagccga tgagggcggt attaccgata ttgagtttat tacccagtat  2580
ctggtgttgc tgcacgcgca tgacaagccg aagctgacgc gctggtcgga taacgtgcgc  2640
attctggaac tgctggcgca aaacgacatt atggacgagc aggaggcgca ggccttaacc  2700
cgtgcctata caacgcttcg cgatgagctc catcatctgg cgttgcagga gcagccggga  2760
cacgtggcgc tggactgttt caccgctgaa cgcgctcagg taacggccag ctggcagaag  2820
tggctggtgg aaccgtgcgt aacaaatcaa gtgtga                           2856

SEQ ID NO: 82          moltype = DNA  length = 1290
FEATURE                Location/Qualifiers
gene                   1..1290
                       note = amtB
source                 1..1290
                       mol_type = genomic DNA
                       organism = Enterobacter sp.
SEQUENCE: 82
atgaagatag caacacttaa aacgggtctg ggttcgctgg cactgctgcc gggcctggcg  60
ctggctgctg cacctgcggt ggcagacaaa gccgataacg cctttatgat gatcagcacc  120
gcgctggtgc tgttcatgtc cattccgggc attgcgctgt tctatggcgg cctgatccgt  180
ggcaaaaacg ttctctccat gctgacgcag gttgccgtaa cgttcgcgct ggtctgcgta  240
ctgtgggtgg tttacggtta ctcgctggct ttcggcacgg gcaacgcgtt ctttggtaac  300
ttcgactggg tgatgctgaa aaatattgaa ctgaccgcgc tgatgggcag tttctaccag  360
tatattcacg ttgctttcca gggctcgttc gcctgcatta ccgtcgggct gattgtaggc  420
gcgcttgccg agcgtattcg tttctctgcg gtcctgatct tcgtggtggt ctggctgacg  480
ctctcctatg tgccgattgc gcacatggtc tggggtggcg gtctgctggc gacgcatggc  540
gcgctggact tcgcgggcgg taccgttgtg cacattaacg ccgcggtagc gggtctggtt  600
ggcgcatacc tgattggcaa acgcgtgggc ttcggtaaag aagcgttcaa accgcacaac  660
ctgccgatgg tcttcaccgg taccgcgatc ctctactttg gctggtttgg tttcaacgcc  720
ggctcagcaa gtgccgcgaa cgaaatcgcc gcgctggcct tcgtgaatac cgttgtggcc  780
acggcaggtg caatcctctc ctgggtcttt ggcgagtggg ctgtgcgcgg taaaccttct  840
ctgctgggtg cctgttcggg ggcgattgct ggtctggtcg gtatcacccc agcatgtggt  900
tatgtcggtg tgggtggcgc gctgctggtc ggcctggtgt caggtctggc gggtctgtgg  960
ggcgtgacgg cgctgaaacg tattctgcgc gttgatgacc cttgcgatgt gtttggcgtg  1020
cacggcgtgt gcggcatcgt cggctgtatc atgaccggta tctttgcagc gaaatcgctg  1080
ggtggcgtgg gctacgcaga aggcgtcacc atggcccatc aggtgctggt gcagctggaa  1140
agtattgctg tcaccgtggt gtggtctgcc gttgtcgctt tcattggcta caaactggcg  1200
gacatgacgg ttggtctgcg cgtgccggaa gagcaggaac gcgaaggtct ggacgtcaac  1260
agccacggcg agaatgcgta taacgcatga                                   1290

SEQ ID NO: 83          moltype = DNA  length = 1299
FEATURE                Location/Qualifiers
gene                   1..1299
                       note = 16S
variation              294
                       note = n is a, c, t, g, unknown or other
variation              299
                       note = n is a, c, t, g, unknown or other
variation              302
                       note = n is a, c, t, g, unknown or other
variation              309..310
                       note = n is a, c, t, g, unknown or other
variation              332
                       note = n is a, c, t, g, unknown or other
variation              346
                       note = n is a, c, t, g, unknown or other
variation              351
                       note = n is a, c, t, g, unknown or other
variation              438
                       note = n is a, c, t, g, unknown or other
variation              445
                       note = n is a, c, t, g, unknown or other
variation              454
                       note = n is a, c, t, g, unknown or other
variation              469
                       note = n is a, c, t, g, unknown or other
variation              477
                       note = n is a, c, t, g, unknown or other
variation              492
                       note = n is a, c, t, g, unknown or other
variation              504
                       note = n is a, c, t, g, unknown or other
variation              555
                       note = n is a, c, t, g, unknown or other
variation              775
                       note = n is a, c, t, g, unknown or other
source                 1..1299
                       mol_type = genomic DNA
                       organism = Azospirillum lipoferum
SEQUENCE: 83
gccgagagag gggcccgcgt cggattaggt agttggtgag gtaatggctc accaagcctt  60
```

```
cgatccgtag ctggtctgag aggatgatca gccacactgg gactgagaca cggcccagac  120
tcctacggga ggcagcagtg gggaatattg gacaatgggc gcaagcctga tccagcaatg  180
ccgcgtgagt gatgaaggcc ttagggttgt aaagctcttt cgcacgcgac gatgatgacg  240
gtagcgtgag aagaagcccc ggctaacttc gtgccagcag ccgcggtaat acgnagggng  300
cnagcgttnn tcggaattac tgggcgtaaa gngcgcgtag gcggcntgtt nagtcagaag  360
tgaaagcccc gggctcaacc tgggaatagc ttttgatact ggcaggcttg agttccggag  420
aggatggtgg aattcccngt gtagnggtga aatncgtaga tattgggang aacaccngtg  480
gcgaaggcgg cnatctggac gganactgac gctgaggcgc gaaagcgtgg ggagcaaaca  540
ggattagata ccctngtagt ccacgccgta aacgatgaat gctagacgtc ggggtgcatg  600
cacttcggtg tcgccgctaa cgcattaagc attccgcctg gggagtacgg ccgcaaggtt  660
aaaactcaaa ggaattgacg gggcccgca caagcggtgg agcatgtggt ttaattcgaa  720
gcaacgcgca gaaccttacc aacccttgac atgtccactt tgggctcgag agatngggtc  780
cttcagttcg gctgggtgga acacaggtgc tgcatggctg tcgtcagctc gtgtcgtgag  840
atgttgggtt aagtcccgca acgagcgcaa cccctaccgt cagttgccat cattcagttg  900
ggcactctgg tggaaccgcc ggtgacaagc cggaggaagg cggggatgac gtcaagtcct  960
catggccctt atgggttggg ctacacacgt gctacaatgg cggtgacagt gggaagcgaa  1020
gtcgcgagat ggagcaaatc cccaaaagcc gtctcagttc ggatcgcact ctgcaactcg  1080
agtgcgtgaa gttggaatcg ctagtaatcg cggatcagca cgccgcggtg aatacgttcc  1140
cgggccttgt acacaccgcc cgtcacacca tgggagttgg ttttacccga aggtggtgcg  1200
ctaaccgcaa ggaggcagcc aaccacggta aggtcagcga ctggggtgaa gtcgtaacaa  1260
ggtagccgta ggggaacctg cggctggatc acctcctttt                       1299
```

```
SEQ ID NO: 84          moltype = DNA  length = 897
FEATURE                Location/Qualifiers
gene                   1..897
                       note = nifH
source                 1..897
                       mol_type = genomic DNA
                       organism = Azospirillum lipoferum
SEQUENCE: 84
atggccaaag cgcctctgcg tcagatcgcc ttttacggca agggcggtat cggcaagtcc  60
accacctctc agaacacgct ggccgcgctg gtcgagctgg atcagaggat cctgatcgtc  120
ggctgcgacc cgaaggccga ctcgacccgc ctgatcctgc acgcaaaggc ccaggacacc  180
gtcctgcatc tggccgccga ggccggctcg gtcgaggatc tggagctcga ggacgttctc  240
aagatcggct acaagaacat caagtgcgtc gagtccggcg gtccggagcc gggggtcggc  300
tgcgccggcc gcggcgtcat cacctcgatc aacttcctgg aagagaacgg cgcctacgac  360
gacgtggact atgtgtccta cgacgtgctg ggcgacgtgg tctgcggcgg cttcgccatg  420
ccgatccgcg agaacaaggc ccaggaaatc tacatcgtca tgtccggcga gatgatggcg  480
ctgtacgccg ccaacaacat cgccaagggc atcctgaagt acgcgcacag cggcggcgtc  540
cgtctcggcg gcctgatctg caacgagcgc cagaccgaca aggaatggga tctggccgac  600
gcgctggcca agcgcctggg ctccaagctg atccacttcg tgccgcgcga caacatcgtc  660
cagcacgccg agctgcgccg catgacggtc atcgagtacg ccccggacag caagcaggcc  720
ggcgaatacc gcgcgctcgc caacaagatc catgcgaact ccggccaggg ttgcatcccg  780
accccgatca ccatggaaga gctggaagag atgctgatgg acttcggcat catgaagacc  840
gaggagcagc agctcgccga gctcgccgcc aaggaagcgg cgaaggccgg cgcctga     897
```

```
SEQ ID NO: 85          moltype = DNA  length = 1440
FEATURE                Location/Qualifiers
gene                   1..1440
                       note = nifD1
source                 1..1440
                       mol_type = genomic DNA
                       organism = Azospirillum lipoferum
SEQUENCE: 85
atgagcctgt ccgagaacac cacggtcgac gtcaagaacc tcgtcaacga agtcctcgaa  60
gcctatcccg aaaaatcccg caagcgccgc gccaagcacc tgaacgtgct ggaggccgag  120
gccaaggact gcggcgtcaa gtcgaacgtc aagtccatcc ccggcgtcat gaccatccgc  180
ggctgcgcct atgccggctc caagggcgtg gtgtggggtc cgatcaagga catgatccac  240
atctcccacg gtccggtcgg ctgcggctac tactcctggt ccggccgccg caactactac  300
atcggcgaca ccggtgtgga cagctggggc acgatgcact tcacctccga cttccaggag  360
aaggacatcg tcttcggcgg cgacaagaag ctgcacaagg tcatcgagga aatcaacgag  420
ctgttcccgc tggtgaacgg catctcgatc cagtcggaat gcccgatcgg cctgatcggc  480
gacgacatcg aggctgtcgc ccgcgccaag tcggcggaaa tcggcaagcc ggtcatcccc  540
gtgcgctgcg aaggcttccg cggcgtgtcc cagtcgctgg gccaccacat cgccaacgac  600
gccatccgag actgggtgtt cgagaagacg gaacccaagg ccggcttcgt ctccaccccc  660
tatgacgtca ccatcatcgg cgactacaac atcggcggcg acgcctggtc gtcccgcatc  720
ctgctggagg agatcggcct gcgcgtgatc gcccagtggt cgggcgacgg cacgctcgcc  780
gaactggaga acacgccgaa ggccaaggtc aacctgatcc actgctaccg ctcgatgaac  840
tacatcgcgc gccacatgga agagaagttc aacattcctt ggatggaata caacttcttc  900
ggcccgagcc agatcgccga atccctgcgc aagatcgccg ctctcttcga cgacaagatc  960
aaggagaacg ccgagaaggt catcgcccgc taccagccga tggtcgatgc ggtcatcgcc  1020
aagtacaagc cgcggctcga aggcaagaag gtcatgatct acgtcggcgg cctgcgtccc  1080
cgccacgtcg tcgatgccta ccatgacctc ggcatggaga tcaccggcac cggctacgag  1140
ttcgcccaca acgacgacta tcagcgcacg cagcactacg tgaaggaagg cacgctgatc  1200
tacgacgacg tcaccgcgtt cgaactggag aagttcgtcg aggcgatgcg tcccgacctc  1260
gtcgcgtcgg gcatcaagga aaagtacgtg ttccagaaga tgggcctgcc gttccgccag  1320
atgcacagct gggactactc cggcccgtac cacggctatg acggcttcgc gatcttcgcc  1380
cgcgacatgg acctggccat caacaacccc gtctggggcg tgatgaaggc cccgttctga  1440
```

```
SEQ ID NO: 86          moltype = DNA  length = 1419
FEATURE                Location/Qualifiers
gene                   1..1419
                       note = nifD2
source                 1..1419
                       mol_type = genomic DNA
                       organism = Azospirillum lipoferum
SEQUENCE: 86
atgctccagg acaagatcca ggatgtcttc aacgaaccgg gctgcgcgac caaccaagcc  60
aaatcggcca aggagaagaa gaagggctgc accaagtcgc tgaaaccggg ggcggcagcc  120
ggcggctgcg cctatgacgg ggcgatgatc gtgctccagc cgatcgccga cgccgcccat  180
ctggtccatg gccccatcgc ctgcctcgga aacagttggg acaaccgcgg ctccaaatcc  240
tccggctcgc agctctaccg caccggcttc accaccgatc tgtcggaact ggacgtcatc  300
ggcggcggcg agaagaagct ctaccgcgcc atcaaggaga tcgttcagca atacgacccg  360
ccggccgtct tcgtctatca gacctgcgtg cccgccatga ccggcgacga catcgccgcg  420
gtctgcaagt tcgccacgca gaagctgggc aagccggtga tcccggtgga ctcgccgggc  480
ttcgtcgggt cgaagaatct cggcaacaag ctggccggcg aagccctgct ggagcatgtc  540
atcggcacgg tcgaaccgga ctacaccacc ccgaccgacg tctgcatcat cggcgaatac  600
aaccttgccg gcgagctgtg gctggtcaag ccgctgctgg acgagatcgg catccgcctc  660
ctgtcctgca tttccggcga cggccgctac cgggaggtgg cgcaggccca ccgcgcccgc  720
gtcaccatga tggtgtgcag ccaggcgctg gtgaatgtcg ggcgcaagat ggaggagcgc  780
tacggcatcc cctatttcga ggggtccttc tacggcgtgt ccgacatgtc ggacaccctg  840
cgcaccatga cccgcatgct ggtggagcgc ggcgccgaca agggcctgat cgaccgggcg  900
gagggcgtga tcgcgcggga ggaaagccgg gtctggcgcc ggctggaacc ctacaagccg  960
cgcttcgacg gcaagcgcgt ccttctcttc accggcggcg tcaagagctg gtcgatggtc  1020
agcgcgctgg agggtgcggg gctgaccatc ctcggcacct ccaccaagaa atcgaccagg  1080
gaggacaagg agcgcatcaa gaagatgaag ggcgaagagt tccaccagtg ggacgatttg  1140
aagccgcgcg acatctacag gatgctggcc gacgatcagg ccgacatcat gatgtccggc  1200
ggccgctcgc agttcatctc gctgaaggcc aaggttccct ggctcgacat caaccaggag  1260
cgccaccacg cctatgccgg ctatgacggc atcgtcaatc tctgcgagga gatcgacaaa  1320
acgctgtcga atccgatctg gcgtcaggtg cgtcagccgg caccgtggga gtccggcgcg  1380
tcctccaccc ttctggcttc ctcgatggcg gcggagtga                         1419

SEQ ID NO: 87          moltype = DNA  length = 1383
FEATURE                Location/Qualifiers
gene                   1..1383
                       note = nifK
source                 1..1383
                       mol_type = genomic DNA
                       organism = Azospirillum lipoferum
SEQUENCE: 87
atgtcccaca tccagcgctt cccctccgcc gccaaggccg cctccaccaa cccgctgaag  60
atgagccagc cgctgggtgc ggctctggcc tatctcggcg tcgaccgctg cctgccgctg  120
ttccatggct cgcagggctg caccgccttc gggctggtcc tgctggtgcg ccatttccgc  180
gaggcgatcc cgctccagac cacggcgatg gatcaggtcg ccaccatcct cggcggctac  240
gacaatctgg agcaggcgat ccgcaccatc gtcgagcgca accagcccgc catgatcggc  300
gtcgccacca ccggcgtcac cgagaccaag ggcgaggata tggccggaca gtacacgctg  360
ttccgccagc gcaaccccga cttggccgac acggccctgg tcttcgccaa cacccccgac  420
ttcgccggcg gcttcgagga cggcttcgcc gccgcggtca ccgcgatggt cgagcggttg  480
gtcgaaccgt cgccggtgcg catcccgacc caggtcaacg tgctggccgg ctgccatctg  540
tcccccggcg acgtggagga actgcgcgac atcatcgaag gcttcggcct gtcgccgatc  600
ttcctgcccg acctgtcgct gtcgatggcg ggccgccagc cggccgactt caccgccacc  660
tcgctgggcg gcgtgaccgt cgatcagatc cgcgccatgg gcgcttcggc cctcaccatc  720
gtggtcggtg agcatatgcg ggtggccggt aacgcgctgg agctgaagac cgacgtgccc  780
agccatttct tcaaccgcct gaccgggctg gaggcgacgg acaagctggt ccggctgctg  840
atggagttgt cgggcaagcc ggcgcccgcc cggctgcggc gccagcgcga aagcctggtc  900
gatgccatgc tcgacgggca tttcttctac agccgcaagc gcatcgccgt cgcgctggag  960
cccgacctgc tctatgccgt caccggcttc ctcgccgaca tgggggccga ggtgatcgcc  1020
gcggtgtccc cgacgcagag cccggtgctg gagcggttga aggccgccac catcatggtc  1080
ggcgatcatt ccgacgtgga gacgctggcc cgcgacgccg acctgatcgt ctccaactcg  1140
cacgggcggc agggagccgc gcggatcggc gtggctctgc accgcatggg cctgccgctg  1200
ttcgaccggc tgggggccgg cctgcgcgtc caggtcggct accgcggcac gcgggaactg  1260
ctgtgcgaca tcggcaacct gttcctcgcc cgcgagatgg accacgagca cgggcacgag  1320
agccacgacc acggggaatc ccacggctgc ggaggcggat catgcggatg caacgccgtc  1380
tga                                                                1383

SEQ ID NO: 88          moltype = DNA  length = 1560
FEATURE                Location/Qualifiers
gene                   1..1560
                       note = nifK1
source                 1..1560
                       mol_type = genomic DNA
                       organism = Azospirillum lipoferum
SEQUENCE: 88
atgaccgaca agctttcgca gagcgccgac aaggtcctcg accactacac cctcttccgg  60
cagcccgaat acgcggcgat gttcgagaag aagaagaccg agttcgagta cggccattcg  120
gacgaggaag tcgcccgcgt gtccgaatgg accaagtccg aggactacaa ggcgaagaac  180
ttcgcccgtg aagcggtcgt catcaacccg accaaggcct gccagccgat cggcgcaatg  240
ttcgccgccc agggcttcga aggcaccctg cccttcgtcc acggctccca gggctgcgtc  300
```

```
gcctattacc gcacccacct gacccgtcac ttcaaggagc cgaacagcgc ggtctcctcg  360
tcgatgacgg aggacgcggc ggtgttcggc ggcctgaaca acatgatcga cggcctggcg  420
aacgcctatg cgctctacaa gccgaagatg atcgcggtga tgaccacctg catggccgaa  480
gtcatcggcg acgatttgca gggcttcatc gccaatgcga agaccaagga cagcgtcccg  540
gccgacttcc cggtccccta cgcccacacc ccggccttcg tcggcagcca catcgtcggc  600
tacgacaaca tgatcaaggg gatcctgacc aacttctggg gtacgtcgga gaatttcgac  660
acacccaaga ccgagcagat caacctgatc ccgggcttcg acggcttcgc cgtcggcaac  720
aaccgcgaac tgaagcgcat cgccggcgaa ttcggcgtga agctgcaaat cctgtccgac  780
gtgtccgaca atttcgacac gccgatggat ggcgagtacc gcatgtatga cggcggcacc  840
accatcgagg agaccaagga ggccctgcac gccaaggcca ccatctccat gcaggagtac  900
aacacgaccc agaccctgca attctgcaag gagaagggtc aggaagtcgc caagttcaac  960
tacccgatgg gcgtcaccgg caccgacgag ctgctgctga agctcgccga actgtcgggc  1020
aagccggtcc cggccagcct gaagctggag cgcggccgtc tggtcgacgc catcgccgac  1080
agccacaccc acatgcacgg caagcgcttc gccgtctatg gcgacccgga cttctgcctg  1140
ggcatgtcca agttcctgct ggagctgggt gcggagccgg tgcacatcct gtcgacgtcg  1200
ggctccaaga agtgggagaa gcaggtccag aaggtgctgg acggctcgcc cttcggcgcc  1260
tcgggcaagg cccatggcgg caaggatctg tggcacctgc gttcgctgat cttcaccgac  1320
aaggtggact acatcatcgg caacagctac ggcaagtatc tggagcgcga caccaaggtt  1380
ccgctgatcc gcctgaccta cccgatcttc gaccgccacc accaccaccg ctacccgacc  1440
tggggctacc agggcgcgct gaacgtgctg gtacggatcc tggaccggat cttcgaggac  1500
atcgacgcca acaccaacat cgtcggccag accgactact cgttcgacct gatccgctga  1560

SEQ ID NO: 89          moltype = DNA  length = 1530
FEATURE                Location/Qualifiers
gene                   1..1530
                       note = nifA
source                 1..1530
                       mol_type = genomic DNA
                       organism = Azospirillum lipoferum
SEQUENCE: 89
atgttgacct ctgatattgt tggcaaattg cgctgcatcg cagcagaccc caaagcgggc  60
atcgcaaggg gcctcgacac cgggacgacg aagatcggtc ccgtttggga gggtgacgtg  120
ggcgacaccg tggatttcga agcgctgcgc cagcgggcgg tccactccct gttcgaacat  180
ctggaatcca tgtgcgtcgg cgccgtcgcc gtcgaccaca ccggccgcat cgcctggatg  240
gacgagaagt acaaggctct gctgggcgtt cccgacgacc cgcgcggccg gcaggtggag  300
gacgtcatcc ccaacagcca gctgcgccgg gtgatcgaca gcggccagcc gcagccgctg  360
gacatcatgg agttcgacga ccggtccttc gtggtgacgc ggatgccgct gttcggcacc  420
gacggttcga tcatcggcgc catcggcttc gtgctgttcg accgcgccga atatctccgc  480
ccgctggtcc gcaaatacga gaagatgcag gaggagctgg cccgcaccca gcaggagctg  540
gcgcatgagc gccgcgccaa atactccttc tcgcagttcc tgggcgccag cgaatcgatc  600
cgcgagatca agcggctggg gcgccgcgcc gcccagatgg attcgaccgt cctgctgctg  660
ggcgaaaccg ggaccggcaa ggagctgctg gcccaggcca tccattccgc cagcccgcgg  720
gcgtccaagc ccttcgtcgg cgtcaatgtc gccgccattc cggaaaccct gctggaggcg  780
gagttcttcg gcgtcgcccc cggcgccttc accggcgccg accgccgcca ccgcgacggc  840
aagttccagc tcgccaacgg cggcaccctg ttcctcgacg agatcggcga catgccgctg  900
ccggtgcagg ccaagcttct gcgcgtgctg caggagcggg agatcgagcc gctcggctcc  960
aacaaggtgg tgcgggtcga tgtccgcatc atcgccgcca ccagccgtga cctgcacgcc  1020
ctggtgcgtg agaagcagtt ccgcgccgac ctctattacc ggctgaatgt ggtgccgatc  1080
accctgccgc cgctgcgcga ccggccggag gacatcgaga gcatcgccga ccgcatcctg  1140
gaacagctgg cgatccagca gggcacgccg ccgcgcgagc tgctggaatc ggcggtgcag  1200
gtgctgcgcg actatgactg gcccggcaat gtgcgcgagc tttacaacac gctggaacgg  1260
gtggtggcgc tgaccgatgc gccgatcctg accgcgccgc acatccgcag cgtgctgccc  1320
ggccagcatc cggccggcgc gtcggccctg ccgctggcgg ccggcgcgcg gccgttgcag  1380
gaggtgctgc acgccgccga gcgccacgcc atcgccgcgg cgcttgagga ggcgaacggc  1440
gtcaaggcgc gggcggcgaa gctgctgggc atttcgcgcg cgtcgctgta cgaacgcatg  1500
gtgacgctgg ggttgggggc gacgcagtag                                  1530

SEQ ID NO: 90          moltype = DNA  length = 3030
FEATURE                Location/Qualifiers
gene                   1..3030
                       note = glnE
source                 1..3030
                       mol_type = genomic DNA
                       organism = Azospirillum lipoferum
SEQUENCE: 90
atgccgagtc ccatcgcgtt ctcaagcccc ttgccgaagc ctttcgacag cgcgcaggcg  60
gcgctgggga tggagcgctg gcgccagcag gccgccgcgg cggagccgga gacccgcgcc  120
tgggcggaag ccttcgccga ttcggagacc ggccgggcgc tgatcggggc ggtgtgcggc  180
aacagcccgt atctcggcca cagcctgacg cgggagttgc ccttcgtcgc ccgtacagtg  240
caggacggct tcgacgacac cttcgccgcg ctgatcgccg ctctccatgc cgagcatggc  300
gaggagaaat cgatggaccg gctgatggcc ggcctgcggg tggcgaagcg gcgggcggcg  360
ctgctgatcg cgctggccga catcgccggc gcgtggccgc tgttccgcgt caccggcgcc  420
ctgtcggagc tggcggagac gggggtgcag ctggccgcga atttcctgct gcgccgcgcc  480
agggaggcgg ggacgctgac gctgccggat ccgcagcgac cgtgggtcgg ttcgggcctg  540
atcgttttgg gcatgggtaa gcttggcggg cgcgaactca actattccag cgacatcgac  600
ctgatcgtcc tgtatgacga cgctgttgtg cagacgcccc agccggacaa cctcgcgcga  660
accttcatca ggctcgcacg cgatcttgtc cgcattatgg atgaacggac caaggacggc  720
tacgtcttcc gcaccgacct tcggcttagg cccgatcccg gcgccacgcc gctggcggtt  780
tccgtctccg cagccgaaat ttattacggc agcgtcggtc agaactggga acgcgcggcg  840
```

```
atgatcaagg cccgtcccat cgccggcgat ctggaggcgg gcgcctcctt tgtccgcttc  900
ctggagccct tcgtctggcg ccgcaacctg gatttcgccg ccatccagga catccattcg  960
atcaaacgcc agatcaacgc ccacaagggc caccgcgagg tgacggtcaa cggccacgac  1020
atcaaggtcg gccgcggcgg catccgcgag atcgagttct tcgcccagac ccagcagctg  1080
atcttcggcg ggcgcgaccc gcgcgtgcga atcgctccga ccctgatggc gaacgaggcg  1140
ctgcgcgacg tcggccgcgt gccgccgcag acggtggaag agcttgccgg ggcctatcat  1200
ttcctgcgcc gtgtcgaaca tcgcatccag atgatcgacg accagcagac ccatcgtatt  1260
cccgccgacg atgccggggt ggcgcatttg gccaccttcc tcggctatga cgaccccgcc  1320
gccttccggg cggaactgct ggcgacgctg gggcaggtgg aggaccgcta tgccgagctg  1380
ttcgaggagg cgccgtcgct ttccggcccc ggcaatctgg tcttcaccgg caccgacccc  1440
gatccgggca cgatggagac gctgaagggc atgggcttcg ccgatccggc ccgcgtcatc  1500
agcgtggtgt cggcctggca tcgcggccgc taccgcgcca cccggtcggg ccgggcgcgg  1560
gagctgctga cggagctgac gccggccctg ctgagtgcgc tgaccaagac cccggccccc  1620
gattcggcgc tgatgaactt cgacgatttc ctcggcaagc tgccggccgg cgtcggtctg  1680
ttctcgctgt tcgtcgccaa tccctggctc ctggagctgg tggcggagat catgggcatc  1740
gcgccgcaga tggcgcagac gctgtcgcgc aacccgtcgc tgctcgacgc cgtgctgtcg  1800
ccggacttct tcgacccgct gccgggcaag gaggacgggc tggccgacga ccacgcccgc  1860
gtgatggcgc cggcccgcga tttcgaggat gcgctgaccc tgtcgcggcg ctggaccaac  1920
gaccagcgct tccgcgccgg ggtgcatatc ctgcgcggca tcaccgatgg cgaccgctgc  1980
ggcgccttcc tggccgatct ggccgacatc gtcgtccccg accttgcccg ccgggtggag  2040
gaggagttcg cccagcgcca cggccatatt cccggcggcg cctgggtggt ggtggcgatg  2100
ggcaagctcg gcagccggca gctgaccatc acgtccgaca tcgacctgat cgtcatctac  2160
gatgtggcgc cgggccaagg gggcgggggc ggtccccgct tgtcggatgg tgccaagccg  2220
ctgtcgccca acgagtatta catcaagctg actcagcgtc tgaccaacgc cattaccgcg  2280
ccgatgggcg acggccggct ctacgaggtc gacatgcggc tgcgcccgtc gggcaacgcc  2340
gggccgctcg ccacctcgct ggacgctttc ctgaaatatc aggcgaccga tgcctggacc  2400
tgggagcata tggccctgac ccgcgcccgg gtgatcggcg gtgatgcgga gctggccggg  2460
cgggtgtcgg cagcgatccg ctcggtgctg acggcgccgc gcgatgccga ccggctgctg  2520
tgggacgtgg ccgacatgcg gcggcggatc gagaaggagt tcgggacgac caatgtctgg  2580
aacgtcaaat acgcccgcgg cggcctgatc gacatcgagt tcatcgccca gtacctgcaa  2640
ctgcgccatg gtcacgagcg gccggacatc ctgcacatcg gcaccgccaa ggcgctgggc  2700
tgcgccgccc ggacgggcgc gctggcgccg gaggtggcgg aggatctgga gacgacgctg  2760
cggctgtggc ggcgggtgca gggctttctg cggttgacca ccgccggggt gctcgatccc  2820
aatcaggtgt cgcccagcct gctggccggg ctggtccgcg ccgcctttcc tgctgacttt  2880
cagggcgagc gtgagcctgg cactgttgac ttccccgaac tggaccacaa aatccgtgcc  2940
gtcgccgccc gcgcccatgg tcatttcaag accctggtcg aggaaccggc gggccgtctg  3000
gccccacccg ccaccacgcc tccagcctga                                  3030
```

```
SEQ ID NO: 91          moltype = DNA  length = 1440
FEATURE                Location/Qualifiers
gene                   1..1440
                       note = amtB1
source                 1..1440
                       mol_type = genomic DNA
                       organism = Azospirillum lipoferum
SEQUENCE: 91
atgaaccgtc tgttccttat ggccgcaccg atgatggcgg ttgctctggg cgcggtcggc  60
atgccggccg cagcccttgc ccaggatccg gcggctgccg ccgctgccgc ggctgcggct  120
gcggctgccg ccgctgctgc cgcaccggcg gctccggcgc tgaatggcgg cgacaccgcc  180
tggatgctca tctccaccgc gctggtgctg atgatgacca tccccggcct ggcgctgttc  240
tacggcggca tggtccgcaa gatgaacgtg ctgtcgacgg tgatgcagag cttcgccatc  300
acctgcctga tcagcgtcct gtggtacgtc atcggctaca gcctggcctt caccggcacc  360
ggtgcctatg tcggcggtct cgaccggctg ttcctcaacg ggctcgactt cacgaaggcc  420
ttcgtgctgg gcgaggcgac cggcgtcggc gtcccgacga ccatccccga gccggtcttc  480
atgatgttcc agatgacctt tgcgatcatc accccggccc tgatcaccgg cgccttcgcc  540
gaccgcatga agttctcctc cctgctggtc ttcaccgcgc tgtggtcgat cgtggtctat  600
gcgccgatcg cccactgggt ctggtacccg tcgggcttcc tgttcggcct gggcgtgctg  660
gacttcgccg gcggcacggt cgtgcacatc aacgccggcg tcgccggcct ggtcgccgcg  720
ctggtgatcg gcaagcgcaa gggctacccg aaggaagcct tcatgccgca caacctggtg  780
ctgtcgctga tcggcgcctc gctgctgtgg gtcggctggt tcggcttcaa cgccggttcg  840
gccctgaccg ccggtccgcg tgccggcatg gcgctggccg ccacgcacat cgccaccgcc  900
ggtgccgcca tgggctggct gttcgcggag tggatcgtca agggcaagcc gtcgatcctc  960
ggcatcatct ccggcgccgt cgccggcctg gtcgcggtga ccccggccgc cggcttcgtc  1020
gacccgacgg gcgccatcgt catcggcatc gtcgccggcg tggtctgctt ctggtcggcc  1080
accagcctca agcacatgct gggctatgac gacagcctgg acgccttcgg cgtgcacggc  1140
gtcggcggcc tgatcggcgc catcctgacc ggcgtcttcg ccaagatgtc ggtgtccaac  1200
agcgaaggcg gcttcgcctc cgtcctgcag gccgacccga aggccacgct gggcctgctg  1260
gaaggcaacg ccgccgccgt ctggatccag gtccagggcg tcctctacac catggtctgg  1320
tgcgccatcg ccaccttcgt cctgctgaag atcgtcgatg tggtcatggg cctgcgcgtc  1380
gaagaggatg tggagcgcga cggtctcgac ctcgccctgc atggcgagag catccactaa  1440
```

```
SEQ ID NO: 92          moltype = DNA  length = 1227
FEATURE                Location/Qualifiers
gene                   1..1227
                       note = amtB2
source                 1..1227
                       mol_type = genomic DNA
                       organism = Azospirillum lipoferum
SEQUENCE: 92
```

```
atggatgcgg caaagacggg tggcgacgtc cttttcgtgc tgatgggcgc ggtgatggtg  60
ctggcgatgc attgcggctt cgccctgctg gaggtcggga cggtccggcg caagaatcag  120
gtcaacgcgc tggtgaagat cctgtcggac ttcgccatgt cgaccatcgc ctattttttc  180
gtcggttatg ccgtggccta cggcatcgac ttcttcgccg acgcccacac gctggtcggc  240
aagggaagcg gcgggttcgc ggcctatggc tacgatctgg tgaagttctt cttcctggcg  300
accttcgccg ccgcggtgcc ggccatcgtc tcgggcggca tcgccgagcg tgctaggttc  360
tggccgcagg ccgccgccac gctggcgctg atcgcgctgt tctatccatt gctggaaggc  420
acggtctggg gcacccgctt cggcctgcaa agctggatgg ccgcgacctt cggccagcct  480
ttccacgact tcgccggatc tgtggtggtg catgccttcg gcggctgggt ggcgctgggt  540
gccgtgctga acctcggcaa ccgccgcggc cgctaccgtc cgaacggctc gctgatcgcc  600
attccgccgt cgaacatccc cttcctggcg ctgggcgcct gggtgctgtg cgtggggtgg  660
ttcggcttca acgtgatgag cgcccaggtg ctggatggcg tgacgggtct ggtggcgctg  720
aactcgctga tggcgatggt cggcggcatc gtcacctcgc tggtgatcag ccgcaccgat  780
cccggcttcg tccacaacgg cgcgctggcc ggtctggtgg cggtctgcgc cgggtccgac  840
gtgatgcacc cgctgggcgc gctggtcacc ggcggcatcg ccgggctgct gttcgtctgg  900
gccttcaaca aatgccagat cgactggaag atcgacgacg tgctgggcgt ctggccgctg  960
cacggtctgt gcggcctgac cggcggcctg ctggccggcg tcttcgggca ggaggcactg  1020
ggcggccttg gcggcgtgtc gatcctcagc cagatcgtcg gcacggcaag cggcgccagc  1080
ttcggattcg tctcgggtct ggcggtctac ggcctgctgc gcgtcaccgt cggcatccgc  1140
ctcgatcccg agcaggagta caagggcgcc gacttgtcgt tgcaccatat caccgcgtac  1200
ccggaagagg acgcgccgac cctgtaa                                      1227
```

```
SEQ ID NO: 93          moltype = DNA  length = 613
FEATURE                Location/Qualifiers
misc_feature           1..613
                       note = Synthetic polynucleotide
misc_feature           1..613
                       note = delta-nifL::PinfC
source                 1..613
                       mol_type = other DNA
                       organism = synthetic construct
SEQUENCE: 93
atgaccctga atatgatgat ggattcttgg ttctctggag cgctttatcg gcatcctgac  60
tgaagaattt gcaggcttct tcccaacctg gcttgcaccc gtgcaggtag ttgtgatgaa  120
catcactgat tcgcaggctg aatacgttaa cgaattgacc cgtaaactgc aaaatgcggg  180
cattcgtgta aaagcagact tgagaaacga gaagattggc tttaaaatcc gcgagcacac  240
tttacgtcgt gtcccttata tgctggtttg tggtgacaaa gaggtcgaag ccggcaaagt  300
tgctgtgcgt acccgtcgcg gtaaagacct gggtagcctg gacgtaaatg atgttatcga  360
gaagctgcaa caagagattc gcagccgcag tcttcaacaa ctggaggaat aaggtattaa  420
aggcggaaaa cgagttcaaa cggcgcgtcc caatcgtatt aatggcgaga ttcgcgccac  480
ggaagttcgc ttaacaggtc tggaaggcga gcagcttggt attgcgatag aactcacttc  540
acgccccgaa gggggaagct gcctgaccct acgattcccg ctatttcatt cactgaccgg  600
aggttcaaaa tga                                                     613
```

```
SEQ ID NO: 94          moltype = DNA  length = 1613
FEATURE                Location/Qualifiers
misc_feature           1..1613
                       note = Synthetic polynucleotide
misc_feature           1..1613
                       note = delta-nifL::PinfC with 500bp flank
source                 1..1613
                       mol_type = other DNA
                       organism = synthetic construct
SEQUENCE: 94
accggataag agagaaaagt gtcgacgtcg gtccggttga tattgaccgg cgcatccgcc  60
agctcgccca gtttttggtg gatctgtttg gcgattttgc gggtcttgcc ggtgtcggtg  120
ccgaaaaaaa taccaatatt tgccataaca cacgctcctg ttgaaaaaga gatcccgcgg  180
ggaaaatgcg gtgaacatgt cagctattgc gaagagtgtg ccagttttgc tcacgggcaa  240
aagctgcacc agaatgggta ttaatgcacc agcctggcgc ttttttcgc ggcacgtccc   300
ctcgctaatg cccgtctggc gcggctttga cgctgataag gcgctgaata ccgatctgga  360
tcaaggtttt gtcgggttat cgtccaaaag gtgcactctt tgcatggtta taagtgcctg  420
acatggtgtc cgggcgaacg tcgccaggtg gcacaaattg tcagaactac gacacgacta  480
accgaccgca ggagtgtgcg atgaccctga atatgatgat ggattcttgg ttctctggag  540
cgctttatcg gcatcctgac tgaagaattt gcaggcttct tcccaacctg gcttgcaccc  600
gtgcaggtag ttgtgatgaa catcactgat tcgcaggctg aatacgttaa cgaattgacc  660
cgtaaactgc aaaatgcggg cattcgtgta aaagcagact tgagaaacga gaagattggc  720
tttaaaatcc gcgagcacac tttacgtcgt gtcccttata tgctggtttg tggtgacaaa  780
gaggtcgaag ccggcaaagt tgctgtgcgt acccgtcgcg gtaaagacct gggtagcctg  840
gacgtaaatg atgttatcga gaagctgcaa caagagattc gcagccgcag tcttcaacaa  900
ctggaggaat aaggtattaa aggcggaaaa cgagttcaaa cggcgcgtcc caatcgtatt  960
aatggcgaga ttcgcgccac ggaagttcgc ttaacaggtc tggaaggcga gcagcttggt  1020
attgcgatag aactcacttc acgccccgaa gggggaagct gcctgaccct acgattcccg  1080
ctatttcatt cactgaccgg aggttcaaaa tgacccagcg aaccgagtcg ggtaataccg  1140
tctggcgctt cgatttatcc cagcagttca ccgcgatgca gcggataagc gtggttctca  1200
gccgggcgac cgaggttgaa cagacactcc agcaggtgct gtgcgtattg cacaatgacg  1260
cctttttgca gcacggcatg atctgtctgt acgacagcca gcaggcgatt ttgactattg  1320
aagcgttgca ggaagccgat cagcagttga tccccggcag ctcgcaaatt cgctaccgtc  1380
cgggtgaagg gctggtcggg acggtgcttt cgcaggggca atcgttagtg ctggcgcgtg  1440
tggctgacga tcagcgcttt cttgaccgcc tgggactgta tgattacaac ctgccgttta  1500
```

```
tcgccgtgcc gctgataggg ccggatgcgc agacttttgg cgtgctgacg gcgcaaccga  1560
tggcgcgtta cgaagagcgg ttacccgcct gcacccgctt tctggaaacg gtc         1613

SEQ ID NO: 95          moltype = DNA  length = 1185
FEATURE                Location/Qualifiers
misc_feature           1..1185
                       note = Synthetic polynucleotide
misc_feature           1..1185
                       note = glnE-delta-AR-2
source                 1..1185
                       mol_type = other DNA
                       organism = synthetic construct
SEQUENCE: 95
tccctgtgcg ccgcgtcgcc gatggtggcc agccaactgg cgcgctaccc gatcctgctc  60
gatgaactgc tcgacccgaa cacgctctat caaccgacgg cgatgaacgc ctatcgcgat  120
gaactgcgac aatacctgtt gcgcgtgccg gaagaggatg aagagcagca actggaggcg  180
ctacggcagt ttaagcaggc gcagttgttg cgcgtagcgg cggcggatat cgccggtacg  240
ttacccgtca tgaaagtgag cgatcactta acctggctgg cggaagcgat tatcgatgcg  300
gtggtgcagc aagcctggaa ccagatggtg gcgcgttacg gccagccgac gcatctgcac  360
gatcgcgaag ggcgcggttt cgccgtggtc ggttacggca aacttggcgg ctgggaatta  420
ggttacagct ccgatctgga tctggtgttc ctgcacgact gccccatgga tgtgatgacc  480
gatggcgagc gtgaaatcga tggccgccag ttctatttgc gcctcgcgca gcgcgtgatg  540
cacctgttca gcacgcgcac gtcgtccggc attctttatg aagtcgatgc gcgtttgcgc  600
ccgtccggcg cggccggaat gctggtgacc actgcggaag cgttcgccga ttatcaaaaa  660
aatgaagcct ggacatggga gcatcaggcg ctggcgcgtg cgcgcgtggt gtacggcgat  720
ccgcaactga ccgccgaatt tgacgccatt cgccgcgata tcctgatgac ctcccgcgat  780
gccgctaccc tgcaaaccga agtgcgggaa atgcgtgaga aaatgcgcgc ccatcttggt  840
aacaagcaca aagaccgttt cgatctgaaa gccgatgaag gcggtatcac cgatattgag  900
tttatcgctc agtatctggt gctgcgcttt gcccatgaga agccgaaact gacgcgctgg  960
tcggataatg tgcgcatcct cgaagggctg gcgcaaaacg gcatcatgga tgagcaggaa  1020
gcgcaggcat tgacgctggc gtacaccacg ttgcgtgatg agctgcacca cctggcgctg  1080
caagagctgc caggacatgt ggcgctctcc tgttttgtcg ccgagcgtgc gcttatcaaa  1140
accagctggg acaagtggct ggtggaaccg tgcgccccgg cgtaa                   1185

SEQ ID NO: 96          moltype = DNA  length = 2085
FEATURE                Location/Qualifiers
misc_feature           1..2085
                       note = Synthetic polynucleotide
misc_feature           1..2085
                       note = glnE-delta-AR-2 with 500bp flank
source                 1..2085
                       mol_type = other DNA
                       organism = synthetic construct
SEQUENCE: 96
taaagcgagc gctcacttac gtgatctgtt gacgcagtcc gaagcgacca ttacttcagc  60
cgtttcagca gatacggcgg tgtggagtgc gcaatcagcc ctggcgaaac tggtgctcac  120
cgagtggtta gtgacgcagg gctggcgaac cttccttgat gaaaaagcgc aggctaagtt  180
tgccgactcc tttaaacgct ttgctgacgt tcatctgtca cgcagcgccg ccgagctgaa  240
aaaagccttt gcccagccgc tgggcgacag ctatcgcgac cagttaccgc ggctggcgcg  300
tgatatcgac agcgcgttat tgctggccgg acattacgat cgcgcgcgcg ccgtggagtg  360
gctggaaaac tggcaggggc ttcagcacgc tattgaaacg cgccagagag ttgaaatcga  420
acatttccgt aataccgcca ttacccagga gccgttctgg ttgcacagcg gaaaacgtta  480
acgaaaggat atttcgcatg tccctgtgcg ccgcgtcgcc gatggtggcc agccaactgg  540
cgcgctaccc gatcctgctc gatgaactgc tcgacccgaa cacgctctat caaccgacgg  600
cgatgaacgc ctatcgcgat gaactgcgac aatacctgtt gcgcgtgccg gaagaggatg  660
aagagcagca actggaggcg ctacggcagt ttaagcaggc gcagttgttg cgcgtagcgg  720
cggcggatat cgccggtacg ttacccgtca tgaaagtgag cgatcactta acctggctgg  780
cggaagcgat tatcgatgcg gtggtgcagc aagcctggaa ccagatggtg gcgcgttacg  840
gccagccgac gcatctgcac gatcgcgaag ggcgcggttt cgccgtggtc ggttacggca  900
aacttggcgg ctgggaatta ggttacagct ccgatctgga tctggtgttc ctgcacgact  960
gccccatgga tgtgatgacc gatggcgagc gtgaaatcga tggccgccag ttctatttgc  1020
gcctcgcgca gcgcgtgatg cacctgttca gcacgcgcac gtcgtccggc attctttatg  1080
aagtcgatgc gcgtttgcgc ccgtccggcg cggccggaat gctggtgacc actgcggaag  1140
cgttcgccga ttatcaaaaa aatgaagcct ggacatggga gcatcaggcg ctggcgcgtg  1200
cgcgcgtggt gtacggcgat ccgcaactga ccgccgaatt tgacgccatt cgccgcgata  1260
tcctgatgac ctcccgcgat gccgctaccc tgcaaaccga agtgcgggaa atgcgtgaga  1320
aaatgcgcgc ccatcttggt aacaagcaca aagaccgttt cgatctgaaa gccgatgaag  1380
gcggtatcac cgatattgag tttatcgctc agtatctggt gctgcgcttt gcccatgaga  1440
agccgaaact gacgcgctgg tcggataatg tgcgcatcct cgaagggctg gcgcaaaacg  1500
gcatcatgga tgagcaggaa gcgcaggcat tgacgctggc gtacaccacg ttgcgtgatg  1560
agctgcacca cctggcgctg caagagctgc caggacatgt ggcgctctcc tgttttgtcg  1620
ccgagcgtgc gcttatcaaa accagctggg acaagtggct ggtggaaccg tgcgccccgg  1680
cgtaagtgtg gtatcatcgc gcgcaaattt tgtatctctc aggagacagg aatgaaagtt  1740
acgctgccag agttcaatca agccggtgtc atggtggtgg gtgatgtgat gctggatcgc  1800
tactggtacg gcccaaccag ccgcatttct ccggaagcgc cagttccggt tgttaaagtc  1860
gatactattg aagagcgacc gggcggtgcg gcaaacgtgg cgatgaacat tgcctcgctg  1920
ggcgcaacgg cgcgtctggt tggcctgact ggcattgatg atgcggcgcg cgcgctgagc  1980
aaagcgctgg cggatgttaa tgttaaatgt gacttcgttt ctgttccgac tcaccccacc  2040
atcactaagc tgcgcgtgct gtcgcgtaac cagcaactga ttcgc                   2085
```

```
SEQ ID NO: 97          moltype = DNA  length = 461
FEATURE                Location/Qualifiers
misc_feature           1..461
                       note = Synthetic polynucleotide
misc_feature           1..461
                       note = delta-nifL::Prm1
source                 1..461
                       mol_type = other DNA
                       organism = synthetic construct
SEQUENCE: 97
atgaccctga atatgatgat ggatgccagc cgttctgtaa taataaccgg acaattcgga  60
ctgattaaaa aagcgccctc gcggcgcttt ttttatattc tcgactccat ttaaaataaa  120
aaatccaatc ggatttcact atttaaactg gccattatct aagatgaatc cgatggaagc  180
tcgctgtttt aacacgcgtt ttttaacctt ttattgaaag tcggtgcttc tttgagcgaa  240
cgatcaaatt taagtggatt cccatcaaaa aaatattctc aacctaaaaa agtttgtgta  300
atacttgtaa cgctacatgg agattaactc aatctagagg gtattaataa tgaatcgtac  360
taaactggta ctgggcgcaa ctcacttcac gccccgaagg gggaagctgc ctgaccctac  420
gattcccgct atttcattca ctgaccggag gttcaaaatg a                      461

SEQ ID NO: 98          moltype = DNA  length = 1461
FEATURE                Location/Qualifiers
misc_feature           1..1461
                       note = Synthetic polynucleotide
misc_feature           1..1461
                       note = delta-nifL::Prm1 with 500bp flank
source                 1..1461
                       mol_type = other DNA
                       organism = synthetic construct
SEQUENCE: 98
accggataag agagaaaagt gtcgacgtcg gtccggttga tattgaccgg cgcatccgcc  60
agctcgccca gtttttggtg gatctgtttg gcgattttgc gggtcttgcc ggtgtcggtg  120
ccgaaaaaaa taccaatatt tgccataaca cacgctcctg ttgaaaaaga gatcccgcgg  180
ggaaaatgcg gtgaacatgt cagctattgc gaagagtgtg ccagttttgc tcacgggcaa  240
aagctgcacc agaatgggta ttaatgcacc agcctggcgc ttttttttcgc ggcacgtccc  300
ctcgctaatg cccgtctggc gcggctttga cgctgataag gcgctgaata ccgatctgga  360
tcaaggtttt gtcgggttat cgtccaaaag gtgcactctt tgcatggtta taagtgcctg  420
acatggtgtc cgggcgaacg tcgccaggtg gcacaaattg tcagaactac gacacgacta  480
accgaccgca ggagtgtgcg atgaccctga atatgatgat ggatgccagc cgttctgtaa  540
taataaccgg acaattcgga ctgattaaaa aagcgccctc gcggcgcttt ttttatattc  600
tcgactccat ttaaaataaa aaatccaatc ggatttcact atttaaactg gccattatct  660
aagatgaatc cgatggaagc tcgctgtttt aacacgcgtt ttttaacctt ttattgaaag  720
tcggtgcttc tttgagcgaa cgatcaaatt taagtggatt cccatcaaaa aaatattctc  780
aacctaaaaa agtttgtgta atacttgtaa cgctacatgg agattaactc aatctagagg  840
gtattaataa tgaatcgtac taaactggta ctgggcgcaa ctcacttcac gccccgaagg  900
gggaagctgc ctgaccctac gattcccgct atttcattca ctgaccggag gttcaaaatg  960
acccagcgaa ccgagtcggg taataccgtc tggcgcttcg atttatccca gcagttcacc  1020
gcgatgcagc ggataagcgt ggttctcagc cgggcgaccg aggttgaaca gacactccag  1080
caggtgctgt gcgtattgca caatgacgcc tttttgcagc acggcatgat ctgtctgtac  1140
gacagccagc aggcgatttt gactattgaa gcgttgcagg aagccgatca gcagttgatc  1200
cccggcagct cgcaaattcg ctaccgtccg ggtgaagggc tggtcgggac ggtgctttcg  1260
caggggcaat cgttagtgct ggcgcgtgtg gctgacgatc agcgctttct tgaccgcctg  1320
ggactgtatg attacaacct gccgtttatc gccgtgccgc tgatagggcc ggatgcgcag  1380
acttttggcg tgctgacggc gcaaccgatg gcgcgttacg aagagcggtt acccgcctgc  1440
acccgctttc tggaaacggt c                                            1461

SEQ ID NO: 99          moltype = DNA  length = 1185
FEATURE                Location/Qualifiers
misc_feature           1..1185
                       note = Synthetic polynucleotide
misc_feature           1..1185
                       note = glnE-delta-AR-2
source                 1..1185
                       mol_type = other DNA
                       organism = synthetic construct
SEQUENCE: 99
tccctgtgcg ccgcgtcgcc gatggtggcc agccaactgg cgcgctaccc gatcctgctc  60
gatgaactgc tcgacccgaa cacgctctat caaccgacgg cgatgaacgc ctatcgcgat  120
gaactgcgac aatacctgtt gcgcgtgccg gaagaggatg aagagcagca actggaggcg  180
ctacggcagt ttaagcaggc gcagttgttg cgcgtagcgg cggcggatat cgccggtacg  240
ttacccgtca tgaaagtgag cgatcactta acctggctgg cggaagcgat tatcgatgcg  300
gtggtgcagc aagcctggaa ccagatggtg gcgcgttacg gccagccgac gcatctgcac  360
gatcgcgaag ggcgcggttt cgccgtggtc ggttacggca aacttggcgg ctgggaatta  420
ggttacagct ccgatctgga tctggtgttc ctgcacgact gccccatgga tgtgatgacc  480
gatggcgagc gtgaaatcga tggccgccag ttctatttgc gcctcgcgca gcgcgtgatg  540
cacctgttca gcacgcgcac gtcgtccggc attctttatg aagtcgatgc gcgtttgcgc  600
ccgtccggcg cggccggaat gctggtgacc actgcggaag cgttcgccga ttatcaaaaa  660
aatgaagcct ggacatggga gcatcaggcg ctggcgcgtg cgcgcgtggt gtacggcgat  720
ccgcaactga ccgccgaatt tgacgccatt cgccgcgata tcctgatgac ctcccgcgat  780
```

```
gccgctaccc tgcaaaccga agtgcgggaa atgcgtgaga aaatgcgcgc ccatcttggt  840
aacaagcaca aagaccgttt cgatctgaaa gccgatgaag gcggtatcac cgatattgag  900
tttatcgctc agtatctggt gctgcgcttt gcccatgaga agccgaaact gacgcgctgg  960
tcggataatg tgcgcatcct cgaagggctg gcgcaaaacg gcatcatgga tgagcaggaa  1020
gcgcaggcat tgacgctggc gtacaccacg ttgcgtgatg agctgcacca cctggcgctg  1080
caagagctgc caggacatgt ggcgctctcc tgttttgtcg ccgagcgtgc gcttatcaaa  1140
accagctggg acaagtggct ggtggaaccg tgcgccccgg cgtaa                 1185

SEQ ID NO: 100         moltype = DNA  length = 2085
FEATURE                Location/Qualifiers
misc_feature           1..2085
                       note = Synthetic polynucleotide
misc_feature           1..2085
                       note = glnE-delta-AR-2 with 500bp flank
source                 1..2085
                       mol_type = other DNA
                       organism = synthetic construct
SEQUENCE: 100
taaagcgagc gctcacttac gtgatctgtt gacgcagtcc gaagcgacca ttacttcagc  60
cgtttcagca gatacggcgg tgtggagtgc gcaatcagcc ctggcgaaac tggtgctcac  120
cgagtggtta gtgacgcagg gctggcgaac cttccttgat gaaaaagcgc aggctaagtt  180
tgccgactcc tttaaacgct ttgctgacgt tcatctgtca cgcagcgccg ccgagctgaa  240
aaaagccttt gcccagccgc tgggcgacag ctatcgcgac cagttaccgc ggctggcgcg  300
tgatatcgac agcgcgttat tgctggccgg acattacgat cgcgcgcgcg ccgtggagtg  360
gctggaaaac tggcaggggc ttcagcacgc tattgaaacg cgccagagag ttgaaatcga  420
acatttccgt aataccgcca ttacccagga gccgttctgg ttgcacagcg gaaaacgtta  480
acgaaaggat atttcgcatg tccctgtgcg ccgcgtcgcc gatggtggcc agccaactgg  540
cgcgctaccc gatcctgctc gatgaactgc tcgacccgaa cacgctctat caaccgacgg  600
cgatgaacgc ctatcgcgat gaactgcgac aatacctgtt gcgcgtgccg gaagaggatg  660
aagagcagca actggaggcg ctacggcagt ttaagcaggc gcagttgttg cgcgtagcgg  720
cggcggatat cgccggtacg ttacccgtca tgaaagtgag cgatcactta acctggctgg  780
cggaagcgat tatcgatgcg gtggtgcagc aagcctggaa ccagatggtg gcgcgttacg  840
gccagccgac gcatctgcac gatcgcgaag ggcgcggttt cgccgtggtc ggttacggca  900
aacttggcgg ctgggaatta ggttacagct ccgatctgga tctggtgttc ctgcacgact  960
gccccatgga tgtgatgacc gatggcgagc gtgaaatcga tggccgccag ttctatttgc  1020
gcctcgcgca gcgcgtgatg cacctgttca gcacgcgcac gtcgtccggc attctttatg  1080
aagtcgatgc gcgtttgcgc ccgtccggcg cggccggaat gctggtgacc actgcggaag  1140
cgttcgccga ttatcaaaaa aatgaagcct ggacatggga gcatcaggcg ctggcgcgtg  1200
cgcgcgtggt gtacggcgat ccgcaactga ccgccgaatt tgacgccatt cgccgcgata  1260
tcctgatgac ctcccgcgat gccgctaccc tgcaaaccga agtgcgggaa atgcgtgaga  1320
aaatgcgcgc ccatcttggt aacaagcaca aagaccgttt cgatctgaaa gccgatgaag  1380
gcggtatcac cgatattgag tttatcgctc agtatctggt gctgcgcttt gcccatgaga  1440
agccgaaact gacgcgctgg tcggataatg tgcgcatcct cgaagggctg gcgcaaaacg  1500
gcatcatgga tgagcaggaa gcgcaggcat tgacgctggc gtacaccacg ttgcgtgatg  1560
agctgcacca cctggcgctg caagagctgc caggacatgt ggcgctctcc tgttttgtcg  1620
ccgagcgtgc gcttatcaaa accagctggg acaagtggct ggtggaaccg tgcgccccgg  1680
cgtaagtgtg gtatcatcgc gcgcaaattt tgtatctctc aggagacagg aatgaaagtt  1740
acgctgccag agttcaatca agccggtgtc atggtggtgg gtgatgtgat gctggatcgc  1800
tactggtacg gcccaaccag ccgcatttct ccggaagcgc cagttccggt tgttaaagtc  1860
gatactattg aagagcgacc gggcggtgcg gcaaacgtgg cgatgaacat tgcctcgctg  1920
ggcgcaacgg cgcgtctggt tggcctgact ggcattgatg atgcggcgcg cgcgctgagc  1980
aaagcgctgg cggatgttaa tgttaaatgt gacttcgttt ctgttccgac tcaccccacc  2040
atcactaagc tgcgcgtgct gtcgcgtaac cagcaactga ttcgc                 2085

SEQ ID NO: 101         moltype = DNA  length = 461
FEATURE                Location/Qualifiers
misc_feature           1..461
                       note = Synthetic polynucleotide
misc_feature           1..461
                       note = delta-nifL::Prm1
source                 1..461
                       mol_type = other DNA
                       organism = synthetic construct
SEQUENCE: 101
atgaccctga atatgatgat ggatgccagc cgttctgtaa taataaccgg acaattcgga  60
ctgattaaaa aagcgccctc gcggcgcttt ttttatattc tcgactccat ttaaaataaa  120
aaatccaatc ggatttcact atttaaactg gccattatct aagatgaatc cgatggaagc  180
tcgctgtttt aacacgcgtt ttttaacctt ttattgaaag tcggtgcttc tttgagcgaa  240
cgatcaaatt taagtggatt cccatcaaaa aaatattctc aacctaaaaa agtttgtgta  300
atacttgtaa cgctacatgg agattaactc aatctagagg gtattaataa tgaatcgtac  360
taaactggta ctgggcgcaa ctcacttcac gccccgaagg gggaagctgc ctgaccctac  420
gattcccgct atttcattca ctgaccggag gttcaaaatg a                     461

SEQ ID NO: 102         moltype = DNA  length = 1461
FEATURE                Location/Qualifiers
misc_feature           1..1461
                       note = Synthetic polynucleotide
misc_feature           1..1461
                       note = delta-nifL::Prm1 with 500bp flank
```

```
source                  1..1461
                        mol_type = other DNA
                        organism = synthetic construct
SEQUENCE: 102
accggataag agagaaaagt gtcgacgtcg gtccggttga tattgaccgg cgcatccgcc  60
agctcgccca gtttttggtg gatctgtttg gcgattttgc gggtcttgcc ggtgtcggtg  120
ccgaaaaaaa taccaatatt tgccataaca cacgctcctg ttgaaaaaga gatcccgcgg  180
ggaaaatgcg gtgaacatgt cagctattgc gaagagtgtg ccagttttgc tcacgggcaa  240
aagctgcacc agaatgggta ttaatgcacc agcctggcgc ttttttttcgc ggcacgtccc  300
ctcgctaatg cccgtctggc gcggctttga cgctgataag gcgctgaata ccgatctgga  360
tcaaggtttt gtcgggttat cgtccaaaag gtgcactctt tgcatggtta taagtgcctg  420
acatggtgtc cgggcgaacg tcgccaggtg gcacaaattg tcagaactac gacacgacta  480
accgaccgca ggagtgtgcg atgaccctga atatgatgat ggatgccagc cgttctgtaa  540
taataaccgg acaattcgga ctgattaaaa aagcgccctc gcggcgcttt ttttatattc  600
tcgactccat ttaaaataaa aaatccaatc ggatttcact atttaaactg gccattatct  660
aagatgaatc cgatggaagc tcgctgtttt aacacgcgtt ttttaacctt ttattgaaag  720
tcggtgcttc tttgagcgaa cgatcaaatt taagtggatt cccatcaaaa aaatattctc  780
aacctaaaaa agtttgtgta atacttgtaa cgctacatgg agattaactc aatctagagg  840
gtattaataa tgaatcgtac taaactggta ctgggcgcaa ctcacttcac gccccgaagg  900
gggaagctgc ctgaccctac gattcccgct atttcattca ctgaccggag gttcaaaatg  960
acccagcgaa ccgagtcggg taataccgtc tggcgcttcg atttatccca gcagttcacc  1020
gcgatgcagc ggataagcgt ggttctcagc cgggcgaccg aggttgaaca gacactccag  1080
caggtgctgt gcgtattgca caatgacgcc tttttgcagc acggcatgat ctgtctgtac  1140
gacagccagc aggcgatttt gactattgaa gcgttgcagg aagccgatca gcagttgatc  1200
cccggcagct cgcaaattcg ctaccgtccg ggtgaagggc tggtcgggac ggtgctttcg  1260
caggggcaat cgttagtgct ggcgcgtgtg gctgacgatc agcgctttct tgaccgcctg  1320
ggactgtatg attacaacct gccgtttatc gccgtgccgc tgatagggcc ggatgcgcag  1380
acttttggcg tgctgacggc gcaaccgatg gcgcgttacg aagagcggtt acccgcctgc  1440
acccgctttc tggaaacggt c                                             1461

SEQ ID NO: 103          moltype = DNA  length = 1185
FEATURE                 Location/Qualifiers
misc_feature            1..1185
                        note = Synthetic polynucleotide
misc_feature            1..1185
                        note = glnE-delta-AR-2
source                  1..1185
                        mol_type = other DNA
                        organism = synthetic construct
SEQUENCE: 103
tccctgtgcg ccgcgtcgcc gatggtggcc agccaactgg cgcgctaccc gatcctgctc  60
gatgaactgc tcgacccgaa cacgctctat caaccgacgg cgatgaacgc ctatcgcgat  120
gaactgcgac aatacctgtt gcgcgtgccg gaagaggatg aagagcagca actggaggcg  180
ctacggcagt ttaagcaggc gcagttgttg cgcgtagcgg cggcggatat cgccggtacg  240
ttacccgtca tgaaagtgag cgatcactta acctggctgg cggaagcgat tatcgatgcg  300
gtggtgcagc aagcctggaa ccagatggtg gcgcgttacg gccagccgac gcatctgcac  360
gatcgcgaag ggcgcggttt cgccgtggtc ggttacggca aacttggcgg ctgggaatta  420
ggttacagct ccgatctgga tctggtgttc ctgcacgact gccccatgga tgtgatgacc  480
gatggcgagc gtgaaatcga tggccgccag ttctatttgc gcctcgcgca gcgcgtgatg  540
cacctgttca gcacgcgcac gtcgtccggc attctttatg aagtcgatgc gcgtttgcgc  600
ccgtccggcg cggccggaat gctggtgacc actgcggaag cgttcgccga ttatcaaaaa  660
aatgaagcct ggacatggga gcatcaggcg ctggcgcgtg cgcgcgtggt gtacggcgat  720
ccgcaactga ccgccgaatt tgacgccatt cgccgcgata tcctgatgac ctcccgcgat  780
gccgctaccc tgcaaaccga agtgcgggaa atgcgtgaga aaatgcgcgc ccatcttggt  840
aacaagcaca aagaccgttt cgatctgaaa gccgatgaag gcggtatcac cgatattgag  900
tttatcgctc agtatctggt gctgcgcttt gcccatgaga agccgaaact gacgcgctgg  960
tcggataatg tgcgcatcct cgaagggctg gcgcaaaacg gcatcatgga tgagcaggaa  1020
gcgcaggcat tgacgctggc gtacaccacg ttgcgtgatg agctgcacca cctggcgctg  1080
caagagctgc caggacatgt ggcgctctcc tgttttgtcg ccgagcgtgc gcttatcaaa  1140
accagctggg acaagtggct ggtggaaccg tgcgccccgg cgtaa                    1185

SEQ ID NO: 104          moltype = DNA  length = 2085
FEATURE                 Location/Qualifiers
misc_feature            1..2085
                        note = Synthetic polynucleotide
misc_feature            1..2085
                        note = glnE-delta-AR-2 with 500bp flank
source                  1..2085
                        mol_type = other DNA
                        organism = synthetic construct
SEQUENCE: 104
taaagcgagc gctcacttac gtgatctgtt gacgcagtcc gaagcgacca ttacttcagc  60
cgtttcagca gatacggcgg tgtggagtgc gcaatcagcc ctggcgaaac tggtgctcac  120
cgagtggtta gtgacgcagg gctggcgaac cttccttgat gaaaaagcgc aggctaagtt  180
tgccgactcc tttaaacgct ttgctgacgt tcatctgtca cgcagcgccg ccgagctgaa  240
aaaagccttt gcccagccgc tgggcgacag ctatcgcgac cagttaccgc ggctggcgcg  300
tgatatcgac agcgcgttat tgctggccgg acattacgat cgcgcgcgcg ccgtggagtg  360
gctggaaaac tggcaggggc ttcagcacgc tattgaaacg cgccagagag ttgaaatcga  420
acatttccgt aataccgcca ttacccagga gccgttctgg ttgcacagcg gaaaacgtta  480
```

```
acgaaaggat atttcgcatg tccctgtgcg ccgcgtcgcc gatggtggcc agccaactgg  540
cgcgctaccc gatcctgctc gatgaactgc tcgacccgaa cacgctctat caaccgacgg  600
cgatgaacgc ctatcgcgat gaactgcgac aatacctgtt gcgcgtgccg gaagaggatg  660
aagagcagca actggaggcg ctacggcagt ttaagcaggc gcagttgttg cgcgtagcgg  720
cggcggatat cgccggtacg ttacccgtca tgaaagtgag cgatcactta acctggctgg  780
cggaagcgat tatcgatgcg gtggtgcagc aagcctggaa ccagatggtg gcgcgttacg  840
gccagccgac gcatctgcac gatcgcgaag ggcgcggttt cgccgtggtc ggttacggca  900
aacttggcgg ctgggaatta ggttacagct ccgatctgga tctggtgttc ctgcacgact  960
gccccatgga tgtgatgacc gatggcgagc gtgaaatcga tggccgccag ttctatttgc  1020
gcctcgcgca gcgcgtgatg cacctgttca gcacgcgcac gtcgtccggc attctttatg  1080
aagtcgatgc gcgtttgcgc ccgtccggcg cggccggaat gctggtgacc actgcggaag  1140
cgttcgccga ttatcaaaaa aatgaagcct ggacatggga gcatcaggcg ctggcgcgtg  1200
cgcgcgtggt gtacggcgat ccgcaactga ccgccgaatt tgacgccatt cgccgcgata  1260
tcctgatgac ctcccgcgat gccgctaccc tgcaaaccga agtgcgggaa atgcgtgaga  1320
aaatgcgcgc ccatcttggt aacaagcaca aagaccgttt cgatctgaaa gccgatgaag  1380
gcggtatcac cgatattgag tttatcgctc agtatctggt gctgcgcttt gcccatgaga  1440
agccgaaact gacgcgctgg tcggataatg tgcgcatcct cgaagggctg gcgcaaaacg  1500
gcatcatgga tgagcaggaa gcgcaggcat tgacgctggc gtacaccacg ttgcgtgatg  1560
agctgcacca cctggcgctg caagagctgc caggacatgt ggcgctctcc tgttttgtcg  1620
ccgagcgtgc gcttatcaaa accagctggg acaagtggct ggtggaaccg tgcgccccgg  1680
cgtaagtgtg gtatcatcgc gcgcaaattt tgtatctctc aggagacagg aatgaaagtt  1740
acgctgccag agttcaatca agccggtgtc atggtggtgg gtgatgtgat gctggatcgc  1800
tactggtacg gcccaaccag ccgcatttct ccggaagcgc cagttccggt tgttaaagtc  1860
gatactattg aagagcgacc gggcggtgcg gcaaacgtgg cgatgaacat tgcctcgctg  1920
ggcgcaacgg cgcgtctggt tggcctgact ggcattgatg atgcggcgcg cgcgctgagc  1980
aaagcgctgg cggatgttaa tgttaaatgt gacttcgttt ctgttccgac tcaccccacc  2040
atcactaagc tgcgcgtgct gtcgcgtaac cagcaactga ttcgc                  2085
```

```
SEQ ID NO: 105         moltype = DNA  length = 452
FEATURE                Location/Qualifiers
misc_feature           1..452
                       note = Synthetic polynucleotide
misc_feature           1..452
                       note = delta-nifL::Prm7
source                 1..452
                       mol_type = other DNA
                       organism = synthetic construct
SEQUENCE: 105
atgaccctga atatgatgat ggatgccagc cgcgtcaggt tgaacgtaaa aaagtcggtc  60
tgcgcaaagc acgtcgtcgt ccgcagttct ccaaacgtta attggtttct gcttcggcag  120
aacgattggc gaaaaaaccc ggtgcgaacc gggttttttt atggataaag atcgtgttat  180
ccacagcaat ccattgatta tctcttcttt ttcagcattt ccagaatccc ctcaccacaa  240
agcccgcaaa atctggtaaa ctatcatcca attttctgcc caaatggctg ggattgttca  300
tttttgttt gccttacaac gagagtgaca gtacgcgcgg gtagttaact caacatctga  360
ccggtcgata actcacttca cgccccgaag gggaagctg cctgacccta cgattcccgc  420
tatttcattc actgaccgga ggttcaaaat ga                                452
```

```
SEQ ID NO: 106         moltype = DNA  length = 1451
FEATURE                Location/Qualifiers
misc_feature           1..1451
                       note = Synthetic polynucleotide
misc_feature           1..1451
                       note = delta-nifL::Prm7 with 500bp flank
source                 1..1451
                       mol_type = other DNA
                       organism = synthetic construct
SEQUENCE: 106
accggataag agagaaaagt gtcgacgtcg gtccggttga tattgaccgg cgcatccgcc  60
agctcgccca gtttttggtg gatctgtttg gcgattttgc gggtcttgcc ggtgtcggtg  120
ccgaaaaaaa taccaatatt tgccataaca cacgctcctg ttgaaaaaga gatcccgcgg  180
ggaaaatgcg gtgaacatgt cagctattgc gaagagtgtg ccagttttgc tcacgggcaa  240
aagctgcacc agaatgggta ttaatgcacc agcctggcgc tttttttcgc ggcacgtccc  300
ctcgctaatg cccgtctggc gcggctttga cgctgataag gcgctgaata ccgatctgga  360
tcaaggtttt gtcgggttat cgtccaaaag gtgcactctt tgcatggtta taagtgcctg  420
acatggtgtc cgggcgaacg tcgccaggtg gcacaaattg tcagaactac gacacgacta  480
accgaccgca ggagtgtgcg atgaccctga atatgatgat ggatgccagc cgcgtcaggt  540
tgaacgtaaa aaagtcggtc tgcgcaaagc acgtcgtcgt ccgcagttct ccaaacgtta  600
attggtttct gcttcggcag aacgattggc gaaaaaaccc ggtgcgaacc gggttttttt  660
atggataaag atcgtgttat ccacagcaat ccattgatta tctcttcttt ttcagcattt  720
ccagaatccc ctcaccacaa agcccgcaaa atctggtaaa ctatcatcca attttctgcc  780
caaatggctg ggattgttca tttttgttt gccttacaac gagagtgaca gtacgcgcgg  840
gtagttaact caacatctga ccggtcgata actcacttca cgccccgaag gggaagctg  900
cctgacccta cgattcccgc tatttcattc actgaccgga ggttcaaaat gacccagcga  960
accgagtcgg gtaataccgt ctggcgcttc gatttatccc agcagttcac cgcgatgcag  1020
cggataagcg tggttctcag ccgggcgacc gaggttgaac agacactcca gcaggtgctg  1080
tgcgtattgc acaatgacgc ctttttgcag cacggcatga tctgtctgta cgacagccag  1140
caggcgattt tgactattga agcgttgcag gaagccgatc agcagttgat ccccggcagc  1200
tcgcaaattc gctaccgtcc gggtgaaggg ctggtcggga cggtgcttte gcaggggcaa  1260
tcgttagtgc tggcgcgtgt ggctgacgat cagcgctttc ttgaccgcct gggactgtat  1320
```

```
gattacaacc tgccgtttat cgccgtgccg ctgatagggc cggatgcgca gacttttggc  1380
gtgctgacgg cgcaaccgat ggcgcgttac gaagagcggt tacccgcctg cacccgcttt  1440
ctggaaacgg t                                                      1451

SEQ ID NO: 107         moltype = DNA  length = 1191
FEATURE                Location/Qualifiers
misc_feature           1..1191
                       note = Synthetic polynucleotide
misc_feature           1..1191
                       note = glnE-delta-AR-2
source                 1..1191
                       mol_type = other DNA
                       organism = synthetic construct
SEQUENCE: 107
atggcgctga agcacctgat cacgctctgc gcggcgtcgc cgatggtcgc cagccagctg  60
gcgcgccacc cgctgctgct ggatgagctg ctggatccca acaccctcta tcagccgacg  120
gcgaccgatg cctatcgcga cgagctgcgc cagtacctgc tgcgcgtgcc ggaagaggat  180
gaagagcagc agctggaggc gttgcgccag tttaagcagg cgcagcagct gcatatcgcg  240
gcggcggata tcgctggtac cctgccggtg atgaaggtca gcgatcactt aacctggctt  300
gccgaagcga tcctcgacgc ggtggtgcag caggcatggg ggcagatggt cgctcgctac  360
ggccagccga cccacctgca cgatcgccag ggtcgcggct tcgccgtcgt cggctacggt  420
aagcttggcg gctgggagct gggctacagc tccgatctcg atctggtgtt cctccatgac  480
tgcccggcgg aggtgatgac cgacggcgag cgggagattg acggccgtca gttctacctg  540
cggctggccc agcggatcat gcacctgttc agcacccgca cctcgtccgg tattctctac  600
gaagtggacg cccggctgcg tccttctggc gcggcgggga tgctggtcac caccgccgac  660
gcgtttgctg actatcagca gaacgaagcc tggacgtggg aacatcaggc gctggtgcgc  720
gcccgcgtgg tctatggcga cccggcgctg caggcgcgct ttgacgccat tcgtcgcgat  780
atcctgacca ccccgcggga ggggatgacc ctgcagaccg aggttcgcga gatgcgcgag  840
aagatgcgcg cccaccttgg caacaaacat cccgatcgtt ttgatatcaa agccgatgcc  900
ggcgggatca ccgatattga atttattact cagtatctgg tcctacgcta tgccagtgac  960
aagccgaagc tgacccgctg gtctgacaac gtgcgtattc ttgagctgct ggcgcagaac  1020
gacatcatgg acgaggagga ggcgcgcgcc ttaacgcatg cgtacaccac cttgcgtgat  1080
gcgctccatc acctggccct gcaggagcag ccgggacacg tggcgccaga ggccttcagc  1140
cgggagcgtc agcaggtcag cgccagctgg cagaagtggc tgatggctta a           1191

SEQ ID NO: 108         moltype = DNA  length = 2191
FEATURE                Location/Qualifiers
misc_feature           1..2191
                       note = Synthetic polynucleotide
misc_feature           1..2191
                       note = glnE-delta-AR-2 with 500bp flank
source                 1..2191
                       mol_type = other DNA
                       organism = synthetic construct
SEQUENCE: 108
cgtaaggcga ccacccagct ccgcgcgttg ctgaacgacg ctgaagccgt tctgctggcc  60
gcggacaccg ccgacgaggc gttattccgc accgaggtcg tcggcgccaa actggccctg  120
actgaatggc tggtccagcg cggctggcgt ccgttcctca acgaggcagg agagaaaaaa  180
atagccggat cgttcaaacg gtttgccgat attaacctct cgcgggtggc ggccgagctg  240
cgcagcgccg tgcagcatct ggcggttgaa gatgccgccg accagttgcc gaagctgtcc  300
cgcgacatcg acagcgtcca gctgctggcg ggcgcctatg gcgacgccgt cgcgccgtgg  360
ctggagaact ggcaggagct tcaccgtgca atagcacatg acgatcgcag cgtctttgaa  420
tatttccgtc gccaggcgct ggctgccgag ccgttctggc tgcatagtgg aaaacgataa  480
tttcaggcca gggagccctt atggcgctga agcacctgat cacgctctgc gcggcgtcgc  540
cgatggtcgc cagccagctg gcgcgccacc cgctgctgct ggatgagctg ctggatccca  600
acaccctcta tcagccgacg gcgaccgatg cctatcgcga cgagctgcgc cagtacctgc  660
tgcgcgtgcc ggaagaggat gaagagcagc agctggaggc gttgcgccag tttaagcagg  720
cgcagcagct gcatatcgcg gcggcggata tcgctggtac cctgccggtg atgaaggtca  780
gcgatcactt aacctggctt gccgaagcga tcctcgacgc ggtggtgcag caggcatggg  840
ggcagatggt cgctcgctac ggccagccga cccacctgca cgatcgccag ggtcgcggct  900
tcgccgtcgt cggctacggt aagcttggcg gctgggagct gggctacagc tccgatctcg  960
atctggtgtt cctccatgac tgcccggcgg aggtgatgac cgacggcgag cgggagattg  1020
acggccgtca gttctacctg cggctggccc agcggatcat gcacctgttc agcacccgca  1080
cctcgtccgg tattctctac gaagtggacg cccggctgcg tccttctggc gcggcgggga  1140
tgctggtcac caccgccgac gcgtttgctg actatcagca gaacgaagcc tggacgtggg  1200
aacatcaggc gctggtgcgc gcccgcgtgg tctatggcga cccggcgctg caggcgcgct  1260
ttgacgccat tcgtcgcgat atcctgacca ccccgcggga ggggatgacc ctgcagaccg  1320
aggttcgcga gatgcgcgag aagatgcgcg cccaccttgg caacaaacat cccgatcgtt  1380
ttgatatcaa agccgatgcc ggcgggatca ccgatattga atttattact cagtatctgg  1440
tcctacgcta tgccagtgac aagccgaagc tgacccgctg gtctgacaac gtgcgtattc  1500
ttgagctgct ggcgcagaac gacatcatgg acgaggagga ggcgcgcgcc ttaacgcatg  1560
cgtacaccac cttgcgtgat gcgctccatc acctggccct gcaggagcag ccgggacacg  1620
tggcgccaga ggccttcagc cgggagcgtc agcaggtcag cgccagctgg cagaagtggc  1680
tgatggctta actataaaat cgggtgtgct attatcgcgc gcaaagtttg cgtctcgcag  1740
gagagagtca tgaaagtaac gctgccggag tttgaacgtg caggagtgtt ggtggtgggt  1800
gatgtgatgc tggaccgcta ctggtacggc cccaccagtc gtatttcccc ggaagccccg  1860
gtgccggtgg tgaaggtgga aaatatcgaa gaacgtcctg gcggcgcggc aaacgtagcg  1920
atgaacatcg cctccctggg ggcaacgtcg cgcctggtgg gattgaccgg gattgatgac  1980
gctgcccgcg cgctgagcca ggcgctggcc aatgtgaatg tgaagtgcga cttcgtctcc  2040
```

```
gtcccgactc acccgaccat caccaagctg cgggtgctgt cgcgcaatca gcagctgatc  2100
cgcctcgact ttgaagaggg cttctccggc gtggatccgc agccgatgca tgagcgcatt  2160
cagcaggcgc tgggagccat tggcgcactg g                                 2191

SEQ ID NO: 109         moltype = DNA  length = 613
FEATURE                Location/Qualifiers
misc_feature           1..613
                       note = Synthetic polynucleotide
misc_feature           1..613
                       note = delta-nifL::PinfC
source                 1..613
                       mol_type = other DNA
                       organism = synthetic construct
SEQUENCE: 109
atgaccctga atatgatgct agaagcgtca ggtaccggtc atgattcacc gtgcgattct  60
cggttccctg gagcgcttca ttggcatcct gaccgaagag ttcgctggct tcttcccaac  120
ctggattgca ccagtgcagg tagtggtcat gaatattacc gattctcagg ctgaatacgt  180
taacgaattg acgcgtaaac tacaaaatgc gggcattcgt gtaaaagcag acttgagaaa  240
tgagaagatt ggctttaaaa tccgcgagca cactttacgt cgtgtcccgt atatgttggt  300
ctgtggcgac aaagaagtcg aagccggcaa agtggccgtg cgcacccgtc gcgggaaaga  360
cctcggcagc atggacgtaa gtgaagtgat tgagaagctg caacaagaga ttcgcagccg  420
cagtcttcaa caactggagg aataaggtat taaaggcgga aaacgagttc aaacggcacg  480
tccgaatcgt atcaatggcg agattcgcgc cctggaagtt cgcgccattg agctggcttc  540
ccgaccgcag ggcggcacct gcctgaccct gcgtttcccg ctgtttaaca ccctgaccgg  600
aggtgaagca tga                                                     613

SEQ ID NO: 110         moltype = DNA  length = 1613
FEATURE                Location/Qualifiers
misc_feature           1..1613
                       note = Synthetic polynucleotide
misc_feature           1..1613
                       note = delta-nifL::PinfC with 500bp flank
source                 1..1613
                       mol_type = other DNA
                       organism = synthetic construct
SEQUENCE: 110
ggccgtcgcc cagcgtcggc gtccccaaca gcagggccgg gtaggccagc aggtccgcca  60
gcgtggcgcg gttaatattg accggggcgg cggcggcctc ccccagctgc ttgtggatca  120
ttttcgcgat cttgcgggtt ttaccggtat cggtaccaaa gaaaatgcca atgttcgcca  180
tagtacgctc ctgtcggaat ggtgttgaaa aaaggaatga cgacagaggt attgcgaagg  240
ctgtgccagg ttgccctgca ccgcgacggc ccatccctgc cccatcagga tcgcttcgca  300
tcacgatgcc gcgcgccaaa ggcgcacccg gcggggcgaa aggtaaaaat ccgtgaattt  360
tccccctgtc ggatcaatgt ttcgcgtggt cgttccgata agggcgcaca ctttgcatgg  420
ttatccgggt tcggcttacc ccgccgcgtt ttgcgcacgg tgtcggacaa tttgtcataa  480
ctgcgacaca ggagtttgcg atgaccctga atatgatgct agaagcgtca ggtaccggtc  540
atgattcacc gtgcgattct cggttccctg gagcgcttca ttggcatcct gaccgaagag  600
ttcgctggct tcttcccaac ctggattgca ccagtgcagg tagtggtcat gaatattacc  660
gattctcagg ctgaatacgt taacgaattg acgcgtaaac tacaaaatgc gggcattcgt  720
gtaaaagcag acttgagaaa tgagaagatt ggctttaaaa tccgcgagca cactttacgt  780
cgtgtcccgt atatgttggt ctgtggcgac aaagaagtcg aagccggcaa agtggccgtg  840
cgcacccgtc gcgggaaaga cctcggcagc atggacgtaa gtgaagtgat tgagaagctg  900
caacaagaga ttcgcagccg cagtcttcaa caactggagg aataaggtat taaaggcgga  960
aaacgagttc aaacggcacg tccgaatcgt atcaatggcg agattcgcgc cctggaagtt  1020
cgcgccattg agctggcttc ccgaccgcag ggcggcacct gcctgaccct gcgtttcccg  1080
ctgtttaaca ccctgaccgg aggtgaagca tgatccctga atccgacccg gacaccaccg  1140
tcagacgctt cgacctctct cagcagttca ccgccatgca gcggataagc gtggtgctga  1200
gccgggccac cgaggccagc aaaacgctgc aggaggtgct cagcgtatta cacaacgatg  1260
cctttatgca gcacgggatg atctgcctgt acgacagcga gcaggagatc ctcagtatcg  1320
aagcgctgca gcaaaccggc cagcagcccc tccccggcag cacgcagatc cgctatcgcc  1380
ccggcgaggg actggtgggg accgtgctgg cccaggggca gtcgctggtg ctgccccggg  1440
tcgccgacga tcagcgtttt ctcgaccgcc tgagcctcta cgattacgat ctgccgttta  1500
tcgccgtacc gttgatgggg cccaacgccc ggccaatagg ggtgctggcg gcccagccga  1560
tggcgcgcca ggaagagcgg ctgccggcct gcacccgttt tctcgaaacc gtc         1613

SEQ ID NO: 111         moltype = DNA  length = 1155
FEATURE                Location/Qualifiers
misc_feature           1..1155
                       note = Synthetic polynucleotide
misc_feature           1..1155
                       note = glnE-delta-AR-2 36bp deletion
source                 1..1155
                       mol_type = other DNA
                       organism = synthetic construct
SEQUENCE: 111
atggcgctga agcacctgat cacgctctgc gcggcgtcgc cgatggtcgc cagccagctg  60
gcgcgccacc cgctgctgct ggatgagctg ctggatccca acaccctcta tcagccgacg  120
gcgaccgatg cctatcgcga cgagctgcgc cagtacctgc tgcgcgtgcc ggaagaggat  180
gaagagcagc agctgcatat cgcggcggcg gatatcgctg gtaccctgcc ggtgatgaag  240
gtcagcgatc acttaacctg gcttgccgaa gcgatcctcg acgcggtggt gcagcaggca  300
```

```
tgggggcaga tggtcgctcg ctacggccag ccgacccacc tgcacgatcg ccagggtcgc  360
ggcttcgccg tcgtcggcta cggtaagctt ggcggctggg agctgggcta cagctccgat  420
ctcgatctgg tgttcctcca tgactgcccg gcggaggtga tgaccgacgg cgagcgggag  480
attgacggcc gtcagttcta cctgcggctg gcccagcgga tcatgcacct gttcagcacc  540
cgcacctcgt ccggtattct ctacgaagtg gacgcccggc tgcgtccttc tggcgcggcg  600
gggatgctgg tcaccaccgc cgacgcgttt gctgactatc agcagaacga agcctggacg  660
tgggaacatc aggcgctggt gcgcgcccgc gtggtctatg gcgacccggc gctgcaggcg  720
cgctttgacg ccattcgtcg cgatatcctg accaccccgc gggaggggat gaccctgcag  780
accgaggttc gcgagatgcg cgagaagatg cgcgcccacc ttggcaacaa acatcccgat  840
cgttttgata tcaaagccga tgccggcggg atcaccgata ttgaatttat tactcagtat  900
ctggtcctac gctatgccag tgacaagccg aagctgaccc gctggtctga caacgtgcgt  960
attcttgagc tgctggcgca gaacgacatc atggacgagg aggaggcgcg cgccttaacg  1020
catgcgtaca ccaccttgcg tgatgcgctc catcacctgg ccctgcagga gcagccggga  1080
cacgtggcgc cagaggcctt cagccgggag cgtcagcagg tcagcgccag ctggcagaag  1140
tggctgatgg cttaa                                                 1155

SEQ ID NO: 112          moltype = DNA  length = 2155
FEATURE                 Location/Qualifiers
misc_feature            1..2155
                        note = Synthetic polynucleotide
misc_feature            1..2155
                        note = glnE-delta-AR-2 36bp deletion
source                  1..2155
                        mol_type = other DNA
                        organism = synthetic construct
SEQUENCE: 112
cgtaaggcga ccacccagct ccgcgcgttg ctgaacgacg ctgaagccgt tctgctggcc  60
gcggacaccg ccgacgaggc gttattccgc accgaggtcg tcggcgccaa actggccctg  120
actgaatggc tggtccagcg cggctggcgt ccgttcctca acgaggcagg agagaaaaaa  180
atagccggat cgttcaaacg gtttgccgat attaacctct cgcgggtggc ggccgagctg  240
cgcagcgccg tgcagcatct ggcggttgaa gatgccgccg accagttgcc gaagctgtcc  300
cgcgacatcg acagcgtcca gctgctggcg ggcgcctatg gcgacgccgt cgcgccgtgg  360
ctggagaact ggcaggagct tcaccgtgca atagcacatg acgatcgcag cgtctttgaa  420
tatttccgtc gccaggcgct ggctgccgag ccgttctggc tgcatagtgg aaaacgataa  480
tttcaggcca gggagccctt atggcgctga agcacctgat cacgctctgc gcggcgtcgc  540
cgatggtcgc cagccagctg gcgcgccacc cgctgctgct ggatgagctg ctggatccca  600
acaccctcta tcagccgacg gcgaccgatg cctatcgcga cgagctgcgc cagtacctgc  660
tgcgcgtgcc ggaagaggat gaagagcagc agctgcatat cgcggcggcg gatatcgctg  720
gtaccctgcc ggtgatgaag gtcagcgatc acttaacctg gcttgccgaa gcgatcctcg  780
acgcggtggt gcagcaggca tgggggcaga tggtcgctcg ctacggccag ccgacccacc  840
tgcacgatcg ccagggtcgc ggcttcgccg tcgtcggcta cggtaagctt ggcggctggg  900
agctgggcta cagctccgat ctcgatctgg tgttcctcca tgactgcccg gcggaggtga  960
tgaccgacgg cgagcgggag attgacggcc gtcagttcta cctgcggctg gcccagcgga  1020
tcatgcacct gttcagcacc cgcacctcgt ccggtattct ctacgaagtg gacgcccggc  1080
tgcgtccttc tggcgcggcg gggatgctgg tcaccaccgc cgacgcgttt gctgactatc  1140
agcagaacga agcctggacg tgggaacatc aggcgctggt gcgcgcccgc gtggtctatg  1200
gcgacccggc gctgcaggcg cgctttgacg ccattcgtcg cgatatcctg accaccccgc  1260
gggaggggat gaccctgcag accgaggttc gcgagatgcg cgagaagatg cgcgcccacc  1320
ttggcaacaa acatcccgat cgttttgata tcaaagccga tgccggcggg atcaccgata  1380
ttgaatttat tactcagtat ctggtcctac gctatgccag tgacaagccg aagctgaccc  1440
gctggtctga caacgtgcgt attcttgagc tgctggcgca gaacgacatc atggacgagg  1500
aggaggcgcg cgccttaacg catgcgtaca ccaccttgcg tgatgcgctc catcacctgg  1560
ccctgcagga gcagccggga cacgtggcgc cagaggcctt cagccgggag cgtcagcagg  1620
tcagcgccag ctggcagaag tggctgatgg cttaactata aaatcgggtg tgctattatc  1680
gcgcgcaaag tttgcgtctc gcaggagaga gtcatgaaag taacgctgcc ggagtttgaa  1740
cgtgcaggag tgttggtggt gggtgatgtg atgctggacc gctactggta cggcccccacc  1800
agtcgtattt ccccggaagc cccggtgccg gtggtgaagg tggaaaatat cgaagaacgt  1860
cctggcggcg cggcaaacgt agcgatgaac atcgcctccc tgggggcaac gtcgcgcctg  1920
gtgggattga ccgggattga tgacgctgcc cgcgcgctga gccaggcgct ggccaatgtg  1980
aatgtgaagt gcgacttcgt ctccgtcccg actcacccga ccatcaccaa gctgcgggtg  2040
ctgtcgcgca atcagcagct gatccgcctc gactttgaag agggcttctc cggcgtggat  2100
ccgcagccga tgcatgagcg cattcagcag gcgctgggag ccattggcgc actgg       2155

SEQ ID NO: 113          moltype = DNA  length = 412
FEATURE                 Location/Qualifiers
misc_feature            1..412
                        note = Synthetic polynucleotide
misc_feature            1..412
                        note = delta-nifL::Prm8.2
source                  1..412
                        mol_type = other DNA
                        organism = synthetic construct
SEQUENCE: 113
atgaccctga atatgatgct cgacgccgtc ctcgcagtac cattgcaacc gactttacag  60
caagaagtga ttctggcacg catggaacaa attcttgcca gtcgggcttt atccgatgac  120
gaacgcgcac agcttttata tgagcgcgga gtgttgtatg atagtctcgg tctgagggca  180
ttagcgcgaa atgatttttc acaagcgctg gcaatccgac ccgatatgcc tgaagtattc  240
aattacttag gcatttactt aacgcaggca ggcaattttg atgctgccta tgaagcgttt  300
gattctgtac ttgagcttga tcgccattga gctggcttcc cgaccgcagg gcggcacctg  360
```

```
cctgaccctg cgtttcccgc tgtttaacac cctgaccgga ggtgaagcat ga         412

SEQ ID NO: 114         moltype = DNA  length = 1389
FEATURE                Location/Qualifiers
misc_feature           1..1389
                       note = Synthetic polynucleotide
misc_feature           1..1389
                       note = delta-nifL::Prm8.2 with 500bp flank
source                 1..1389
                       mol_type = other DNA
                       organism = synthetic construct
SEQUENCE: 114
cccaacagca gggccgggta ggccagcagg tccgccagcg tggcgcggtt aatattgacc  60
ggggcggcgg cggcctcccc cagctgcttg tggatcattt tcgcgatctt gcgggtttta  120
ccggtatcgg taccaaagaa aatgccaatg ttcgccatag tacgctcctg tcggaatggt  180
gttgaaaaaa ggaatgacga cagaggtatt gcgaaggctg tgccaggttg ccctgcaccg  240
cgacggccca tccctgcccc atcaggatcg cttcgcatca cgatgccgcg cgccaaaggc  300
gcacccggcg gggcgaaagg taaaaatccg tgaattttcc ccctgtcgga tcaatgtttc  360
gcgtggtcgt tccgataagg gcgcacactt tgcatggtta tccgggttcg gcttaccccg  420
ccgcgttttg cgcacggtgt cggacaattt gtcataactg cgacacagga gtttgcgatg  480
accctgaata tgatgctcga cgccgtcctc gcagtaccat tgcaaccgac tttacagcaa  540
gaagtgattc tggcacgcat ggaacaaatt cttgccagtc gggctttatc cgatgacgaa  600
cgcgcacagc ttttatatga gcgcggagtg ttgtatgata gtctcggtct gagggcatta  660
gcgcgaaatg atttttcaca agcgctggca atccgacccg atatgcctga agtattcaat  720
tacttaggca tttacttaac gcaggcaggc aattttgatg ctgcctatga agcgtttgat  780
tctgtacttg agcttgatcg ccattgagct ggcttcccga ccgcagggcg gcacctgcct  840
gaccctgcgt ttcccgctgt ttaacaccct gaccggaggt gaagcatgat ccctgaatcc  900
gacccggaca ccaccgtcag acgcttcgac ctctctcagc agttcaccgc catgcagcgg  960
ataagcgtgg tgctgagccg ggccaccgag gccagcaaaa cgctgcagga ggtgctcagc  1020
gtattacaca acgatgcctt tatgcagcac gggatgatct gcctgtacga cagcgagcag  1080
gagatcctca gtatcgaagc gctgcagcaa accggccagc agcccctccc cggcagcacg  1140
cagatccgct atcgccccgg cgagggactg gtggggaccg tgctggccca ggggcagtcg  1200
ctggtgctgc cccgggtcgc cgacgatcag cgttttctcg accgcctgag cctctacgat  1260
tacgatctgc cgtttatcgc cgtaccgttg atggggccca acgcccggcc aataggggtg  1320
ctggcggccc agccgatggc gcgccaggaa gagcggctgc cggcctgcac ccgttttctc  1380
gaaaccgtc                                                         1389

SEQ ID NO: 115         moltype = DNA  length = 1155
FEATURE                Location/Qualifiers
misc_feature           1..1155
                       note = Synthetic polynucleotide
misc_feature           1..1155
                       note = glnE-delta-AR-2 36bp deletion
source                 1..1155
                       mol_type = other DNA
                       organism = synthetic construct
SEQUENCE: 115
atggcgctga agcacctgat cacgctctgc gcggcgtcgc cgatggtcgc cagccagctg  60
gcgcgccacc cgctgctgct ggatgagctg ctggatccca acaccctcta tcagccgacg  120
gcgaccgatg cctatcgcga cgagctgcgc cagtacctgc tgcgcgtgcc ggaagaggat  180
gaagagcagc agctgcatat cgcggcggcg gatatcgctg gtaccctgcc ggtgatgaag  240
gtcagcgatc acttaacctg gcttgccgaa gcgatcctcg acgcggtggt gcagcaggca  300
tgggggcaga tggtcgctcg ctacggccag ccgacccacc tgcacgatcg ccagggtcgc  360
ggcttcgccg tcgtcggcta cggtaagctt ggcggctggg agctgggcta cagctccgat  420
ctcgatctgg tgttcctcca tgactgcccg gcggaggtga tgaccgacgg cgagcgggag  480
attgacggcc gtcagttcta cctgcggctg gcccagcgga tcatgcacct gttcagcacc  540
cgcacctcgt ccggtattct ctacgaagtg gacgcccggc tgcgtccttc tggcgcggcg  600
gggatgctgg tcaccaccgc cgacgcgttt gctgactatc agcagaacga agcctggacg  660
tgggaacatc aggcgctggt gcgcgcccgc gtggtctatg gcgacccggc gctgcaggcg  720
cgctttgacg ccattcgtcg cgatatcctg accaccccgc gggaggggat gaccctgcag  780
accgaggttc gcgagatgcg cgagaagatg cgcgcccacc ttggcaacaa acatcccgat  840
cgttttgata tcaaagccga tgccggcggg atcaccgata ttgaatttat tactcagtat  900
ctggtcctac gctatgccag tgacaagccg aagctgaccc gctggtctga caacgtgcgt  960
attcttgagc tgctggcgca gaacgacatc atggacgagg aggaggcgcg cgccttaacg  1020
catgcgtaca ccaccttgcg tgatgcgctc catcacctgg ccctgcagga gcagccggga  1080
cacgtggcgc cagaggcctt cagccgggag cgtcagcagg tcagcgccag ctggcagaag  1140
tggctgatgg cttaa                                                  1155

SEQ ID NO: 116         moltype = DNA  length = 2155
FEATURE                Location/Qualifiers
misc_feature           1..2155
                       note = Synthetic polynucleotide
misc_feature           1..2155
                       note = glnE-delta-AR-2 36bp deletion
source                 1..2155
                       mol_type = other DNA
                       organism = synthetic construct
SEQUENCE: 116
cgtaaggcga ccacccagct ccgcgcgttg ctgaacgacg ctgaagccgt tctgctggcc  60
```

```
gcggacaccg ccgacgaggc gttattccgc accgaggtcg tcggcgccaa actggccctg  120
actgaatggc tggtccagcg cggctggcgt ccgttcctca acgaggcagg agagaaaaaa  180
atagccggat cgttcaaacg gtttgccgat attaacctct cgcgggtggc ggccgagctg  240
cgcagcgccg tgcagcatct ggcggttgaa gatgccgccg accagttgcc gaagctgtcc  300
cgcgacatcg acagcgtcca gctgctggcg ggcgcctatg gcgacgccgt cgcgccgtgg  360
ctggagaact ggcaggagct tcaccgtgca atagcacatg acgatcgcag cgtctttgaa  420
tatttccgtc gccaggcgct ggctgccgag ccgttctggc tgcatagtgg aaaacgataa  480
tttcaggcca gggagccctt atggcgctga agcacctgat cacgctctgc gcggcgtcgc  540
cgatggtcgc cagccagctg gcgcgccacc cgctgctgct ggatgagctg ctggatccca  600
acaccctcta tcagccgacg gcgaccgatg cctatcgcga cgagctgcgc cagtacctgc  660
tgcgcgtgcc ggaagaggat gaagagcagc agctgcatat cgcggcggcg gatatcgctg  720
gtaccctgcc ggtgatgaag gtcagcgatc acttaacctg gcttgccgaa gcgatcctcg  780
acgcggtggt gcagcaggca tgggggcaga tggtcgctcg ctacggccag ccgacccacc  840
tgcacgatcg ccagggtcgc ggcttcgccg tcgtcggcta cggtaagctt ggcggctggg  900
agctgggcta cagctccgat ctcgatctgg tgttcctcca tgactgcccg gcggaggtga  960
tgaccgacgg cgagcgggag attgacggcc gtcagttcta cctgcggctg gcccagcgga  1020
tcatgcacct gttcagcacc cgcacctcgt ccggtattct ctacgaagtg gacgcccggc  1080
tgcgtccttc tggcgcggcg gggatgctgg tcaccaccgc cgacgcgttt gctgactatc  1140
agcagaacga agcctggacg tgggaacatc aggcgctggt gcgcgcccgc gtggtctatg  1200
gcgacccggc gctgcaggcg cgctttgacg ccattcgtcg cgatatcctg accaccccgc  1260
gggaggggat gaccctgcag accgaggttc gcgagatgcg cgagaagatg cgcgcccacc  1320
ttggcaacaa acatcccgat cgttttgata tcaaagccga tgccggcggg atcaccgata  1380
ttgaatttat tactcagtat ctggtcctac gctatgccag tgacaagccg aagctgaccc  1440
gctggtctga caacgtgcgt attcttgagc tgctggcgca gaacgacatc atggacgagg  1500
aggaggcgcg cgccttaacg catgcgtaca ccaccttgcg tgatgcgctc catcacctgg  1560
ccctgcagga gcagccggga cacgtggcgc cagaggcctt cagccgggag cgtcagcagg  1620
tcagcgccag ctggcagaag tggctgatgg cttaactata aaatcgggtg tgctattatc  1680
gcgcgcaaag tttgcgtctc gcaggagaga gtcatgaaag taacgctgcc ggagtttgaa  1740
cgtgcaggag tgttggtggt gggtgatgtg atgctggacc gctactggta cggcccccacc  1800
agtcgtattt ccccggaagc cccggtgccg gtggtgaagg tggaaaatat cgaagaacgt  1860
cctggcggcg cggcaaacgt agcgatgaac atcgcctccc tgggggcaac gtcgcgcctg  1920
gtgggattga ccgggattga tgacgctgcc cgcgcgctga gccaggcgct ggccaatgtg  1980
aatgtgaagt gcgacttcgt ctccgtcccg actcacccga ccatcaccaa gctgcgggtg  2040
ctgtcgcgca atcagcagct gatccgcctc gactttgaag agggcttctc cggcgtggat  2100
ccgcagccga tgcatgagcg cattcagcag gcgctgggag ccattggcgc actgg       2155
```

```
SEQ ID NO: 117          moltype = DNA  length = 413
FEATURE                 Location/Qualifiers
misc_feature            1..413
                        note = Synthetic polynucleotide
misc_feature            1..413
                        note = delta-nifL::Prm6.2
source                  1..413
                        mol_type = other DNA
                        organism = synthetic construct
SEQUENCE: 117
atgaccctga atatgatgct cgagctaaag ttctcggcta atcgctgata acatttgacg  60
caatgcgcaa taaaagggca tcatttgatg ccctttttgc acgctttcat accagaacct  120
ggctcatcag tgattttttt tgtcataatc attgctgaga caggctctga agagggcgtt  180
tatacaccaa accattcgag cggtagcgcg acggcaagtc agcgttctcc tttgcaatag  240
cagggaagag gcgccagaac cgccagcgtt gaagcagttt gaacgcgttc agtgtataat  300
ccgaaactta atttcggttt ggagccattg agctggcttc ccgaccgcag ggcggcacct  360
gcctgaccct gcgtttcccg ctgtttaaca ccctgaccgg aggtgaagca tga         413
```

```
SEQ ID NO: 118          moltype = DNA  length = 1413
FEATURE                 Location/Qualifiers
misc_feature            1..1413
                        note = Synthetic polynucleotide
misc_feature            1..1413
                        note = delta-nifL::Prm6.2 with 500bp flank
source                  1..1413
                        mol_type = other DNA
                        organism = synthetic construct
SEQUENCE: 118
ggccgtcgcc cagcgtcggc gtccccaaca gcagggccgg gtaggccagc aggtccgcca  60
gcgtggcgcg gttaatattg accggggcgg cggcggcctc ccccagctgc ttgtggatca  120
ttttcgcgat cttgcgggtt ttaccggtat cggtaccaaa gaaaatgcca atgttcgcca  180
tagtacgctc ctgtcggaat ggtgttgaaa aaaggaatga cgacagaggt attgcgaagg  240
ctgtgccagg ttgccctgca ccgcgacggc ccatccctgc cccatcagga tcgcttcgca  300
tcacgatgcc gcgcgccaaa ggcgcacccg gcggggcgaa aggtaaaaat ccgtgaattt  360
tccccctgtc ggatcaatgt ttcgcgtggt cgttccgata agggcgcaca ctttgcatgg  420
ttatccgggt tcggcttacc ccgccgcgtt ttgcgcacgg tgtcggacaa tttgtcataa  480
ctgcgacaca ggagtttgcg atgaccctga atatgatgct cgagctaaag ttctcggcta  540
atcgctgata acatttgacg caatgcgcaa taaaagggca tcatttgatg ccctttttgc  600
acgctttcat accagaacct ggctcatcag tgattttttt tgtcataatc attgctgaga  660
caggctctga agagggcgtt tatacaccaa accattcgag cggtagcgcg acggcaagtc  720
agcgttctcc tttgcaatag cagggaagag gcgccagaac cgccagcgtt gaagcagttt  780
gaacgcgttc agtgtataat ccgaaactta atttcggttt ggagccattg agctggcttc  840
ccgaccgcag ggcggcacct gcctgaccct gcgtttcccg ctgtttaaca ccctgaccgg  900
```

```
aggtgaagca tgatccctga atccgacccg gacaccaccg tcagacgctt cgacctctct  960
cagcagttca ccgccatgca gcggataagc gtggtgctga gccgggccac cgaggccagc  1020
aaaacgctgc aggaggtgct cagcgtatta cacaacgatg cctttatgca gcacgggatg  1080
atctgcctgt acgacagcga gcaggagatc ctcagtatcg aagcgctgca gcaaaccggc  1140
cagcagcccc tccccggcag cacgcagatc cgctatcgcc ccggcgaggg actggtgggg  1200
accgtgctgg cccaggggca gtcgctggtg ctgccccggg tcgccgacga tcagcgtttt  1260
ctcgaccgcc tgagcctcta cgattacgat ctgccgttta tcgccgtacc gttgatgggg  1320
cccaacgccc ggccaatagg ggtgctggcg gcccagccga tggcgcgcca ggaagagcgg  1380
ctgccggcct gcacccgttt tctcgaaacc gtc                               1413

SEQ ID NO: 119          moltype = DNA  length = 513
FEATURE                 Location/Qualifiers
misc_feature            1..513
                        note = Synthetic polynucleotide
misc_feature            1..513
                        note = delta-nifL::Prm1.2
source                  1..513
                        mol_type = other DNA
                        organism = synthetic construct
SEQUENCE: 119
atgaccctga atatgatgct cgagcccgct gaccgaccag aacttccacc ttggactcgg  60
ctataccctt ggcgtgacgg cgcgcgataa ctgggactac atccccattc cggtgatctt  120
accattggcg tcaataggtt acggtccggc gactttccag atgacctata ttcccggcac  180
ctacaataac ggtaacgttt acttcgcctg ggctcgtata cagttttaat tcgctaagtc  240
ttagcaataa atgagataag cggtgtgtct tgtggaaaaa caaggactaa agcgttaccc  300
actaaaaaag atagcgactt ttatcacttt ttagcaaagt tgcactggac aaaaggtacc  360
acaattggtg tactgatact cgacacagca ttagtgtcga tttttcatat aaaggtaatt  420
ttggccattg agctggcttc ccgaccgcag ggcggcacct gcctgaccct gcgtttcccg  480
ctgtttaaca ccctgaccgg aggtgaagca tga                               513

SEQ ID NO: 120          moltype = DNA  length = 1513
FEATURE                 Location/Qualifiers
misc_feature            1..1513
                        note = Synthetic polynucleotide
misc_feature            1..1513
                        note = delta-nifL::Prm1.2 with 500bp flank
source                  1..1513
                        mol_type = other DNA
                        organism = synthetic construct
SEQUENCE: 120
ggccgtcgcc cagcgtcggc gtccccaaca gcagggccgg gtaggccagc aggtccgcca  60
gcgtggcgcg gttaatattg accggggcgg cggcggcctc ccccagctgc ttgtggatca  120
ttttcgcgat cttgcgggtt ttaccggtat cggtaccaaa gaaaatgcca atgttcgcca  180
tagtacgctc ctgtcggaat ggtgttgaaa aaaggaatga cgacagaggt attgcgaagg  240
ctgtgccagg ttgccctgca ccgcgacggc ccatccctgc cccatcagga tcgcttcgca  300
tcacgatgcc gcgcgccaaa ggcgcacccg gcggggcgaa aggtaaaaat ccgtgaattt  360
tccccctgtc ggatcaatgt ttcgcgtggt cgttccgata agggcgcaca ctttgcatgg  420
ttatccgggt tcggcttacc ccgccgcgtt ttgcgcacgg tgtcggacaa tttgtcataa  480
ctgcgacaca ggagtttgcg atgaccctga atatgatgct cgagcccgct gaccgaccag  540
aacttccacc ttggactcgg ctataccctt ggcgtgacgg cgcgcgataa ctgggactac  600
atccccattc cggtgatctt accattggcg tcaataggtt acggtccggc gactttccag  660
atgacctata ttcccggcac ctacaataac ggtaacgttt acttcgcctg ggctcgtata  720
cagttttaat tcgctaagtc ttagcaataa atgagataag cggtgtgtct tgtggaaaaa  780
caaggactaa agcgttaccc actaaaaaag atagcgactt ttatcacttt ttagcaaagt  840
tgcactggac aaaaggtacc acaattggtg tactgatact cgacacagca ttagtgtcga  900
tttttcatat aaaggtaatt ttggccattg agctggcttc ccgaccgcag ggcggcacct  960
gcctgaccct gcgtttcccg ctgtttaaca ccctgaccgg aggtgaagca tgatccctga  1020
atccgacccg gacaccaccg tcagacgctt cgacctctct cagcagttca ccgccatgca  1080
gcggataagc gtggtgctga gccgggccac cgaggccagc aaaacgctgc aggaggtgct  1140
cagcgtatta cacaacgatg cctttatgca gcacgggatg atctgcctgt acgacagcga  1200
gcaggagatc ctcagtatcg aagcgctgca gcaaaccggc cagcagcccc tccccggcag  1260
cacgcagatc cgctatcgcc ccggcgaggg actggtgggg accgtgctgg cccaggggca  1320
gtcgctggtg ctgccccggg tcgccgacga tcagcgtttt ctcgaccgcc tgagcctcta  1380
cgattacgat ctgccgttta tcgccgtacc gttgatgggg cccaacgccc ggccaatagg  1440
ggtgctggcg gcccagccga tggcgcgcca ggaagagcgg ctgccggcct gcacccgttt  1500
tctcgaaacc gtc                                                     1513

SEQ ID NO: 121          moltype = DNA  length = 1155
FEATURE                 Location/Qualifiers
misc_feature            1..1155
                        note = Synthetic polynucleotide
misc_feature            1..1155
                        note = glnE-delta-AR-2 36bp deletion
source                  1..1155
                        mol_type = other DNA
                        organism = synthetic construct
SEQUENCE: 121
atggcgctga agcacctgat cacgctctgc gcggcgtcgc cgatggtcgc cagccagctg  60
gcgcgccacc cgctgctgct ggatgagctg ctggatccca acaccctcta tcagccgacg  120
```

```
gcgaccgatg cctatcgcga cgagctgcgc cagtacctgc tgcgcgtgcc ggaagaggat  180
gaagagcagc agctgcatat cgcggcggcg gatatcgctg gtaccctgcc ggtgatgaag  240
gtcagcgatc acttaacctg gcttgccgaa gcgatcctcg acgcggtggt gcagcaggca  300
tgggggcaga tggtcgctcg ctacggccag ccgacccacc tgcacgatcg ccagggtcgc  360
ggcttcgccg tcgtcggcta cggtaagctt ggcggctggg agctgggcta cagctccgat  420
ctcgatctgg tgttcctcca tgactgcccg gcggaggtga tgaccgacgg cgagcgggag  480
attgacggcc gtcagttcta cctgcggctg gcccagcgga tcatgcacct gttcagcacc  540
cgcacctcgt ccggtattct ctacgaagtg gacgcccggc tgcgtccttc tggcgcggcg  600
gggatgctgg tcaccaccgc cgacgcgttt gctgactatc agcagaacga agcctggacg  660
tgggaacatc aggcgctggt gcgcgcccgc gtggtctatg gcgacccggc gctgcaggcg  720
cgctttgacg ccattcgtcg cgatatcctg accaccccgc gggaggggat gaccctgcag  780
accgaggttc gcgagatgcg cgagaagatg cgcgcccacc ttggcaacaa acatcccgat  840
cgttttgata tcaaagccga tgccggcggg atcaccgata ttgaatttat tactcagtat  900
ctggtcctac gctatgccag tgacaagccg aagctgaccc gctggtctga caacgtgcgt  960
attcttgagc tgctggcgca gaacgacatc atggacgagg aggaggcgcg cgccttaacg  1020
catgcgtaca ccaccttgcg tgatgcgctc catcacctgg ccctgcagga gcagccggga  1080
cacgtggcgc cagaggcctt cagccgggag cgtcagcagg tcagcgccag ctggcagaag  1140
tggctgatgg cttaa                                                  1155
```

| | |
|---|---|
| SEQ ID NO: 122 | moltype = DNA length = 2155 |
| FEATURE | Location/Qualifiers |
| misc_feature | 1..2155 |
| | note = Synthetic polynucleotide |
| misc_feature | 1..2155 |
| | note = glnE-delta-AR-2 36bp deletion |
| source | 1..2155 |
| | mol_type = other DNA |
| | organism = synthetic construct |

SEQUENCE: 122

```
cgtaaggcga ccacccagct ccgcgcgttg ctgaacgacg ctgaagccgt tctgctggcc  60
gcggacaccg ccgacgaggc gttattccgc accgaggtcg tcggcgccaa actggccctg  120
actgaatggc tggtccagcg cggctggcgt ccgttcctca acgaggcagg agagaaaaaa  180
atagccggat cgttcaaacg gtttgccgat attaacctct cgcgggtggc ggccgagctg  240
cgcagcgccg tgcagcatct ggcggttgaa gatgccgccg accagttgcc gaagctgtcc  300
cgcgacatcg acagcgtcca gctgctggcg ggcgcctatg gcgacgccgt cgcgccgtgg  360
ctggagaact ggcaggagct tcaccgtgca atagcacatg acgatcgcag cgtctttgaa  420
tatttccgtc gccaggcgct ggctgccgag ccgttctggc tgcatagtgg aaaacgataa  480
tttcaggcca gggagccctt atggcgctga agcacctgat cacgctctgc gcggcgtcgc  540
cgatggtcgc cagccagctg gcgcgccacc cgctgctgct ggatgagctg ctggatccca  600
acaccctcta tcagccgacg gcgaccgatg cctatcgcga cgagctgcgc cagtacctgc  660
tgcgcgtgcc ggaagaggat gaagagcagc agctgcatat cgcggcggcg gatatcgctg  720
gtaccctgcc ggtgatgaag gtcagcgatc acttaacctg gcttgccgaa gcgatcctcg  780
acgcggtggt gcagcaggca tgggggcaga tggtcgctcg ctacggccag ccgacccacc  840
tgcacgatcg ccagggtcgc ggcttcgccg tcgtcggcta cggtaagctt ggcggctggg  900
agctgggcta cagctccgat ctcgatctgg tgttcctcca tgactgcccg gcggaggtga  960
tgaccgacgg cgagcgggag attgacggcc gtcagttcta cctgcggctg gcccagcgga  1020
tcatgcacct gttcagcacc cgcacctcgt ccggtattct ctacgaagtg gacgcccggc  1080
tgcgtccttc tggcgcggcg gggatgctgg tcaccaccgc cgacgcgttt gctgactatc  1140
agcagaacga agcctggacg tgggaacatc aggcgctggt gcgcgcccgc gtggtctatg  1200
gcgacccggc gctgcaggcg cgctttgacg ccattcgtcg cgatatcctg accaccccgc  1260
gggaggggat gaccctgcag accgaggttc gcgagatgcg cgagaagatg cgcgcccacc  1320
ttggcaacaa acatcccgat cgttttgata tcaaagccga tgccggcggg atcaccgata  1380
ttgaatttat tactcagtat ctggtcctac gctatgccag tgacaagccg aagctgaccc  1440
gctggtctga caacgtgcgt attcttgagc tgctggcgca gaacgacatc atggacgagg  1500
aggaggcgcg cgccttaacg catgcgtaca ccaccttgcg tgatgcgctc catcacctgg  1560
ccctgcagga gcagccggga cacgtggcgc cagaggcctt cagccgggag cgtcagcagg  1620
tcagcgccag ctggcagaag tggctgatgg cttaactata aaatcgggtg tgctattatc  1680
gcgcgcaaag tttgcgtctc gcaggagaga gtcatgaaag taacgctgcc ggagtttgaa  1740
cgtgcaggag tgttggtggt gggtgatgtg atgctggacc gctactggta cggcccccacc 1800
agtcgtattt ccccggaagc cccggtgccg gtggtgaagg tggaaaatat cgaagaacgt  1860
cctggcggcg cggcaaacgt agcgatgaac atcgcctccc tgggggcaac gtcgcgcctg  1920
gtgggattga ccgggattga tgacgctgcc cgcgcgctga gccaggcgct ggccaatgtg  1980
aatgtgaagt gcgacttcgt ctccgtcccg actcacccga ccatcaccaa gctgcgggtg  2040
ctgtcgcgca atcagcagct gatccgcctc gactttgaag agggcttctc cggcgtggat  2100
ccgcagccga tgcatgagcg cattcagcag gcgctgggag ccattggcgc actgg       2155
```

| | |
|---|---|
| SEQ ID NO: 123 | moltype = DNA length = 613 |
| FEATURE | Location/Qualifiers |
| misc_feature | 1..613 |
| | note = Synthetic polynucleotide |
| misc_feature | 1..613 |
| | note = delta-nifL::PinfC |
| source | 1..613 |
| | mol_type = other DNA |
| | organism = synthetic construct |

SEQUENCE: 123

```
atgaccctga atatgatgct agaagcgtca ggtaccggtc atgattcacc gtgcgattct  60
cggttccctg gagcgcttca ttggcatcct gaccgaagag ttcgctggct tcttcccaac  120
ctggattgca ccagtgcagg tagtggtcat gaatattacc gattctcagg ctgaatacgt  180
```

```
taacgaattg acgcgtaaac tacaaaatgc gggcattcgt gtaaaagcag acttgagaaa  240
tgagaagatt ggctttaaaa tccgcgagca cactttacgt cgtgtcccgt atatgttggt  300
ctgtggcgac aaagaagtcg aagccggcaa agtggccgtg cgcacccgtc gcgggaaaga  360
cctcggcagc atggacgtaa gtgaagtgat tgagaagctg caacaagaga ttcgcagccg  420
cagtcttcaa caactggagg aataaggtat taaaggcgga aaacgagttc aaacggcacg  480
tccgaatcgt atcaatggcg agattcgcgc cctggaagtt cgcgccattg agctggcttc  540
ccgaccgcag ggcggcacct gcctgaccct gcgtttcccg ctgtttaaca ccctgaccgg  600
aggtgaagca tga                                                     613

SEQ ID NO: 124         moltype = DNA  length = 1613
FEATURE                Location/Qualifiers
misc_feature           1..1613
                       note = Synthetic polynucleotide
misc_feature           1..1613
                       note = delta-nifL::PinfC with 500bp flank
source                 1..1613
                       mol_type = other DNA
                       organism = synthetic construct
SEQUENCE: 124
ggccgtcgcc cagcgtcggc gtccccaaca gcagggccgg gtaggccagc aggtccgcca  60
gcgtggcgcg gttaatattg accggggcgg cggcggcctc ccccagctgc ttgtggatca  120
ttttcgcgat cttgcgggtt ttaccggtat cggtaccaaa gaaaatgcca atgttcgcca  180
tagtacgctc ctgtcggaat ggtgttgaaa aaaggaatga cgacagaggt attgcgaagg  240
ctgtgccagg ttgccctgca ccgcgacggc ccatccctgc cccatcagga tcgcttcgca  300
tcacgatgcc gcgcgccaaa ggcgcacccg gcggggcgaa aggtaaaaat ccgtgaattt  360
tccccctgtc ggatcaatgt ttcgcgtggt cgttccgata agggcgcaca ctttgcatgg  420
ttatccgggt tcggcttacc ccgccgcgtt ttgcgcacgg tgtcggacaa tttgtcataa  480
ctgcgacaca ggagtttgcg atgaccctga atatgatgct agaagcgtca ggtaccggtc  540
atgattcacc gtgcgattct cggttccctg gagcgcttca ttggcatcct gaccgaagag  600
ttcgctggct tcttcccaac ctggattgca ccagtgcagg tagtggtcat gaatattacc  660
gattctcagg ctgaatacgt taacgaattg acgcgtaaac tacaaaatgc gggcattcgt  720
gtaaaagcag acttgagaaa tgagaagatt ggctttaaaa tccgcgagca cactttacgt  780
cgtgtcccgt atatgttggt ctgtggcgac aaagaagtcg aagccggcaa agtggccgtg  840
cgcacccgtc gcgggaaaga cctcggcagc atggacgtaa gtgaagtgat tgagaagctg  900
caacaagaga ttcgcagccg cagtcttcaa caactggagg aataaggtat taaaggcgga  960
aaacgagttc aaacggcacg tccgaatcgt atcaatggcg agattcgcgc cctggaagtt  1020
cgcgccattg agctggcttc ccgaccgcag ggcggcacct gcctgaccct gcgtttcccg  1080
ctgtttaaca ccctgaccgg aggtgaagca tgatccctga atccgacccg gacaccaccg  1140
tcagacgctt cgacctctct cagcagttca ccgccatgca gcggataagc gtggtgctga  1200
gccgggccac cgaggccagc aaaacgctgc aggaggtgct cagcgtatta cacaacgatg  1260
cctttatgca gcacgggatg atctgcctgt acgacagcga gcaggagatc ctcagtatcg  1320
aagcgctgca gcaaaccggc cagcagcccc tccccggcag cacgcagatc cgctatcgcc  1380
ccggcgaggg actggtgggg accgtgctgg cccaggggca gtcgctggtg ctgccccggg  1440
tcgccgacga tcagcgtttt ctcgaccgcc tgagcctcta cgattacgat ctgccgttta  1500
tcgccgtacc gttgatgggg cccaacgccc ggccaatagg ggtgctggcg gcccagccga  1560
tggcgcgcca ggaagagcgg ctgccggcct gcacccgttt tctcgaaacc gtc         1613

SEQ ID NO: 125         moltype = DNA  length = 1191
FEATURE                Location/Qualifiers
misc_feature           1..1191
                       note = Synthetic polynucleotide
misc_feature           1..1191
                       note = glnE-delta-AR-2
source                 1..1191
                       mol_type = other DNA
                       organism = synthetic construct
SEQUENCE: 125
atggcgctga agcacctgat cacgctctgc gcggcgtcgc cgatggtcgc cagccagctg  60
gcgcgccacc cgctgctgct ggatgagctg ctggatccca acaccctcta tcagccgacg  120
gcgaccgatg cctatcgcga cgagctgcgc cagtacctgc tgcgcgtgcc ggaagaggat  180
gaagagcagc agctggaggc gttgcgccag tttaagcagg cgcagcagct gcatatcgcg  240
gcggcggata tcgctggtac cctgccggtg atgaaggtca gcgatcactt aacctggctt  300
gccgaagcga tcctcgacgc ggtggtgcag caggcatggg ggcagatggt cgctcgctac  360
ggccagccga cccacctgca cgatcgccag ggtcgcggct tcgccgtcgt cggctacggt  420
aagcttggcg gctgggagct gggctacagc tccgatctcg atctggtgtt cctccatgac  480
tgcccggcgg aggtgatgac cgacggcgag cgggagattg acggccgtca gttctacctg  540
cggctggccc agcggatcat gcacctgttc agcacccgca cctcgtccgg tattctctac  600
gaagtggacg cccggctgcg tccttctggc gcggcgggga tgctggtcac caccgccgac  660
gcgtttgctg actatcagca gaacgaagcc tggacgtggg aacatcaggc gctggtgcgc  720
gcccgcgtgg tctatggcga cccggcgctg caggcgcgct ttgacgccat tcgtcgcgat  780
atcctgacca ccccgcggga ggggatgacc ctgcagaccg aggttcgcga gatgcgcgag  840
aagatgcgcg cccaccttgg caacaaacat cccgatcgtt ttgatatcaa agccgatgcc  900
ggcgggatca ccgatattga atttattact cagtatctgg tcctacgcta tgccagtgac  960
aagccgaagc tgacccgctg gtctgacaac gtgcgtattc ttgagctgct ggcgcagaac  1020
gacatcatgg acgaggagga ggcgcgcgcc ttaacgcatg cgtacaccac cttgcgtgat  1080
gcgctccatc acctggccct gcaggagcag ccgggacacg tggcgccaga ggccttcagc  1140
cgggagcgtc agcaggtcag cgccagctgg cagaagtggc tgatggctta a           1191

SEQ ID NO: 126         moltype = DNA  length = 2191
```

```
FEATURE                Location/Qualifiers
misc_feature           1..2191
                       note = Synthetic polynucleotide
misc_feature           1..2191
                       note = glnE-delta-AR-2 with 500bp flank
source                 1..2191
                       mol_type = other DNA
                       organism = synthetic construct
SEQUENCE: 126
cgtaaggcga ccacccagct ccgcgcgttg ctgaacgacg ctgaagccgt tctgctggcc  60
gcggacaccg ccgacgaggc gttattccgc accgaggtcg tcggcgccaa actggccctg  120
actgaatggc tggtccagcg cggctggcgt ccgttcctca acgaggcagg agagaaaaaa  180
atagccggat cgttcaaacg gtttgccgat attaacctct cgcgggtggc ggccgagctg  240
cgcagcgccg tgcagcatct ggcggttgaa gatgccgccg accagttgcc gaagctgtcc  300
cgcgacatcg acagcgtcca gctgctggcg ggcgcctatg gcgacgccgt cgcgccgtgg  360
ctggagaact ggcaggagct tcaccgtgca atagcacatg acgatcgcag cgtctttgaa  420
tatttccgtc gccaggcgct ggctgccgag ccgttctggc tgcatagtgg aaaacgataa  480
tttcaggcca gggagccctt atggcgctga agcacctgat cacgctctgc gcggcgtcgc  540
cgatggtcgc cagccagctg gcgcgccacc cgctgctgct ggatgagctg ctggatccca  600
acaccctcta tcagccgacg gcgaccgatg cctatcgcga cgagctgcgc cagtacctgc  660
tgcgcgtgcc ggaagaggat gaagagcagc agctggaggc gttgcgccag tttaagcagg  720
cgcagcagct gcatatcgcg gcggcggata tcgctggtac cctgccggtg atgaaggtca  780
gcgatcactt aacctggctt gccgaagcga tcctcgacgc ggtggtgcag caggcatggg  840
ggcagatggt cgctcgctac ggccagccga cccacctgca cgatcgccag ggtcgcggct  900
tcgccgtcgt cggctacggt aagcttggcg gctgggagct gggctacagc tccgatctcg  960
atctggtgtt cctccatgac tgcccggcgg aggtgatgac cgacggcgag cgggagattg  1020
acggccgtca gttctacctg cggctggccc agcggatcat gcacctgttc agcacccgca  1080
cctcgtccgg tattctctac gaagtggacg cccggctgcg tccttctggc gcggcgggga  1140
tgctggtcac caccgccgac gcgtttgctg actatcagca gaacgaagcc tggacgtggg  1200
aacatcaggc gctggtgcgc gcccgcgtgg tctatggcga cccggcgctg caggcgcgct  1260
ttgacgccat tcgtcgcgat atcctgacca ccccgcggga ggggatgacc ctgcagaccg  1320
aggttcgcga gatgcgcgag aagatgcgcg cccaccttgg caacaaacat cccgatcgtt  1380
ttgatatcaa agccgatgcc ggcgggatca ccgatattga atttattact cagtatctgg  1440
tcctacgcta tgccagtgac aagccgaagc tgacccgctg gtctgacaac gtgcgtattc  1500
ttgagctgct ggcgcagaac gacatcatgg acgaggagga ggcgcgcgcc ttaacgcatg  1560
cgtacaccac cttgcgtgat gcgctccatc acctggccct gcaggagcag ccgggacacg  1620
tggcgccaga ggccttcagc cgggagcgtc agcaggtcag cgccagctgg cagaagtggc  1680
tgatggctta actataaaat cggtgtgct attatcgcgc gcaaagtttg cgtctcgcag  1740
gagagagtca tgaaagtaac gctgccggag tttgaacgtg caggagtgtt ggtggtgggt  1800
gatgtgatgc tggaccgcta ctggtacggc cccaccagtc gtatttcccc ggaagccccg  1860
gtgccggtgg tgaaggtgga aaatatcgaa gaacgtcctg gcggcgcggc aaacgtagcg  1920
atgaacatcg cctccctggg ggcaacgtcg cgcctggtgg gattgaccgg gattgatgac  1980
gctgcccgcg cgctgagcca ggcgctggcc aatgtgaatg tgaagtgcga cttcgtctcc  2040
gtcccgactc acccgaccat caccaagctg cgggtgctgt cgcgcaatca gcagctgatc  2100
cgcctcgact ttgaagaggg cttctccggc gtggatccgc agccgatgca tgagcgcatt  2160
cagcaggcgc tgggagccat tggcgcactg g                                2191

SEQ ID NO: 127         moltype = DNA  length = 1188
FEATURE                Location/Qualifiers
misc_feature           1..1188
                       note = Synthetic polynucleotide
misc_feature           1..1188
                       note = glnE-delta-AR-2
source                 1..1188
                       mol_type = other DNA
                       organism = synthetic construct
SEQUENCE: 127
atggcgctca aacagttaat ccgtctgtgt gccgcctcgc cgatggtcgc gacacaactt  60
gcacgtcatc ctttattgct cgatgaactg ctcgacccgc gcacgcttta ccagccgatt  120
gagccgggcg cttaccgcga cgaactgcgt cagtatctga tgcgggtgcc aacagaagac  180
gaagaacagc agcttgaagc cgtgcgccag ttcaaacagg cccagcattt gcgtatcgca  240
gccgggggata tttccggggc attgccggtg atgaaagtca gtgaccattt aacctacctt  300
gccgaggcca ttctcgatgt cgtggtgcag catgcgtggg aacaaatggt cgtaaaatac  360
gggcagcccg cgcatcttca gcaccgtgag gggcgcggtt ttgccgtggt cggttacggg  420
aaactcggtg gctgggagct gggttatagc tcagatctgg atctggtctt cctgctcgat  480
tgcgcgccgg aggtgatgac ggacggcgaa cgcagcatcg acggacgtca gttttatctt  540
cggctggcgc agcgcattat gcacttattc agcacccgga catcgtcagg cattctttac  600
gaggttgatc cgcgtctgcg accttccggc gcatccggca tgctggtcag taccattgaa  660
gcgtttgcag attatcaggc caatgaagcc tggacgtggg agcatcaggc gctggttcgc  720
gcgcgcgtgg tttacgggga tccgcaactg acacagcaat ttaacgccac gcgtcgcgac  780
attctttgcc gccagcgcga tggcgacggc ctgcgtaagg aggtccgtga aatgcgcgag  840
aaaatgtatg cccatctggg gagtaaaaaa gcccacgagt ttgatctgaa agccgatccg  900
ggtggcatca cggatattga attcattgca caatacctgg ttctgcgttt cgcgcatgat  960
gagccgaagc tgacgcgctg gtctgataac gtgcggattt ttgaactgat ggcacgatat  1020
gacatcatgc cggaagagga agcgcgccat ctgacgcagg cttatgtgac gctgcgcgat  1080
gaaattcatc atctggcgtt gcaggaacac agcgggaaag tggccgcgga cagctttgct  1140
actgagcgcg cgcagatccg tgccagctgg gcaaagtggc tcggctga              1188

SEQ ID NO: 128         moltype = DNA  length = 2188
```

```
FEATURE                 Location/Qualifiers
misc_feature            1..2188
                        note = Synthetic polynucleotide
misc_feature            1..2188
                        note = glnE-delta-AR-2 with 500bp flank
source                  1..2188
                        mol_type = other DNA
                        organism = synthetic construct
SEQUENCE: 128
cggtactgga acagaaatcg gcggatgcgc aggaaatttg ttatgacacg gcctgtctga  60
agtgcaagtt agtgcttact tcctggctgg caacctcagg ctggacgccg tttattgatg  120
ataaatctgc gaagaaactg gacgcttcct tcaaacgttt tgctgacatc atgctcggtc  180
gtaccgcagc ggatctgaaa gaagcctttg cgcagccact gacggaagaa ggttatcgcg  240
atcagctggc gcgcctgaaa cgccagatca ttaccttcca tttgcttgcc ggtgcttacc  300
ctgaaaaaga cgtcgatgcg tatattgccg gctgggtgga cctgcaacag gccatcgttc  360
agcagcaaca cgcctgggag gattcggccc gttctcacgc ggtgatgatg gatgcttttct  420
ggttaaacgg gcaacctcgt taactgactg actagcctgg gcaaactgcc cgggcttttt  480
tttgcaagga atctgatttc atggcgctca aacagttaat ccgtctgtgt gccgcctcgc  540
cgatggtcgc gacacaactt gcacgtcatc ctttattgct cgatgaactg ctcgacccgc  600
gcacgcttta ccagccgatt gagccgggcg cttaccgcga cgaactgcgt cagtatctga  660
tgcgggtgcc aacagaagac gaagaacagc agcttgaagc cgtgcgccag ttcaaacagg  720
cccagcattt gcgtatcgca gccggggata tttccggggc attgccggtg atgaaagtca  780
gtgaccattt aacctacctt gccgaggcca ttctcgatgt cgtggtgcag catgcgtggg  840
aacaaatggt cgtaaaatac gggcagcccg cgcatcttca gcaccgtgag ggcgcggtt  900
ttgccgtggt cggttacggg aaactcggtg gctgggagct gggttatagc tcagatctgg  960
atctggtctt cctgctcgat tgcgcgccgg aggtgatgac ggacggcgaa cgcagcatcg  1020
acggacgtca gttttatctt cggctggcgc agcgcattat gcacttattc agcacccgga  1080
catcgtcagg cattctttac gaggttgatc cgcgtctgcg accttccggc gcatccggca  1140
tgctggtcag taccattgaa gcgtttgcag attatcaggc caatgaagcc tggacgtggg  1200
agcatcaggc gctggttcgc gcgcgcgtgg tttacgggga tccgcaactg acacagcaat  1260
ttaacgccac gcgtcgcgac attctttgcc gccagcgcga tggcgacggc ctgcgtaagg  1320
aggtccgtga aatgcgcgag aaaatgtatg cccatctggg gagtaaaaaa gcccacgagt  1380
ttgatctgaa agccgatccg ggtggcatca cggatattga attcattgca caatacctgg  1440
ttctgcgttt cgcgcatgat gagccgaagc tgacgcgctg gtctgataac gtgcggattt  1500
ttgaactgat ggcacgatat gacatcatgc cggaagagga agcgcgccat ctgacgcagg  1560
cttatgtgac gctgcgcgat gaaattcatc atctggcgtt gcaggaacac agcgggaaag  1620
tggccgcgga cagctttgct actgagcgcg cgcagatccg tgccagctgg gcaaagtggc  1680
tcggctgagg gtttttattc ggctaacagg cgcttgtgat attatccggc gcattgtatt  1740
tacccgattt gatttatctg ttttggagtc ttgggatgaa agtgactttg cctgattttc  1800
accgcgcagg tgtgctggtt gtcggtgacg taatgttaga ccgttactgg tatggcccga  1860
ccaatcgtat ttctccggaa gctccggtgc cggtggtgaa ggtcagtacc attgaagagc  1920
ggcctggcgg tgcagctaac gtggcgatga acatttcatc tctgggcgcc tcttcctgtc  1980
tgatcggcct gaccggcgta gacgacgctg cgcgtgccct cagtgagcgt ctggcagaag  2040
tgaaagttaa ctgcgatttc gtcgcactat ccacacatcc taccatcacc aaactgcgaa  2100
ttttgtcccg taaccagcaa ctgatccgcc tcgactttga ggaaggtttt gaaggcgttg  2160
atctcgagcc gatgctgacc aaaataga                                    2188

SEQ ID NO: 129          moltype = DNA  length = 635
FEATURE                 Location/Qualifiers
misc_feature            1..635
                        note = Synthetic polynucleotide
misc_feature            1..635
                        note = delta-nifL::Prm6.1
source                  1..635
                        mol_type = other DNA
                        organism = synthetic construct
SEQUENCE: 129
atgagcatca cggcgttatc agcatcattt cctgaggggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg aattttttt cacaaagcgt  240
agcgttattg aatcgcacat tttaaactgt tggccgctgt ggaagcgaat attggtgaaa  300
ggtgcggttt taaggccttt ttctttgact ctctgtcgtt acaaagttaa tatgcgcgcc  360
ctccgtctct gaagctctcg gtgaacattg ttgcgaggca ggatgcgagc tggttgtgtt  420
ttgacattac cgataatgtg ccgcgtgaac gggtgcgtta tgcccgcccg gaagcggcgt  480
tttcccgtcc ggggaatggc atggagctgc gccttatcca gacgctgatc gcccatcatc  540
gcggttcttt agatctctcg gtccgccctg atggcggcac cttgctgacg ttacgcctgc  600
cggtacagca ggttatcacc ggaggcttaa aatga                            635

SEQ ID NO: 130          moltype = DNA  length = 1635
FEATURE                 Location/Qualifiers
misc_feature            1..1635
                        note = Synthetic polynucleotide
misc_feature            1..1635
                        note = delta-nifL::Prm6.1 with 500bp flank
source                  1..1635
                        mol_type = other DNA
                        organism = synthetic construct
SEQUENCE: 130
```

```
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
aatttttttt cacaaagcgt agcgttattg aatcgcacat tttaaactgt tggccgctgt  780
ggaagcgaat attggtgaaa ggtgcggttt taaggccttt ttctttgact ctctgtcgtt  840
acaaagttaa tatgcgcgcc ctccgtctct gaagctctcg gtgaacattg ttgcgaggca  900
ggatgcgagc tggttgtgtt ttgacattac cgataatgtg ccgcgtgaac gggtgcgtta  960
tgcccgcccg gaagcggcgt ttcccgtcc ggggaatggc atggagctgc gccttatcca  1020
gacgctgatc gcccatcatc gcggttcttt agatctctcg gtccgccctg atggcggcac  1080
cttgctgacg ttacgcctgc cggtacagca ggttatcacc ggaggcttaa aatgacccag  1140
ttacctaccg cgggcccggt tatccggcgc tttgatatgt ctgcccagtt tacggcgctt  1200
tatcgcatca gcgtggcgct gagtcaggaa agcaacaccg ggcgcgcact ggcggcgatc  1260
ctcgaagtgc ttcacgatca tgcatttatg caatacggca tggtgtgtct gtttgataaa  1320
gaacgcaatg cactctttgt ggaatccctg catggcatcg acggcgaaag gaaaaaagag  1380
acccgccatg tccgttaccg catgggggaa ggcgtgatcg gcgcggtgat gagccagcgt  1440
caggcgctgg tgttaccgcg catttcagac gatcagcgtt ttctcgaccg cctgaatatt  1500
tacgattaca gcctgccgtt gattggcgtg ccgatccccg gtgcggataa tcagccatcg  1560
ggcgtgctgg tggcacagcc gatggcgttg cacgaagacc ggctgactgc cagtacgcgg  1620
tttttagaaa tggtc                                                   1635
```

```
SEQ ID NO: 131         moltype = DNA  length = 635
FEATURE                Location/Qualifiers
misc_feature           1..635
                       note = Synthetic polynucleotide
misc_feature           1..635
                       note = delta-nifL::Prm6.1
source                 1..635
                       mol_type = other DNA
                       organism = synthetic construct
SEQUENCE: 131
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg aatttttttt cacaaagcgt  240
agcgttattg aatcgcacat tttaaactgt tggccgctgt ggaagcgaat attggtgaaa  300
ggtgcggttt taaggccttt ttctttgact ctctgtcgtt acaaagttaa tatgcgcgcc  360
ctccgtctct gaagctctcg gtgaacattg ttgcgaggca ggatgcgagc tggttgtgtt  420
ttgacattac cgataatgtg ccgcgtgaac gggtgcgtta tgcccgcccg gaagcggcgt  480
tttcccgtcc ggggaatggc atggagctgc gccttatcca gacgctgatc gcccatcatc  540
gcggttcttt agatctctcg gtccgccctg atggcggcac cttgctgacg ttacgcctgc  600
cggtacagca ggttatcacc ggaggcttaa aatga                             635
```

```
SEQ ID NO: 132         moltype = DNA  length = 1635
FEATURE                Location/Qualifiers
misc_feature           1..1635
                       note = Synthetic polynucleotide
misc_feature           1..1635
                       note = delta-nifL::Prm6.1 with 500bp flank
source                 1..1635
                       mol_type = other DNA
                       organism = synthetic construct
SEQUENCE: 132
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
aatttttttt cacaaagcgt agcgttattg aatcgcacat tttaaactgt tggccgctgt  780
ggaagcgaat attggtgaaa ggtgcggttt taaggccttt ttctttgact ctctgtcgtt  840
acaaagttaa tatgcgcgcc ctccgtctct gaagctctcg gtgaacattg ttgcgaggca  900
ggatgcgagc tggttgtgtt ttgacattac cgataatgtg ccgcgtgaac gggtgcgtta  960
tgcccgcccg gaagcggcgt tttcccgtcc ggggaatggc atggagctgc gccttatcca  1020
gacgctgatc gcccatcatc gcggttcttt agatctctcg gtccgccctg atggcggcac  1080
```

```
cttgctgacg ttacgcctgc cggtacagca ggttatcacc ggaggcttaa aatgacccag  1140
ttacctaccg cgggcccggt tatccggcgc tttgatatgt ctgcccagtt tacggcgctt  1200
tatcgcatca gcgtggcgct gagtcaggaa agcaacaccg ggcgcgcact ggcggcgatc  1260
ctcgaagtgc ttcacgatca tgcatttatg caatacggca tggtgtgtct gtttgataaa  1320
gaacgcaatg cactctttgt ggaatccctg catggcatcg acggcgaaag gaaaaaagag  1380
acccgccatg tccgttaccg catgggggaa ggcgtgatcg gcgcggtgat gagccagcgt  1440
caggcgctgg tgttaccgcg catttcagac gatcagcgtt ttctcgaccg cctgaatatt  1500
tacgattaca gcctgccgtt gattggcgtg ccgatccccg gtgcggataa tcagccatcg  1560
ggcgtgctgg tggcacagcc gatggcgttg cacgaagacc ggctgactgc cagtacgcgg  1620
tttttagaaa tggtc                                                  1635

SEQ ID NO: 133         moltype = DNA  length = 786
FEATURE                Location/Qualifiers
misc_feature           1..786
                       note = Synthetic polynucleotide
misc_feature           1..786
                       note = delta-nifL::Prm7.1
source                 1..786
                       mol_type = other DNA
                       organism = synthetic construct
SEQUENCE: 133
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg ttaaaaacgt gaccacgagc  240
attaataaac gccacgaaat gtggcgttta tttattcaaa aagtatcttc tttcataaaa  300
agtgctaaat gcagtagcag caaaattggg ataagtccca tggaatacgg ctgttttcgc  360
tgcaattttt aactttttcg taaaaaaaga tgtttctttg agcgaacgat caaaatatag  420
cgttaaccgg caaaaaatta ttctcattag aaaatagttt gtgtaatact tgtaacgcta  480
catggagatt aacttaatct agagggtttt ataccgtctc tgaagctctc ggtgaacatt  540
gttgcgaggc aggatgcgag ctggttgtgt tttgacatta ccgataatgt gccgcgtgaa  600
cgggtgcgtt atgcccgccc ggaagcggcg ttttcccgtc cggggaatgg catggagctg  660
cgccttatcc agacgctgat cgcccatcat cgcggttctt tagatctctc ggtccgccct  720
gatggcggca ccttgctgac gttacgcctg ccggtacagc aggttatcac cggaggctta  780
aaatga                                                            786

SEQ ID NO: 134         moltype = DNA  length = 1786
FEATURE                Location/Qualifiers
misc_feature           1..1786
                       note = Synthetic polynucleotide
misc_feature           1..1786
                       note = delta-nifL::Prm7.1 with 500bp flank
source                 1..1786
                       mol_type = other DNA
                       organism = synthetic construct
SEQUENCE: 134
gtttcgtctc gaggccgggc aactgagcgg ccccgttgaa accgacctgg gctggcatct  60
gttgttgtgc gaacaaattc gcctgccgca acccttgccg aaagccgaag ccttaacgcg  120
ggtgcgtcag caactgattg cccggcaaca gaaacattat cagcgccagt ggctgcaaca  180
actgatcaac gcctgagcct gttctccttc ttgttgatgc agacgggtta atgcccgttt  240
tgcacgaaaa atgcacataa attgcctgcg ttgccttata acagcgcagg gaaatcctgc  300
ctccggcctt gtgccacacc gcgctttgcc tggtttgtgg taaaaactgg cccgctttgc  360
atcctgatgc ttaaaacacc ccgttcagat caacctttgg gcagataagc ccgcgaaagg  420
cctgcaaatt gcacggttat tccgggtgag tatatgtgtg atttgggttc cggcattgcg  480
caataaaggg gagaaagaca tgagcatcac ggcgttatca gcatcatttc ctgaggggaa  540
tatcgccagc cgcttgtcgc tgcaacatcc ttcactgttt tataccgtgg ttgaacaatc  600
ttcggtggcg atttcgctga ccgatccgca ggcgcgcatt tgttatgcca atccggcatt  660
ctgccgccag acgggttttg cacttgagac acttttgggc gagaaccacc gtctgctggt  720
taaaaacgtg accacgagca ttaataaacg ccacgaaatg tggcgtttat ttattcaaaa  780
agtatcttct ttcataaaaa gtgctaaatg cagtagcagc aaaattggga taagtcccat  840
ggaatacggc tgttttcgct gcaattttta actttttcgt aaaaaaagat gtttctttga  900
gcgaacgatc aaaatatagc gttaaccggc aaaaaattat tctcattaga aaatagtttg  960
tgtaatactt gtaacgctac atggagatta acttaatcta gagggtttta taccgtctct  1020
gaagctctcg gtgaacattg ttgcgaggca ggatgcgagc tggttgtgtt ttgacattac  1080
cgataatgtg ccgcgtgaac gggtgcgtta tgcccgcccg gaagcggcgt tttcccgtcc  1140
ggggaatggc atggagctgc gccttatcca gacgctgatc gcccatcatc gcggttcttt  1200
agatctctcg gtccgccctg atggcggcac cttgctgacg ttacgcctgc cggtacagca  1260
ggttatcacc ggaggcttaa aatgacccag ttacctaccg cgggcccggt tatccggcgc  1320
tttgatatgt ctgcccagtt tacggcgctt tatcgcatca gcgtggcgct gagtcaggaa  1380
agcaacaccg ggcgcgcact ggcggcgatc ctcgaagtgc ttcacgatca tgcatttatg  1440
caatacggca tggtgtgtct gtttgataaa gaacgcaatg cactctttgt ggaatccctg  1500
catggcatcg acggcgaaag gaaaaaagag acccgccatg tccgttaccg catgggggaa  1560
ggcgtgatcg gcgcggtgat gagccagcgt caggcgctgg tgttaccgcg catttcagac  1620
gatcagcgtt ttctcgaccg cctgaatatt tacgattaca gcctgccgtt gattggcgtg  1680
ccgatccccg gtgcggataa tcagccatcg ggcgtgctgg tggcacagcc gatggcgttg  1740
cacgaagacc ggctgactgc cagtacgcgg tttttagaaa tggtcg                1786

SEQ ID NO: 135         moltype = DNA  length = 993
FEATURE                Location/Qualifiers
```

```
misc_feature          1..993
                      note = Synthetic polynucleotide
misc_feature          1..993
                      note = delta-nifL::Prm1.2
source                1..993
                      mol_type = other DNA
                      organism = synthetic construct
SEQUENCE: 135
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg tgaacatcac tgatgcacaa  240
gctacctatg tcgaagaatt aactaaaaaa ctgcaagatg caggcattcg cgttaaagcc  300
gacttgagaa atgagaagat tggctttaaa attcgcgaac acacgctacg ccgtgttcct  360
tatatgttag tttgtggcga taaagaggtc gaagcaggca aagttgctgt tcgtacccgc  420
cgcggcaaag acttaggaag catggatgtt agcgaagtcg ttgacaaact gctggcggaa  480
atccgcagca gaagtcttca tcaactggag gaataaagta ttaaaggcgg aaaacgagtt  540
caaccggcgc gtcctaatcg cattaacaaa gagattcgcg cgcaagaagt tcgcctcaca  600
ggcgtcgatg gcgagcagat tggtattgtc agtctgaatg aagctcttga aaaagctgag  660
gaagcgggcg tcgatttagt agaaatcagt ccgaatgccg agccgccagt ttgtcgaatc  720
ccgtctctga agctctcggt gaacattgtt gcgaggcagg atgcgagctg gttgtgtttt  780
gacattaccg ataatgtgcc gcgtgaacgg gtgcgttatg cccgcccgga agcggcgttt  840
tcccgtccgg ggaatggcat ggagctgcgc cttatccaga cgctgatcgc ccatcatcgc  900
ggttctttag atctctcggt ccgccctgat ggcggcacct tgctgacgtt acgcctgccg  960
gtacagcagg ttatcaccgg aggcttaaaa tga                                993

SEQ ID NO: 136        moltype = DNA  length = 1993
FEATURE               Location/Qualifiers
misc_feature          1..1993
                      note = Synthetic polynucleotide
misc_feature          1..1993
                      note = delta-nifL::Prm1.2 with 500bp flank
source                1..1993
                      mol_type = other DNA
                      organism = synthetic construct
SEQUENCE: 136
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
tgaacatcac tgatgcacaa gctacctatg tcgaagaatt aactaaaaaa ctgcaagatg  780
caggcattcg cgttaaagcc gacttgagaa atgagaagat tggctttaaa attcgcgaac  840
acacgctacg ccgtgttcct tatatgttag tttgtggcga taaagaggtc gaagcaggca  900
aagttgctgt tcgtacccgc cgcggcaaag acttaggaag catggatgtt agcgaagtcg  960
ttgacaaact gctggcggaa atccgcagca gaagtcttca tcaactggag gaataaagta  1020
ttaaaggcgg aaaacgagtt caaccggcgc gtcctaatcg cattaacaaa gagattcgcg  1080
cgcaagaagt tcgcctcaca ggcgtcgatg gcgagcagat tggtattgtc agtctgaatg  1140
aagctcttga aaaagctgag gaagcgggcg tcgatttagt agaaatcagt ccgaatgccg  1200
agccgccagt ttgtcgaatc ccgtctctga agctctcggt gaacattgtt gcgaggcagg  1260
atgcgagctg gttgtgtttt gacattaccg ataatgtgcc gcgtgaacgg gtgcgttatg  1320
cccgcccgga agcggcgttt tcccgtccgg ggaatggcat ggagctgcgc cttatccaga  1380
cgctgatcgc ccatcatcgc ggttctttag atctctcggt ccgccctgat ggcggcacct  1440
tgctgacgtt acgcctgccg gtacagcagg ttatcaccgg aggcttaaaa tgacccagtt  1500
acctaccgcg ggcccggtta tccggcgctt tgatatgtct gcccagttta cggcgcttta  1560
tcgcatcagc gtggcgctga gtcaggaaag caacaccggg cgcgcactgg cggcgatcct  1620
cgaagtgctt cacgatcatg catttatgca atacggcatg gtgtgtctgt ttgataaaga  1680
acgcaatgca ctctttgtgg aatccctgca tggcatcgac ggcgaaagga aaaaagagac  1740
ccgccatgtc cgttaccgca tggggaaggg cgtgatcggc gcggtgatga gccagcgtca  1800
ggcgctggtg ttaccgcgca tttcagacga tcagcgtttt ctcgaccgcc tgaatattta  1860
cgattacagc ctgccgttga ttggcgtgcc gatccccggt gcggataatc agccatcggg  1920
cgtgctggtg gcacagccga tggcgttgca cgaagaccgg ctgactgcca gtacgcggtt  1980
tttagaaatg gtc                                                      1993

SEQ ID NO: 137        moltype = DNA  length = 993
FEATURE               Location/Qualifiers
misc_feature          1..993
                      note = Synthetic polynucleotide
misc_feature          1..993
                      note = delta-nifL::Prm1.2
source                1..993
                      mol_type = other DNA
```

```
                         organism = synthetic construct
SEQUENCE: 137
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg tgaacatcac tgatgcacaa  240
gctacctatg tcgaagaatt aactaaaaaa ctgcaagatg caggcattcg cgttaaagcc  300
gacttgagaa atgagaagat tggctttaaa attcgcgaac acacgctacg ccgtgttcct  360
tatatgttag tttgtggcga taaagaggtc gaagcaggca aagttgctgt tcgtacccgc  420
cgcggcaaag acttaggaag catggatgtt agcgaagtcg ttgacaaact gctggcggaa  480
atccgcagca gaagtcttca tcaactggag gaataaagta ttaaaggcgg aaaacgagtt  540
caaccggcgc gtcctaatcg cattaacaaa gagattcgcg cgcaagaagt tcgcctcaca  600
ggcgtcgatg gcgagcagat tggtattgtc agtctgaatg aagctcttga aaaagctgag  660
gaagcgggcg tcgatttagt agaaatcagt ccgaatgccg agccgccagt ttgtcgaatc  720
ccgtctctga agctctcggt gaacattgtt gcgaggcagg atgcgagctg gttgtgtttt  780
gacattaccg ataatgtgcc gcgtgaacgg gtgcgttatg cccgcccgga agcggcgttt  840
tcccgtccgg ggaatggcat ggagctgcgc cttatccaga cgctgatcgc ccatcatcgc  900
ggttctttag atctctcggt ccgccctgat ggcggcacct tgctgacgtt acgcctgccg  960
gtacagcagg ttatcaccgg aggcttaaaa tga                               993

SEQ ID NO: 138           moltype = DNA  length = 1993
FEATURE                  Location/Qualifiers
misc_feature             1..1993
                         note = Synthetic polynucleotide
misc_feature             1..1993
                         note = delta-nifL::Prm1.2 with 500bp flank
source                   1..1993
                         mol_type = other DNA
                         organism = synthetic construct
SEQUENCE: 138
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
tgaacatcac tgatgcacaa gctacctatg tcgaagaatt aactaaaaaa ctgcaagatg  780
caggcattcg cgttaaagcc gacttgagaa atgagaagat tggctttaaa attcgcgaac  840
acacgctacg ccgtgttcct tatatgttag tttgtggcga taaagaggtc gaagcaggca  900
aagttgctgt tcgtacccgc cgcggcaaag acttaggaag catggatgtt agcgaagtcg  960
ttgacaaact gctggcggaa atccgcagca gaagtcttca tcaactggag gaataaagta  1020
ttaaaggcgg aaaacgagtt caaccggcgc gtcctaatcg cattaacaaa gagattcgcg  1080
cgcaagaagt tcgcctcaca ggcgtcgatg gcgagcagat tggtattgtc agtctgaatg  1140
aagctcttga aaaagctgag gaagcgggcg tcgatttagt agaaatcagt ccgaatgccg  1200
agccgccagt ttgtcgaatc ccgtctctga agctctcggt gaacattgtt gcgaggcagg  1260
atgcgagctg gttgtgtttt gacattaccg ataatgtgcc gcgtgaacgg gtgcgttatg  1320
cccgcccgga agcggcgttt tcccgtccgg ggaatggcat ggagctgcgc cttatccaga  1380
cgctgatcgc ccatcatcgc ggttctttag atctctcggt ccgccctgat ggcggcacct  1440
tgctgacgtt acgcctgccg gtacagcagg ttatcaccgg aggcttaaaa tgacccagtt  1500
acctaccgcg ggcccggtta tccggcgctt tgatatgtct gcccagttta cggcgcttta  1560
tcgcatcagc gtggcgctga gtcaggaaag caacaccggg cgcgcactgg cggcgatcct  1620
cgaagtgctt cacgatcatg catttatgca atacggcatg gtgtgtctgt ttgataaaga  1680
acgcaatgca ctctttgtgg aatccctgca tggcatcgac ggcgaaagga aaaaagagac  1740
ccgccatgtc cgttaccgca tgggggaagg cgtgatcggc gcggtgatga gccagcgtca  1800
ggcgctggtg ttaccgcgca tttcagacga tcagcgtttt ctcgaccgcc tgaatattta  1860
cgattacagc ctgccgttga ttggcgtgcc gatccccggt gcggataatc agccatcggg  1920
cgtgctggtg gcacagccga tggcgttgca cgaagaccgg ctgactgcca gtacgcggtt  1980
tttagaaatg gtc                                                     1993

SEQ ID NO: 139           moltype = DNA  length = 1188
FEATURE                  Location/Qualifiers
misc_feature             1..1188
                         note = Synthetic polynucleotide
misc_feature             1..1188
                         note = glnE-delta-AR-2
source                   1..1188
                         mol_type = other DNA
                         organism = synthetic construct
SEQUENCE: 139
atggcgctca aacagttaat ccgtctgtgt gccgcctcgc cgatggtcgc gacacaactt  60
gcacgtcatc ctttattgct cgatgaactg ctcgacccgc gcacgcttta ccagccgatt  120
gagccgggcg cttaccgcga cgaactgcgt cagtatctga tgcgggtgcc aacagaagac  180
gaagaacagc agcttgaagc cgtgcgccag ttcaaacagg cccagcattt gcgtatcgca  240
```

```
gccggggata tttccggggc attgccggtg atgaaagtca gtgaccattt aacctacctt  300
gccgaggcca ttctcgatgt cgtggtgcag catgcgtggg aacaaatggt cgtaaaatac  360
gggcagcccg cgcatcttca gcaccgtgag gggcgcggtt ttgccgtggt cggttacggg  420
aaactcggtg gctgggagct gggttatagc tcagatctgg atctggtctt cctgctcgat  480
tgcgcgccgg aggtgatgac ggacggcgaa cgcagcatcg acggacgtca gttttatctt  540
cggctggcgc agcgcattat gcacttattc agcacccgga catcgtcagg cattctttac  600
gaggttgatc cgcgtctgcg accttccggc gcatccggca tgctggtcag taccattgaa  660
gcgtttgcag attatcaggc caatgaagcc tggacgtggg agcatcaggc gctggttcgc  720
gcgcgcgtgg tttacgggga tccgcaactg acacagcaat ttaacgccac gcgtcgcgac  780
attctttgcc gccagcgcga tggcgacggc ctgcgtaagg aggtccgtga aatgcgcgag  840
aaaatgtatg cccatctggg gagtaaaaaa gcccacgagt ttgatctgaa agccgatccg  900
ggtggcatca cggatattga attcattgca caatacctgg ttctgcgttt cgcgcatgat  960
gagccgaagc tgacgcgctg gtctgataac gtgcggattt ttgaactgat ggcacgatat  1020
gacatcatgc cggaagagga agcgcgccat ctgacgcagg cttatgtgac gctgcgcgat  1080
gaaattcatc atctggcgtt gcaggaacac agcgggaaag tggccgcgga cagctttgct  1140
actgagcgcg cgcagatccg tgccagctgg gcaaagtggc tcggctga              1188
```

```
SEQ ID NO: 140          moltype = DNA  length = 2188
FEATURE                 Location/Qualifiers
misc_feature            1..2188
                        note = Synthetic polynucleotide
misc_feature            1..2188
                        note = glnE-delta-AR-2 with 500bp flank
source                  1..2188
                        mol_type = other DNA
                        organism = synthetic construct
SEQUENCE: 140
cggtactgga acagaaatcg gcggatgcgc aggaaatttg ttatgacacg gcctgtctga  60
agtgcaagtt agtgcttact tcctggctgg caacctcagg ctggacgccg tttattgatg  120
ataaatctgc gaagaaactg gacgcttcct tcaaacgttt tgctgacatc atgctcggtc  180
gtaccgcagc ggatctgaaa gaagcctttg cgcagccact gacggaagaa ggttatcgcg  240
atcagctggc gcgcctgaaa cgccagatca ttaccttcca tttgcttgcc ggtgcttacc  300
ctgaaaaaga cgtcgatgcg tatattgccg gctgggtgga cctgcaacag gccatcgttc  360
agcagcaaca cgcctgggag gattcggccc gttctcacgc ggtgatgatg gatgctttct  420
ggttaaacgg gcaacctcgt taactgactg actagcctgg gcaaactgcc cgggcttttt  480
tttgcaagga atctgatttc atggcgctca aacagttaat ccgtctgtgt gccgcctcgc  540
cgatggtcgc gacacaactt gcacgtcatc ctttattgct cgatgaactg ctcgacccgc  600
gcacgcttta ccagccgatt gagccgggcg cttaccgcga cgaactgcgt cagtatctga  660
tgcgggtgcc aacagaagac gaagaacagc agcttgaagc cgtgcgccag ttcaaacagg  720
cccagcattt gcgtatcgca gccggggata tttccggggc attgccggtg atgaaagtca  780
gtgaccattt aacctacctt gccgaggcca ttctcgatgt cgtggtgcag catgcgtggg  840
aacaaatggt cgtaaaatac gggcagcccg cgcatcttca gcaccgtgag gggcgcggtt  900
ttgccgtggt cggttacggg aaactcggtg gctgggagct gggttatagc tcagatctgg  960
atctggtctt cctgctcgat tgcgcgccgg aggtgatgac ggacggcgaa cgcagcatcg  1020
acggacgtca gttttatctt cggctggcgc agcgcattat gcacttattc agcacccgga  1080
catcgtcagg cattctttac gaggttgatc cgcgtctgcg accttccggc gcatccggca  1140
tgctggtcag taccattgaa gcgtttgcag attatcaggc caatgaagcc tggacgtggg  1200
agcatcaggc gctggttcgc gcgcgcgtgg tttacgggga tccgcaactg acacagcaat  1260
ttaacgccac gcgtcgcgac attctttgcc gccagcgcga tggcgacggc ctgcgtaagg  1320
aggtccgtga aatgcgcgag aaaatgtatg cccatctggg gagtaaaaaa gcccacgagt  1380
ttgatctgaa agccgatccg ggtggcatca cggatattga attcattgca caatacctgg  1440
ttctgcgttt cgcgcatgat gagccgaagc tgacgcgctg gtctgataac gtgcggattt  1500
ttgaactgat ggcacgatat gacatcatgc cggaagagga agcgcgccat ctgacgcagg  1560
cttatgtgac gctgcgcgat gaaattcatc atctggcgtt gcaggaacac agcgggaaag  1620
tggccgcgga cagctttgct actgagcgcg cgcagatccg tgccagctgg gcaaagtggc  1680
tcggctgagg gtttttattc ggctaacagg cgcttgtgat attatccggc gcattgtatt  1740
tacccgattt gatttatctg ttttggagtc ttgggatgaa agtgactttg cctgattttc  1800
accgcgcagg tgtgctggtt gtcggtgacg taatgttaga ccgttactgg tatggcccga  1860
ccaatcgtat ttctccggaa gctccggtgc cggtggtgaa ggtcagtacc attgaagagc  1920
ggcctggcgg tgcagctaac gtggcgatga acatttcatc tctgggcgcc tcttcctgtc  1980
tgatcggcct gaccggcgta gacgacgctg cgcgtgccct cagtgagcgt ctggcagaag  2040
tgaaagttaa ctgcgatttc gtcgcactat ccacacatcc taccatcacc aaactgcgaa  2100
ttttgtcccg taaccagcaa ctgatccgcc tcgactttga ggaaggtttt gaaggcgttg  2160
atctcgagcc gatgctgacc aaaataga                                    2188
```

```
SEQ ID NO: 141          moltype = DNA  length = 663
FEATURE                 Location/Qualifiers
misc_feature            1..663
                        note = Synthetic polynucleotide
misc_feature            1..663
                        note = delta-nifL::Prm3.1
source                  1..663
                        mol_type = other DNA
                        organism = synthetic construct
SEQUENCE: 141
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg tacagtagcg cctctcaaaa  240
```

```
atagataaac ggctcatgta cgtgggccgt ttattttttc tacccataat cgggaaccgg  300
tgttataatg ccgcgccctc atattgtggg gatttcttaa tgacctatcc tgggtcctaa  360
agttgtagtt gacattagcg gagcactaac ccgtctctga agctctcggt gaacattgtt  420
gcgaggcagg atgcgagctg gttgtgtttt gacattaccg ataatgtgcc gcgtgaacgg  480
gtgcgttatg cccgcccgga agcggcgttt tcccgtccgg ggaatggcat ggagctgcgc  540
cttatccaga cgctgatcgc ccatcatcgc ggttctttag atctctcggt ccgccctgat  600
ggcggcacct tgctgacgtt acgcctgccg gtacagcagg ttatcaccgg aggcttaaaa  660
tga                                                               663

SEQ ID NO: 142         moltype = DNA  length = 1663
FEATURE                Location/Qualifiers
misc_feature           1..1663
                       note = Synthetic polynucleotide
misc_feature           1..1663
                       note = delta-nifL::Prm3.1 with 500bp flank
source                 1..1663
                       mol_type = other DNA
                       organism = synthetic construct
SEQUENCE: 142
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
tacagtagcg cctctcaaaa atagataaac ggctcatgta cgtgggccgt ttattttttc  780
tacccataat cgggaaccgg tgttataatg ccgcgccctc atattgtggg gatttcttaa  840
tgacctatcc tgggtcctaa agttgtagtt gacattagcg gagcactaac ccgtctctga  900
agctctcggt gaacattgtt gcgaggcagg atgcgagctg gttgtgtttt gacattaccg  960
ataatgtgcc gcgtgaacgg gtgcgttatg cccgcccgga agcggcgttt tcccgtccgg  1020
ggaatggcat ggagctgcgc cttatccaga cgctgatcgc ccatcatcgc ggttctttag  1080
atctctcggt ccgccctgat ggcggcacct tgctgacgtt acgcctgccg gtacagcagg  1140
ttatcaccgg aggcttaaaa tgacccagtt acctaccgcg ggcccggtta tccggcgctt  1200
tgatatgtct gcccagttta cggcgcttta tcgcatcagc gtggcgctga gtcaggaaag  1260
caacaccggg cgcgcactgg cggcgatcct cgaagtgctt cacgatcatg catttatgca  1320
atacggcatg gtgtgtctgt ttgataaaga acgcaatgca ctctttgtgg aatccctgca  1380
tggcatcgac ggcgaaagga aaaaagagac ccgccatgtc cgttaccgca tgggggaagg  1440
cgtgatcggc gcggtgatga gccagcgtca ggcgctggtg ttaccgcgca tttcagacga  1500
tcagcgtttt ctcgaccgcc tgaatattta cgattacagc ctgccgttga ttggcgtgcc  1560
gatccccggt gcggataatc agccatcggg cgtgctggtg gcacagccga tggcgttgca  1620
cgaagaccgg ctgactgcca gtacgcggtt tttagaaatg gtc                   1663

SEQ ID NO: 143         moltype = DNA  length = 1188
FEATURE                Location/Qualifiers
misc_feature           1..1188
                       note = Synthetic polynucleotide
misc_feature           1..1188
                       note = glnE-delta-AR-2
source                 1..1188
                       mol_type = other DNA
                       organism = synthetic construct
SEQUENCE: 143
atggcgctca aacagttaat ccgtctgtgt gccgcctcgc cgatggtcgc gacacaactt  60
gcacgtcatc ctttattgct cgatgaactg ctcgacccgc gcacgcttta ccagccgatt  120
gagccgggcg cttaccgcga cgaactgcgt cagtatctga tgcgggtgcc aacagaagac  180
gaagaacagc agcttgaagc cgtgcgccag ttcaaacagg cccagcattt gcgtatcgca  240
gccggggata tttccggggc attgccggtg atgaaagtca gtgaccattt aacctacctt  300
gccgaggcca ttctcgatgt cgtggtgcag catgcgtggg aacaaatggt cgtaaaatac  360
gggcagcccg cgcatcttca gcaccgtgag ggcgcggtt ttgccgtggt cggttacggg  420
aaactcggtg gctgggagct gggttatagc tcagatctgg atctggtctt cctgctcgat  480
tgcgcgccgg aggtgatgac ggacggcgaa cgcagcatcg acggacgtca gttttatctt  540
cggctggcgc agcgcattat gcacttattc agcacccgga catcgtcagg cattctttac  600
gaggttgatc cgcgtctgcg accttccggc gcatccggca tgctggtcag taccattgaa  660
gcgtttgcag attatcaggc caatgaagcc tggacgtggg agcatcaggc gctggttcgc  720
gcgcgcgtgg tttacgggga tccgcaactg acacagcaat ttaacgccac gcgtcgcgac  780
attctttgcc gccagcgcga tggcgacggc ctgcgtaagg aggtccgtga aatgcgcgag  840
aaaatgtatg cccatctggg gagtaaaaaa gcccacgagt ttgatctgaa agccgatccg  900
ggtggcatca cggatattga attcattgca caatacctgg ttctgcgttt cgcgcatgat  960
gagccgaagc tgacgcgctg gtctgataac gtgcggattt ttgaactgat ggcacgatat  1020
gacatcatgc cggaagagga agcgcgccat ctgacgcagg cttatgtgac gctgcgcgat  1080
gaaattcatc atctggcgtt gcaggaacac agcgggaaag tggccgcgga cagctttgct  1140
actgagcgcg cgcagatccg tgccagctgg gcaaagtggc tcggctga              1188
```

```
SEQ ID NO: 144          moltype = DNA  length = 2188
FEATURE                 Location/Qualifiers
misc_feature            1..2188
                        note = Synthetic polynucleotide
misc_feature            1..2188
                        note = glnE-delta-AR-2 with 500bp flank
source                  1..2188
                        mol_type = other DNA
                        organism = synthetic construct
SEQUENCE: 144
cggtactgga acagaaatcg gcggatgcgc aggaaatttg ttatgacacg gcctgtctga  60
agtgcaagtt agtgcttact tcctggctgg caacctcagg ctggacgccg tttattgatg  120
ataaatctgc gaagaaactg gacgcttcct tcaaacgttt tgctgacatc atgctcggtc  180
gtaccgcagc ggatctgaaa gaagcctttg cgcagccact gacggaagaa ggttatcgcg  240
atcagctggc gcgcctgaaa cgccagatca ttaccttcca tttgcttgcc ggtgcttacc  300
ctgaaaaaga cgtcgatgcg tatattgccg gctgggtgga cctgcaacag gccatcgttc  360
agcagcaaca cgcctgggag gattcggccc gttctcacgc ggtgatgatg gatgctttct  420
ggttaaacgg gcaacctcgt taactgactg actagcctgg gcaaactgcc cgggcttttt  480
tttgcaagga atctgatttc atggcgctca aacagttaat ccgtctgtgt gccgcctcgc  540
cgatggtcgc gacacaactt gcacgtcatc ctttattgct cgatgaactg ctcgacccgc  600
gcacgcttta ccagccgatt gagccgggcg cttaccgcga cgaactgcgt cagtatctga  660
tgcgggtgcc aacagaagac gaagaacagc agcttgaagc cgtgcgccag ttcaaacagg  720
cccagcattt gcgtatcgca gccggggata tttccggggc attgccggtg atgaaagtca  780
gtgaccattt aacctacctt gccgaggcca ttctcgatgt cgtggtgcag catgcgtggg  840
aacaaatggt cgtaaaatac gggcagcccg cgcatcttca gcaccgtgag ggcgcggtt  900
ttgccgtggt cggttacggg aaactcggtg gctgggagct gggttatagc tcagatctgg  960
atctggtctt cctgctcgat tgcgcgccgg aggtgatgac ggacggcgaa cgcagcatcg  1020
acggacgtca gttttatctt cggctggcgc agcgcattat gcacttattc agcacccgga  1080
catcgtcagg cattctttac gaggttgatc cgcgtctgcg accttccggc gcatccggca  1140
tgctggtcag taccattgaa gcgtttgcag attatcaggc caatgaagcc tggacgtggg  1200
agcatcaggc gctggttcgc gcgcgcgtgg tttacgggga tccgcaactg acacagcaat  1260
ttaacgccac gcgtcgcgac attctttgcc gccagcgcga tggcgacggc ctgcgtaagg  1320
aggtccgtga aatgcgcgag aaaatgtatg cccatctggg gagtaaaaaa gcccacgagt  1380
ttgatctgaa agccgatccg ggtggcatca cggatattga attcattgca caatacctgg  1440
ttctgcgttt cgcgcatgat gagccgaagc tgacgcgctg gtctgataac gtgcggattt  1500
ttgaactgat ggcacgatat gacatcatgc cggaagagga agcgcgccat ctgacgcagg  1560
cttatgtgac gctgcgcgat gaaattcatc atctggcgtt gcaggaacac agcgggaaag  1620
tggccgcgga cagctttgct actgagcgcg cgcagatccg tgccagctgg gcaaagtggc  1680
tcggctgagg gtttttattc ggctaacagg cgcttgtgat attatccggc gcattgtatt  1740
taccccgattt gatttatctg ttttggagtc ttgggatgaa agtgactttg cctgattttc  1800
accgcgcagg tgtgctggtt gtcggtgacg taatgttaga ccgttactgg tatggcccga  1860
ccaatcgtat ttctccggaa gctccggtgc cggtggtgaa ggtcagtacc attgaagagc  1920
ggcctggcgg tgcagctaac gtggcgatga acatttcatc tctgggcgcc tcttcctgtc  1980
tgatcggcct gaccggcgta gacgacgctg cgcgtgccct cagtgagcgt ctggcagaag  2040
tgaaagttaa ctgcgatttc gtcgcactat ccacacatcc taccatcacc aaactgcgaa  2100
ttttgtcccg taaccagcaa ctgatccgcc tcgactttga ggaaggtttt gaaggcgttg  2160
atctcgagcc gatgctgacc aaaataga                                  2188

SEQ ID NO: 145          moltype = DNA  length = 613
FEATURE                 Location/Qualifiers
misc_feature            1..613
                        note = Synthetic polynucleotide
misc_feature            1..613
                        note = delta-nifL::PinfC
source                  1..613
                        mol_type = other DNA
                        organism = synthetic construct
SEQUENCE: 145
atgagcatca cggcgttatc agctgaatat cactgactca caagctacct atgtcgaaga  60
attaactaaa aaactgcaag atgcaggcat tcgcgttaaa gccgacttga gaaatgagaa  120
gattggcttt aaaattcgcg aacacacgct acgccgtgtt ccttatatgt tagtttgtgg  180
cgataaagag gtcgaagcag gcaaagttgc tgttcgtact cgtcgcggca aagacttagg  240
aagcatggat gttagcgaag tcgttgacaa actgctggcg gaaatccgca gcagaagtca  300
tcatcaactg gaggaataaa gtattaaagg cggaaaacga gttcaaccgg cgcgtcctaa  360
tcgcattaac aaagagattc gcgcgcaaga agttcgcctc accggcgtcg atggcgagca  420
gattggtatt gtcagtctga atgaagctct tgaaaaagct gaggaagcgg gcgtcgattt  480
agtagaaatc agtccgaatg ccgagccgcc agtttgtcga atctctttag atctctcggt  540
ccgccctgat ggcggcacct tgctgacgtt acgcctgccg gtacagcagg ttatcaccgg  600
aggcttaaaa tga                                                  613

SEQ ID NO: 146          moltype = DNA  length = 1613
FEATURE                 Location/Qualifiers
misc_feature            1..1613
                        note = Synthetic polynucleotide
misc_feature            1..1613
                        note = delta-nifL::PinfC with 500bp flank
source                  1..1613
                        mol_type = other DNA
                        organism = synthetic construct
```

```
SEQUENCE: 146
tgtttcgtct cgaagccggg caactgagca gccccgttga aaccgaactg ggctggcatc  60
tgttgttgtg cgaacaaatt cgcctgccgc aacccttgcc gaaagccgag gccttaacgc  120
gggtgcgtca gcaactgatt gcccggcaac agaatcatta tcagcgccag tggctgcaac  180
aactgatcaa cgcctgagcc tgttctcctt cttgttggtg cagacgggtt aatgcccgtt  240
ttgcacgaaa aatgcacata aactgccttc gctgccttat aacagcgcat ggaaatcctg  300
cctcctgcct tgtgccacgc cgcgctttgc ctggtttgtg gtaaaaactg gcccgctttg  360
catcctgatg tttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agctgaatat cactgactca  540
caagctacct atgtcgaaga attaactaaa aaactgcaag atgcaggcat tcgcgttaaa  600
gccgacttga gaaatgagaa gattggcttt aaaattcgcg aacacacgct acgccgtgtt  660
ccttatatgt tagtttgtgg cgataaagag gtcgaagcag gcaaagttgc tgttcgtact  720
cgtcgcggca aagacttagg aagcatggat gttagcgaag tcgttgacaa actgctggcg  780
gaaatccgca gcagaagtca tcatcaactg gaggaataaa gtattaaagg cggaaaacga  840
gttcaaccgg cgcgtcctaa tcgcattaac aaagagattc gcgcgcaaga agttcgcctc  900
accggcgtcg atggcgagca gattggtatt gtcagtctga atgaagctct tgaaaaagct  960
gaggaagcgg gcgtcgattt agtagaaatc agtccgaatg ccgagccgcc agtttgtcga  1020
atctctttag atctctcggt ccgccctgat ggcggcacct tgctgacgtt acgcctgccg  1080
gtacagcagg ttatcaccgg aggcttaaaa tgacccagtt acctaccgcg ggcccggtta  1140
tccggcgctt tgatatgtct gcccagttta cggcgcttta tcgcatcagc gtggcgctga  1200
gtcaggaaag caataccgcg cgcgcactgg cggcgatcct cgaagtgctt cacgatcatg  1260
catttatgca atacggcatg gtgtgtctgt tcgataaaga acgcaatgca ctgtttgtgg  1320
aatccctgca tggcatcgac ggcgaaagga aaaaagaaac ccgccatgtc cgttaccgca  1380
tgggggaagg cgtgatcggc gcggtgatga gccagcgtca ggcgctggtg ttaccgcgca  1440
tttcagacga tcagcgtttt ctcgaccgcc tgaatattta cgattacagc ctgccgctga  1500
ttggtgtgcc gatccccggt gcggataatc agcctgcggg tgtgctggtg gcacagccga  1560
tggcgttgca cgaagaccgg ctggctgcca gtacgcggtt tttagaaatg gtc         1613

SEQ ID NO: 147          moltype = DNA  length = 426
FEATURE                 Location/Qualifiers
misc_feature            1..426
                        note = Synthetic polynucleotide
misc_feature            1..426
                        note = delta-nifL::Prm5
source                  1..426
                        mol_type = other DNA
                        organism = synthetic construct
SEQUENCE: 147
atgaccctga atatgatgat ggatgccggc ggacatcatc gcgacaaaca atattaatac  60
cggcaaccac accggcaatt tacgagactg cgcaggcatc ctttctcccg tcaatttctg  120
tcaaataaag taaaagaggc agtctacttg aattaccccc ggctggttga gcgtttgttg  180
aaaaaaagta actgaaaaat ccgtagaata gcgccactct gatggttaat taacctattc  240
aattaagaat tatctggatg aatgtgccat taaatgcgca gcataatggt gcgttgtgcg  300
ggaaaactgc tttttttga aagggttggt cagtagcgga aacaactcac ttcacacccc  360
gaagggggaa gttgcctgac cctacgattc ccgctatttc attcactgac cggaggttca  420
aaatga                                                             426

SEQ ID NO: 148          moltype = DNA  length = 1426
FEATURE                 Location/Qualifiers
misc_feature            1..1426
                        note = Synthetic polynucleotide
misc_feature            1..1426
                        note = delta-nifL::Prm5 with 500bp flank
source                  1..1426
                        mol_type = other DNA
                        organism = synthetic construct
SEQUENCE: 148
accggatacg agagaaaagt gtctacatcg gttcggttga tattgaccgg cgcatccgcc  60
agcccgccca gtttctggtg gatctgtttg gcgattttgc gggtcttgcc ggtgtcggtg  120
ccgaaaaaaa taccaatatt tgccataaca cacgctcctg ttgaaaaaga gatcccgccg  180
ggaaatgcgg tgaacgtgtc tgatattgcg aagagtgtgc cagttttggt cgcgggcaaa  240
acctgcacca gtttggttat taatgcacca gtctggcgct tttttcgcc gagtttctcc  300
tcgctaatgc ccgccaggcg cggctttggc gctgatagcg cgctgaatac cgatctggat  360
caaggttttg tcgggttatc agccaaaagg tgcactcttt gcatggttat acgtgcctga  420
catgttgtcc gggcgacaaa cggcctggtg gcacaaattg tcagaactac gacacgacta  480
actgaccgca ggagtgtgcg atgaccctga atatgatgat ggatgccggc ggacatcatc  540
gcgacaaaca atattaatac cggcaaccac accggcaatt tacgagactg cgcaggcatc  600
ctttctcccg tcaatttctg tcaaataaag taaaagaggc agtctacttg aattaccccc  660
ggctggttga gcgtttgttg aaaaaaagta actgaaaaat ccgtagaata gcgccactct  720
gatggttaat taacctattc aattaagaat tatctggatg aatgtgccat taaatgcgca  780
gcataatggt gcgttgtgcg ggaaaactgc tttttttga aagggttggt cagtagcgga  840
aacaactcac ttcacacccc gaagggggaa gttgcctgac cctacgattc ccgctatttc  900
attcactgac cggaggttca aaatgaccca gcgaaccgag tcgggtaata ccgtctggcg  960
cttcgatttg tcccagcagt tcactgcgat gcagcgcata agcgtggtac tcagccgggc  1020
gaccgaggtc gatcagacgc tccagcaagt gctgtgcgta ttgcacaatg acgccttttt  1080
gcagcacggc atgatctgtc tgtacgacag ccagcaggcg attttgaata ttgaagcgtt  1140
gcaggaagcc gatcagcagt taatccccgg cagctcgcaa atccgctatc gtccgggcga  1200
agggctggtc gggacggtgc tttcgcaggg ccaatcatta gtgctggcgc gcgttgctga  1260
```

```
cgatcagcgc tttcttgacc ggctcgggtt gtatgattac aacctgccgt ttatcgccgt  1320
gccgctgata gggccagatg cgcagacttt cggtgtgctg acggcacaac ccatggcgcg  1380
ttacgaagag cgattacccg cctgcacccg ctttctggaa acggtc                 1426

SEQ ID NO: 149         moltype = DNA  length = 461
FEATURE                Location/Qualifiers
misc_feature           1..461
                       note = Synthetic polynucleotide
misc_feature           1..461
                       note = delta-nifL::Prm1
source                 1..461
                       mol_type = other DNA
                       organism = synthetic construct
SEQUENCE: 149
atgaccctga atatgatgat ggatgccggc cgtcctgtaa taataaccgg acaattcgga  60
ctgattaaaa aagcgccctt gtggcgcttt ttttatattc ccgcctccat ttaaaataaa  120
aaatccaatc ggatttcact atttaaactg gccattatct aagatgaatc cgatggaagc  180
tcgctgtttt aacacgcgtt ttttaacctt ttattgaaag tcggtgcttc tttgagcgaa  240
cgatcaaatt taagtggatt cccatcaaaa aaatattctc aacctaaaaa agtttgtgta  300
atacttgtaa cgctacatgg agattaactc aatctagagg gtattaataa tgaatcgtac  360
taaactggta ctgggcgcaa ctcacttcac accccgaagg gggaagttgc ctgaccctac  420
gattcccgct atttcattca ctgaccggag gttcaaaatg a                      461

SEQ ID NO: 150         moltype = DNA  length = 1461
FEATURE                Location/Qualifiers
misc_feature           1..1461
                       note = Synthetic polynucleotide
misc_feature           1..1461
                       note = delta-nifL::Prm1 with 500bp flank
source                 1..1461
                       mol_type = other DNA
                       organism = synthetic construct
SEQUENCE: 150
accggatacg agagaaaagt gtctacatcg gttcggttga tattgaccgg cgcatccgcc  60
agcccgccca gtttctggtg gatctgtttg gcgattttgc gggtcttgcc ggtgtcggtg  120
ccgaaaaaaa taccaatatt tgccataaca cacgctcctg ttgaaaaaga gatcccgccg  180
ggaaatgcgg tgaacgtgtc tgatattgcg aagagtgtgc cagttttggt cgcgggcaaa  240
acctgcacca gtttggttat taatgcacca gtctggcgct ttttttcgcc gagtttctcc  300
tcgctaatgc ccgccaggcg cggctttggc gctgatagcg cgctgaatac cgatctggat  360
caaggttttg tcgggttatc agccaaaagg tgcactcttt gcatggttat acgtgcctga  420
catgttgtcc gggcgacaaa cggcctggtg gcacaaattg tcagaactac gacacgacta  480
actgaccgca ggagtgtgcg atgaccctga atatgatgat ggatgccggc cgtcctgtaa  540
taataaccgg acaattcgga ctgattaaaa aagcgccctt gtggcgcttt ttttatattc  600
ccgcctccat ttaaaataaa aaatccaatc ggatttcact atttaaactg gccattatct  660
aagatgaatc cgatggaagc tcgctgtttt aacacgcgtt ttttaacctt ttattgaaag  720
tcggtgcttc tttgagcgaa cgatcaaatt taagtggatt cccatcaaaa aaatattctc  780
aacctaaaaa agtttgtgta atacttgtaa cgctacatgg agattaactc aatctagagg  840
gtattaataa tgaatcgtac taaactggta ctgggcgcaa ctcacttcac accccgaagg  900
gggaagttgc ctgaccctac gattcccgct atttcattca ctgaccggag gttcaaaatg  960
acccagcgaa ccgagtcggg taataccgtc tggcgcttcg atttgtccca gcagttcact  1020
gcgatgcagc gcataagcgt ggtactcagc cgggcgaccg aggtcgatca gacgctccag  1080
caagtgctgt gcgtattgca caatgacgcc tttttgcagc acggcatgat ctgtctgtac  1140
gacagccagc aggcgatttt gaatattgaa gcgttgcagg aagccgatca gcagttaatc  1200
cccggcagct cgcaaatccg ctatcgtccg ggcgaagggc tggtcgggac ggtgctttcg  1260
cagggccaat cattagtgct ggcgcgcgtt gctgacgatc agcgctttct tgaccggctc  1320
gggttgtatg attacaacct gccgtttatc gccgtgccgc tgatagggcc agatgcgcag  1380
actttcggtg tgctgacggc acaacccatg gcgcgttacg aagagcgatt acccgcctgc  1440
acccgctttc tggaaacggt c                                            1461

SEQ ID NO: 151         moltype = DNA  length = 461
FEATURE                Location/Qualifiers
misc_feature           1..461
                       note = Synthetic polynucleotide
misc_feature           1..461
                       note = delta-nifL::Prm1
source                 1..461
                       mol_type = other DNA
                       organism = synthetic construct
SEQUENCE: 151
atgaccctga atatgatgat ggatgccggc cgtcctgtaa taataaccgg acaattcgga  60
ctgattaaaa aagcgccctt gtggcgcttt ttttatattc ccgcctccat ttaaaataaa  120
aaatccaatc ggatttcact atttaaactg gccattatct aagatgaatc cgatggaagc  180
tcgctgtttt aacacgcgtt ttttaacctt ttattgaaag tcggtgcttc tttgagcgaa  240
cgatcaaatt taagtggatt cccatcaaaa aaatattctc aacctaaaaa agtttgtgta  300
atacttgtaa cgctacatgg agattaactc aatctagagg gtattaataa tgaatcgtac  360
taaactggta ctgggcgcaa ctcacttcac accccgaagg gggaagttgc ctgaccctac  420
gattcccgct atttcattca ctgaccggag gttcaaaatg a                      461

SEQ ID NO: 152         moltype = DNA  length = 1461
```

```
FEATURE                Location/Qualifiers
misc_feature           1..1461
                       note = Synthetic polynucleotide
misc_feature           1..1461
                       note = delta-nifL::Prm1 with 500bp flank
source                 1..1461
                       mol_type = other DNA
                       organism = synthetic construct
SEQUENCE: 152
accggatacg agagaaaagt gtctacatcg gttcggttga tattgaccgg cgcatccgcc  60
agcccgccca gtttctggtg gatctgtttg gcgattttgc gggtcttgcc ggtgtcggtg  120
ccgaaaaaaa taccaatatt tgccataaca cacgctcctg ttgaaaaaga gatcccgccg  180
ggaaatgcgg tgaacgtgtc tgatattgcg aagagtgtgc cagttttggt cgcgggcaaa  240
acctgcacca gtttggttat taatgcacca gtctggcgct ttttttcgcc gagtttctcc  300
tcgctaatgc ccgccaggcg cggctttggc gctgatagcg cgctgaatac cgatctggat  360
caaggttttg tcgggttatc agccaaaagg tgcactcttt gcatggttat acgtgcctga  420
catgttgtcc gggcgacaaa cggcctggtg gcacaaattg tcagaactac gacacgacta  480
actgaccgca ggagtgtgcg atgaccctga atatgatgat ggatgccggc cgtcctgtaa  540
taataaccgg acaattcgga ctgattaaaa aagcgccctt gtggcgcttt ttttatattc  600
ccgcctccat ttaaaataaa aaatccaatc ggatttcact atttaaactg gccattatct  660
aagatgaatc cgatggaagc tcgctgtttt aacacgcgtt ttttaacctt ttattgaaag  720
tcggtgcttc tttgagcgaa cgatcaaatt taagtggatt cccatcaaaa aaatattctc  780
aacctaaaaa agtttgtgta atacttgtaa cgctacatgg agattaactc aatctagagg  840
gtattaataa tgaatcgtac taaactggta ctgggcgcaa ctcacttcac accccgaagg  900
gggaagttgc ctgaccctac gattcccgct atttcattca ctgaccggag gttcaaaatg  960
acccagcgaa ccgagtcggg taataccgtc tggcgcttcg atttgtccca gcagttcact  1020
gcgatgcagc gcataagcgt ggtactcagc cgggcgaccg aggtcgatca gacgctccag  1080
caagtgctgt gcgtattgca caatgacgcc tttttgcagc acggcatgat ctgtctgtac  1140
gacagccagc aggcgatttt gaatattgaa gcgttgcagg aagccgatca gcagttaatc  1200
cccggcagct cgcaaatccg ctatcgtccg ggcgaagggc tggtcgggac ggtgctttcg  1260
cagggccaat cattagtgct ggcgcgcgtt gctgacgatc agcgctttct tgaccggctc  1320
gggttgtatg attacaacct gccgtttatc gccgtgccgc tgatagggcc agatgcgcag  1380
actttcggtg tgctgacggc acaacccatg gcgcgttacg aagagcgatt acccgcctgc  1440
acccgctttc tggaaacggt c                                            1461

SEQ ID NO: 153         moltype = DNA  length = 1188
FEATURE                Location/Qualifiers
misc_feature           1..1188
                       note = Synthetic polynucleotide
misc_feature           1..1188
                       note = glnE-delta-AR-2
source                 1..1188
                       mol_type = other DNA
                       organism = synthetic construct
SEQUENCE: 153
atggcactga aacacctcat ttccctgtgt gccgcgtcgc cgatggttgc cagtcagctg  60
gcgcgctacc cgatcctgct tgatgaattg ctcgacccga atacgctcta tcaaccgacg  120
gcgatgaatg cctatcgcga tgagctgcgc caatacctgc tgcgcgtgcc ggaagatgat  180
gaagagcaac agcttgaggc gctgcggcag tttaagcagg cgcagttgct gcgcgtggcg  240
gcggcggata ttgccggtac gttgccagta atgaaagtga gcgatcactt aacctggctg  300
gcggaagcga ttattgatgc ggtggtgcag caagcctggg ggcagatggt ggcgcgttat  360
ggccagccaa cgcatctgca cgatcgcgaa gggcgcggtt ttgcggtggt cggttatggc  420
aagctgggcg gctgggagct gggttacagc tccgatctgg atctggtatt cctgcacgac  480
tgcccgatgg atgtgatgac cgatggcgag cgtgaaatcg atggtcgcca gttctatttg  540
cgtctcgcgc agcgcgtgat gcacctgttt agcacgcgca cgtcgtccgg catcctttat  600
gaagttgatg cgcgtctgcg tccatctggc gctgcgggga tgctggtcac tactacggaa  660
tcgttcgccg attaccagca aaacgaagcc tggacgtggg aacatcaggc gctggcccgt  720
gcgcgcgtgg tgtacggcga tccgcaactg accgccgaat ttgacgccat tcgccgcgat  780
attctgatga cgcctcgcga cggcgcaacg ctgcaaaccg acgtgcgaga aatgcgcgag  840
aaaatgcgtg cccatcttgg caacaagcat aaagaccgct tcgatctgaa agccgatgaa  900
ggcggtatca ccgacatcga gtttatcgcc caatatctgg tgctgcgctt tgcccatgac  960
aagccgaaac tgacgcgctg gtcggataat gtgcgcattc tcgaagggct ggcgcaaaac  1020
ggcatcatgg aggagcagga agcgcaggca ttgacgctgg cgtacaccac attgcgtgat  1080
gagctgcacc acctggcgct gcaagagttg ccgggacatg tggcgctctc ctgttttgtc  1140
gccgagcgtg cgcttattaa aaccagctgg gacaagtggc tggtggaa               1188

SEQ ID NO: 154         moltype = DNA  length = 2206
FEATURE                Location/Qualifiers
misc_feature           1..2206
                       note = Synthetic polynucleotide
misc_feature           1..2206
                       note = glnE-delta-AR-2 with 500bp flank
source                 1..2206
                       mol_type = other DNA
                       organism = synthetic construct
SEQUENCE: 154
gcgcaaagcg agtgctcact tacgtgatct gttgacacaa tctgaagcga ccataacttc  60
tgccgtttca gcgaatacgg cggtgtggag cgcacaatca gccctggcga agctggtgct  120
caccgagtgg ctagtgacgc agggctggcg aaccttcctt gatgaaaaag cgcaggccaa  180
```

```
attcgccgac tcctttaaac gctttgctga catccatctg tcacgcagcg ccgccgagct  240
gaaaaaagcc tttgcccaac cgctgggcga cagctatcgc gaccagttgc cgcgcctggc  300
gcgtgatatc gactgcgcgt tactgctggc cgggcattac gatcgcgcgc gcgccgtgga  360
atggctggaa aactggcagg ggcttcagca cgccattgaa acgcgccaga gagtcgaaat  420
cgaacatttc cgtaataccg cgattaccca ggagccgttc tggttgcaca gcggaaaacg  480
ttaacgaaag gatatttcgc atggcactga aacacctcat ttccctgtgt gccgcgtcgc  540
cgatggttgc cagtcagctg gcgcgctacc cgatcctgct tgatgaattg ctcgacccga  600
atacgctcta tcaaccgacg gcgatgaatg cctatcgcga tgagctgcgc caatacctgc  660
tgcgcgtgcc ggaagatgat gaagagcaac agcttgaggc gctgcggcag tttaagcagg  720
cgcagttgct gcgcgtggcg gcggcggata ttgccggtac gttgccagta atgaaagtga  780
gcgatcactt aacctggctg gcggaagcga ttattgatgc ggtggtgcag caagcctggg  840
ggcagatggt ggcgcgttat ggccagccaa cgcatctgca cgatcgcgaa gggcgcggtt  900
ttgcggtggt cggttatggc aagctgggcg gctgggagct gggttacagc tccgatctgg  960
atctggtatt cctgcacgac tgcccgatgg atgtgatgac cgatggcgag cgtgaaatcg  1020
atggtcgcca gttctatttg cgtctcgcgc agcgcgtgat gcacctgttt agcacgcgca  1080
cgtcgtccgg catcctttat gaagttgatg cgcgtctgcg tccatctggc gctgcgggga  1140
tgctggtcac tactacggaa tcgttcgccg attaccagca aaacgaagcc tggacgtggg  1200
aacatcaggc gctggcccgt gcgcgcgtgg tgtacggcga tccgcaactg accgccgaat  1260
ttgacgccat tcgccgcgat attctgatga cgcctcgcga cggcgcaacg ctgcaaaccg  1320
acgtgcgaga aatgcgcgag aaaatgcgtg cccatcttgg caacaagcat aaagaccgct  1380
tcgatctgaa agccgatgaa ggcggtatca ccgacatcga gtttatcgcc caatatctgg  1440
tgctgcgctt tgcccatgac aagccgaaac tgacgcgctg gtcggataat gtgcgcattc  1500
tcgaagggct ggcgcaaaac ggcatcatgg aggagcagga agcgcaggca ttgacgctgg  1560
cgtacaccac attgcgtgat gagctgcacc acctggcgct gcaagagttg ccgggacatg  1620
tggcgctctc ctgttttgtc gccgagcgtg cgcttattaa aaccagctgg gacaagtggc  1680
tggtggaacc gtgcgccccg gcgtaagtgt ggtatcatcg cgcgcaaatt ttgtatctct  1740
caggagacag gaatgaaagt gacgctgcca gagtttaagc aagccggtgt aatggtggtg  1800
ggtgatgtga tgctggatcg ttactggtat ggcccaacca gccgtatctc tccggaagcg  1860
ccagtcccgg ttgttaaagt cgataccatt gaagagcgtc ctggcggcgc ggcaaacgtg  1920
gcgatgaata tcgcctcact gggcgccacg gcgcgtctgg ttggcctgac tggcattgac  1980
gatgcggcgc gcgcgctgag caaagcgctg gccgatgtta acgttaaatg tgacttcgtt  2040
tctgttccga cgcatcccac catcactaag ctgcgcgtgc tgtcgcgtaa ccagcagctg  2100
attcgcctgg actttgaaga gggttttgaa ggagtcgatc cgcaaccgat gcatgaacgc  2160
atcagccagg cgcttggtaa tattggcgcg ctggtgctgt cggatt                2206
```

```
SEQ ID NO: 155          moltype = DNA  length = 1563
FEATURE                 Location/Qualifiers
misc_feature            1..1563
                        note = Synthetic polynucleotide
misc_feature            1..1563
                        note = glnE-delta-AR-1
source                  1..1563
                        mol_type = other DNA
                        organism = synthetic construct
SEQUENCE: 155
atgtttaacg atctgattgg cgatgatgaa acggattcgc cggaagatgc gctttctgag  60
agctggcgcg aattgtggca ggatgcgttg caggaggagg attccacgcc cgtgctggcg  120
catctctcag aggacgatcg ccgccgcgtg gtggcgctga ttgccgattt tcgcaaagag  180
ttggataaac gcaccattgg cccgcgaggg cggcaggtac tcgatcactt aatgccgcat  240
ctgctcagcg atgtatgctc gcgcgacgat gcgccagtac cgctgtcacg cctgacgccg  300
ctgctcaccg gaattattac ccgcaccact taccttgagc tgctaagtga atttcccggc  360
gcactgaaac acctcatttc cctgtgtgcc gcgtcgccga tggttgccag tcagctggcg  420
cgctacccga tcctgcttga tgaattgctc gacccgaata cgctctatca accgacggcg  480
atgaatgcct atcgcgatga gctgcgccaa tacctgctgc gcgtgccgga agatgatgaa  540
gagcaacagc ttgaggcgct gcggcagttt aagcaggcgc agttgctgcg cgtggcggcg  600
gcggatattg ccggtacgtt gccagtaatg aaagtgagcg atcacttaac ctggctggcg  660
gaagcgatta ttgatgcggt ggtgcagcaa gcctgggggc agatggtggc gcgttatggc  720
cagccaacgc atctgcacga tcgcgaaggg cgcggttttg cggtggtcgg ttatggcaag  780
ctgggcggct gggagctggg ttacagctcc gatctggatc tggtattcct gcacgactgc  840
ccgatggatg tgatgaccga tggcgagcgt gaaatcgatg gtcgccagtt ctatttgcgt  900
ctcgcgcagc gcgtgatgca cctgtttagc acgcgcacgt cgtccggcat cctttatgaa  960
gttgatgcgc gtctgcgtcc atctggcgct gcggggatgc tggtcactac tacggaatcg  1020
ttcgccgatt accagcaaaa cgaagcctgg acgtgggaac atcaggcgct ggcccgtgcg  1080
cgcgtggtgt acggcgatcc gcaactgacc gccgaatttg acgccattcg ccgcgatatt  1140
ctgatgacgc ctcgcgacgg cgcaacgctg caaaccgacg tgcgagaaat gcgcgagaaa  1200
atgcgtgccc atcttggcaa caagcataaa gaccgcttcg atctgaaagc cgatgaaggc  1260
ggtatcaccg acatcgagtt tatcgcccaa tatctggtgc tgcgctttgc ccatgacaag  1320
ccgaaactga cgcgctggtc ggataatgtg cgcattctcg aagggctggc gcaaaacggc  1380
atcatggagg agcaggaagc gcaggcattg acgctggcgt acaccacatt gcgtgatgag  1440
ctgcaccacc tggcgctgca agagttgccg ggacatgtgg cgctctcctg ttttgtcgcc  1500
gagcgtgcgc ttattaaaac cagctgggac aagtggctgg tggaaccgtg cgccccggcg  1560
taa                                                               1563
```

```
SEQ ID NO: 156          moltype = DNA  length = 461
FEATURE                 Location/Qualifiers
misc_feature            1..461
                        note = Synthetic polynucleotide
misc_feature            1..461
                        note = delta-nifL::Prm1
```

```
source                1..461
                      mol_type = other DNA
                      organism = synthetic construct
SEQUENCE: 156
atgaccctga atatgatgat ggatgccggc cgtcctgtaa taataaccgg acaattcgga  60
ctgattaaaa aagcgccctt gtggcgcttt ttttatattc ccgcctccat ttaaaataaa  120
aaatccaatc ggatttcact atttaaactg gccattatct aagatgaatc cgatggaagc  180
tcgctgtttt aacacgcgtt ttttaacctt ttattgaaag tcggtgcttc tttgagcgaa  240
cgatcaaatt taagtggatt cccatcaaaa aaatattctc aacctaaaaa agtttgtgta  300
atacttgtaa cgctacatgg agattaactc aatctagagg gtattaataa tgaatcgtac  360
taaactggta ctgggcgcaa ctcacttcac accccgaagg gggaagttgc ctgaccctac  420
gattcccgct atttcattca ctgaccggag gttcaaaatg a                     461

SEQ ID NO: 157        moltype = DNA  length = 1461
FEATURE               Location/Qualifiers
misc_feature          1..1461
                      note = Synthetic polynucleotide
misc_feature          1..1461
                      note = delta-nifL::Prm1 with 500bp flank
source                1..1461
                      mol_type = other DNA
                      organism = synthetic construct
SEQUENCE: 157
accggatacg agagaaaagt gtctacatcg gttcggttga tattgaccgg cgcatccgcc  60
agcccgccca gtttctggtg gatctgtttg gcgattttgc gggtcttgcc ggtgtcggtg  120
ccgaaaaaaa taccaatatt tgccataaca cacgctcctg ttgaaaaaga gatcccgccg  180
ggaaatgcgg tgaacgtgtc tgatattgcg aagagtgtgc cagttttggt cgcgggcaaa  240
acctgcacca gtttggttat taatgcacca gtctggcgct ttttttcgcc gagtttctcc  300
tcgctaatgc ccgccaggcg cggctttggc gctgatagcg cgctgaatac cgatctggat  360
caaggttttg tcgggttatc agccaaaagg tgcactcttt gcatggttat acgtgcctga  420
catgttgtcc gggcgacaaa cggcctggtg gcacaaattg tcagaactac gacacgacta  480
actgaccgca ggagtgtgcg atgaccctga atatgatgat ggatgccggc cgtcctgtaa  540
taataaccgg acaattcgga ctgattaaaa aagcgccctt gtggcgcttt ttttatattc  600
ccgcctccat ttaaaataaa aaatccaatc ggatttcact atttaaactg gccattatct  660
aagatgaatc cgatggaagc tcgctgtttt aacacgcgtt ttttaacctt ttattgaaag  720
tcggtgcttc tttgagcgaa cgatcaaatt taagtggatt cccatcaaaa aaatattctc  780
aacctaaaaa agtttgtgta atacttgtaa cgctacatgg agattaactc aatctagagg  840
gtattaataa tgaatcgtac taaactggta ctgggcgcaa ctcacttcac accccgaagg  900
gggaagttgc ctgaccctac gattcccgct atttcattca ctgaccggag gttcaaaatg  960
acccagcgaa ccgagtcggg taataccgtc tggcgcttcg atttgtccca gcagttcact  1020
gcgatgcagc gcataagcgt ggtactcagc cgggcgaccg aggtcgatca gacgctccag  1080
caagtgctgt gcgtattgca caatgacgcc tttttgcagc acggcatgat ctgtctgtac  1140
gacagccagc aggcgatttt gaatattgaa gcgttgcagg aagccgatca gcagttaatc  1200
cccggcagct cgcaaatccg ctatcgtccg ggcgaagggc tggtcgggac ggtgctttcg  1260
cagggccaat cattagtgct ggcgcgcgtt gctgacgatc agcgctttct tgaccggctc  1320
gggttgtatg attacaacct gccgtttatc gccgtgccgc tgatagggcc agatgcgcag  1380
actttcggtg tgctgacggc acaacccatg gcgcgttacg aagagcgatt acccgcctgc  1440
acccgctttc tggaaacggt c                                           1461

SEQ ID NO: 158        moltype = DNA  length = 2563
FEATURE               Location/Qualifiers
misc_feature          1..2563
                      note = Synthetic polynucleotide
misc_feature          1..2563
                      note = glnE-delta-AR-1 with 500bp flank
source                1..2563
                      mol_type = other DNA
                      organism = synthetic construct
SEQUENCE: 158
gcgcaaagcg agtgctcact tacgtgatct gttgacacaa tctgaagcga ccataacttc  60
tgccgtttca gcgaatacgg cggtgtggag cgcacaatca gccctggcga agctggtgct  120
caccgagtgg ctagtgacgc agggctggcg aaccttcctt gatgaaaaag cgcaggccaa  180
attcgccgac tcctttaaac gctttgctga catccatctg tcacgcagcg ccgccgagct  240
gaaaaaagcc tttgcccaac cgctgggcga cagctatcgc gaccagttgc cgcgcctggc  300
gcgtgatatc gactgcgcgt tactgctggc cgggcattac gatcgcgcgc gcgccgtgga  360
atggctggaa aactggcagg ggcttcagca cgccattgaa acgcgccaga gagtcgaaat  420
cgaacatttc cgtaataccg cgattaccca ggagccgttc tggttgcaca gcggaaaacg  480
ttaacgaaag gatatttcgc atgtttaacg atctgattgg cgatgatgaa acggattcgc  540
cggaagatgc gctttctgag agctggcgcg aattgtggca ggatgcgttg caggaggagg  600
attccacgcc cgtgctggcg catctctcag aggacgatcg ccgccgcgtg gtggcgctga  660
ttgccgattt tcgcaaagag ttggataaac gcaccattgg cccgcgaggg cggcaggtac  720
tcgatcactt aatgccgcat ctgctcagcg atgtatgctc gcgcgacgat gcgccagtac  780
cgctgtcacg cctgacgccg ctgctcaccg gaattattac ccgcaccact taccttgagc  840
tgctaagtga atttcccggc gcactgaaac acctcatttc cctgtgtgcc gcgtcgccga  900
tggttgccag tcagctggcg cgctacccga tcctgcttga tgaattgctc gacccgaata  960
cgctctatca accgacggcg atgaatgcct atcgcgatga gctgcgccaa tacctgctgc  1020
gcgtgccgga agatgatgaa gagcaacagc ttgaggcgct gcggcagttt aagcaggcgc  1080
agttgctgcg cgtggcggcg gcggatattg ccggtacgtt gccagtaatg aaagtgagcg  1140
atcacttaac ctggctggcg gaagcgatta ttgatgcggt ggtgcagcaa gcctgggggc  1200
```

```
agatggtggc gcgttatggc cagccaacgc atctgcacga tcgcgaaggg cgcggttttg  1260
cggtggtcgg ttatggcaag ctgggcggct gggagctggg ttacagctcc gatctggatc  1320
tggtattcct gcacgactgc ccgatggatg tgatgaccga tggcgagcgt gaaatcgatg  1380
gtcgccagtt ctatttgcgt ctcgcgcagc gcgtgatgca cctgtttagc acgcgcacgt  1440
cgtccggcat cctttatgaa gttgatgcgc gtctgcgtcc atctggcgct gcggggatgc  1500
tggtcactac tacggaatcg ttcgccgatt accagcaaaa cgaagcctgg acgtgggaac  1560
atcaggcgct ggcccgtgcg cgcgtggtgt acggcgatcc gcaactgacc gccgaatttg  1620
acgccattcg ccgcgatatt ctgatgacgc ctcgcgacgg cgcaacgctg caaaccgacg  1680
tgcgagaaat gcgcgagaaa atgcgtgccc atcttggcaa caagcataaa gaccgcttcg  1740
atctgaaagc cgatgaaggc ggtatcaccg acatcgagtt tatcgcccaa tatctggtgc  1800
tgcgctttgc ccatgacaag ccgaaactga cgcgctggtc ggataatgtg cgcattctcg  1860
aagggctggc gcaaaacggc atcatggagg agcaggaagc gcaggcattg acgctggcgt  1920
acaccacatt gcgtgatgag ctgcaccacc tggcgctgca agagttgccg ggacatgtgg  1980
cgctctcctg ttttgtcgcc gagcgtgcgc ttattaaaac cagctgggac aagtggctgg  2040
tggaaccgtg cgcccggcg taagtgtggt atcatcgcgc gcaaattttg tatctctcag  2100
gagacaggaa tgaaagtgac gctgccagag tttaagcaag ccggtgtaat ggtggtgggt  2160
gatgtgatgc tggatcgtta ctggtatggc ccaaccagcc gtatctctcc ggaagcgcca  2220
gtcccggttg ttaaagtcga taccattgaa gagcgtcctg gcggcgcggc aaacgtggcg  2280
atgaatatcg cctcactggg cgccacggcg cgtctggttg gcctgactgg cattgacgat  2340
gcggcgcgcg cgctgagcaa agcgctggcc gatgttaacg ttaaatgtga cttcgtttct  2400
gttccgacgc atcccaccat cactaagctg cgcgtgctgt cgcgtaacca gcagctgatt  2460
cgcctggact ttgaagaggg ttttgaagga gtcgatccgc aaccgatgca tgaacgcatc  2520
agccaggcgc ttggtaatat tggcgcgctg gtgctgtcgg att                    2563
```

```
SEQ ID NO: 159          moltype = DNA  length = 1563
FEATURE                 Location/Qualifiers
misc_feature            1..1563
                        note = Synthetic polynucleotide
misc_feature            1..1563
                        note = glnE-delta-AR-1
source                  1..1563
                        mol_type = other DNA
                        organism = synthetic construct
SEQUENCE: 159
atgtttaacg atctgattgg cgatgatgaa acggattcgc cggaagatgc gctttctgag  60
agctggcgcg aattgtggca ggatgcgttg caggaggagg attccacgcc cgtgctggcg  120
catctctcag aggacgatcg ccgccgcgtg gtggcgctga ttgccgattt tcgcaaagag  180
ttggataaac gcaccattgg cccgcgaggg cggcaggtac tcgatcactt aatgccgcat  240
ctgctcagcg atgtatgctc gcgcgacgat gcgccagtac cgctgtcacg cctgacgccg  300
ctgctcaccg gaattattac ccgcaccact taccttgagc tgctaagtga atttcccggc  360
gcactgaaac acctcatttc cctgtgtgcc gcgtcgccga tggttgccag tcagctggcg  420
cgctacccga tcctgcttga tgaattgctc gacccgaata cgctctatca accgacggcg  480
atgaatgcct atcgcgatga gctgcgccaa tacctgctgc gcgtgccgga agatgatgaa  540
gagcaacagc ttgaggcgct gcggcagttt aagcaggcgc agttgctgcg cgtggcggcg  600
gcggatattg ccggtacgtt gccagtaatg aaagtgagcg atcacttaac ctggctggcg  660
gaagcgatta ttgatgcggt ggtgcagcaa gcctgggggc agatggtggc gcgttatggc  720
cagccaacgc atctgcacga tcgcgaaggg cgcggttttg cggtggtcgg ttatggcaag  780
ctgggcggct gggagctggg ttacagctcc gatctggatc tggtattcct gcacgactgc  840
ccgatggatg tgatgaccga tggcgagcgt gaaatcgatg gtcgccagtt ctatttgcgt  900
ctcgcgcagc gcgtgatgca cctgtttagc acgcgcacgt cgtccggcat cctttatgaa  960
gttgatgcgc gtctgcgtcc atctggcgct gcggggatgc tggtcactac tacggaatcg  1020
ttcgccgatt accagcaaaa cgaagcctgg acgtgggaac atcaggcgct ggcccgtgcg  1080
cgcgtggtgt acggcgatcc gcaactgacc gccgaatttg acgccattcg ccgcgatatt  1140
ctgatgacgc ctcgcgacgg cgcaacgctg caaaccgacg tgcgagaaat gcgcgagaaa  1200
atgcgtgccc atcttggcaa caagcataaa gaccgcttcg atctgaaagc cgatgaaggc  1260
ggtatcaccg acatcgagtt tatcgcccaa tatctggtgc tgcgctttgc ccatgacaag  1320
ccgaaactga cgcgctggtc ggataatgtg cgcattctcg aagggctggc gcaaaacggc  1380
atcatggagg agcaggaagc gcaggcattg acgctggcgt acaccacatt gcgtgatgag  1440
ctgcaccacc tggcgctgca agagttgccg ggacatgtgg cgctctcctg ttttgtcgcc  1500
gagcgtgcgc ttattaaaac cagctgggac aagtggctgg tggaaccgtg cgcccggcg  1560
taa                                                                1563
```

```
SEQ ID NO: 160          moltype = DNA  length = 2563
FEATURE                 Location/Qualifiers
misc_feature            1..2563
                        note = Synthetic polynucleotide
misc_feature            1..2563
                        note = glnE-delta-AR-1 with 500bp flank
source                  1..2563
                        mol_type = other DNA
                        organism = synthetic construct
SEQUENCE: 160
gcgcaaagcg agtgctcact tacgtgatct gttgacacaa tctgaagcga ccataacttc  60
tgccgtttca gcgaatacgg cggtgtggag cgcacaatca gccctggcga agctggtgct  120
caccgagtgg ctagtgacgc agggctggcg aaccttcctt gatgaaaaag cgcaggccaa  180
attcgccgac tcctttaaac gctttgctga catccatctg tcacgcagcg ccgccgagct  240
gaaaaaagcc tttgcccaac cgctgggcga cagctatcgc gaccagttgc cgcgcctggc  300
gcgtgatatc gactgcgcgt tactgctggc cgggcattac gatcgcgcgc gcgccgtgga  360
atggctggaa aactggcagg ggcttcagca cgccattgaa acgcgccaga gagtcgaaat  420
```

```
cgaacatttc cgtaataccg cgattaccca ggagccgttc tggttgcaca gcggaaaacg  480
ttaacgaaag gatatttcgc atgtttaacg atctgattgg cgatgatgaa acggattcgc  540
cggaagatgc gctttctgag agctggcgcg aattgtggca ggatgcgttg caggaggagg  600
attccacgcc cgtgctggcg catctctcag aggacgatcg ccgccgcgtg gtggcgctga  660
ttgccgattt tcgcaaagag ttggataaac gcaccattgg cccgcgaggg cggcaggtac  720
tcgatcactt aatgccgcat ctgctcagcg atgtatgctc gcgcgacgat gcgccagtac  780
cgctgtcacg cctgacgccg ctgctcaccg gaattattac ccgcaccact taccttgagc  840
tgctaagtga atttcccggc gcactgaaac acctcatttc cctgtgtgcc gcgtcgccga  900
tggttgccag tcagctggcg cgctacccga tcctgcttga tgaattgctc gacccgaata  960
cgctctatca accgacggcg atgaatgcct atcgcgatga gctgcgccaa tacctgctgc  1020
gcgtgccgga agatgatgaa gagcaacagc ttgaggcgct gcggcagttt aagcaggcgc  1080
agttgctgcg cgtggcggcg gcggatattg ccggtacgtt gccagtaatg aaagtgagcg  1140
atcacttaac ctggctggcg gaagcgatta ttgatgcggt ggtgcagcaa gcctgggggc  1200
agatggtggc gcgttatggc cagccaacgc atctgcacga tcgcgaaggg cgcggttttg  1260
cggtggtcgg ttatggcaag ctgggcggct gggagctggg ttacagctcc gatctggatc  1320
tggtattcct gcacgactgc ccgatggatg tgatgaccga tggcgagcgt gaaatcgatg  1380
gtcgccagtt ctatttgcgt ctcgcgcagc gcgtgatgca cctgtttagc acgcgcacgt  1440
cgtccggcat cctttatgaa gttgatgcgc gtctgcgtcc atctggcgct gcggggatgc  1500
tggtcactac tacggaatcg ttcgccgatt accagcaaaa cgaagcctgg acgtgggaac  1560
atcaggcgct ggcccgtgcg cgcgtggtgt acggcgatcc gcaactgacc gccgaatttg  1620
acgccattcg ccgcgatatt ctgatgacgc ctcgcgacgg cgcaacgctg caaaccgacg  1680
tgcgagaaat gcgcgagaaa atgcgtgccc atcttggcaa caagcataaa gaccgcttcg  1740
atctgaaagc cgatgaaggc ggtatcaccg acatcgagtt tatcgcccaa tatctggtgc  1800
tgcgctttgc ccatgacaag ccgaaactga cgcgctggtc ggataatgtg cgcattctcg  1860
aagggctggc gcaaaacggc atcatggagg agcaggaagc gcaggcattg acgctggcgt  1920
acaccacatt gcgtgatgag ctgcaccacc tggcgctgca agagttgccg ggacatgtgg  1980
cgctctcctg ttttgtcgcc gagcgtgcgc ttattaaaac cagctgggac aagtggctgg  2040
tggaaccgtg cgcccggcg taagtgtggt atcatcgcgc gcaaattttg tatctctcag  2100
gagacaggaa tgaaagtgac gctgccagag tttaagcaag ccggtgtaat ggtggtgggt  2160
gatgtgatgc tggatcgtta ctggtatggc ccaaccagcc gtatctctcc ggaagcgcca  2220
gtcccggttg ttaaagtcga taccattgaa gagcgtcctg gcggcgcggc aaacgtggcg  2280
atgaatatcg cctcactggg cgccacggcg cgtctggttg gcctgactgg cattgacgat  2340
gcggcgcgcg cgctgagcaa agcgctggcc gatgttaacg ttaaatgtga cttcgtttct  2400
gttccgacgc atcccaccat cactaagctg cgcgtgctgt cgcgtaacca gcagctgatt  2460
cgcctggact ttgaagaggg ttttgaagga gtcgatccgc aaccgatgca tgaacgcatc  2520
agccaggcgc ttggtaatat tggcgcgctg gtgctgtcgg att                    2563
```

```
SEQ ID NO: 161         moltype = DNA  length = 426
FEATURE                Location/Qualifiers
misc_feature           1..426
                       note = Synthetic polynucleotide
misc_feature           1..426
                       note = delta-nifL::Prm5
source                 1..426
                       mol_type = other DNA
                       organism = synthetic construct
SEQUENCE: 161
atgaccctga atatgatgat ggatgccggc ggacatcatc gcgacaaaca atattaatac  60
cggcaaccac accggcaatt tacgagactg cgcaggcatc ctttctcccg tcaatttctg  120
tcaaataaag taaaagaggc agtctacttg aattaccccc ggctggttga gcgtttgttg  180
aaaaaaagta actgaaaaat ccgtagaata gcgccactct gatggttaat taacctattc  240
aattaagaat tatctggatg aatgtgccat taaatgcgca gcataatggt gcgttgtgcg  300
ggaaaactgc tttttttga aagggttggt cagtagcgga aacaactcac ttcacacccc  360
gaagggggaa gttgcctgac cctacgattc ccgctatttc attcactgac cggaggttca  420
aaatga                                                            426
```

```
SEQ ID NO: 162         moltype = DNA  length = 1426
FEATURE                Location/Qualifiers
misc_feature           1..1426
                       note = Synthetic polynucleotide
misc_feature           1..1426
                       note = delta-nifL::Prm5 with 500bp flank
source                 1..1426
                       mol_type = other DNA
                       organism = synthetic construct
SEQUENCE: 162
accggatacg agagaaaagt gtctacatcg gttcggttga tattgaccgg cgcatccgcc  60
agcccgccca gtttctggtg gatctgtttg gcgattttgc gggtcttgcc ggtgtcggtg  120
ccgaaaaaaa taccaatatt tgccataaca cacgctcctg ttgaaaaaga gatcccgccg  180
ggaaatgcgg tgaacgtgtc tgatattgcg aagagtgtgc cagttttggt cgcgggcaaa  240
acctgcacca gtttggttat taatgcacca gtctggcgct ttttttcgcc gagtttctcc  300
tcgctaatgc ccgccaggcg cggctttggc gctgatagcg cgctgaatac cgatctggat  360
caaggttttg tcgggttatc agccaaaagg tgcactcttt gcatggttat acgtgcctga  420
catgttgtcc gggcgacaaa cggcctggtg gcacaaattg tcagaactac gacacgacta  480
actgaccgca ggagtgtgcg atgaccctga atatgatgat ggatgccggc ggacatcatc  540
gcgacaaaca atattaatac cggcaaccac accggcaatt tacgagactg cgcaggcatc  600
ctttctcccg tcaatttctg tcaaataaag taaaagaggc agtctacttg aattaccccc  660
ggctggttga gcgtttgttg aaaaaaagta actgaaaaat ccgtagaata gcgccactct  720
gatggttaat taacctattc aattaagaat tatctggatg aatgtgccat taaatgcgca  780
```

```
gcataatggt gcgttgtgcg ggaaaactgc ttttttttga aagggttggt cagtagcgga  840
aacaactcac ttcacacccc gaagggggaa gttgcctgac cctacgattc ccgctatttc  900
attcactgac cggaggttca aaatgaccca gcgaaccgag tcgggtaata ccgtctggcg  960
cttcgatttg tcccagcagt tcactgcgat gcagcgcata agcgtggtac tcagccgggc  1020
gaccgaggtc gatcagacgc tccagcaagt gctgtgcgta ttgcacaatg acgccttttt  1080
gcagcacggc atgatctgtc tgtacgacag ccagcaggcg attttgaata ttgaagcgtt  1140
gcaggaagcc gatcagcagt taatccccgg cagctcgcaa atccgctatc gtccgggcga  1200
agggctggtc gggacggtgc tttcgcaggg ccaatcatta gtgctggcgc gcgttgctga  1260
cgatcagcgc tttcttgacc ggctcgggtt gtatgattac aacctgccgt ttatcgccgt  1320
gccgctgata gggccagatg cgcagacttt cggtgtgctg acggcacaac ccatggcgcg  1380
ttacgaagag cgattacccg cctgcacccg ctttctggaa acggtc                1426

SEQ ID NO: 163         moltype = DNA  length = 461
FEATURE                Location/Qualifiers
misc_feature           1..461
                       note = Synthetic polynucleotide
misc_feature           1..461
                       note = delta-nifL::Prm1
source                 1..461
                       mol_type = other DNA
                       organism = synthetic construct
SEQUENCE: 163
atgaccctga atatgatgat ggatgccggc cgtcctgtaa taataaccgg acaattcgga  60
ctgattaaaa aagcgccctt gtggcgcttt ttttatattc ccgcctccat ttaaaataaa  120
aaatccaatc ggatttcact atttaaactg gccattatct aagatgaatc cgatggaagc  180
tcgctgtttt aacacgcgtt ttttaacctt ttattgaaag tcggtgcttc tttgagcgaa  240
cgatcaaatt taagtggatt cccatcaaaa aaatattctc aacctaaaaa agtttgtgta  300
atacttgtaa cgctacatgg agattaactc aatctagagg gtattaataa tgaatcgtac  360
taaactggta ctgggcgcaa ctcacttcac accccgaagg gggaagttgc ctgaccctac  420
gattcccgct atttcattca ctgaccggag gttcaaaatg a                     461

SEQ ID NO: 164         moltype = DNA  length = 1461
FEATURE                Location/Qualifiers
misc_feature           1..1461
                       note = Synthetic polynucleotide
misc_feature           1..1461
                       note = delta-nifL::Prm1 with 500bp flank
source                 1..1461
                       mol_type = other DNA
                       organism = synthetic construct
SEQUENCE: 164
accggatacg agagaaaagt gtctacatcg gttcggttga tattgaccgg cgcatccgcc  60
agcccgccca gtttctggtg gatctgtttg gcgattttgc gggtcttgcc ggtgtcggtg  120
ccgaaaaaaa taccaatatt tgccataaca cacgctcctg ttgaaaaaga gatcccgccg  180
ggaaatgcgg tgaacgtgtc tgatattgcg aagagtgtgc cagttttggt cgcgggcaaa  240
acctgcacca gtttggttat taatgcacca gtctggcgct ttttttcgcc gagtttctcc  300
tcgctaatgc ccgccaggcg cggctttggc gctgatagcg cgctgaatac cgatctggat  360
caaggttttg tcgggttatc agccaaaagg tgcactcttt gcatggttat acgtgcctga  420
catgttgtcc gggcgacaaa cggcctggtg gcacaaattg tcagaactac gacacgacta  480
actgaccgca ggagtgtgcg atgaccctga atatgatgat ggatgccggc cgtcctgtaa  540
taataaccgg acaattcgga ctgattaaaa aagcgccctt gtggcgcttt ttttatattc  600
ccgcctccat ttaaaataaa aaatccaatc ggatttcact atttaaactg gccattatct  660
aagatgaatc cgatggaagc tcgctgtttt aacacgcgtt ttttaacctt ttattgaaag  720
tcggtgcttc tttgagcgaa cgatcaaatt taagtggatt cccatcaaaa aaatattctc  780
aacctaaaaa agtttgtgta atacttgtaa cgctacatgg agattaactc aatctagagg  840
gtattaataa tgaatcgtac taaactggta ctgggcgcaa ctcacttcac accccgaagg  900
gggaagttgc ctgaccctac gattcccgct atttcattca ctgaccggag gttcaaaatg  960
acccagcgaa ccgagtcggg taataccgtc tggcgcttcg atttgtccca gcagttcact  1020
gcgatgcagc gcataagcgt ggtactcagc cgggcgaccg aggtcgatca gacgctccag  1080
caagtgctgt gcgtattgca caatgacgcc tttttgcagc acggcatgat ctgtctgtac  1140
gacagccagc aggcgatttt gaatattgaa gcgttgcagg aagccgatca gcagttaatc  1200
cccggcagct cgcaaatccg ctatcgtccg ggcgaagggc tggtcgggac ggtgctttcg  1260
cagggccaat cattagtgct ggcgcgcgtt gctgacgatc agcgctttct tgaccggctc  1320
gggttgtatg attacaacct gccgtttatc gccgtgccgc tgatagggcc agatgcgcag  1380
actttcggtg tgctgacggc acaacccatg gcgcgttacg aagagcgatt acccgcctgc  1440
acccgctttc tggaaacggt c                                           1461

SEQ ID NO: 165         moltype = DNA  length = 1188
FEATURE                Location/Qualifiers
misc_feature           1..1188
                       note = Synthetic polynucleotide
misc_feature           1..1188
                       note = glnE-delta-AR-2
source                 1..1188
                       mol_type = other DNA
                       organism = synthetic construct
SEQUENCE: 165
atggcactga aacacctcat ttccctgtgt gccgcgtcgc cgatggttgc cagtcagctg  60
gcgcgctacc cgatcctgct tgatgaattg ctcgacccga atacgctcta tcaaccgacg  120
```

```
gcgatgaatg cctatcgcga tgagctgcgc caatacctgc tgcgcgtgcc ggaagatgat  180
gaagagcaac agcttgaggc gctgcggcag tttaagcagg cgcagttgct gcgcgtggcg  240
gcggcggata ttgccggtac gttgccagta atgaaagtga gcgatcactt aacctggctg  300
gcggaagcga ttattgatgc ggtggtgcag caagcctggg ggcagatggt ggcgcgttat  360
ggccagccaa cgcatctgca cgatcgcgaa gggcgcggtt ttgcggtggt cggttatggc  420
aagctgggcg gctgggagct gggttacagc tccgatctgg atctggtatt cctgcacgac  480
tgcccgatgg atgtgatgac cgatggcgag cgtgaaatcg atggtcgcca gttctatttg  540
cgtctcgcgc agcgcgtgat gcacctgttt agcacgcgca cgtcgtccgg catcctttat  600
gaagttgatg cgcgtctgcg tccatctggc gctgcgggga tgctggtcac tactacggaa  660
tcgttcgccg attaccagca aaacgaagcc tggacgtggg aacatcaggc gctggcccgt  720
gcgcgcgtgg tgtacggcga tccgcaactg accgccgaat ttgacgccat tcgccgcgat  780
attctgatga cgcctcgcga cggcgcaacg ctgcaaaccg acgtgcgaga aatgcgcgag  840
aaaatgcgtg cccatcttgg caacaagcat aaagaccgct tcgatctgaa agccgatgaa  900
ggcggtatca ccgacatcga gtttatcgcc caatatctgg tgctgcgctt tgcccatgac  960
aagccgaaac tgacgcgctg gtcggataat gtgcgcattc tcgaagggct ggcgcaaaac  1020
ggcatcatgg aggagcagga agcgcaggca ttgacgctgg cgtacaccac attgcgtgat  1080
gagctgcacc acctggcgct gcaagagttg ccgggacatg tggcgctctc ctgttttgtc  1140
gccgagcgtg cgcttattaa aaccagctgg gacaagtggc tggtggaa              1188
```

```
SEQ ID NO: 166          moltype = DNA  length = 2206
FEATURE                 Location/Qualifiers
misc_feature            1..2206
                        note = Synthetic polynucleotide
misc_feature            1..2206
                        note = glnE-delta-AR-2 with 500bp flank
source                  1..2206
                        mol_type = other DNA
                        organism = synthetic construct
SEQUENCE: 166
gcgcaaagcg agtgctcact tacgtgatct gttgacacaa tctgaagcga ccataacttc  60
tgccgtttca gcgaatacgg cggtgtggag cgcacaatca gccctggcga agctggtgct  120
caccgagtgg ctagtgacgc agggctggcg aaccttcctt gatgaaaaag cgcaggccaa  180
attcgccgac tcctttaaac gctttgctga catccatctg tcacgcagcg ccgccgagct  240
gaaaaaagcc tttgcccaac cgctgggcga cagctatcgc gaccagttgc cgcgcctggc  300
gcgtgatatc gactgcgcgt tactgctggc cgggcattac gatcgcgcgc gcgccgtgga  360
atggctggaa aactggcagg ggcttcagca cgccattgaa acgcgccaga gagtcgaaat  420
cgaacatttc cgtaataccg cgattaccca ggagccgttc tggttgcaca gcggaaaacg  480
ttaacgaaag gatatttcgc atggcactga aacacctcat ttccctgtgt gccgcgtcgc  540
cgatggttgc cagtcagctg gcgcgctacc cgatcctgct tgatgaattg ctcgacccga  600
atacgctcta tcaaccgacg gcgatgaatg cctatcgcga tgagctgcgc caatacctgc  660
tgcgcgtgcc ggaagatgat gaagagcaac agcttgaggc gctgcggcag tttaagcagg  720
cgcagttgct gcgcgtggcg gcggcggata ttgccggtac gttgccagta atgaaagtga  780
gcgatcactt aacctggctg gcggaagcga ttattgatgc ggtggtgcag caagcctggg  840
ggcagatggt ggcgcgttat ggccagccaa cgcatctgca cgatcgcgaa gggcgcggtt  900
ttgcggtggt cggttatggc aagctgggcg gctgggagct gggttacagc tccgatctgg  960
atctggtatt cctgcacgac tgcccgatgg atgtgatgac cgatggcgag cgtgaaatcg  1020
atggtcgcca gttctatttg cgtctcgcgc agcgcgtgat gcacctgttt agcacgcgca  1080
cgtcgtccgg catcctttat gaagttgatg cgcgtctgcg tccatctggc gctgcgggga  1140
tgctggtcac tactacggaa tcgttcgccg attaccagca aaacgaagcc tggacgtggg  1200
aacatcaggc gctggcccgt gcgcgcgtgg tgtacggcga tccgcaactg accgccgaat  1260
ttgacgccat tcgccgcgat attctgatga cgcctcgcga cggcgcaacg ctgcaaaccg  1320
acgtgcgaga aatgcgcgag aaaatgcgtg cccatcttgg caacaagcat aaagaccgct  1380
tcgatctgaa agccgatgaa ggcggtatca ccgacatcga gtttatcgcc caatatctgg  1440
tgctgcgctt tgcccatgac aagccgaaac tgacgcgctg gtcggataat gtgcgcattc  1500
tcgaagggct ggcgcaaaac ggcatcatgg aggagcagga agcgcaggca ttgacgctgg  1560
cgtacaccac attgcgtgat gagctgcacc acctggcgct gcaagagttg ccgggacatg  1620
tggcgctctc ctgttttgtc gccgagcgtg cgcttattaa aaccagctgg gacaagtggc  1680
tggtggaacc gtgcgccccg gcgtaagtgt ggtatcatcg cgcgcaaatt ttgtatctct  1740
caggagacag gaatgaaagt gacgctgcca gagtttaagc aagccggtgt aatggtggtg  1800
ggtgatgtga tgctggatcg ttactggtat ggcccaacca gccgtatctc tccggaagcg  1860
ccagtcccgg ttgttaaagt cgataccatt gaagagcgtc ctggcggcgc ggcaaacgtg  1920
gcgatgaata tcgcctcact gggcgccacg gcgcgtctgg ttggcctgac tggcattgac  1980
gatgcggcgc gcgcgctgag caaagcgctg gccgatgtta acgttaaatg tgacttcgtt  2040
tctgttccga cgcatcccac catcactaag ctgcgcgtgc tgtcgcgtaa ccagcagctg  2100
attcgcctgg actttgaaga gggttttgaa ggagtcgatc cgcaaccgat gcatgaacgc  2160
atcagccagg cgcttggtaa tattggcgcg ctggtgctgt cggatt                2206
```

```
SEQ ID NO: 167          moltype = DNA  length = 199
FEATURE                 Location/Qualifiers
misc_feature            1..199
                        note = Synthetic polynucleotide
misc_feature            1..199
                        note = delta-amtB
source                  1..199
                        mol_type = other DNA
                        organism = synthetic construct
SEQUENCE: 167
tttcgctgaa ggtgtgacca tgggccatca ggtgctggtg cagctggaaa gtgttgccat  60
cactatcgtg tggtctggcg tggtggcctt tattggttac aaactggcgg acatgacggt  120
```

```
aggcctgcgc gtaccggaag aacaagaacg tgaagggctg gatgtaaaca gccacggcga  180
aaacgcctat aacgcctga                                               199

SEQ ID NO: 168          moltype = DNA  length = 1199
FEATURE                 Location/Qualifiers
misc_feature            1..1199
                        note = Synthetic polynucleotide
misc_feature            1..1199
                        note = delta-amtB with 500bp flank
source                  1..1199
                        mol_type = other DNA
                        organism = synthetic construct
SEQUENCE: 168
tttcctttct gactctgccc gtccgggcgc actaacggcc tgaaatactc cctcttttca  60
ttcctggcac aacgattgca atgtctgttg cgtgttagct gcggccatta tcgaattcga  120
ctggaggggg atctatgaag ctggttaccg tggtgattaa gccattcaaa cttgaagacg  180
tgcgtgaagc gctttcttct attggtattc aagggttgac cgtaactgaa gtgaaaggct  240
ttggccgtca gaagggtcac gctgagctgt accgcggtgc ggaatatagc gttaatttcc  300
tgccgaaagt gaaaattgat gtggcgatcg ctgacgatca actcgatgaa gtaatcgatg  360
tgatcagcaa agcggcctac accggaaaaa ttggcgacgg caaaattttc gttgctgagc  420
tgcaacgcgt cattcgtatt cgtaccggcg aagccgacga agcggcactg taatacaaga  480
cacacagtga tggggatcgg tttcgctgaa ggtgtgacca tgggccatca ggtgctggtg  540
cagctggaaa gtgttgccat cactatcgtg tggtctggcg tggtggcctt tattggttac  600
aaactggcgg acatgacggt aggcctgcgc gtaccggaag aacaagaacg tgaagggctg  660
gatgtaaaca gccacggcga aaacgcctat aacgcctgat tgcgttgagt tatctcctga  720
gcataaaaaa gcctccattc ggaggctttt cttttttaa gtttaaagcg cggttagttg  780
cgattgcgca tgacgccttc ctgcacgctg gacgcgacca gcacaccctc ttgcgtatag  840
aactcgccgc gcacaaaacc gcgagcgctg gaggctgacg tgctttccac actgtagagc  900
agccattcgt tcatattaaa cggcgatgg aaccacatgg agtggtcaat ggtggcaacc  960
tgcataccgc gctcaaggaa gcccacgccg tgcggctgaa gtgcaaccgg caggaagtta  1020
aagtctgagg catatccaag cagatattga tgtacgcgaa aatcgtccgg caccgtgccg  1080
tttgcgcgga tccatacctg gcgggtggga tcggcaacgt ggcctttcag cgggttatga  1140
aactcaaccg ggcggatctc cagtggttta tcactaagaa acttctcttt ggcctgcgg   1199

SEQ ID NO: 169          moltype = DNA  length = 1563
FEATURE                 Location/Qualifiers
misc_feature            1..1563
                        note = Synthetic polynucleotide
misc_feature            1..1563
                        note = glnE-delta-AR-1
source                  1..1563
                        mol_type = other DNA
                        organism = synthetic construct
SEQUENCE: 169
atgtttaacg atctgattgg cgatgatgaa acggattcgc cggaagatgc gctttctgag  60
agctggcgcg aattgtggca ggatgcgttg caggaggagg attccacgcc cgtgctggcg  120
catctctcag aggacgatcg ccgccgcgtg gtggcgctga ttgccgattt tcgcaaagag  180
ttggataaac gcaccattgg cccgcgaggg cggcaggtac tcgatcactt aatgccgcat  240
ctgctcagcg atgtatgctc gcgcgacgat gcgccagtac cgctgtcacg cctgacgccg  300
ctgctcaccg gaattattac ccgcaccact taccttgagc tgctaagtga atttcccggc  360
gcactgaaac acctcatttc cctgtgtgcc gcgtcgccga tggttgccag tcagctggcg  420
cgctacccga tcctgcttga tgaattgctc gacccgaata cgctctatca accgacggcg  480
atgaatgcct atcgcgatga gctgcgccaa tacctgctgc gcgtgccgga agatgatgaa  540
gagcaacagc ttgaggcgct gcggcagttt aagcaggcgc agttgctgcg cgtggcggcg  600
gcggatattg ccggtacgtt gccagtaatg aaagtgagcg atcacttaac ctggctggcg  660
gaagcgatta ttgatgcggt ggtgcagcaa gcctgggggc agatggtggc gcgttatggc  720
cagccaacgc atctgcacga tcgcgaaggg cgcggttttg cggtggtcgg ttatggcaag  780
ctgggcggct gggagctggg ttacagctcc gatctggatc tggtattcct gcacgactgc  840
ccgatggatg tgatgaccga tggcgagcgt gaaatcgatg gtcgccagtt ctatttgcgt  900
ctcgcgcagc gcgtgatgca cctgtttagc acgcgcacgt cgtccggcat cctttatgaa  960
gttgatgcgc gtctgcgtcc atctggcgct gcggggatgc tggtcactac tacggaatcg  1020
ttcgccgatt accagcaaaa cgaagcctgg acgtgggaac atcaggcgct ggcccgtgcg  1080
cgcgtggtgt acggcgatcc gcaactgacc gccgaatttg acgccattcg ccgcgatatt  1140
ctgatgacgc ctcgcgacgg cgcaacgctg caaaccgacg tgcgagaaat gcgcgagaaa  1200
atgcgtgccc atcttggcaa caagcataaa gaccgcttcg atctgaaagc cgatgaaggc  1260
ggtatcaccg acatcgagtt tatcgcccaa tatctggtgc tgcgctttgc ccatgacaag  1320
ccgaaactga cgcgctggtc ggataatgtg cgcattctcg aagggctggc gcaaaacggc  1380
atcatggagg agcaggaagc gcaggcattg acgctggcgt acaccacatt gcgtgatgag  1440
ctgcaccacc tggcgctgca agagttgccg ggacatgtgg cgctctcctg ttttgtcgcc  1500
gagcgtgcgc ttattaaaac cagctgggac aagtggctgg tggaaccgtg cgccccggcg  1560
taa                                                                1563

SEQ ID NO: 170          moltype = DNA  length = 2563
FEATURE                 Location/Qualifiers
misc_feature            1..2563
                        note = Synthetic polynucleotide
misc_feature            1..2563
                        note = glnE-delta-AR-1 with 500bp flank
source                  1..2563
```

```
                        mol_type = other DNA
                        organism = synthetic construct
SEQUENCE: 170
gcgcaaagcg agtgctcact tacgtgatct gttgacacaa tctgaagcga ccataacttc  60
tgccgtttca gcgaatacgg cggtgtggag cgcacaatca gccctggcga agctggtgct  120
caccgagtgg ctagtgacgc agggctggcg aaccttcctt gatgaaaaag cgcaggccaa  180
attcgccgac tcctttaaac gctttgctga catccatctg tcacgcagcg ccgccgagct  240
gaaaaaagcc tttgcccaac cgctgggcga cagctatcgc gaccagttgc cgcgcctggc  300
gcgtgatatc gactgcgcgt tactgctggc cgggcattac gatcgcgcgc gcgccgtgga  360
atggctggaa aactggcagg ggcttcagca cgccattgaa acgcgccaga gagtcgaaat  420
cgaacatttc cgtaataccg cgattaccca ggagccgttc tggttgcaca gcggaaaacg  480
ttaacgaaag gatatttcgc atgtttaacg atctgattgg cgatgatgaa acggattcgc  540
cggaagatgc gctttctgag agctggcgcg aattgtggca ggatgcgttg caggaggagg  600
attccacgcc cgtgctggcg catctctcag aggacgatcg ccgccgcgtg gtggcgctga  660
ttgccgattt tcgcaaagag ttggataaac gcaccattgg cccgcgaggg cggcaggtac  720
tcgatcactt aatgccgcat ctgctcagcg atgtatgctc gcgcgacgat gcgccagtac  780
cgctgtcacg cctgacgccg ctgctcaccg gaattattac ccgcaccact taccttgagc  840
tgctaagtga atttcccggc gcactgaaac acctcatttc cctgtgtgcc gcgtcgccga  900
tggttgccag tcagctggcg cgctacccga tcctgcttga tgaattgctc gacccgaata  960
cgctctatca accgacggcg atgaatgcct atcgcgatga gctgcgccaa tacctgctgc  1020
gcgtgccgga agatgatgaa gagcaacagc ttgaggcgct gcggcagttt aagcaggcgc  1080
agttgctgcg cgtggcggcg gcggatattg ccggtacgtt gccagtaatg aaagtgagcg  1140
atcacttaac ctggctggcg gaagcgatta ttgatgcggt ggtgcagcaa gcctgggggc  1200
agatggtggc gcgttatggc cagccaacgc atctgcacga tcgcgaaggg cgcggttttg  1260
cggtggtcgg ttatggcaag ctgggcggct gggagctggg ttacagctcc gatctggatc  1320
tggtattcct gcacgactgc ccgatggatg tgatgaccga tggcgagcgt gaaatcgatg  1380
gtcgccagtt ctatttgcgt ctcgcgcagc gcgtgatgca cctgtttagc acgcgcacgt  1440
cgtccggcat cctttatgaa gttgatgcgc gtctgcgtcc atctggcgct gcggggatgc  1500
tggtcactac tacggaatcg ttcgccgatt accagcaaaa cgaagcctgg acgtgggaac  1560
atcaggcgct ggcccgtgcg cgcgtggtgt acggcgatcc gcaactgacc gccgaatttg  1620
acgccattcg ccgcgatatt ctgatgacgc ctcgcgacgg cgcaacgctg caaaccgacg  1680
tgcgagaaat gcgcgagaaa atgcgtgccc atcttggcaa caagcataaa gaccgcttcg  1740
atctgaaagc cgatgaaggc ggtatcaccg acatcgagtt tatcgcccaa tatctggtgc  1800
tgcgctttgc ccatgacaag ccgaaactga cgcgctggtc ggataatgtg cgcattctcg  1860
aagggctggc gcaaaacggc atcatggagg agcaggaagc gcaggcattg acgctggcgt  1920
acaccacatt gcgtgatgag ctgcaccacc tggcgctgca agagttgccg ggacatgtgg  1980
cgctctcctg ttttgtcgcc gagcgtgcgc ttattaaaac cagctgggac aagtggctgg  2040
tggaaccgtg cgcccccggcg taagtgtggt atcatcgcgc gcaaattttg tatctctcag  2100
gagacaggaa tgaaagtgac gctgccagag tttaagcaag ccggtgtaat ggtggtgggt  2160
gatgtgatgc tggatcgtta ctggtatggc ccaaccagcc gtatctctcc ggaagcgcca  2220
gtcccggttg ttaaagtcga taccattgaa gagcgtcctg gcggcgcggc aaacgtggcg  2280
atgaatatcg cctcactggg cgccacggcg cgtctggttg gcctgactgg cattgacgat  2340
gcggcgcgcg cgctgagcaa agcgctggcc gatgttaacg ttaaatgtga cttcgtttct  2400
gttccgacgc atcccaccat cactaagctg cgcgtgctgt cgcgtaacca gcagctgatt  2460
cgcctggact ttgaagaggg ttttgaagga gtcgatccgc aaccgatgca tgaacgcatc  2520
agccaggcgc ttggtaatat tggcgcgctg gtgctgtcgg att                   2563

SEQ ID NO: 171          moltype = DNA  length = 461
FEATURE                 Location/Qualifiers
misc_feature            1..461
                        note = Synthetic polynucleotide
misc_feature            1..461
                        note = delta-nifL::Prm1
source                  1..461
                        mol_type = other DNA
                        organism = synthetic construct
SEQUENCE: 171
atgaccctga atatgatgat ggatgccggc cgtcctgtaa taataaccgg acaattcgga  60
ctgattaaaa aagcgccctt gtggcgcttt ttttatattc ccgcctccat ttaaaataaa  120
aaatccaatc ggatttcact atttaaactg gccattatct aagatgaatc cgatggaagc  180
tcgctgtttt aacacgcgtt ttttaacctt ttattgaaag tcggtgcttc tttgagcgaa  240
cgatcaaatt taagtggatt cccatcaaaa aaatattctc aacctaaaaa agtttgtgta  300
atacttgtaa cgctacatgg agattaactc aatctagagg gtattaataa tgaatcgtac  360
taaactggta ctgggcgcaa ctcacttcac accccgaagg gggaagttgc ctgaccctac  420
gattcccgct atttcattca ctgaccggag gttcaaaatg a                     461

SEQ ID NO: 172          moltype = DNA  length = 1461
FEATURE                 Location/Qualifiers
misc_feature            1..1461
                        note = Synthetic polynucleotide
misc_feature            1..1461
                        note = delta-nifL::Prm1 with 500bp flank
source                  1..1461
                        mol_type = other DNA
                        organism = synthetic construct
SEQUENCE: 172
accggatacg agagaaaagt gtctacatcg gttcggttga tattgaccgg cgcatccgcc  60
agcccgccca gtttctggtg gatctgtttg gcgattttgc gggtcttgcc ggtgtcggtg  120
ccgaaaaaaa taccaatatt tgccataaca cacgctcctg ttgaaaaaga gatcccgccg  180
```

```
ggaaatgcgg tgaacgtgtc tgatattgcg aagagtgtgc cagttttggt cgcgggcaaa  240
acctgcacca gtttggttat taatgcacca gtctggcgct ttttttcgcc gagtttctcc  300
tcgctaatgc ccgccaggcg cggctttggc gctgatagcg cgctgaatac cgatctggat  360
caaggttttg tcgggttatc agccaaaagg tgcactcttt gcatggttat acgtgcctga  420
catgttgtcc gggcgacaaa cggcctggtg gcacaaattg tcagaactac gacacgacta  480
actgaccgca ggagtgtgcg atgaccctga atatgatgat ggatgccggc cgtcctgtaa  540
taataaccgg acaattcgga ctgattaaaa aagcgccctt gtggcgcttt ttttatattc  600
ccgcctccat ttaaaataaa aaatccaatc ggatttcact atttaaactg gccattatct  660
aagatgaatc cgatggaagc tcgctgtttt aacacgcgtt ttttaacctt ttattgaaag  720
tcggtgcttc tttgagcgaa cgatcaaatt taagtggatt cccatcaaaa aaatattctc  780
aacctaaaaa agtttgtgta atacttgtaa cgctacatgg agattaactc aatctagagg  840
gtattaataa tgaatcgtac taaactggta ctgggcgcaa ctcacttcac accccgaagg  900
gggaagttgc ctgaccctac gattcccgct atttcattca ctgaccggag gttcaaaatg  960
acccagcgaa ccgagtcggg taataccgtc tggcgcttcg atttgtccca gcagttcact  1020
gcgatgcagc gcataagcgt ggtactcagc cgggcgaccg aggtcgatca gacgctccag  1080
caagtgctgt gcgtattgca caatgacgcc tttttgcagc acggcatgat ctgtctgtac  1140
gacagccagc aggcgatttt gaatattgaa gcgttgcagg aagccgatca gcagttaatc  1200
cccggcagct cgcaaatccg ctatcgtccg ggcgaagggc tggtcgggac ggtgctttcg  1260
cagggccaat cattagtgct ggcgcgcgtt gctgacgatc agcgctttct tgaccggctc  1320
gggttgtatg attacaacct gccgtttatc gccgtgccgc tgatagggcc agatgcgcag  1380
actttcggtg tgctgacggc acaacccatg gcgcgttacg aagagcgatt acccgcctgc  1440
acccgctttc tggaaacggt c                                            1461
```

```
SEQ ID NO: 173         moltype = DNA  length = 199
FEATURE                Location/Qualifiers
misc_feature           1..199
                       note = Synthetic polynucleotide
misc_feature           1..199
                       note = delta-amtB
source                 1..199
                       mol_type = other DNA
                       organism = synthetic construct
SEQUENCE: 173
tttcgctgaa ggtgtgacca tggccatca ggtgctggtg cagctggaaa gtgttgccat  60
cactatcgtg tggtctggcg tggtggcctt tattggttac aaactggcgg acatgacggt  120
aggcctgcgc gtaccggaag aacaagaacg tgaagggctg gatgtaaaca gccacggcga  180
aaacgcctat aacgcctga                                              199
```

```
SEQ ID NO: 174         moltype = DNA  length = 1199
FEATURE                Location/Qualifiers
misc_feature           1..1199
                       note = Synthetic polynucleotide
misc_feature           1..258
                       note = delta-amtB with 500bp flank
source                 1..1199
                       mol_type = other DNA
                       organism = synthetic construct
SEQUENCE: 174
tttcctttct gactctgccc gtccgggcgc actaacggcc tgaaatactc cctcttttca  60
ttcctggcac aacgattgca atgtctgttg cgtgttagct gcggccatta tcgaattcga  120
ctggaggggg atctatgaag ctggttaccg tggtgattaa gccattcaaa cttgaagacg  180
tgcgtgaagc gctttcttct attggtattc aagggttgac cgtaactgaa gtgaaaggct  240
ttggccgtca gaagggtcac gctgagctgt accgcggtgc ggaatatagc gttaatttcc  300
tgccgaaagt gaaaattgat gtggcgatcg ctgacgatca actcgatgaa gtaatcgatg  360
tgatcagcaa agcggcctac accggaaaaa ttggcgacgg caaaattttc gttgctgagc  420
tgcaacgcgt cattcgtatt cgtaccggcg aagccgacga agcggcactg taatacaaga  480
cacacagtga tggggatcgg tttcgctgaa ggtgtgacca tggccatca ggtgctggtg  540
cagctggaaa gtgttgccat cactatcgtg tggtctggcg tggtggcctt tattggttac  600
aaactggcgg acatgacggt aggcctgcgc gtaccggaag aacaagaacg tgaagggctg  660
gatgtaaaca gccacggcga aaacgcctat aacgcctgat tgcgttgagt tatctcctga  720
gcataaaaaa gcctccattc ggaggctttt cttttttaa gtttaaagcg cggttagttg  780
cgattgcgca tgacgccttc ctgcacgctg gacgcgacca gcacaccctc ttgcgtatag  840
aactcgccgc gcacaaaacc gcgagcgctg gaggctgacg tgctttccac actgtagagc  900
agccattcgt tcatattaaa cgggcgatgg aaccacatgg agtggtcaat ggtggcaacc  960
tgcataccgc gctcaaggaa gcccacgccg tgcggctgaa gtgcaaccgg caggaagtta  1020
aagtctgagg catatccaag cagatattga tgtacgcgaa aatcgtccgg caccgtgccg  1080
tttgcgcgga tccatacctg gcgggtggga tcggcaacgt ggcctttcag cgggttatga  1140
aactcaaccg ggcggatctc cagtggttta tcactaagaa acttctcttt ggcctgcgg  1199
```

```
SEQ ID NO: 175         moltype = DNA  length = 607
FEATURE                Location/Qualifiers
misc_feature           1..607
                       note = Synthetic polynucleotide
misc_feature           1..607
                       note = delta-nifL::PinfC
source                 1..607
                       mol_type = other DNA
                       organism = synthetic construct
SEQUENCE: 175
```

```
atgaccttta atatgatgcc tggggtcact ggagcgcttt atcggcatcc tgaccgaaga  60
atttgccggt ttcttcccga cctggctggc ccctgttcag gttgtggtga tgaatatcac  120
tgattctcaa gctgaatatg tcaacgaatt gacccgtaaa ttgcaaaatg cgggcattcg  180
tgtaaaagcg gacttgagaa acgagaagat tggctttaaa atccgcgagc acactttacg  240
tcgtgtccct tatatgttgg tctgtggtga taaagaggtg gaagcaggca aagtggccgt  300
tcgcacccgc cgcggtaaag acctgggcag cctggacgta agtgaagtga ttgagaagct  360
gcaacaagag attcgcagcc gcagtcttca acaactggag gaataaggta ttaaaggcgg  420
aaaacgagtt caaacggcac gtccgaatcg tatcaatggc gagattcgcg cccaggaagt  480
tcgcttaact ggtctggaag gtgagcagct gggtattgca atagaactaa ctacccgccc  540
tgaaggcggt acctgcctga ccctgcgatt cccgttattt cattcactga ccggaggccc  600
acgatga                                                            607

SEQ ID NO: 176         moltype = DNA  length = 1607
FEATURE                Location/Qualifiers
misc_feature           1..1607
                       note = Synthetic polynucleotide
misc_feature           1..1607
                       note = delta-nifL::PinfC with 500bp flank
source                 1..1607
                       mol_type = other DNA
                       organism = synthetic construct
SEQUENCE: 176
ggtacgacaa aaacgtctcc agcgacgtgc ggttaatatt gactggcgca tccgccacat  60
cccccagttt ttgctggatc agtttggcga ttttgcgggt ttttcccgtg tcactgccaa  120
aaaaaatacc aatgttagcc atgtcgcgct cctgttgaga aagaataagg ccgcctgcaa  180
acggcggata tcccttctcc tgttgcgaag gctgtgccag gttttttaa ggccttctgt  240
gcactgaaat gggtgaaaaa atgactcttt tttgtgcagg caccgtcctc tctccgctat  300
ccagacctgc tttgaaggcc tctgagggcc aaatcagggc caaaacacga atcaggatca  360
atgtttcggc gcgttacctg ttcgaaaggt gcactctttg catggttaat cacacccaat  420
cagggctgcg gatgtcgggc gtttcacaac acaaaatgtt gtaaatgcga cacagccggg  480
cctgaaacca ggagcgtgtg atgaccttta atatgatgcc tggggtcact ggagcgcttt  540
atcggcatcc tgaccgaaga atttgccggt ttcttcccga cctggctggc ccctgttcag  600
gttgtggtga tgaatatcac tgattctcaa gctgaatatg tcaacgaatt gacccgtaaa  660
ttgcaaaatg cgggcattcg tgtaaaagcg gacttgagaa acgagaagat tggctttaaa  720
atccgcgagc acactttacg tcgtgtccct tatatgttgg tctgtggtga taaagaggtg  780
gaagcaggca aagtggccgt tcgcacccgc cgcggtaaag acctgggcag cctggacgta  840
agtgaagtga ttgagaagct gcaacaagag attcgcagcc gcagtcttca acaactggag  900
gaataaggta ttaaaggcgg aaaacgagtt caaacggcac gtccgaatcg tatcaatggc  960
gagattcgcg cccaggaagt tcgcttaact ggtctggaag gtgagcagct gggtattgca  1020
atagaactaa ctacccgccc tgaaggcggt acctgcctga ccctgcgatt cccgttattt  1080
cattcactga ccggaggccc acgatgaccc agcgacccga gtcgggcacc accgtctggc  1140
gttttgatct ctcacagcaa tttaccgcca tgcagcgcat cagcgtggtg ttgagtcgcg  1200
caaccgagat aagccagacg ctgcaggagg tgctgtgtgt tctgcataat gacgcattta  1260
tgcaacacgg catgctgtgt ctgtatgaca accagcagga aattctgagt attgaagcct  1320
tgcaggaggc agaccaacat ctgatccccg gcagctcgca aattcgctat cgccctggcg  1380
aagggctggt aggagccgta ctgtcccagg gacaatctct tgtgctgccg cgtgtcgccg  1440
acgatcaacg ctttctcgac aggcttggca tctatgatta caacctgccg tttatcgccg  1500
tcccccttaat ggggccaggc gcgcagacga ttggcgtgct cgccgcgcag ccgatggcgc  1560
gtctggagga gcggcttcct tcctgtacgc gctttctgga aaccgtc               1607

SEQ ID NO: 177         moltype = DNA  length = 1536
FEATURE                Location/Qualifiers
gene                   1..1536
                       note = 16S-1
source                 1..1536
                       mol_type = genomic DNA
                       organism = Kosakonia sacchari
SEQUENCE: 177
ttgaagagtt tgatcatggc tcagattgaa cgctggcggc aggcctaaca catgcaagtc  60
gaacggtagc acagagagct tgctctcggg tgacgagtgg cggacgggtg agtaatgtct  120
gggaaactgc ctgatggagg gggataacta ctggaaacgg tagctaatac cgcataacgt  180
cgcaagacca aagaggggga ccttcgggcc tcttgccatc agatgtgccc agatgggatt  240
agctagtagg tggggtaacg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtgtgaagaa ggccttcggg  420
ttgtaaagca ctttcagcgg ggaggaaggg agtaaggtta ataaccttat tcattgacgt  480
tacccgcaga agaagcaccg gctaactccg tgccagcagc cgcggtaata cggagggtgc  540
aagcgttaat cggaattact gggcgtaaag cgcacgcagg cggtctgtca agtcggatgt  600
gaaatccccg ggctcaacct gggaactgca tccgaaactg gcaggcttga gtctcgtaga  660
gggaggtaga attccaggtg tagcggtgaa atgcgtagag atctggagga ataccggtgg  720
cgaaggcggc ctcctggacg aagactgacg ctcaggtgcg aaagcgtggg gagcaaacag  780
gattagatac cctggtagtc cacgccgtaa acgatgtcta tttggaggtt gtgcccttga  840
ggcgtggctt ccggagctaa cgcgttaaat agaccgcctg gggagtacgg ccgcaaggtt  900
aaaactcaaa tgaattgacg ggggcccgca caagcggtgg agcatgtggt ttaattcgat  960
gcaacgcgaa gaaccttacc tggtcttgac atccacagaa ctttccagag atggattggt  1020
gccttcggga actgtgagac aggtgctgca tggctgtcgt cagctcgtgt tgtgaaatgt  1080
tgggttaagt cccgcaacga gcgcaaccct tatcctttgt tgccagcggt ccggccggga  1140
actcaaagga gactgccagt gataaactgg aggaaggtgg ggatgacgtc aagtcatcat  1200
ggcccttacg accagggcta cacacgtgct acaatggcgc atacaaagag aagcgacctc  1260
```

```
gcgagagtaa gcggacctca taaagtgcgt cgtagtccgg attggagtct gcaactcgac  1320
tccatgaagt cggaatcgct agtaatcgtg gatcagaatg ccacggtgaa tacgttcccg  1380
ggccttgtac acaccgcccg tcacaccatg ggagtgggtt gcaaaagaag taggtagctt  1440
aaccttcggg agggcgctta ccactttgtg attcatgact ggggtgaagt cgtaacaagg  1500
taaccgtagg ggaacctgcg gttggatcac ctcctt                            1536

SEQ ID NO: 178         moltype = DNA  length = 1537
FEATURE                Location/Qualifiers
gene                   1..1537
                       note = 16S-2
variation              450
                       note = n is a, c, t, g, unknown or other
variation              452
                       note = n is a, c, t, g, unknown or other
variation              455
                       note = n is a, c, t, g, unknown or other
variation              473
                       note = n is a, c, t, g, unknown or other
source                 1..1537
                       mol_type = genomic DNA
                       organism = Kosakonia sacchari
SEQUENCE: 178
ttgaagagtt tgatcatggc tcagattgaa cgctggcggc aggcctaaca catgcaagtc  60
gaacggtagc acagagagct tgctctcggg tgacgagtgg cggacgggtg agtaatgtct  120
gggaaactgc ctgatggagg gggataacta ctggaaacgg tagctaatac cgcataacgt  180
cgcaagacca aagaggggga ccttcgggcc tcttgccatc agatgtgccc agatgggatt  240
agctagtagg tggggtaacg gctcacctag gcgacgatcc ctagctggtc tgagaggatg  300
accagccaca ctggaactga gacacggtcc agactcctac gggaggcagc agtggggaat  360
attgcacaat gggcgcaagc ctgatgcagc catgccgcgt gtgtgaagaa ggccttcggg  420
ttgtaaagca ctttcagcgg ggaggaaggn antanggtta ataacctgtg ttnattgacg  480
ttacccgcag aagaagcacc ggctaactcc gtgccagcag ccgcggtaat acggagggtg  540
caagcgttaa tcggaattac tgggcgtaaa gcgcacgcag gcggtctgtc aagtcggatg  600
tgaaatcccc gggctcaacc tgggaactgc atccgaaact ggcaggcttg agtctcgtag  660
agggaggtag aattccaggt gtagcggtga aatgcgtaga gatctggagg aataccggtg  720
gcgaaggcgg cctcctggac gaagactgac gctcaggtgc gaaagcgtgg ggagcaaaca  780
ggattagata ccctggtagt ccacgccgta aacgatgtct atttggaggt tgtgcccttg  840
aggcgtggct tccggagcta acgcgttaaa tagaccgcct ggggagtacg gccgcaaggt  900
taaaactcaa atgaattgac gggggcccgc acaagcggtg gagcatgtgg tttaattcga  960
tgcaacgcga agaaccttac ctggtcttga catccacaga acttagcaga gatgctttgg  1020
tgccttcggg aactgtgaga caggtgctgc atggctgtcg tcagctcgtg ttgtgaaatg  1080
ttgggttaag tcccgcaacg agcgcaaccc ttatcctttg ttgccagcgg ttaggccggg  1140
aactcaaagg agactgccag tgataaactg gaggaaggtg gggatgacgt caagtcatca  1200
tggcccttac gaccagggct acacacgtgc tacaatggcg catacaaaga gaagcgacct  1260
cgcgagagta agcggacctc ataaagtgcg tcgtagtccg gattggagtc tgcaactcga  1320
ctccatgaag tcggaatcgc tagtaatcgt ggatcagaat gccacggtga atacgttccc  1380
gggccttgta cacaccgccc gtcacaccat gggagtgggt tgcaaaagaa gtaggtagct  1440
taaccttcgg gagggcgctt accactttgt gattcatgac tggggtgaag tcgtaacaag  1500
gtaaccgtag gggaacctgc ggttggatca cctcctt                           1537

SEQ ID NO: 179         moltype = DNA  length = 882
FEATURE                Location/Qualifiers
gene                   1..882
                       note = nifH
source                 1..882
                       mol_type = genomic DNA
                       organism = Kosakonia sacchari
SEQUENCE: 179
atgaccatgc gtcaatgcgc catttacggc aaaggtggga tcggcaaatc gaccaccaca  60
cagaacctgg tcgccgcgct ggcggagatg ggtaaaaaag tcatgattgt cggctgtgac  120
ccgaaagccg attccacgcg tttgatcctg catgcgaaag cgcagaacac cattatggag  180
atggctgctg aagtcggctc cgtggaagac ctggagttag aagacgtgct gcaaatcggt  240
tacggcggcg tgcgctgcgc agagtccggc ggcccggagc caggcgtggg ctgtgccggt  300
cgcggggtga tcaccgcgat taacttcctc gaagaagaag gcgcttacgt gccggatctc  360
gattttgttt tctacgacgt gctgggcgac gtggtatgcg gtggtttcgc catgccgatt  420
cgtgaaaaca aagcgcagga gatctacatc gtttgctctg gcgaaatgat ggcgatgtac  480
gccgccaaca acatctccaa aggcatcgtg aaatacgcca aatccggtaa agtgcgcctc  540
ggcgggctga tttgtaactc gcgccagacc gaccgtgaag atgaactgat cattgcgctg  600
gcagaaaaac tcggcacgca gatgatccac tttgttcccc gcgacaacat tgtgcagcgt  660
gcggaaatcc gccgtatgac ggttatcgaa tatgacccga cctgcaatca ggcgaacgaa  720
tatcgcagcc ttgccagcaa aatcgtcaac aacaccaaaa tggtggtgcc cacccccctgc  780
accatggatg aactggaaga actgctgatg gagttcggca ttatggatgt ggaagacacc  840
agcatcattg gtaaaaccgc cgccgaagaa aacgccgtct ga                      882

SEQ ID NO: 180         moltype = DNA  length = 1449
FEATURE                Location/Qualifiers
gene                   1..1449
                       note = nifD2
source                 1..1449
                       mol_type = genomic DNA
```

```
                          organism = Kosakonia sacchari
SEQUENCE: 180
atgagcaatg caacaggcga acgcaacctg gagataatcg agcaggtgct cgaggttttc  60
ccggagaaga cgcgcaaaga acgcagaaaa cacatgatgg tgacggaccc ggagcaggaa  120
agcgtcggta agtgcatcat ctctaaccgc aaatcgcagc caggcgtgat gaccgtgcgc  180
ggctgctcgt atgccggttc gaaaggggtg gtatttgggc caatcaagga tatggcgcat  240
atctcgcatg gcccaatcgg ctgcggccaa tactcccgcg ccgggcggcg gaactactac  300
accggcgtca gcggcgtgga cagcttcggc acgctcaact tcacctccga ttttcaggag  360
cgcgacatcg tgtttggcgg cgataaaaag ctcgccaaac tgattgaaga gctggaagag  420
ctgttcccgc tgaccaaagg catttcgatt cagtcggaat gcccggtcgg cctgattggc  480
gatgacattg aggccgtcgc gaacgccagc cgcaaagcca tcaacaaacc ggttattccg  540
gtgcgttgcg aaggctttcg cggcgtgtcg caatccctcg gtcaccatat tgccaacgat  600
gtgatccgcg actgggtgct ggataaccgc gaaggcaaac cgttcgaatc cacccccttac  660
gatgtggcga tcatcggcga ttacaacatc ggcggcgatg cctgggcttc gcgcattttg  720
ctcgaagaga tgggcttgcg ggtggtggca cagtggtctg gcgacggtac gctggtggag  780
atggaaaaca cgccgttcgt caaactgaac ctggtgcatt gttaccgctc aatgaactac  840
atctcgcgcc atatggagga gaagcacggt attccgtgga tggaatacaa cttctttggt  900
ccgacgaaaa tcgcggaatc gctgcgcaaa atcgccgacc agtttgacga caccattcgc  960
gccaacgccg aagcggtgat cgccagatac caggcgcaaa acgacgccat tatcgccaaa  1020
tatcgcccgc gtctggaggg gcgcaaagtg ctgctttata tgggcgggct gcgtccgcgc  1080
catgtgattg gcgcctatga agacctggga atggagatca tcgctgccgg ttatgagttc  1140
ggtcataacg atgattacga ccgcaccttg ccggatctga aagagggcac gctgctgttt  1200
gatgatgcca gcagttatga gctggaggcg ttcgtcaacg cgctgaaacc ggatctcatc  1260
ggttccggca tcaaagagaa gtacatcttt cagaaaatgg gcgtgccgtt tcgccagatg  1320
cactcctggg attactccgg cccgtaccac ggctatgacg gcttcgccat cttcgcccgc  1380
gatatggata tgacgctcaa caaccccgcg tggggccagt tgaccgcgcc gtggctgaaa  1440
tccgcctga                                                    1449

SEQ ID NO: 181           moltype = DNA  length = 1563
FEATURE                  Location/Qualifiers
gene                     1..1563
                         note = nifK2
source                   1..1563
                         mol_type = genomic DNA
                         organism = Kosakonia sacchari
SEQUENCE: 181
atgagccaga ctgctgagaa aatacagaat tgccatcccc tgtttgaaca ggatgcttac  60
cagacgctgt ttgccggtaa acgggcactc gaagaggcgc actcgccgga gcgggtgcag  120
gaagtgtttc aatggaccac taccccggaa tatgaagcgc tgaactttaa acgcgaagcg  180
ctgactatcg acccggcaaa agcctgccag ccgctgggcg cggtgctctg ttcgctgggg  240
tttgccaata ccctaccgta tgtgcacggt tcacagggtt gcgtggccta tttccgcacg  300
tactttaacc gccactttaa agaaccggtg gcctgcgtgt cggattcaat gacggaagac  360
gcggcggtgt tcggcgggaa taacaacctc aacaccggct tacaaaacgc cagcgcgctg  420
tataaaccgg agattatcgc cgtctctacc acctgtatgg cggaagtgat cggtgatgat  480
ttgcaggcct ttatcgccaa cgccaaaaaa gatggttttc tcgatgccgc catccccgtg  540
ccctacgcgc acacccccag ttttatcggc agccatatca ccggctggga taacatgttt  600
gaaggttttg cccggacctt tacggcagac catgaagctc agcccggcaa actttcacgc  660
atcaacctgg tgaccgggtt tgaaacctat ctcggcaatt tccgcgtgct gaaacgcatg  720
atggaacaaa tggaggtgcc ggcgagtgtg ctctccgatc cgtcggaagt gctggatact  780
cccgccaacg ggcattacca gatgtacgcg ggcgggacga cgcagcaaga gatgcgcgag  840
gcgccggatg ctatcgacac cctgttgctg cagccctggc aactggtgaa aagcaaaaaa  900
gtggtgcagg agatgtggaa tcagcccgcc accgaggttt ctgttcccgt tgggctggca  960
ggaacagacg aactgttgat ggcgattagc cagttaaccg gcaaggccat tcccgattca  1020
ctggcgctgg agcgcgggcg gctggtcgat atgatgctcg attcccacac ctggttgcac  1080
ggtaaaaaat tcggcctgtt tggcgatccg gattttgtca tgggattgac ccgtttcctg  1140
ctggagctgg gctgcgaacc gaccgttatc ctctgccaca acggtaacaa acgctggcag  1200
aaagcaatga agaaaatgct tgacgcctcg ccgtacggcc aggagagcga agtgtttatc  1260
aactgcgatt tgtggcattt ccgctcgctg atgtttaccc gccagccgga ttttatgatt  1320
ggcaactcgt acggcaagtt cattcagcgc gacaccttag ccaaaggcga gcagtttgaa  1380
gttccgctga tccgcctcgg ttttcccctg ttcgaccgcc accatctgca ccgccagacc  1440
acctggggct acgagggcgc catgagcatt ctcactaccc ttgtgaatgc ggtactggag  1500
aaagtggaca aagagaccat caagctcggc aaaaccgact acagcttcga tcttatccgt  1560
taa                                                          1563

SEQ ID NO: 182           moltype = DNA  length = 1488
FEATURE                  Location/Qualifiers
gene                     1..1488
                         note = nifL
source                   1..1488
                         mol_type = genomic DNA
                         organism = Kosakonia sacchari
SEQUENCE: 182
atgaccctga atatgatgat ggatgccggc gcgcccgagg caatcgccgg tgcgctttcg  60
cgacaccatc ctgggctgtt ttttaccatc gttgaagaag cgcccgtcgc catttcgctg  120
actgatgccg acgcacgcat tgtctatgcc aacccggctt tctgccgcca gaccggctat  180
gaactagaag cgttgttgca gcaaaatccc cgcctgcttg caagtcgcca aaccccacgg  240
gaaatctatc aggatatgtg gcacaccttg ttacaacgcc gaccgtggcg cgggcaattg  300
attaaccgcc accgcgacgg cagcctgtat ctggtcgaga tcgatatcac cccggtgatt  360
aacccgtttg gcgaactgga acactacctg gcaatgcagc gcgatatcag cgccagttat  420
```

```
gcgctggagc agcggttgcg caatcacatg acgctgaccg aagcggtgct gaataacatt  480
ccggcggcgg tggttgtagt ggatgaacgc gatcatgtgg ttatggataa ccttgcctac  540
aaaacgttct gtgccgactg cggcggaaaa gagctcctga gcgaactcaa tttttcagcc  600
cgaaaagcgg agctggcaaa cggccaggtc ttaccggtgg tgctgcgcgg tgaggtgcgc  660
tggttgtcgg tgacctgctg ggcgctgccg ggcgtcagcg aagaagccag tcgctacttt  720
attgataaca ggctgacgcg cacgctggtg gtgatcaccg acgacaccca acaacgccag  780
cagcaggaac agggccgact tgaccgcctt aaacagcaga tgaccaacgg caaactactg  840
gcagcgatcc gcgaagcgct tgacgccgcg ctgatccagc ttaactgccc catcaatatg  900
ctggcggcgg cgcgacgttt aaacggcagt gataacaaca atgtggcgct cgacgccgcg  960
tggcgcgaag gtgaagaggc gatggcgcgg ctgaaacgtt gccgcccgtc gctggaactg  1020
gaaagtgcgg ccgtctggcc gctgcaaccc ttttttgacg atctgcgcgc gctttatcac  1080
acccgctacg agcaggggaa aaatttgcag gtcacgctgg attcccatca tctggtggga  1140
tttggtcagc gtacgcaact gttagcctgc ctgagtctgt ggctcgatcg cacgctggat  1200
attgccgccg ggctgggtga tttcaccgcg caaacgcaga tttacgcccg cgaagaagag  1260
ggctggctct ctttgtatat cactgacaat gtgccgctga tcccgctgcg ccacacccac  1320
tcgccggatg cgcttaacgc tccgggaaaa ggcatggagc tgcgcctgat ccagacgctg  1380
gtggcacacc accacggcgc aatagaactc acttcacacc ccgaaggggg aagttgcctg  1440
accctacgat tcccgctatt tcattcactg accggaggtt caaaatga              1488
```

```
SEQ ID NO: 183         moltype = DNA  length = 1575
FEATURE                Location/Qualifiers
gene                   1..1575
                       note = nifA
source                 1..1575
                       mol_type = genomic DNA
                       organism = Kosakonia sacchari
SEQUENCE: 183
atgacccagc gaaccgagtc gggtaatacc gtctggcgct tcgatttgtc ccagcagttc  60
actgcgatgc agcgcataag cgtggtactc agccgggcga ccgaggtcga tcagacgctc  120
cagcaagtgc tgtgcgtatt gcacaatgac gccttttttgc agcacggcat gatctgtctg  180
tacgacagcc agcaggcgat tttgaatatt gaagcgttgc aggaagccga tcagcagtta  240
atccccggca gctcgcaaat ccgctatcgt ccgggcgaag ggctggtcgg gacggtgctt  300
tcgcagggcc aatcattagt gctggcgcgc gttgctgacg atcagcgctt tcttgaccgg  360
ctcgggttgt atgattacaa cctgccgttt atcgccgtgc cgctgatagg gccagatgcg  420
cagactttcg gtgtgctgac ggcacaaccc atggcgcgtt acgaagagcg attacccgcc  480
tgcacccgct ttctggaaac ggtcgctaac ctggtcgcgc aaaccgtgcg tttgatggca  540
ccaccggcag tgcgcccttc cccgcgcgcc gccataacac aggccgccag cccgaaatcc  600
tgcacggcct cacgcgcatt tggttttgaa aatatggtcg gtaacagtcc ggcgatgcgc  660
cagaccatgg agattatccg tcaggtttcg cgctgggaca ccaccgttct ggtacgcggc  720
gagagtggca ccggcaagga gctgattgcc aacgccatcc accaccattc gccgcgtgcc  780
ggtgcgccat ttgtgaaatt caactgtgcg gcgctgccgg acacactgct ggaaagcgaa  840
ttgttcggtc acgagaaagg ggcatttacc ggcgcggtac gccagcgtaa aggccgtttt  900
gagctggccg atggcggcac gctgtttctt gacgagatcg gcgagagtag cgcctcgttt  960
caggctaagc tgctgcgcat tttgcaggaa ggcgaaatgg aacgcgtcgg cggcgacgag  1020
acattgcaag tgaatgtgcg cattattgcc gcgacgaacc gcaatcttga agatgaagtc  1080
cggctggggc actttcgcga agatctctat tatcgcctga atgtgatgcc catcgccctg  1140
ccgccactac gcgaacgcca ggaggacatt gccgagctgg cgcactttct ggtgcgtaaa  1200
atcgcccata accagagccg tacgctgcgc attagcgagg gcgctatccg cctgctgatg  1260
agctacaact ggcccggtaa tgtgcgcgaa ctggaaaact gccttgagcg ctcagcggtg  1320
atgtcggaga acggtctgat cgatcgggat gtgattttgt ttaatcatcg cgaccagcca  1380
gccaaaccgc cagttatcag cgtctcgcat gatgataact ggctcgataa caaccttgac  1440
gagcgccagc ggctgattgc ggcgctggaa aaagcgggat gggtacaagc caaagccgcg  1500
cgcttgctgg ggatgacgcc gcgccaggtc gcctatcgta ttcagacgat ggatataacc  1560
ctgccaaggc tataa                                                  1575
```

```
SEQ ID NO: 184         moltype = DNA  length = 2850
FEATURE                Location/Qualifiers
gene                   1..2850
                       note = glnE
source                 1..2850
                       mol_type = genomic DNA
                       organism = Kosakonia sacchari
SEQUENCE: 184
atgccgcacc acgcaggatt gtcgcagcac tggcaaacgg tattttctcg tctgccggaa  60
tcgctcaccg cgcagccatt gagcgcgcag gcgcagtcag tgctcacttt tagtgatttt  120
gttcaggaca gcatcatcgc gcatcctgag tggctggcag agcttgaaag cgcgccgccg  180
cctgcgaacg aatggcaaca ctatgcgcaa tggctgcaag cggcgctgga tggcgtcacc  240
gatgaagcct cgctgatgcg cgcgctgcgg ctgtttcgcc gtcgcatcat ggtgcgcatc  300
gcctggagcc aggcgttaca gttggtggcg gaagaagata tcctgcaaca gcttagcgtg  360
ctggcggaaa ccctgatcgt cgccgcgcgc gactggcttt atgaggcctg ctgccgtgag  420
tggggaacgc cgagcaatcc acaaggcgtg gcgcagccga tgctggtact cggcatgggc  480
aaactgggtg gcggcgaact caatttctca tccgatatcg atttgatttt cgcctggccg  540
gaaaatggcg caacgcgcgg tggacgccgt gagctggata acgcgcaatt tttcactcgc  600
cttggtcaac ggctgattaa agtcctcgac cagccaacgc aggatggctt tgtctaccgc  660
gtcgatatgc gcttgcgccc gtttggcgac agcggcccgc tggtgctgag ctttgccgcg  720
ctggaagatt actaccagga gcaggggcgc gattgggaac gctacgcgat ggtgaaagcg  780
cgcattatgg gcgataacga cggcgaccat gcgcgggagt tgcgcgcaat gctgcgcccg  840
tttgttttcc gccgttatat cgacttcagc gtgattcagt ccctgcgtaa catgaaaggc  900
atgattgccc gcgaagtgcg tcgccgtggc ctgaaggaca acattaagct cggcgcgggc  960
```

```
gggatccgcg aaatagaatt tatcgtccag gttttccagc tgattcgcgg cggtcgcgag  1020
cctgcactgc aatcgcgttc actgttgccg acgcttgctg ccatagatca actgcatctg  1080
ctgccggatg gcgacgcaac ccggctgcgc gaggcgtatt tgtggctgcg acggctggag  1140
aacctgctgc aaagcatcaa tgacgaacag acacagacgc tgccgggcga tgaactgaat  1200
cgcgcgcgcc tcgcctgggg aatgggcaaa gatagctggg aagcgctctg cgaaacgctg  1260
gaagcgcata tgtcggcggt gcgtcagata tttaacgatc tgattggcga tgatgaaacg  1320
gattcgccgg aagatgcgct ttctgagagc tggcgcgaat tgtggcagga tgcgttgcag  1380
gaggaggatt ccacgcccgt gctggcgcat ctctcagagg acgatcgccg ccgcgtggtg  1440
gcgctgattg ccgattttcg caaagagttg gataaacgca ccattggccc gcgagggcgg  1500
caggtactcg atcacttaat gccgcatctg ctcagcgatg tatgctcgcg cgacgatgcg  1560
ccagtaccgc tgtcacgcct gacgccgctg ctcaccggaa ttattacccg caccacttac  1620
cttgagctgc taagtgaatt tcccggcgca ctgaaacacc tcatttccct gtgtgccgcg  1680
tcgccgatgg ttgccagtca gctggcgcgc tacccgatcc tgcttgatga attgctcgac  1740
ccgaatacgc tctatcaacc gacggcgatg aatgcctatc gcgatgagct gcgccaatac  1800
ctgctgcgcg tgccggaaga tgatgaagag caacagcttg aggcgctgcg gcagtttaag  1860
caggcgcagt tgctgcgcgt ggcggcggcg gatattgccg gtacgttgcc agtaatgaaa  1920
gtgagcgatc acttaacctg gctggcggaa gcgattattg atgcggtggt gcagcaagcc  1980
tgggggcaga tggtggcgcg ttatggccag ccaacgcatc tgcacgatcg cgaagggcgc  2040
ggttttgcgg tggtcggtta tggcaagctg ggcggctggg agctgggtta cagctccgat  2100
ctggatctgg tattcctgca cgactgcccg atggatgtga tgaccgatgg cgagcgtgaa  2160
atcgatggtc gccagttcta tttgcgtctc gcgcagcgcg tgatgcacct gtttagcacg  2220
cgcacgtcgt ccggcatcct ttatgaagtt gatgcgcgtc tgcgtccatc tggcgctgcg  2280
gggatgctgg tcactactac ggaatcgttc gccgattacc agcaaaacga agcctggacg  2340
tgggaacatc aggcgctggc ccgtgcgcgc gtggtgtacg gcgatccgca actgaccgcc  2400
gaatttgacg ccattcgccg cgatattctg atgacgcctc gcgacggcgc aacgctgcaa  2460
accgacgtgc gagaaatgcg cgagaaaatg cgtgcccatc ttggcaacaa gcataaagac  2520
cgcttcgatc tgaaagccga tgaaggcggt atcaccgaca tcgagtttat cgcccaatat  2580
ctggtgctgc gctttgccca tgacaagccg aaactgacgc gctggtcgga taatgtgcgc  2640
attctcgaag ggctggcgca aaacggcatc atggaggagc aggaagcgca ggcattgacg  2700
ctggcgtaca ccacattgcg tgatgagctg caccacctgg cgctgcaaga gttgccggga  2760
catgtggcgc tctcctgttt tgtcgccgag cgtgcgctta ttaaaaccag ctgggacaag  2820
tggctggtgg aaccgtgcgc cccggcgtaa                                 2850
```

```
SEQ ID NO: 185          moltype = DNA  length = 1536
FEATURE                 Location/Qualifiers
gene                    1..1536
                        note = 16S-3
variation               766..776
                        note = n is a, c, t, g, unknown or other
variation               905
                        note = n is a, c, t, g, unknown or other
source                  1..1536
                        mol_type = genomic DNA
                        organism = Kosakonia sacchari
SEQUENCE: 185
attgaagagt ttgatcatgg ctcagattga acgctggcgg caggcctaac acatgcaagt  60
cgaacggtag cacagagagc ttgctctcgg gtgacgagtg gcggacgggt gagtaatgtc  120
tgggaaactg cctgatggag ggggataact actggaaacg gtagctaata ccgcataacg  180
tcgcaagacc aaagaggggg accttcgggc ctcttgccat cagatgtgcc cagatgggat  240
tagctagtag gtggggtaac ggctcaccta ggcgacgatc cctagctggt ctgagaggat  300
gaccagccac actggaactg agacacggtc cagactccta cgggaggcag cagtggggaa  360
tattgcacaa tgggcgcaag cctgatgcag ccatgccgcg tgtgtgaaga aggccttcgg  420
gttgtaaagc actttcagcg gggaggaagg gagtaaggtt aataaccttg ctcattgacg  480
ttacccgcag aagaagcacc ggctaactcc gtgccagcag ccgcggtaat acggagggtg  540
caagcgttaa tcggaattac tgggcgtaaa gcgcacgcag gcggtctgtc aagtcggatg  600
tgaaatcccc gggctcaacc tgggaactgc atccgaaact ggcaggcttg agtctcgtag  660
agggaggtag aattccaggt gtagcggtga aatgcgtaga gatctggagg aataccggtg  720
gcgaaggcgg cctcctggac gaagactgac gctcaggtgc gaaagnnnnn nnnnnnaaca  780
ggattagata ccctggtagt ccatgccgta aacgatgtct actagccgtt ggggcctttg  840
aggctttagt ggcgcagcta acgcgataag tagaccgcct ggggagtacg gtcgcaagac  900
taaanctcaa atgaattgac gggggcccgc acaagcggtg gagcatgtgg tttaattcga  960
tgcaacgcga agaaccttac ctggccttga catagtaaga attttccaga gatggattgg  1020
tgccttcggg aacttacata caggtgctgc atggctgtcg tcagctcgtg tcgtgagatg  1080
ttgggttaag tcccgcaacg agcgcaaccc ttgtcattag ttgctacatt tagttgggca  1140
ctctaatgag actgccggtg acaaaccgga ggaaggtggg gatgacgtca agtcctcatg  1200
gcccttatag gtggggctac acacgtcata caatggctgg tacaaagggt tgccaacccg  1260
cgagggggag ctaatcccat aaaaccagtc gtagtccgga tcgcagtctg caactcgact  1320
gcgtgaagtc ggaatcgcta gtaatcgtgg atcagaatgt cacggtgaat acgttcccgg  1380
gtcttgtaca caccgcccgt cacaccatgg gagcgggttc tgccagaagt agttagctta  1440
accgcaagga gggcgattac cacggcaggg ttcgtgactg gggtgaagtc gtaacaaggt  1500
agccgtatcg gaaggtgcgg ctggatcacc tccttt                          1536
```

```
SEQ ID NO: 186          moltype = DNA  length = 882
FEATURE                 Location/Qualifiers
gene                    1..882
                        note = nifD1
source                  1..882
                        mol_type = genomic DNA
                        organism = Kosakonia sacchari
```

```
SEQUENCE: 186
atgaccatgc gtcaatgcgc catttacggc aaaggtggga tcggcaaatc gaccaccaca  60
cagaacctgg tcgccgcgct ggcggagatg ggtaaaaaag tcatgattgt cggctgtgac  120
ccgaaagccg attccacgcg tttgatcctg catgcgaaag cgcagaacac cattatggag  180
atggctgctg aagtcggctc cgtggaagac ctggagttag aagacgtgct gcaaatcggt  240
tacggcggcg tgcgctgcgc agagtccggc ggcccggagc caggcgtggg ctgtgccggt  300
cgcggggtga tcaccgcgat taacttcctc gaagaagaag gcgcttacgt gccggatctc  360
gattttgttt tctacgacgt gctgggcgac gtggtatgcg gtggtttcgc catgccgatt  420
cgtgaaaaca aagcgcagga gatctacatc gtttgctctg gcgaaatgat ggcgatgtac  480
gccgccaaca acatctccaa aggcatcgtg aaatacgcca aatccggtaa agtgcgcctc  540
ggcgggctga tttgtaactc gcgccagacc gaccgtgaag atgaactgat cattgcgctg  600
gcagaaaaac tcggcacgca gatgatccac tttgttcccc gcgacaacat tgtgcagcgt  660
gcggaaatcc gccgtatgac ggttatcgaa tatgacccga cctgcaatca ggcgaacgaa  720
tatcgcagcc ttgccagcaa aatcgtcaac aacaccaaaa tggtggtgcc cacccccctgc  780
accatggatg aactggaaga actgctgatg gagttcggca ttatggatgt ggaagacacc  840
agcatcattg gtaaaaccgc cgccgaagaa aacgccgtct ga                     882

SEQ ID NO: 187          moltype = DNA  length = 1386
FEATURE                 Location/Qualifiers
gene                    1..1386
                        note = nifK1
source                  1..1386
                        mol_type = genomic DNA
                        organism = Kosakonia sacchari
SEQUENCE: 187
atggccgaaa ttctgcgcag taaaaaaccg ctggcggtca gcccgataaa aagcggccag  60
ccgctggggg cgatcctcgc aagcctgggt gtcgaacagt gcataccgct ggtacacggc  120
gcacagggat gtagcgcgtt cgcgaaggtg ttctttattc aacattttca cgatccgatc  180
ccgctgcaat cgacggcgat ggatccgact tccaccatta tgggcgccga tgaaaacatt  240
tttaccgcgc tcaatgtgct ctgccagcgc aacgccgcga aagccattgt gctgctcagc  300
accgggcttt cagaagccca gggcagcgac atttcgcggg tggtgcgcca gtttcgtgat  360
gattttcccc ggcataaagg cgttgcgctg ctcaccgtca acacacccga tttctacggc  420
tcgctggaaa acggctacag cgccgtgctg gaaagcatga ttgaacagtg ggtacccgca  480
cagcccgccg ccagcctgcg caaccgccgt gtcaacctgc tggtcagcca tttactgaca  540
ccaggcgata tcgaactgtt gcgcagttat gttgaagcct tcggcctgca accggtgatt  600
gtgccggatc tgtcgctgtc gctggacggg catctggcag acggtgattt ttcgcctgtt  660
acccaagggg gaacatcgct gcgcatgatt gaacagatgg ggcaaaacct ggccaccttt  720
gtgattggcg cctcgctggg ccgtgcggcg gcgttactgg cgcagcgcag ccgtggcgag  780
gtgatcgccc tgccgcatct gatgacgctt gcagcctgcg acacgtttat tcatcgactg  840
aaaaccctct ccgggcgcga tgtccccgcg tggattgagc gccagcgcgg ccaagttcag  900
gatgcgatga tcgattgcca tatgtggctg cagggtgcgg ctatcgccat ggcagcagaa  960
ggcgatcacc tggcggcatg gtgcgatttc gcccgcagcc agggcatgat ccccggcccg  1020
attgtcgcac cggtcagcca gccggggttg caaaatctgc cggttgaaac cgtggttatc  1080
ggcgatctgg aagatatgca ggatcggctt tgcgcgacgc ccgccgcgtt actggtggcc  1140
aattctcatg ccgccgatct cgccacgcag tttgatttgt cacttatccg cgccgggttc  1200
ccggtgtatg accggctggg ggaatttcgt cgcctgcgcc aggggtacag cggcattcgt  1260
gacacgctgt ttgagctggc gaatgtgatg cgcgagcgcc atcacccgct tgcaacctac  1320
cgctcgccgc tgcgccagca cgccgacgac aacgttacgc ctggagatct gtatgccgca  1380
tgttaa                                                              1386

SEQ ID NO: 188          moltype = DNA  length = 1287
FEATURE                 Location/Qualifiers
gene                    1..1287
                        note = amtB
source                  1..1287
                        mol_type = genomic DNA
                        organism = Kosakonia sacchari
SEQUENCE: 188
atgaaaaaca caacattaaa aacagcgctt gcttcgctgg cgttactgcc tggcctggcg  60
atggcggctc ccgctgtggc ggataaagcc gacaacggct ttatgatgat ttgcaccgcg  120
ctggtgctgt ttatgaccat tccgggcatt gcgctgttct acggcggttt gatccgcggt  180
aaaaacgtgc tgtcgatgct gacgcaggtt gccgtcacct tcgcactggt gtgcattctg  240
tgggtggtgt atggctactc gctggcattt ggcgagggca acagcttctt cgggagtttt  300
aactgggcga tgttgaaaaa catcgaactg aaagccgtga tgggcagcat ttatcagtat  360
atccacgtgg cgttccaggg ttccttcgcc tgtatcaccg ttggcctgat tgtcggtgca  420
ctggctgagc gtattcgctt ctctgcggtg ctgatttttg tggtggtatg gctgacgctt  480
tcttacgtgc cgattgcaca catggtgtgg ggcggcggtc tgctggcaac ccacggtgcg  540
ctggatttcg caggcggtac ggttgttcac atcaacgctg cgattgcagg tctggtgggg  600
gcttacctga ttggcaaacg cgtgggcttt ggcaaagaag cattcaaacc gcataacctg  660
ccgatggtct tcactggcac cgctatcctg tatgttggct ggtttggttt caacgccggc  720
tccgcaagct cggcgaacga aattgctgcg ctggccttcg tgaacactgt cgttgccact  780
gctgccgcta ttctggcgtg ggtatttggc gaatgggcaa tgcgcggcaa gccgtctctg  840
ctcggtgcct gttctggtgc catcgcgggt ctggttggta tcacccccgc ctgtggttat  900
gtgggtgtcg gcggtgcgct gattgtgggt ctgattgccg gtctggctgg gctgtggggc  960
gttactgcgc tgaaacgtat gttgcgtgtc gatgacccgt gtgacgtatt cggtgtgcac  1020
ggcgtgtgcg gcatcgtggg ctgtatcctg acgggtatct tcgcctctac gtcgctgggt  1080
ggtgtcggtt tcgctgaagg tgtgaccatg ggccatcagg tgctggtgca gctggaaagt  1140
gttgccatca ctatcgtgtg gtctggcgtg gtggccttta ttggttacaa actggcggac  1200
atgacggtag gcctgcgcgt accggaagaa caagaacgtg aagggctgga tgtaaacagc  1260
```

```
cacggcgaaa acgcctataa cgcctga                                   1287

SEQ ID NO: 189         moltype = DNA  length = 348
FEATURE                Location/Qualifiers
gene                   1..348
                       note = Prm1
source                 1..348
                       mol_type = genomic DNA
                       organism = Kosakonia sacchari
SEQUENCE: 189
cgtcctgtaa taataaccgg acaattcgga ctgattaaaa aagcgccctt gtggcgcttt  60
ttttatattc ccgcctccat ttaaaataaa aaatccaatc ggatttcact atttaaactg  120
gccattatct aagatgaatc cgatggaagc tcgctgtttt aacacgcgtt ttttaacctt  180
ttattgaaag tcggtgcttc tttgagcgaa cgatcaaatt taagtggatt cccatcaaaa  240
aaatattctc aacctaaaaa agtttgtgta atacttgtaa cgctacatgg agattaactc  300
aatctagagg gtattaataa tgaatcgtac taaactggta ctgggcgc              348

SEQ ID NO: 190         moltype = DNA  length = 313
FEATURE                Location/Qualifiers
gene                   1..313
                       note = Prm5
source                 1..313
                       mol_type = genomic DNA
                       organism = Kosakonia sacchari
SEQUENCE: 190
ggacatcatc gcgacaaaca atattaatac cggcaaccac accggcaatt tacgagactg  60
cgcaggcatc ctttctcccg tcaatttctg tcaaataaag taaaagaggc agtctacttg  120
aattaccccc ggctggttga gcgtttgttg aaaaaaagta actgaaaaat ccgtagaata  180
gcgccactct gatggttaat taacctattc aattaagaat tatctggatg aatgtgccat  240
taaatgcgca gcataatggt gcgttgtgcg ggaaaactgc ttttttttga aagggttggt  300
cagtagcgga aac                                                    313

SEQ ID NO: 191         moltype = DNA  length = 1485
FEATURE                Location/Qualifiers
gene                   1..1485
                       note = nifL
source                 1..1485
                       mol_type = genomic DNA
                       organism = Rahnella aquatilis
SEQUENCE: 191
atgaccctga atatgatgct cgataacgcc gcgccggagg ccatcgccgg cgcgctgact  60
caacaacatc cggggctgtt ttttaccatg gtggaacagg cctcggtggc catctccctc  120
accgatgcca gcgccaggat catttacgcc aacccggcgt tttgccgcca gaccggctat  180
tcgctggcgc aattgttaaa ccagaacccg cgcctgctgg ccagcagcca gacgccgcgc  240
gagatctatc aggagatgtg gcataccctg ctccagcgtc agccctggcg cggtcagctg  300
attaatcagc gtcgggacgg cggcctgtac ctggtggaga ttgacatcac cccggtgctt  360
agcccgcaag gggaactgga gcattatctg gcgatgcagc gggatatcag cgtcagctac  420
accctcgaac agcggctgcg caaccatatg accctgatgg aggcggtgct gaataatatc  480
cccgccgccg tggtagtggt ggacgagcag gatcgggtgg tgatggacaa cctcgcctac  540
aaaaccttct gcgctgactg cggcggccgg gagctgctca ccgagctgca ggtctcccct  600
ggccggatga cgcccggcgt ggaggcgatc ctgccggtgg cgctgcgcgg ggccgcgcgc  660
tggctgtcgg taacctgctg gccgttgccc ggcgtcagtg aagaggccag ccgctacttt  720
atcgacagcg cgctggcgcg gaccctggtg gtgatcgccg actgtaccca gcagcgtcag  780
cagcaggagc aagggcgcct tgaccggctg aagcagcaaa tgaccgccgg caagctgctg  840
gcggcgatcc gcgagtcgct ggacgccgcg ctgatccagc tgaactgccc gattaatatg  900
ctggcggcag cccgtcggct gaacggcgag ggaagcggga atgtggcgct ggaggccgcc  960
tggcgtgaag gggaagaggc gatggcgcgg ctccagcgct gtcgcccatc gctggaactc  1020
gaaaaccccg ccgtctggcc gctgcagccc tttttcgacg atctgtgcgc cctctaccgt  1080
acacgcttcg atcccgacgg gctgcaggtc gacatggcct caccgcatct gatcggcttt  1140
ggccagcgca ccccactgct ggcgtgctta agcctgtggc tcgatcgcac cctggccctc  1200
gccgccgaac tcccctccgt gccgctggcg atgcagctct acgccgagga gaacgacggc  1260
tggctgtcgc tgtatctgac tgacaacgta ccgctgctgc aggtgcgcta cgctcactcc  1320
cccgacgcgc tgaactcgcc gggcaaaggc atggagctgc ggctgatcca gaccctggtg  1380
gcgcaccatc gcggggccat tgagctggct tcccgaccgc agggcggcac ctgcctgacc  1440
ctgcgtttcc cgctgtttaa caccctgacc ggaggtgaag catga                 1485

SEQ ID NO: 192         moltype = DNA  length = 1575
FEATURE                Location/Qualifiers
gene                   1..1575
                       note = nifA
source                 1..1575
                       mol_type = genomic DNA
                       organism = Rahnella aquatilis
SEQUENCE: 192
atgatccctg aatccgaccc ggacaccacc gtcagacgct tcgacctctc tcagcagttc  60
accgccatgc agcggataag cgtggtgctg agccgggcca ccgaggccag caaaacgctg  120
caggaggtgc tcagcgtatt acacaacgat gcctttatgc agcacgggat gatctgcctg  180
tacgacagcg agcaggagat cctcagtatc gaagcgctgc agcaaaccgg ccagcagccc  240
ctccccggca gcacgcagat ccgctatcgc cccggcgagg gactggtggg gaccgtgctg  300
```

```
gcccaggggc agtcgctggt gctgccccgg gtcgccgacg atcagcgttt tctcgaccgc  360
ctgagcctct acgattacga tctgccgttt atcgccgtac cgttgatggg gcccaacgcc  420
cggccaatag gggtgctggc ggcccagccg atggcgcgcc aggaagagcg gctgccggcc  480
tgcacccgtt ttctcgaaac cgtcgccaac ctcgtcgccc agaccatccg gctgatgatc  540
cttccggcct cacccgccct gtcgagccgc cagccgccga aggtggaacg gccgccggcc  600
tgctcgtcgt cgcgcggcgt gggccttgac aatatggtcg gcaagagccc ggcgatgcgc  660
cagatcgtgg aggtgatccg tcaggtttcg cgctgggaca ccaccgtgct ggtacgcggc  720
gaaagcggca ccgggaaaga gctgatcgcc aacgccatcc atcaccattc gccacgggct  780
ggcgccgcct tcgtcaaatt taactgcgcg gcgctgccgg acaccctgct ggaaagcgaa  840
ctgttcggcc atgagaaagg cgcctttacc ggggcggtgc gtcagcgtaa aggacgtttt  900
gagctggcgg atggcggcac cctgttcctc gatgagattg gtgaaagcag cgcctcgttc  960
caggccaagc tgctgcgtat cctccaggag ggggagatgg agcgggtcgg cggcgatgag  1020
accctgcggg tgaatgtccg catcatcgcc gccaccaacc gtcacctgga ggaggaggtc  1080
cggctgggcc atttccgcga ggatctctac tatcgtctga acgtgatgcc catcgccctg  1140
cccccgctgc gcgagcgtca ggaggacatc gccgagctgg cgcacttcct ggtgcgcaaa  1200
atcggccagc atcaggggcg cacgctgcgg atcagcgagg gcgcgatccg cctgctgatg  1260
gagtacagct ggccgggtaa cgttcgcgaa ctggagaact gcctcgaacg atcggcggtg  1320
atgtcggaga gtggcctgat cgatcgcgac gtgatcctct tcactcacca ggatcgtccc  1380
gccaaagccc tgcctgccag cggccagcg gaagacagct ggctggacaa cagcctggac  1440
gaacgtcagc gactgatcgc cgcgctggaa aaagccggct gggtgcaggc caaggcggca  1500
cggctgctgg ggatgacgcc gcgccaggtc gcttatcgga tccagatcat ggatatcacc  1560
ctgccgcgtc tgtag                                                 1575

SEQ ID NO: 193         moltype = DNA  length = 1540
FEATURE                Location/Qualifiers
gene                   1..1540
                       note = 16S-1
source                 1..1540
                       mol_type = genomic DNA
                       organism = Rahnella aquatilis
SEQUENCE: 193
attgaagagt ttgatcatgg ctcagattga acgctggcgg caggcctaac acatgcaagt  60
cgagcggcag cgggaagtag cttgctactt tgccggcgag cggcggacgg gtgagtaatg  120
tctgggaaac tgcctgatgg agggggataa ctactggaaa cggtagctaa taccgcatga  180
cctcgaaaga gcaaagtggg ggatcttcgg acctcacgcc atcggatgtg cccagatggg  240
attagctagt aggtgaggta atggctcacc taggcgacga tccctagctg gtctgagagg  300
atgaccagcc acactggaac tgagacacgg tccagactcc tacgggaggc agcagtgggg  360
aatattgcac aatgggcgca agcctgatgc agccatgccg cgtgtgtgaa gaaggcctta  420
gggttgtaaa gcactttcag cgaggaggaa ggcatcatac ttaatacgtg tggtgattga  480
cgttactcgc agaagaagca ccggctaact ccgtgccagc agccgcggta atacggaggg  540
tgcaagcgtt aatcggaatt actgggcgta aagcgcacgc aggcggtttg ttaagtcaga  600
tgtgaaatcc ccgagcttaa cttgggaact gcatttgaaa ctggcaagct agagtcttgt  660
agaggggggt agaattccag gtgtagcggt gaaatgcgta gagatctgga ggaataccgg  720
tggcgaaggc ggccccctgg acaaagactg acgctcaggt gcgaaagcgt ggggagcaaa  780
caggattaga taccctggta gtccacgctg taaacgatgt cgacttggag gttgtgccct  840
tgaggcgtgg cttccggagc taacgcgtta agtcgaccgc ctggggagta cggccgcaag  900
gttaaaactc aaatgaattg acgggggccc gcacaagcgg tggagcatgt ggtttaattc  960
gatgcaacgc gaagaacctt acctactctt gacatccaga gaatttgcca gagatggcga  1020
agtgccttcg ggaactctga gacaggtgct gcatggctgt cgtcagctcg tgttgtgaaa  1080
tgttgggtta agtcccgcaa cgagcgcaac ccttatcctt tgttgccagc acgtaatggt  1140
gggaactcaa aggagactgc cggtgataaa ccggaggaag gtggggatga cgtcaagtca  1200
tcatggccct tacgagtagg gctacacacg tgctacaatg gcatatacaa agagaagcga  1260
actcgcgaga gcaagcggac ctcataaagt atgtcgtagt ccggattgga gtctgcaact  1320
cgactccatg aagtcggaat cgctagtaat cgtagatcag aatgctacgg tgaatacgtt  1380
cccgggcctt gtacacaccg cccgtcacac catgggagtg ggttgcaaaa gaagtaggta  1440
gcttaacctt cgggagggcg cttaccactt tgtgattcat gactggggtg aagtcgtaac  1500
aaggtaaccg taggggaacc tgcggttgga tcacctcctt                      1540

SEQ ID NO: 194         moltype = DNA  length = 1540
FEATURE                Location/Qualifiers
gene                   1..1540
                       note = 16S-2
variation              267
                       note = n is a, c, t, g, unknown or other
source                 1..1540
                       mol_type = genomic DNA
                       organism = Rahnella aquatilis
SEQUENCE: 194
attgaagagt ttgatcatgg ctcagattga acgctggcgg caggcctaac acatgcaagt  60
cgagcggcat cgggaagtag cttgctactt tgccggcgag cggcggacgg gtgagtaatg  120
tctgggaaac tgcctgatgg agggggataa ctactggaaa cggtagctaa taccgcatga  180
cctcgaaaga gcaaagtggg ggatcttcgg acctcacgcc atcggatgtg cccagatggg  240
attagctagt aggtgaggta atggctnacc taggcgacga tccctagctg gtctgagagg  300
atgaccagcc acactggaac tgagacacgg tccagactcc tacgggaggc agcagtgggg  360
aatattgcac aatgggcgca agcctgatgc agccatgccg cgtgtgtgaa gaaggcctta  420
gggttgtaaa gcactttcag cgaggaggaa ggcatcatac ttaatacgtg tggtgattga  480
cgttactcgc agaagaagca ccggctaact ccgtgccagc agccgcggta atacggaggg  540
tgcaagcgtt aatcggaatt actgggcgta aagcgcacgc aggcggtttg ttaagtcaga  600
tgtgaaatcc ccgagcttaa cttgggaact gcatttgaaa ctggcaagct agagtcttgt  660
```

-continued

```
agagggggt agaattccag gtgtagcggt gaaatgcgta gagatctgga ggaataccgg  720
tggcgaaggc ggcccctgg acaaagactg acgctcaggt gcgaaagcgt ggggagcaaa  780
caggattaga taccctggta gtccacgctg taaacgatgt cgacttggag gttgtgccct  840
tgaggcgtgg cttccggagc taacgcgtta agtcgaccgc ctggggagta cggccgcaag  900
gttaaaactc aaatgaattg acgggggccc gcacaagcgg tggagcatgt ggtttaattc  960
gatgcaacgc gaagaacctt acctactctt gacatccaga gaatttgcca gagatggcga  1020
agtgccttcg ggaactctga gacaggtgct gcatggctgt cgtcagctcg tgttgtgaaa  1080
tgttgggtta agtcccgcaa cgagcgcaac ccttatcctt tgttgccagc acgtgatggt  1140
gggaactcaa aggagactgc cggtgataaa ccggaggaag gtggggatga cgtcaagtca  1200
tcatggccct tacgagtagg gctacacacg tgctacaatg gcatatacaa agagaagcga  1260
actcgcgaga gcaagcggac ctcataaagt atgtcgtagt ccggattgga gtctgcaact  1320
cgactccatg aagtcggaat cgctagtaat cgtagatcag aatgctacgg tgaatacgtt  1380
cccgggcctt gtacacaccg cccgtcacac catgggagtg ggttgcaaaa gaagtaggta  1440
gcttaacctt cgggagggcg cttaccactt tgtgattcat gactggggtg aagtcgtaac  1500
aaggtaaccg taggggaacc tgcggttgga tcacctcctt                       1540

SEQ ID NO: 195          moltype = DNA  length = 1540
FEATURE                 Location/Qualifiers
gene                    1..1540
                        note = 16S-3
variation               455
                        note = n is a, c, t, g, unknown or other
source                  1..1540
                        mol_type = genomic DNA
                        organism = Rahnella aquatilis
SEQUENCE: 195
attgaagagt ttgatcatgg ctcagattga acgctggcgg caggcctaac acatgcaagt  60
cgagcggcag cgggaagtag cttgctactt tgccggcgag cggcggacgg gtgagtaatg  120
tctgggaaac tgcctgatgg agggggataa ctactggaaa cggtagctaa taccgcatga  180
cctcgaaaga gcaaagtggg ggatcttcgg acctcacgcc atcggatgtg cccagatggg  240
attagctagt aggtgaggta atggctcacc taggcgacga tccctagctg gtctgagagg  300
atgaccagcc acactggaac tgagacacgg tccagactcc tacgggaggc agcagtgggg  360
aatattgcac aatgggcgca agcctgatgc agccatgccg cgtgtgtgaa gaaggcctta  420
gggttgtaaa gcactttcag cgaggaggaa ggcancatac ttaatacgtg tggtgattga  480
cgttactcgc agaagaagca ccggctaact ccgtgccagc agccgcggta atacggaggg  540
tgcaagcgtt aatcggaatt actgggcgta aagcgcacgc aggcggtttg ttaagtcaga  600
tgtgaaatcc ccgagcttaa cttgggaact gcatttgaaa ctggcaagct agagtcttgt  660
agagggggt agaattccag gtgtagcggt gaaatgcgta gagatctgga ggaataccgg  720
tggcgaaggc ggcccctgg acaaagactg acgctcaggt gcgaaagcgt ggggagcaaa  780
caggattaga taccctggta gtccacgctg taaacgatgt cgacttggag gttgtgccct  840
tgaggcgtgg cttccggagc taacgcgtta agtcgaccgc ctggggagta cggccgcaag  900
gttaaaactc aaatgaattg acgggggccc gcacaagcgg tggagcatgt ggtttaattc  960
gatgcaacgc gaagaacctt acctactctt gacatccaga gaatttgcca gagatggcga  1020
agtgccttcg ggaactctga gacaggtgct gcatggctgt cgtcagctcg tgttgtgaaa  1080
tgttgggtta agtcccgcaa cgagcgcaac ccttatcctt tgttgccagc acgtgatggt  1140
gggaactcaa aggagactgc cggtgataaa ccggaggaag gtggggatga cgtcaagtca  1200
tcatggccct tacgagtagg gctacacacg tgctacaatg gcatatacaa agagaagcga  1260
actcgcgaga gcaagcggac ctcataaagt atgtcgtagt ccggattgga gtctgcaact  1320
cgactccatg aagtcggaat cgctagtaat cgtagatcag aatgctacgg tgaatacgtt  1380
cccgggcctt gtacacaccg cccgtcacac catgggagtg ggttgcaaaa gaagtaggta  1440
gcttaacctt cgggagggcg cttaccactt tgtgattcat gactggggtg aagtcgtaac  1500
aaggtaaccg taggggaacc tgcggttgga tcacctcctt                       1540

SEQ ID NO: 196          moltype = DNA  length = 1540
FEATURE                 Location/Qualifiers
gene                    1..1540
                        note = 16S-4
variation               70
                        note = n is a, c, t, g, unknown or other
source                  1..1540
                        mol_type = genomic DNA
                        organism = Rahnella aquatilis
SEQUENCE: 196
attgaagagt ttgatcatgg ctcagattga acgctggcgg caggcctaac acatgcaagt  60
cgagcggcan cgggaagtag cttgctactt tgccggcgag cggcggacgg gtgagtaatg  120
tctgggaaac tgcctgatgg agggggataa ctactggaaa cggtagctaa taccgcatga  180
cctcgaaaga gcaaagtggg ggatcttcgg acctcacgcc atcggatgtg cccagatggg  240
attagctagt aggtgaggta atggcttacc taggcgacga tccctagctg gtctgagagg  300
atgaccagcc acactggaac tgagacacgg tccagactcc tacgggaggc agcagtgggg  360
aatattgcac aatgggcgca agcctgatgc agccatgccg cgtgtgtgaa gaaggcctta  420
gggttgtaaa gcactttcag cgaggaggaa ggcatcacac ttaatacgtg tggtgattga  480
cgttactcgc agaagaagca ccggctaact ccgtgccagc agccgcggta atacggaggg  540
tgcaagcgtt aatcggaatt actgggcgta aagcgcacgc aggcggtttg ttaagtcaga  600
tgtgaaatcc ccgagcttaa cttgggaact gcatttgaaa ctggcaagct agagtcttgt  660
agagggggt agaattccag gtgtagcggt gaaatgcgta gagatctgga ggaataccgg  720
tggcgaaggc ggcccctgg acaaagactg acgctcaggt gcgaaagcgt ggggagcaaa  780
caggattaga taccctggta gtccacgctg taaacgatgt cgacttggag gttgtgccct  840
tgaggcgtgg cttccggagc taacgcgtta agtcgaccgc ctggggagta cggccgcaag  900
gttaaaactc aaatgaattg acgggggccc gcacaagcgg tggagcatgt ggtttaattc  960
```

```
gatgcaacgc gaagaacctt acctactctt gacatccaga gaatttgcca gagatggcga  1020
agtgccttcg ggaactctga gacaggtgct gcatggctgt cgtcagctcg tgttgtgaaa  1080
tgttgggtta agtcccgcaa cgagcgcaac ccttatcctt tgttgccagc acgtgatggt  1140
gggaactcaa aggagactgc cggtgataaa ccggaggaag gtggggatga cgtcaagtca  1200
tcatggccct tacgagtagg gctacacacg tgctacaatg gcatatacaa agagaagcga  1260
actcgcgaga gcaagcggac ctcataaagt atgtcgtagt ccggattgga gtctgcaact  1320
cgactccatg aagtcggaat cgctagtaat cgtagatcag aatgctacgg tgaatacgtt  1380
cccgggcctt gtacacaccg cccgtcacac catgggagtg ggttgcaaaa gaagtaggta  1440
gcttaacctt cgggagggcg cttaccactt tgtgattcat gactggggtg aagtcgtaac  1500
aaggtaaccg taggggaacc tgcggttgga tcacctcctt                        1540

SEQ ID NO: 197         moltype = DNA  length = 1540
FEATURE                Location/Qualifiers
gene                   1..1540
                       note = 16S-5
source                 1..1540
                       mol_type = genomic DNA
                       organism = Rahnella aquatilis
SEQUENCE: 197
attgaagagt ttgatcatgg ctcagattga acgctggcgg caggcctaac acatgcaagt  60
cgagcggcag cgggaagtag cttgctactt tgccggcgag cggcggacgg gtgagtaatg  120
tctgggaaac tgcctgatgg agggggataa ctactggaaa cggtagctaa taccgcatga  180
cctcgaaaga gcaaagtggg ggatcttcgg acctcacgcc atcggatgtg cccagatggg  240
attagctagt aggtgaggta atggctcacc taggcgacga tccctagctg gtctgagagg  300
atgaccagcc acactggaac tgagacacgg tccagactcc tacgggaggc agcagtgggg  360
aatattgcac aatgggcgca agcctgatgc agccatgccg cgtgtgtgaa gaaggcctta  420
gggttgtaaa gcactttcag cgaggaggaa ggcatcacac ttaatacgtg tgttgattga  480
cgttactcgc agaagaagca ccggctaact ccgtgccagc agccgcggta atacggaggg  540
tgcaagcgtt aatcggaatt actgggcgta aagcgcacgc aggcggtttg ttaagtcaga  600
tgtgaaatcc ccgagcttaa cttgggaact gcatttgaaa ctggcaagct agagtcttgt  660
agaggggggt agaattccag gtgtagcggt gaaatgcgta gagatctgga ggaataccgg  720
tggcgaaggc ggccccctgg acaaagactg acgctcaggt gcgaaagcgt ggggagcaaa  780
caggattaga taccctggta gtccacgctg taaacgatgt cgacttggag gttgtgccct  840
tgaggcgtgg cttccggagc taacgcgtta agtcgaccgc ctggggagta cggccgcaag  900
gttaaaactc aaatgaattg acgggggccc gcacaagcgg tggagcatgt ggtttaattc  960
gatgcaacgc gaagaacctt acctactctt gacatccaga gaatttgcca gagatggcga  1020
agtgccttcg ggaactctga gacaggtgct gcatggctgt cgtcagctcg tgttgtgaaa  1080
tgttgggtta agtcccgcaa cgagcgcaac ccttatcctt tgttgccagc acgtgatggt  1140
gggaactcaa aggagactgc cggtgataaa ccggaggaag gtggggatga cgtcaagtca  1200
tcatggccct tacgagtagg gctacacacg tgctacaatg gcatatacaa agagaagcga  1260
actcgcgaga gcaagcggac ctcataaagt atgtcgtagt ccggattgga gtctgcaact  1320
cgactccatg aagtcggaat cgctagtaat cgtagatcag aatgctacgg tgaatacgtt  1380
cccgggcctt gtacacaccg cccgtcacac catgggagtg ggttgcaaaa gaagtaggta  1440
gcttaacctt cgggagggcg cttaccactt tgtgattcat gactggggtg aagtcgtaac  1500
aaggtaaccg taggggaacc tgcggttgga tcacctcctt                        1540

SEQ ID NO: 198         moltype = DNA  length = 1009
FEATURE                Location/Qualifiers
gene                   1..1009
                       note = 16S-6
variation              296
                       note = n is a, c, t, g, unknown or other
variation              311
                       note = n is a, c, t, g, unknown or other
variation              973
                       note = n is a, c, t, g, unknown or other
source                 1..1009
                       mol_type = genomic DNA
                       organism = Rahnella aquatilis
SEQUENCE: 198
gtagctaata ccgcatgacc tcgaaagagc aaagtggggg atcttcggac ctcacgccat  60
cggatgtgcc cagatgggat tagctagtag gtgaggtaat ggctcaccta ggcgacgatc  120
cctagctggt ctgagaggat gaccagccac actggaactg agacacggtc cagactccta  180
cgggaggcag cagtggggaa tattgcacaa tgggcgcaag cctgatgcag ccatgccgcg  240
tgtgtgaaga aggccttagg gttgtaaagc actttcagcg aggaggaagg catcanactt  300
aatacgtgtg ntgattgacg ttactcgcag aagaagcacc ggctaactcc gtgccagcag  360
ccgcggtaat acggagggtg caagcgttaa tcggaattac tgggcgtaaa gcgcacgcag  420
gcggtttgtt aagtcagatg tgaaatcccc gagcttaact tgggaactgc atttgaaact  480
ggcaagctag agtcttgtag aggggggtag aattccaggt gtagcggtga aatgcgtaga  540
gatctggagg aataccggtg gcgaaggcgg ccccctggac aaagactgac gctcaggtgc  600
gaaagcgtgg ggagcaaaca ggattagata ccctggtagt ccacgctgta aacgatgtcg  660
acttggaggt tgtgcccttg aggcgtggct tccggagcta acgcgttaag tcgaccgcct  720
ggggagtacg gccgcaaggt taaaactcaa atgaattgac gggggcccgc acaagcggtg  780
gagcatgtgg tttaattcga tgcaacgcga agaaccttac ctactcttga catccagaga  840
atttgccaga gatggcgaag tgccttcggg aactctgaga caggtgctgc atggctgtcg  900
tcagctcgtg ttgtgaaatg ttgggttaag tcccgcaacg agcgcaaccc ttatcctttg  960
ttgccagcac gtnatggtgg gaactcaaag gagactgccg gtgataaac               1009

SEQ ID NO: 199         moltype = DNA  length = 1519
```

```
FEATURE                 Location/Qualifiers
gene                    1..1519
                        note = 16S-7
source                  1..1519
                        mol_type = genomic DNA
                        organism = Rahnella aquatilis
SEQUENCE: 199
attgaagagt ttgatcatgg ctcagattga acgctggcgg caggcctaac acatgcaagt  60
cgagcggcag cgggaagtag cttgctactt tgccggcgag cggcggacgg gtgagtaatg  120
tcctgatgga ggggataact actggaacgg tagctaatac cgcacctcga aagagcaaag  180
tgggggatct tcggacctca cgccatcgga tgtgcccaga tgggattagc tagtaggtga  240
ggtaatggct cacctaggcg acgatcccta gctggtctga gaggatgacc agccacactg  300
gaactgagac acggtccaga ctcctacggg aggcagcagt ggggaatatt gcacaatggg  360
cgcaagcctg atgcagccat gccgcgtgtg tgaagaaggc cttagggttg taaagcactt  420
tcagcgagga ggaaggcatc atacttaata cgtgtggtga ttgacgttac tcgcagaaga  480
agcaccggct aactccgtgc cagcagccgc ggtaatacgg agggtgcaag cttaatcgga  540
attactgggc gtaaagcgca cgcaggcggt tgttaagtca gatgtgaaat ccccgagctt  600
aacttgggaa ctgcatttga aactggcaag ctagagtctt gtagaggggg gtagaattcc  660
aggtgtagcg gtgaaatgcg tagagatctg gaggaatacc ggtggcgaag gcggccccct  720
ggacaaagac tgacgctcag gtgcgaaagc gtggggagca aacaggatta ataccctggt  780
agtccacgct gtaacgatgt cgacttggag gttgtgccct gaggcgtggc ttccggagct  840
aacgcgttaa gtcgaccgcc tggggagtac ggccgcaagg ttaaaactca aatgaattga  900
cgggggcccg cacaagcggt ggagcatgtg gtttaattcg atgcaacgcg aagaacctta  960
cctactcttg acatccagag aatttgccag agatggcgaa gtgccttcgg gaactctgag  1020
acaggtgctg catggctgtc gtcagctcgt gttgtgaaat gttgggttaa gtcccgcaac  1080
gagcgcaacc cttatccttt gttgccagca cgtaatggtg ggaactcaaa ggagactgcc  1140
ggtgataaac cggaggaagg tggggatgac gtcaagtcat catggccctt acgagtaggg  1200
ctacacacgt gctacaatgg catatacaaa gagaagcgaa ctcgcgagag caagcggacc  1260
tcataaagta tgtcgtagtc cggattggag tctgcaactc gactccatga agtcggaatc  1320
gctagtaatc gtagatcaga atgctacggt gaatacgttc ccgggccttg tacacaccgc  1380
ccgtcacacc atgggagtgg gttgcaaaag aagtaggtag cttaaccttc gggagggcgc  1440
ttaccacttt gtgattcatg actggggtga agtcgtaaca aggtaaccgt aggggaacct  1500
gcggttggat cacctcctt                                                 1519

SEQ ID NO: 200          moltype = DNA  length = 882
FEATURE                 Location/Qualifiers
gene                    1..882
                        note = nifH1
source                  1..882
                        mol_type = genomic DNA
                        organism = Rahnella aquatilis
SEQUENCE: 200
atgaccatgc gtcaatgcgc tatctacggt aaaggcggta tcggtaaatc caccaccacc  60
cagaatctcg tcgcggccct cgccgagatg ggtaagaaag tgatgatcgt cggctgcgat  120
ccgaaagcgg attccacccg tctgatcctc cacgctaaag cccagaacac catcatggag  180
atggcggcgg aagtgggctc ggtcgaggat ctggagctcg aagacgttct gcaaatcggc  240
tatggcgatg tccgttgcgc cgaatccggc ggcccggagc caggcgtcgg ctgcgccgga  300
cgcggggtga tcaccgccat caacttcctc gaggaagaag gcgcctatga agaagatttg  360
gatttcgtct tctatgacgt cctcggcgac gtggtctgcg gcggcttcgc tatgccgatc  420
cgcgaaaaca aagcccagga gatctacatc gtctgctccg gcgagatgat ggcgatgtat  480
gccgccaaca atatctccaa agggatcgtg aagtacgcca aatccggcaa ggtgcgcctc  540
ggcggcctga tctgtaactc gcgcaaaacc gaccgggaag acgaactgat catcgccctg  600
gcggagaagc ttggcacgca gatgatccac ttcgttcccc gcgacaacat tgtgcagcgc  660
gcggagatcc gccggatgac ggtgatcgag tacgacccga cctgtcagca ggcgaatgaa  720
tatcgtcaac tggcgcagaa gatcgtcaat aacaccaaaa aagtggtgcc gacgccgtgc  780
accatggacg agctggaatc gctgctgatg gagttcggca tcatggaaga agaagacacc  840
agcatcattg gtaaaaccgc cgctgaagaa aacgcggcct ga                       882

SEQ ID NO: 201          moltype = DNA  length = 1113
FEATURE                 Location/Qualifiers
gene                    1..1113
                        note = nifH2
source                  1..1113
                        mol_type = genomic DNA
                        organism = Rahnella aquatilis
SEQUENCE: 201
atggttagga aaagtagaag taaaaataca aatatagaac taactgaaca tgaccattta  60
ttaataagtc aaataaaaaa gcttaaaaca caaaccactt gctttttaa taataaagga  120
ggggttggga agactacatt agtagcaaat ttaggagcag agctatcaat aaactttagt  180
gcaaaagttc ttattgtgga tgccgaccct caatgtaatc tcacgcagta tgtattaagt  240
gatgaagaaa ctcaggactt atatgggcaa gaaaatccag atagtattta tacagtaata  300
agaccactat cctttggtaa aggatatgaa agtgacctcc ctataaggca tgtagagaat  360
ttcggttttg acataattgt cggtgaccct agacttgctt tacaggaaga cctttagct  420
ggagactggc gagatgccaa aggcggtggg atgcgaggaa ttaggacaac ttttgtattt  480
gcagagttaa ttaagaaagc tcgtgagcta aattatgatt ttgttttctt tgacatggga  540
ccatcattag gcgcaatcaa cagggcagta ttactggcaa tggaattctt tgtcgtccca  600
atgtcaatcg atgtattttc actatgggct attaaaaata ttggctccac ggtttcaata  660
tggaaaaaag aattagacac agggattcgg ctctcagagg aacctagcga attatcacaa  720
ttatcacctc aaggaaaact aaagtttctc ggttacgtca cccaacaaca taaagaacgc  780
```

```
tctggatacg atacaattca gcttgagaat actgaggaag aaataaaatc gaaacgtcgg  840
gtaaaggcgt atgaagacat tggagaggtg tttccttcta aaattactga gcatctttct  900
aaactttatg catcaaaaga tatgaaccca caccttggag atatacgtca tttaggtagt  960
ttagctccga aatcacaatc acaacacgtt ccgatgatat cagtgtctgg tacaggaaat  1020
tacaccagac ttagaaaaag cgcgcgtgaa ctttatcgag atattgcaag aagatactta  1080
gagaacattc agactgctaa tggcgagaaa tag                               1113

SEQ ID NO: 202         moltype = DNA  length = 1374
FEATURE                Location/Qualifiers
gene                   1..1374
                       note = nifD1
source                 1..1374
                       mol_type = genomic DNA
                       organism = Rahnella aquatilis
SEQUENCE: 202
atgaagggaa aggaaattct ggcgctgctg gacgaacccg cctgcgagca caaccagaag  60
caaaaatccg gctgcagcgc ccctaagccc ggcgctaccg ccggcggttg cgccttcgac  120
ggcgcgcaga taacgctcct gcccatcgcc gacgtcgcgc acctggtgca cggccccatc  180
ggctgcgcgg gcagctcgtg ggataaccgc ggcagcgtca gcgccggccc ggccctcaac  240
cggctcggct ttaccaccga tcttaacgaa caggatgtga ttatgggccg cggcgaacgc  300
cgcctgttcc acgccgtgcg tcacatcgtc gaccgctatc atccggcggc ggtctttatc  360
tacaacacct gcgtaccggc gatggagggc gatgacatcg aggcggtctg ccaggccgca  420
cagaccgcca ccggcgtccc ggtcatcgct attgacgccg ccggtttcta cggcagtaaa  480
aatcttggca accgaatggc gggcgacgtg atgctcaggc aggtgattgg ccagcgcgaa  540
ccggccccgt ggccagacaa cacgcccttt gccccggccc agcgccacga tatcggcctg  600
attggcgaat tcaatatcgc cggcgagttc tggcaggtcc agccgctgct cgacgagctg  660
gggatccgcg tcctcggcag cctctccggc gacggccgct ttgccgagat ccagaccctg  720
caccgggcgc aggccaatat gctggtgtgc tcgcgcgcgc tgatcaacgt cgcccggggg  780
ctggagctgc gctacggcac gccgtggttt gaaggcagct tctacgggat ccgcgccacc  840
tccgacgcct tgcgccagct ggcgacgctg ctgggggatg acgacctgcg ccgccgcacc  900
gaggcgctga tcgcccgcga agagcaggcg gcggagcagg ctcttgcgcc gtggcgtgag  960
cagctccgcg ggcgcaaagt gctgctctat accggcggcg tgaaatcctg gtcggtggta  1020
tcggccctgc aggatctcgg catgaccgtg gtggccaccg gcacgcgcaa atccaccgag  1080
gaggacaaac agcggatccg tgagctgatg ggcgacgagg cggtgatgct tgaggagggc  1140
aatgcccgca ccctgctcga cgtggtgtac cgctatcagg ccgacctgat gatcgccggc  1200
ggacgcaata tgtacaccgc ctggaaagcc cggctgccgt ttctcgatat caatcaggag  1260
cgcgagcacg cctacgccgg ctatcagggc atcatcaccc tcgcccgcca gctctgtctg  1320
accctcgcca gccccgtctg gccgcaaacg catacccgcg ccccgtggcg ctag        1374

SEQ ID NO: 203         moltype = DNA  length = 1449
FEATURE                Location/Qualifiers
gene                   1..1449
                       note = nifD2
source                 1..1449
                       mol_type = genomic DNA
                       organism = Rahnella aquatilis
SEQUENCE: 203
atgaccaacg caacaggcga acgtaacctt gcgctcatcc aggaagtcct ggaggtgttt  60
cccgaaaccg cgcgcaaaga gcgcagaaag cacatgatga tcagcgatcc gcagatggag  120
agcgtcggca agtgcattat ctcgaaccgt aaatcgcagc ccggggtgat gaccgtgcgc  180
ggctgcgcct atgcgggctc gaaaggggtg gtgtttgggc caatcaaaga catggcccat  240
atctcgcacg gccccatcgg ctgcggccag tattcccgcg ccggacggcg caactactat  300
accggcgtca gcggtgtcga cagcttcggc accctgaact tcacctctga ttttcaggag  360
cgcgatattg ttttcggcgg cgataaaaag ctgaccaaac tgatcgaaga gatggagctg  420
ctgttcccgc tgaccaaagg gatcaccatc cagtcggagt gcccggtggg cctgatcggc  480
gatgacatca gcgccgtagc caacgccagc agcaaggcgc tggataaacc ggtgatcccg  540
gtgcgctgcg aaggctttcg cggcgtatcg caatcgctgg gccaccatat cgccaacgac  600
gtggtgcgcg actgggtgct gaacaatcgc gaagggcagc cgtttgccag caccccgtac  660
gatgttgcca tcattggcga ttacaacatc ggcggcgacg cctgggcctc gcgcattctg  720
ctggaagaga tggggctgcg cgtagtggcg cagtggtccg gcgacggcac cctggtggag  780
atggagaaca ccccattcgt taagcttaac ctcgtccact gctaccgttc gatgaactat  840
atcgcccgcc atatggagga gaaacatcag atcccatgga tggaatataa cttcttcggc  900
ccgaccaaaa tcgccgaatc gctgcgcaag atcgccgatc aatttgatga caccattcgc  960
gccaatgcgg aagcggtgat cgccaaatat gaggggcaga tggcggccat catcgccaaa  1020
tatcgcccgc ggctggaggg gcgcaaagtg ctgctgtaca tgggggggct gcggccgcgc  1080
cacgtcatcg gcgcctatga ggatctcggg atggagatca tcgccgccgg ctacgagttt  1140
gcccataacg atgattacga ccgcaccctg ccggacctga aagagggcac cctgctgttt  1200
gacgatgcca gcagctatga gctggaggcc ttcgtcaaag cgctgaaacc tgacctcatc  1260
ggctccggga tcaaagagaa atatatcttc cagaaaatgg gggtgccgtt ccgccagatg  1320
cactcctggg actattccgg cccctatcac ggctatgacg gcttcgccat ctttgcccgc  1380
gatatggata tgaccctgaa caatccggcg tggaacgaac tgactgcccc gtggctgaag  1440
tctgcgtga                                                          1449

SEQ ID NO: 204         moltype = DNA  length = 1386
FEATURE                Location/Qualifiers
gene                   1..1386
                       note = nifK1
source                 1..1386
                       mol_type = genomic DNA
```

```
                         organism = Rahnella aquatilis
SEQUENCE: 204
atggcagata ttatccgcag tgaaaaaccg ctggcggtga gcccgattaa aaccgggcaa  60
ccgctcgggg cgatcctcgc cagcctcggg ctggcccagg ccatcccgct ggtccacggc  120
gcccagggct gcagcgcctt cgccaaagtt ttctttattc agcatttcca tgacccggtg  180
ccgctgcagt cgacggccat ggatccgacc gccacgatca tgggggccga cggcaatatc  240
ttcaccgcgc tcgacaccct ctgccagcgc cacagcccgc aggccatcgt gctgctcagc  300
accggtctgg cggaagcgca gggcagcgat atcgcccggg tggtgcgcca gtttcgcgag  360
gcgcatccgc gccataacgg cgtggcgatc ctcaccgtca ataccccgga tttttttggc  420
tctatggaaa acggctacag cgcggtgatc gagagcgtga tcgagcagtg ggtcgcgccg  480
acgccgcgtc cggggcagcg gccccggcgg gtcaacctgc tggtcagcca cctctgttcg  540
ccaggggata tcgaatggct gggcgctgc gtggaggcct ttggcctgca gccggtgatc  600
ctgccggacc tctcgcagtc aatggatggc cacctcggtg aaggggattt tacgcccctg  660
acccagggcg gcgcctcgct gcgccagatt gcccagatgg gccagagtct gggcagcttc  720
gccattggcg tgtcgctcca gcgggcggca tcgctcctga cccaacgcag ccgcggcgac  780
gtgatcgccc tgccgcatct gatgaccctc gaccattgcg atacctttat ccatcagctg  840
gcgaagatgt ccggacgccg cgtaccggcc tggattgagc gccagcgtgg ccagctgcag  900
gatgcgatga tcgactgcca tatgtggctt cagggccagc gcatggcgat ggcggcggag  960
ggcgacctgc tggcggcgtg gtgtgatttc gcccgcagcc aggggatgca gcccggcccg  1020
ctggtcgccc ccaccagcca ccccagcctg cgccagctgc cggtcgagca agtcgtgccg  1080
ggggatcttg aggatctgca gcagctgctg agccaccaac ccgccgatct gctggtggct  1140
aactctcacg cccgcgatct ggcggagcag tttgccctgc cgctgatccg cgtcggtttt  1200
cccctcttcg accggctcgg tgagtttcgt cgcgtccgcc aggggtacgc cggtatgcga  1260
gatacgctgt ttgaactggc caatctgctg cgcgaccgcc atcaccacac cgccctctac  1320
cgctcgccgc ttcgccaggg cgccgacccc cagccggctt caggagacgc ttatgccgcc  1380
cattaa                                                             1386

SEQ ID NO: 205           moltype = DNA  length = 1563
FEATURE                  Location/Qualifiers
gene                     1..1563
                         note = nifK2
source                   1..1563
                         mol_type = genomic DNA
                         organism = Rahnella aquatilis
SEQUENCE: 205
atgagccaaa cgatcgataa aattcacagc tgttatccgc tgtttgaaca ggatgaatac  60
cagaccctgt tccagaataa aaagaccctt gaagaggcgc acgacgcgca gcgtgtgcag  120
gaggtttttg cctggaccac caccgccgag tatgaagcgc tgaacttcca gcgcgaggcg  180
ctgaccgtcg acccggccaa agcctgccag ccgctcggcg ccgtactctg cgcgctgggg  240
ttcgccggca ccctgcccta cgtgcacggc tcccagggct gcgtcgccta ttttcgcacc  300
tactttaacc gccattttaa agagccggtc gcctgcgtct ccgactccat gaccgaggac  360
gcggcggtgt tcggcggcaa caacaacatg aatctgggcc tgcagaatgc cagcgcgctg  420
tataaacccg agattatcgc cgtctccacc acctgtatgg ccgaggtgat cggcgacgat  480
ctgcaggcgt ttatcgccaa cgccaaaaaa gagggatttg ttgacgaccg catcgccatt  540
ccttacgccc atacccccag ctttatcggc agccatgtca ccggctggga caatatgttc  600
gaagggttcg cgaagacctt taccgctgac tacgccgggc agccgggcaa acagcaaaag  660
ctcaatctgg tgaccggatt tgagacctat ctcggcaact tccgcgtgct gaagcggatg  720
atggcgcaga tggatgtccc gtgcagcctg ctctccgacc catcagaggt gctcgacacc  780
cccgccgacg gccattaccg gatgtacgcc ggcggcacca gccagcagga gatcaaaacc  840
gcgccggacg ccattgacac cctgctgctg cagccgtggc agctggtgaa aagcaaaaag  900
gtggttcagg agatgtggaa ccagcccgcc accgaggtgg ccgttccgct gggcctggcc  960
gccaccgacg cgctgctgat gaccgtcagt cagctgaccg gcaaaccgat cgccgacgct  1020
ctgaccctgg agcgcggccg gctggtcgac atgatgctgg attcccacac ctggctgcat  1080
ggcaaaaaat tcggcctcta cggcgatccg gatttcgtga tggggctgac gcgcttcctg  1140
ctggagctgg gctgcgagcc gacggtgatc ctcagtcata acgccaataa acgctggcaa  1200
aaagcgatga agaaaatgct cgatgcctcg ccgtacggtc aggaaagcga agtgttcatc  1260
aactgcgacc tgtggcactt ccggtcgctg atgttcaccc gtcagccgga ctttatgatc  1320
ggtaactcct acggcaagtt tatccagcgc gataccctgg caaagggcaa agccttcgaa  1380
gtgccgctga tccgtctggg ctttccgctg ttcgaccgcc atcatctgca ccgccagacc  1440
acctggggct atgaaggcgc aatgaacatc gtcacgacgc tggtgaacgc cgtgctggaa  1500
aaactggacc acgacaccag ccagttgggc aaaaccgatt acagcttcga cctcgttcgt  1560
taa                                                                1563

SEQ ID NO: 206           moltype = DNA  length = 2838
FEATURE                  Location/Qualifiers
gene                     1..2838
                         note = glnE
source                   1..2838
                         mol_type = genomic DNA
                         organism = Rahnella aquatilis
SEQUENCE: 206
atgatgccgc tttctccgca attacagcag cactggcaga cggtcgctga ccgtctgcca  60
gcggattttc ccattgccga actgagccca caggccaggt cggtcatggc gttcagcgat  120
tttgtcgaac agagtgtgat cgcccagccg ggctggctga atgagcttgc ggactcctcg  180
ccggaggcgg aagagtggcg gcattacgag gcctggctgc aggatcgcct gcaggccgtc  240
actgacgaag cggggttgat gcgagagctg cgtctcttcc gccgccagat gatggtccgc  300
atcgcctggg cgcaggcgct gtcgctggtg agcgaagaag agactctgca gcagctgagc  360
gtcctggcgg agaccctgat tgtcgccgcc cgcgactggc tgtacgccgc ctgctgtaag  420
gagtggggaa cgccatgcaa tgccgagggc cagccgcagc cgctgctgat cctcgggatg  480
```

```
ggaaagctgg gcggcggcga gctgaacttc tcttccgata tcgatctgat ctttgcctgg  540
cctgagcatg gcgccacccg cggcggccgc cgcgagctgg ataacgccca gttctttacc  600
cgtctggggc agcggctgat caaggccctt gaccagccga cgcaggacgg ctttgtctat  660
cgggttgaca tgcgcctgcg gccgtttggc gacagtgggc cgctggtact cagttttgcg  720
gcgctggaag attattacca ggagcagggt cgggactggg aacgctatgc gatggtgaaa  780
gcgcggatca tgggcgataa cgacggcgtg tacgccagcg agttgcgcgc gatgctccgt  840
cctttcgtct tccgccgtta tatcgacttc agcgtgatcc agtcgctgcg taacatgaaa  900
ggcatgatcg cccgcgaagt gcggcgtcgc gggctgaaag acaacatcaa gctcggcgcc  960
ggcgggatcc gtgaaattga gtttatcgtt caggtctttc aactgatccg cggtggtcgc  1020
gaacctgcac tgcagcagcg cgccctgctg ccgacgctgg cggcgattga tgagctacat  1080
ctgctgccgg aaggcgacgc ggcgctgctg cgcgaggcct atctgttcct gcgccggctg  1140
gaaaacctgc tgcaaagcat caacgatgag cagacccaga ccctgccgca ggatgaactt  1200
aaccgcgcca ggctggcgtg gggatgcat accgaagact gggagacgct gagcgcgcag  1260
ctggcgagcc agatggccaa cgtgcggcga gtgtttaatg aactgatcgg cgatgatgag  1320
gatcagtccc cggatgagca actggccgag tactggcgcg agctgtggca ggatgcgctg  1380
gaagaagatg acgccagccc ggcgctggcg catttaaacg ataccgaccg ccgtagcgtg  1440
ctggcgctga ttgccgattt tcgtaaagag ctggatcggc gcaccatcgg cccgcgcggc  1500
cgccaggtgc tggatcagct gatgccgcat ctgctgagcg aaatctgctc gcgcgccgat  1560
gcgccgctgc ctctggcgcg gatcacgccg ctgttgaccg ggatcgtcac ccgtaccacc  1620
tatcttgagc tgctgagcga attccccggc gcgctgaagc acctgatcac gctctgcgcg  1680
gcgtcgccga tggtcgccag ccagctggcg cgccacccgc tgctgctgga tgagctgctg  1740
gatcccaaca ccctctatca gccgacggcg accgatgcct atcgcgacga gctgcgccag  1800
tacctgctgc gcgtgccgga agaggatgaa gagcagcagc tggaggcgtt gcgccagttt  1860
aagcaggcgc agcagctgca tatcgcggcg gcggatatcg ctggtaccct gccggtgatg  1920
aaggtcagcg atcacttaac ctggcttgcc gaagcgatcc tcgacgcggt ggtgcagcag  1980
gcatgggggc agatggtcgc tcgctacggc cagccgaccc acctgcacga tcgccagggt  2040
cgcggcttcg ccgtcgtcgg ctacggtaag cttggcggct gggagctggg ctacagctcc  2100
gatctcgatc tggtgttcct ccatgactgc ccggcggagg tgatgaccga cggcgagcgg  2160
gagattgacg gccgtcagtt ctacctgcgg ctggcccagc ggatcatgca cctgttcagc  2220
acccgcacct cgtccggtat tctctacgaa gtggacgccc ggctgcgtcc ttctggcgcg  2280
gcggggatgc tggtcaccac cgccgacgcg tttgctgact atcagcagaa cgaagcctgg  2340
acgtgggaac atcaggcgct ggtgcgcgcc cgcgtggtct atggcgaccc ggcgctgcag  2400
gcgcgctttg acgccattcg tcgcgatatc ctgaccaccc cgcgggaggg gatgaccctg  2460
cagaccgagg ttcgcgagat gcgcgagaag atgcgcgccc accttggcaa caaacatccc  2520
gatcgttttg atatcaaagc cgatgccggc gggatcaccg atattgaatt tattactcag  2580
tatctggtcc tacgctatgc cagtgacaag ccgaagctga cccgctggtc tgacaacgtg  2640
cgtattcttg agctgctggc gcagaacgac atcatggacg aggaggaggc gcgcgcctta  2700
acgcatgcgt acaccacctt gcgtgatgcg ctccatcacc tggccctgca ggagcagccg  2760
ggacacgtgg cgccagaggc cttcagccgg gagcgtcagc aggtcagcgc cagctggcag  2820
aagtggctga tggcttaa                                                2838
```

```
SEQ ID NO: 207          moltype = DNA  length = 449
FEATURE                 Location/Qualifiers
gene                    1..449
                        note = Prm4
source                  1..449
                        mol_type = genomic DNA
                        organism = Rahnella aquatilis
SEQUENCE: 207
agtctgaact catcctgcgg cagtcggtga gacgtatttt tgaccaaaga gtgatctaca  60
tcacggaatt ttgtggttgt tgctgcttaa aagggcaaat ctacccttag aatcaactgt  120
tatatcaggg ggattcagag agatattagg aatttgcaca agcgcacaat ttaaccacat  180
catgataacg ccatgtaaaa caaagataaa aaaacaaaat gcagtgactt acatcgcaag  240
caaggcattt tcttatccaa ttgctcaaag tttggccttt catatcgcaa cgaaaatgcg  300
taatatacgc gcccttgcgg acatcagtat ggtcattcct agttcatgcg catcggacac  360
caccagctta caaattgcct gattgcggcc ccgatggccg gtatcactga ccgaccattt  420
cgtgccttat gtcatgcgat gggggctgg                                    449
```

```
SEQ ID NO: 208          moltype = DNA  length = 500
FEATURE                 Location/Qualifiers
gene                    1..500
                        note = Prm1.2
source                  1..500
                        mol_type = genomic DNA
                        organism = Rahnella aquatilis
SEQUENCE: 208
tgaacatcac tgatgcacaa gctacctatg tcgaagaatt aactaaaaaa ctgcaagatg  60
caggcattcg cgttaaagcc gacttgagaa atgagaagat tggctttaaa attcgcgaac  120
acacgctacg ccgtgttcct tatatgttag tttgtggcga taaagaggtc gaagcaggca  180
aagttgctgt tcgtacccgc cgcggcaaag acttaggaag catggatgtt agcgaagtcg  240
ttgacaaact gctggcggaa atccgcagca gaagtcttca tcaactggag gaataaagta  300
ttaaaggcgg aaaacgagtt caaccggcgc gtcctaatcg cattaacaaa gagattcgcg  360
cgcaagaagt tcgcctcaca ggcgtcgatg gcgagcagat tggtattgtc agtctgaatg  420
aagctcttga aaaagctgag gaagcgggcg tcgatttagt agaaatcagt ccgaatgccg  480
agccgccagt ttgtcgaatc                                              500
```

```
SEQ ID NO: 209          moltype = DNA  length = 170
FEATURE                 Location/Qualifiers
gene                    1..170
```

```
                        note = Prm3.1
source                  1..170
                        mol_type = genomic DNA
                        organism = Rahnella aquatilis
SEQUENCE: 209
tacagtagcg cctctcaaaa atagataaac ggctcatgta cgtgggccgt ttattttttc  60
tacccataat cgggaaccgg tgttataatg ccgcgccctc atattgtggg gatttcttaa  120
tgacctatcc tgggtcctaa agttgtagtt gacattagcg gagcactaac             170

SEQ ID NO: 210          moltype = DNA  length = 142
FEATURE                 Location/Qualifiers
gene                    1..142
                        note = Prm6.1
source                  1..142
                        mol_type = genomic DNA
                        organism = Rahnella aquatilis
SEQUENCE: 210
aatttttttt cacaaagcgt agcgttattg aatcgcacat tttaaactgt tggccgctgt  60
ggaagcgaat attggtgaaa ggtgcggttt taaggccttt ttctttgact ctctgtcgtt  120
acaaagttaa tatgcgcgcc ct                                           142

SEQ ID NO: 211          moltype = DNA  length = 293
FEATURE                 Location/Qualifiers
gene                    1..293
                        note = Prm7.1
source                  1..293
                        mol_type = genomic DNA
                        organism = Rahnella aquatilis
SEQUENCE: 211
ttaaaaacgt gaccacgagc attaataaac gccacgaaat gtggcgttta tttattcaaa  60
aagtatcttc tttcataaaa agtgctaaat gcagtagcag caaaattggg ataagtccca  120
tggaatacgg ctgttttcgc tgcaattttt aactttttcg taaaaaaaga tgtttctttg  180
agcgaacgat caaaatatag cgttaaccgg caaaaaatta ttctcattag aaaatagttt  240
gtgtaatact tgtaacgcta catggagatt aacttaatct agagggtttt ata         293

SEQ ID NO: 212          moltype = DNA  length = 1188
FEATURE                 Location/Qualifiers
misc_feature            1..1188
                        note = Synthetic polynucleotide
misc_feature            1..1188
                        note = glnE-delta-AR-2
source                  1..1188
                        mol_type = other DNA
                        organism = synthetic construct
SEQUENCE: 212
atggcgctca aacagttaat ccgtctgtgt gccgcctcgc cgatggtcgc gacacaactt  60
gcacgtcatc ctttattgct cgatgaactg ctcgacccgc gcacgcttta ccagccgatt  120
gagccgggcg cttaccgcga cgaactgcgt cagtatctga tgcgggtgcc aacagaagac  180
gaagaacagc agcttgaagc cgtgcgccag ttcaaacagg cccagcattt gcgtatcgca  240
gccggggata tttccggggc attgccggtg atgaaagtca gtgaccattt aacctacctt  300
gccgaggcca ttctcgatgt cgtggtgcag catgcgtggg aacaaatggt cgtaaaatac  360
gggcagcccg cgcatcttca gcaccgtgag ggcgcggttt ttgccgtggt cggttacggg  420
aaactcggtg gctgggagct gggttatagc tcagatctgg atctggtctt cctgctcgat  480
tgcgcgccgg aggtgatgac ggacggcgaa cgcagcatcg acggacgtca gttttatctt  540
cggctggcgc agcgcattat gcacttattc agcacccgga catcgtcagg cattctttac  600
gaggttgatc cgcgtctgcg accttccggc gcatccggca tgctggtcag taccattgaa  660
gcgtttgcag attatcaggc caatgaagcc tggacgtggg agcatcaggc gctggttcgc  720
gcgcgcgtgg tttacgggga tccgcaactg acacagcaat ttaacgccac gcgtcgcgac  780
attctttgcc gccagcgcga tggcgacggc ctgcgtaagg aggtccgtga aatgcgcgag  840
aaaatgtatg cccatctggg gagtaaaaaa gcccacgagt ttgatctgaa agccgatccg  900
ggtggcatca cggatattga attcattgca caatacctgg ttctgcgttt cgcgcatgat  960
gagccgaagc tgacgcgctg gtctgataac gtgcggattt ttgaactgat ggcacgatat  1020
gacatcatgc cggaagagga agcgcgccat ctgacgcagg cttatgtgac gctgcgcgat  1080
gaaattcatc atctggcgtt gcaggaacac agcgggaaag tggccgcgga cagctttgct  1140
actgagcgcg cgcagatccg tgccagctgg gcaaagtggc tcggctga               1188

SEQ ID NO: 213          moltype = DNA  length = 2188
FEATURE                 Location/Qualifiers
misc_feature            1..2188
                        note = Synthetic polynucleotide
misc_feature            1..2188
                        note = glnE-delta-AR-2 with 500bp flank
source                  1..2188
                        mol_type = other DNA
                        organism = synthetic construct
SEQUENCE: 213
cggtactgga acagaaatcg gcggatgcgc aggaaatttg ttatgacacg gcctgtctga  60
agtgcaagtt agtgcttact tcctggctgg caacctcagg ctggacgccg tttattgatg  120
ataaatctgc gaagaaactg gacgcttcct tcaaacgttt tgctgacatc atgctcggtc  180
```

```
gtaccgcagc ggatctgaaa gaagcctttg cgcagccact gacggaagaa ggttatcgcg  240
atcagctggc gcgcctgaaa cgccagatca ttaccttcca tttgcttgcc ggtgcttacc  300
ctgaaaaaga cgtcgatgcg tatattgccg gctgggtgga cctgcaacag gccatcgttc  360
agcagcaaca cgcctgggag gattcggccc gttctcacgc ggtgatgatg gatgcttttct  420
ggttaaacgg gcaacctcgt taactgactg actagcctgg gcaaactgcc cgggcttttt  480
tttgcaagga atctgatttc atggcgctca aacagttaat ccgtctgtgt gccgcctcgc  540
cgatggtcgc gacacaactt gcacgtcatc ctttattgct cgatgaactg ctcgacccgc  600
gcacgcttta ccagccgatt gagccgggcg cttaccgcga cgaactgcgt cagtatctga  660
tgcgggtgcc aacagaagac gaagaacagc agcttgaagc cgtgcgccag ttcaaacagg  720
cccagcattt gcgtatcgca gccggggata tttccggggc attgccggtg atgaaagtca  780
gtgaccattt aacctacctt gccgaggcca ttctcgatgt cgtggtgcag catgcgtggg  840
aacaaatggt cgtaaaatac gggcagcccg cgcatcttca gcaccgtgag gggcgcggtt  900
ttgccgtggt cggttacggg aaactcggtg gctgggagct gggttatagc tcagatctgg  960
atctggtctt cctgctcgat tgcgcgccgg aggtgatgac ggacggcgaa cgcagcatcg  1020
acggacgtca gttttatctt cggctggcgc agcgcattat gcacttattc agcacccgga  1080
catcgtcagg cattctttac gaggttgatc cgcgtctgcg accttccggc gcatccggca  1140
tgctggtcag taccattgaa gcgtttgcag attatcaggc caatgaagcc tggacgtggg  1200
agcatcaggc gctggttcgc gcgcgcgtgg tttacgggga tccgcaactg acacagcaat  1260
ttaacgccac gcgtcgcgac attctttgcc gccagcgcga tggcgacggc ctgcgtaagg  1320
aggtccgtga aatgcgcgag aaaatgtatg cccatctggg gagtaaaaaa gcccacgagt  1380
ttgatctgaa agccgatccg ggtggcatca cggatattga attcattgca caatacctgg  1440
ttctgcgttt cgcgcatgat gagccgaagc tgacgcgctg gtctgataac gtgcggattt  1500
ttgaactgat ggcacgatat gacatcatgc cggaagagga agcgcgccat ctgacgcagg  1560
cttatgtgac gctgcgcgat gaaattcatc atctggcgtt gcaggaacac agcgggaaag  1620
tggccgcgga cagctttgct actgagcgcg cgcagatccg tgccagctgg gcaaagtggc  1680
tcggctgagg gtttttattc ggctaacagg cgcttgtgat attatccggc gcattgtatt  1740
tacccgattt gatttatctg ttttggagtc ttgggatgaa agtgactttg cctgattttc  1800
accgcgcagg tgtgctggtt gtcggtgacg taatgttaga ccgttactgg tatggcccga  1860
ccaatcgtat ttctccggaa gctccggtgc cggtggtgaa ggtcagtacc attgaagagc  1920
ggcctggcgg tgcagctaac gtggcgatga acatttcatc tctgggcgcc tcttcctgtc  1980
tgatcggcct gaccggcgta gacgacgctg cgcgtgccct cagtgagcgt ctggcagaag  2040
tgaaagttaa ctgcgatttc gtcgcactat ccacacatcc taccatcacc aaactgcgaa  2100
ttttgtcccg taaccagcaa ctgatccgcc tcgactttga ggaaggtttt gaaggcgttg  2160
atctcgagcc gatgctgacc aaaataga                                  2188
```

```
SEQ ID NO: 214          moltype = DNA  length = 524
FEATURE                 Location/Qualifiers
misc_feature            1..524
                        note = Synthetic polynucleotide
misc_feature            1..524
                        note = delta-nifL::null-v1
source                  1..524
                        mol_type = other DNA
                        organism = synthetic construct
SEQUENCE: 214
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg agtctgaact catcctgcga  240
tgggggctgg gccgtctctg aagctctcgg tgaacattgt tgcgaggcag gatgcgagct  300
ggttgtgttt tgacattacc gataatgtgc cgcgtgaacg ggtgcgttat gcccgcccgg  360
aagcggcgtt ttcccgtccg gggaatggca tggagctgcg ccttatccag acgctgatcg  420
cccatcatcg cggttcttta gatctctcgg tccgccctga tggcggcacc ttgctgacgt  480
tacgcctgcc ggtacagcag gttatcaccg gaggcttaaa atga                 524
```

```
SEQ ID NO: 215          moltype = DNA  length = 1524
FEATURE                 Location/Qualifiers
misc_feature            1..1524
                        note = Synthetic polynucleotide
misc_feature            1..1524
                        note = delta-nifL::null-v1 with 500bp flank
source                  1..1524
                        mol_type = other DNA
                        organism = synthetic construct
SEQUENCE: 215
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
agtctgaact catcctgcga tgggggctgg gccgtctctg aagctctcgg tgaacattgt  780
tgcgaggcag gatgcgagct ggttgtgttt tgacattacc gataatgtgc cgcgtgaacg  840
```

```
ggtgcgttat gcccgcccgg aagcggcgtt ttcccgtccg gggaatggca tggagctgcg  900
ccttatccag acgctgatcg cccatcatcg cggttcttta gatctctcgg tccgccctga  960
tggcggcacc ttgctgacgt tacgcctgcc ggtacagcag gttatcaccg gaggcttaaa  1020
atgacccagt tacctaccgc gggcccggtt atccggcgct ttgatatgtc tgcccagttt  1080
acggcgcttt atcgcatcag cgtggcgctg agtcaggaaa gcaacaccgg gcgcgcactg  1140
gcggcgatcc tcgaagtgct tcacgatcat gcatttatgc aatacggcat ggtgtgtctg  1200
tttgataaag aacgcaatgc actctttgtg gaatccctgc atggcatcga cggcgaaagg  1260
aaaaaagaga cccgccatgt ccgttaccgc atgggggaag gcgtgatcgg cgcggtgatg  1320
agccagcgtc aggcgctggt gttaccgcgc atttcagacg atcagcgttt tctcgaccgc  1380
ctgaatattt acgattacag cctgccgttg attggcgtgc cgatccccgg tgcggataat  1440
cagccatcgg gcgtgctggt ggcacagccg atggcgttgc acgaagaccg gctgactgcc  1500
agtacgcggt ttttagaaat ggtc                                        1524
```

```
SEQ ID NO: 216          moltype = DNA  length = 266
FEATURE                 Location/Qualifiers
misc_feature            1..266
                        note = Synthetic polynucleotide
misc_feature            1..266
                        note = delta-nifL::null-v2
source                  1..266
                        mol_type = other DNA
                        organism = synthetic construct
SEQUENCE: 216
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg ttaaagcctg ccggtacagc  240
aggttatcac cggaggctta aaatga                                      266
```

```
SEQ ID NO: 217          moltype = DNA  length = 1266
FEATURE                 Location/Qualifiers
misc_feature            1..1266
                        note = Synthetic polynucleotide
misc_feature            1..1266
                        note = delta-nifL::null-v2 with 500bp flank
source                  1..1266
                        mol_type = other DNA
                        organism = synthetic construct
SEQUENCE: 217
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
ttaaagcctg ccggtacagc aggttatcac cggaggctta aaatgaccca gttacctacc  780
gcgggcccgg ttatccggcg ctttgatatg tctgcccagt ttacggcgct ttatcgcatc  840
agcgtggcgc tgagtcagga aagcaacacc gggcgcgcac tggcggcgat cctcgaagtg  900
cttcacgatc atgcatttat gcaatacggc atggtgtgtc tgtttgataa agaacgcaat  960
gcactctttg tggaatccct gcatggcatc gacggcgaaa ggaaaaaaga gacccgccat  1020
gtccgttacc gcatggggga aggcgtgatc ggcgcggtga tgagccagcg tcaggcgctg  1080
gtgttaccgc gcatttcaga cgatcagcgt tttctcgacc gcctgaatat ttacgattac  1140
agcctgccgt tgattggcgt gccgatcccc ggtgcggata atcagccatc gggcgtgctg  1200
gtggcacagc cgatggcgtt gcacgaagac cggctgactg ccagtacgcg gtttttagaa  1260
atggtc                                                            1266
```

```
SEQ ID NO: 218          moltype = DNA  length = 943
FEATURE                 Location/Qualifiers
misc_feature            1..943
                        note = Synthetic polynucleotide
misc_feature            1..943
                        note = delta-nifL::Prm4
source                  1..943
                        mol_type = other DNA
                        organism = synthetic construct
SEQUENCE: 218
atgagcatca cggcgttatc agcatcattt cctgagggga atatcgccag ccgcttgtcg  60
ctgcaacatc cttcactgtt ttataccgtg gttgaacaat cttcggtggc gatttcgctg  120
accgatccgc aggcgcgcat ttgttatgcc aatccggcat tctgccgcca gacgggtttt  180
gcacttgaga cacttttggg cgagaaccac cgtctgctgg agtctgaact catcctgcgg  240
cagtcggtga gacgtatttt tgaccaaaga gtgatctaca tcacggaatt ttgtggttgt  300
tgctgcttaa aagggcaaat ctacccttag aatcaactgt tatatcaggg ggattcagag  360
agatattagg aatttgcaca agcgcacaat ttaaccacat catgataacg ccatgtaaaa  420
```

```
caaagataaa aaaacaaaat gcagtgactt acatcgcaag caaggcattt tcttatccaa  480
ttgctcaaag tttggccttt catatcgcaa cgaaaatgcg taatatacgc gcccttgcgg  540
acatcagtat ggtcattcct agttcatgcg catcggacac caccagctta caaattgcct  600
gattgcggcc ccgatggccg gtatcactga ccgaccattt cgtgccttat gtcatgcgat  660
gggggctggg ccgtctctga agctctcggt gaacattgtt gcgaggcagg atgcgagctg  720
gttgtgtttt gacattaccg ataatgtgcc gcgtgaacgg gtgcgttatg cccgcccgga  780
agcggcgttt tcccgtccgg ggaatggcat ggagctgcgc cttatccaga cgctgatcgc  840
ccatcatcgc ggttctttag atctctcggt ccgccctgat ggcggcacct tgctgacgtt  900
acgcctgccg gtacagcagg ttatcaccgg aggcttaaaa tga                    943

SEQ ID NO: 219          moltype = DNA  length = 1943
FEATURE                 Location/Qualifiers
misc_feature            1..1943
                        note = Synthetic polynucleotide
misc_feature            1..1943
                        note = delta-nifL::Prm4 with 500bp flank
source                  1..1943
                        mol_type = other DNA
                        organism = synthetic construct
SEQUENCE: 219
tgtttcgtct cgaggccggg caactgagcg gccccgttga aaccgacctg ggctggcatc  60
tgttgttgtg cgaacaaatt cgcctgccgc aacccttgcc gaaagccgaa gccttaacgc  120
gggtgcgtca gcaactgatt gcccggcaac agaaacatta tcagcgccag tggctgcaac  180
aactgatcaa cgcctgagcc tgttctcctt cttgttgatg cagacgggtt aatgcccgtt  240
ttgcacgaaa aatgcacata aattgcctgc gttgccttat aacagcgcag ggaaatcctg  300
cctccggcct tgtgccacac cgcgctttgc ctggtttgtg gtaaaaactg gcccgctttg  360
catcctgatg cttaaaacac cccgttcaga tcaacctttg ggcagataag cccgcgaaag  420
gcctgcaaat tgcacggtta ttccgggtga gtatatgtgt gatttgggtt ccggcattgc  480
gcaataaagg ggagaaagac atgagcatca cggcgttatc agcatcattt cctgagggga  540
atatcgccag ccgcttgtcg ctgcaacatc cttcactgtt ttataccgtg gttgaacaat  600
cttcggtggc gatttcgctg accgatccgc aggcgcgcat ttgttatgcc aatccggcat  660
tctgccgcca gacgggtttt gcacttgaga cacttttggg cgagaaccac cgtctgctgg  720
agtctgaact catcctgcgg cagtcggtga gacgtatttt tgaccaaaga gtgatctaca  780
tcacggaatt ttgtggttgt tgctgcttaa aagggcaaat ctacccttag aatcaactgt  840
tatatcaggg ggattcagag agatattagg aatttgcaca agcgcacaat ttaaccacat  900
catgataacg ccatgtaaaa caaagataaa aaaacaaaat gcagtgactt acatcgcaag  960
caaggcattt tcttatccaa ttgctcaaag tttggccttt catatcgcaa cgaaaatgcg  1020
taatatacgc gcccttgcgg acatcagtat ggtcattcct agttcatgcg catcggacac  1080
caccagctta caaattgcct gattgcggcc ccgatggccg gtatcactga ccgaccattt  1140
cgtgccttat gtcatgcgat gggggctggg ccgtctctga agctctcggt gaacattgtt  1200
gcgaggcagg atgcgagctg gttgtgtttt gacattaccg ataatgtgcc gcgtgaacgg  1260
gtgcgttatg cccgcccgga agcggcgttt tcccgtccgg ggaatggcat ggagctgcgc  1320
cttatccaga cgctgatcgc ccatcatcgc ggttctttag atctctcggt ccgccctgat  1380
ggcggcacct tgctgacgtt acgcctgccg gtacagcagg ttatcaccgg aggcttaaaa  1440
tgacccagtt acctaccgcg ggcccggtta tccggcgctt tgatatgtct gcccagttta  1500
cggcgcttta tcgcatcagc gtggcgctga gtcaggaaag caacaccggg cgcgcactgg  1560
cggcgatcct cgaagtgctt cacgatcatg catttatgca atacggcatg gtgtgtctgt  1620
ttgataaaga acgcaatgca ctctttgtgg aatccctgca tggcatcgac ggcgaaagga  1680
aaaaagagac ccgccatgtc cgttaccgca tgggggaagg cgtgatcggc gcggtgatga  1740
gccagcgtca ggcgctggtg ttaccgcgca tttcagacga tcagcgtttt ctcgaccgcc  1800
tgaatattta cgattacagc ctgccgttga ttggcgtgcc gatccccggt gcggataatc  1860
agccatcggg cgtgctggtg gcacagccga tggcgttgca cgaagaccgg ctgactgcca  1920
gtacgcggtt tttagaaatg gtc                                          1943

SEQ ID NO: 220          moltype = DNA  length = 2864
FEATURE                 Location/Qualifiers
gene                    1..2864
                        note = glnD with flanking sequences
source                  1..2864
                        mol_type = genomic DNA
                        organism = Kosakonia sacchari
SEQUENCE: 220
ttctgacatt agcaaacgcg ataaacggtc cgctctgcgg gccgtttttt ttaccgctct  60
tccctgcagc gtcatacata taaacgactt ttcattttc attatctctt ttaagttgtt  120
ttgctatgca tatgcactcc agacgggtgg cccataatga gcaacatcac ttcagaacaa  180
tttgtcagcg cggtacaacc caccccttccc ggccagcctg aatatccagg ggtttggtca  240
caagacgaat tccagtgcgc caatatcaaa gcgcatattg aggctttcca gcagtggctc  300
gggcacgtct ttgacgccgg aatttcagcc gagcaattaa ttgaagcgcg caccgaattt  360
attgatcaac ttctgcaacg cttatgctg gagtacggtt ttggcgacgt cagtgatacc  420
gcgctggttg cggtaggcgg ttacggtcgc ggcgaactgc atccgctatc ggatattgat  480
ttactgatcc tcagccgcag caaactttcc gacgaacaag cgcagaagat tggcgaactg  540
ctcacgctgc tgtgggatgt caaactcgaa gtgggacaca gcgttcgtac gctggatgag  600
tgcttacagg aagggttatc ggatctcact gtcgcgacca acttaattga atcacgtctg  660
ctgattggcg acgtcgcgct gtttctggaa ctgcaaaagc atatttttag cgacagcttc  720
tggccatcgg aaacttttt cccggcaaaa gtggcggaac aaaacgagcg ccaccagcgt  780
tatcacggca ccagttataa cctggaaccc gacataaaaa gtagccctgg tggtctgcgc  840
gatattcaca ccctgcaatg ggttgctcgc cgtcactttg gtgccacatc gctggatgaa  900
atggtgggct ttggctttct gaccgaagcc gagcgcaatg agctgaacga gtgtctgcac  960
ctgctttggc gtatccgctt cgcgctgcat ctggaagtga gccgctacga caaccgcctg  1020
```

```
ctgttcgacc gccaactgag cgtagcgcag cgtctgaatt atgtcggtga aggcaaccag  1080
cctgtcgaac atatgatgaa ggatttcttc cgcgttaccc gccgcgtcgc ggagctgaac  1140
cagatgctgt tacagctctt tgatgaagcg attctggcgc tgaccaccga cgagaaaccg  1200
cgcccgattg acgatgaatt ccaactgcgc ggttcgctta tcgatctgcg tgacgaaacg  1260
ctgtttatcc gtgagccgca ggccatcctg cgcatgttct atatcatggt gcgcaacagc  1320
accattaccg gcatctactc caccacgctg cgccacttgc gccacgcccg ccgccatctg  1380
acgcagccgc tgtgttacat cgcggaagca cgctctattt tcctcagcat gttgcgccat  1440
ccaggcgccg tcagccgcgg tttgctgccg atgcaccgcc acagcgtgtt gtgggcttat  1500
atgccacagt ggtcgcacat cgtcggtcag atgcagtttg acctgttcca cgcctatacc  1560
gtggatgagc acaccattcg cgtattgctg aagctggaaa gttttgccaa agaagagacg  1620
cgcaataagc accctctatg cgtggaactg tggccgcgtt tgacccaccc ggagctgatc  1680
ctgatcgcgg cgttgttcca tgatatcgcc aaaggacgcg gcggcgacca ctcggtgctg  1740
ggtgcgcagg atgtgctgaa gttcgctgaa ttacacgggc ttaactcacg cgaaacccag  1800
ctggttgcct ggctggtgcg ccatcatctg ttgatgtcgg tcaccgccca gcgccgtgat  1860
attcaggatc cggaagtcat caagcagttt gccgaagagg tgcaaacgga aaaccgtctg  1920
cgcttcctcg tctgtctgac cgtggcggat atctgtgcca ccaacgaaac cctgtggaac  1980
agttggaagc agagcttgct gcgcgagctc tatttcgcga ctgaaaaaca gctgcgtcgc  2040
ggcatgcaaa acacgccgga tatgcgcgaa cgcgtgcgcc atcaccagct tcaggcgctg  2100
gcgttgctgc gtatggataa tattgatgaa gagcagttgc atcagatttg ggcgcgctgt  2160
cgggcgaact attttgttcg ccatagccca aaccagcttg cctggcatgc gcgccacctg  2220
ctgcaacatg atctgagcaa gccgatgatt ttgctcagcc cacaggctac gcgcggcggc  2280
accgagatct ttatctggag cccggatcgc ccgtatctgt ttgcagcggt gtgcgccgag  2340
cttgatcgtc gcaacctgag cgttcacgac gcgcagattt ttaccacccg cgacggcatg  2400
gcaatggata cctttattgt gctggaaccg gacggaagcc cgctctccgc cgatcgccac  2460
gacgcgattt gtttcgggct ggagcaggcc attacgcaac acacctggca gccgccgcaa  2520
ccgcgccgtc agcctgccaa attgcgccac tttaccgtcg ataccgaagt gaatttcctg  2580
ccaacccata ccgacagaaa atcgtttctt gaattgattg cccttgacca gccagggctg  2640
cttgcccgcg tcgggcaggt gtttgcggat ctgggaattt cgctgcacgg ggcgagaatt  2700
acaaccattg gtgagcgagt agaagattta tttataatcg cgactgccga ccggcgtggc  2760
cttaataatg cgctgcaaaa ggaggtacaa caacggttga cagaggccct caatccaaac  2820
gataaagggt gattattttt ttacacagat ggaaagagta aaca                  2864
```

```
SEQ ID NO: 221         moltype = DNA  length = 426
FEATURE                Location/Qualifiers
misc_feature           1..426
                       note = delta-nifL::Prm5
source                 1..426
                       mol_type = other DNA
                       organism = synthetic construct
SEQUENCE: 221
atgaccctga atatgatgat ggatgccggc ggacatcatc gcgacaaaca atattaatac  60
cggcaaccac accggcaatt tacgagactg cgcaggcatc ctttctcccg tcaatttctg  120
tcaaataaag taaaagaggc agtctacttg aattaccccc ggctggttga gcgtttgttg  180
aaaaaaagta actgaaaaat ccgtagaata gcgccactct gatggttaat taacctattc  240
aattaagaat tatctggatg aatgtgccat taaatgcgca gcataatggt gcgttgtgcg  300
ggaaaactgc ttttttttga aagggttggt cagtagcgga aacaactcac ttcacacccc  360
gaagggggaa gttgcctgac cctacgattc ccgctatttc attcactgac cggaggttca  420
aaatga                                                             426
```

```
SEQ ID NO: 222         moltype = DNA  length = 1563
FEATURE                Location/Qualifiers
misc_feature           1..1563
                       note = glnE-delta-AR
source                 1..1563
                       mol_type = other DNA
                       organism = synthetic construct
SEQUENCE: 222
atgtttaacg atctgattgg cgatgatgaa acggattcgc cggaagatgc gctttctgag  60
agctggcgcg aattgtggca ggatgcgttg caggaggagg attccacgcc cgtgctggcg  120
catctctcag aggacgatcg ccgccgcgtg gtggcgctga ttgccgattt tcgcaaagag  180
ttggataaac gcaccattgg cccgcgaggg cggcaggtac tcgatcactt aatgccgcat  240
ctgctcagcg atgtatgctc gcgcgacgat gcgccagtac cgctgtcacg cctgacgccg  300
ctgctcaccg gaattattac ccgcaccact taccttgagc tgctaagtga atttcccggc  360
gcactgaaac acctcatttc cctgtgtgcc gcgtcgccga tggttgccag tcagctggcg  420
cgctacccga tcctgcttga tgaattgctc gacccgaata cgctctatca accgacggcg  480
atgaatgcct atcgcgatga gctgcgccaa tacctgctgc gcgtgccgga agatgatgaa  540
gagcaacagc ttgaggcgct gcggcagttt aagcaggcgc agttgctgcg cgtggcggcg  600
gcggatattg ccggtacgtt gccagtaatg aaagtgagcg atcacttaac ctggctggcg  660
gaagcgatta ttgatgcggt ggtgcagcaa gcctgggggc agatggtggc gcgttatggc  720
cagccaacgc atctgcacga tcgcgaaggg cgcggttttg cggtggtcgg ttatggcaag  780
ctgggcggct gggagctggg ttacagctcc gatctggatc tggtattcct gcacgactgc  840
ccgatggatg tgatgaccga tggcgagcgt gaaatcgatg gtcgccagtt ctatttgcgt  900
ctcgcgcagc gcgtgatgca cctgtttagc acgcgcacgt cgtccggcat cctttatgaa  960
gttgatgcgc gtctgcgtcc atctggcgct gcggggatgc tggtcactac tacggaatcg  1020
ttcgccgatt accagcaaaa cgaagcctgg acgtgggaac atcaggcgct ggcccgtgcg  1080
cgcgtggtgt acggcgatcc gcaactgacc gccgaatttg acgccattcg ccgcgatatt  1140
ctgatgacgc ctcgcgacgg cgcaacgctg caaaccgacg tgcgagaaat gcgcgagaaa  1200
atgcgtgccc atcttggcaa caagcataaa gaccgcttcg atctgaaagc cgatgaaggc  1260
ggtatcaccg acatcgagtt tatcgcccaa tatctggtgc tgcgctttgc ccatgacaag  1320
```

-continued

```
ccgaaactga cgcgctggtc ggataatgtg cgcattctcg aagggctggc gcaaaacggc  1380
atcatggagg agcaggaagc gcaggcattg acgctggcgt acaccacatt gcgtgatgag  1440
ctgcaccacc tggcgctgca agagttgccg ggacatgtgg cgctctcctg ttttgtcgcc  1500
gagcgtgcgc ttattaaaac cagctgggac aagtggctgg tggaaccgtg cgccccggcg  1560
taa                                                                1563

SEQ ID NO: 223          moltype = DNA  length = 188
FEATURE                 Location/Qualifiers
misc_feature            1..188
                        note = delta-glnD
source                  1..188
                        mol_type = other DNA
                        organism = synthetic construct
SEQUENCE: 223
ttctgacatt agcaaacgcg ataaacggtc cgctctgcgg gccgtttttt ttaccgctct  60
tccctgcagc gtcatacata taaacgactt ttcatttttc attatctctt ttaagttgtt  120
ttgctatgca tatgcactcc agacgggtgg cccatattat ttttttacac agatggaaag  180
agtaaaca                                                           188
```

STABLE LIQUID FORMULATIONS FOR NITROGEN-FIXING MICROORGANISMS

CROSS-REFERENCE TO RELATED APPLICATIONS

This application is a continuation of International Application No. PCT/US2021/029993 entitled "STABLE LIQUID FORMULATIONS FOR NITROGEN-FIXING MICROORGANISMS" filed Apr. 29, 2021, which claims the benefit of U.S. Provisional Application No. 63/019,096, entitled "STABLE LIQUID FORMULATIONS FOR NITROGEN-FIXING MICROORGANISMS" filed on May 1, 2020. The contents of each of the aforementioned documents are incorporated by reference herein in their entirety.

REFERENCE TO AN ELECTRONIC SEQUENCE LISTING

The contents of the electronic sequence listing (PIVO_020_01US_SeqList_ST26.xml; Size: 638,663 bytes; and Date of Creation: Oct. 27, 2022) is herein incorporated by reference in its entirety.

FIELD OF THE DISCLOSURE

The present disclosure relates to agronomically stable liquid agricultural compositions comprising nitrogen-fixing microorganisms, methods of formulation thereof, and methods of use thereof. The agricultural compositions may have improved stability at room temperature, allowing for greater ease of storage and use for agricultural crops. Also provided are methods of formulating agricultural compositions with improved stability comprising varying one or more parameters of the formulation process and/or ingredients. The agricultural compositions may be used to improve one or more aspects of the agricultural crop to which they are exposed, including yield and productivity.

BACKGROUND

Plant beneficial microbes, such as gram-negative bacteria, have the potential to increase growth and increase yields of crops under a variety of environmental stresses. These beneficial microbes, specifically those used for nitrogen fixation, must be cultured and transplanted to the soil near the root structure of the plant. Existing agricultural formulations for administering such microbes to agricultural plant tissues or their environment face ongoing problems with microbial stability, shelf life, and ease of use.

Most existing agricultural formulations comprising nitrogen-fixing microorganisms come in either dry or liquid forms. Dry powders have the benefit of improved stability and ease of storage, but often require the steps of mixing with a liquid carrier and activation by the user—steps that can compromise the viability of the formulation if incorrectly performed. After activation, many of these formulations also suffer from a limited shelf life in liquid form, which can lead to further difficulties in their use. Liquid formulations of nitrogen-fixing microorganisms allow for more complete control over the formulation process and greater ease of application by the user, but suffer from poor shelf life, complicating their storage and delivery.

There is an unmet need for improved liquid agricultural formulations comprising nitrogen-fixing bacteria for improving one or more traits of agricultural crops.

BRIEF SUMMARY

In one aspect, the present disclosure provides an agronomically stable liquid agricultural composition, comprising: a) a diazotrophic bacterium; b) a buffering agent; c) a microbial stabilizer; and d) a physical stabilizer, wherein the composition has a room temperature shelf life of at least 30 days.

In some embodiments, the microbial stability of the composition is greater than the microbial stability of the composition absent one or more of the buffering agent, microbial stabilizer, and physical stabilizer.

In some embodiments, the shelf life is at least two months, at least three months, at least four months, or at least five months.

In some embodiments, the shelf life is at least three months.

In some embodiments, the log loss of CFU/mL over the shelf life of the composition is less than 0.2.

In some embodiments, the bacterium is present at a cellular density that provides an acceptable rate of decay over the shelf life of the composition.

In some embodiments, the bacterium is present at a cellular density that minimizes the rate of decay over the shelf life of the composition.

In some embodiments, the bacterium is present at a cellular density that provides a reduced, but not minimized rate of decay.

In some embodiments, the bacterium is present at a cellular density that provides a rate of decay of less than 1.0 log loss of CFU/mL over 30 days in the agricultural composition absent the buffering agent, microbial stabilizer, and physical stabilizer.

In some embodiments, the bacterium is present at a cellular density of about 3E9-6E9 CFU/mL.

In some embodiments, the buffering agent maintains the pH of the composition over the shelf life of the composition.

In some embodiments, the buffering agent maintains the pH of the composition at about pH 6-8 over the shelf life of the composition.

In some embodiments, the buffering agent maintains the pH of the composition at about pH 6.5 over the shelf life of the composition.

In some embodiments, the buffering agent is selected from the list consisting of phosphate buffered saline (PBS); modified, high buffering capacity PBS; 3-Morpholinopropane-1-sulfonic acid (MOPS); and 2-[4-(2-hydroxyethyl)piperazin-1-yl]ethanesulfonic acid (HEPES).

In some embodiments, the buffering agent is modified, high buffering capacity PBS.

In some embodiments, the microbial stabilizer slows the doubling rate of the diazotrophic bacterium.

In some embodiments, the microbial stabilizer slows the toxin accumulation rate within the composition.

In some embodiments, the microbial stabilizer is a monosaccharide, disaccharide, polysaccharide, pentose, hexose, oligosaccharide, oligofructose, sugar alcohol, amino acid, protein or protein hydrolysate, or polymer.

In some embodiments, the microbial stabilizer is a monosaccharide or a disaccharide selected from the list consisting of glucose, fructose, trehalose, sucrose, lactose, melibiose, and lactulose.

In some embodiments, the microbial stabilizer is fructose or trehalose.

In some embodiments, the microbial stabilizer is fructose.

In some embodiments, the microbial stabilizer is fructose and is present in the composition at a concentration of about 0.5-2.5% w/v.

In some embodiments, the microbial stabilizer is fructose and is present in the composition at a concentration of about 1.3% w/v.

In some embodiments, the physical stabilizer decreases the local density of the diazotrophic bacterium within the composition.

In some embodiments, the physical stabilizer is a polysaccharide, protein or protein hydrolysate, polymer, or a natural gum or its derivative.

In some embodiments, the physical stabilizer is a polysaccharide.

In some embodiments, the physical stabilizer is a polysaccharide selected from the list consisting of maltodextrin, polyethylene glycol (PEG), xanthan gum, pectin, alginates, microcrystalline cellulose, and dextran.

In some embodiments, the physical stabilizer is xanthan gum.

In some embodiments, the physical stabilizer is xanthan gum and is present in the composition at a concentration of about 0.001-0.2% w/v.

In some embodiments, the physical stabilizer is xanthan gum and is present in the composition at a concentration of about 0.1% w/v.

In some embodiments, the bacterium is a gram-negative bacterium.

In some embodiments, the bacterium is of a genus selected from the group consisting of: *Acetobacter, Achromobacter, Aerobacter, Anabaena, Azoarcus, Azomonas, Azorhizobium, Azospirillum, Azotobacter, Beijernickia, Bradyrhizobium, Burkholderia, Citrobacter, Derxia, Enterobacter, Herbaspirillum, Klebsiella, Kluyvera, Kosakonia, Mesorhizobium, Metakosakonia, Paraburkholderia, Nostoc, Rahnella, Rhizobium, Rhodobacter, Rhodopseudomonas, Rhodospirillum, Serratia Sinorhizobium, Spirillum, Trichodesmium*, and *Xanthomonas*.

In some embodiments, the bacterium is of a species selected from the group consisting of: *Achromobacter marplatensis, Achromobacter spiritinus, Azospirillum lipoferum, Enterobacter sacchari, Herbaspirillum aquaticum, Klebsiella variicola, Kluyvera intermedia, Kosakonia pseudosacchari, Kosakonia sacchari, Metakosakonia intestini, Paraburkholderia tropica, Rahnella aquatilis*, and combinations thereof.

In some embodiments, the bacterium is a gram-positive bacterium.

In some embodiments, the bacterium is of a genus selected from the group consisting of: *Arthrobacter, Agromyces, Bacillus, Clostridium, Corynebacterium, Frankia, Heliobacillus, Heliobacterium, Heliophilum, Heliorestis Methanobacterium, Microbacterium, Micrococcus, Micromonospora, Mycobacterium, Paenibacillus, Propionibacterium*, and *Streptomyces*.

In some embodiments, the bacterium is of a species selected from the group consisting of: *Bacillus amyloliquefaciens, Bacillus macerans, Bacillus pumilus, Bacillus thuringiensis, Clostridium acetobutylicum, Corynebacterium autitrophicum Methanobacterium formicicum, Methanobacterium omelionski, Microbacterium murale, Mycobacterium flavum, Paenibacillus polymyxa, Paenibacillus riograndensis, Propionibacterium acidipropio, Propionibacterium freudenreichii, Streptococcus lactis, Streptomyces griseus*, and combinations thereof.

In some embodiments, the bacterium is of the genus *Klebsiella*.

In some embodiments, the bacterium is of the species *Klebsiella variicola*.

In some embodiments, the bacterium is of the strain *Klebsiella variicola* NCMA 201712002.

In some embodiments, the bacterium is of the genus *Kosakonia*.

In some embodiments, the bacterium is of the species *Kosakonia sacchari*.

In some embodiments, the bacterium is of the strain *Kosakonia sacchari* ATCC PTA-126743.

In some embodiments, the bacterium is endophytic, epiphytic, or rhizospheric.

In some embodiments, the bacterium is a wild type bacterium.

In some embodiments, the bacterium is an engineered bacterium.

In some embodiments, the bacterium is a transgenic bacterium.

In some embodiments, the bacterium is an intragenic bacterium.

In some embodiments, the bacterium is a remodeled bacterium.

In some embodiments, the bacterium comprises a non-intergeneric genomic modification.

In some embodiments, the bacterium is an engineered bacterium capable of fixing atmospheric nitrogen in the presence of exogenous nitrogen.

In some embodiments, the bacterium is an engineered bacterium comprising at least one genetic variation introduced into at least one gene, or non-coding polynucleotide, of the nitrogen fixation or assimilation genetic regulatory network.

In some embodiments, the bacterium is an engineered bacterium comprising an introduced control sequence operably linked to at least one gene of the nitrogen fixation or assimilation genetic regulatory network.

In some embodiments, the bacterium is an engineered bacterium comprising a heterologous promoter operably linked to at least one gene of the nitrogen fixation or assimilation genetic regulatory network.

In some embodiments, the bacterium is an engineered bacterium comprising at least one genetic variation selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifJU, nifS, nifV, nifW, nifZ, nifM, nifF, nifB, nifQ, a gene associated with biosynthesis of a nitrogenase enzyme, and combinations thereof.

In some embodiments, the bacterium is an engineered bacterium comprising at least one genetic variation introduced into at least one gene, or non-coding polynucleotide, of the nitrogen fixation or assimilation genetic regulatory network that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased expression or uridylyl-removing activity of GlnD.

In some embodiments, the bacterium is an engineered bacterium comprising a mutated nifL gene that has been altered to comprise a heterologous promoter inserted into said nifL gene.

In some embodiments, the bacterium is an engineered bacterium comprising a mutated glnE gene that results in a truncated GlnE protein lacking an adenylyl-removing (AR) domain.

In some embodiments, the bacterium is an engineered bacterium comprising a mutated glnD gene that results in the lack of expression of said glnD gene.

In some embodiments, the bacterium is an engineered bacterium comprising a mutated amtB gene that results in the lack of expression of said amtB gene.

In some embodiments, the bacterium is an engineered bacterium comprising at least one of: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; a mutated glnD gene that results in the lack of expression of said glnD gene; and combinations thereof.

In some embodiments, the bacterium is an engineered bacterium comprising at least one genetic variation introduced into genes involved in a pathway selected from the group consisting of: exopolysaccharide production, endo-polygalaturonase production, trehalose production, and glutamine conversion.

In some embodiments, the bacterium is an engineered bacterium comprising at least one genetic variation introduced into genes selected from the group consisting of: bcsii, bcsiii, yjbE, fhaB, pehA, otsB, treZ, glsA2, and combinations thereof.

In some embodiments, the bacterium is selected from Table 1, or a variant, mutant, or derivative thereof.

In some embodiments, the bacterium comprises a nucleic acid sequence that shares at least about 90%, 95%, or 99% sequence identity to a nucleic acid sequence selected from SEQ ID NOs: 1-223.

In some embodiments, the bacterium comprises a nucleic acid sequence selected from SEQ ID NOs: 1-223.

In one aspect, the present disclosure provides an agronomically stable liquid agricultural composition with a room temperature shelf life of at least 3 months, comprising: a) a diazotrophic bacterium at a cellular density that provides a decay rate of less than 0.2 log loss CFU/mL over the shelf life of the composition; b) a buffering agent that maintains the pH of the composition around pH 6.7 over the shelf life of the composition; c) a microbial stabilizer that slows the doubling rate of the diazotrophic bacterium; and d) a physical stabilizer that decreases the local density of the diazotrophic bacterium within the composition, wherein the stability of the composition is greater than, and the presence of toxic byproducts is less than, the composition absent one or more of the buffering agent, microbial stabilizer, and physical stabilizer.

In one aspect, the present disclosure provides an agronomically stable liquid agricultural composition with a room temperature shelf life of at least 3 months, comprising: a) *Klebsiella variicola* at a concentration of at least about 4.5E9 CFU/mL; b) modified, high buffering capacity PBS; c) fructose at a concentration of at least about 1% w/v; and d) xanthan gum at a concentration of at least about 0.05% w/v.

In one aspect, the present disclosure provides an agronomically stable liquid agricultural composition with a room temperature shelf life of at least 3 months, comprising: a) *Kosakonia sacchari* at a concentration of about 3E9 CFU/mL; b) modified, high buffering capacity PBS; and c) fructose at a concentration of at least about 1% w/v.

In one aspect, the present disclosure provides agricultural plant tissue comprising the agronomically stable liquid agricultural composition of any of the foregoing embodiments.

In some embodiments, the agricultural plant is a legume or cereal grain.

In some embodiments, the agricultural plant is alfalfa, clover, bean, pea, chickpea, lentil, lupin, mesquite, carob, soybean, peanut, rooibos, or tamarind.

In some embodiments, the agricultural plant is corn, rice, wheat, barley, sorghum, millet, oats, or rye.

In some embodiments, the agricultural plant is corn.

In one aspect, the present disclosure provides a method for applying a diazotrophic bacterium to agricultural plant tissues comprising applying the composition of any one of the foregoing embodiments to agricultural plant tissues or the environs thereof.

In one aspect, the present disclosure provides a method for maintaining a population of a diazotrophic bacterium on an agricultural plant tissue comprising applying the composition of any one of the foregoing embodiments to said plant tissue or the environs thereof.

In one aspect, the present disclosure provides a method of increasing agricultural plant crop yield comprising applying the composition of any one of the foregoing embodiments to the agricultural plant tissues or the environs thereof prior to, during, or immediately following planting, thereby increasing the crop yield of the agricultural plant once planted.

In one aspect, the present disclosure provides a method of providing fixed atmospheric nitrogen to a cereal plant, comprising applying the composition of any one of the foregoing embodiments to the cereal plant tissues or the environs thereof.

In one aspect, the present disclosure provides a method of providing fixed atmospheric nitrogen to a corn plant that eliminates the need for the addition of in-season exogenous nitrogen application, comprising applying the composition of any one of the foregoing embodiments to the corn plant tissues or the environs thereof.

In one aspect, the present disclosure provides a method for increasing corn yield per acre, comprising applying the composition of any one of the foregoing embodiments to the corn plant tissues or the environs thereof.

In one aspect, the present disclosure provides a method for reducing infield variability for corn yield per acre, comprising applying the composition of any one of the foregoing embodiments to the corn plant tissues or the environs thereof, wherein the standard deviation of corn mean yield measured in bushels per acre is lower than for control plants to which the composition has not been applied.

In some embodiments, the method comprises: a) applying the composition to a locus; and b) providing to the locus a plurality of the plants.

In some embodiments, the composition comprises a plurality of said diazotrophic bacteria, wherein the diazotrophic bacteria comprise engineered bacteria, and wherein the engineered bacteria colonize the root surface of said plurality of plants and supply the plants with fixed nitrogen.

In some embodiments, the composition comprises a plurality of said diazotrophic bacteria, wherein the diazotrophic bacteria comprise engineered bacteria, and wherein the engineered bacteria colonize the root surface of said plurality of plants and supply the plants with fixed nitrogen, and wherein the plurality of engineered bacteria produce in the aggregate at least about 15 pounds of fixed nitrogen per acre over the course of at least about 10 days to about 60 days.

In some embodiments, exogenous nitrogen is not applied to the plant tissues or the environs thereof after the composition is applied.

In some embodiments, the agricultural plant is a legume or cereal grain.

In some embodiments, the agricultural plant is alfalfa, clover, bean, pea, chickpea, lentil, lupin, mesquite, carob, soybean, peanut, rooibos, or tamarind.

In some embodiments, the agricultural plant is corn, rice, wheat, barley, sorghum, millet, oats, or rye.

In some embodiments, the agricultural plant is corn.

In some embodiments, the method increases the crop yield of the agricultural plant.

In some embodiments, the method increases the crop yield of the agricultural plant with a win rate of greater than 65%.

In some embodiments, the method increases the crop yield of the agricultural plant with a win rate of about 75%.

In some embodiments, the method increases the crop yield of the agricultural plant by more than 3 bushels/acre.

In some embodiments, the method increases the crop yield of the agricultural plant by about 3 bushels/acre.

In some embodiments, the method reduces infield variability for the agricultural plant crop yield per acre.

In some embodiments, the method reduces infield variability for the agricultural plant crop yield per acre with a win rate of greater than 65%.

In some embodiments, the method reduces infield variability for the agricultural plant crop yield per acre with a win rate of about 75%.

In some embodiments, the method reduces infield variability for the agricultural plant crop yield per acre with a variance improvement of greater than 2 bushels/acre.

In one aspect, the present disclosure provides a method of preparing an agronomically stable liquid agricultural composition comprising a diazotrophic bacterium, the method comprising the steps of: a) providing a diazotrophic bacterium; b) selecting for inclusion in the composition a cellular density of the diazotrophic bacterium that provides an acceptable rate of decay of the bacterium; c) selecting a buffering agent for inclusion in the composition; d) selecting a microbial stabilizer for inclusion in the composition; and e) selecting a physical stabilizer for inclusion in the composition, wherein the composition is stable at room temperature for a period of more than 30 days, and wherein the stability of the composition is greater than the composition absent one or more of the buffering agent, microbial stabilizer, an physical stabilizer.

In one aspect, the present disclosure provides a method for improving the stability of a liquid agricultural composition comprising a diazotrophic bacterium, the method comprising the steps of a) providing a diazotrophic bacterium; b) selecting for inclusion in the composition a cellular density of the diazotrophic bacterium that provides an acceptable rate of decay of the bacterium; c) selecting a buffering agent for inclusion in the composition; d) selecting a microbial stabilizer for inclusion in the composition; and e) selecting a physical stabilizer for inclusion in the composition, wherein the composition has a room temperature shelf life of at least 30 days.

In some embodiments, step (b) comprises generating a titration curve to determine cellular density versus decay rate of the diazotrophic bacterium and selecting a cellular density that provides an acceptable decay rate.

In some embodiments, steps (c)-(e) can be performed in any order.

In some embodiments, any subset of steps (c)-(e) can be performed serially or in parallel.

In some embodiments, step (c) comprises selecting a buffering agent that improves microbial stability when included in the agricultural composition, either in the presence or absence of the microbial and/or physical stabilizer.

In some embodiments, step (c) comprises comparing two or more buffering agents and selecting the buffering agent that provides greater improvement to the microbial stability when included in the agricultural composition, either in the presence or absence of the microbial and/or physical stabilizer.

In some embodiments, step (d) comprises selecting a microbial stabilizer that improves microbial stability when included in the agricultural composition, either in the presence or absence of the buffering agent and/or physical stabilizer In some embodiments, step (d) comprises comparing two or more microbial stabilizers and selecting the microbial stabilizer that provides greater improvement to the microbial stability when included in the agricultural composition, either in the presence or absence of the buffering agent and/or physical stabilizer.

In some embodiments, step (e) comprises selecting a physical stabilizer that improves microbial stability when included in the agricultural composition, either in the presence or absence of the buffering agent and/or microbial stabilizer.

In some embodiments, step (e) comprises comparing two or more physical stabilizers and selecting the physical stabilizer that provides greater improvement to the microbial stability when included in the agricultural composition, either in the presence or absence of the buffering agent and/or microbial stabilizer.

In some embodiments, the selections of the microbial stabilizer and the physical stabilizer in steps (d) and (e) are performed simultaneously.

In some embodiments, the method increases the shelf life of the liquid agricultural composition by a factor of at least 2, at least 3, or at least 4.

In some embodiments, any one of steps (b)-(e) alone provides less improvement to the microbial stability of the composition than all of the steps together.

In some embodiments, the composition is for application to agricultural plant tissues or the environs thereof.

In some embodiments, the method decreases the accumulation of toxic byproducts in the composition over the course of its shelf life.

In some embodiments, the method decreases the accumulation of ammonia in the composition over the course of its shelf life.

In some embodiments, the method decreases the accumulation of ammonia in the composition by at least two-fold over the course of its shelf life as compared to an agricultural composition absent the microbial stabilizer and buffering agent.

In some embodiments, the composition at the end of its' shelf life has a colonization potential approximately equal to the colonization potential of the composition when freshly formulated.

In some embodiments, the microbial stability of the composition is greater than the microbial stability of the composition absent one or more of the buffering agent, microbial stabilizer, and physical stabilizer.

In some embodiments, the composition has a shelf life of at least two months, at least three months, at least four months, or at least five months.

In some embodiments, the composition has a shelf life of at least three months.

In some embodiments, the log loss of CFU/mL over the shelf life of the composition is less than 0.2.

In some embodiments, the cellular density of the bacterium minimizes the rate of decay over the shelf life of the composition.

In some embodiments, the cellular density of the bacterium provides a reduced, but not minimized rate of decay.

In some embodiments, the cellular density of the bacterium provides a rate of decay of less than 1.0 log loss of CFU/mL over 30 days in the agricultural composition absent the buffering agent, microbial stabilizer, and physical stabilizer.

In some embodiments, the bacterium is present at a cellular density of about 3E9-6E9 CFU/mL.

In some embodiments, the buffering agent maintains the pH of the composition over the shelf life of the composition.

In some embodiments, the buffering agent maintains the pH of the composition at about pH 6-8 over the shelf life of the composition.

In some embodiments, the buffering agent maintains the pH of the composition at about pH 6.5 over the shelf life of the composition.

In some embodiments, the buffering agent is selected from the list consisting of phosphate buffered saline (PBS); modified, high buffering capacity PBS; 3-Morpholinopropane-1-sulfonic acid (MOPS); and 2-[4-(2-hydroxyethyl) piperazin-1-yl]ethanesulfonic acid (HEPES).

In some embodiments, the buffering agent is modified, high buffering capacity PBS.

In some embodiments, the microbial stabilizer slows the doubling rate of the diazotrophic bacterium.

In some embodiments, the microbial stabilizer slows the toxin accumulation rate within the composition.

In some embodiments, the microbial stabilizer is a monosaccharide, disaccharide, polysaccharide, pentose, hexose, oligosaccharide, oligofructose, sugar alcohol, amino acid, protein or protein hydrolysate, or polymer.

In some embodiments, the microbial stabilizer is a monosaccharide or a disaccharide selected from the list consisting of glucose, fructose, trehalose, sucrose, lactose, melibiose, and lactulose.

In some embodiments, the microbial stabilizer is fructose or trehalose.

In some embodiments, the microbial stabilizer is fructose.

In some embodiments, the microbial stabilizer is fructose and is selected for inclusion in the composition at a concentration of about 0.5-2.5% w/v.

In some embodiments, the microbial stabilizer is fructose and is selected for inclusion in the composition at a concentration of about 1.3% w/v.

In some embodiments, the physical stabilizer decreases the local density of the diazotrophic bacterium within the composition.

In some embodiments, the physical stabilizer is a polysaccharide, protein or protein hydrolysate, polymer, or a natural gum or its derivative.

In some embodiments, the physical stabilizer is a polysaccharide.

In some embodiments, the physical stabilizer is a polysaccharide selected from the list consisting of maltodextrin, polyethylene glycol (PEG), xanthan gum, pectin, alginates, microcrystalline cellulose, and dextran.

In some embodiments, the physical stabilizer is xanthan gum.

In some embodiments, the physical stabilizer is xanthan gum and is selected for inclusion in the composition at a concentration of about 0.001-0.2% w/v.

In some embodiments, the physical stabilizer is xanthan gum and is selected for inclusion in the composition at a concentration of about 0.1% w/v.

In some embodiments, the bacterium is a gram-negative bacterium.

In some embodiments, the bacterium is of a genus selected from the group consisting of: *Acetobacter, Achromobacter, Aerobacter, Anabaena, Azoarcus, Azomonas, Azorhizobium, Azospirillum, Azotobacter, Beijernickia, Bradyrhizobium, Burkholderia, Citrobacter, Derxia, Enterobacter, Herbaspirillum, Klebsiella, Kluyvera, Kosakonia, Mesorhizobium, Metakosakonia, Paraburkholderia, Nostoc, Rahnella, Rhizobium, Rhodobacter, Rhodopseudomonas, Rhodospirillum, Serratia Sinorhizobium, Spirillum, Trichodesmium*, and *Xanthomonas*.

In some embodiments, the bacterium is of a species selected from the group consisting of: *Achromobacter marplatensis, Achromobacter spiritinus, Azospirillum lipoferum, Enterobacter sacchari, Herbaspirillum aquaticum, Klebsiella variicola, Kluyvera intermedia, Kosakonia pseudosacchari, Kosakonia sacchari, Metakosakonia intestini, Paraburkholderia tropica, Rahnella aquatilis*, and combinations thereof.

In some embodiments, the bacterium is a gram-positive bacterium.

In some embodiments, the bacterium is of a genus selected from the group consisting of: *Arthrobacter, Agromyces, Bacillus, Clostridium, Corynebacterium, Frankia, Heliobacillus, Heliobacterium, Heliophilum, Heliorestis Methanobacterium, Microbacterium, Micrococcus, Micromonospora, Mycobacterium, Paenibacillus, Propionibacterium*, and *Streptomyces*.

In some embodiments, the bacterium is of a species selected from the group consisting of: *Bacillus amyloliquefaciens, Bacillus macerans, Bacillus pumilus, Bacillus thuringiensis, Clostridium acetobutylicum, Corynebacterium autitrophicum Methanobacterium formicicum, Methanobacterium omelionski, Microbacterium murale, Mycobacterium flavum, Paenibacillus polymyxa, Paenibacillus riograndensis, Propionibacterium acidipropio, Propionibacterium freudenreichii, Streptococcus lactis, Streptomyces griseus*, and combinations thereof.

In some embodiments, the bacterium is of the genus *Klebsiella*.

In some embodiments, the bacterium is of the species *Klebsiella variicola*.

In some embodiments, the bacterium is of the strain *Klebsiella variicola* NCMA 201712002.

In some embodiments, the bacterium is of the genus *Kosakonia*.

In some embodiments, the bacterium is of the species *Kosakonia sacchari*.

In some embodiments, the bacterium is of the strain *Kosakonia sacchari* ATCC PTA-126743.

In some embodiments, the bacterium is endophytic, epiphytic, or rhizospheric.

In some embodiments, the bacterium is a wild type bacterium.

In some embodiments, the bacterium is an engineered bacterium.

In some embodiments, the bacterium is a transgenic bacterium.

In some embodiments, the bacterium is an intragenic bacterium.

In some embodiments, the bacterium is a remodeled bacterium.

In some embodiments, the bacterium comprises a non-intergeneric genomic modification.

In some embodiments, the bacterium is an engineered bacterium capable of fixing atmospheric nitrogen in the presence of exogenous nitrogen.

In some embodiments, the bacterium is an engineered bacterium comprising at least one genetic variation introduced into at least one gene, or non-coding polynucleotide, of the nitrogen fixation or assimilation genetic regulatory network.

In some embodiments, the bacterium is an engineered bacterium comprising an introduced control sequence operably linked to at least one gene of the nitrogen fixation or assimilation genetic regulatory network.

In some embodiments, the bacterium is an engineered bacterium comprising a heterologous promoter operably linked to at least one gene of the nitrogen fixation or assimilation genetic regulatory network.

In some embodiments, the bacterium is an engineered bacterium comprising at least one genetic variation selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, a gene associated with biosynthesis of a nitrogenase enzyme, and combinations thereof.

In some embodiments, the bacterium is an engineered bacterium comprising at least one genetic variation introduced into at least one gene, or non-coding polynucleotide, of the nitrogen fixation or assimilation genetic regulatory network that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased expression or uridylyl-removing activity of GlnD.

In some embodiments, the bacterium is an engineered bacterium comprising a mutated nifL gene that has been altered to comprise a heterologous promoter inserted into said nifL gene.

In some embodiments, the bacterium is an engineered bacterium comprising a mutated glnE gene that results in a truncated GlnE protein lacking an adenylyl-removing (AR) domain.

In some embodiments, the bacterium is an engineered bacterium comprising a mutated glnD gene that results in the lack of expression of said glnD gene.

In some embodiments, the bacterium is an engineered bacterium comprising a mutated amtB gene that results in the lack of expression of said amtB gene.

In some embodiments, the bacterium is an engineered bacterium comprising at least one of: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; a mutated glnD gene that results in the lack of expression of said glnD gene; and combinations thereof.

In some embodiments, the bacterium is an engineered bacterium comprising at least one genetic variation introduced into genes involved in a pathway selected from the group consisting of: exopolysaccharide production, endo-polygalaturonase production, trehalose production, and glutamine conversion.

In some embodiments, the bacterium is an engineered bacterium comprising at least one genetic variation introduced into genes selected from the group consisting of: bcsii, bcsiii, yjbE, fhaB, pehA, otsB, treZ, glsA2, and combinations thereof.

In some embodiments, the bacterium is selected from Table 1, or a variant, mutant, or derivative thereof.

In some embodiments, the bacterium comprises a nucleic acid sequence that shares at least about 90%, 95%, or 99% sequence identity to a nucleic acid sequence selected from SEQ ID NOs: 1-223.

In some embodiments, the bacterium comprises a nucleic acid sequence selected from SEQ ID NOs: 1-223.

Figure 10:
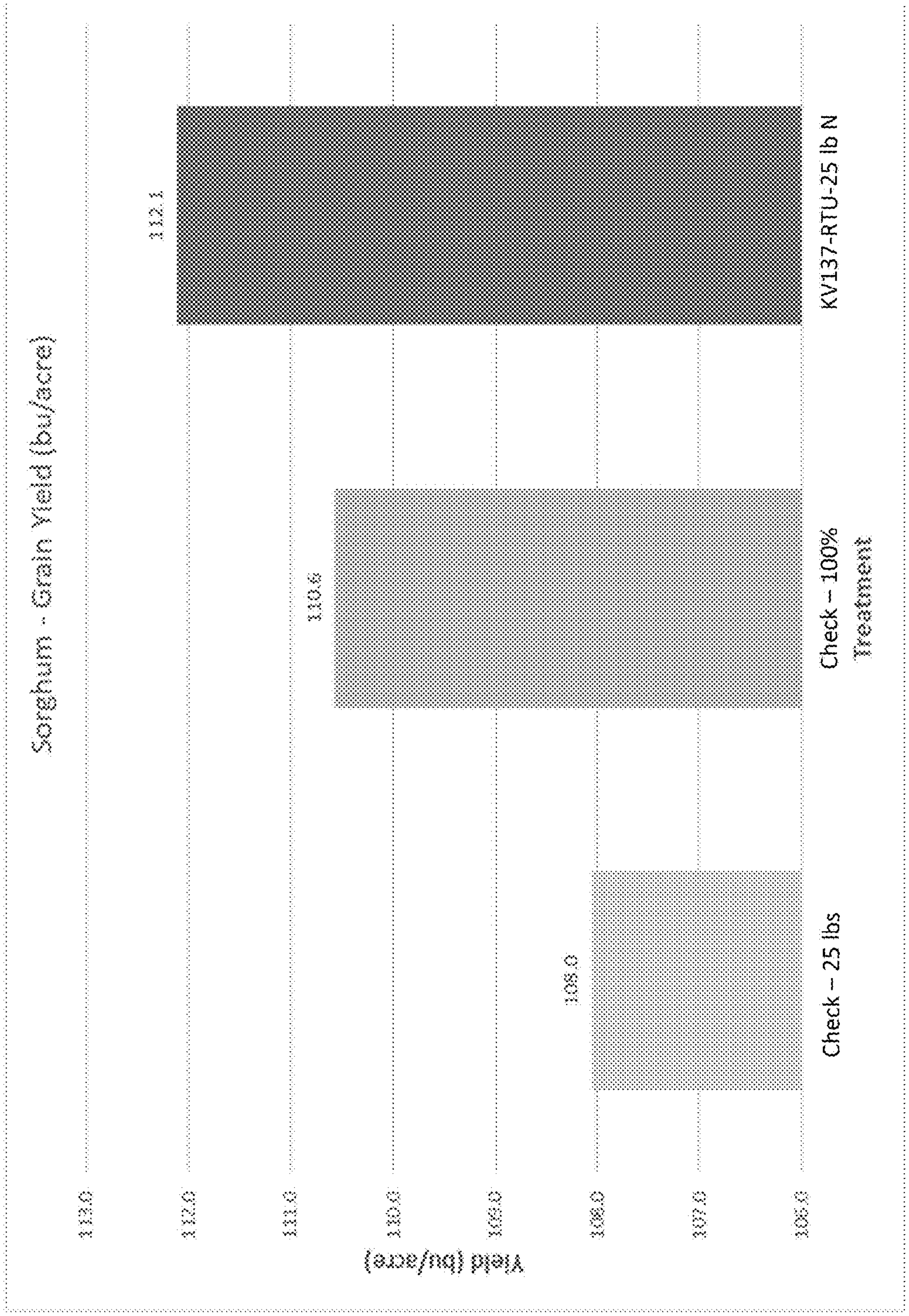

FIG. 10 shows a bar graph of sorghum yield. *K. variicola* deposited strain NCMA 201708001 ("KV137-RTU") was tested at ten trial locations where nitrogen was reduced by 25 pounds and compared to (1) a control which received 100% of the recommended nitrogen rate and (2) a reduced nitrogen control containing nitrogen reduced by 25 pounds.

Figure 11:
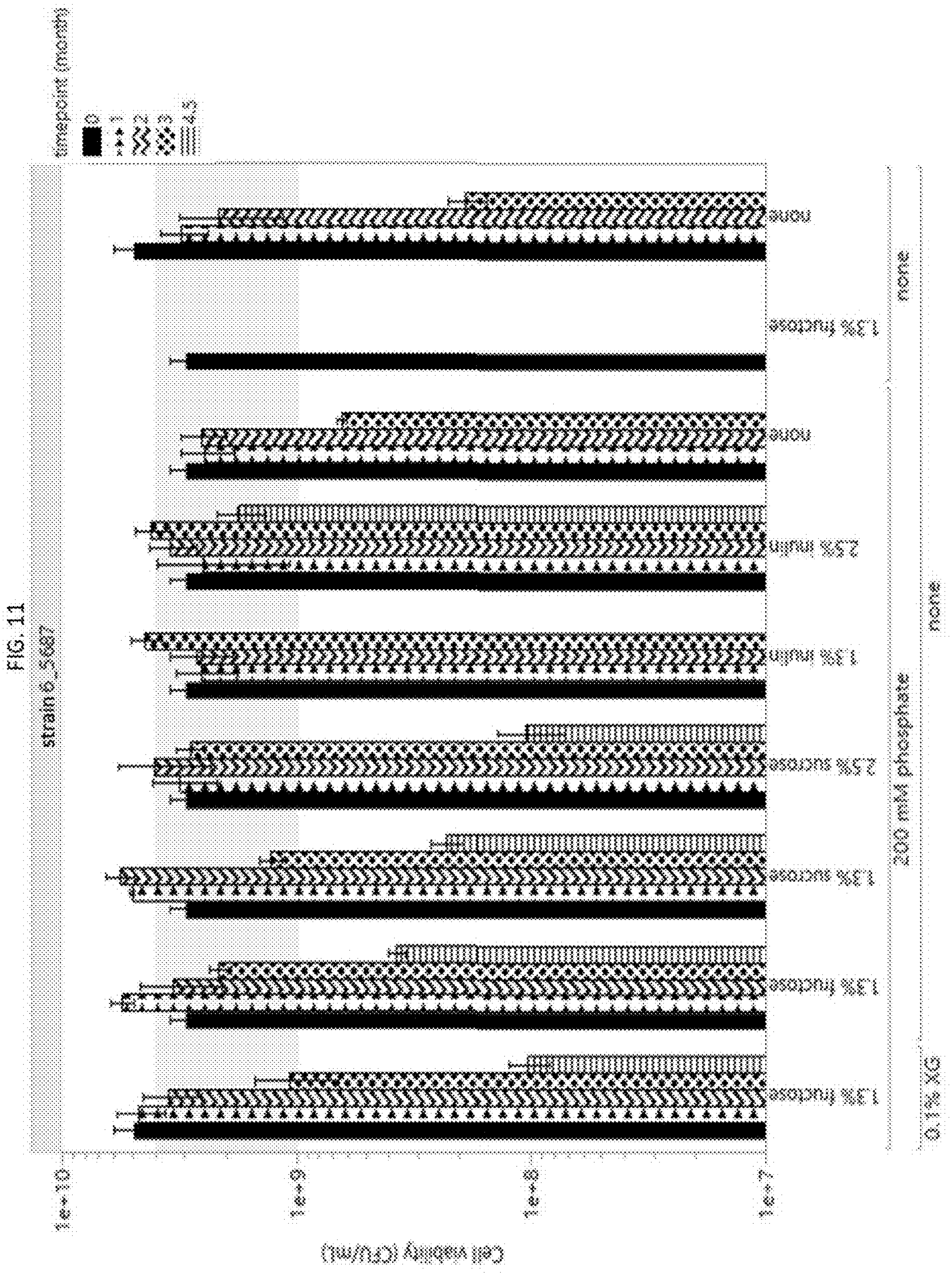

FIG. 11 shows a bar graph of the cell viability of strain ATCC PTA126743 over the course of several months with different stabilizers.

DETAILED DESCRIPTION

The present disclosure provides agronomically stable liquid agricultural compositions comprising nitrogen-fixing microorganisms and one or more of buffering agents, microbial stabilizers, and physical stabilizers. Also provided are methods of formulating these agronomically stable liquid agricultural compositions and methods of applying the same. The present disclosure also provides agricultural plant tissues comprising the agronomically stable liquid agricultural compositions.

Definitions

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

As used herein, the term "about" is used synonymously with the term "approximately." Illustratively, the use of the term "about" with regard to an amount indicates that values slightly outside the cited values, e.g., plus or minus 0.1% to 10%.

"Plant tissues," as used herein, refers to any part of the plant during any aspect of the growing cycle, including seeds, seedlings, plants, or plant parts. Plant parts include leaves, roots, root hairs, rhizomes, stems, seed, ovules, pollen, flowers, fruit, cuttings, tubers, bulbs, etc. An agricultural plant tissue "comprising" an agronomically stable liquid agricultural composition of the disclosure includes agricultural plant tissues to which the agricultural composition has been applied by any of the means set forth herein, e.g., spraying, in-furrow application, seed treatment, etc.

"Plant productivity" refers generally to any aspect of growth or development of a plant that is a reason for which the plant is grown. For food crops, such as grains or vegetables, "plant productivity" can refer to the yield of grain or fruit harvested from a particular crop. As used herein, improved plant productivity refers broadly to improvements in yield of grain, fruit, flowers, or other plant parts harvested for various purposes, improvements in growth of plant parts, including stems, leaves and roots, promotion of plant growth, maintenance of high chlorophyll content in leaves, increasing fruit or seed numbers, increasing fruit or seed unit weight, and similar improvements of the growth and development of plants. Plant productivity, in the context of agricultural compositions with nitrogen fixing bacteria, is determined by comparing the productivity (e.g., yield) of a treated plant (e.g., via in furrow application), vs. a plant with no composition applied, and no additional fertilizer beyond what is provided to the treated plant. Thus, in some embodiments, the agricultural compositions of the present disclosure result in reductions in $NO_2$ emission due to reduced nitrogen fertilizer usage.

Microbes in and around food crops can influence the traits of those crops. Plant traits that may be influenced by microbes include: yield (e.g., grain production, biomass generation, fruit development, flower set); nutrition (e.g., nitrogen, phosphorus, potassium, iron, micronutrient acquisition); abiotic stress management (e.g., drought tolerance, salt tolerance, heat tolerance); and biotic stress management (e.g., pest, weeds, insects, fungi, and bacteria). Strategies for altering crop traits include: increasing key metabolite concentrations; changing temporal dynamics of microbe influence on key metabolites; linking microbial metabolite production/degradation to new environmental cues; reducing negative metabolites; and improving the balance of metabolites or underlying proteins.

As used herein, "in planta" may refer to in the plant, on the plant, or intimately associated with the plant, depending upon context of usage (e.g. endophytic, epiphytic, or rhizospheric associations). The plant may comprise plant parts, tissue, leaves, roots, root hairs, rhizomes, stems, seed, ovules, pollen, flowers, fruit, etc.

As used herein, "introduced" refers to the introduction by means of modern biotechnology, and not a naturally occurring introduction.

In some embodiments, the bacteria of the present disclosure have been modified such that they are not naturally occurring bacteria.

Fertilizers and exogenous nitrogen of the present disclosure may comprise the following nitrogen-containing molecules: ammonium, nitrate, nitrite, ammonia, glutamine, etc. Nitrogen sources of the present disclosure may include anhydrous ammonia, ammonia sulfate, urea, diammonium phosphate, urea-form, monoammonium phosphate, ammonium nitrate, nitrogen solutions, calcium nitrate, potassium nitrate, sodium nitrate, etc.

As used herein, "exogenous nitrogen" refers to non-atmospheric nitrogen readily available in the soil, field, or growth medium that is present under non-nitrogen limiting conditions, including ammonia, ammonium, nitrate, nitrite, urea, uric acid, ammonium acids, etc.

As used herein, "non-nitrogen limiting conditions" refers to non-atmospheric nitrogen available in the soil, field, media at concentrations greater than about 4 mM nitrogen, as disclosed by Kant et al. (2010. J. Exp. Biol. 62(4):1499-1509), which is incorporated herein by reference.

As used herein, an "intergeneric microorganism" is a microorganism that is formed by the deliberate combination of genetic material originally isolated from organisms of different taxonomic genera. An "intergeneric mutant" can be used interchangeably with "intergeneric microorganism". An exemplary "intergeneric microorganism" includes a microorganism containing a mobile genetic element which was first identified in a microorganism in a genus different from the recipient microorganism. Further explanation can be found, inter alia, in 40 C.F.R. § 725.3.

In aspects, microbes taught herein are "non-intergeneric," which means that the microbes are not intergeneric.

As used herein, an "intrageneric microorganism" is a microorganism that is formed by the deliberate combination of genetic material originally isolated from organisms of the same taxonomic genera. An "intrageneric mutant" can be used interchangeably with "intrageneric microorganism."

As used herein, an "intragenic" microorganism, is a microorganism that is engineered to comprise a genetic edit, or genetic modification, or genetic element, or genetic material (e.g. a nucleic acid sequence), that has been sourced from within the organism's own genome.

As used herein, a "transgenic" microorganism, is a microorganism that is engineered to comprise a genetic edit, or genetic modification, or genetic element, or genetic material (e.g. a nucleic acid sequence), that has been sourced from outside the organism's own species.

As used herein, in the context of non-intergeneric microorganisms, the term "remodeled" is used synonymously with the term "engineered". Consequently, a "non-intergeneric remodeled microorganism" has a synonymous meaning to "non-intergeneric engineered microorganism," and will be utilized interchangeably.

A "wild type microbe," e.g., a "wild type bacterium," as used herein refers to a microbe that has not been genetically modified. Wild type microbes may be isolated and cultivated from a natural source. Wild type microbes may be selected for specific naturally occurring traits.

A "diazotroph" is a microbe that fixes atmospheric nitrogen gas into a more usable form, such as ammonia. A diazotroph is a microorganism that is able to grow without external sources of fixed nitrogen. All diazotrophs contain iron-molybdenum or -vanadium nitrogenase systems.

In some embodiments, the increase of nitrogen fixation and/or the production of 1% or more of the nitrogen in the plant are measured relative to control plants, which have not been exposed to the bacteria of the present disclosure. All increases or decreases in bacteria are measured relative to control bacteria. All increases or decreases in plants are measured relative to control plants.

In aspects, "applying," "coating," and "treating" agricultural plant tissues or the environs thereof with the present agricultural compositions includes any means by which the plant tissues or the environs thereof are made to come into contact (i.e. exposed) to said agricultural compositions. Consequently, "applying" includes any of the following means of exposure to said agricultural compositions: spraying, dripping, submerging, applying as a seed coat, applying to a field that will then be planted with seed, applying to a field already planted with seed, etc. For the purposes of this disclosure, "the environs" of agricultural plant tissues include the elements of the vicinity around the agricultural plant tissues that come into contact with the agricultural plant tissues. For example, application to the environs of agricultural plant tissues would include soil application and in-furrow application means.

As used herein the term "plant" can include plant parts, tissue, leaves, roots, root hairs, rhizomes, stems, seeds, ovules, pollen, flowers, fruit, etc. Thus, when the disclosure discusses providing a plurality of corn plants to a particular locus, it is understood that this may entail planting a corn seed at a particular locus.

As used herein the terms "microorganism" or "microbe" should be taken broadly. These terms, used interchangeably, include but are not limited to, the two prokaryotic domains, Bacteria and Archaea. The term may also encompass eukaryotic fungi and protists.

As used herein, when the disclosure discuses a particular microbial deposit by accession number, it is understood that the disclosure also contemplates a microbial strain having all of the identifying characteristics of said deposited microbe, and/or a mutant thereof.

In certain aspects of the disclosure, the isolated microbes exist as "isolated and biologically pure cultures." It will be appreciated by one of skill in the art, that an isolated and biologically pure culture of a particular microbe, denotes that said culture is substantially free of other living organisms and contains only the individual microbe in question. The culture can contain varying concentrations of said microbe. The present disclosure notes that isolated and biologically pure microbes often "necessarily differ from less pure or impure materials." See, e.g. *In re Bergstrom,* 427 F.2d 1394, (CCPA 1970)(discussing purified prostaglandins), see also, *In re Bergy,* 596 F.2d 952 (CCPA 1979) (discussing purified microbes), see also, *Parke-Davis & Co. v. H.K. Mulford & Co.,* 189 F. 95 (S.D.N.Y. 1911) (Learned Hand discussing purified adrenaline), aff'd in part, rev'd in part, 196 F. 496 (2d Cir. 1912), each of which are incorporated herein by reference. Furthermore, in some aspects, the disclosure provides for certain quantitative measures of the concentration, or purity limitations, that must be found within an isolated and biologically pure microbial culture. The presence of these purity values, in certain embodiments, is a further attribute that distinguishes the presently disclosed microbes from those microbes existing in a natural state. See, e.g., *Merck & Co. v. Olin Mathieson Chemical Corp.,* 253 F.2d 156 (4th Cir. 1958) (discussing purity limitations for vitamin B12 produced by microbes), incorporated herein by reference.

Microbes of the present disclosure may include spores and/or vegetative cells. In some embodiments, microbes of the present disclosure include microbes in a viable but non-culturable (VBNC) state. As used herein, "spore" or "spores" refer to structures produced by bacteria and fungi that are adapted for survival and dispersal. Spores are generally characterized as dormant structures; however, spores are capable of differentiation through the process of germination. Germination is the differentiation of spores into vegetative cells that are capable of metabolic activity, growth, and reproduction. The germination of a single spore results in a single fungal or bacterial vegetative cell. Fungal spores are units of asexual reproduction, and In some embodiments are necessary structures in fungal life cycles. Bacterial spores are structures for surviving conditions that may ordinarily be nonconducive to the survival or growth of vegetative cells.

As used herein, the term "agronomically stable" refers to an agricultural composition comprising microorganisms that maintains the viability of the microorganisms over time. An agronomically stable agricultural composition may exhibit a decline in the bacterial concentration over time, but at a reduced rate compared to traditional liquid formulations. Loss of bacterial concentration may be measured in log loss of CFU per unit over time.

As used herein, the "shelf life" of an agricultural composition refers to the period of time over which the composition can be stored and still retain a desired level of efficacy for its intended purpose, e.g., application to agricultural plant tissues or the environs thereof for delivery of fixed nitrogen to the agricultural plant. In some embodiments, the shelf life is the period of time over which an agricultural composition can be stored at room temperature and experience less than log loss CFU/mL of 1. In some embodiments, the shelf life is the period of time over which an agricultural composition can be stored at room temperature and experience less than log loss CFU/mL of 0.5-2. In some embodiments, the shelf life is the period of time over which an agricultural composition can be stored and experience less than 50% loss of cell density in CFU/mL. In some embodiments, the shelf life is the period of time over which an agricultural composition can be stored and experience less than 90% loss of cell density in CFU/mL. In some embodiments, the shelf life is measured at room temperature. In some embodiments, the shelf life is measured at 4° C. In some embodiments, the temperature varies over the course of the period of storage over which shelf life is measured.

As used herein, a "seed treatment" refers to a substance that may be applied to agricultural seeds. The seed treatment may provide one or more benefits to the seed and/or plant resulting from the seed. Without limitation, seed treatments may include pesticides, herbicides, insecticides, nematicides, plant-growth promoting factors, fertilizers, compositions of the disclosure comprising diazotrophic microbes, and the like.

As used herein, the terms "formulation," "composition," "agricultural treatment," and the like may be used interchangeably to refer to the agronomically stable liquid agricultural compositions of the present disclosure.

The term "colony forming unit" or "CFU" as used herein is a unit used to estimate the number of viable microbial cells in a sample. Viable is defined as the ability to multiply under the controlled conditions. Counting colony-forming units requires culturing the microbes and counting only viable cells, in contrast with microscopic examination which counts all cells, living or dead. The visual appearance of a colony in a cell culture requires significant growth and may result from the growth of individual or multiple viable cells.

As used herein, a "buffering agent," "buffer solution," or "buffer," also known as a "pH buffer" or "hydrogen ion buffer," is an aqueous solution consisting of a mixture of a weak acid and its conjugate base, or a weak base and its conjugate acid. Its pH changes very little when a small amount of strong acid or base is added to it. Buffering agents are used as a means of keeping pH at a nearly constant value, or within a certain pH range, over a period of time. Herein, "a buffering agent" may refer to either a chemical compound used to buffer a formulation or to a buffering system comprising a combination of acids, bases, and/or salts.

Aronomically Stable Liquid Agricultural Compositions and Methods of Formulation Thereof The present disclosure provides agronomically stable liquid agricultural compositions. The agricultural compositions comprise plant-beneficial, nitrogen-fixing microorganisms. The agricultural compositions also comprise one or more of buffering agents, microbial stabilizers, and physical stabilizers. The present disclosure also provides methods of formulating and improving the stability of liquid agricultural compositions comprising nitrogen-fixing microorganisms and one or more of buffering agents, microbial stabilizers, and physical stabilizers.

In some embodiments, the agricultural compositions are cost effective, scalable liquid formulations for providing nitrogen-fixing microorganisms to agricultural plants in the form most preferred within the agricultural industry with improved stability compared to existing liquid formulations. Unlike a dry powder, the agricultural composition does not require suspension or activation prior to use, thus allowing for improved consistency in quality and application results. In some embodiments, the agricultural composition is ready to use as-is. In some embodiments, the agricultural composition is concentrated and is diluted prior to use. When the agricultural composition is ready to use as-is or with dilution, in some embodiments, its use does not require consistent compliance in the activation steps taken by the user. In some embodiments, the ready to use formulation of the agricultural compositions decreases variance in the quality of the agricultural composition between different users.

In some embodiments, the present formulation methods produce agricultural compositions with improved shelf stability. In some embodiments, the agricultural composition has improved shelf stability compared to existing liquid formulations comprising nitrogen-fixing microorganisms. In some embodiments, this shelf stability is determined by measuring microbial viability as a function of time. In some embodiments, the agricultural composition is shelf stable for a period of three to six months. In some embodiments, the agricultural composition is shelf stable for a period of at least three months. In some embodiments, the agricultural composition is shelf stable for a period of at least four months. In some embodiments, the agricultural composition is shelf stable for a period of at least five months. In some embodiments, the agricultural composition is shelf stable for a period of at least six months.

Without wishing to be bound by theory, it is believed that the improved stability of the disclosed agricultural compositions is a result of the combination of formulation ingredients, e.g., as selected using a formulation method disclosed herein. In some embodiments, the agricultural composition components address different underlying causes of decay that lead to poor shelf stability for other liquid formulations. In some embodiments, the causes of decay are: high densities of microbial cells, toxins produced by the cells, and cells entering long-term stationary phase. In some embodiments, the present agricultural compositions address these causes of decay by comprising: an initial density of cells selected to provide a decreased decay rate; physical stabilizers that improve the uniform distribution of cells and decrease the local accumulation of high densities and/or toxin levels; microbial stabilizers that protect the cells, potentially by putting them into a semi-dormant state; and buffering agents that prevent pH fluctuations.

These components and the selection thereof for inclusion in the agricultural compositions of the disclosure are described in greater detail in the following sections.

Microorganisms

The agricultural compositions of the present disclosure comprise plant-beneficial microorganisms, particularly nitrogen-fixing microorganisms. In some embodiments, microbes useful in the methods and agricultural compositions disclosed herein are obtained from any source.

In some embodiments, microbes are bacteria, archaea, protozoa, algae, or fungi. In some embodiments, the microbes of this disclosure are nitrogen fixing microbes, for example nitrogen fixing bacteria, nitrogen fixing archaea, nitrogen fixing fungi, nitrogen fixing yeast, nitrogen fixing algae, or nitrogen fixing protozoa. In some embodiments, microbes useful in the methods and agricultural compositions disclosed herein are spore forming microbes, for example spore forming bacteria. In some embodiments, bacteria useful in the methods and agricultural compositions disclosed herein are Gram positive bacteria or Gram negative bacteria. In some embodiments, the bacteria are endospore forming bacteria of the Firmicute phylum. In some embodiments, the bacteria are diazotrophs. In some embodiments, the bacteria are not diazotrophs.

In some embodiments, the methods and agricultural compositions of the disclosure are used with an archaea, such as, for example, *Methanothermobacter thermoautotrophicus, Methanosarcina barkeri, Methanospirillum hungatei, Methanobacterium bryantii, Methanococcus thermolithotrophicus*, and *Methanococcus maripaludis.*

In some embodiments, bacteria which are useful for inclusion in the agricultural compositions of the disclosure include, but are not limited to, *Agrobacterium radiobacter, Bacillus acidocaldarius, Bacillus acidoterrestris, Bacillus agri, Bacillus aizawai, Bacillus albolactis, Bacillus alcalophilus, Bacillus alvei, Bacillus aminoglucosidicus, Bacillus aminovorans, Bacillus amylolyticus* (also known as *Paenibacillus amylolyticus*) *Bacillus amyloliquefaciens, Bacillus aneurinolyticus, Bacillus atrophaeus, Bacillus azotoformans, Bacillus badius, Bacillus cereus* (synonyms: *Bacillus endorhythmos, Bacillus medusa*), *Bacillus chitinosporus, Bacillus circulans, Bacillus coagulans, Bacillus endoparasiticus Bacillus fastidiosus, Bacillus firmus, Bacillus kurstaki, Bacillus lacticola, Bacillus lactimorbus, Bacillus lactis, Bacillus laterosporus* (also known as *Brevibacillus laterosporus*), *Bacillus lautus, Bacillus lentimorbus, Bacillus lentus, Bacillus licheniformis, Bacillus maroccanus, Bacillus megaterium, Bacillus metiens, Bacillus mycoides, Bacillus natto, Bacillus nematocida, Bacillus nigrificans, Bacillus nigrum, Bacillus pantothenticus, Bacillus popillae, Bacillus psychrosaccharolyticus, Bacillus pumilus, Bacillus siamensis, Bacillus smithii, Bacillus sphaericus, Bacillus subtilis, Bacillus thuringiensis, Bacillus uniflagellatus, Bradyrhizobium japonicum, Brevibacillus brevis, Brevibacillus laterosporus* (formerly *Bacillus laterosporus*), *Chromobacterium subtsugae, Delftia acidovorans, Lactobacillus acidophilus, Lysobacter antibioticus, Lysobacter enzymogenes, Paenibacillus alvei, Paenibacillus polymyxa, Paenibacillus popilliae* (formerly *Bacillus popilliae*), *Pantoea agglomerans, Pasteuria penetrans* (formerly *Bacillus penetrans*), *Pasteuria usgae, Pectobacterium carotovorum* (formerly *Erwinia carotovora*), *Pseudomonas aeruginosa, Pseudomonas aureofaciens, Pseudomonas cepacia* (formerly known as *Burkholderia cepacia*), *Pseudomonas chlororaphis, Pseudomonas fluorescens, Pseudomonas proradix, Pseudomonas putida, Pseudomonas syringae, Serratia entomophila, Serratia marcescens, Streptomyces colombiensis, Streptomyces galbus, Streptomyces goshikiensis, Streptomyces griseoviridis, Streptomyces lavendulae, Streptomyces prasinus, Streptomyces saraceticus, Streptomyces venezuelae, Xanthomonas campestris, Xenorhabdus luminescens, Xenorhabdus nematophila, Rhodococcus globerulus* AQ719 (NRRL Accession No. B-21663), *Bacillus* sp. AQ175 (ATCC Accession No. 55608), *Bacillus* sp. AQ 177 (ATCC Accession No. 55609), *Bacillus* sp. AQ178 (ATCC Accession No. 53522), and *Streptomyces* sp. strain NRRL Accession No. B-30145. In some embodiments, the bacterium is *Azotobacter chroococcum, Methanosarcina barkeri, Klesiella pneumoniae, Azotobacter vinelandii, Rhodobacter spharoides, Rhodobacter capsulatus, Rhodobcter palustris, Rhodosporillum rubrum, Rhizobium leguminosarum* or *Rhizobium etli.*

In some embodiments, the bacterium is a species of *Clostridium*, for example *Clostridium pasteurianum, Clostridium beijerinckii, Clostridium perfringens, Clostridium tetani, Clostridium acetobutylicum.*

In some embodiments, bacteria used with the methods and agricultural compositions of the present disclosure are cyanobacteria. Examples of cyanobacterial genuses include *Anabaena* (for example *Anagaena* sp. PCC7120), *Nostoc* (for example *Nostoc punctiforme*), or *Synechocystis* (for example *Synechocystis* sp. PCC6803).

In some embodiments, bacteria used with the methods and agricultural compositions of the present disclosure belong to the phylum Chlorobi, for example *Chlorobium tepidum.*

In some embodiments, microbes used with the methods and agricultural compositions of the present disclosure comprise a gene homologous to a known NifH gene. Sequences of known NifH genes may be found in, for example, the Zehr lab NifH database, (wwwzehr.pmc.ucsc.edu/nifH_Database_Public/, Apr. 4, 2014), or the Buckley lab NifH database (www.css.cornell.edu/faculty/buckley/nifh.htm, and Gaby, John Christian, and Daniel H. Buckley. "A comprehensive aligned nifH gene database: a multipurpose tool for studies of nitrogen-fixing bacteria." Database 2014 (2014): bau001). In some embodiments, microbes used with the methods and agricultural compositions of the present disclosure comprise a sequence which encodes a polypeptide with at least 60%, 70%, 80%, 85%, 90%, 95%, 96%, 96%, 98%, 99% or more than 99% sequence identity to a sequence from the Zehr lab NifH database, (wwwzehr.pmc.ucsc.edu/nifH_Database_Public/, Apr. 4, 2014). In some embodiments, microbes used with the methods and agricultural compositions of the present disclosure comprise a sequence which encodes a polypeptide with at least 60%, 70%, 80%, 85%, 90%, 95%, 96%, 96%, 98%, 99% or more than 99% sequence identity to a sequence from the Buckley lab NifH database, (Gaby, John Christian, and Daniel H. Buckley. "A comprehensive aligned nifH gene database: a multipurpose tool for studies of nitrogen-fixing bacteria." *Database* 2014 (2014): bau001).

In some embodiments, the methods and agricultural compositions described herein make use of bacteria that are able to self-propagate efficiently on the leaf surface, root surface, or inside plant tissues without inducing a damaging plant defense reaction, or bacteria that are resistant to plant defense responses. In some embodiments, the bacteria described herein are isolated by culturing a plant tissue extract or leaf surface wash in a medium with no added nitrogen.

In some embodiments, the bacteria described herein is an endophyte or an epiphyte or a bacterium inhabiting the plant rhizosphere (rhizospheric bacteria). Endophytes are organisms that enter the interior of plants without causing disease symptoms or eliciting the formation of symbiotic structures, and are of agronomic interest because they can enhance plant growth and improve the nutrition of plants (e.g., through nitrogen fixation). The bacteria can be a seed-borne endophyte. Seed-borne endophytes include bacteria associated with or derived from the seed of a grass or plant, such as a seed-borne bacterial endophyte found in mature, dry, undamaged (e.g., no cracks, visible fungal infection, or prematurely germinated) seeds. The seed-borne bacterial endophyte can be associated with or derived from the surface of the seed; alternatively, or in addition, it can be associated with or derived from the interior seed compartment (e.g., of a surface-sterilized seed). In some embodiments, a seed-borne bacterial endophyte is capable of replicating within the plant tissue, for example, the interior of the seed. Also, In some embodiments, the seed-borne bacterial endophyte is capable of surviving desiccation.

The bacterial used in methods or agricultural compositions of the disclosure, can comprise a plurality of different bacterial taxa in combination. By way of example, the bacteria may include Proteobacteria (such as *Pseudomonas, Enterobacter, Stenotrophomonas, Burkholderia, Rhizobium, Herbaspirillum, Pantoea, Serratia, Rahnella, Azospirillum, Azorhizobium, Azotobacter, Duganella, Delftia, Bradyrhizobiun, Sinorhizobium* and *Halomonas*), Firmicutes (such as *Bacillus, Paenibacillus, Lactobacillus, Mycoplasma*, and *Acetabacterium*),and Actinobacteria (such as *Streptomyces, Rhodacoccus, Microbacterium*, and *Curtobacterium*). The bacteria used in methods and agricultural compositions of this disclosure may include nitrogen fixing bacterial consortia of two or more species. In some embodiments, one or more bacterial species of the bacterial consortia may be capable of fixing nitrogen. In some embodiments, one or more species of the bacterial consortia facilitate or enhance the ability of other bacteria to fix nitrogen. The bacteria which fix nitrogen and the bacteria which enhance the ability of other bacteria to fix nitrogen may be the same or different. In some embodiments, a bacterial strain is able to fix nitrogen when in combination with a different bacterial strain, or in a certain bacterial consortia, but may be unable to fix nitrogen in a monoculture. Examples of bacterial genuses which may be found in a nitrogen fixing bacterial consortia include, but are not limited to, *Herbaspirillum, Azospirillum, Enterobacter*, and *Bacillus.*

Bacteria that can be used in the agricultural compositions and methods disclosed herein include *Azotobacter* sp., *Bradyrhizobium* sp., *Klebsiella* sp., and *Sinorhizobium* sp. In some embodiments, the bacteria are selected from the group consisting of: *Azotobacter vinelandii, Bradyrhizobium japonicum, Klebsiella pneumoniae*, and *Sinorhizobium meliloti*. In some embodiments, the bacteria are of the genus *Enterobacter* or *Rahnella*. In some embodiments, the bacteria are of the genus *Frankia*, or *Clostridium*. Examples of bacteria of the genus *Clostridium* include, but are not limited to, *Clostridium acetobutilicum, Clostridium pasteurianum, Clostridium beijerinckii, Clostridium perfringens*, and *Clostridium tetani*. In some embodiments, the bacteria are of the genus *Paenibacillus*, for example *Paenibacillus azotofixans, Paenibacillus borealis, Paenibacillus durus, Paenibacillus macerans, Paenibacillus polymyxa, Paenibacillus alvei, Paenibacillus amylolyticus, Paenibacillus campinasensis, Paenibacillus chibensis, Paenibacillus glucanolyticus, Paenibacillus illinoisensis, Paenibacillus larvae* subsp. Larvae, *Paenibacillus larvae* subsp. *Pulvifaciens, Paenibacillus lautus, Paenibacillus macerans, Paenibacillus macquariensis, Paenibacillus macquariensis, Paenibacillus pabuli, Paenibacillus peoriae*, or *Paenibacillus polymyxa.*

In some embodiments, bacteria for use in the present compositions and methods can be a member of one or more of the following taxa: *Achromobacter, Acidithiobacillus, Acidovorax, Acidovoraz, Acinetobacter, Actinoplanes, Adlercreutzia, Aerococcus, Aeromonas, Afipia, Agromyces, Ancylobacter, Arthrobacter, Atopostipes, Azospirillum, Bacillus, Bdellovibrio, Beijerinckia, Bosea, Bradyrhizobium, Brevibacillus, Brevundimonas, Burkholderia, Candidatus Haloredivivus, Caulobacter, Cellulomonas, Cellvibrio, Chryseobacterium, Citrobacter, Clostridium, Coraliomargarita, Corynebacterium, Cupriavidus, Curtobacterium, Curvibacter, Deinococcus, Delftia, Desemzia, Devosia, Dokdonella, Dyella, Enhydrobacter, Enterobacter, Enterococcus, Erwinia, Escherichia, Escherichia Shigella, Exiguobacterium, Ferroglobus, Filimonas, Finegoldia, Flavisolibacter, Flavobacterium, Frigoribacterium, Gluconacetobacter, Hafnia, Halobaculum, Halomonas, Halosimplex, Herbaspirillum, Hymenobacter, Klebsiella, Kocuria, Kosakonia, Lactobacillus, Leclercia, Lentzea, Luteibacter, Luteimonas, Massilia, Mesorhizobium, Methylobacterium, Microbacterium, Micrococcus, Microvirga, Mycobacterium, Neisseria, Nocardia, Oceanibaculum, Ochrobactrum, Okibacterium, Oligotropha, Oryzihumus, Oxalophagus, Paenibacillus, Panteoa, Pantoea, Pelomonas, Perlucidibaca, Plantibacter, Polynucleobacter, Propionibacterium, Propioniciclava, Pseudoclavibacter, Pseudomonas, Pseudonocardia, Pseudoxanthomonas, Psychrobacter, Rahnella, Ralstonia, Rheinheimera, Rhizobium, Rhodococcus, Rhodopseudomonas, Roseateles, Ruminococcus, Sebaldella, Sediminibacillus, Sediminibacterium, Serratia, Shigella, Shinella, Sinorhizobium, Sinosporangium, Sphingobacterium, Sphingomonas, Sphingopyxis, Sphingosinicella, Staphylococcus, Stenotrophomonas, Strenotrophomonas, Streptococcus, Streptomyces, Stygiolobus, Sulfurisphaera, Tatumella, Tepidimonas, Thermomonas, Thiobacillus, Variovorax*, WPS-2 genera incertae *sedis, Xanthomonas*, and *Zimmermannella.*

In some embodiments, the bacteria are gram-negative bacteria of a genus selected from the following list: *Acetobacter, Achromobacter, Aerobacter, Anabaena, Azoarcus, Azomonas, Azorhizobium, Azospirillum, Azotobacter, Beijernickia, Bradyrhizobium, Burkholderia, Citrobacter, Derxia, Enterobacter, Herbaspirillum, Klebsiella, Kluyvera, Kosakonia, Nostoc, Mesorhizobium, Rahnella, Rhizobium, Rhodobacter, Rhodopseudomonas, Rhodospirillum, Serratia Sinorhizobium, Spirillum, Trichodesmium*, and *Xanthomonas.*

In some embodiments, a bacterial species selected from at least one of the following genera are utilized: *Enterobacter, Klebsiella, Kosakonia*, and *Rahnella*. In some embodiments, a combination of bacterial species from the following genera are utilized: *Enterobacter, Klebsiella, Kosakonia*, and *Rahnella*. In some embodiments, the species utilized can be one or more of: *Enterobacter sacchari, Klebsiella variicola, Kosakonia sacchari*, and *Rahnella aquatilis.*

In some embodiments, a Gram positive microbe may have a Molybdenum-Iron nitrogenase system comprising: nifH, nifD, nifK, nifB, nifE, nif, nifX, hesA, nif, niW, nifU, nifS, nifI1, and nifI2. In some embodiments, a Gram positive microbe may have a vanadium nitrogenase system comprising: vnfDG, vnfK, vnfE, vnfN, vupC, vupB, vupA, vnfV, vnfR1, vnfH, vnfR2, vnfA (transcriptional regulator). In some embodiments, a Gram positive microbe may have an iron-only nitrogenase system comprising: anfK, anfG, anfD, anfH, anfA (transcriptional regulator). In some embodiments, a Gram positive microbe may have a nitrogenase system comprising glnB, and glnK (nitrogen signaling proteins). Some examples of enzymes involved in nitrogen metabolism in Gram positive microbes include glnA (glutamine synthetase), gdh (glutamate dehydrogenase), bdh (3-hydroxybutyrate dehydrogenase), glutaminase, gltAB/gltB/gltS (glutamate synthase), asnA/asnB (aspartate-ammonia ligase/asparagine synthetase), and ansA/ansZ (asparaginase). Some examples of proteins involved in nitrogen transport in Gram positive microbes include amtB (ammonium transporter), glnK (regulator of ammonium transport), glnPHQ/glnQHMP (ATP-dependent glutamine/glutamate transporters), glnT/alsT/yrbD/yflA (glutamine-like proton symport transporters), and gltP/gltT/yhcl/nqt (glutamate-like proton symport transporters).

Examples of Gram positive microbes for use within the present agricultural compositions include *Paenibacillus polymixa, Paenibacillus riograndensis, Paenibacillus* sp., *Frankia* sp., *Heliobacterium* sp., *Heliobacterium chlorum,*

*Heliobacillus* sp., *Heliophilum* sp., *Heliorestis* sp., *Clostridium acetobutylicum, Clostridium* sp., *Methanobacterium* sp., *Micrococcus* sp., *Mycobacterium flavum, Mycobacterium* sp., *Arthrobacter* sp., *Agromyces* sp., *Corynebacterium autitrophicum, Corynebacterium* sp., *Micromonospora* sp., *Propionibacteria* sp., *Streptomyces* sp., and *Microbacterium* sp.

In some embodiments, microorganisms are present in agricultural compositions of the present disclosure at a concentration of between $10^4$ to $10^{12}$ CFU/ml. In some embodiments, the microorganisms are at an initial concentration of $10^4$ to $10^{12}$ CFU/ml. In some embodiments, the microorganisms are at an initial concentration of $10^8$ to $10^{10}$ CFU/ml. In some embodiments, the microorganisms are at an initial concentration of about $10^4$, $10^5$, $10^6$, $10^7$, $10^8$, $10^9$, $10^{10}$, $10^{11}$, or $10^{12}$ CFU/mL. In some embodiments, the microorganisms are at an initial concentration of about $10^8$. In some embodiments, the microorganisms are at an initial concentration of about $10^9$. In some embodiments, the microorganisms are at an initial concentration of about $10^{10}$.

Genetic Alterations

In some embodiments, the agricultural compositions of the present disclosure comprise a microbe capable of fixing nitrogen. In some embodiments, the microbe can naturally fix nitrogen. In some embodiments the microbe is genetically modified to fix nitrogen. In some embodiments, the organism is genetically modified to provide improved nitrogen fixation capabilities. Thus, in some embodiments, the microbes comprise one or more genetic variations introduced into one or more genes regulating nitrogen fixation. The genetic variation may be introduced into a gene selected from the group consisting of nifA, nifL, ntrB, ntrC, glutamine synthetase, glnA, glnB, glnK, draT, amtB, glutaminase, glnD, glnE, nifJ, nifH, nifD, nifK, nifY, nifE, nifN, nifU, nifS, nifV, nifW, nifZ, nifM, nifF, nifB, and nifQ. The genetic variation may be a variation in a gene encoding a protein with functionality selected from the group consisting of: glutamine synthetase, glutaminase, glutamine synthetase adenylyltransferase, transcriptional activator, anti-transcriptional activator, pyruvate flavodoxin oxidoreductase, flavodoxin, and NAD+-dinitrogen-reductase aDP-D-ribosyltransferase. The genetic variation may be a mutation that results in one or more of: increased expression or activity of nifA or glutaminase; decreased expression or activity of nifL, ntrB, glutamine synthetase, glnB, glnK, draT, amtB; decreased adenylyl-removing activity of GlnE; decreased expression of GlnD; or decreased uridylyl-removing activity of GlnD. The genetic variation may be a variation in a gene selected from the group consisting of: bcsii, bcsiii, yjbE, jhaB, pehA, otsB, treZ, glsA2, and combinations thereof.

In some embodiments, the microbe has a disrupted (e.g., deleted or partially deleted) nifL gene. In some embodiments, the microbe has a nifL gene that has been disrupted with the introduction of a promoter sequence that acts on the nifA gene. In some embodiments, e.g., when the microbe is a strain of *K. variicola*, the promoter is a *K. variicola* PinfC promoter. In some embodiments, e.g., when the microbe is a strain of *K. sacchari*, the promoter is a *K. sacchari* Prm5 promoter. In some embodiments, the microbe has a glnE gene that has been altered to remove the adenylyl-removing (AR) domain, while leaving the coding region for the adenyltransferase (AT) domain, which is functionally expressed. In some embodiments, the microbe has a deletion of the glnD gene.

The genetic variation introduced into one or more bacteria of the agricultural compositions disclosed herein may be a knock-out mutation or it may abolish a regulatory sequence of a target gene, or it may comprise insertion of a heterologous regulatory sequence, for example, insertion of a regulatory sequence found within the genome of the same bacterial species or genus. The regulatory sequence can be chosen based on the expression level of a gene in a bacterial culture or within plant tissue. The genetic variation may be produced by chemical mutagenesis. The plants grown may be exposed to biotic or abiotic stressors. However, in some embodiments, the methods disclosed herein also envision altering the impact of ATP or $O_2$ on the circuitry, or replacing the circuitry with other regulatory cascades in the cell, or altering genetic circuits other than nitrogen fixation. Gene clusters can be re-engineered to generate functional products under the control of a heterologous regulatory system. By eliminating native regulatory elements outside of, and within, coding sequences of gene clusters, and replacing them with alternative regulatory systems, the functional products of complex genetic operons and other gene clusters can be controlled and/or moved to heterologous cells, including cells of different species other than the species from which the native genes were derived. Once re-engineered, the synthetic gene clusters can be controlled by genetic circuits or other inducible regulatory systems, thereby controlling the products' expression as desired. The expression cassettes can be designed to act as logic gates, pulse generators, oscillators, switches, or memory devices. The controlling expression cassette can be linked to a promoter such that the expression cassette functions as an environmental sensor, such as an oxygen, temperature, touch, osmotic stress, membrane stress, or redox sensor.

As an example, the nifL, nifA, nifT, and nifX genes can be eliminated from the nif gene cluster. Synthetic genes can be designed by codon randomizing the DNA encoding each amino acid sequence. Codon selection is performed, specifying that codon usage be as divergent as possible from the codon usage in the native gene. Proposed sequences are scanned for any undesired features, such as restriction enzyme recognition sites, transposon recognition sites, repetitive sequences, sigma 54 and sigma 70 promoters, cryptic ribosome binding sites, and rho independent terminators. Synthetic ribosome binding sites are chosen to match the strength of each corresponding native ribosome binding site, such as by constructing a fluorescent reporter plasmid in which the 150 bp surrounding a gene's start codon (from −60 to +90) is fused to a fluorescent gene. This chimera can be expressed under control of the Ptac promoter, and fluorescence measured via flow cytometry. To generate synthetic ribosome binding sites, a library of reporter plasmids using 150 bp (−60 to +90) of a synthetic expression cassette is generated. Briefly, a synthetic expression cassette can consist of a random DNA spacer, a degenerate sequence encoding an RBS library, and the coding sequence for each synthetic gene. Multiple clones are screened to identify the synthetic ribosome binding site that best matched the native ribosome binding site. Synthetic operons that consist of the same genes as the native operons are thus constructed and tested for functional complementation. A further exemplary description of synthetic operons is provided in US20140329326.

Some examples of genetic alterations which may be made in Gram positive microbes include: deleting glnR to remove negative regulation of BNF in the presence of environmental nitrogen, inserting different promoters directly upstream of the nif cluster to eliminate regulation by GlnR in response to environmental nitrogen, mutating glnA to reduce the rate of ammonium assimilation by the GS-GOGAT pathway, deleting amtB to reduce uptake of ammonium from the media, mutating glnA so it is constitutively in the feedback-inhibited (FBI-GS) state, to reduce ammonium assimilation by the GS-GOGAT pathway.

In some embodiments, glnR is the main regulator of N metabolism and fixation in, e.g., *Paenibacillus* species. In some embodiments, the genome of a *Paenibacillus* species does not contain a gene to produce glnR. In some embodiments, the genome of a *Paenibacillus* species does not contain a gene to produce glnE or glnD. In some embodiments, the genome of a *Paenibacillus* species does contain a gene to produce glnB or glnK. For example, *Paenibacillus* sp. WLY78 doesn't contain a gene for glnB, or its homologs found in the archaeon *Methanococcus maripaludis*, nifI1 and nifI2. In some embodiments, the genomes of *Paenibacillus* species are variable. For example, *Paenibacillus polymixa* E681 lacks glnK and gdh, has several nitrogen compound transporters, but only amtB appears to be controlled by GlnR. In another example, *Paenibacillus* sp. JDR2 has glnK, gdh and most other central nitrogen metabolism genes, has many fewer nitrogen compound transporters, but does have glnPHQ controlled by GlnR. *Paenibacillus riograndensis* SBR5 contains a standard glnRA operon, an fdx gene, a main nifoperon, a secondary nif operon, and an anf operon (encoding iron-only nitrogenase). Putative glnR/tnrA sites were found upstream of each of these operons. GlnR may regulate all of the above operons, except the anf operon. GlnR may bind to each of these regulatory sequences as a dimer.

*Paenibacillus* N-fixing strains may fall into two subgroups: Subgroup I, which contains only a minimal nf gene cluster and subgroup II, which contains a minimal cluster, plus an uncharacterized gene between nifX and hesA, and often other clusters duplicating some of the nf genes, such as nifH, nifHDK, nifBEN, or clusters encoding vanadaium nitrogenase (vnf) or iron-only nitrogenase (anf) genes.

In some embodiments, the genome of a *Paenibacillus* species may not contain a gene to produce glnB or glnK. In some embodiments, the genome of a *Paenibacillus* species may contain a minimal nif cluster with 9 genes transcribed from a sigma-70 promoter. In some embodiments, a *Paenibacillus* nif cluster is negatively regulated by nitrogen or oxygen. In some embodiments, the genome of a *Paenibacillus* species does not contain a gene to produce sigma-54. For example, *Paenibacillus* sp. WLY78 does not contain a gene for sigma-54. In some embodiments, a nif cluster is regulated by glnR, and/or TnrA. In some embodiments, activity of a nif cluster is altered by altering activity of glnR, and/or TnrA.

In Bacilli, glutamine synthetase (GS) is feedback-inhibited by high concentrations of intracellular glutamine, causing a shift in confirmation (referred to as FBI-GS). Nif clusters contain distinct binding sites for the regulators GlnR and TnrA in several Bacilli species. GlnR binds and represses gene expression in the presence of excess intracellular glutamine and AMP. A role of GlnR may be to prevent the influx and intracellular production of glutamine and ammonium under conditions of high nitrogen availability. TnrA may bind and/or activate (or repress) gene expression in the presence of limiting intracellular glutamine, and/or in the presence of FBI-GS. In some embodiments, the activity of a Bacilli nif cluster is altered by altering the activity of GlnR.

Feedback-inhibited glutamine synthetase (FBI-GS) may bind GlnR and stabilize binding of GlnR to recognition sequences. Several bacterial species have a GlnR/TnrA binding site upstream of the mf cluster. Altering the binding of FBI-GS and GlnR may alter the activity of the nif pathway.

Additional genetic modifications suitable for the microbes of the present disclosure may be found in International Patent Application No. PCT/US2019/039528, the contents of which are herein incorporated by reference in their entirety.

Sources of Microbes

Microbes of the present disclosure can be obtained from any source, including environmental and commercial sources. The bacteria (or any microbe according to the disclosure) may be obtained from any general terrestrial environment, including its soils, plants, fungi, animals (including invertebrates) and other biota, including the sediments, water and biota of lakes and rivers; from the marine environment, its biota and sediments (for example, sea water, marine muds, marine plants, marine invertebrates (for example, sponges), marine vertebrates (for example, fish)); the terrestrial and marine geosphere (regolith and rock, for example, crushed subterranean rocks, sand and clays); the cryosphere and its meltwater; the atmosphere (for example, filtered aerial dusts, cloud and rain droplets); urban, industrial and other man-made environments (for example, accumulated organic and mineral matter on concrete, roadside gutters, roof surfaces, and road surfaces).

The plants from which the bacteria (or any microbe according to the disclosure) are obtained may be a plant having one or more desirable traits, for example a plant which naturally grows in a particular environment or under certain conditions of interest. By way of example, a certain plant may naturally grow in sandy soil or sand of high salinity, or under extreme temperatures, or with little water, or it may be resistant to certain pests or disease present in the environment, and it may be desirable for a commercial crop to be grown in such conditions, particularly if they are, for example, the only conditions available in a particular geographic location. By way of further example, the bacteria may be collected from commercial crops grown in such environments, or more specifically from individual crop plants best displaying a trait of interest amongst a crop grown in any specific environment: for example the fastest-growing plants amongst a crop grown in saline-limiting soils, or the least damaged plants in crops exposed to severe insect damage or disease epidemic, or plants having desired quantities of certain metabolites and other compounds, including fiber content, oil content, and the like, or plants displaying desirable colors, taste or smell. The bacteria may be collected from a plant of interest or any material occurring in the environment of interest, including fungi and other animal and plant biota, soil, water, sediments, and other elements of the environment as referred to previously.

The bacteria (or any microbe according to the disclosure) may be isolated from plant tissue. This isolation can occur from any appropriate tissue in the plant, including for example root, stem and leaves, and plant reproductive tissues. Non-limiting examples of plant tissues include a seed, seedling, leaf, cutting, plant, bulb, tuber, root, and rhizomes. In some embodiments, microorganisms are isolated from a seed. In some embodiments, microorganisms are isolated from a root.

Persons having skill in the art will be familiar with techniques for recovering microbes from various environmental sources. For example, microbes useful in the methods and agricultural compositions disclosed herein can be obtained by extracting microbes from surfaces or tissues of native plants; grinding seeds to isolate microbes; planting seeds in diverse soil samples and recovering microbes from tissues; or inoculating plants with exogenous microbes and determining which microbes appear in plant tissues. The parameters for processing samples may be varied to isolate different types of associative microbes, such as rhizospheric, epiphytes, or endophytes. By way of example, some methods for isolation from plants include the sterile excision of the plant material of interest (e.g. root or stem lengths, leaves), surface sterilization with an appropriate solution (e.g. 2% sodium hypochlorite), after which the plant material is placed on nutrient medium for microbial growth. Alternatively, the surface-sterilized plant material can be crushed in a sterile liquid (usually water) and the liquid suspension, including small pieces of the crushed plant material spread over the surface of a suitable solid agar medium, or media, which may or may not be selective (e.g. contain only phytic acid as a source of phosphorus). This approach is especially useful for bacteria which form isolated colonies and can be picked off individually to separate plates of nutrient medium, and further purified to a single species by well-known methods. Alternatively, the plant root or foliage samples may not be surface sterilized but only washed gently thus including surface-dwelling epiphytic microorganisms in the isolation process, or the epiphytic microbes can be isolated separately, by imprinting and lifting off pieces of plant roots, stem or leaves onto the surface of an agar medium and then isolating individual colonies as above. This approach is especially useful for bacteria, for example. Alternatively, the roots may be processed without washing off small quantities of soil attached to the roots, thus including microbes that colonize the plant rhizosphere. Otherwise, soil adhering to the roots can be removed, diluted and spread out onto agar of suitable selective and non-selective media to isolate individual colonies of rhizospheric bacteria.

Microbes may also be sourced from a repository, such as environmental strain collections, instead of initially isolating from a first plant. The microbes can be genotyped and phenotyped, via sequencing the genomes of isolated microbes; profiling the composition of communities in planta; characterizing the transcriptomic functionality of communities or isolated microbes; or screening microbial features using selective or phenotypic media (e.g., nitrogen fixation or phosphate solubilization phenotypes). Selected candidate strains or populations can be obtained via sequence data; phenotype data; plant data (e.g., genome, phenotype, and/or yield data); soil data (e.g., pH, N/P/K content, and/or bulk soil biotic communities); or any combination of these.

Budapest Treaty on the International Recognition of the Deposit of Microorganisms for the Purpose of Patent Procedures The microbial deposits of the present disclosure were made under the provisions of the Budapest Treaty on the International Recognition of the Deposit of Microorganisms for the Purpose of Patent Procedure (Budapest Treaty).

Applicants state that pursuant to 37 C.F.R. § 1.808(a)(2) "all restrictions imposed by the depositor on the availability to the public of the deposited material will be irrevocably removed upon the granting of the patent." This statement is subject to paragraph (b) of this section (i.e. 37 C.F.R. § 1.808(b)).

The *Enterobacter sacchari* has now been reclassified as *Kosakonia sacchari*, the name for the organism may be used interchangeably throughout the present disclosure.

Some microbes of the present disclosure are derived from two wild-type strains. Strain CI006 is a bacterial species previously classified in the genus *Enterobacter* (see aforementioned reclassification into *Kosakonia*). Strain CI019 is a bacterial species classified in the genus *Rahnella*. The deposit information for the CI006 *Kosakonia* wild type (WT) and CI019 *Rahnella* WT are found in Table 1.

Some microorganisms described in this application were deposited on Jan. 6, 2017 or Aug. 11, 2017 with the Bigelow National Center for Marine Algae and Microbiota (NCMA), located at 60 Bigelow Drive, East Boothbay, Maine 04544, USA. As aforementioned, all deposits were made under the terms of the Budapest Treaty on the International Recognition of the Deposit of Microorganisms for the Purposes of Patent Procedure. The Bigelow National Center for Marine Algae and Microbiota accession numbers and dates of deposit for the aforementioned Budapest Treaty deposits are provided in Table 1.

Biologically pure cultures of *Kosakonia sacchari* (WT), *Rahnella aquatilis* (WT), and a variant/remodeled *Kosakonia sacchari* strain were deposited on Jan. 6, 2017 with the Bigelow National Center for Marine Algae and Microbiota (NCMA), located at 60 Bigelow Drive, East Boothbay, Maine 04544, USA, and assigned NCMA Patent Deposit Designation numbers 201701001, 201701003, and 201701002, respectively. The applicable deposit information is found below in Table 1.

Biologically pure cultures of variant/remodeled *Kosakonia sacchari* strains were deposited on Aug. 11, 2017 with the Bigelow National Center for Marine Algae and Microbiota (NCMA), located at 60 Bigelow Drive, East Boothbay, Maine 04544, USA, and assigned NCMA Patent Deposit Designation numbers 201708004, 201708003, and 201708002, respectively. The applicable deposit information is found below in Table 1.

A biologically pure culture of *Klebsiella variicola* (WT) was deposited on Aug. 11, 2017 with the Bigelow National Center for Marine Algae and Microbiota (NCMA), located at 60 Bigelow Drive, East Boothbay, Maine 04544, USA, and assigned NCMA Patent Deposit Designation number 201708001. Biologically pure cultures of two *Klebsiella variicola* variants/remodeled strains were deposited on Dec. 20, 2017 with the Bigelow National Center for Marine Algae and Microbiota (NCMA), located at 60 Bigelow Drive, East Boothbay, Maine 04544, USA, and assigned NCMA Patent Deposit Designation numbers 201712001 and 201712002, respectively. The applicable deposit information is found below in Table 1.

Biologically pure cultures of two *Kosakonia sacchari* variants/remodeled strains were deposited on Dec. 23, 2019 with the American Type Culture Collection (ATCC), located at University Boulevard, Manassas, Virginia 20110-2209, USA and assigned ATCC Patent Deposit Numbers PTA-126575 and PTA-126576. Biologically pure cultures of four *Klebsiella variicola* variants/remodeled strains were deposited on Dec. 23, 2019 with the American Type Culture Collection (ATCC), located at 10801 University Boulevard, Manassas, Virginia 20110-2209, USA and assigned ATCC Patent Deposit Numbers PTA-126577, PTA-126578, PTA-126579 and PTA-126580. A biologically pure culture of a *Paenibacillus polymyxa* (WT) strain was deposited on Dec. 23, 2019 with the American Type Culture Collection (ATCC), located at 10801 University Boulevard, Manassas, Virginia 20110-2209, USA and assigned ATCC Patent Deposit Number PTA-126581. A biologically pure culture of a *Paraburkholderia tropica* (WT) strain was deposited on Dec. 23, 2019 with the American Type Culture Collection (ATCC), located at 10801 University Boulevard, Manassas, Virginia 20110-2209, USA and assigned ATCC Patent Deposit Number PTA-126582. A biologically pure culture of a *Herbaspirillum aquaticum* (WT) strain was deposited on Dec. 23, 2019 with the American Type Culture Collection (ATCC), located at 10801 University Boulevard, Manassas, Virginia 20110-2209, USA and assigned ATCC Patent Deposit Number PTA-126583. Biologically pure cultures of four *Metakosakonia intestini* variants/remodeled strains were deposited on Dec. 23, 2019 with the American Type Culture Collection (ATCC), located at 10801 University Boulevard, Manassas, Virginia 20110-2209, USA and assigned ATCC Patent Deposit Numbers PTA-126584, PTA-126586, PTA-126587 and PTA-126588. A biologically pure culture of a *Metakosakonia intestini* (WT) strain was deposited on Dec. 23, 2019 with the American Type Culture Collection (ATCC), located at 10801 University Boulevard, Manassas, Virginia 20110-2209, USA and assigned ATCC Patent Deposit Number PTA-126585. A biologically pure culture of a *Klebsiella variicola* variant/remodeled strain was deposited on Mar. 25, 2020 with the American Type Culture Collection (ATCC), located at 10801 University Boulevard, Manassas, Virginia 20110-2209, USA and assigned ATCC Patent Deposit Number PTA-126740. A biologically pure culture of a *Kosakonia sacchari* variant/remodeled strain was deposited on Mar. 25, 2020 with the American Type Culture Collection (ATCC), located at 10801 University Boulevard, Manassas, Virginia 20110-2209, USA and assigned ATCC Patent Deposit Number PTA-126743. The applicable deposit information is found below in Table 1.

TABLE 1

Microorganisms Deposited under the Budapest Treaty

| Depository | Pivot Strain Designation (some strains have multiple designations) | Taxonomy | Accession Number | Date of Deposit |
|---|---|---|---|---|
| NCMA | CI006, PBC6.1 | *Kosakonia sacchari* (WT) | NCMA 201701001 | Jan. 6, 2017 |
| NCMA | CI019 | *Rahnella aquatilis* (WT) | NCMA 201701003 | Jan. 6, 2017 |
| NCMA | CM029 | *Kosakonia sacchari* | NCMA 201701002 | Jan. 6, 2017 |
| NCMA | CM037 | *Kosakonia sacchari* | NCMA 201708004 | Aug. 11, 2017 |
| NCMA | CM38, PBC6.38 | *Kosakonia sacchari* | NCMA 201708003 | Aug. 11, 2017 |
| NCMA | CM094, PBC6.94 | *Kosakonia sacchari* | NCMA 201708002 | Aug. 11, 2017 |
| NCMA | CI137, 137, PB137 | *Klebsiella variicola* (WT) | NCMA 201708001 | Aug. 11, 2017 |
| NCMA | | *Klebsiella variicola* | NCMA 201712001 | Dec. 20, 2017 |
| NCMA | | *Klebsiella variicola* | NCMA 201712002 | Dec. 20, 2017 |
| ATCC | | *Kosakonia sacchari* | PTA-126575 | Dec. 23, 2019 |
| ATCC | | *Kosakonia sacchari* | PTA-126576 | Dec. 23, 2019 |
| ATCC | | *Klebsiella variicola* | PTA-126577 | Dec. 23, 2019 |
| ATCC | | *Klebsiella variicola* | PTA-126578 | Dec. 23, 2019 |
| ATCC | | *Klebsiella variicola* | PTA-126579 | Dec. 23, 2019 |
| ATCC | | *Klebsiella variicola* | PTA-126580 | Dec. 23, 2019 |
| ATCC | | *Paenibacillus polymyxa* (WT) | PTA-126581 | Dec. 23, 2019 |
| ATCC | CI8 | *Paraburkholderia tropica* (WT) | PTA-126582 | Dec. 23, 2019 |

TABLE 1-continued

Microorganisms Deposited under the Budapest Treaty

| Depository | Pivot Strain Designation (some strains have multiple designations) | Taxonomy | Accession Number | Date of Deposit |
|---|---|---|---|---|
| ATCC | CI3069 | *Herbaspirillum aquaticum* (WT) | PTA-126583 | Dec. 23, 2019 |
| ATCC | | *Metakosakonia intestine* | PTA-126584 | Dec. 23, 2019 |
| ATCC | CI910 | *Metakosakonia intestini* (WT) | PTA-126585 | Dec. 23, 2019 |
| ATCC | | *Metakosakonia intestine* | PTA-126586 | Dec. 23, 2019 |
| ATCC | | *Metakosakonia intestine* | PTA-126587 | Dec. 23, 2019 |
| ATCC | | *Metakosakonia intestine* | PTA-126588 | Dec. 23, 2019 |
| ATCC | | *Klebsiella variicola* | PTA-126740 | Mar. 25, 2020 |
| ATCC | | *Kosakonia sacchari* | PTA-126743 | Mar. 25, 2020 |

The present disclosure, in certain embodiments, provides isolated and biologically pure microorganisms that have applications, inter alia, in agriculture. The disclosed microorganisms can be utilized in their isolated and biologically pure states, as well as being formulated into compositions (see below section for exemplary composition descriptions). Furthermore, the disclosure provides microbial compositions containing at least two members of the disclosed isolated and biologically pure microorganisms, as well as methods of utilizing said microbial compositions. Furthermore, the disclosure provides for methods of modulating nitrogen fixation in plants via the utilization of the disclosed isolated and biologically pure microbes.

In some aspects, the isolated and biologically pure microorganisms of the disclosure are those from Table 1. In other aspects, the isolated and biologically pure microorganisms of the disclosure are derived from a microorganism of Table 1. For example, a strain, child, mutant, or derivative, of a microorganism from Table 1 are provided herein. The disclosure contemplates all possible combinations of microbes listed in Table 1, said combinations sometimes forming a microbial consortia. The microbes from Table 1, either individually or in any combination, can be combined with any plant, active molecule (synthetic, organic, etc.), adjuvant, carrier, supplement, or biological, mentioned in the disclosure.

Initial Cell Density

In some embodiments, the present formulation methods comprise the step of selecting an initial cell density to provide an acceptable rate of microbial decay. In some embodiments, the initial cell density of the agricultural composition is varied to identify an initial cell density that lowers the rate of decay compared to an existing formulation. In some embodiments, the initial cell density of the agricultural composition is varied to identify an initial cell density that minimizes the rate of decay while maximizing the cell density. In some embodiments, the present agricultural compositions comprise an initial cell density with an acceptable rate of microbial decay, a rate of decay that is lower than existing formulations, or a rate of decay that is minimized while maximizing cell density.

In some embodiments, the initial cell density is selected to provide an acceptable rate of decay based on a target cell density at a later time point. For example, for an agricultural composition that is targeted to have at least a three-month shelf life, an acceptable rate of decay would be one that results in the three-month old agricultural composition comprising a microbial density above the target threshold given the value of the initial cell density.

To provide a non-limiting illustrative example of a calculation to identify an acceptable rate of decay, suppose the initial cell density is 1E10 CFU/mL; the acceptable threshold for cell density for the purposes of application to agricultural plant tissues or the environs thereof is 1E9 CFU/mL; and the target shelf life is at least three months. Then an acceptable rate of decay would be one that resulted in a composition having the cell density of 1E9 CFU/mL at the three month time point. Assuming that decay is approximately linear for the log of the cell density, this would be a decay rate that was less than or equal to the decay rate r that satisfied the equation $\log_{10} T_f = \log_{10} T_i - r \times t$, where $T_f$ is the final cell density threshold in CFU/mL at the target shelf-life time point, $T_i$ is the initial cell density in CFU/mL, r is the decay rate in $\log_{10}$ loss of CFU/mL per day, and t is the number of days at the target shelf-life time point. For this example, that would translate to: $\log_{10}$ 1E9=$\log_{10}$ 1E10−r×90, which is satisfied when r is 1/90≈0.011 $\log_{10}$ loss of CFU/mL per day.

In some embodiments, the method comprises testing multiple initial cell densities and monitoring microbial viability over a period of time. In some embodiments, this comprises generating a titration curve of initial cell density versus microbial decay rate. In some embodiments, the initial cell density is selected to be one associated with an acceptable rate of decay.

In some embodiments, the parameter of initial cell density is varied within the method and selected separately from the other parameters. In some embodiments, the parameter of initial cell density is varied at the same time as one or more other parameters, such as microbial stabilizer, physical stabilizer, or buffering agent.

Buffering Agents

In some embodiments, the methods of the present disclosure comprise the step of selecting a buffering agent. In some embodiments, the agricultural compositions of the present disclosure comprise a buffering agent. In some embodiments, the buffering agent provides consistency in the pH of the agricultural composition. In some embodiments, the buffering agent prevents fluctuations in the pH of the agricultural composition that are detrimental to the nitrogen-fixing microorganisms comprised by the agricultural composition. In some embodiments, the buffering agent prevents toxic levels of acidity. In some embodiments, the buffering agent prevents toxic levels of basicity.

In some embodiments, the buffering agent is selected based on its ability to maintain the pH of the agricultural composition within an acceptable range for at least three months. In some embodiments, the buffering agent maintains the pH of the agricultural composition within an acceptable range for at least three months, at least four months, at least five months, or at least six months.

In some embodiments, the buffering agent maintains the pH of the agricultural composition in the pH range of pH 5-9, pH 5-8, pH 5-7, pH 5-6, pH 6-9, pH 6-8, pH 6-7, pH 7-9, or pH 7-8. In some embodiments, the buffering agent maintains the pH of the agricultural composition in the pH range of pH 6-8.

In some embodiments, the agricultural composition is buffered to the desired pH using conventional buffering agents. Non-limiting examples of buffering agents suitable for use within the disclosed agricultural compositions include sodium citrate, ascorbate, succinate, lactate, citric acid, boric acid, borax, hydrochloric acid, disodium hydrogen phosphate, acetic acid, formic acid, glycine, bicarbonate, phosphate, tartaric acid, Tris-glycine, Tris-NaCl, Tris-ethylenediamine tetraacetic acid ("EDTA"), Tris-borate, Tris-borate-EDTA, Tris-acetate-EDTA ("TAB"), Tris-buffered saline, 4-(2-hydroxyethyl)-1-piperazineethanesulfonic acid ("HEPES"), 3-(N-morpholino) propanesulfonic acid ("MOPS"), piperazine-1,4-bis(2-ethanesulfonic acid) ("PIPES"), 2-(N-morpholino)ethanesulfonic acid ("MES"), and phosphate buffered saline ("PBS"). Table 2 also provides exemplary buffering agents for use in the agricultural compositions of the disclosure, as well as their pKa values and useful pH ranges. In some embodiments, an agricultural composition of the present disclosure comprises a buffering agent disclosed in Table 2. In some embodiments, an agricultural composition of the present disclosure comprises one or more buffering agents disclosed in Table 2.

TABLE 2

Exemplary buffering agents

| Common name and/or chemical name | pKa at 25° C. | Useful pH range |
|---|---|---|
| ACES | 6.78 | 6.1-7.5 |
| Acetic acid (Ethanoic acid) | 4.8 | 3.8-5.8 |
| ADA | 6.59 | 6.0-7.2 |
| AMP | 9.7 | 9.0-10.5 |
| AMPD | 8.8 | 7.8-9.7 |
| AMPSO | 9 | 8.3-9.7 |
| BES | 7.09 | 6.4-7.8 |
| Bicine (2-(bis(2-hydroxyethyl) amino)acetic acid) | 8.35 | 7.6-9.0 |
| Bis-Tris | 6.5 | 5.8-7.2 |
| Bis-Tris Propane | 6.8,9.0 | 6.3-9.5 |
| Boric acid | 9.24 | 8.25-10.25 |
| CABS | 10.7 | 10.0-11.4 |
| Cacodylate (dimethylarsenic acid) | 6.27 | 5.0-7.4 |
| CAPS | 10.4 | 9.7-11.1 |
| CAPSO | 9.6 | 8.9-10.3 |
| CHES (N-Cyclohexyl-2-aminoethanesulfonic acid) | 9.3 | 8.3-10.3 |
| Citric acid (2-Hydroxypropane-1,2,3-tricarboxylic acid) | 3.13, 4.76, 6.40 | 2.1-7.4 |
| DIPSO | 7.6 | 7.0-8.2 |
| EPPS | 8 | 7.3-8.7 |
| Gly-Gly | 8.2 | 7.5-8.9 |
| HEPBS | 8.3 | 7.6-9.0 |
| HEPES (4-(2-hydroxyethyl)-1-piperazineethanesulfonic acid) | 7.48 | 2.5-3.5 or 6.8-8.2 |
| HEPPSO | 7.8 | 7.1-8.5 |
| KH2PO4 (Monopotassium phosphate) | 7.2 | 6.2-8.2 |
| MES (2-(N-morpholino)ethanesulfonic acid) | 6.15 | 5.5-6.7 |
| MOBS | 7.6 | 6.9-8.3 |
| MOPS (3-(N-morpholino)propanesulfonic acid) | 7.2 | 6.5-7.9 |
| MOPSO | 6.9 | 6.2-7.6 |
| PBS or high buffering capacity PBS | | 5.8-8.0 |
| PIPES | 6.76 | 6.1-7.5 |
| PIPES (piperazine-N,N'-bis(2-ethanesulfonic acid)) | 6.76 | 6.1-7.5 |
| POPSO | 7.8 | 7.2-8.5 |
| TABS | 8.9 | 8.2-9.6 |
| TAPS ([tris(hydroxymethyl) methylamino]propanesulfonic acid) | 8.43 | 7.7-9.1 |
| TAPSO (3-[N-tris(hydroxymethyl) methylamino]-2-hydroxypropane-sulfonic acid) | 7.635 | 7.0-8.2 |
| TEA | 7.8 | 7.3-8.3 |
| TES (2-[[1,3-dihydroxy-2-(hydroxymethyl) propan-2-yl]amino]ethanesulfonic acid) | 7.4 | 6.8-8.2 |
| Tricine (N-[tris(hydroxymethyl)methyl] glycine) | 8.05 | 7.4-8.8 |

TABLE 2-continued

| Exemplary buffering agents | | |
|---|---|---|
| Common name and/or chemical name | pKa at 25° C. | Useful pH range |
| Tris (tris(hydroxymethyl)aminomethane) or (2-amino-2-(hydroxymethyl)propane-1,3-diol) | 8.07 | 7.1-9.1 |

Additional buffers and instructions on how to prepare them can be found in, e.g., "Common Buffers and Stock Solutions" (2011) *Current Protocols in Nucleic Acid Chemistry*, A.2A.1-A.2A.14 and in the Sigma Aldrich "Buffer Reference Center" www.sigmaaldrich.com/life-science/core-bioreagents/biological-buffers/learning-center/buffer-reference-center.html, the contents of each of which are incorporated herein in their entirety.

In some embodiments, the buffering agent is one with a high buffering capacity. In some embodiments, the buffering agent is a modified, high buffering capacity version of any one of the buffering agents disclosed herein. In some embodiments, the buffering agent is PBS. In some embodiments, the buffering agent is modified, high buffering capacity PBS as described in the Examples herein.

In some embodiments, the formulation method comprises the step of varying the buffering agent. In some embodiments, the formulation method comprises the step of varying the concentration/molarity of the buffering agent.

Microbial Stabilizers

In some embodiments, the method of formulation comprises the step of selecting a microbial stabilizer. In some embodiments, the agricultural composition comprises a microbial stabilizer. A microbial stabilizer is an agent that acts to stabilize the microorganism population within the agricultural composition. In some embodiments, the microbial stabilizer decreases or slows the decay rate of the microbial population. In some embodiments, the microbial stabilizer accomplishes this change in the decay rate by maintaining the microorganisms in a semi-dormant state. In a semi-dormant state, microorganisms do not respond to environmental conditions as rapidly as they would in an active state.

In some embodiments, the microbial stabilizer improves microbial survival rate, decreases microbial decay, improves microbial metabolic activity, improves microbial catabolic gene expression, improves the microbial colonization rate, or decreases toxin accumulation within the agricultural composition after 1-6 months of storage compared to the agricultural composition without the microbial stabilizer.

In some embodiments, the microbial stabilizer increases the survival rate of microbial cells comprised by the agricultural composition after storage, e.g., after 1, 2, 3, 4, 5, or 6 months of storage. In some embodiments, the log loss of CFU/mL of microbes after the storage period is less than 1. In some embodiments, the log loss is less than 1, 0.9, 0.8, 0.7, 0.6, 0.5, 0.4, 0.3, or 0.2.

In some embodiments, the microbial stabilizer improves the metabolic activity and/or catabolic gene expression of the microorganisms comprised by the agricultural composition after the storage period. In some embodiments, the microbes are more metabolically and/or catabolically active than microbes from the agricultural composition without the microbial stabilizer.

In some embodiments, the microbial stabilizer improves the colonization rate of the microorganisms in the agricultural plant after the storage period compared to the agricultural composition minus the microbial stabilizer. In some embodiments, microbial colonization is unaffected by the storage period for the agricultural composition comprising the microbial stabilizer.

In some embodiments, the microbial stabilizer decreases toxin accumulation. In some embodiments, the toxin is a direct product or byproduct of nitrogen fixation. In some embodiments, the toxin is ammonia or ammonium. In some embodiments, the toxin is produced during cell growth/division.

In some embodiments, the microbial stabilizer decreases toxin accumulation at least two-fold over the target time period, e.g., three months, compared to the agricultural composition absent the microbial stabilizer. In some embodiments, the microbial stabilizer decreases toxin accumulation at least two-fold to at least ten-fold compared to the agricultural composition without the microbial stabilizer. In some embodiments, the microbial stabilizer decreases toxin accumulation at least two-fold, at least three-fold, at least four-fold, at least five-fold, at least six-fold, at least seven-fold, at least eight-fold, at least nine-fold, or at least ten-fold. In some embodiments, the microbial stabilizer decreases toxin accumulation about two-fold, about three-fold, about four-fold, about five-fold, about six-fold, about seven-fold, about eight-fold, about nine-fold, or about ten-fold.

In some embodiments, the microbial stabilizer is a sugar. In some embodiments, the microbial stabilizer is a non-reducing sugar. In some embodiments, the microbial stabilizer is a monosaccharide. Monosaccharides suitable for use include, but are not limited to, glucose and fructose. In some embodiments, the microbial stabilizer is fructose. In some embodiments, the microbial stabilizer is a disaccharide. Monosaccharides suitable for use include, but are not limited to, trehalose, sucrose, lactose, melibiose, and lactulose. In some embodiments, the microbial stabilizer is trehalose. In some embodiments, the microbial stabilizer is a polysaccharide. Polysaccharides suitable for use include, but are not limited to, maltodextrin, microcrystalline cellulose, and dextran. Additional carbohydrates suitable for use as microbial stabilizers within the agricultural compositions of the present disclosure include, but are not limited to, pentoses (e.g., ribose, xylose), hexoses (e.g., mannose, sorbose), oligosaccharides (e.g., raffinose), and oligofructoses. In some embodiments, the microbial stabilizer is a sugar alcohol. Sugar alcohols suitable for use include, but are not limited to, glycerol, mannitol, and sorbitol.

In some embodiments, the microbial stabilizer is an amino acid. In some embodiments, the microbial stabilizer is glycine, proline, glutamate, or cysteine. In some embodiments, the microbial stabilizer is a protein or protein hydrolysate. Proteins or protein hydrolysates suitable for use as microbial stabilizers within the agricultural composition of the present disclosure include, but are not limited to, malt extract, milk powder, casein, whey powder, and yeast extract. In some embodiments, the microbial stabilizer is skimmed milk, starch, humic acid, chitosan, CMC, corn steep liquor, molasses, paraffin, pinolene, NFSM, $MgSO_4$, liquid growth medium, horse serum, or Ficoll.

In some embodiments, the microbial stabilizer is a desiccant. As used herein, a "desiccant" can include any compound or mixture of compounds that can be classified as a desiccant regardless of whether the compound or compounds are used in such concentrations that they in fact have a desiccating effect on the liquid inoculant. Such desiccants are ideally compatible with the microbial population used, and should promote the ability of the microbial population to survive application on the agricultural plant tissues or the environs thereof and to survive desiccation. Examples of suitable desiccants include one or more of trehalose, sucrose, glycerol, and methylene glycol. Other suitable desiccants include, but are not limited to, non-reducing sugars and sugar alcohols (e.g., mannitol or sorbitol).

In some embodiments, the microbial stabilizer comprised by the agricultural composition also acts as a physical stabilizer. In some embodiments, the substance acting as a microbial stabilizer within the agricultural composition has properties of a thickening agent and therefore also acts as a physical stabilizer. In some embodiments, an agricultural composition of the present disclosure comprising both a physical and a microbial stabilizer does so by comprising the same agent that has characteristics of both types of stabilizer.

In some embodiments, the concentration of microbial stabilizer comprised by the agricultural composition ranges from about 0.1% w/v to about 20% w/v. In some embodiments, the concentration of microbial stabilizer comprised by the agricultural composition is in the range of 0.1-1.0% w/v, 1.0-5.0% w/v, 5.0-10% w/v, or 10-20% w/v. In some embodiments, the microbial stabilizer is present at a concentration of about 0.5-10% w/v. In some embodiments, the microbial stabilizer is present at a concentration of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0% w/v. In some embodiments, the microbial stabilizer is present at a concentration of about 1.0% w/v. In some embodiments, the microbial stabilizer is present at a concentration of about 1.3% w/v. In some embodiments, the microbial stabilizer is present at a concentration of about 2.5% w/v.

Physical Stabilizers

In some embodiments, the method of formulation comprises the step of selecting a physical stabilizer. In some embodiments, the agricultural composition comprises a physical stabilizer. As used herein, a "physical stabilizer" refers to a substance that improves the homogeneity of the agricultural composition, such that the microbial cells are at a similar density throughout the liquid composition. By increasing homogeneity, the physical stabilizer prevents high concentrations of cells and/or toxins from accumulating in any one sub-volume of the agricultural composition.

In some embodiments, the physical stabilizer increases the viscosity of the liquid agricultural composition. In some embodiments, the physical stabilizer is a thickening agent. In some embodiments, the physical stabilizer is an anti-settling agent. In some embodiments, the physical stabilizer is a suspension aid. In some embodiments, the physical stabilizer acts to maintain microbial cells in suspension, improving the cell's resistance to settle statically and flow under shear or rheological shear-thinning. In some embodiments, a physical stabilizer may also have properties of a microbial stabilizer and vice versa. In some embodiments, the agricultural composition comprises more than one physical stabilizer.

In some embodiments, the physical stabilizer is a polysaccharide. Polysaccharides suitable for use as physical stabilizers include, but are not limited to, polyethylene glycol (PEG), xanthan gum, pectin, and alginates. In some embodiments, the physical stabilizer is xanthan gum. In some embodiments, the physical stabilizer is a protein or protein hydrolysate. Proteins or protein hydrolysates suitable for use as physical stabilizers within the agricultural composition of the present disclosure include, but are not limited to, gluten, collagen, gelatin, elastin, keratin, and albumin. In some embodiments, the physical stabilizer is a polymer. Polymers suitable for use as physical stabilizers include, but are not limited to, Carbopol® (CBP) polymers, methylene glycol, polyvinyl alcohol (PVA), polyvinylpyrrolidone (PVP), polyacrylate, hydroxyethyl cellulose, or hydroxypropyl methylcellulose. In some embodiments, the physical stabilizer is a gum or its derivative. Gums and their derivatives suitable for use as physical stabilizers within the agricultural composition of the present disclosure include, but are not limited to, guar gum, gum Arabic, gum tragacanth, xanthan gum, derivitized guar, hydroxypropyl guar, and polysaccharide gums. In some embodiments, the physical stabilizer is a CBP polymer.

In some embodiments, the physical stabilizer is a suspension aid. Suitable suspension aids for use as physical stabilizers in the agricultural compositions of the present disclosure include, but are not limited to, water soluble polymers such as acrylamide homo- and copolymers, acrylic acid homo- and copolymer, cellulose, methyl cellulose, ethyl cellulose, carboxymethyl cellulose (sodium and other salts), carboxymethyl hydroxyethyl cellulose, hydroxyethyl cellulose, hydrophobically modified hydroxyethyl cellulose, hydroxypropyl cellulose, hydroxypropyl methylcellulose, water-soluble cellulose ethers, carboxy-vinyl copolymers, alginic acid, polyacrylic acid, sodium polyacrylate, partially and fully hydrolyzed polyvinyl alcohols, partially neutralized polyacrylic acid, polyalkylene glycol, polyvinylpyrrolidone and derivatives, starch and its derivatives, vinylpyrrolidone homo- and copolymers, polyacrylamide, attapulgite, montmorillonite, organically modified montmorillonite clays, alumina, precipitated silica, or any mixture thereof.

In some embodiments, the concentration of physical stabilizer comprised by the agricultural composition ranges from about 0.01% w/v to about 30% w/v. In some embodiments, the concentration of physical stabilizer comprised by the agricultural composition is in the range of 0.01-0.1% w/v, 0.1-1.0% w/v, 1.0-5.0% w/v, 5.0-10% w/v, 10-15%, 15-20%, 20-25%, or 25-30% w/v. In some embodiments, the physical stabilizer is present at a concentration of about 0.01-2.0% w/v. In some embodiments, the physical stabilizer is present at a concentration of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0% w/v. In some embodiments, the physical stabilizer is present at a concentration of about 0.1% w/v. In some embodiments, the physical stabilizer is present at a concentration of about 0.2% w/v.

Additional Agricultural Composition Components and/or Treatments

The present liquid agricultural compositions comprise plant-beneficial, nitrogen-fixing microorganisms and one or more of a buffering agent, a microbial stabilizer, and a physical stabilizer. In some embodiments, the formulation methods of the present disclosure comprise the step of selecting additional components. In some embodiments, the agricultural compositions of the present disclosure comprise additional components. In some embodiments, the additional ingredients are separately added to the liquid agricultural composition. In some embodiments, the agricultural plant tissues or environs thereof of the present disclosure are separately treated with an additional component before, during, or after application of the agricultural compositions of the present disclosure. These additional components may include protectants and beneficial ingredients including but not limited to animal and bird repellants, attractants, baits, herbicides, herbicide safeners, antidessicants, anti-transpirants, frost prevention aids, inoculants, dyes, brighteners, markers, synergists, pigments, UV protectants, anti-oxidants, leaf polish, pigmentation stimulants and inhibitors, surfactants, moisture retention aids, humic acids and humates, lignins and lignates, bitter flavors, irritants, malodorous ingredients, molluscicides (e.g., slugs and snails), nematicides, rodenticides, defoliants, desiccants, sticky traps, IPM (integrated pest management) lures, chemosterilants, plant defense boosters (harpin protein and chitosan), and other beneficial or detrimental agents applied to the surface of the plant tissue or the environs thereof. In some embodiments, multiple active agents are readily formulated within a given agricultural composition, for example, multiple active agents may include two or more of any of the following fungicides, fertilizers, pesticides, herbicides, and any type of active ingredient or class of active ingredient.

Suitable additional ingredients for the agricultural compositions of the present disclosure include, but are not limited to, the following:

Insecticides: A1) the class of carbamates consisting of aldicarb, alanycarb, benfuracarb, carbaryl, carbofuran, carbosulfan, methiocarb, methomyl, oxamyl, pirimicarb, propoxur and thiodicarb; A2) the class of organophosphates consisting of acephate, azinphos-ethyl, azinphos-methyl, chlorfenvinphos, chlorpyrifos, chlorpyrifos-methyl, demeton-S-methyl, diazinon, dichlorvos/DDVP, dicrotophos, dimethoate, disulfoton, ethion, fenitrothion, fenthion, isoxathion, malathion, methamidaphos, methidathion, mevinphos, monocrotophos, oxymethoate, oxydemeton-methyl, parathion, parathion-methyl, phenthoate, phorate, phosalone, phosmet, phosphamidon, pirimiphos-methyl, quinalphos, terbufos, tetrachlorvinphos, triazophos and trichlorfon; A3) the class of cyclodiene organochlorine compounds such as endosulfan; A4) the class of fiproles consisting of ethiprole, fipronil, pyrafluprole and pyriprole; A5) the class of neonicotinoids consisting of acetamiprid, chlothianidin, dinotefuran, imidacloprid, nitenpyram, thiacloprid and thiamethoxam; A6) the class of spinosyns such as spinosad and spinetoram; A7) chloride channel activators from the class of mectins consisting of abamectin, emamectin benzoate, ivermectin, lepimectin and milbemectin; A8) juvenile hormone mimics such as hydroprene, kinoprene, methoprene, fenoxycarb and pyriproxyfen; A9) selective homopteran feeding blockers such as pymetrozine, flonicamid and pyrifluquinazon; A10) mite growth inhibitors such as clofentezine, hexythiazox and etoxazole; A11) inhibitors of mitochondrial ATP synthase such as diafenthiuron, fenbutatin oxide and propargite; uncouplers of oxidative phosphorylation such as chlorfenapyr; A12) nicotinic acetylcholine receptor channel blockers such as bensultap, cartap hydrochloride, thiocyclam and thiosultap sodium; A13) inhibitors of the chitin biosynthesis type 0 from the benzoylurea class consisting of bistrifluron, diflubenzuron, flufenoxuron, hexaflumuron, lufenuron, novaluron and teflubenzuron; A14) inhibitors of the chitin biosynthesis type 1 such as buprofezin; A15) moulting disruptors such as cyromazine; A16) ecdyson receptor agonists such as methoxyfenozide, tebufenozide, halofenozide and chromafenozide; A17) octopamin receptor agonists such as amitraz; A18) mitochondrial complex electron transport inhibitors pyridaben, tebufenpyrad, tolfenpyrad, flufenerim, cyenopyrafen, cyflumetofen, hydramethylnon, acequinocyl or fluacrypyrim; A19) voltage-dependent sodium channel blockers such as indoxacarb and metaflumizone; A20) inhibitors of the lipid synthesis such as spirodiclofen, spiromesifen and spirotetramat; A21) ryanodine receptor-modulators from the class of diamides consisting of flubendiamide, the phthalamide compounds (R)-3-Chlor-N1-{2-methyl-4-[1,2,2,2-tetrafluor-1-(trifluormethyl)ethyl]phenyl}-N2-(1-methyl-2-methyl sulfonylethyl)phthalamid and (S)-3-Chlor-N1-{2-methyl-4-[1,2,2,2-tetrafluor-1-(trifluormethyl)ethyl] phenyl}-N2-(1-methyl-2-methylsulfonylethyl)phthalamid, chloranthraniliprole and cyantraniliprole; A22) compounds of unknown or uncertain mode of action such as azadirachtin, amidoflumet, bifenazate, fluensulfone, piperonyl butoxide, pyridalyl, sulfoxaflor; or A23) sodium channel modulators from the class of pyrethroids consisting of acrinathrin, allethrin, bifenthrin, cyfluthrin, gamma-cyhalothrin, lambda-cyhalothrin, cypermethrin, alpha-cypermethrin, beta-cypermethrin, zeta-cypermethrin, deltamethrin, esfenvalerate, etofenprox, fenpropathrin, fenvalerate, flucythrinate, tau-fluvalinate, permethrin, silafluofen, tefluthrin and tralomethrin and any suitable combinations thereof.

Fungicides: B1) azoles selected from the group consisting of bitertanol, bromuconazole, cyproconazole, difenoconazole, diniconazole, enilconazole, epoxiconazole, fluquinconazole, fenbuconazole, flusilazole, flutriafol, hexaconazole, imibenconazole, ipconazole, metconazole, myclobutanil, penconazole, propiconazole, prothioconazole, simeconazole, triadimefon, triadimenol, tebuconazole, tetraconazole, triticonazole, prochloraz, pefurazoate, imazalil, triflumizole, cyazofamid, benomyl, carbendazim, thiabendazole, fuberidazole, ethaboxam, etridiazole and hymexazole, azaconazole, diniconazole-M, oxpoconazol, paclobutrazol, uniconazol, 1-(4-chloro-phenyl)-2-([1,2,4] triazol-1-yl)-cycloheptanol and imazalilsulfphate; B2) strobilurins selected from the group consisting of azoxystrobin, dimoxystrobin, enestroburin, fluoxastrobin, kresoxim-methyl, methominostrobin, orysastrobin, picoxystrobin, pyraclostrobin, trifloxystrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl] benzyl)carbamate and methyl 2-(ortho-(2,5-dimethylphenyloxymethylene)-phenyl)-3-methoxyacrylate, 2-(2-(6-(3-chloro-2-methyl-phenoxy)-5-fluoro-pyrimidin-4-yloxy)-phenyl)-2-methoxyimino-N-methyl-acetamide and 3-methoxy-2-(2-(N-(4-methoxy-phenyl)-cyclopropanecarboximidoylsulfanylmethyl)-phenyl)-acrylic acid methyl ester; B3) carboxamides selected from the group consisting of carboxin, benalaxyl, benalaxyl-M, fenhexamid, flutolanil, furametpyr, mepronil, metalaxyl, mefenoxam, ofurace, oxadixyl, oxycarboxin, penthiopyrad, isopyrazam, thifluzamide, tiadinil, 3,4-dichloro-N-(2-cyanophenyl)isothiazole-5-carboxamide, dimethomorph, flumorph, flumetover, fluopicolide (picobenzamid), zoxamide, carpropamid, diclocymet, mandipropamid, N-(2-(443-(4-chlorophenyl)prop-2-ynyloxy]-3-methoxyphenyl)ethyl)-2-methanesulfonyl-amino-3-methylbutyramide, N-(2-(4-[3-(4-chloro-phenyl)prop-2-ynyloxy]-3-methoxy-phenyl)ethyl)-2-ethanesulfonylamino-3-methylbutyramide, methyl 3-(4-chlorophenyl)-3-(2-isopropoxycarbonyl-amino-3-methyl-butyrylamino) propionate, N-(4'-bromobiphenyl-2-yl)-4-difluoromethylA-methylthiazole-6-carboxamide, N-(4'-trifluoromethyl-biphenyl-2-yl)-4-difluoromethyl-2-methylthiazole-5-carboxamide, N-(4'-chloro-3'-fluorobiphenyl-2-yl)-4-difluoromethyl-2-methyl-thiazole-5-carboxamide, N-(3',4'-dichloro-4-fluorobiphenyl-2-yl)-3-difluoro-methyl-1-methyl-pyrazole-4-carboxamide, N-(3',4'-dichloro-5-fluorobiphenyl-2-yl)-3-difluoromethyl-1-methylpyrazole-4-carboxamide, N-(2-cyano-phenyl)-3,4-dichloroisothiazole-5-carboxamide, 2-amino-4-methyl-thiazole-5-carboxanilide, 2-chloro-N-(1,1,3-trimethyl-indan-4-yl)-nicotinamide, N-(2-(1,3-dimethylbutyl)-phenyl)-1,3-dimethyl-5-fluoro-1H-pyrazole-4-carboxamide, N-(4'-chloro-3', 5-difluoro-biphenyl-2-yl)-3-difluoromethyl-1-methyl-1H-pyrazole-4-carboxamide, N-(4'-chloro-3', 5-difluoro-biphenyl-2-yl)-3-trifluoromethyl-1-methyl-1H-pyrazole-4-carboxamide, N-(3', 4'-dichloro-5-fluoro-biphenyl-2-yl)-3-trifluoromethyl-1-methyl-1H-pyrazole-4-carboxamide, N-(3', 5-difluoro-4'-methyl-biphenyl-2-yl)-3-difluoromethyl-1-methyl-1H-pyrazole-4-carboxamide, N-(3', 5-difluoro-4'-methyl-biphenyl-2-yl)-3-trifluoromethyl-1-methyl-1H-pyrazole-4-carboxamide, N-(cis-2-bicyclopropyl-2-yl-phenyl)-3-difluoromethyl-1-methyl-1H-pyrazole-4-carboxamide, N-(trans-2-bicyclopropyl-2-yl-phenyl)-3-difluoro-methyl-1-methyl-1H-pyrazole-4-carboxamide, fluopyram, N-(3-ethyl-3,5-5-trimethyl-cyclohexyl)-3-formylamino-2-hydroxy-benzamide, oxytetracyclin, silthiofam, N-(6-methoxy-pyridin-3-yl) cyclopropanecarboxamide, 2-iodo-N-phenyl-benzamide, N-(2-bicyclo-propyl-2-yl-phenyl)-3-difluormethyl-1-methylpyrazol-4-ylcarboxamide, N-(3',4',5'-trifluorobiphenyl-2-yl)-1,3-dimethylpyrazol-4-ylcarboxamide, N-(3',4',5'-trifluorobiphenyl-2-yl)-1,3-dimethyl-5-fluoropyrazol-4-yl-carboxamide, N-(3',4',5'-trifluorobiphenyl-2-yl)-5-chloro-1,3-dimethyl-pyrazol-4-ylcarboxamide, N-(3',4',5'-trifluorobiphenyl-2-yl)-3-fluoromethyl-1-methylpyrazol-4-ylcarboxamide, N-(3',4',5'-trifluorobiphenyl-2-yl)-3-(chlorofluoromethyl)-1-methylpyrazol-4-ylcarboxamide,N-(3',4',5'-trifluorobiphenyl-2-yl)-3-difluoromethyl-1-methylpyrazol-4-ylcarboxamide, N-(3',4',5'-trifluorobiphenyl-2-yl)-3-difluoromethyl-5-fluoro-1-methylpyrazol-4-ylcarboxamide, N-(3',4',5'-trifluorobiphenyl-2-yl)-5-chloro-3-difluoromethyl-1-methylpyrazol-4-ylcarboxamide, N-(3',4',5'-trifluorobiphenyl-2-yl)-3-(chlorodifluoromethyl)-1-methylpyrazol-4-ylcarboxamide, N-(3',4',5'-trifluorobiphenyl-2-yl)-1-methyl-3-trifluoromethylpyrazol-4-ylcarboxamide, N-(3',4',5'-trifluorobiphenyl-2-yl)-5-fluoro-1-methyl-3-trifluoromethylpyrazol-4-ylcarboxamide, N-(3',4',5'-trifluorobiphenyl-2-yl)-5-chloro-1-methyl-3-trifluoromethylpyrazol-4-ylcarboxamide, N-(2',4',5'-trifluorobiphenyl-2-yl)-1,3-dimethylpyrazol-4-ylcarboxamide, N-(2',4',5'-trifluorobiphenyl-2-yl)-1,3-dimethyl-5-fluoropyrazol-4-ylcarboxamide, N-(2',4',5'-trifluorobiphenyl-2-yl)-5-chloro-1,3-dimethylpyrazol-4-ylcarboxamide, N-(2',4',5'-trifluorobiphenyl-2-yl)-3-fluoromethyl-1-methylpyrazol-4-ylcarboxamide, N-(2',4',5'-trifluorobiphenyl-2-yl)-3-(chlorofluoromethyl)-1-methylpyrazol-4-ylcarboxamide,N-(2',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-5-fluoro-1-methylpyrazol-4-ylcarboxamide, N-(2',4',5'-trifluorobiphenyl-2-yl)-5-chloro-3-difluoromethyl-1-methylpyrazol-4-ylcarboxamide, N-(2',4',5'-trifluorobiphenyl-2-yl)-3-(chlorodifluoromethyl)-1-methylpyrazol-4-ylcarboxamide, N-(2',4',5'-trifluorobiphenyl-2-yl)-1-methyl-3-trifluoromethylpyrazol-4-ylcarboxamide, N-(2',4',5'-trifluorobiphenyl-2-yl)-5-fluoro-1-methyl-3-trifluoromethylpyrazol-4-ylcarboxamide, N-(2',4',5'-trifluorobiphenyl-2-yl)-5-chloro-1-methyl-3-trifluoromethylpyrazol-4-ylcarboxamide, N-(3',4'-dichloro-3-fluorobiphenyl-2-yl)-1-methyl-3-trifluoromethyl-1H-pyrazole-4-carboxamide, N-(3',4'-dichloro-3-fluorobiphenyl-2-yl)-1-methyl-3-difluoromethyl-1H-pyrazole-4-carboxamide, N-(3',4'-difluoro-3-fluorobiphenyl-2-yl)-1-methyl-3-trifluoromethyl-1H-pyrazole-4-carboxamide, N-(3',4'-difluoro-3-fluorobiphenyl-2-yl)-1-methyl-S-difluoromethyl-1H-pyrazole-4-carboxamide, N-(3'-chloro-4'-fluoro-3-fluorobiphenyl-2-yl)-1-methyl-3-difluoromethyl-1H-pyrazole-4-carboxamide, N-(3',4'-dichloro-4-fluorobiphenyl-2-yl)-1-methyl-3-trifluoromethyl-1H-pyrazole-4-carboxamide, N-(3',4'-difluoro-4-fluorobiphenyl-2-yl)-1-methyl-S-trifluoromethyl-1H-pyrazole-4-carboxamide, N-(3',4'-dichloro-4-fluorobiphenyl-2-yl)-1-methyl-3-difluoromethyl-1H-pyrazole-4-carboxamide, N-(3',4'-difluoro-4-fluorobiphenyl-2-yl)-1-methyl-3-difluoromethyl-1H-pyrazole-4-carboxamide, N-(3'-chloro-4'-fluoro-4-fluorobiphenyl-2-yl)-1-methyl-S-difluoromethyl-1H-pyrazole-4-carboxamide, N-(3',4'-dichloro-5-fluorobiphenyl-2-yl)-1-methyl-3-trifluoromethyl-1H-pyrazole-4-carboxamide, N-(3',4'-difluoro-5-fluorobiphenyl-2-yl)-1-methyl-3-trifluoromethyl-1H-pyrazole-4-carboxamide, N-(3',4'-dichloro-5-fluorobiphenyl-2-yl)-1-methyl-S-difluoromethyl-1H-pyrazole-carboxamide, N-(3',4'-difluoro-5-fluorobiphenyl-2-yl)-1-methyl-3-difluoromethyl-1H-pyrazole-4-carboxamide, N-(3',4'-dichloro-5-fluorobiphenyl-2-yl)-1,3-dimethyl-1H-pyrazole-4-carboxamide, N-(3'-chloro-4'-fluoro-5-fluorobiphenyl-2-yl)-1-methyl-3-difluoromethyl-1H-pyrazole-4-carboxamide, N-(4'-fluoro-4-fluorobiphenyl-2-yl)-1-methyl-3-trifluoromethyl-1H-pyrazole-4-carboxamide, N-(4'-fluoro-5-fluorobiphenyl-2-yl)-1-methyl-3-trifluoromethyl-1H-pyrazole-4-carboxamide, N-(4'-chloro-5-fluorobiphenyl-2-yl)-1-methyl-3-trifluoromethyl-1H-pyrazole-4-carboxamide, N-(4'-methyl-5-fluorobiphenyl-2-yl)-1-methyl-3-trifluoromethyl-1H-pyrazole-4-carboxamide, N-(4'-fluoro-5-fluorobiphenyl-2-yl)-1,3-dimethyl-1H-pyrazole-4-carboxamide, N-(4'-chloro-5-fluorobiphenyl-2-yl)-1,3-dimethyl-1H-pyrazole-4-carboxamide, N-(4'-methyl-5-fluorobiphenyl-2-yl)-1,3-dimethyl-1H-pyrazole-4-carboxamide, N-(4'-fluoro-6-fluorobiphenyl-2-yl)-1-methyl-3-trifluoromethyl-1H-pyrazole-4-carboxamide, N-(4'-chloro-6-fluorobiphenyl-2-yl)-1-methyl-3-trifluoromethyl-1H-pyrazole-4-carboxamide, N-[2-(1,1,2,3,3,3-hexafluoropropoxy)-phenyl]-3-difluoromethyl-1-methyl-1H-pyrazole-4-carboxamide, N-[4'-(trifluoromethylthio)-biphenyl-2-yl]-3-difluoromethyl-1-methyl-1H-pyrazole-4-carboxamide and N44'-(trifluoromethylthio)-biphenyl-2-yl]-1-methyl-3-trifluoromethyl-1-methyl-1H-pyrazole-4-carboxamide; B4) heterocyclic compounds selected from the group consisting of fluazinam, pyrifenox, bupirimate, cyprodinil, fenarimol, ferimzone, mepanipyrim, nuarimol, pyrimethanil, triforine, fenpiclonil, fludioxonil, aldimorph, dodemorph, fenpropimorph, tridemorph, fenpropidin, iprodione, procymidone, vinclozolin, famoxadone, fenamidone, octhilinone, proben-azole, 5-chloro-7-(4-methyl-piperidin-1-yl)-6-(2,4,6-trifluorophenyl)41,2,4]triazolo[1,5-a]pyrimidine, anilazine, diclomezine, pyroquilon, proquinazid, tricyclazole, 2-butoxy-6-iodo-3-propyl-chromen-4-one, acibenzolar-S-methyl, captafol, captan, dazomet, folpet, fenoxanil, quinoxyfen, N,N-dimethyl-3-(3-bromo-6-fluoro-2-methylindole-1-sulfonyl)-[1,2,4]triazole-1-sulfonamide, 5-ethyl-6-octyl41,2,4]triazolo[1 2,3,5,6-tetrachloro-4-methanesulfonyl-pyridine, 3,4,5-trichloro-pyridine-2,6-di-carbonitrile, N-(1-(5-bromo-3-chloro-pyridin-2-yl)-ethyl)-2,4-dichloro-nicotinamide, N-((5-bromo-3-chloro pyridin-2-yl)-methyl)-2,4-dichloro-nicotinamide, diflumetorim, nitrapyrin, dodemorphacetate, fluoroimid, blasticidin-S, chinomethionat, debacarb, difenzoquat, difenzoquat-methylsulphat, oxolinic acid and piperalin; B5) carbamates selected from the group consisting of mancozeb, maneb, metam, methasulphocarb, metiram, ferbam, propineb, thiram, zineb, ziram, diethofencarb, iprovalicarb, benthiavalicarb, propamocarb, propamocarb hydrochlorid, 4-fluorophenyl N-(1-(1-(4-cyanophenyl)- ethanesulfonyl)but-2-yl)carbamate, methyl 3-(4-chloro-phenyl)-3-(2-isopropoxycarbonylamino-3-methyl-butyrylamino)propanoate; or B6) other fungicides selected from the group consisting of guanidine, dodine, dodine free base, iminoctadine, guazatine, antibiotics: kasugamycin, streptomycin, polyoxin, validamycin A, nitrophenyl derivatives: binapacryl, dinocap, dinobuton, sulfur-containing heterocyclyl compounds: dithianon, isoprothiolane, organometallic compounds: fentin salts, organophosphorus compounds: edifenphos, iprobenfos, fosetyl, fosetyl-aluminum, phosphorous acid and its salts, pyrazophos, tolclofos-methyl, organochlorine compounds: dichlofluanid, flusulfamide, hexachloro-benzene, phthalide, pencycuron, quintozene, thiophanate-methyl, tolylfluanid, others: cyflufenamid, cymoxanil, dimethirimol, ethirimol, furalaxyl, metrafenone and spiroxamine, guazatine-acetate, iminoc-tadine-triacetate, iminoctadine-tris(albesilate), kasugamycin hydrochloride hydrate, dichlorophen, pentachlorophenol and its salts, N-(4-chloro-2-nitro-phenyl)-N-ethyl-4-methyl-benzenesulfonamide, did nitrothal-isopropyl, tecnazen, biphenyl, bronopol, diphenylamine, mildiomycin, oxincopper, prohexadione calcium, N-(cyclopropylmethoxyimino-(6-difluoromethoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluormethyl-4-(3-trimethyl-silanyl-propoxy)-phenyl)-N-ethyl-N-methylformamidine and N'-(5-difluormethyl-2-methyl-4-(3-trimethylsilanyl-propoxy)-phenyl)-N-ethyl-N-methyl formamidine, and any combinations thereof Herbicides: C1) acetyl-CoA carboxylase inhibitors (ACC), for example cyclohexenone oxime ethers, such as alloxydim, clethodim, cloproxydim, cycloxydim, sethoxydim, tralkoxydim, butroxydim, clefoxydim or tepraloxydim; phenoxyphenoxypropionic esters, such as clodinafop-propargyl, cyhalofop-butyl, diclofop-methyl, fenoxaprop-ethyl, fenoxaprop-P-ethyl, fenthiapropethyl, fluazifop-butyl, fluazifop-P-butyl, haloxyfop-ethoxyethyl, haloxyfop-methyl, haloxyfop-P-methyl, isoxapyrifop, propaquizafop, quizalofop-ethyl, quizalofop-P-ethyl or quizalofop-tefuryl; or arylaminopropionic acids, such as flamprop-methyl or flamprop-isopropyl; C2 acetolactate synthase inhibitors (ALS), for example imidazolinones, such as imazapyr, imazaquin, imazamethabenz-methyl (imazame), imazamox, imazapic or imazethapyr; pyrimidyl ethers, such as pyrithiobac-acid, pyrithiobac-sodium, bispyribac-sodium. KIH-6127 or pyribenzoxym; sulfonamides, such as florasulam, flumetsulam or metosulam; or sulfonylureas, such as amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flazasulfuron, halosulfuron-methyl, imazosulfuron, metsulfuron-methyl, nicosulfuron, primisulfuron-methyl, prosulfuron, pyrazosulfuron-ethyl, rimsulfuron, sulfometuron-methyl, thifensulfuron-methyl, triasulfuron, tribenuron-methyl, triflusulfuron-methyl, tritosulfuron, sulfosulfuron, foramsulfuron or iodosulfuron; C3) amides, for example allidochlor (CDAA), benzoylprop-ethyl, bromobutide, chiorthiamid. diphenamid, etobenzanidibenzchlomet), fluthiamide, fosamin or monalide; C4) auxin herbicides, for example pyridinecarboxylic acids, such as clopyralid or picloram; or 2,4-D or benazolin; C5) auxin transport inhibitors, for example naptalame or diflufenzopyr; C6) carotenoid biosynthesis inhibitors, for example benzofenap, clomazone (dimethazone), diflufenican, fluorochloridone, fluridone, pyrazolynate, pyrazoxyfen, isoxaflutole, isoxachlortole, mesotrione, sulcotrione (chlormesulone), ketospiradox, flurtamone, norflurazon or amitrol; C7) enolpyruvylshikimate-3-phosphate synthase inhibitors (EPSPS), for example glyphosate or sulfosate; C8) glutamine synthetase inhibitors, for example bilanafos (bialaphos) or glufosinate-ammonium; C9) lipid biosynthesis inhibitors, for example anilides, such as anilofos or mefenacet; chloroacetanilides, such as dimethenamid, S-dimethenamid, acetochlor, alachlor, butachlor, butenachlor, diethatyl-ethyl, dimethachlor, metazachlor, metolachlor, S-metolachlor, pretilachlor, propachlor, prynachlor, terbuchlor, thenylchlor or xylachlor; thioureas, such as butylate, cycloate, di-allate, dimepiperate, EPTC. esprocarb, molinate, pebulate, prosulfocarb, thiobencarb (benthiocarb), triallate or vemolate; or benfuresate or perfluidone; C10) mitosis inhibitors, for example carbamates, such as asulam, carbetamid, chlorpropham, orbencarb, pronamid (propyzamid), propham or tiocarbazil; dinitroanilines, such as benefin, butralin, dinitramin, ethalfluralin, fluchloralin, oryzalin, pendimethalin, prodiamine or trifluralin; pyridines, such as dithiopyr or thiazopyr; or butamifos, chlorthal-dimethyl (DCPA) or maleic hydrazide; C11) protoporphyrinogen IX oxidase inhibitors, for example diphenyl ethers, such as acifluorfen, acifluorfen-sodium, aclonifen, bifenox, chlomitrofen (CNP), ethoxyfen, fluorodifen, fluoroglycofen-ethyl, fomesafen, furyloxyfen, lactofen, nitrofen, nitrofluorfen or oxyfluorfen; oxadiazoles, such as oxadiargyl or oxadiazon; cyclic imides, such as azafenidin, butafenacil, carfentrazone-ethyl, cinidon-ethyl, flumiclorac-pentyl, flumioxazin, flumipropyn, flupropacil, fluthiacet-methyl, sulfentrazone or thidiazimin; or pyrazoles, such as ET-751.JV 485 or nipyraclofen; C12) photosynthesis inhibitors, for example propanil, pyridate or pyridafol; benzothiadiazinones, such as bentazone; dinitrophenols, for example bromofenoxim, dinoseb, dinoseb-acetate, dinoterb or DNOC; dipyridylenes, such as cyperquat-chloride, difenzoquat-methyl sulfate, diquat or paraquat-dichloride; ureas, such as chlorbromuron, chlorotoluron, difenoxuron, dimefuron, diuron, ethidimuron, fenuron, fluometuron, isoproturonisouron, linuron, methabenzthiazuron, methazole, metobenzuron, metoxuron, monolinuron, neburon, siduron or tebuthiuron; phenols, such as bromoxynil or ioxynil; chloridazon; triazines, such as ametryn, atrazine, cyanazine, desmein, dimethamethryn, hexazinone, prometon, prometryn, propazine, simazine, simetryn, terbumeton, terbutryn, terbutylazine or trietazine; triazinones, such as metamitron or metribuzin; uracils, such as bromacil, lenacil or terbacil; or biscarbamates, such as desmedipham or phenmedipham; C13) synergists, for example oxiranes, such as tridiphane; C14) CIS cell wall synthesis inhibitors, for example isoxaben or dichlobenil; C16) various other herbicides, for example dichloropropionic acids, such as dalapon; dihydrobenzofurans, such as ethofumesate; phenylacetic acids, such as chlorfenac (fenac); or aziprotryn, barban, bensulide, benzthiazuron, benzofluor, buminafos, buthidazole, buturon, cafenstrole, chlorbufam, chlorfenprop-methyl, chloroxuron, cinmethylin, cumyluron, cycluron, cyprazine, cyprazole, dibenzyluron, dipropetryn, dymron, eglinazin-ethyl, endothall, ethiozin, flucabazone, fluorbentranil, flupoxam, isocarbamid, isopropalin, karbutilate, mefluidide, monuron, napropamide, napropanilide, nitralin, oxaciclomefone, phenisopham, piperophos, procyazine, profluralin, pyributicarb, secbumeton, sulfallate (CDEC), terbucarb, triaziflam, triazofenamid or trimeturon; or their environmentally compatible salts or combinations thereof.

Nematicides: Benomyl, cloethocarb, aldoxycarb, tirpate, diamidafos, fenamiphos, cadusafos, dichlofenthion, ethoprophos, fensulfothion, fosthiazate, heterophos, isamidofof, isazofos, phosphocarb, thionazin, imicyafos, mecarphon, acetoprole, benclothiaz, chloropicrin, dazomet, fluensulfone, oxamyl, terbufos and suitable combinations thereof.

Plant Growth Regulators: D1) Antiauxins, such as clofibric acid, 2,3,5-triiodobenzoic acid; D2) Auxins such as 4-CPA, 2,4-D, 2,4-DB, 2,4-DEP, dichlorprop, fenoprop, IAA, IBA, naphthaleneacetamide, α-naphthaleneacetic acids, 1-naphthol, naphthoxyacetic acids, potassium naphthenate, sodium naphthenate, 2,4,5-T; D3) cytokinins, such as 21P, benzyladenine, 4-hydroxyphenethyl alcohol, kinetin, zeatin; D4) defoliants, such as calcium cyanamide, dimethipin, endothal, ethephon, merphos, metoxuron, pentachlorophenol, thidiazuron, tribufos; D5) ethylene inhibitors, such as aviglycine, 1-methylcyclopropene; D6) ethylene releasers, such as ACC, etacelasil, ethephon, glyoxime; D7) gametocides, such as fenridazon, maleic hydrazide; D8) gibberellins, such as gibberellins, gibberellic acid; D9) growth inhibitors, such as abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, tiaojiean, 2,3,5-tri-iodobenzoic acid; D10) morphactins, such as chlorfluren, chlorflurenol, dichlorflurenol, flurenol; D11) growth retardants, such as chlormequat, daminozide, flurprimidol, mefluidide, paclobutrazol, tetcyclacis, uniconazole; D12) growth stimulators, such as brassinolide, brassinolide-ethyl, DCPTA, forchlorfenuron, hymexazol, prosuler, triacontanol; D13) unclassified plant growth regulators, such as bachmedesh, benzofluor, buminafos, carvone, choline chloride, ciobutide, clofencet, cyanamide, cyclanilide, cycloheximide, cyprosulfamide, epocholeone, ethychlozate, ethylene, fuphenthiourea, furalane, heptopargil, holosulf, inabenfide, karetazan, lead arsenate, methasulfocarb, prohexadione, pydanon, sintofen, triapenthenol, trinexapac.

Fertilizers, Nitrogen Stabilizers, and Urease Inhibitors

The agricultural compositions of the disclosure, which may comprise any microbe taught herein, may be combined with one or more of a: fertilizer, nitrogen stabilizer, or urease inhibitor.

In some embodiments, fertilizers are used in combination with the methods and bacteria of the present disclosure. Fertilizers include anhydrous ammonia, urea, ammonium nitrate, and urea-ammonium nitrate (UAN) compositions, among many others. In some embodiments, pop-up fertilization and/or starter fertilization is used in combination with the methods and bacteria of the present disclosure.

In some embodiments, nitrogen stabilizers are used in combination with the methods and bacteria of the present disclosure. Nitrogen stabilizers include nitrapyrin, 2-chloro-6-(trichloromethyl) pyridine, N-SERVE 24, INSTINCT, dicyandiamide (DCD).

In some embodiments, urease inhibitors are used in combination with the methods and bacteria of the present disclosure. Urease inhibitors include N-(n-butyl)-thiophosphoric triamide (NBPT), AGROTAIN, AGROTAIN PLUS, and AGROTAIN PLUS SC. Further, the disclosure contemplates utilization of AGROTAIN ADVANCED 1.0, AGROTAIN DRI-MAXX, and AGROTAIN ULTRA.

Further, stabilized forms of fertilizer can be used. For example, a stabilized form of fertilizer is SUPER U, containing 46% nitrogen in a stabilized, urea-based granule, SUPERU contains urease and nitrification inhibitors to guard from denitrification, leaching, and volatilization. Stabilized and targeted foliar fertilizer such as NITAMIN may also be used herein.

Pop-up fertilizers are commonly used in corn fields. Pop-up fertilization comprises applying a few pounds of nutrients with the seed at planting. Pop-up fertilization is used to increase seedling vigor.

Slow- or controlled-release fertilizer that may be used herein entails: A fertilizer containing a plant nutrient in a form which delays its availability for plant uptake and use after application, or which extends its availability to the plant significantly longer than a reference 'rapidly available nutrient fertilizer' such as ammonium nitrate or urea, ammonium phosphate or potassium chloride. Such delay of initial availability or extended time of continued availability may occur by a variety of mechanisms. These include controlled water solubility of the material by semi-permeable coatings, occlusion, protein materials, or other chemical forms, by slow hydrolysis of water-soluble low molecular weight compounds, or by other unknown means.

Stabilized nitrogen fertilizer that may be used herein entails: A fertilizer to which a nitrogen stabilizer has been added. A nitrogen stabilizer is a substance added to a fertilizer which extends the time the nitrogen component of the fertilizer remains in the soil in the urea-N or ammoniacal-N form.

Nitrification inhibitor that may be used herein entails: A substance that inhibits the biological oxidation of ammoniacal-N to nitrate-N. Some examples include: (1) 2-chloro-6-(trichloromethyl-pyridine), common name Nitrapyrin, manufactured by Dow Chemical; (2) 4-amino-1,2,4-6-triazole-HCl, common name ATC, manufactured by Ishihada Industries; (3) 2,4-diamino-6-trichloro-methyltriazine, common name CI-1580, manufactured by American Cyanamid; (4) Dicyandiamide, common name DCD, manufactured by Showa Denko; (5) Thiourea, common name TU, manufactured by Nitto Ryuso; (6) 1-mercapto-1,2,4-triazole, common name MT, manufactured by Nippon; (7) 2-amino-4-chloro-6-methyl-pyramidine, common name AM, manufactured by Mitsui Toatsu; (8) 3,4-dimethylpyrazole phosphate (DMPP), from BASF; (9) 1-amide-2-thiourea (ASU), from Nitto Chemical Ind.; (10) Ammoniumthiosulphate (ATS); (11) 1H-1,2,4-triazole (HPLC); (12) 5-ethylene oxide-3-trichloro-methlyl,2,4-thiodiazole (Terrazole), from Olin Mathieson; (13) 3-methylpyrazole (3-MP); (14) 1-carbamoyle-3-methyl-pyrazole (CMP); (15) Neem; and (16) DMPP.

Urease inhibitor that may be used herein entails: A substance that inhibits hydrolytic action on urea by the enzyme urease. Thousands of chemicals have been evaluated as soil urease inhibitors (Kiss and Simihaian, 2002). However, only a few of the many compounds tested meet the necessary requirements of being nontoxic, effective at low concentration, stable, and compatible with urea (solid and solutions), degradable in the soil and inexpensive. They can be classified according to their structures and their assumed interaction with the enzyme urease (Watson, 2000, 2005). Four main classes of urease inhibitors have been proposed: (a) reagents which interact with the sulphydryl groups (sulphydryl reagents), (b) hydroxamates, (c) agricultural crop protection chemicals, and (d) structural analogues of urea and related compounds. N-(n-Butyl) thiophosphoric triamide (NBPT), phenylphosphorodiamidate (PPD/PPDA), and hydroquinone are probably the most thoroughly studied urease inhibitors (Kiss and Simihaian, 2002). Research and practical testing has also been carried out with N-(2-nitrophenyl) phosphoric acid triamide (2-NPT) and ammonium thiosulphate (ATS). The organo-phosphorus compounds are structural analogues of urea and are some of the most effective inhibitors of urease activity, blocking the active site of the enzyme (Watson, 2005).

In some embodiments, compositions are supplemented with trace metal ions, such as molybdenum ions, iron ions, manganese ions, or combinations of these ions. The concentration of ions in examples of compositions as described herein may between about 0.1 mM and about 50 mM.

Some examples of agricultural compositions may also include additional carriers, besides those involved in the formulation process. Additional carriers may include beta-glucan, carboxylmethyl cellulose (CMC), bacterial extracellular polymeric substance (EPS), sugar, trehalose, maltose, animal milk, milk powder, or other suitable carriers. In some embodiments, peat or planting materials can be used as a carrier, or biopolymers in which a composition is entrapped in the biopolymer can be used as a carrier.

Agricultural compositions described herein may include additional agriculturally acceptable carriers, in addition to the microbial stabilizers, physical stabilizers, and/or buffering agents included in the formulation process. Additional ingredients useful for these embodiments may include at least one member selected from the group consisting of a tackifier, a fungicide, an antibacterial agent, a preservative, a stabilizer, a surfactant, an anti-complex agent, an herbicide, a nematicide, an insecticide, a plant growth regulator, a fertilizer, a rodenticide, a desiccant, a bactericide, a nutrient, or any combination thereof. For example, any of the agricultural compositions described herein can include an agriculturally acceptable carrier (e.g., one or more of a fertilizer such as a non-naturally occurring fertilizer, an adhesion agent such as a non-naturally occurring adhesion agent, and a pesticide such as a non-naturally occurring pesticide). A non-naturally occurring adhesion agent can be, for example, a polymer, copolymer, or synthetic wax. For example, any of the coated plant tissues or the environs thereof described herein can contain such an agriculturally acceptable carrier in their coating. In any of the agricultural compositions or methods described herein, an agriculturally acceptable carrier can be or can include a non-naturally occurring compound (e.g., a non-naturally occurring fertilizer, a non-naturally occurring adhesion agent such as a polymer, copolymer, or synthetic wax, or a non-naturally occurring pesticide). Non-limiting examples of agriculturally acceptable carriers are described below. Additional examples of agriculturally acceptable carriers are known in the art.

In some cases, microbes are mixed with an additional agriculturally acceptable carrier. The carrier can be a solid carrier or liquid carrier, and in various forms including microspheres, powders, emulsions and the like. The carrier may be any one or more of a number of carriers that confer a variety of properties, such as increased stability, wettability, or dispersability. Wetting agents such as natural or synthetic surfactants, which can be nonionic or ionic surfactants, or a combination thereof can be included in the agricultural composition. Suitable formulations that may be prepared include wettable powders, granules, gels, agar strips or pellets, thickeners, and the like, microencapsulated particles, and the like, liquids such as aqueous flowables, aqueous suspensions, water-in-oil emulsions, etc. The formulation may include grain or legume products, for example, ground grain or beans, broth or flour derived from grain or beans, starch, sugar, or oil.

In some embodiments, the agricultural carrier is a soil or a plant growth medium. Other agricultural carriers that may be used include water, fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Agricultural compositions may include food sources for the bacteria, such as barley, rice, or other biological materials such as seed, plant parts, sugar cane bagasse, hulls or stalks from grain processing, ground plant material or wood from building site refuse, sawdust or small fibers from recycling of paper, fabric, or wood.

For example, a fertilizer can be used to help promote the growth or provide nutrients to a plant tissue, e.g., a seed, seedling, or plant. Non-limiting examples of fertilizers include nitrogen, phosphorous, potassium, calcium, sulfur, magnesium, boron, chloride, manganese, iron, zinc, copper, molybdenum, and selenium (or a salt thereof). Additional examples of fertilizers include one or more amino acids, salts, carbohydrates, vitamins, glucose, NaCl, yeast extract, $NH_4H_2PO_4$, $(NH_4)_2SO_4$, glycerol, valine, L-leucine, lactic acid, propionic acid, succinic acid, malic acid, citric acid, KH tartrate, xylose, lyxose, and lecithin. In one embodiment, the agricultural composition can include a tackifier or adherent (referred to as an adhesive agent) to help bind other active agents to a substance (e.g., a surface of a plant tissue or the environs thereof). Such agents are useful for combining microbes with carriers that can contain other compounds (e.g., control agents that are not biologic), to yield a coating composition. Such compositions help create coatings around the plant tissues or the environs thereof to maintain contact between the microbe and other agents with the plant tissues or the environs thereof. In one embodiment, adhesives are selected from the group consisting of: alginate, gums, starches, lecithins, formononetin, polyvinyl alcohol, alkali formononetinate, hesperetin, polyvinyl acetate, cephalins, Gum Arabic, Xanthan Gum, Mineral Oil, Polyethylene Glycol (PEG), Polyvinyl pyrrolidone (PVP), Arabino-galactan, Methyl Cellulose, PEG 400, Chitosan, Polyacrylamide, Polyacrylate, Polyacrylonitrile, Glycerol, Triethylene glycol, Vinyl Acetate, Gellan Gum, Polystyrene, Polyvinyl, Carboxymethyl cellulose, Gum Ghatti, and polyoxyethylene-polyoxybutylene block copolymers.

In some embodiments, the adhesives can be, e.g. a wax such as carnauba wax, beeswax, Chinese wax, shellac wax, spermaceti wax, candelilla wax, castor wax, ouricury wax, and rice bran wax, a polysaccharide (e.g., starch, dextrins, maltodextrins, alginate, and chitosans), a fat, oil, a protein (e.g., gelatin and zeins), gum arables, and shellacs. Adhesive agents can be non-naturally occurring compounds, e.g., polymers, copolymers, and waxes. For example, non-limiting examples of polymers that can be used as an adhesive agent include: polyvinyl acetates, polyvinyl acetate copolymers, ethylene vinyl acetate (EVA) copolymers, polyvinyl alcohols, polyvinyl alcohol copolymers, celluloses (e.g., ethylcelluloses, methylcelluloses, hydroxymethylcelluloses, hydroxypropylcelluloses, and carboxymethylcelluloses), polyvinylpyrolidones, vinyl chloride, vinylidene chloride copolymers, calcium lignosulfonates, acrylic copolymers, polyvinylacrylates, polyethylene oxide, acylamide polymers and copolymers, polyhydroxyethyl acrylate, methylacrylamide monomers, and polychloroprene.

In some embodiments, one or more of the adhesion agents, anti-fungal agents, growth regulation agents, and pesticides (e.g., insecticide) are non-naturally occurring compounds (e.g., in any combination). Additional examples of agriculturally acceptable carriers include dispersants (e.g., polyvinylpyrrolidone/vinyl acetate PVPIVA S-630), surfactants, binders, and filler agents.

The agricultural composition can also contain a surfactant. Non-limiting examples of surfactants include nitrogen-surfactant blends such as Prefer 28 (Cenex), Surf-N(US), Inhance (Brandt), P-28 (Wilfarm) and Patrol (Helena); esterified seed oils include Sun-It II (AmCy), MSO (UAP), Scoil (Agsco), Hasten (Wilfarm) and Mes-100 (Drexel); and organo-silicone surfactants include Silwet L77 (UAP), Silikin (Terra), Dyne-Amic (Helena), Kinetic (Helena), Sylgard 309 (Wilbur-Ellis) and Century (Precision). In one embodiment, the surfactant is present at a concentration of between 0.01% v/v to 10% v/v. In another embodiment, the surfactant is present at a concentration of between 0.1% v/v to 1% v/v.

In some embodiments, a fungicide includes a compound or agent, whether chemical or biological, that can inhibit the growth of a fungus or kill a fungus. In some embodiments, a fungicide includes compounds that may be fungistatic or fungicidal. In some embodiments, a fungicide is a protectant, or agent that is effective predominantly on the surface of plant tissues or the environs thereof. In some embodiments, a fungicide is a protectant, or agent that is effective predominantly on the seed surface, providing protection against seed surface-borne pathogens and providing some level of control of soil-borne pathogens. Non-limiting examples of protectant fungicides include captan, maneb, thiram, or fludioxonil.

In some embodiments, fungicide can be a systemic fungicide, which can be absorbed into the emerging seedling and inhibit or kill the fungus inside host plant tissues. Systemic fungicides used for agricultural treatment include, but are not limited to the following: azoxystrobin, carboxin, mefenoxam, metalaxyl, thiabendazole, trifloxystrobin, and various triazole fungicides, including difenoconazole, ipconazole, tebuconazole, and triticonazole. Mefenoxam and metalaxyl are primarily used to target the water mold fungi *Pythium* and *Phytophthora*. Some fungicides are preferred over others, depending on the plant species, either because of subtle differences in sensitivity of the pathogenic fungal species, or because of the differences in the fungicide distribution or sensitivity of the plants. In some embodiments, fungicide can be a biological control agent, such as a bacterium or fungus. Such organisms may be parasitic to the pathogenic fungi, or secrete toxins or other substances which can kill or otherwise prevent the growth of fungi. Any type of fungicide, particularly ones that are commonly used on plants, can be used as a control agent in an agricultural composition.

In some embodiments, the agricultural composition comprises a control agent which has antibacterial properties. In one embodiment, the control agent with antibacterial properties is selected from the compounds described herein elsewhere. In another embodiment, the compound is Streptomycin, oxytetracycline, oxolinic acid, or gentamicin. Other examples of antibacterial compounds which can be used as part of an agricultural composition include those based on dichlorophene and benzylalcohol hemi formal (Proxel® from ICI or Acticide® RS from Thor Chemie and Kathon® MK 25 from Rohm & Haas) and isothiazolinone derivatives such as alkylisothiazolinones and benzisothiazolinones (Acticide® MBS from Thor Chemie).

In some embodiments, growth regulator is selected from the group consisting of: Abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione phosphorotrithioate, 2,3,5-triiodobenzoic acid, trinexapac-ethyl and uniconazole. Additional non-limiting examples of growth regulators include brassinosteroids, cytokinines (e.g., kinetin and zeatin), auxins (e.g., indolylacetic acid and indolylacetyl aspartate), flavonoids and isoflavanoids (e.g., formononetin and diosmetin), phytoaixins (e.g., glyceolline), and phytoalexin-inducing oligosaccharides (e.g., pectin, chitin, chitosan, polygalacuronic acid, and oligogalacturonic acid), and gibellerins. Such agents are ideally compatible with the agricultural plant tissues or the environs thereof onto which the agricultural composition is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

Some examples of nematode-antagonistic biocontrol agents include ARF18; 30 *Arthrobotrys* spp.; *Chaetomium* spp.; *Cylindrocarpon* spp.; *Exophilia* spp.; *Fusarium* spp.; *Gliocladium* spp.; *Hirsutella* spp.; *Lecanicillium* spp.; *Monacrosporium* spp.; *Myrothecium* spp.; *Neocosmospora* spp.; *Paecilomyces* spp.; *Pochonia* spp.; *Stagonospora* spp.; vesicular-arbuscular mycorrhizal fungi, *Burkholderia* spp.; *Pasteuria* spp., *Brevibacillus* spp.; *Pseudomonas* spp.; and *Rhizobacteria*. Particularly preferred nematode-antagonistic biocontrol agents include ARF18, *Arthrobotrys oligospora, Arthrobotrys dactyloides, Chaetomium globosum, Cylindrocarpon heteronema, Exophilia jeanselmei, Exophilia pisciphila, Fusarium aspergilus, Fusarium solani, Gliocladium catenulatum, Gliocladium roseum, Gliocladium vixens, Hirsutella rhossiliensis, Hirsutella minnesotensis, Lecanicillium lecanii, Monacrosporium drechsleri, Monacrosporium gephyropagum, Myrotehcium verrucaria, Neocosmospora vasinfecta, Paecilomyces lilacinus, Pochonia chlamydosporia, Stagonospora heteroderae, Stagonospora phaseoli*, vesicular-arbuscular mycorrhizal fungi, *Burkholderia cepacia, Pasteuria penetrans, Pasteuria thornei, Pasteuria nishizawae, Pasteuria ramosa, Pastrueia usage, Brevibacillus laterosporus* strain G4, *Pseudomonas fluorescens* and *Rhizobacteria.*

Some examples of nutrients can be selected from the group consisting of a nitrogen fertilizer including, but not limited to Urea, Ammonium nitrate, Ammonium sulfate, Non-pressure nitrogen solutions, Aqua ammonia, Anhydrous ammonia, Ammonium thiosulfate, Sulfur-coated urea, Urea-formaldehydes, IBDU, Polymer-coated urea, Calcium nitrate, Ureaform, and Methylene urea, phosphorous fertilizers such as Diammonium phosphate, Monoammonium phosphate, Ammonium polyphosphate, Concentrated superphosphate and Triple superphosphate, and potassium fertilizers such as Potassium chloride, Potassium sulfate, Potassium-magnesium sulfate, Potassium nitrate. Such compositions can exist as free salts or ions within the agricultural composition. Alternatively, nutrients/fertilizers can be complexed or chelated to provide sustained release over time.

Some examples of rodenticides may include selected from the group of substances consisting of 2-isovalerylindan-1, 3-dione, 4-(quinoxalin-2-ylamino) benzenesulfonamide, alpha-chlorohydrin, aluminum phosphide, antu, arsenous oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin and zinc phosphide.

In the liquid form, for example, solutions or suspensions, bacterial populations can be mixed or suspended in suitable liquid carriers. Suitable liquid diluents or carriers include water, buffered solvents, oils, petroleum distillates, or other liquid carriers.

Solid compositions can be prepared by dispersing the bacterial populations in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

The solid carriers used upon formulation include, for example, mineral carriers such as kaolin clay, pyrophyllite, bentonite, montmorillonite, diatomaceous earth, acid white soil, vermiculite, and pearlite, and inorganic salts such as ammonium sulfate, ammonium phosphate, ammonium nitrate, urea, ammonium chloride, and calcium carbonate. Also, organic fine powders such as wheat flour, wheat bran, and rice bran may be used. The liquid carriers include vegetable oils such as soybean oil and cottonseed oil, glycerol, ethylene glycol, polyethylene glycol, propylene glycol, polypropylene glycol, etc.

The agricultural composition can be fabricated in bioreactors such as continuous stirred tank reactors, batch reactors, and on the farm. In some embodiments, compositions can be stored in a container, such as a jug or in mini bulk. In some embodiments, compositions are stored within an object selected from the group consisting of a bottle, jar, ampule, package, vessel, bag, box, bin, envelope, carton, container, silo, shipping container, truck bed, and/or case.

Additional agricultural composition components for inclusion in the compositions disclosed herein may be found in International Patent Application No. PCT/US2019/039217, the contents of which are herein incorporated by reference in their entirety.

Methods of Formulating Agronomically Stable Liquid Agricultural Compositions

As referenced in the foregoing sections, the present disclosure provides methods of formulating the disclosed agronomically stable liquid agricultural compositions, e.g., methods of improving the stability of liquid agricultural compositions comprising nitrogen-fixing microorganisms. These methods comprise the steps of varying and/or optimizing the agricultural composition along different parameters. In some embodiments, these parameters include the selection of an initial cell density, the choice of microbial stabilizer, the choice of physical stabilizer, and the choice of buffering agent, each of which components is described in detail in its respective section.

In some embodiments, the selection of the initial cell density with an acceptable decay rate, the selection of the buffering agent, the selection of the microbial stabilizer, and the selection of the physical stabilizer are performed in any order. In some embodiments, these selection steps are performed in parallel. In some embodiments, these selection steps are performed serially. In some embodiments, the selection of the initial cell density with an acceptable decay rate is performed first. Selection of the initial cell density is described in detail in the present application disclosure.

In some embodiments, the selections of the buffering agent, microbial stabilizer, and physical stabilizer are performed in tandem through screening assays comprising different combinations. In some embodiments, the selections of any two of the buffering agent, microbial stabilizer, and physical stabilizer are performed in tandem. In some embodiments, when tested in tandem, the method comprises selecting combinations that have an additive or synergistic effect on microbial stability. In some embodiments, the selections of the buffering agent, microbial stabilizer, and physical stabilizer are performed separately through screening assays varying each parameter individually. In some embodiments, the method comprises varying each parameter by assaying two or more possible components of each type. In some embodiments, the method comprises varying each parameter by assaying two or more concentrations of each component.

In some embodiments, the method comprises comparing possible components and/or concentrations of components against each other in one or more screening assays. In some embodiments, the agricultural composition is screened for microbial viability. In some embodiments, microbial viability is measured in CFU/mL via a standard plating assay. In some embodiments, the agricultural composition is screened for colonization potential. In some embodiments, the agricultural composition is screened for colonization potential in log 10 copies per gram of fresh weight via a root colonization assay, as describe in Example 1. In some embodiments, the agricultural composition is screened for toxin accumulation. In some embodiments, the composition is screened for toxin concentrations at a given time point, e.g., the target shelf life time point. In some embodiments, the results of any one or more screening assays are used to select the buffering agent, microbial stabilizer, and physical stabilizer for inclusion in the agricultural composition.

In terms of selection of the buffering agent, in some embodiments, a screening assay compares different buffering agents, different pH levels of buffering agents, different buffering capacities of a given buffering agent, and/or different molarities of buffering agents. In terms of selection of the microbial stabilizer, in some embodiments, a screening assay compares different microbial stabilizers and/or different concentrations of a given microbial stabilizer. In terms of selection of the physical stabilizer, in some embodiments, a screening assay compares different physical stabilizers and/or different concentrations of a given physical stabilizer. In some embodiments, the physical stabilizers and microbial stabilizers are assayed in tandem.

In some embodiments, the method improves the shelf life of the agricultural composition at least 2-fold, at least 3-fold, or at least 4-fold. In some embodiments, the method produces a liquid agricultural composition with a shelf life of at least 30 days, at least 2 months, at least 3 months, at least 4 months, at least 5 months, or at least 6 months.

Methods of Application

The present disclosure provides methods for improving one or more aspects of agricultural plant characteristics through the application of the disclosed agronomically stable agricultural compositions to agricultural plant tissues or the environs thereof. More generally, provided herein are methods of applying the disclosed agricultural compositions to agricultural plant tissues or the environs thereof. Such application may improve one or more characteristics of the agricultural plant. In some embodiments, the methods are used for improving the health, yield, yield variance, stress resistance, growth, or agronomic characteristics of a plant, the methods comprising contacting the plant tissues or the environs thereof before or during planting with the disclosed agronomically stable liquid agricultural compositions.

In some embodiments, provided are methods for providing a diazotrophic bacterium to agricultural plant tissues or the environs thereof, the method comprising formulating an agricultural composition according to the present disclosure and applying said agricultural composition to said agricultural plant tissues or the environs thereof. In some embodiments, the agricultural composition is applied in-furrow. In some embodiments, the agricultural composition is applied as a seed coat. In some embodiments, the present methods are used to increase agricultural plant crop yield and/or decrease agricultural plant crop yield variance.

In some embodiments, the methods comprise applying one or more of the disclosed agricultural compositions to agricultural plant tissues or the environs thereof. In some embodiments, one or more compositions are applied to the surface of a seed, seedling, plant, plant part, or the environs thereof. In some embodiments, one or more compositions are applied as a seed coat on a seed. In some embodiments, one or more compositions are applied as a layer above a surface of a seed, seedling, plant, plant part, or the environs thereof. In some embodiments, one or more compositions is applied to a seed, seedling, plant, plant part, or the environs thereof by spraying, immersing, coating, misting, sprinkling, rolling and/or encapsulating the seed, seedling, plant, plant part, or the environs thereof with the one or more compositions. Similarly, applying the composition to the seed, seedling, plant, plant part, or the environs thereof comprises any means of application, including dipping, rolling, spraying, shaking, immersing, flowing, misting, painting, brushing, and washing. As used herein, the term "applying" or "application" refers to placing or distributing an agricultural composition of the present disclosure onto an area, volume, or quantity of agricultural plant tissues or the environs thereof. For example, application may be accomplished by hand broadcast, machine spreading, brushing, spraying, machine broadcasting, irrigating, top dressing vehicle, and the like, onto agricultural plant tissues or the environs thereof.

In some embodiments, the methods provide an effective amount of a disclosed composition to plant tissues or the environs thereof. In general, an effective amount is an amount sufficient to result in plants with improved traits (e.g. a desired level of nitrogen fixation). An effective amount of the agricultural composition can be used to populate the sub-soil region around seeds, seedlings, plants, or plant parts with viable bacterial growth, or populate the seeds, seedlings, plants, or plant parts with viable bacterial growth.

In some embodiments, the present methods result in a higher concentration of microbes surviving through storage, delivery, and/or transport until planting.

In some embodiments, the agricultural compositions disclosed herein may be applied to any plant part or the environs thereof. Non-limiting examples of plant tissues include a seed, seedling, leaf, cutting, plant, bulb, tuber, root, and rhizomes. In some embodiments, agricultural compositions are applied to a seed. In some embodiments, agricultural compositions are applied to a seedling. In some embodiments, agricultural compositions are applied to plant roots. In some embodiments, agricultural compositions are applied in-furrow.

Concentrations and Rates of Application of Agricultural Compositions

As aforementioned, the agricultural compositions of the present disclosure, which comprise a nitrogen-fixing microorganism, can be applied as an agricultural composition to a seed, seedling, plant, plant part, or the environs thereof.

The microbes of the disclosure can be present on the seed, seedling, plant, plant part, or the environs thereof in a variety of concentrations. In some embodiments, the agricultural composition is applied as a seed treatment in a variety of concentrations. For example, the microbes can be found in a seed treatment at a CFU concentration per seed of: $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, or more. In particular aspects, the seed treatment compositions comprise about $1\times10^4$ to about $1\times10^8$ CFU per seed. In other particular aspects, the seed treatment compositions comprise about $1\times10^5$ to about $1\times10^7$ CFU per seed. In other aspects, the seed treatment compositions comprise about $1\times10^6$ CFU per seed.

In the United States, about 10% of corn acreage is planted at a seed density of above about 36,000 seeds per acre; ⅓ of the corn acreage is planted at a seed density of between about 33,000 to 36,000 seeds per acre; ⅓ of the corn acreage is planted at a seed density of between about 30,000 to 33,000 seeds per acre, and the remainder of the acreage is variable. See, "Corn Seeding Rate Considerations," written by Steve Butzen, available at: www.pioneer.com/home/site/us/agronomy/library/corn-seeding-rate-considerations/

Table 3 below utilizes various CFU concentrations per seed in a contemplated seed treatment embodiment (rows across) and various seed acreage planting densities (1st column: 15K-41K) to calculate the total amount of CFU per acre, which would be utilized in various agricultural scenarios (i.e. seed treatment concentration per seed×seed density planted per acre). Thus, if one were to utilize a seed treatment with $1\times10^6$ CFU per seed and plant 30,000 seeds per acre, then the total CFU content per acre would be $3\times10^{10}$ (i.e. 30K*$1\times10^6$).

TABLE 3

Total CFU Per Acre Calculation for Seed Treatment Embodiments

| Corn Population (i.e. seeds per acre) | 1.00E+02 | 1.00E+03 | 1.00E+04 | 1.00E+05 | 1.00E+06 | 1.00E+07 | 1.00E+08 | 1.00E+09 |
|---|---|---|---|---|---|---|---|---|
| 15,000 | 1.50E+06 | 1.50E+07 | 1.50E+08 | 1.50E+09 | 1.50E+10 | 1.50E+11 | 1.50E+12 | 1.50E+13 |
| 16,000 | 1.60E+06 | 1.60E+07 | 1.60E+08 | 1.60E+09 | 1.60E+10 | 1.60E+11 | 1.60E+12 | 1.60E+13 |
| 17,000 | 1.70E+06 | 1.70E+07 | 1.70E+08 | 1.70E+09 | 1.70E+10 | 1.70E+11 | 1.70E+12 | 1.70E+13 |
| 18,000 | 1.80E+06 | 1.80E+07 | 1.80E+08 | 1.80E+09 | 1.80E+10 | 1.80E+11 | 1.80E+12 | 1.80E+13 |
| 19,000 | 1.90E+06 | 1.90E+07 | 1.90E+08 | 1.90E+09 | 1.90E+10 | 1.90E+11 | 1.90E+12 | 1.90E+13 |

TABLE 3-continued

Total CFU Per Acre Calculation for Seed Treatment Embodiments

| Corn Population (i.e. seeds per acre) | 1.00E+02 | 1.00E+03 | 1.00E+04 | 1.00E+05 | 1.00E+06 | 1.00E+07 | 1.00E+08 | 1.00E+09 |
|---|---|---|---|---|---|---|---|---|
| 20,000 | 2.00E+06 | 2.00E+07 | 2.00E+08 | 2.00E+09 | 2.00E+10 | 2.00E+11 | 2.00E+12 | 2.00E+13 |
| 21,000 | 2.10E+06 | 2.10E+07 | 2.10E+08 | 2.10E+09 | 2.10E+10 | 2.10E+11 | 2.10E+12 | 2.10E+13 |
| 22,000 | 2.20E+06 | 2.20E+07 | 2.20E+08 | 2.20E+09 | 2.20E+10 | 2.20E+11 | 2.20E+12 | 2.20E+13 |
| 23,000 | 2.30E+06 | 2.30E+07 | 2.30E+08 | 2.30E+09 | 2.30E+10 | 2.30E+11 | 2.30E+12 | 2.30E+13 |
| 24,000 | 2.40E+06 | 2.40E+07 | 2.40E+08 | 2.40E+09 | 2.40E+10 | 2.40E+11 | 2.40E+12 | 2.40E+13 |
| 25,000 | 2.50E+06 | 2.50E+07 | 2.50E+08 | 2.50E+09 | 2.50E+10 | 2.50E+11 | 2.50E+12 | 2.50E+13 |
| 26,000 | 2.60E+06 | 2.60E+07 | 2.60E+08 | 2.60E+09 | 2.60E+10 | 2.60E+11 | 2.60E+12 | 2.60E+13 |
| 27,000 | 2.70E+06 | 2.70E+07 | 2.70E+08 | 2.70E+09 | 2.70E+10 | 2.70E+11 | 2.70E+12 | 2.70E+13 |
| 28,000 | 2.80E+06 | 2.80E+07 | 2.80E+08 | 2.80E+09 | 2.80E+10 | 2.80E+11 | 2.80E+12 | 2.80E+13 |
| 29,000 | 2.90E+06 | 2.90E+07 | 2.90E+08 | 2.90E+09 | 2.90E+10 | 2.90E+11 | 2.90E+12 | 2.90E+13 |
| 30,000 | 3.00E+06 | 3.00E+07 | 3.00E+08 | 3.00E+09 | 3.00E+10 | 3.00E+11 | 3.00E+12 | 3.00E+13 |
| 31,000 | 3.10E+06 | 3.10E+07 | 3.10E+08 | 3.10E+09 | 3.10E+10 | 3.10E+11 | 3.10E+12 | 3.10E+13 |
| 32,000 | 3.20E+06 | 3.20E+07 | 3.20E+08 | 3.20E+09 | 3.20E+10 | 3.20E+11 | 3.20E+12 | 3.20E+13 |
| 33,000 | 3.30E+06 | 3.30E+07 | 3.30E+08 | 3.30E+09 | 3.30E+10 | 3.30E+11 | 3.30E+12 | 3.30E+13 |
| 34,000 | 3.40E+06 | 3.40E+07 | 3.40E+08 | 3.40E+09 | 3.40E+10 | 3.40E+11 | 3.40E+12 | 3.40E+13 |
| 35,000 | 3.50E+06 | 3.50E+07 | 3.50E+08 | 3.50E+09 | 3.50E+10 | 3.50E+11 | 3.50E+12 | 3.50E+13 |
| 36,000 | 3.60E+06 | 3.60E+07 | 3.60E+08 | 3.60E+09 | 3.60E+10 | 3.60E+11 | 3.60E+12 | 3.60E+13 |
| 37,000 | 3.70E+06 | 3.70E+07 | 3.70E+08 | 3.70E+09 | 3.70E+10 | 3.70E+11 | 3.70E+12 | 3.70E+13 |
| 38,000 | 3.80E+06 | 3.80E+07 | 3.80E+08 | 3.80E+09 | 3.80E+10 | 3.80E+11 | 3.80E+12 | 3.80E+13 |
| 39,000 | 3.90E+06 | 3.90E+07 | 3.90E+08 | 3.90E+09 | 3.90E+10 | 3.90E+11 | 3.90E+12 | 3.90E+13 |
| 40,000 | 4.00E+06 | 4.00E+07 | 4.00E+08 | 4.00E+09 | 4.00E+10 | 4.00E+11 | 4.00E+12 | 4.00E+13 |
| 41,000 | 4.10E+06 | 4.10E+07 | 4.10E+08 | 4.10E+09 | 4.10E+10 | 4.10E+11 | 4.10E+12 | 4.10E+13 |

For in-furrow embodiments, in some embodiments, the microbes of the disclosure are applied at a CFU concentration per acre of about 1E9-1E13 CFU/acre. In some embodiments, the microbes of the disclosure are applied at a CFU concentration per acre of about: 3E9, 1.5E10, 3E10, 1.5E11, 3E11, 8E11, 1.5E12, 3E12, or more. In some embodiments, the liquid in-furrow compositions are applied at a concentration of between about 3E9 to about 3E12 CFU per acre.

In some aspects, the in-furrow compositions are contained in a liquid agricultural composition. In the liquid in-furrow embodiments, the microbes can be present at a CFU concentration per milliliter of: $1\times10^{1}$, $1\times10^{2}$, $1\times10^{3}$, $1\times10^{4}$, $1\times10^{5}$, $1\times10^{6}$, $1\times10^{7}$, $1\times10^{8}$, $1\times10^{9}$, $1\times10^{10}$, $1\times10^{11}$, $1\times10^{12}$, $1\times10^{13}$, or more. In certain aspects, the liquid in-furrow compositions comprise microbes at a concentration of about $1\times10^{6}$ to about $1\times10^{11}$ CFU per milliliter. In other aspects, the liquid in-furrow compositions comprise microbes at a concentration of about $1\times10^{7}$ to about $1\times10^{10}$ CFU per milliliter. In other aspects, the liquid in-furrow compositions comprise microbes at a concentration of about $1\times10^{8}$ to about $1\times10^{9}$ CFU per milliliter. In other aspects, the liquid in-furrow compositions comprise microbes at a concentration of up to about $1\times10^{13}$ CFU per milliliter.

Improvement of Plant Traits

Methods and agricultural compositions of the present disclosure may be employed to introduce or improve one or more of a variety of desirable traits in a plant through application of the disclosed compositions to a seed, seedling, plant, plant part, or the environs thereof prior to or during planting. Examples of traits that may be introduced or improved include: root biomass, root length, height, shoot length, leaf number, water use efficiency, overall biomass, yield, fruit size, grain size, photosynthesis rate, tolerance to drought, heat tolerance, salt tolerance, resistance to nematode stress, resistance to a fungal pathogen, resistance to a bacterial pathogen, resistance to a viral pathogen, level of a metabolite, and proteome expression. The desirable traits, including height, overall biomass, root and/or shoot biomass, seed germination, seedling survival, photosynthetic efficiency, transpiration rate, seed/fruit number or mass, plant grain or fruit yield, leaf chlorophyll content, photosynthetic rate, root length, or any combination thereof, can be used to measure growth, and compared with the growth rate of reference agricultural plants (e.g., plants without the improved traits) grown under identical conditions. In some embodiments, the methods and agricultural compositions described herein can improve plant traits, such as promoting plant growth, maintaining high chlorophyll content in leaves, increasing fruit or seed numbers, and increasing fruit or seed unit weight. In some embodiments, the plant has improved health, yield, stress resistance, growth, or agronomic characteristics relative to a control plant.

A preferred trait to be introduced or improved is nitrogen fixation, as described herein. A second preferred trait to be introduced or improved is colonization potential, as described herein. In some embodiments, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under the same conditions in the soil. In additional examples, a plant resulting from the methods described herein exhibits a difference in the trait that is at least about 5% greater, for example at least about 5%, at least about 8%, at least about 10%, at least about 15%, at least about 20%, at least about 25%, at least about 30%, at least about 40%, at least about 50%, at least about 60%, at least about 75%, at least about 80%, at least about 80%, at least about 90%, or at least 100%, at least about 200%, at least about 300%, at least about 400% or greater than a reference agricultural plant grown under similar conditions in the soil.

The trait to be improved may be assessed under conditions including the application of one or more biotic or abiotic stressors. Examples of stressors include abiotic stresses (such as heat stress, salt stress, drought stress, cold stress, and low nutrient stress) and biotic stresses (such as nematode stress, insect herbivory stress, fungal pathogen stress, bacterial pathogen stress, and viral pathogen stress).

The trait improved by methods and agricultural compositions of the present disclosure may be nitrogen fixation, including in a plant not previously capable of nitrogen fixation. In some embodiments, bacteria isolated according to a method described herein produce 1% or more (e.g. 2%, 3%, 4%, 5%, 6%, 7%, 8%, 9%, 10%, 15%, 20%, or more) of a plant's nitrogen, which may represent an increase in nitrogen fixation capability of at least 2-fold (e.g. 3-fold, 4-fold, 5-fold, 6-fold, 7-fold, 8-fold, 9-fold, 10-fold, 20-fold, 50-fold, 100-fold, 1000-fold, or more) as compared to bacteria isolated from the first plant before introducing any genetic variation. In some embodiments, the bacteria produce 5% or more of a plant's nitrogen. The desired level of nitrogen fixation may be achieved after repeating the steps of introducing genetic variation, exposure to a plurality of plants, and isolating bacteria from plants with an improved trait one or more times (e.g. 1, 2, 3, 4, 5, 10, 15, 25, or more times). In some embodiments, enhanced levels of nitrogen fixation are achieved in the presence of fertilizer supplemented with glutamine, ammonia, or other chemical source of nitrogen. Methods for assessing degree of nitrogen fixation are known and may be employed to assess the methods described herein.

Agricultural Plant Tissue Compositions

In one aspect, the present disclosure provides agricultural plant tissues, e.g., seeds, comprising the disclosed compositions. In some embodiments, the plant tissues have been subject to a method of application disclosed herein. The methods and agricultural compositions described herein are suitable for plant tissues from any of a variety of plants, such as plants in the genera *Hordeum, Oryza, Zea*, and *Triticeae*. Other non-limiting examples of suitable plants include mosses, lichens, and algae. In some embodiments, the plants have economic, social and/or environmental value, such as food crops, fiber crops, oil crops, plants in the forestry or pulp and paper industries, feedstock for biofuel production and/or ornamental plants. In some embodiments, plants are used to produce economically valuable products such as a grain, a flour, a starch, a syrup, a meal, an oil, a film, a packaging, a nutraceutical product, a pulp, an animal feed, a fish fodder, a bulk material for industrial chemicals, a cereal product, a processed human-food product, a sugar, an alcohol, and/or a protein. Non-limiting examples of crop plants include maize, rice, wheat, barley, sorghum, millet, oats, rye triticale, buckwheat, sweet corn, sugar cane, onions, tomatoes, strawberries, asparagus, canola, soybean, potato, vegetables, cereals, and oilseeds. Plant tissues as provided herein can be genetically modified organisms (GMO), non-GMO, organic, or conventional. In some embodiments, the methods and agricultural compositions described herein are suitable for plant tissues from any of a variety of transgenic plants, non-transgenic plants, and hybrid plants thereof.

In some embodiments, plant tissues that are treated using the methods and agricultural composition disclosed herein include plant tissues from plants that are important or interesting for agriculture, horticulture, biomass for the production of biofuel molecules and other chemicals, and/or forestry. Some examples of these plants may include pineapple, banana, coconut, lily, grasspeas and grass; and dicotyledonous plants, such as, for example, peas, alfalfa, tomatillo, melon, chickpea, chicory, clover, kale, lentil, soybean, tobacco, potato, sweet potato, radish, cabbage, rape, apple trees, grape, cotton, sunflower, thale cress, canola, citrus (including orange, mandarin, kumquat, lemon, lime, grapefruit, tangerine, tangelo, citron, and pomelo), pepper, bean, lettuce, *Panicum virgatum* (switch), *Sorghum bicolor* (sorghum, sudan), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), *Pennisetum glaucum* (pearl millet), *Panicum* spp. *Sorghum* spp., *Miscanthus* spp., *Saccharum* spp., *Erianthus* spp., *Populus* spp., *Secale cereale* (rye), Salix spp. (willow), *Eucalyptus* spp. (*eucalyptus*), *Triticosecale* spp. (triticum-25 wheat X rye), *bamboo, Carthamus tinctorius* (safflower), *Jatropha curcas* (Jatropha), *Ricinus communis* (castor), *Elaeis guineensis* (oil palm), *Phoenix dactylifera* (date palm), *Archontophoenix cunninghamiana* (king palm), *Syagrus romanzoffiana* (queen palm), *Linum usitatissimum* (flax), *Brassica juncea, Manihot esculenta* (cassaya), *Lycopersicon esculentum* (tomato), *Lactuca saliva* (lettuce), *Musa paradisiaca* (banana), *Solanum tuberosum* (potato), *Brassica oleracea* (broccoli, cauliflower, brussel sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Papaver somniferum* (opium poppy), *Papaver orientale, Taxus baccata, Taxus brevifolia, Artemisia annua, Cannabis saliva, Camptotheca acuminate, Catharanthus roseus, Vinca rosea, Cinchona officinalis, Coichicum autumnale, Veratrum californica, Digitalis lanata, Digitalis purpurea, Dioscorea* 5 spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii, Tanacetum parthenium, Parthenium argentatum* (guayule), *Hevea* spp. (rubber), *Mentha spicata* (mint), *Mentha piperita* (mint), *Bixa orellana, Alstroemeria* spp., *Rosa* spp. (rose), *Dianthus caryophyllus* (carnation), *Petunia* spp. (*petunia*), Poinsettia *pulcherrima* (poinsettia), *Nicotiana tabacum* (tobacco), *Lupinus albus* (lupin), *Uniola paniculata* (oats), *Hordeum vulgare* (barley), and *Lolium* spp. (rye).

In some embodiments, plant tissues or plant parts, e.g., seeds, from a monocotyledonous plant are treated. Monocotyledonous plants belong to the orders of the Alismatales, Arales, Arecales, Bromeliales, Commelinales, Cyclanthales, Cyperales, Eriocaulales, Hydrocharitales, Juncales, Lilliales, Najadales, Orchidales, Pandanales, Poales, Restionales, Triuridales, Typhales, and Zingiberales. Plants belonging to the class of the Gymnospermae are Cycadales, Ginkgoales, Gnetales, and Pinales. In some embodiments, the monocotyledonous plant can be selected from the group consisting of a maize, rice, wheat, barley, and sugarcane.

In some embodiments, plant tissues or plant parts, e.g., seeds, from a dicotyledonous plant are treated, including those belonging to the orders of the Aristochiales, Asterales, Batales, Campanulales, Capparales, Caryophyllales, Casuarinales, Celastrales, Cornales, Diapensales, Dilleniales, Dipsacales, Ebenales, Ericales, Eucomiales, Euphorbiales, Fabales, Fagales, Gentianales, Geraniales, Haloragales, Hamamelidales, Middles, Juglandales, Lamiales, Laurales, Lecythidales, Leitneriales, Magniolales, Malvales, Myricales, Myrtales, Nymphaeales, Papeverales, Piperales, Plantaginales, Plumb aginales, Podostemales, Polemoniales, Polygalales, Polygonales, Primulales, Proteales, Rafflesiales, Ranunculales, Rhamnales, Rosales, Rubiales, Salicales, Santales, Sapindales, Sarraceniaceae, Scrophulariales, Theales, Trochodendrales, Umbellales, Urticales, and Violates. In some embodiments, the dicotyledonous plant can be selected from the group consisting of cotton, soybean, pepper, and tomato.

In some embodiments, the plant to be improved is not readily amenable to experimental conditions. For example, a crop plant may take too long to grow enough to practically assess an improved trait serially over multiple iterations. Accordingly, a first plant from which bacteria are initially isolated, and/or the plurality of plants to which genetically manipulated bacteria are applied may be a model plant, such as a plant more amenable to evaluation under desired conditions. Non-limiting examples of model plants include *Setaria, Brachypodium*, and *Arabidopsis*. Ability of bacteria isolated according to a method of the disclosure using a model plant may then be applied to plant tissues, e.g., seeds, of a plant of another type (e.g. a crop plant) to confirm conferral of the improved trait.

Traits that may be improved by the methods and agricultural compositions disclosed herein include any observable characteristic of the seed or the plant resulting therefrom, including, for example, growth rate, height, weight, color, taste, smell, changes in the production of one or more compounds by the plant (including for example, metabolites, proteins, drugs, carbohydrates, oils, and any other compounds). Selecting agricultural plant tissues based on genotypic information is also envisaged (for example, including the pattern of plant gene expression in response to the bacteria, or identifying the presence of genetic markers, such as those associated with increased nitrogen fixation). Plants from which the plant tissues are obtained may also be selected based on the absence, suppression or inhibition of a certain feature or trait (such as an undesirable feature or trait) as opposed to the presence of a certain feature or trait (such as a desirable feature or trait). Additional plants and seeds acceptable for use within the methods and compositions of the present disclosure may be found in International Application Nos. PCT/US2019/039528 and PCT/US2019/039217, the contents of each of which are herein incorporated by reference in their entirety.

Non-Genetically Modified Maize

The methods and agricultural compositions described herein are suitable for any of a variety of non-genetically modified maize plants or parts thereof. In some embodiments, the corn is organic. The methods and agricultural compositions described herein are suitable for plant tissues, e.g., seeds, or for in-furrow application, to any non-genetically modified hybrids, varieties, lineages, etc. In some embodiments, corn varieties generally fall under six categories: sweet corn, flint corn, popcorn, dent corn, pod corn, and flour corn.

Genetically Modified Maize

The methods and agricultural compositions described herein are suitable for plant tissues, e.g., seeds, or for in-furrow application, of any of a hybrid, variety, lineage, etc. of genetically modified maize plants or part thereof.

Furthermore, the methods and agricultural compositions described herein are suitable for any of the following genetically modified maize events, which have been approved in one or more countries, or any new genetically modified corn event, which may include Bt traits, glufosinate resistance, glyphosate resistance, etc.: 32138 (32138 SPT Maintainer), 3272 (ENOGEN), 3272×Bt11, 3272×bt11×GA21, 3272×Bt11×MIR604, 3272×Bt11×MIR604×GA21, 3272×Bt11×MIR604×TC1507×5307×GA21, 3272×GA21, 3272×MIR604, 3272×MIR604×GA21, 4114, 5307 (AGRISURE Duracade), 5307×GA21, 5307×MIR604×Bt11×TC1507×GA21 (AGRISURE Duracade 5122), 5307×MIR604×Bt11×TC1507×GA21×MIR162 (AGRISURE Duracade 5222), 59122 (Herculex RW), 59122×DAS40278, 59122×GA21, 59122×MIR604, 59122×MIR604×GA21, 59122×MIR604×TC1507, 59122×MIR604×TC1507×GA21, 59122×MON810, 59122×MON810×MIR604, 59122×MON810×NK603, 59122×MON810×NK603×MIR604, 59122×MON88017, 59122×MON88017×DAS40278, 59122×NK603 (Herculex RW ROUNDUP READY 2), 59122×NK603×MIR604, 59122×TC1507×GA21, 676, 678, 680, 3751 IR, 98140, 98140×59122, 98140×TC1507, 98140×TC1507×59122, Bt10 (Bt10), Bt11 [X4334CBR, X4734CBR] (AGRISURE CB/LL), Bt11×5307, Bt11×5307×GA21, Bt11×59122×MIR604, Br11×59122×MIR604×GA21, Bt11×59122×MIR604×TC1507, M53, M56, DAS-59122-7, Bt11×59122×MIR604×TC1507×GA21, Bt11×59122×TC1507, TC1507×DAS-59122-7, Bt11×59122×TC1507×GA21, Bt11×GA21 (AGRISURE GT/CB/LL), Bt11×MIR162 (AGRISURE Viptera 2100), BT11×MIR162×5307, Bt11×MIR162×5307×GA21, Bt11×MIR162×GA21 (AGRISURE Viptera 3110), Bt11×MIR162×MIR604 (AGRISURE Viptera 3100), Bt11×MIR162×MIR604×5307, Bt11×MIR162×MIR604×5307×GA21, Bt11×MIR162×MIR604×GA21 (AGRISURE Viptera 3111/AGRISURE Viptera 4), Bt11, MIR162×MIR604×MON89034×5307×GA21, Bt11×MIR162×MIR604×TC1507, Bt11×MIR162×MIR604×TC1507×5307, Bt11×MIR162×MIR604×TC1507×GA21, Bt11×MIR162×MON89034, Bt11×MIR162×MON89034×GA21, Bt11×MIR162×TC1507, Bt11×MIR162×TC1507×5307, Bt11×MIR162×TC1507×5307×GA21, Bt11×MR162×TC1507×GA21 (AGRISURE Viptera 3220), BT11×MIR604 (Agrisure BC/LL/RW), Bt11×MIR604×5307, Bt11×MIR604×5307×GA21, Bt11×MIR604×GA21, Bt11×MIR604×TC1507, Bt11×MIR604×TC1507×5307, Bt11×MIR604×TC1507×GA21, Bt11×MON89034×GA21, Bt11×TC1507, Bt11×TC1507×5307, Bt11×TC1507×GA21, Bt176 [176] (NaturGard KnockOut/Maximizer), BVLA430101, CBH-351 (STARLINK Maize), DAS40278 (ENLIST Maize), DAS40278×NK603, DBT418 (Bt Xtra Maize), DLL25 [B16], GA21 (ROUNDUP READY Maize/AGRISURE GT), GA21×MON810 (ROUNDUP READY Yieldgard Maize), GA21×T25, HCEM485, LY038 (MAVERA Maize), LY038×MON810 (MAVERA Yieldgard Maize), MIR162 (AGRISURE Viptera), MIR162×5307, MIR162×5307×GA21, MIR162×GA21, MIR162×MIR604, MIR162×MIR604×5307, MIR162×MIR604×5307×GA21, MIR162×MIR604×GA21, MIR162×MIR604×TC1507×5307, MIR162×MIR604×TC1507×5307×GA21, MIR162×MIR604×TC1507×GA21, MIR162×MON89034, MIR162×NK603, MIR162×TC1507, MIR162×TC1507×5307, MIR162×TC1507×5307×GA21, MIR162×TC1507×GA21, MIR604 (AGRISURE RW), MIR604×5307, MIR604×5307×GA21, MIR604×GA21 (AGRISURE GT/RW), MIR604×NK603, MIR604×TC1507, MIR604×TC1507×5307, MIR604×TC1507×5307×GA21, MIR604×TC1507×GA21, MON801 [MON80100], MON802, MON809, MON810 (YIELDGARD, MAIZEGARD), MON810×MIR162, MON810×MIR162×NK603, MON810×MIR604, MON810×MON88017 (YIELDGARD VT Triple), MON810×NK603×MIR604, MON832 (ROUNDUP READY Maize), MON863 (YIELDGARD Rootworm RW, MAXGARD), MON863×MON810 (YIELDGARD Plus), MON863×MON810×NK603 (YIELDGARD Plus with RR), MON863×NK603 (YIELDGARD RW+RR), MON87403, MON87411, MON87419, MON87427 (ROUNDUP READY Maize), MON87427×59122, MON87427×MON88017, MON87427×MON88017×59122, MON87427×MON89034, MON87427×MON89034×59122, MON87427×MON89034×MIR162×MON87411, MON87427×MON89034×MON88017, MON87427×MON89034×MON88017×59122, MON87427×MON89034×NK603, MON87427×MON89034×TC1507, MON87427×MON89034×TC1507×59122, MON87427×MON89034×TC1507×MON87411×59122, MON87427×MON89034×TC1507×MON87411×59122×DAS40278, MON87427×MON89034×TC1507×MON88017, MON87427×MON89034×MIR162×NK603, MON87427×MON89034×TC1507×MON88017×59122, MON87427×TC1507, MON87427×TC1507×59122, MON87427×TC1507×MON88017, MON87427×TC1507×MON88017×59122, MON87460 (GENUITY DROUGHTGARD), MON87460×MON88017, MON87460×MON89034×MON88017, MON87460×MON89034×NK603, MON87460×NK603, MON88017, MON88017×DAS40278, MON89034, MON89034×59122, MON89034×59122×DAS40278, MON89034×59122×MON88017, MON89034×59122×MON88017×DAS40278, MON89034×DAS40278, MON89034×MON87460, MON89034×MON88017 (GENUITY VT Triple Pro), MON89034×MON88017×DAS40278, MON89034×NK603 (GENUITY VT Double Pro), MON89034×NK603×DAS40278, MON89034×TC1507, MON89034×TC1507×59122, MON89034×TC1507×59122×DAS40278, MON89034×TC1507×DAS40278, MON89034×TC1507×MON88017, MON89034×TC1507×MON88017×59122 (GENUITY SMARTSTAX), MON89034×TC1507×MON88017×59122×DAS40278, MON89034×TC1507×MON88017×DAS40278, MON89034×TC1507×NK603 (POWER CORE), MON89034×TC1507×NK603×DAS40278, MON89034×TC1507×NK603×MIR162, MON89034×TC1507×NK603×MIR162×DAS40278, MON89034×GA21, MS3 (INVIGOR Maize), MS6 (INVIGOR Maize), MZHGOJG, MZIRO98, NK603 (ROUNDUP READY 2 Maize), NK603×MON810×4114×MIR604, NK603×MON810 (YIELDGARD CB+RR), NK603×T25 (ROUNDUP READY LIBERTY LINK Maize), T14 (LIBERTY LINK Maize), T25 (LIBERTY LINK Maize), T25×MON810 (LIBERTY LINK YIELDGARD Maize), TC1507 (HERCULEX I, HERCULEX CB), TC1507×59122×MON810×MIR604×NK603 (OPTIMUM INTRASECT XTREME), TC1507×MON810×MIR604×NK603, TC1507×5307, TC1507×5307×GA21, TC1507×59122 (HERCULEX XTRA), TC1507×59122×DAS40278, TC1507×59122×MON810, TC1507×59122×MON810×MIR604, TC1507×59122×MON810×NK603 (OPTIMUM INTRASECT XTRA), TC1507×59122×MON88017, TC1507×59122×MON88017×DAS40278, TC1507×59122×NK603 (HERCULEX XTRA RR), TC1507×59122×NK603×MIR604, TC1507×DAS40278, TC1507×GA21, TC1507×MIR162×NK603, TC1507×MIR604×NK603 (OPTIMUM TRISECT), TC1507×MON810, TC1507×MON810×MIR162, TC1507×MON810×MIR162×NK603, TC1507×MON810×MIR604, TC1507×MON810×NK603 (OPTIMUM INTRASECT), TC1507×MON810×NK603×MIR604, TC1507×MON88017, TC1507×MON88017×DAS40278, TC1507×NK603 (HERCULEX I RR), TC1507×NK603×DAS40278, TC6275, and VCO-01981-5.

Remodeled Microbes of the Disclosure

The present disclosure provides engineered microbes for use in the disclosed agricultural compositions and methods. In some embodiments, the microbes are non-intergeneric remodeled microbes. The term "non-intergeneric" indicates that the genetic variations introduced into the host do not contain nucleic acid sequences from outside the host genus (e.g., no transgenic DNA). Therefore, in some embodiments, the microbes are not transgenic. For example, for non-transgenic microbes with varied promoters, promoters for promoter swapping are selected from within the microbe's genome, or genus.

Exemplary non-intergeneric genetic variations include a mutation in the gene of interest that may improve the function of the protein encoded by the gene; a constitutionally active promoter that can replace the endogenous promoter of the gene of interest to increase the expression of the gene; a mutation that will inactivate the gene of interest; the insertion of a promoter from within the host's genome into a heterologous location, e.g. insertion of the promoter into a gene that results in inactivation of said gene and upregulation of a downstream gene; and the like. The mutations can be point mutations, insertions, and/or deletions (full or partial deletion of the gene). For example, in some embodiments, to improve the nitrogen fixation activity of the host microbe, a genetic variation may comprise an inactivating mutation of the nifL gene (negative regulator of nitrogen fixation pathway) and/or comprise replacing the endogenous promoter of the nifA and/or nifH gene (nitrogenase iron protein that catalyzes a key reaction to fix atmospheric nitrogen) with a constitutionally active promoter that will drive the expression of the nifA and/or nifH gene constitutively. Additional genetic variations of interest are described further in the foregoing "Genetic alterations" section.

Exemplary wild-type and modified sequences of microbes for use in the agricultural compositions and methods of the present disclosure are provided in Table 4.

TABLE 4

Wild-type and modified sequences for use in microbes of the disclosure

| SEQ ID NO | Genotype | Description |
|---|---|---|
| SEQ ID NO 1 | 16S | N/A |
| SEQ ID NO 2 | nifH | N/A |
| SEQ ID NO 3 | nifD1 | 1 of 2 unique genes annotated as nifD in 63 genome |
| SEQ ID NO 4 | nifD2 | 2 of 2 unique genes annotated as nifD in 63 genome |

TABLE 4-continued

Wild-type and modified sequences for use in microbes of the disclosure

| SEQ ID NO | Genotype | Description |
|---|---|---|
| SEQ ID NO 5 | nifK1 | 1 of 2 unique genes annotated as nifK in 63 genome |
| SEQ ID NO 6 | nifK2 | 2 of 2 unique genes annotated as nifK in 63 genome |
| SEQ ID NO 7 | nifL | N/A |
| SEQ ID NO 8 | nifA | N/A |
| SEQ ID NO 9 | glnE | N/A |
| SEQ ID NO 10 | amtB | N/A |
| SEQ ID NO 11 | PinfC | 500 bp immediately upstream of the ATG start codon of the infC gene |
| SEQ ID NO 12 | 16S | N/A |
| SEQ ID NO 13 | nifH1 | 1 of 2 unique genes annotated as nifH in 137 genome |
| SEQ ID NO 14 | nifH2 | 2 of 2 unique genes annotated as nifH in 137 genome |
| SEQ ID NO 15 | nifD1 | 1 of 2 unique genes annotated as nifD in 137 genome |
| SEQ ID NO 16 | nifD2 | 2 of 2 unique genes annotated as nifD in 137 genome |
| SEQ ID NO 17 | nifK1 | 1 of 2 unique genes annotated as nifK in 137 genome |
| SEQ ID NO 18 | nifK2 | 2 of 2 unique genes annotated as nifK in 137 genome |
| SEQ ID NO 19 | nifL | N/A |
| SEQ ID NO 20 | nifA | N/A |
| SEQ ID NO 21 | glnE | N/A |
| SEQ ID NO 22 | PinfC | 500 bp immediately upstream of the TTG start codon of infC |
| SEQ ID NO 23 | amtB | N/A |
| SEQ ID NO 24 | Prm8.2 | internal promoter located in nlpI gene; 299 bp starting at 81 bp after the A of the ATG of the nlpI gene |
| SEQ ID NO 25 | Prm6.2 | 300 bp upstream of the secE gene starting at 57 bp upstream of the A of the ATG of secE |
| SEQ ID NO 26 | Prm1.2 | 400 bp immediately upstream of the ATG of cspE gene |
| SEQ ID NO 27 | 16S | N/A |
| SEQ ID NO 28 | nifH | N/A |
| SEQ ID NO 29 | nifD1 | 1 of 2 unique genes annotated as nifD in 728 genome |
| SEQ ID NO 30 | nifD2 | 2 of 2 unique genes annotated as nifD in 728 genome |
| SEQ ID NO 31 | nifK1 | 1 of 2 unique genes annotated as nifK in 728 genome |
| SEQ ID NO 32 | nifK2 | 2 of 2 unique genes annotated as nifK in 728 genome |
| SEQ ID NO 33 | nifL | N/A |
| SEQ ID NO 34 | nifA | N/A |
| SEQ ID NO 35 | glnE | N/A |
| SEQ ID NO 36 | amtB | N/A |
| SEQ ID NO 37 | 16S | N/A |
| SEQ ID NO 38 | 16S | N/A |
| SEQ ID NO 39 | 16S | N/A |
| SEQ ID NO 40 | 16S | N/A |
| SEQ ID NO 41 | nifH | N/A |
| SEQ ID | Dinitrogenase | N/A |

TABLE 4-continued

Wild-type and modified sequences for use in microbes of the disclosure

| SEQ ID NO | Genotype | Description |
|---|---|---|
| NO 42 | iron-molybdenum cofactor CDS | |
| SEQ ID NO 43 | nifD1 | N/A |
| SEQ ID NO 44 | nifD2 | N/A |
| SEQ ID NO 45 | nifK1 | N/A |
| SEQ ID NO 46 | nifK2 | N/A |
| SEQ ID NO 47 | nifL | N/A |
| SEQ ID NO 48 | nifA | N/A |
| SEQ ID NO 49 | glnE | N/A |
| SEQ ID NO 50 | amtB | N/A |
| SEQ ID NO 51 | PinfC | 498 bp immediately upstream of the ATG of the infC gene |
| SEQ ID NO 52 | 16S | N/A |
| SEQ ID NO 53 | nifH | N/A |
| SEQ ID NO 54 | nifD1 | 1 of 2 unique genes annotated as nifD in 126585 genome |
| SEQ ID NO 55 | nifD2 | 2 of 2 unique genes annotated as nifD in 126585 genome |
| SEQ ID NO 56 | nifK1 | 1 of 2 unique genes annotated as nifK in 126585 genome |
| SEQ ID NO 57 | nifK2 | 2 of 2 unique genes annotated as nifK in 126585 genome |
| SEQ ID NO 58 | nifL | N/A |
| SEQ ID NO 59 | nifA | N/A |
| SEQ ID NO 60 | glnE | N/A |
| SEQ ID NO 61 | amtB | N/A |
| SEQ ID NO 62 | PinfC | 500 bp immediately upstream of the ATG start codon of the infC gene |
| SEQ ID NO 63 | Prm1 | 348 bp includes the 319 bp immediately upstream of the ATG start codon of the 1 pp gene and the first 29 bp of the 1 pp gene |
| SEQ ID NO 64 | Prm7 | 339 bp upstream of the sspA gene, ending at 46 bp upstream of the ATG of the sspA gene |
| SEQ ID NO 65 | 16S | N/A |
| SEQ ID NO 66 | nifH | N/A |
| SEQ ID NO 67 | nifD1 | 1 of 2 unique genes annotated as nifD in 1113 genome |
| SEQ ID NO 68 | nifD2 | 2 of 2 unique genes annotated as nifD in 1113 genome |
| SEQ ID NO 69 | nifK | N/A |
| SEQ ID NO 70 | nifL | N/A |
| SEQ ID NO 71 | nifA partial gene | due to a gap in the sequence assembly, we can only identify a partial gene from the 1113 genome |
| SEQ ID NO 72 | glnE | N/A |
| SEQ ID NO 73 | 16S | |
| SEQ ID NO 74 | nifH | |
| SEQ ID NO 75 | nifD1 | 1 of 2 unique genes annotated as nifD in 1116 genome |
| SEQ ID NO 76 | nifD2 | 2 of 2 unique genes annotated as nifD in 1116 genome |

TABLE 4-continued

| Wild-type and modified sequences for use in microbes of the disclosure | | |
|---|---|---|
| SEQ ID NO | Genotype | Description |
| SEQ ID NO 77 | nifK1 | 1 of 2 unique genes annotated as nifK in 1116 genome |
| SEQ ID NO 78 | nifK2 | 2 of 2 unique genes annotated as nifK in 1116 genome |
| SEQ ID NO 79 | nifL | N/A |
| SEQ ID NO 80 | nifA | N/A |
| SEQ ID NO 81 | glnE | N/A |
| SEQ ID NO 82 | amtB | N/A |
| SEQ ID NO 83 | 16S | N/A |
| SEQ ID NO 84 | nifH | N/A |
| SEQ ID NO 85 | nifD1 | 1 of 2 unique genes annotated as nifD in 1293 genome |
| SEQ ID NO 86 | nifD2 | 2 of 2 unique genes annotated as nifD in 1293 genome |
| SEQ ID NO 87 | nifK | 1 of 2 unique genes annotated as nifK in 1293 genome |
| SEQ ID NO 88 | nifK1 | 2 of 2 unique genes annotated as nifK in 1293 genome |
| SEQ ID NO 89 | nifA | N/A |
| SEQ ID NO 90 | glnE | N/A |
| SEQ ID NO 91 | amtB1 | 1 of 2 unique genes annotated as amtB in 1293 genome |
| SEQ ID NO 92 | amtB2 | 2 of 2 unique genes annotated as amtB in 1293 genome |
| SEQ ID NO 93 | ΔnifL:PinfC | starting at 24 bp after the A of the ATG start codon, 1375 bp of nifL have been deleted and replaced with the 1021 PinfC promoter sequence |
| SEQ ID NO 94 | ΔnifL:PinfC with 500 bp flank | starting at 24 bp after the A of the ATG start codon, 1375 bp of nifL have been deleted and replaced with the 1021 PinfC promoter sequence; 500 bp flanking the nifL gene upstream and downstream are included |
| SEQ ID NO 95 | glnEΔAR-2 | glnE gene with 1673 bp immediately downstream of the ATG start codon deleted, resulting in a truncated glnE protein lacking the adenylyl-removing (AR) domain |
| SEQ ID NO 96 | glnEΔAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included |
| SEQ ID NO 97 | ΔnifL::Prm1 | starting at 24 bp after the A of the ATG start codon, 1375 bp of nifL have been deleted and replaced with the 1021 Prm1 promoter sequence |
| SEQ ID NO 98 | ΔnifL::Prm1 with 500 bp flank | starting at 24 bp after the A of the ATG start codon, 1375 bp of nifL have been deleted and replaced with the 1021 rml promoter sequence; 500 bp flanking the nifL gene upstream and downstream are included |
| SEQ ID NO 99 | glnEΔAR-2 | glnE gene with 1673 bp immediately downstream of the ATG start codon deleted, resulting in a truncated glnE protein lacking the adenylyl-removing (AR) domain |
| SEQ ID NO 100 | glnEΔAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included |
| SEQ ID NO 101 | ΔnifL::Prm1 | starting at 24 bp after the A of the ATG start codon, 1375 bp of nifL have been deleted and replaced with the 1021 Prm1 promoter sequence |
| SEQ ID NO 102 | ΔnifL::Prm1 with 500 bp flank | starting at 24 bp after the A of the ATG start codon, 1375 bp of nifL have been deleted and replaced with the 1021 rml promoter sequence; 500 bp flanking the nifL gene upstream and downstream are included |
| SEQ ID NO 103 | glnEΔAR-2 | glnE gene with 1673 bp immediately downstream of the ATG start codon deleted, resulting in a truncated glnE protein lacking the adenylyl-removing (AR) domain |

TABLE 4-continued

Wild-type and modified sequences for use in microbes of the disclosure

| SEQ ID NO | Genotype | Description |
|---|---|---|
| SEQ ID NO 104 | glnEΔAR-2 with 500 bp flank | glnE gene with 1673 bp immediately downstream of the ATG start codon deleted, resulting in a truncated glnE protein lacking the adenylyl-removing (AR) domain; 500 bp flanking the glnE gene upstream and downstream are included |
| SEQ ID NO 105 | ΔnifL::Prm7 | starting at 24 bp after the A of the ATG start codon, 1375 bp of nifL have been deleted and replaced with the 1021 Prm7 promoter sequence |
| SEQ ID NO 106 | ΔnifL::Prm7 with 500 bp flank | starting at 24 bp after the A of the ATG start codon, 1375 bp of nifL have been deleted and replaced with the 1021 rm7 promoter sequence; 500 bp flanking the nifL gene upstream and downstream are included |
| SEQ ID NO 107 | glnEΔAR-2 | glnE gene with 1290 bp immediately downstream of the ATG start codon deleted, resulting in a truncated glnE protein lacking the adenylyl-removing (AR) domain |
| SEQ ID NO 108 | glnEΔAR-2 with 500 bp flank | glnE gene with 1290 bp immediately downstream of the ATG start codon deleted, resulting in a truncated glnE protein lacking the adenylyl-removing (AR) domain; 500 bp flanking the glnE gene upstream and downstream are included |
| SEQ ID NO 109 | ΔnifL:PinfC | starting at 24 bp after the A of the ATG start codon, 1372 bp of nifL have been deleted and replaced with the 137 PinfC promoter sequence |
| SEQ ID NO 110 | ΔnifL:PinfC with 500 bp flank | starting at 24 bp after the A of the ATG start codon, 1372 bp of nifL have been deleted and replaced with the 137 PinfC promoter sequence; 500 bp flanking the nifL gene upstream and downstream are included |
| SEQ ID NO ill | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain |
| SEQ ID NO 112 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain; 500 bp flanking the nifL gene upstream and downstream are included |
| SEQ ID NO 113 | ΔnifL::Prm8.2 | starting at 24 bp after the A of the ATG start codon, 1372 bp of nifL have been deleted and replaced with the 137 Prm8.2 promoter sequence |
| SEQ ID NO 114 | ΔnifL::Prm8.2 with 500 bp flank | starting at 24 bp after the A of the ATG start codon, 1372 bp of nifL have been deleted and replaced with the 137 Prm8.2 promoter sequence; 500 bp flanking the nifL gene upstream and downstream are included |
| SEQ ID NO 115 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain |
| SEQ ID NO 116 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain; 500 bp flanking the nifL gene upstream and downstream are included |
| SEQ ID NO 117 | ΔnifL::Prm6.2 | starting at 24 bp after the A of the ATG start codon, 1372 bp of nifL have been deleted and replaced with the 137 Prm6.2 promoter sequence |
| SEQ ID NO | Genotype | Description |
| SEQ ID NO 118 | ΔnifL::Prm6.2 with 500 bp flank | starting at 24 bp after the A of the ATG start codon, 1372 bp of nifL have been deleted and replaced with the 137 Prm6.2 promoter sequence; 500 bp flanking the nifL gene upstream and downstream are included |
| SEQ ID NO 119 | ΔnifL::Prm1.2 | starting at 24 bp after the A of the ATG start codon, 1372 bp of nifL have been deleted and replaced with the 137 Prm1.2 promoter sequence |
| SEQ ID NO 120 | ΔnifL::Prm1.2 with 500 bp flank | starting at 24 bp after the A of the ATG start codon, 1372 bp of nifL have been deleted and replaced with the 137 Prm1.2 promoter sequence; 500 bp flanking the nifL gene upstream and downstream are included |
| SEQ ID NO 121 | glnEΔAR-2 36 bp deletion | glnE gene with 1290 bp immediately downstream of the ATG start codon deleted AND 36 bp deleted beginning at 1472 bp downstream of the start codon, resulting in a |

TABLE 4-continued

Wild-type and modified sequences for use in microbes of the disclosure

| SEQ ID NO | Genotype | Description |
|---|---|---|
| | | truncated glnE protein lacking the adenylyl-removing (AR) domain |
| SEQ ID NO 122 | glnEΔAR-2 36 bp deletion | glnE gene with 1290 bp immediately downstream of the ATG start codon deleted AND 36 bp deleted beginning at 1472 bp downstream of the start codon, resulting in a truncated glnE protein lacking the adenylyl-removing (AR) domain; 500 bp flanking the nifL gene upstream and downstream are included |
| SEQ ID NO 123 | ΔnifL:PinfC | starting at 24 bp after the A of the ATG start codon, 1372 bp of nifL have been deleted and replaced with the 137 PinfC promoter sequence |
| SEQ ID NO 124 | ΔnifL:PinfC with 500 bp flank | starting at 24 bp after the A of the ATG start codon, 1372 bp of nifL have been deleted and replaced with the 137 PinfC promoter sequence; 500 bp flanking the nifL gene upstream and downstream are included |
| SEQ ID NO 125 | glnEΔAR-2 | glnE gene with 1290 bp immediately downstream of the ATG start codon deleted, resulting in a truncated glnE protein lacking the adenylyl-removing (AR) domain |
| SEQ ID NO 126 | glnEΔAR-2 with 500 bp flank | glnE gene with 1290 bp immediately downstream of the ATG start codon deleted, resulting in a truncated glnE protein lacking the adenylyl-removing (AR) domain; 500 bp flanking the glnE gene upstream and downstream are included |
| SEQ ID NO 127 | glnEΔAR-2 | glnE gene with 1650 bp immediately downstream of the ATG start codon deleted, resulting in a truncated glnE protein lacking the adenylyl-removing (AR) domain |
| SEQ ID NO 128 | glnEΔAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included |
| SEQ ID NO 129 | ΔnifL::Prm6.1 | starting at 221 bp after the A of the ATG start codon, 845 bp of nifL have been deleted and replaced with the NCMA 201701003 Prm6.1 promoter sequence |
| SEQ ID NO 130 | ΔnifL::Prm6.1 with 500 bp flank | starting at 221 bp after the A of the ATG start codon, 845 bp of nifL have been deleted and replaced with the NCMA 201701003 Prm6.1promoter sequence; 500 bp flanking the nifL gene upstream and downstream are included |
| SEQ ID NO 131 | ΔnifL::Prm6.1 | starting at 221 bp after the A of the ATG start codon, 845 bp of nifL have been deleted and replaced with the NCMA 201701003 Prm6.1 promoter sequence |
| SEQ ID NO 132 | ΔnifL::Prm6.1 with 500 bp flank | starting at 221 bp after the A of the ATG start codon, 845 bp of nifL have been deleted and replaced with the NCMA 201701003 Prm6.1promoter sequence; 500 bp flanking the nifL gene upstream and downstream are included |
| SEQ ID NO 133 | ΔnifL::Prm7.1 | starting at 221 bp after the A of the ATG start codon, 845 bp of nifL have been deleted and replaced with the NCMA 201701003 Prm7.1 promoter sequence |
| SEQ ID NO 134 | ΔnifL::Prm7.1 with 500 bp flank | starting at 221 bp after the A of the ATG start codon, 845 bp of nifL have been deleted and replaced with the NCMA 201701003 Prm76.1promoter sequence; 500 bp flanking the nifL gene upstream and downstream are included |
| SEQ ID NO 135 | ΔnifL::Prm1.2 | starting at 221 bp after the A of the ATG start codon, 845 bp of nifL have been deleted and replaced with the NCMA 201701003 Prm1.2 promoter sequence |
| SEQ ID NO 136 | ΔnifL::Prm1.2 with 500 bp flank | starting at 221 bp after the A of the ATG start codon, 845 bp of nifL have been deleted and replaced with the NCMA 201701003 Prm1.2 promoter sequence; 500 bp flanking the nifL gene upstream and downstream are included |
| SEQ ID NO 137 | ΔnifL::Prm1.2 | starting at 221 bp after the A of the ATG start codon, 845 bp of nifL have been deleted and replaced with the NCMA 201701003 Prm1.2 promoter sequence |
| SEQ ID NO 138 | ΔnifL::Prm1.2 with 500 bp flank | starting at 221 bp after the A of the ATG start codon, 845 bp of nifL have been deleted and replaced with the NCMA 201701003 Prm1.2 promoter sequence; 500 bp flanking the nifL gene upstream and downstream are included |

TABLE 4-continued

Wild-type and modified sequences for use in microbes of the disclosure

| SEQ ID NO | Genotype | Description |
|---|---|---|
| SEQ ID NO 139 | glnEΔAR-2 | glnE gene with 1650 bp immediately downstream of the ATG start codon deleted, resulting in a truncated glnE protein lacking the adenylyl-removing (AR) domain |
| SEQ ID NO 140 | glnEΔAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included |
| SEQ ID NO 141 | ΔnifL::Prm3.1 | starting at 221 bp after the A of the ATG start codon, 845 bp of nifL have been deleted and replaced with the NCMA 201701003 Prm3.1 promoter sequence |
| SEQ ID NO 142 | ΔnifL::Prm3.1 with 500 bp flank | starting at 221 bp after the A of the ATG start codon, 845 bp of nifL have been deleted and replaced with the NCMA 201701003 Prm3.1 promoter sequence; 500 bp flanking the nifL gene upstream and downstream are included |
| SEQ ID NO 143 | glnEΔAR-2 | glnE gene with 1650 bp immediately downstream of the ATG start codon deleted, resulting in a truncated glnE protein lacking the adenylyl-removing (AR) domain |
| SEQ ID NO 144 | glnEΔAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included |
| SEQ ID NO 145 | ΔnifL:PinfC | starting at 24 bp after the A of the ATG start codon, 1375 bp of nifL have been deleted and replaced with the 63 PinfC promoter sequence |
| SEQ ID NO 146 | ΔnifL:PinfC with 500 bp flank | starting at 24 bp after the A of the ATG start codon, 1375 bp of nifL have been deleted and replaced with the 63 PinfC promoter sequence; 500 bp flanking the nifL gene upstream and downstream are included |
| SEQ ID NO 147 | ΔnifL::Prm5 | starting at 31 bp after the A of the ATG start codon, 1375 bp of nifL have been deleted and replaced with the NCMA 201701001 Prm5 promoter sequence |
| SEQ ID NO 148 | ΔnifL::Prm5 with 500 bp flank | starting at 31 bp after the A of the ATG start codon, 1375 bp of nifL have been deleted and replaced with the NCMA 201701001 Prm5 promoter sequence; 500 bp flanking the nifL gene upstream and downstream are included |
| SEQ ID NO 149 | ΔnifL::Prm1 | starting at 31 bp after the A of the ATG start codon, 1375 bp of nifL have been deleted and replaced with the NCMA 201701001 Prm1 promoter sequence |
| SEQ ID NO 150 | ΔnifL::Prm1 with 500 bp flank | starting at 31 bp after the A of the ATG start codon, 1375 bp of nifL have been deleted and replaced with the NCMA 201701001 Prm1 promoter sequence; 500 bp flanking the nifL gene upstream and downstream are included |
| SEQ ID NO 151 | ΔnifL::Prm1 | starting at 31 bp after the A of the ATG start codon, 1375 bp of nifL have been deleted and replaced with the NCMA 201701001 Prm1 promoter sequence |
| SEQ ID NO 152 | ΔnifL::Prm1 with 500 bp flank | starting at 31 bp after the A of the ATG start codon, 1375 bp of nifL have been deleted and replaced with the NCMA 201701001 Prm1 promoter sequence; 500 bp flanking the nifL gene upstream and downstream are included |
| SEQ ID NO 153 | glnEΔAR-2 | glnE gene with 1644 bp immediately downstream of the ATG start codon deleted, resulting in a truncated glnE protein lacking the adenylyl-removing (AR) domain |
| SEQ ID NO 154 | glnEΔAR-2 with 500 bp flank | glnE gene with 1644 bp immediately downstream of the ATG start codon deleted, resulting in a truncated glnE protein lacking the adenylyl-removing (AR) domain; 500 bp flanking the glnE gene upstream and downstream are included |
| SEQ ID NO 155 | glnEΔAR-1 | glnE gene with 1287 bp immediately downstream of the ATG start codon deleted, resulting in a truncated glnE protein lacking the adenylyl-removing (AR) domain |
| SEQ ID NO 156 | ΔnifL::Prm1 | starting at 31 bp after the A of the ATG start codon, 1375 bp of nifL have been deleted and replaced with the NCMA 201701001 Prm1 promoter sequence |
| SEQ ID NO 157 | ΔnifL::Prm1 with 500 bp flank | starting at 31 bp after the A of the ATG start codon, 1375 bp of nifL have been deleted and replaced with the NCMA 201701001 Prm1 promoter sequence; 500 bp flanking the nifL gene upstream and downstream are included |

TABLE 4-continued

Wild-type and modified sequences for use in microbes of the disclosure

| SEQ ID NO | Genotype | Description |
|---|---|---|
| SEQ ID NO 158 | glnEΔAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included |
| SEQ ID NO 159 | glnEΔAR-1 | glnE gene with 1287 bp immediately downstream of the ATG start codon deleted, resulting in a truncated glnE protein lacking the adenylyl-removing (AR) domain |
| SEQ ID NO 160 | glnEΔAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included |
| SEQ ID NO 161 | ΔnifL::Prm5 | starting at 31 bp after the A of the ATG start codon, 1375 bp of nifL have been deleted and replaced with the NCMA 201701001 Prm5 promoter sequence |
| SEQ ID NO 162 | ΔnifL::Prm5 with 500 bp flank | starting at 31 bp after the A of the ATG start codon, 1375 bp of nifL have been deleted and replaced with the NCMA 201701001 Prm5 promoter sequence; 500 bp flanking the nifL gene upstream and downstream are included |
| SEQ ID NO 163 | ΔnifL::Prm1 | starting at 31 bp after the A of the ATG start codon, 1375 bp of nifL have been deleted and replaced with the NCMA 201701001 Prm1 promoter sequence |
| SEQ ID NO 164 | ΔnifL::Prm1 with 500 bp flank | starting at 31 bp after the A of the ATG start codon, 1375 bp of nifL have been deleted and replaced with the NCMA 201701001 Prm1 promoter sequence; 500 bp flanking the nifL gene upstream and downstream are included |
| SEQ ID NO 165 | glnEΔAR-2 | glnE gene with 1644 bp immediately downstream of the ATG start codon deleted, resulting in a truncated glnE protein lacking the adenylyl-removing (AR) domain |
| SEQ ID NO 166 | glnEΔAR-2 with 500 bp flank | glnE gene with 1644 bp immediately downstream of the ATG start codon deleted, resulting in a truncated glnE protein lacking the adenylyl-removing (AR) domain; 500 bp flanking the glnE gene upstream and downstream are included |
| SEQ ID NO 167 | ΔamtB | First 1088 bp of amtB gene and 4 bp upstream of start codon deleted; 199 bp of gene remaining lacks a start codon; no amtB protein is translated |
| SEQ ID NO 168 | ΔamtB with 500 bp flank | First 1088 bp of amtB gene and 4 bp upstream of start codon deleted; 199 bp of gene remaining lacks a start codon; no amtB protein is translated |
| SEQ ID NO 169 | glnEΔAR-1 | glnE gene with 1287 bp immediately downstream of the ATG start codon deleted, resulting in a truncated glnE protein lacking the adenylyl-removing (AR) domain |
| SEQ ID NO 170 | glnEΔAR-1 with 500 bp flank | glnE gene with 1287 bp immediately downstream of the ATG start codon deleted, resulting in a truncated glnE protein lacking the adenylyl-removing (AR) domain; 500 bp flanking the glnE gene upstream and downstream are included |
| SEQ ID NO 171 | ΔnifL::Prm1 | starting at 31 bp after the A of the ATG start codon, 1375 bp of nifL have been deleted and replaced with the NCMA 201701001 Prm1 promoter sequence |
| SEQ ID NO 172 | ΔnifL::Prm1 with 500 bp flank | starting at 31 bp after the A of the ATG start codon, 1375 bp of nifL have been deleted and replaced with the NCMA 201701001 Prm1 promoter sequence; 500 bp flanking the nifL gene upstream and downstream are included |
| SEQ ID NO 173 | ΔamtB | First 1088 bp of amtB gene and 4 bp upstream of start codon deleted; 199 bp of gene remaining lacks a start codon; no amtB protein is translated |
| SEQ ID NO 174 | ΔamtB with 500 bp flank | First 1088 bp of amtB gene and 4 bp upstream of start codon deleted; 199 bp of gene remaining lacks a start codon; no amtB protein is translated |
| SEQ ID NO 175 | ΔnifL:PinfC | starting at 20 bp after the A of the ATG start codon, 1379 bp of nifL have been deleted and replaced with the PTA-126585 PinfC promoter sequence |
| SEQ ID NO 176 | ΔnifL:PinfC with 500 bp flank | starting at 20 bp after the A of the ATG start codon, 1379 bp of nifL have been deleted and replaced with the PTA-126585 PinfC promoter sequence; 500 bp flanking the nifL gene upstream and downstream are included |
| SEQ ID NO 177 | 16S-1 | 1 of 3 unique 16S rDNA genes in the NCMA 201701001 genome |

TABLE 4-continued

Wild-type and modified sequences for use in microbes of the disclosure

| SEQ ID NO | Genotype | Description |
|---|---|---|
| SEQ ID NO 178 | 16S-2 | 2 of 3 unique 16S rDNA genes in the NCMA 201701001 genome |
| SEQ ID NO 179 | nifH | N/A |
| SEQ ID NO 180 | nifD2 | 2 of 2 unique genes annotated as nifD in NCMA 201701001 genome |
| SEQ ID NO 181 | nifK2 | 2 of 2 unique genes annotated as nifK in NCMA 201701001 genome |
| SEQ ID NO 182 | nifL | N/A |
| SEQ ID NO 183 | nifA | N/A |
| SEQ ID NO 184 | glnE | N/A |
| SEQ ID NO 185 | 16S-3 | 3 of 3 unique 16S rDNA genes in the NCMA 201701001 genome |
| SEQ ID NO 186 | nifD1 | 1 of 2 unique genes annotated as nifD in NCMA 201701001 genome |
| SEQ ID NO 187 | nifK1 | 1 of 2 unique genes annotated as nifK in NCMA 201701001 genome |
| SEQ ID NO 188 | amtB | N/A |
| SEQ ID NO 189 | Prm1 | 348 bp includes the 319 bp immediately upstream of the ATG start codon of the 1 pp gene and the first 29 bp of the 1 pp gene |
| SEQ ID NO 190 | Prm5 | 313 bp starting at 432 bp upstream of the ATG start codon of the ompX gene and ending 119 bp upstream of the ATG start codon of the ompX gene |
| SEQ ID NO 191 | nifL | N/A |
| SEQ ID NO 192 | nifA | N/A |
| SEQ ID NO 193 | 16S-1 | 1 of 7 unique 16S rDNA genes in the NCMA 201701003 genome |
| SEQ ID NO 194 | 16S-2 | 2 of 7 unique 16S rDNA genes in the NCMA 201701003 genome |
| SEQ ID NO 195 | 16S-3 | 3 of 7 unique 16S rDNA genes in the NCMA 201701003 genome |
| SEQ ID NO 196 | 16S-4 | 4 of 7 unique 16S rDNA genes in the NCMA 201701003 genome |
| SEQ ID NO 197 | 16S-5 | 5 of 7 unique 16S rDNA genes in the NCMA 201701003 genome |
| SEQ ID NO 198 | 16S-6 | 6 of 7 unique 16S rDNA genes in the NCMA 201701003 genome |
| SEQ ID NO 199 | 16S-7 | 7 of 7 unique 16S rDNA genes in the NCMA 201701003 genome |
| SEQ ID NO 200 | nifH1 | 1 of 2 unique genes annotated as nifH in NCMA 201701003 genome |
| SEQ ID NO 201 | nifH2 | 2 of 2 unique genes annotated as nifH in NCMA 201701003 genome |
| SEQ ID NO 202 | nifD1 | 1 of 2 unique genes annotated as nifD in NCMA 201701003 genome |
| SEQ ID NO 203 | nifD2 | 2 of 2 unique genes annotated as nifD in NCMA 201701003 genome |
| SEQ ID NO 204 | nifK1 | 1 of 2 unique genes annotated as nifK in NCMA 201701003 genome |
| SEQ ID NO 205 | nifK2 | 2 of 2 unique genes annotated as nifK in NCMA 201701003 genome |
| SEQ ID NO 206 | glnE | N/A |
| SEQ ID NO 207 | Prm4 | 449 bp immediately upstream of the ATG of the dscC 2 gene |
| SEQ ID NO 208 | Prm1.2 | 500 bp immediately upstream of the TTG start codon of the infC gene |
| SEQ ID NO 209 | Prm3.1 | 170 bp immediately upstream of the ATG start codon of the rpIN gene |
| SEQ ID NO 210 | Prm6.1 | 142 bp immediately upstream of the ATG of a highly-expressed hypothetical protein (annotated as PROKKA 00662 in NCMA 201701003 assembly 82) |
| SEQ ID NO 211 | Prm7.1 | 293 bp immediately upstream of the ATG of the 1 pp gene |

TABLE 4-continued

| Wild-type and modified sequences for use in microbes of the disclosure | | |
|---|---|---|
| SEQ ID NO | Genotype | Description |
| SEQ ID NO 212 | glnEΔAR-2 | glnE gene with 1650 bp immediately downstream of the ATG start codon deleted, resulting in a truncated glnE protein lacking the adenylyl-removing (AR) domain |
| SEQ ID NO 213 | glnEΔAR-2 with 500 bp flank | glnE gene with 1650 bp immediately downstream of the ATG start codon deleted, resulting in a truncated glnE protein lacking the adenylyl-removing (AR) domain; 500 bp flanking the glnE gene upstream and downstream are included |
| SEQ ID NO 214 | ΔnifL::null-v1 | starting at 221 bp after the A of the ATG start codon, 845 bp of nifL have been deleted and replaced with the 31 bp sequence "GGAGTCTGAACTCATCCTGCGATGGGGGCTG" |
| SEQ ID NO 215 | ΔnifL::null-v1 with 500 bp flank | starting at 221 bp after the A of the ATG start codon, 845 bp of nifL have been deleted and replaced with the 31 bp sequence "GGAGTCTGAACTCATCCTGCGATGGGGGCTG"; 500 bp flanking the nifL gene upstream and downstream are included |
| SEQ ID NO 216 | ΔnifL::null-v2 | starting at 221 bp after the A of the ATG start codon, 845 bp of nifL have been deleted and replaced with the 5 bp sequence "TTAAA" |
| SEQ ID NO 217 | ΔnifL::null-v2 with 500 bp flank | starting at 221 bp after the A of the ATG start codon, 845 bp of nifL have been deleted and replaced with the 5 bp sequence "TTAAA"; 500 bp flanking the nifL gene upstream and downstream are included |
| SEQ ID NO 218 | ΔnifL::Prm4 | starting at 221 bp after the A of the ATG start codon, 845 bp of nifL have been deleted and replaced with the CI19 Prm4 sequence |
| SEQ ID NO 219 | ΔnifL::Prm4 with 500 bp flank | starting at 221 bp after the A of the ATG start codon, 845 bp of nifL have been deleted and replaced with the CI19 Prm4 sequence; 500 bp flanking the nifL gene upstream and downstream are included |
| SEQ ID NO 220 | glnD with flanking sequences | glnD gene with upstream and downstream flanking sequences included |
| SEQ ID NO 221 | ΔnifL::Prm5 | Retaining the first 30 bp and the last 83 bp, the middle region of nifL is deleted and replaced with the NCMA 201701001 Prm5 promoter sequence. |
| SEQ ID NO 222 | glnEΔAR | Deletion of the first 1287 bp after the ATG start codon of the glnE gene. Resulting GlnE protein lacks AR domain, but expresses ATase domain. |
| SEQ ID NO 223 | ΔglnD with flanking sequences | Deletion of glnD gene by removing all 2676 nucleotides, including start and stop codons. Upstream and downstream flanking sequences are included. |
| | ΔnifL:PinfC | Deletion of the nifL gene from 20 bp after the ATG (start) to 87 bp before the TGA (stop) of the gene. A 500 bp fragment of the region upstream of the infC gene was inserted (PinfC) upstream of nifA replacing the deleted portion. |
| | ΔglnE$_{AR}$-KO2 | Deletion of 1647 bp after the start codon of the glnE gene. |
| | ΔnifL:PinfC | Deletion of the nifL gene from 20 bp after the ATG (start) to 87 bp before the TGA (stop) of the gene. A 500 bp fragment of the region upstream of the infC gene was inserted (PinfC) upstream of nifA replacing the deleted portion. |
| | glnE$_{AR}$-DxD | Modification of the "GAT" found 513 bp after the start codon of glnE to a "GCG" codon. |
| | ΔnifL::Prm8.2 | Deletion of the nifL gene from 20 bp after the ATG (start) to 87 bp before the TGA (stop) of the gene. A 299 bp fragment (Prm8.2), found 77 bp after the start codon of nipl to 376 bp after the start codon of nipl was inserted upstream of nifA replacing the deleted portion. |
| | ΔglnE$_{AR}$-KO2 | Deletion of 1647 bp after the start codon of the glnE gene. |
| | ΔnifL:PinfC | Deletion of the nifL gene from 20 bp after the ATG (start) to 87 bp before the TGA (stop) of the gene. A 500 bp fragment of the region upstream of the infC gene was inserted (PinfC) upstream of nifA replacing the deleted portion. |
| | ΔglnE$_{AR}$-KO2 | Deletion of 1647 bp after the start codon of the glnE gene. |
| | ΔnifL::Prm1.2 | Deletion of the nifL gene from 20 bp after the ATG (start) to 87 bp before the TGA (stop) of the gene. A 400 bp fragment from the region upstream of the cspE |

TABLE 4-continued

Wild-type and modified sequences for use in microbes of the disclosure

| SEQ ID NO | Genotype | Description |
| --- | --- | --- |
| | | gene was inserted (Prm1.2) upstream of nifA replacing the deleted portion. |
| | ΔglnE$_{AR}$-KO2 | Deletion of 1647 bp after the start codon of the glnE gene. |
| | ΔnifL::Prm1.2 | Deletion of the nifL gene from 20 bp after the ATG (start) to 87 bp before the TGA (stop) of the gene. A 400 bp fragment from the region upstream of the cspE gene was inserted (Prm1.2) upstream of nifA replacing the deleted portion. |
| | ΔglnE$_{AR}$-KO2 | Deletion of 1647 bp after the start codon of the glnE gene. |
| | rpoN-Prm8.2 | Deletion of the 47bo between ibtB2 and rpoN and insertion of a fragment (Prm8.2), found 77 bp after the start codon of nipl to 376 bp after the start codon of nipl, directly upstream of rpoN. |
| | ΔnifL::Prm1.2 | Deletion of the nifL gene from 20 bp after the ATG (start) to 87 bp before the TGA (stop) of the gene. A 400 bp fragment from the region upstream of the cspE gene was inserted (Prm1.2) upstream of nifA replacing the deleted portion. |
| | ΔglnE$_{AR}$-KO2 | Deletion of 1647 bp after the start codon of the glnE gene. |
| | ΔglnD$_{ACT1/2}$ | Deletion of the 546 bp before the stop codon of the glnD gene. |

TABLE 5

Further Descriptions of Deposited Strains from the Disclosure

| Strain ID | Mutagenic DNA Description | Genotype |
| --- | --- | --- |
| NCMA 201701001 | Wildtype parent *Kosakonia sacchari* | WT |
| NCMA 201708001 | Wildtype parent *Klebsiella variicola* | WT |
| PTA-126585 | Wildtype parent *Metakosakonia intestini* | WT |
| PTA-126582 | Wildtype parent *Paraburkholderia tropica* | WT |
| PTA-126581 | Wildtype parent *Paenibacillus polymyxa* | WT |
| PTA-126583 | Wildtype parent *Herbaspirillum aquaticum* | WT |
| NCMA 201708004 | Disruption of nifL gene with a fragment of the region upstream of the lpp gene inserted (Prm1) upstream of nifA. Deletion of the 1647 bp after the start codon of the glnE gene containing the adenylyl-removing domain of glutamate-ammonia-ligase adenylyltransferase (ΔglnE-AR_KO2). | ΔnifL::Prm1, ΔglnE-AR_KO2 |
| PTA-126575 | Disruption of nifL gene with a fragment of the region upstream of the lpp gene inserted (Prm1) upstream of nifA. Deletion of the 987 bp after the start codon of the glnD gene containing the uridylyltransferase (UT) domain of the bifunctional uridylyltransferase/uridylyl-removing enzyme (ΔglnD-UT_truncation) | ΔnifL::Prm1, ΔglnD_UT_truncation |
| PTA-126576 | Disruption of nifL gene with a fragment of the region upstream of the Ipp gene inserted (Prm1) upstream of nifA. Deactivation of the | ΔnifL::Prm1, ΔglnD_UT_deactivation |

TABLE 5-continued

Further Descriptions of Deposited Strains from the Disclosure

| Strain ID | Mutagenic DNA Description | Genotype |
| --- | --- | --- |
| | uridylyltransferase (UT) domain of the bifunctional uridylyltransferase/uridylyl-removing enzyme, glnD, by mutating amino acid residues 90 and 91 from GG to DV as well as residue 104 from D to A. | |
| NCMA 201712001 | Deletion of the 1647 bp after the start codon of the glnE gene containing the adenylyl-removing domain of glutamate-ammonia-ligase adenylyltransferase (ΔglnE-AR_KO2). | ΔglnE-AR_KO2 |
| PTA-126577 | Deletion of the native dctA1 promoter and insertion of a fragment (Prm8.2), found 77 bp after the start codon of nipI to 376 bp after the start codon of nlpI, directly upstream of dctA1. Deletion of the 1647bp after the start codon of the glnE gene containing the adenylyl-removing domain of glutamate-ammonia-ligase adenylyltransferase (ΔglnE-AR_KO2). | ΔnifL::P8.2, ΔglnE-AR_KO2 |
| PTA-126578 | Disruption of nifL gene with a fragment of the region upstream of the cspE gene inserted (Prm1.2) upstream of nifA. Deletion of the 1647 bp after the start codon of the glnE gene containing the adenylyl-removing domain of glutamate-ammonia-ligase adenylyltransferase (ΔglnE- | ΔnifL::Prm1.2 ΔglnE-AR_KO2, ΔglnD_ACT 12_ truncation |

TABLE 5-continued

Further Descriptions of Deposited Strains from the Disclosure

| Strain ID | Mutagenic DNA Description | Genotype |
|---|---|---|
| | AR_KO2). Deletion of the 546 bp before the stop codon of the glnD gene containing the ACT1/2 domain of the bifunctional uridylyltransferase/uridylyl-removing enzyme (ΔglnD-ACT12_truncation) | |
| PTA-126579 | Disruption of nifL gene with a fragment of the region upstream of the espE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glsA2 promoter and insertion of a fragment (Prm1.2) directly upstream of the glsA2 CDS. | ΔnifL::Prm1.2, ΔglnE-AR_KO2, glsA2::Prm1.2 |
| PTA-126580 | Disruption of nifL gene with a fragment of the region upstream of the espE gene inserted (Prm1.2) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native rpoN promoter and insertion of a fragment (Prm1.2) directly upstream of the rpoN CDS. | ΔnifL::Prm1.2, ΔglnE-AR_KO2, rpoN::Prm1.2 |
| PTA-126588 | Disruption of nifL gene with a fragment of the region upstream of the rmF gene inserted (Prm2.1) upstream of nifA. Deletion of the 1647 bp after the start codon of the glnE gene containing the adenylyl-removing domain of glutamate-ammonia-ligase adenylyltransferase (ΔglnE-AR_KO2). Deletion of the native glsA2 promoter and insertion of a fragment upstream of the csrA gene (Prm1.1) directly upstream of the glsA2 CDS. | ΔnifL::Prm2.1, ΔglnE-AR_KO2, glsA2::Prm1.1 |
| PTA-126586 | Disruption of nifL gene with a fragment of the region upstream of the rmF gene inserted (Prm2.1) upstream of nifA. Deletion of the 1647 bp after the start codon of the glnE gene containing the adenylyl-removing domain of glutamate-ammonia-ligase adenylyltransferase (ΔglnE-AR_KO2). Deletion of the 987 bp after the start codon of the glnD gene containing the uridylyltransferase (UT) domain of the bifunctional uridylyltransferase/uridylyl-removing enzyme (ΔglnD-UT_truncation) | ΔnifL::Prm2.1, ΔglnE-AR_KO2, ΔglnD_UT_truncation |
| PTA-126584 | Disruption of nifL gene with a fragment of the region upstream of the rmF gene inserted (Prm2.1) upstream of nifA. Deletion of the 1647 bp after the start codon of the glnE gene containing the adenylyl-removing domain of glutamate-ammonia-ligase adenylyltransferase (ΔglnE-AR_KO2). | ΔnifL::Prm2.1, ΔglnE-AR_KO2 |
| PTA-126587 | Disruption of nifL gene with a fragment of the region upstream of the rmF gene inserted (Prm2.1) upstream of nifA. Deletion of the 987 bp after the start codon of the glnD gene containing the uridylyltransferase (UT) domain of the bifunctional uridylyltransferase/uridylyl-removing enzyme (ΔglnD-UT_truncation). | ΔnifL::Prm2.1, ΔglnD_UT_truncation |
| PTA-126743 | Disruption of nifL gene with a promoter that natively drives ompX (Prm5) inserted upstream of nifA. Deletion of the 1287 bp after the start codon of the glnE gene containing the adenylyl-removing domain of glutamate-ammonia-ligase adenylyltransferase Deletion of entire glnD gene. | ΔnifL::Prm5, glnEΔAR, ΔglnD |

EXAMPLES

Example 1: Exemplary Method for Improving Stability of Liquid Agricultural Composition Comprising Nitrogen-Fixing Gram Negative Bacteria To overcome the limitations of existing dry and liquid formulations of nitrogen-fixing microorganisms, novel formulation methods were developed to produce agronomically stable agricultural compositions for delivering nitrogen-fixing microorganism to agricultural plant tissues or the environs thereof. An exemplary implementation of a method according to the present disclosure involved varying four different parameters of the liquid agricultural composition, each of which proved to contribute to the stability of the composition. The four parameters were: (1) cell density of the nitrogen-fixing microorganism at time of formulation and selection and inclusion of (2) a microbial stabilizer, (3) a physical stabilizer, and (4) a buffering agent. The combination of the microbial stabilizer and the physical stabilizer was observed to have a direct impact on toxin accumulation.

In this example, the nitrogen-fixing microorganism was the diazotrophic bacterium *Klebsiella variicola* strain NCMA 201712002.

Cell Density at Time of Formulation

To determine the effects of initial cell density on the stability of the bacteria within the liquid agricultural composition, a titration curve was created to measure the relationship between initial cell density and decay rate. Cellular densities between ~9.4 and ~10.85 (given in log CFU/mL) were tested with water used as a diluent. The decay rate for each sample was determined by taking measurements of the initial cellular density and the cellular density at the 30 day time point, using standard plating methods, which measurements were used to determine an overall average rate of decay, given in log loss of CFU/mL per day).

Figure 1:
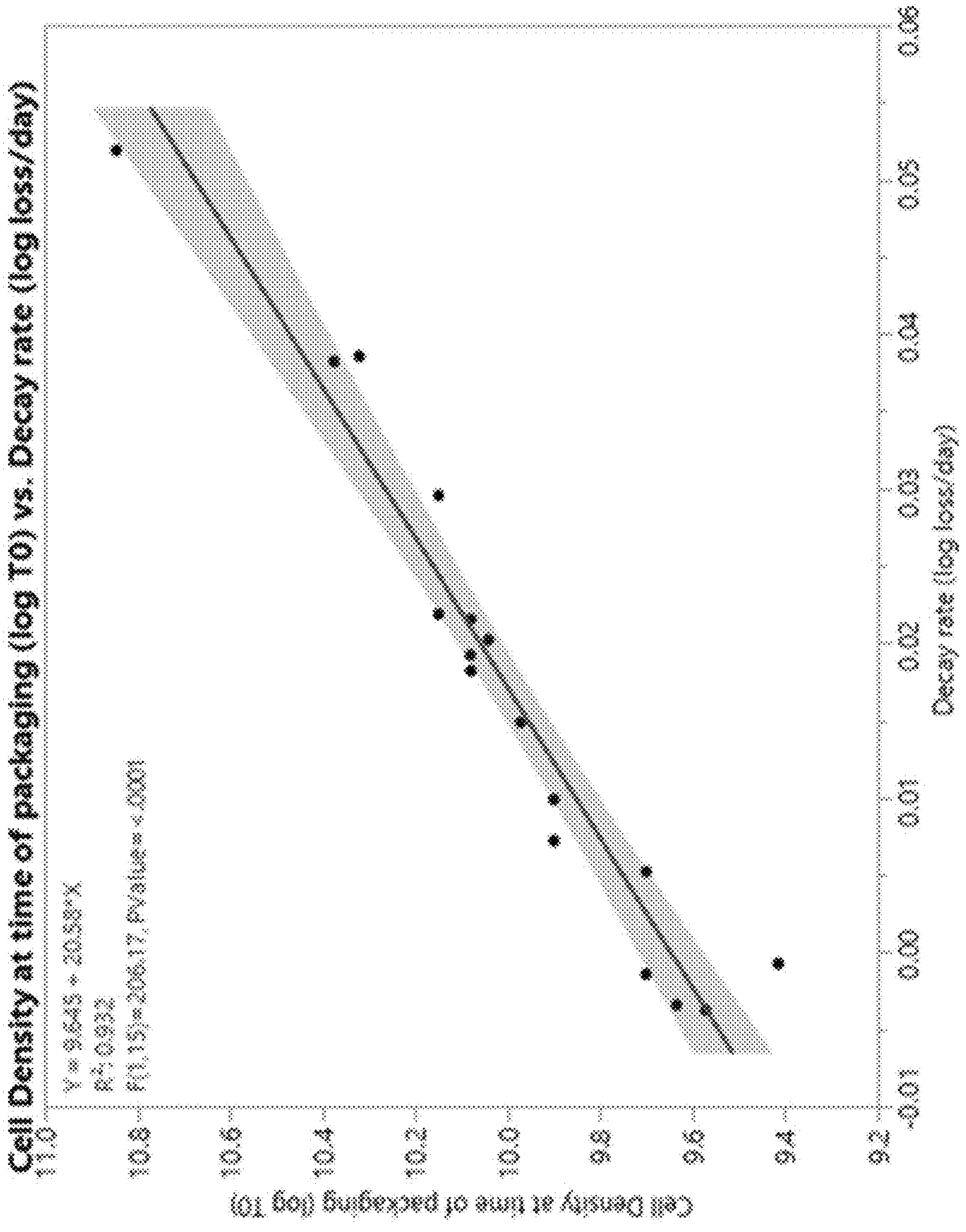
FIG. 1 shows a graph of cell density (log CFU/mL) at the time of formulation of an illustrative agricultural composition versus the decay rate in log loss of CFU/mL per day.

FIG. 1 shows the results of this assay, demonstrating that initial cellular densities between ~9.4 and ~9.7 log CFU/mL did not experience any average measurable decay over the 30 day period of observation, while higher initial cellular densities led to decay, with an initial cellular density of ~10.85, for example, leading to a decay rate of ~0.055 log loss of CFU/mL per day. This data shows a significant correlation ($p<0.0001$) between the cell density of the nitrogen-fixing microorganisms at the time of formulation of the agricultural composition and the decay rate of the microorganisms. Because of this, initial dilution had a significant impact on improving product stability while decreasing the required fermentation volume. Since the typical bacterial titer at the end of fermentation was around 1.5E10 CFU/mL, and the target cell density for the agricultural composition based on these results was around 4.5E9-5.5E9 CFU/mL, this provided the ability to dilute the fermentation volume 3-fold, thereby decreasing the fermentation needs 3-fold as well.

However, while packaging density was observed to affect the stability of the agricultural composition, other factors also affected stability beyond 30 days.

Ammonia Toxin Accumulation Over Time

The inventors theorized that in addition to the effects of cellular density, another key mechanism of failure in the stability of the agricultural composition over time could be a high level of toxin accumulation during storage. Ammonia is a byproduct of media breakdown during fermentation and may also accumulate during storage due to nitrogen fixation by the bacteria. Ammonia is toxic to *Klebsiella variicola* NCMA 201712002 at concentrations above 50 mM, as determined by measuring the final cellular OD in a metabolite screen, results shown in Table 6.

TABLE 6

Ammonia toxicity in *Klebsiella variicola* NCMA 201712002.

| [Ammonia] mM | Final OD |
|---|---|
| 10 | 2.0874 |
| 50 | 2.1558 |
| 100 | 0.4435 |

To test the possibility that ammonia accumulation could be linked to the deterioration of the agricultural composition's stability over time, average ammonia concentrations (averaged across triplicate samples) were measured in the supernatant of samples stored under different conditions for a period of 90 days, with measurements taken at 0, 35, and 90 days post-harvest. The conditions that varied were:

- Dilution level: normal fermentation broth at 1E10 CFU/mL ("broth") versus half broth/half PBS at 5E9 CFU/mL ("halfbroth"), neither one with stabilizers present;
- Storage container: bladder ("bladder") versus bottle ("bottle"); and
- Storage temperature: 4° C. ("4C") versus room temperature ("RT"), with one sample testing the condition of moving from 4° C. to RT at 35 days ("4CtoRT").

Figure 2:
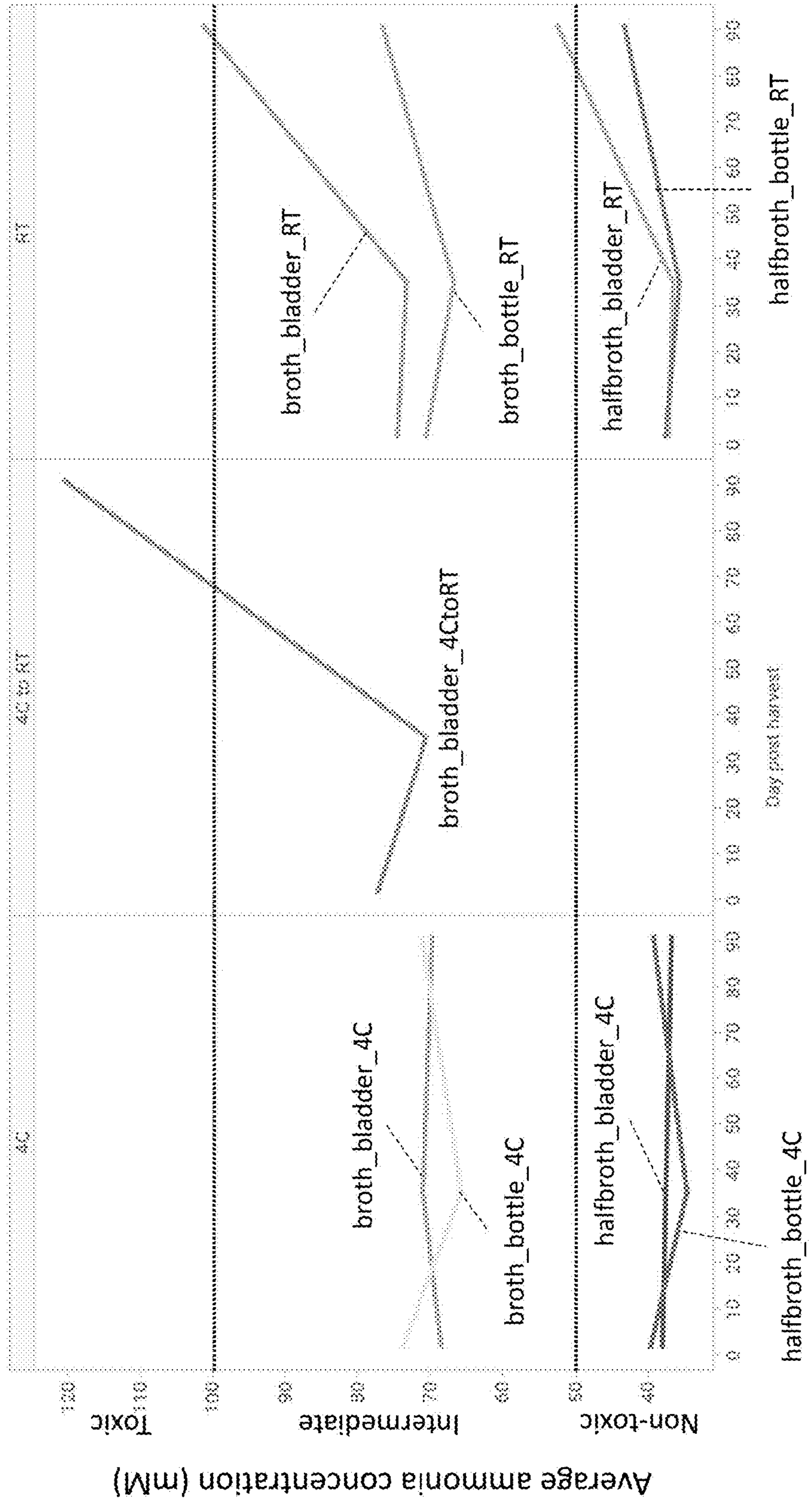
FIG. 2 shows the results of an ammonia toxicity assay. Sample identifiers are indicated in the graph. Toxicity ranges of ammonia for *Klebsiella variicola* NCMA 201708001 are shown in dotted lines: non-toxic from 0-50 mM; intermediate toxicity, 50-100 mM; and toxic, 100 mM and above.

FIG. 2 shows the results of this experiment. In all room temperature samples, ammonia accumulated over time, with the average ammonia concentration at 90 days exceeding the starting value. This ammonia accumulation suggests that cells are metabolically active during storage in room temperature samples. On the other hand, samples stored at 4° C. did not experience a significant increase in ammonia concentration over the 90 day period. The greatest ammonia accumulation was observed in the sample that was moved from 4° C. to room temperature, which may indicate that the temperature shift upregulates cell metabolism.

Microbial Stabilizer & Physical Stabilizer

To improve the stability of the agricultural composition beyond the 30 day period, 82 combinations of microbial and physical stabilizers were explored. The samples comprised fermentation broth at two different initial cell densities (2× and 3× dilution), all in high buffering capacity PBS, along with the combination of stabilizers. The samples were stored at room temperature. Stability and functionality were monitored for a period of 5 months. The stability of the product was measured using a room temperature measurement of cellular viability in units of CFU/mL.

During this time, various stabilizer combinations resulted in different levels of stability, with fructose and xanthan gum at a final concentration of 1.3% and 0.1%, respectively, producing the best results in terms of long term stability: this combination resulted in an agricultural composition that maintained its bacterial viability for the full 3 month period, with less than 0.2 log loss of CFU/mL over the 3 month time frame.

Four agricultural compositions were also tested in an inplanta microbial colonization assay at the three month time point. The four compositions comprised the following combinations of microbial and physical stabilizers: (A) 100 mM PBS, no stabilizers; (B) 1.3% fructose+0.2% CBP; (C) 1.3% fructose+0.1% xanthan gum, and (D) HEPES, no stabilizers. Most of the other combinations of microbial and physical stabilizers produced results below the target of 1E9 CFU/mL at 3 months' time.

The root colonization assay was performed as in International Patent Application No. PCT/US2019/039528, the contents of which are incorporated herein by reference in their entirety. Briefly, four days after planting, 1 ml of a bacterial overnight culture (approximately $10^9$ CFU) was applied to the soil above the planted seed. Seedlings were fertilized three times weekly with 25 ml modified Hoagland's solution supplemented with 0.5 mM ammonium nitrate. Four weeks after planting, root samples were collected and the total genomic DNA (gDNA) was extracted. Root colonization was quantified using qPCR with primers designed to amplify unique regions of either the wild type or derivative strain genome. QPCR reaction efficiency was measured using a standard curve generated from a known quantity of gDNA from the target genome. Data was normalized to genome copies per g fresh weight using the tissue weight and extraction volume. The 3-month old A-D samples were compared to a negative control (untreated control seedlings, no microbe added) and a positive control (fresh culture without stabilizers or buffers).

Figure 3:
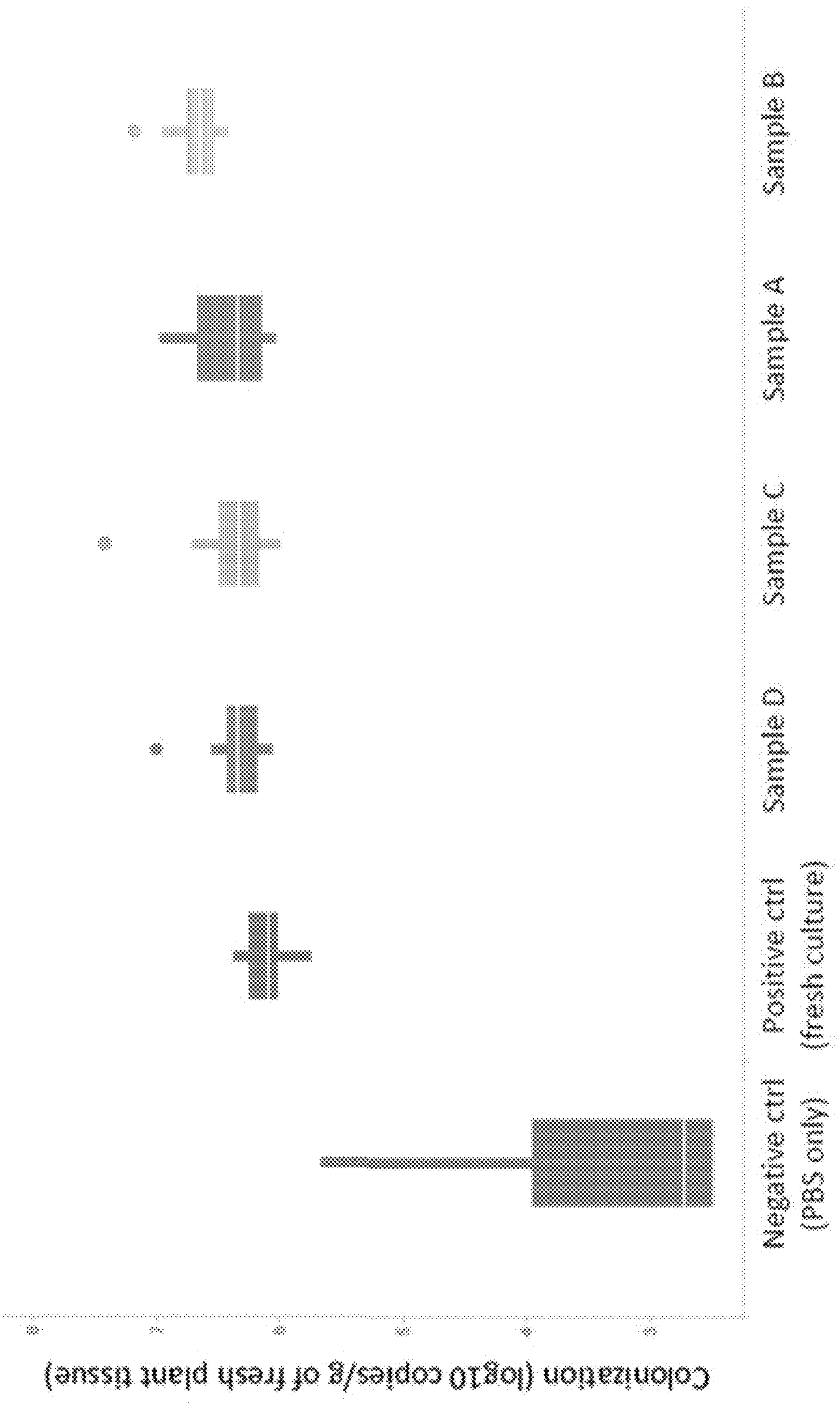
FIG. 3 shows the results of an in planta microbial colonization assay. From left to right, the six tested conditions corresponded to: negative control (no microbe added), positive control (fresh culture), sample D, sample C, sample A, and sample B. The horizontal line shows the median colonization observed among the replicates for each condition.

FIG. 3 and Table 7 show the results of this assay: all four 3-month old compositions had the same colonization performance as a fresh culture of bacteria.

TABLE 7

| Colonization performance of 3-month old agricultural compositions comprising high-performing combinations of physical and microbial stabilizers. | | | | | | |
|---|---|---|---|---|---|---|
| Condition | Negative control | Positive control | Sample D | Sample C | Sample A | Sample B |
| No. of replicates | 11 | 12 | 11 | 12 | 12 | 12 |
| Avg. colonization (log10 copies/g fresh weight) | 3.29 | 6.10 | 6.34 | 6.40 | 6.41 | 6.68 |

In addition to testing the colonization potential of the top-performing agricultural compositions, the supernatants of six different formulation conditions were assayed for soluble ammonia accumulation at the three month time point and compared to a control sample without stabilizers. These six formulations and control formulation comprised the following combinations of physical and microbial stabilizers:

(Sample 1) physical stabilizer: 0.1% xanthan gum; microbial stabilizer: 1.3% fructose;

(Sample 2) physical stabilizer: 0.1% xanthan gum; microbial stabilizer: 2.5% trehalose;

(Sample 3) physical stabilizer: 0.1% xanthan gum; microbial stabilizer: none;

(Sample 4) physical stabilizer: 0.2% CBP; microbial stabilizer: 1% fructose;

(Sample 5) physical stabilizer: 0.2% CBP; microbial stabilizer: 2.5% trehalose; and (Sample 6) physical stabilizer: 0.2% CBP; microbial stabilizer: none.

(Control) physical stabilizer: none; microbial stabilizer: none.

Figure 4:
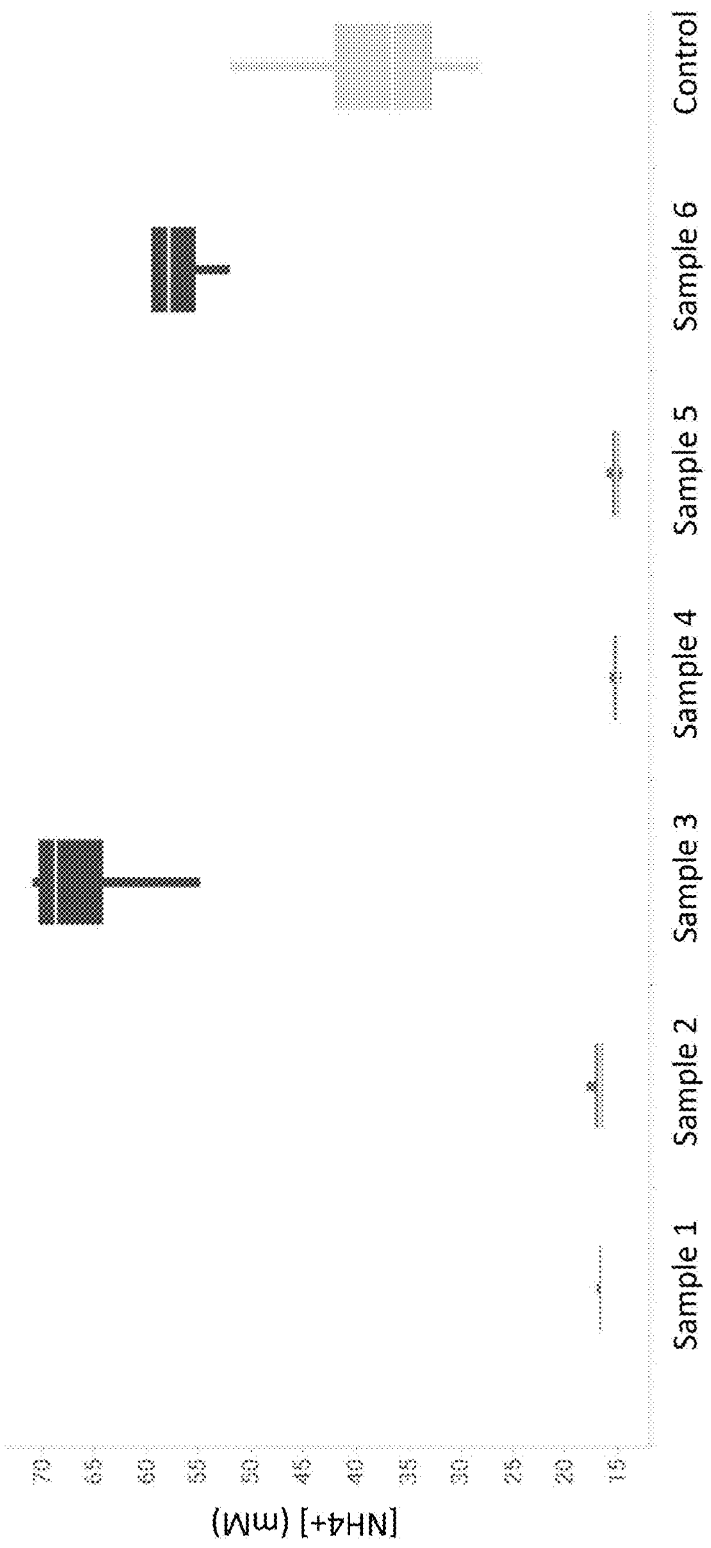
FIG. 4 shows the results of a soluble ammonia accumulation assay in 3-month old samples comprising various combinations of physical and microbial stabilizers. The control condition comprises no stabilizers. The horizontal lines indicate the median ammonia accumulation among the replicates for each condition.

The results of this assay are shown in FIG. 4 and Table 8. These results show that the physical stabilizer alone was not sufficient to decrease ammonia accumulation over the 3-month time frame; in fact, the 0.1% xanthan gum alone condition and the 0.2% CBP alone condition both led to increased soluble ammonia production compared to the control condition without stabilizers. By contrast, the combinations of physical and microbial stabilizers reduced soluble ammonia accumulation four-fold compared to the physical stabilizers alone. In the presence of these combinations, the soluble ammonia accumulation dropped to non-toxic levels, well below the 50 mM threshold. In fact, a comparison of the results in FIG. 4 with those shown in FIG. 2 demonstrates that these combinations of stabilizers (in high buffering capacity PBS with an initial cell density selected to provide a lower decay rate) brought ammonia concentrations down to below 20 mM levels as compared to levels above 75 mM for the full broth, room temperature conditions shown in FIG. 2, a more than 3-fold decrease in ammonia concentration.

TABLE 8

| Soluble ammonia accumulation in 3-month old agricultural compositions. | | | | | | | |
|---|---|---|---|---|---|---|---|
| Condition | Sample 1 | Sample 2 | Sample 3 | Sample 4 | Sample 5 | Sample 6 | Control |
| Median [NH4+] (mM) | 16.51 | 16.70 | 68.77 | 15.02 | 15.08 | 57.94 | 36.53 |

Buffering Agent

In addition to testing different combinations of stabilizers, various buffers were also assayed within the agricultural composition formulation to determine the effect of the choice of buffer on microbial stability. The buffers included: phosphate buffered saline (PBS); modified, high buffering capacity PBS; 3-Morpholinopropane-1-sulfonic acid (MOPS); 2-[4-(2-hydroxyethyl)piperazin-1-yl]ethanesulfonic acid (HEPES); and reverse osmosis water. The modified, high buffering capacity PBS had a higher concentration of $KH_2PO_4$ than the standard PBS recipe, with the following overall composition: 23 g/L $KH_2PO_4$, 7.5 g/L NaCl, 0.2 g/L KCl, and 1.4 g/L dibasic $Na_2HPO_4$. Each of the buffers was tested alone within the agricultural composition and in combination with various stabilizers. The samples all comprised the same initial cellular density of 3-5E9 CFU/mL selected to decrease the decay rate based on the results of the assay shown in FIG. 1.

The stability of the agricultural compositions was measured over time via room temperature measurements of cellular viability (CFU/mL). The 1-month time point was chosen as the deselection timeline, at which point it was determined that a target cell density of 3-5E9 CFU/mL was required for a stable product. For samples within that target cell density range at time of packaging, at the one month time point, the microbial stability was the same across all samples, regardless of the buffer or stabilizers comprised by the composition. At the two month time point, the combination of a buffer and a microbial stabilizer provided improved stability compared to conditions without those agents (regardless of the physical stabilizer). At the three month time point, the importance of the physical stabilizer type became apparent, and the fructose and xanthan gum combination of stabilizers outperformed other stabilizer combinations for preserving bacterial viability within the composition. Finally, at the four month time point, the combination of all four components was able to preserve bacterial viability: an initial cell density between 3-5E9 CFU/mL, high buffering capacity PBS, 0.1% xanthan gum and 1.3% fructose.

Results

The inventors of the present application sought to identify novel liquid agricultural compositions of nitrogen-fixing microbes with improved stability at room temperature compared to existing formulations, ideally for a period of at least three months. To do so, four different parameters of the composition were varied: initial cell density, microbial stabilizer, physical stabilizer, and buffering agent. Addressing only a single variable did not lead to the maximal period of microbial stability. Instead, the final agricultural composition achieved greater than four months of bacterial stability at room temperature by addressing all four parameters: selection of an initial cellular density chosen to decrease microbial decay rate; presence of a microbial stabilizer (fructose 1.3%); presence of a physical stabilizer (xanthan gum 0.1%); and selection of a buffering system (high buffering capacity modified PBS).

This exemplary method of modifying the aforementioned combination of four parameters is able to improve microbial stability and decrease accumulation of toxic metabolites produced during storage of an agricultural composition comprising nitrogen-fixing microorganisms. Selecting the proper cell density at time of packaging was a component in producing a stable product. Next, addition of a microbial and physical stabilizer, as well as having a buffer with a high buffering capacity, were all elements in providing long term shelf life. Microbial stabilizers protect the cells by potentially putting them in a semi-dormant state, so that the cells do not respond to environmental conditions as rapidly as they would in an active state; an appropriate buffering system prevents deleterious pH fluctuations; and physical stabilizers create homogeneous solutions, where the cells are at similar density throughout the liquid. Each component individually functioned to improve stability to some extent, but it was the combination of all four factors that provided the most significant long-term improvement in microbial stability.

Example 2: Formulation of Exemplary Agronomically Stable Liquid Agricultural Composition The present example provides the formulation steps and components for the exemplary agricultural composition developed according to Example 1.

Fermentation, Formulation, and Packaging

Fermentation: *Klebsiella variicola* NCMA 201712002 was fermented at 30° C. in stirred tank reactors (STR) to generate a high cell density robust broth by batch process. Cells were harvested at a cell density of 1.2 to 2.0E10 CFU/mL.

Formulation: After fermentation, cells were diluted in modified, high buffering capacity PBS to a cellular density of 4.5-5.5E9 CFU/mL with fructose and xanthan gum added to final concentrations of 1.3% and 0.1%, respectively. The concentrations of the chemical components of the final product are provided in Table 9.

TABLE 9

Components and concentrations in final liquid agricultural composition product

| Description | Concentration (% in final product) |
|---|---|
| Fructose | 1.3 |
| Xanthan gum | 0.1 |
| monobasic $KH_2PO_4$ | 1.53 |
| NaCl | 0.5 |
| KCl | 0.013 |
| dibasic $Na_2HPO_4$ | 0.09 |

Packaging: product was packaged and stored in breathable bags/bladders with 20% headspace.

Bacterial Stability

Figure 5:
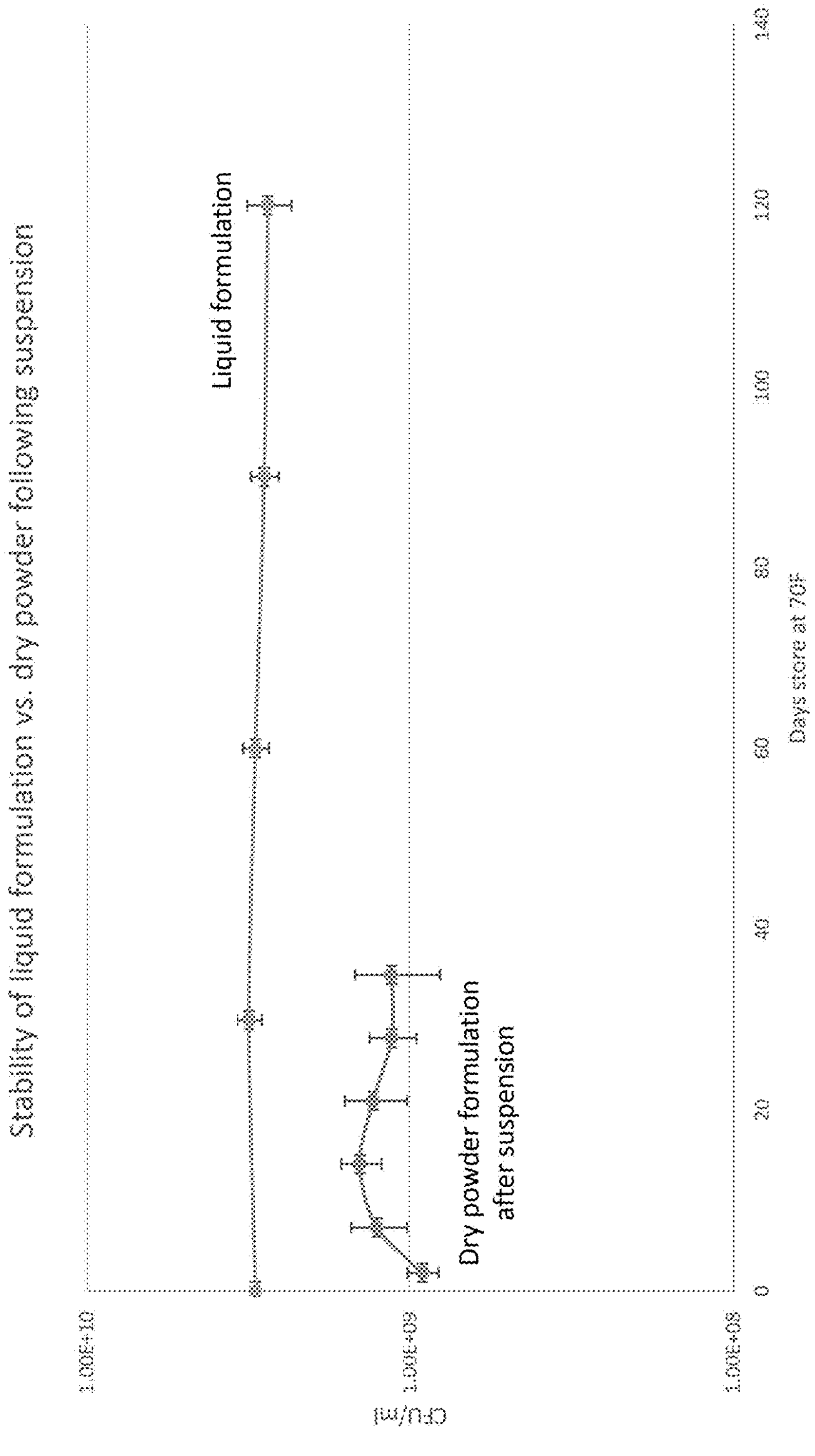
FIG. 5 shows a comparison between the bacterial stability of an exemplary liquid agricultural composition according to the present disclosure and the bacterial propagation of a suspended and activated dry formulation comprising the same bacterial strain.

The microbial stability within the liquid agricultural composition was compared to a dry formulation (Pivot Bio PROVEN™ 2019 dry formulation) comprising the same bacterial strain. The liquid agricultural composition was prepared according to the foregoing formulation steps, while the dry formulation was suspended and activated in a liquid medium according to packaging instructions. The microbial stability of the liquid formulation was monitored on a monthly basis for four months, while the bacterial propagation of the activated and suspended dry formulation was monitored for a period of 35 days. FIG. 5 shows the results of this comparison. The liquid formulation was stable, with almost no change in bacterial viability over the entire tested period of four months, while the bacteria within the suspended dry formulation initially grow after activation, but then start to slowly decay after more than 30 days. This is consistent with the packaging instructions for the dry formulation, which recommend use within 30 days after activation. By contrast, the liquid formulation provides a longer stability timeframe within its liquid form, allowing for greater ease of storage and delivery, without the need for activation and use within a short period.

Bacterial Titer

The improved stability and functionality of the agronomically stable liquid agricultural composition also allowed for an increased bacterial titer within the final product as compared to the dry formulation after liquid suspension. The liquid agricultural composition had a bacterial titer high enough to provide sufficient microbes for 20 acres of land with only 8 L of product—four-fold higher than for the suspended dry powder formulation, which provided sufficient microbes for only 5 acres of land with 8 L of product.

Example 3: Formulation of Exemplary Agronomically Stable Agricultural Composition Comprising Alternative Bacterium The formulation ingredients selected in Example 1 and the formulation steps carried out in Example 2 were applied with a different strain of bacterium, *Kosakonia sacchari* PTA-126743, with the aim of improving microbial stability and shelf life, and decreasing toxin accumulation for the agricultural composition comprising that bacterium.

The PTA-126743 strain agricultural composition was formulated with a 3×diluted initial cell density of about 3E9 CFU/mL, 1.3% fructose, and 0.1% xanthan gum in high buffering capacity PBS. This agricultural composition was compared to the normal fermentation broth in terms of ammonia accumulation, bacterial stability, and pH stability. All samples were tested in triplicate, and the results were averaged.

Average ammonia concentration was measured at the 0 and 3 month time points, with results shown in Table 10. The results demonstrate that the agricultural composition had lower average ammonia concentrations at both time points, with less than half the amount of ammonia accumulation over the course of three months compared to the non-optimized fermentation broth.

TABLE 10

Ammonia accumulation in broth vs. agricultural composition comprising *Kosakonia sacchari* PTA-126743.

| Formulation | Strain | Initial Avg. [NH4+] (mM) | 3 Mo. Avg. [NH4+] (mM) | 3 Mo. Std. Dev. | 3 Mo. Change [NH4+] (mM) |
|---|---|---|---|---|---|
| Broth | PTA-126743 | 78.7 | 95.8 | 2.3 | 17.2 |
| Agricultural composition | PTA-126743 | 20.7 | 28.6 | 4.3 | 7.8 |

The bacterial stability was also compared between the broth and the agricultural composition, results shown in Table 11. Cell density was measured at 0, 1, and 3 months, and the 1 month log loss and 3 month log loss were computed based on these values. The initial cell density of the agricultural composition was one third that of the broth because of the dilution step within the formulation of the agricultural composition. At 1 month, the broth experienced 0.93 log loss of CFU/mL, while the agricultural composition experienced only 0.22 log loss of CFU/mL. At 3 months, the broth experienced 1.28 log loss of CFU/mL compared to the 0.69 log loss of CFU/mL for the agricultural composition, such that the agricultural composition experienced roughly 50% less viability loss over the 3 month time period. By the 3 month time point, the cell density of the agricultural composition was higher than that of the broth, even though it started out as a one third dilution, because of the much lower decay rate. In fact, due to some measurement uncertainty, it is believed that the cell density of the agricultural composition at 3 months was even higher than reported.

TABLE 11

Bacterial stability in broth vs. agricultural composition comprising *Kosakonia sacchari* PTA-126743.

| Formulation | Strain | Storage Temp | Initial CFU/ml | 1 month CFU/ml | 1 month log loss | 3 month CFU/ml | 3 month log loss |
|---|---|---|---|---|---|---|---|
| Broth | PTA-126743 | RT | 7.83E+09 | 9.24E+08 | 0.93 | 4.12E+08 | 1.28 |
| Agricultural composition | PTA-126743 | RT | 2.72E+09 | 1.64E+09 | 0.22 | 5.55E+08 | 0.69 |

The pH stability of the agricultural composition over the 3 month time period was also compared to that of the broth, results shown in Table 12. Overall, the pH of the agricultural composition changed by less than 0.3 at either time point compared to the original pH, while the pH of the broth continued to increase over the 3 month window, with a final difference of 1.31 compared to the initial pH measurement.

TABLE 12

Bacterial stability in broth vs. agricultural composition comprising *Kosakonia sacchari* PTA-126743.

| Formulation | Strain | Storage Temp | Initial pH | 1 month pH | 1 month pH change | 3 month PH | 3 month pH change |
|---|---|---|---|---|---|---|---|
| Broth | PTA-126743 | RT | 6.74 | 7.72 | 0.98 | 8.05 | 1.31 |
| Agricultural composition | PTA-126743 | RT | 6.52 | 6.25 | −0.27 | 6.73 | 0.21 |

These results show that the agricultural composition maintained its microbial viability, pH level, and low ammonia concentration better than the non-optimized fermentation broth over the course of 3 months.

Example 4: Field Application of Exemplary Liquid Agricultural Composition

The exemplary agronomically stable liquid agricultural composition developed according to the method of Example 1 and prepared according to the formulation steps of Example 2 was evaluated in eight corn fields.

Data Collection

Corn yields with the grower standard nitrogen fertilization practice were compared to corn yields with the liquid agricultural composition added to the system as an in-furrow application at planting. These trials took place in 4 different states: 3 in Illinois, 2 in Missouri, 2 in Minnesota, and 1 in Iowa. Farmers were instructed to split fields in three with the liquid agricultural composition on one third of the field, the Grower Standard Practice (untreated control) on the next third, and a suspended and activated dry formulation (Pivot Bio PROVEN™, as referenced in Example 2) on the remaining third.

Trial participants provided digital as-planted (planter monitor) and harvest (combine yield monitor) maps identifying the two treatment zones and the control zone. ArcGIS software was used to analyze data and compare yield differences between the zones.

The yield data from the harvest combine monitors were used to examine changes in yield variability between liquid formulation-treated field areas, suspended dry formulation-treated field areas, and untreated control areas by analyzing the yield homogeneity of variance and standard deviation.

Figure 6:
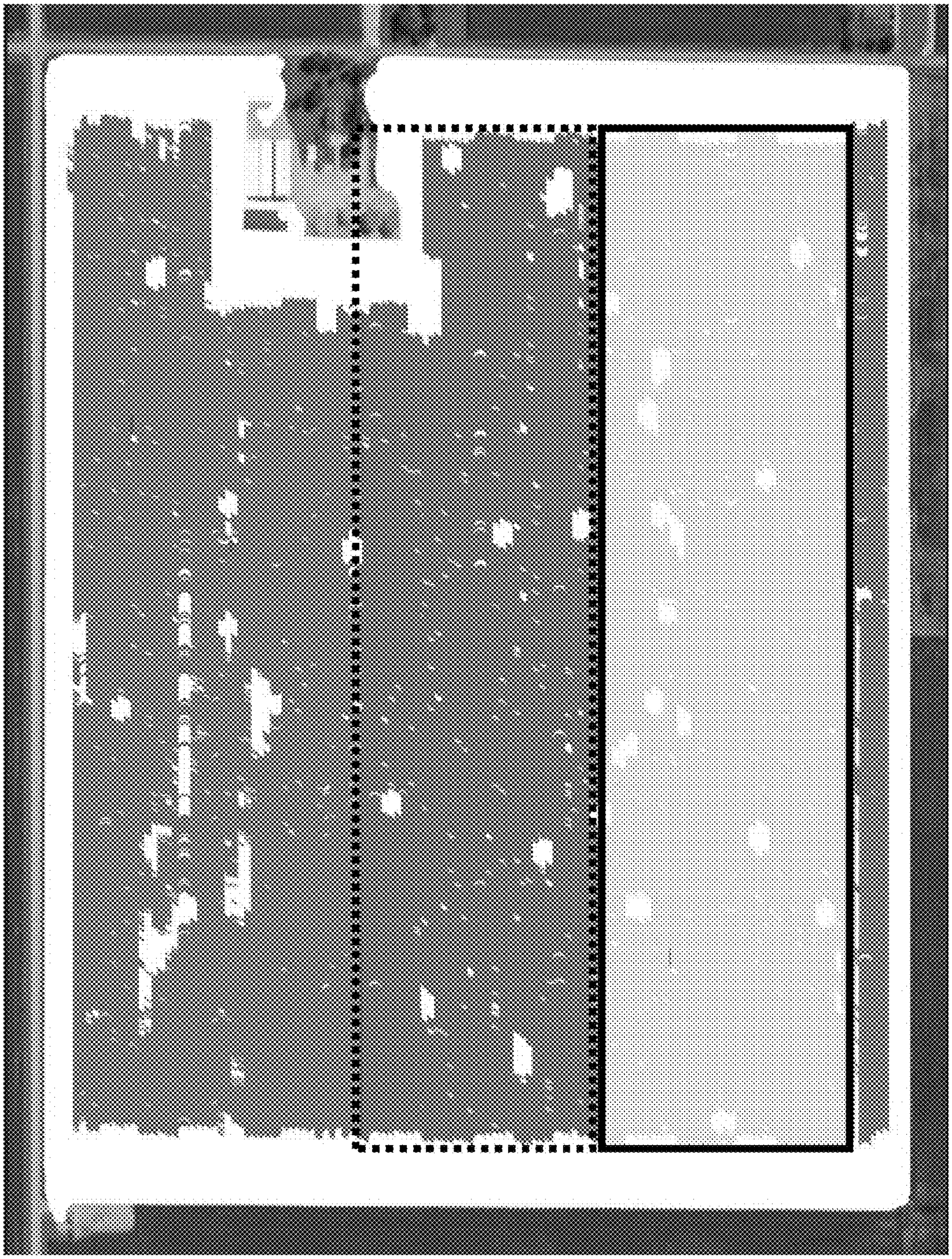
FIG. 6 shows the data collection and quality control for harvest combine monitor data for an exemplary field trial comparing an exemplary liquid agricultural composition of the present disclosure to a suspended dry formulation and an untreated control. White areas correspond to data that were removed because they corresponded to header rows, or because they corresponded to areas where the harvest combine did not have a steady velocity or direction. The area outlined in a dotted line was treated with the exemplary liquid agricultural composition; the area outline in a solid line was treated with the suspended, activated dry formulation; and the remaining areas were the untreated control areas.

Additional QA/QC procedures were applied to combine data ensuring representative comparisons from both treated and untreated field regions. Header rows, which are typically lower in yield, more prone to damage and have a varying incident solar radiation profile, were removed from field data sets. This can be seen in FIG. 6, which shows the data collection and quality control for an exemplary corn field. In this figure, the perimeter of the field is white, showing areas that were excluded from the data analysis. In addition, the most reliable data from combine harvest monitors occurs in areas where the combine is moving at a steady velocity. Thus, data points were removed with automated filters in areas where the combine was accelerating or where the combine had to slow down to pass obstacles like field drains or terraces—these are shown as white patches within the illustrative field depicted in FIG. 6. A total of 54,623 yield harvest data points total were analyzed in this field. Table 13 contains the summary of data points and acreage collected for the treatment and control areas across all 8 trials.

TABLE 13

| Data points by treatment type across the 8 field trials. | | | | |
|---|---|---|---|---|
| | Untreated Control | Suspended dry formulation | Liquid formulation | Total |
| Total monitor data points | 385,361 | 188,451 | 182,231 | 756,043 |
| Total area (acres) | 637 | 293 | 272 | 1,202 |

Results

The performance of the exemplary liquid agricultural composition was evaluated along two metrics: average yield within a field and yield consistency across the field.

Increasing average yield in a field increases the overall production. Furthermore, uniform crop development is an important factor in maximizing yields and an important driver of within field yield variance. Corn is more responsive to nitrogen than other nutrients. Consequently, differences in nitrogen availability within fields contribute greatly to yield variance. The agronomically stable liquid agricultural compositions of the present disclosure can serve as a baseline nitrogen source that doesn't leach from the soil and that delivers nitrogen to the corn plant in a more consistent and reliable manner compared to traditional synthetic nitrogen sources.

Figure 7:
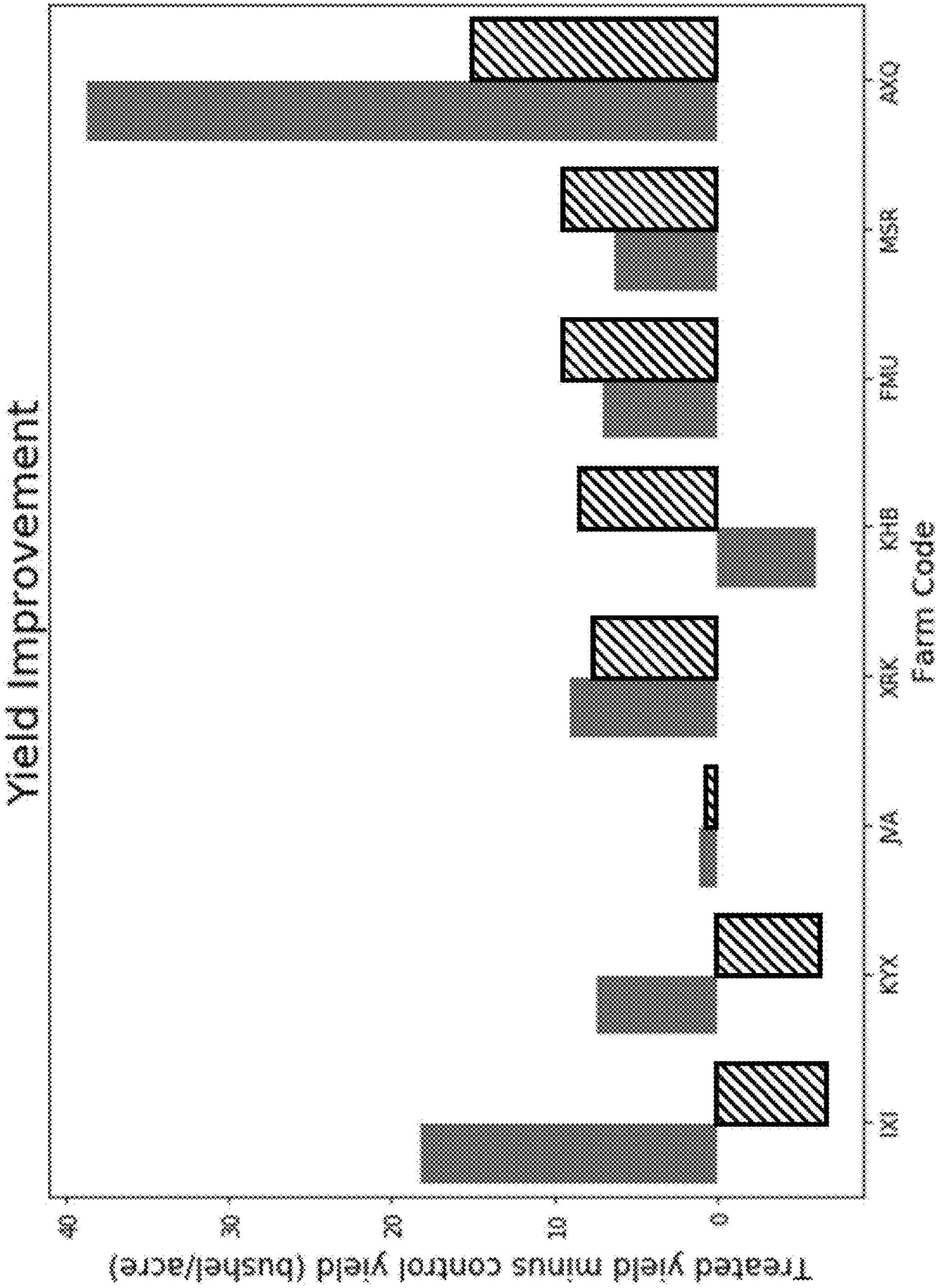
FIG. 7 shows the yield improvement across the eight field trials for a commercially available dry formulation, Pivot Bio PROVEN™ 2019 (solid bars) and an exemplary liquid agricultural composition (bars with diagonal lines).

In terms of average yield, the dry formulation has shown a 76% win rate for increasing yields across 37 large scale field trials, with an average improvement of 5.8 bushels/acre. The exemplary liquid agricultural composition was tested in a smaller set of 8 field trials side by side with the dry formulation. It showed a similar win rate of 75% and an average improvement of 4.7 bushels/acre, as shown in FIG. 7. The activated dry formulation had a yield improvement of 10.2 bushels/acre and a win rate of 88% in the same subset of trials. This shows that the liquid agricultural composition achieved a similar win rate and average yield improvement compared to the overall win rate and average yield improvement for the commercially available dry formulation, while having improved liquid shelf stability and ease of transportation, storage, and use.

Figure 8:
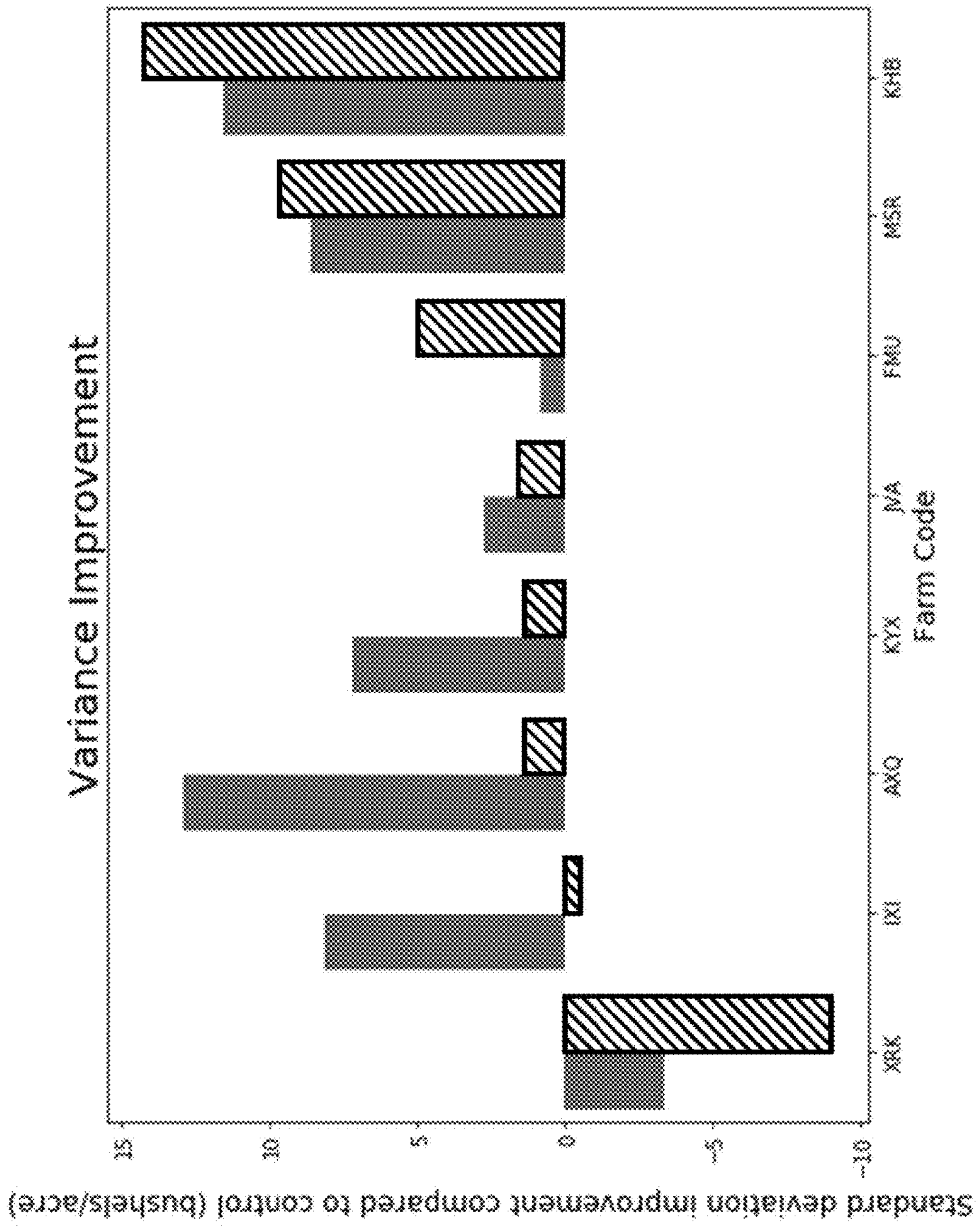
FIG. 8 shows the variance improvement across the eight field trials for a commercially available dry formulation, Pivot Bio PROVEN™ 2019 (solid bars) and an exemplary liquid agricultural composition (bars with diagonal lines).

In terms of yield consistency, the dry formulation has improved uniform yield consistency in 70% of the 37 large scale field trials by reducing the standard deviation of the yield points in treated areas. FIG. 8 shows a similar yield variance improvement for the exemplary liquid agricultural composition, which achieved a win rate of 75% and a variance improvement of 2.9 bushels/acre in the 8 trials. The dry formulation showed a variance improvement of 6.1 bushels/acre and a win rate of 88% in the same trials. This comparison shows that the liquid agricultural composition achieved a higher win rate for yield variance improvement than the historical average for the commercially available dry formulation.

Overall, in its 8 field trials, the liquid agricultural composition performed comparably to the historical average for the commercially available dry formulation comprising the same strain of nitrogen-fixing gram negative bacteria. These similar results were achieved in spite of the fact that the liquid agricultural composition was two-months old upon application to the fields compared to the suspended dry formulation, which was freshly activated. These trial demonstrate the suitability of the liquid agricultural composition for use in improving the average yield and yield consistency of corn crops. Furthermore, it accomplished these results without the need for activation and suspension by the farmers, and with much greater shelf stability in liquid form.

Example 5: Wheat Field Application of Exemplary Liquid Agricultural Composition The exemplary agronomically stable liquid agricultural composition developed according to the method of Example 1 and prepared according to the formulation steps of Example 2 was evaluated in ten trial locations in common spring wheat production areas.

Data Collection

Wheat yields with the grower standard nitrogen fertilization practice were compared to wheat yields with the liquid agricultural composition added to the system as an in-furrow application at planting. The trial was a large replicated complete block design with four repetitions. There was one untreated control which received 100% of the recommended nitrogen rate (labeled "check 100%" in FIG. 9). The other treatments, included a reduced nitrogen control, in which nitrogen was reduced by 25 pounds and a experimental treatment in which the reduced nitrogen control sample was supplemented with the liquid agricultural composition (non-treated control labeled "check −25 lbs" and treated labeled "KV137-RTU-25 lbs" in FIG. 9).

Results

Figure 9:
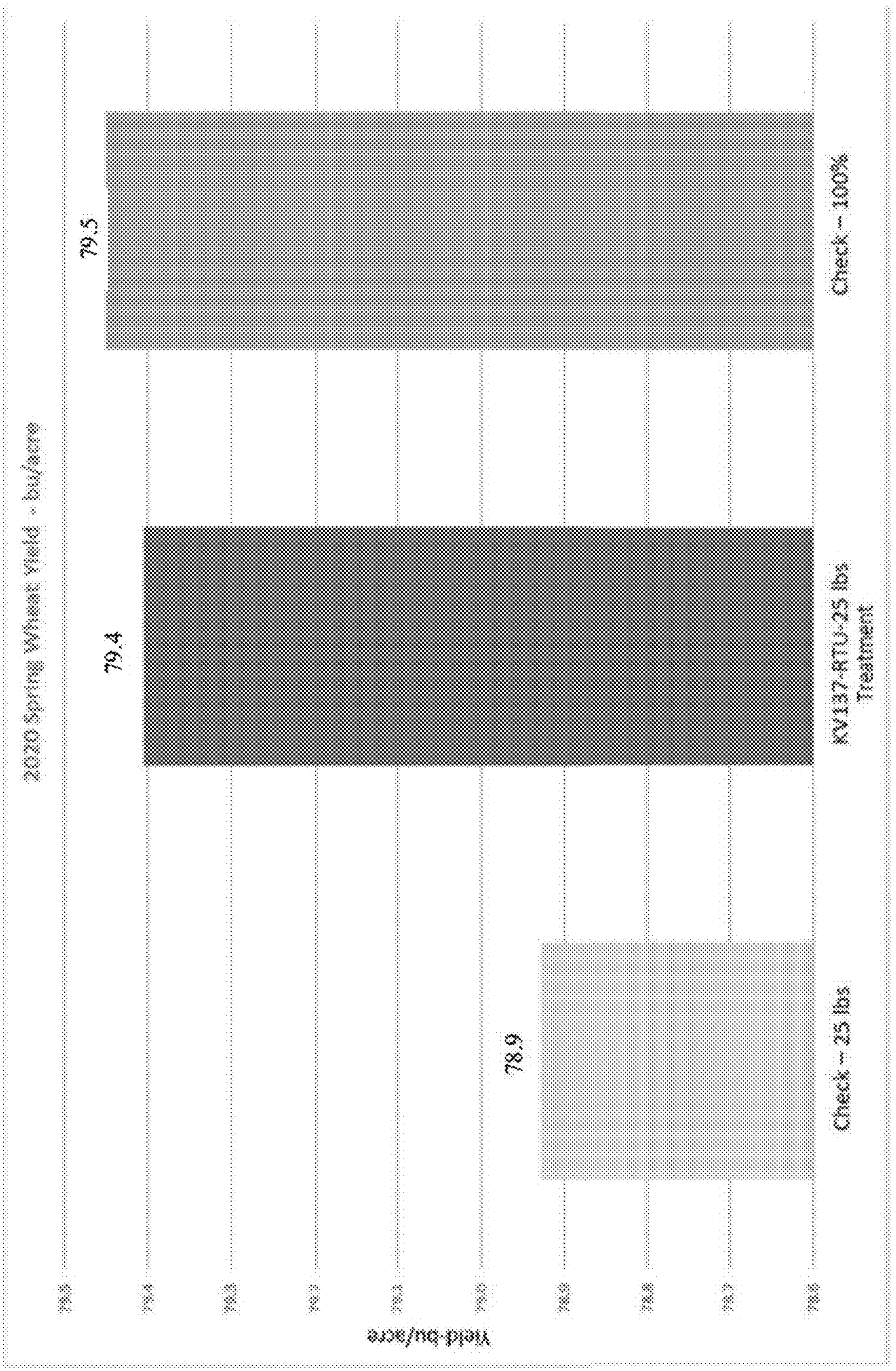
FIG. 9 shows a bar graph of wheat yield. *K. variicola* deposited strain NCMA 201708001 ("KV137-RTU") was tested at ten trial locations where nitrogen was reduced by 25 pounds and compared to (1) a control which received 100% of the recommended nitrogen rate and (2) a reduced nitrogen control containing nitrogen reduced by 25 pounds.

The performance of the exemplary liquid agricultural composition was evaluated by average yield in bushels per acre (FIG. 9). In the reduced nitrogen fertilizer setting, KV137-RTU had an average yield response 0.6 bu/acre higher compared to the reduced nitrogen "check −25 lbs" and was within 0.1 bu/acre of wheat treated with the grower standard nitrogen fertilization practice.

Overall, these trials demonstrate the suitability of the liquid agricultural composition for use in producing wheat with reduced nitrogen fertilizer.

Example 6: Sorghum Field Application of Exemplary Liquid Agricultural Composition The exemplary agronomically stable liquid agricultural composition developed according to the method of Example 1 and prepared according to the formulation steps of Example 2 was evaluated in ten trial locations in common grain sorghum production areas.

Data Collection

Sorghum yields with the grower standard nitrogen fertilization practice were compared to sorghum yields with the liquid agricultural composition added to the system as an in-furrow application at planting. The trial was a large replicated complete block design with four repetitions. There was one untreated control which received 100% of the recommended nitrogen rate (labeled "check 100%" in FIG. 10). The other treatments, included a nontreated control and an experimental treatment, were reduced by 25 pounds of nitrogen alone, or in the case of the experimental treatment, were supplemented with the liquid nutritional composition (nontreated control labeled "check −25 lbs" and treated labeled "KV137-RTU-25 lbs" in FIG. 10).

Results

The performance of the exemplary liquid agricultural composition was evaluated by average yield in bushels per acre (FIG. 10). In the reduced nitrogen fertilizer setting, KV137-RTU had an average yield increase of 4.1 bu/acre over the "check −25 lbs" with a win rate of 71% and a 1.5 bu/acre advantage over the sorghum treated with the grower standard nitrogen fertilization practice with a win rate of 30%.

Overall, these trials demonstrate the suitability of the liquid agricultural composition for use in producing sorghum with reduced nitrogen fertilizer.

Example 7: Formulation of Exemplary Agronomically Stable Liquid Agricultural Composition The present example provides the formulation components for an exemplary agricultural composition developed with *K. sacchari* PTA-126743.

Fermentation, Formulation, and Packaging

Fermentation: *K. sacchari* PTA-126743 was fermented at 30° C. in stirred tank reactors (STR) to generate a high cell density robust broth by batch process.

Formulation: After fermentation, cells were diluted in modified, high buffering capacity PBS. Formulations were generated with different combinations of stabilizers (3 stabilizers each at 2 concentrations), one physical stabilizer and 2 carrier buffers (water as control and optimized PBS buffer). Specifically, combinations of fructose (1.3%), xanthan gum (0.1%), sucrose (1.3% or 2.5%), inulin (1.3% or 2.5%), and 200 mM phosphate, all in comparison with a control having no buffer or stabilizer.

Packaging: product was packaged and stored in breathable bags/bladders with 20% headspace.

Bacterial Stability

Stability of formulated material was monitored at room temperature for up to 4.5 months with monthly sample taken and analyzed for viability, pH and purity (cell viability (CFU/mL) shown in FIG. 11). The results indicate that a microbial stabilizer and buffer can maintain viability of the product beyond 3 months.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as an acknowledgment or any form of suggestion that they constitute valid prior art or form part of the common general knowledge in any country in the world.

Numbered Embodiments of the Invention

Notwithstanding the appended claims, the disclosure sets forth the following numbered embodiments:

1. An agronomically stable liquid agricultural composition, comprising:

a) a diazotrophic bacterium;

b) a buffering agent;

c) a microbial stabilizer; and d) a physical stabilizer, wherein the composition has a room temperature shelf life of at least 30 days.

2. The composition of embodiment 1, wherein the microbial stability of the composition is greater than the microbial stability of the composition absent one or more of the buffering agent, microbial stabilizer, and physical stabilizer.

3. The composition of any one of embodiments 1-2, wherein the shelf life is at least two months, at least three months, at least four months, or at least five months.

4. The composition of any one of embodiments 1-3, wherein the shelf life is at least three months.

5. The composition of any one of embodiments 1-4, wherein the log loss of CFU/mL over the shelf life of the composition is less than 0.2.

6. The composition of any one of embodiments 1-5, wherein the bacterium is present at a cellular density that provides an acceptable rate of decay over the shelf life of the composition.

7. The composition of any one of embodiments 1-6, wherein the bacterium is present at a cellular density that minimizes the rate of decay over the shelf life of the composition.

8. The composition of any one of embodiments 1-7, wherein the bacterium is present at a cellular density that provides a reduced, but not minimized rate of decay.

9. The composition of any one of embodiments 1-8, wherein the bacterium is present at a cellular density that provides a rate of decay of less than 1.0 log loss of CFU/mL over 30 days in the agricultural composition absent the buffering agent, microbial stabilizer, and physical stabilizer.

10. The composition of any one of embodiments 1-9, wherein the bacterium is present at a cellular density of about 3E9-6E9 CFU/mL.

11. The composition of any one of embodiments 1-10, wherein the buffering agent maintains the pH of the composition over the shelf life of the composition.

12. The composition of any one of embodiments 1-11, wherein the buffering agent maintains the pH of the composition at about pH 6-8 over the shelf life of the composition.

13. The composition of any one of embodiments 1-12, wherein the buffering agent maintains the pH of the composition at about pH 6.5 over the shelf life of the composition.

14. The composition of any one of embodiments 1-13, wherein the buffering agent is selected from the list consisting of phosphate buffered saline (PBS); modified, high buffering capacity PBS; 3-Morpholinopropane-1-sulfonic acid (MOPS); and 2-[4-(2-hydroxyethyl)piperazin-1-yl]ethanesulfonic acid (HEPES).

15. The composition of any one of embodiments 1-14, wherein the buffering agent is modified, high buffering capacity PBS.

16. The composition of any one of embodiments 1-15, wherein the microbial stabilizer slows the doubling rate of the diazotrophic bacterium.

17. The composition of any one of embodiments 1-16, wherein the microbial stabilizer slows the toxin accumulation rate within the composition.

18. The composition of any one of embodiments 1-17, wherein the microbial stabilizer is a monosaccharide, disaccharide, polysaccharide, pentose, hexose, oligosaccharide, oligofructose, sugar alcohol, amino acid, protein or protein hydrolysate, or polymer.

19. The composition of any one of embodiments 1-18, wherein the microbial stabilizer is a monosaccharide or a disaccharide selected from the list consisting of glucose, fructose, trehalose, sucrose, lactose, melibiose, and lactulose.

20. The composition of any one of embodiments 1-19, wherein the microbial stabilizer is fructose or trehalose.

21. The composition of any one of embodiments 1-20, wherein the microbial stabilizer is fructose.

22. The composition of any one of embodiments 1-21, wherein the microbial stabilizer is fructose and is present in the composition at a concentration of about 0.5-2.5% w/v.

23. The composition of any one of embodiments 1-22, wherein the microbial stabilizer is fructose and is present in the composition at a concentration of about 1.3% w/v.

24. The composition of any one of embodiments 1-23, wherein the physical stabilizer decreases the local density of the diazotrophic bacterium within the composition.

25. The composition of any one of embodiments 1-24, wherein the physical stabilizer is a polysaccharide, protein or protein hydrolysate, polymer, or a natural gum or its derivative.

26. The composition of any one of embodiments 1-25, wherein the physical stabilizer is a polysaccharide.

27. The composition of any one of embodiments 1-26, wherein the physical stabilizer is a polysaccharide selected from the list consisting of maltodextrin, polyethylene glycol (PEG), xanthan gum, pectin, alginates, microcrystalline cellulose, and dextran.

28. The composition of any one of embodiments 1-27, wherein the physical stabilizer is xanthan gum.

29. The composition of any one of embodiments 1-28, wherein the physical stabilizer is xanthan gum and is present in the composition at a concentration of about 0.001-0.2% w/v.

30. The composition of any one of embodiments 1-29, wherein the physical stabilizer is xanthan gum and is present in the composition at a concentration of about 0.1% w/v.

31. The composition of any one of embodiments 1-30, wherein the bacterium is a gram-negative bacterium.

32. The composition of any one of embodiments 1-31, wherein the bacterium is of a genus selected from the group consisting of: *Acetobacter, Achromobacter, Aerobacter, Anabaena, Azoarcus, Azomonas, Azorhizobium, Azospirillum, Azotobacter, Beijernickia, Bradyrhizobium, Burkholderia, Citrobacter, Derxia, Enterobacter, Herbaspirillum, Klebsiella, Kluyvera, Kosakonia, Mesorhizobium, Metakosakonia, Paraburkholderia, Nostoc, Rahnella, Rhizobium, Rhodobacter, Rhodopseudomonas, Rhodospirillum, Serratia Sinorhizobium, Spirillum, Trichodesmium*, and *Xanthomonas*.

33. The composition of any one of embodiments 1-32, wherein the bacterium is of a species selected from the group consisting of: *Achromobacter marplatensis, Achromobacter spiritinus, Azospirillum lipoferum, Enterobacter sacchari, Herbaspirillum aquaticum, Klebsiella variicola, Kluyvera intermedia, Kosakonia pseudosacchari, Kosakonia sacchari, Metakosakonia intestini, Paraburkholderia tropica, Rahnella aquatilis*, and combinations thereof.

34. The composition of any one of embodiments 1-33, wherein the bacterium is a gram-positive bacterium.

35. The composition of any one of embodiments 1-34, wherein the bacterium is of a genus selected from the group consisting of: *Arthrobacter, Agromyces, Bacillus, Clostridium, Corynebacterium, Frankia, Heliobacillus, Heliobacterium, Heliophilum, Heliorestis Methanobacterium, Microbacterium, Micrococcus, Micromonospora, Mycobacterium, Paenibacillus, Propionibacterium*, and *Streptomyces*.

36. The composition of any one of embodiments 1-35, wherein the bacterium is of a species selected from the group consisting of: *Bacillus amyloliquefaciens, Bacillus macerans, Bacillus pumilus, Bacillus thuringiensis, Clostridium acetobutylicum, Corynebacterium autitrophicum Methanobacterium formicicum, Methanobacterium omelionski, Microbacterium murale, Mycobacterium flavum, Paenibacillus polymyxa, Paenibacillus riograndensis, Propionibacterium acidipropio, Propionibacterium freudenreichii, Streptococcus lactis, Streptomyces griseus*, and combinations thereof.

37. The composition of any one of embodiments 1-36, wherein the bacterium is of the genus *Klebsiella*.

38. The composition of any one of embodiments 1-37, wherein the bacterium is of the species *Klebsiella variicola*.

39. The composition of any one of embodiments 1-38, wherein the bacterium is of the strain *Klebsiella variicola* NCMA 201712002.

40. The composition of any one of embodiments 1-39, wherein the bacterium is of the genus *Kosakonia*.

41. The composition of any one of embodiments 1-40, wherein the bacterium is of the species *Kosakonia sacchari*.

42. The composition of any one of embodiments 1-41, wherein the bacterium is of the strain *Kosakonia sacchari* PTA-126743.

43. The composition of any one of embodiments 1-42, wherein the bacterium is endophytic, epiphytic, or rhizospheric.

44. The composition of any one of embodiments 1-43, wherein the bacterium is a wild type bacterium.

45. The composition of any one of embodiments 1-44, wherein the bacterium is an engineered bacterium.

46. The composition of any one of embodiments 1-45, wherein the bacterium is a transgenic bacterium.

47. The composition of any one of embodiments 1-46, wherein the bacterium is an intragenic bacterium.

48. The composition of any one of embodiments 1-47, wherein the bacterium is a remodeled bacterium.

49. The composition of any one of embodiments 1-48, wherein the bacterium comprises a non-intergeneric genomic modification.

50. The composition of any one of embodiments 1-49, wherein the bacterium is an engineered bacterium capable of fixing atmospheric nitrogen in the presence of exogenous nitrogen.

51. The composition of any one of embodiments 1-50, wherein the bacterium is an engineered bacterium comprising at least one genetic variation introduced into at least one gene, or non-coding polynucleotide, of the nitrogen fixation or assimilation genetic regulatory network.

52. The composition of any one of embodiments 1-51, wherein the bacterium is an engineered bacterium comprising an introduced control sequence operably linked to at least one gene of the nitrogen fixation or assimilation genetic regulatory network.

53. The composition of any one of embodiments 1-52, wherein the bacterium is an engineered bacterium comprising a heterologous promoter operably linked to at least one gene of the nitrogen fixation or assimilation genetic regulatory network.

54. The composition of any one of embodiments 1-53, wherein the bacterium is an engineered bacterium comprising at least one genetic variation selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, a gene associated with biosynthesis of a nitrogenase enzyme, and combinations thereof.

55. The composition of any one of embodiments 1-54, wherein the bacterium is an engineered bacterium comprising at least one genetic variation introduced into at least one gene, or non-coding polynucleotide, of the nitrogen fixation or assimilation genetic regulatory network that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased expression or uridylyl-removing activity of GlnD.

56. The composition of any one of embodiments 1-55, wherein the bacterium is an engineered bacterium comprising a mutated nifL gene that has been altered to comprise a heterologous promoter inserted into said nifL gene.

57. The composition of any one of embodiments 1-56, wherein the bacterium is an engineered bacterium comprising a mutated glnE gene that results in a truncated GlnE protein lacking an adenylyl-removing (AR) domain.

58. The composition of any one of embodiments 1-57, wherein the bacterium is an engineered bacterium comprising a mutated glnD gene that results in the lack of expression of said glnD gene.

59. The composition of any one of embodiments 1-58, wherein the bacterium is an engineered bacterium comprising a mutated amtB gene that results in the lack of expression of said amtB gene.

60. The composition of any one of embodiments 1-59, wherein the bacterium is an engineered bacterium comprising at least one of: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; a mutated glnD gene that results in the lack of expression of said glnD gene; and combinations thereof.

61. The composition of any one of embodiments 1-60, wherein the bacterium is an engineered bacterium comprising at least one genetic variation introduced into genes involved in a pathway selected from the group consisting of: exopolysaccharide production, endo-polygalaturonase production, trehalose production, and glutamine conversion.

62. The composition of any one of embodiments 1-61, wherein the bacterium is an engineered bacterium comprising at least one genetic variation introduced into genes selected from the group consisting of: bcsii, bcsiii, yjbE, fhaB, pehA, otsB, treZ, glsA2, and combinations thereof.

63. The composition of any one of embodiments 1-62, wherein the bacterium is selected from Table 1, or a variant, mutant, or derivative thereof.

64. The composition of any one of embodiments 1-63, wherein the bacterium comprises a nucleic acid sequence that shares at least about 90%, 95%, or 99% sequence identity to a nucleic acid sequence selected from SEQ ID NOs: 1-223.

65. The composition of any one of embodiments 1-64, wherein the bacterium comprises a nucleic acid sequence selected from SEQ ID NOs: 1-223.

66. An agronomically stable liquid agricultural composition with a room temperature shelf life of at least 3 months, comprising:

a) a diazotrophic bacterium at a cellular density that provides a decay rate of less than 0.2 log loss CFU/mL over the shelf life of the composition;

b) a buffering agent that maintains the pH of the composition around pH 6.7 over the shelf life of the composition;

c) a microbial stabilizer that slows the doubling rate of the diazotrophic bacterium; and d) a physical stabilizer that decreases the local density of the diazotrophic bacterium within the composition, wherein the stability of the composition is greater than, and the presence of toxic byproducts is less than, the composition absent one or more of the buffering agent, microbial stabilizer, and physical stabilizer.

67. An agronomically stable liquid agricultural composition with a room temperature shelf life of at least 3 months, comprising:

a) *Klebsiella variicola* at a concentration of at least about 4.5E9 CFU/mL;

b) modified, high buffering capacity PBS;

c) fructose at a concentration of at least about 1% w/v; and d) xanthan gum at a concentration of at least about 0.05% w/v.

68. An agronomically stable liquid agricultural composition with a room temperature shelf life of at least 3 months, comprising:

a) *Kosakonia sacchari* at a concentration of about 3E9 CFU/mL;

b) modified, high buffering capacity PBS; and c) fructose at a concentration of at least about 1% w/v.

69. The composition of any one of embodiments 1-68, wherein the bacterium is a non-intergeneric remodeled bacterium.

70. Agricultural plant tissue comprising the agronomically stable liquid agricultural composition of any of embodiments 1-69.

71. The tissue of embodiment 70, wherein the agricultural plant is a legume or cereal grain.

72. The tissue of embodiment 70 or 71, wherein the agricultural plant is alfalfa, clover, bean, pea, chickpea, lentil, lupin, mesquite, carob, soybean, peanut, rooibos, or tamarind.

73. The tissue of any one of embodiments 70-72, wherein the agricultural plant is corn, rice, wheat, barley, sorghum, millet, oats, or rye.

74. The tissue of any one of embodiments 70-73, wherein the agricultural plant is corn.

75. A method for applying a diazotrophic bacterium to agricultural plant tissues comprising applying the composition of any one of embodiments 1-69 to agricultural plant tissues or the environs thereof.

76. A method for maintaining a population of a diazotrophic bacterium on an agricultural plant tissue comprising applying the composition of any one of embodiments 1-69 to said plant tissue or the environs thereof.

77. A method of increasing agricultural plant crop yield comprising applying the composition of any one of embodiments 1-69 to the agricultural plant tissues or the environs thereof prior to, during, or immediately following planting, thereby increasing the crop yield of the agricultural plant once planted.

78. A method of providing fixed atmospheric nitrogen to a cereal plant, comprising applying the composition of any one of embodiments 1-69 to the cereal plant tissues or the environs thereof.

79. A method of providing fixed atmospheric nitrogen to a corn plant that eliminates the need for the addition of in-season exogenous nitrogen application, comprising applying the composition of any one of embodiments 1-69 to the corn plant tissues or the environs thereof.

80. A method for increasing corn yield per acre, comprising applying the composition of any one of embodiments 1-69 to the corn plant tissues or the environs thereof.

81. A method for reducing infield variability for corn yield per acre, comprising applying the composition of any one of embodiments 1-69 to the corn plant tissues or the environs thereof, wherein the standard deviation of corn mean yield measured in bushels per acre is lower than for control plants to which the composition has not been applied.

82. The method of any one of embodiments 75-81, wherein the method comprises: a) applying the composition to a locus; and b) providing to the locus a plurality of the plants.

83. The method of any one of embodiments 75-82, wherein the composition comprises a plurality of said diazotrophic bacteria, wherein the diazotrophic bacteria comprise engineered bacteria, and wherein the engineered bacteria colonize the root surface of said plurality of plants and supply the plants with fixed nitrogen.

84. The method of any one of embodiments 75-83, wherein the composition comprises a plurality of said diazotrophic bacteria, wherein the diazotrophic bacteria comprise engineered bacteria, and wherein the engineered bacteria colonize the root surface of said plurality of plants and supply the plants with fixed nitrogen, and wherein the plurality of engineered bacteria produce in the aggregate at least about 15 pounds of fixed nitrogen per acre over the course of at least about 10 days to about 60 days.

85. The method of any one of embodiments 75-84, wherein exogenous nitrogen is not applied to the plant tissues or the environs thereof after the composition is applied.

86. The method of any one of embodiments 75-85, wherein the agricultural plant is a legume or cereal grain.

87. The method of any one of embodiments 75-86, wherein the agricultural plant is alfalfa, clover, bean, pea, chickpea, lentil, lupin, mesquite, carob, soybean, peanut, rooibos, or tamarind.

88. The method of any one of embodiments 75-87, wherein the agricultural plant is corn, rice, wheat, barley, sorghum, millet, oats, or rye.

89. The method of any one of embodiments 75-88, wherein the agricultural plant is corn.

90. The method of any one of embodiments 75-89, wherein the method increases the crop yield of the agricultural plant.

91. The method of any one of embodiments 75-90, wherein the method increases the crop yield of the agricultural plant with a win rate of greater than 65%.

92. The method of any one of embodiments 75-91, wherein the method increases the crop yield of the agricultural plant with a win rate of about 75%.

93. The method of any one of embodiments 75-92, wherein the method increases the crop yield of the agricultural plant by more than 3 bushels/acre.

94. The method of any one of embodiments 75-93, wherein the method increases the crop yield of the agricultural plant by about 3 bushels/acre.

95. The method of any one of embodiments 75-94, wherein the method reduces infield variability for the agricultural plant crop yield per acre.

96. The method of any one of embodiments 75-95, wherein the method reduces infield variability for the agricultural plant crop yield per acre with a win rate of greater than 65%.

97. The method of any one of embodiments 75-96, wherein the method reduces infield variability for the agricultural plant crop yield per acre with a win rate of about 75%.

98. The method of any one of embodiments 75-97, wherein the method reduces infield variability for the agricultural plant crop yield per acre with a variance improvement of greater than 2 bushels/acre.

99. A method of preparing an agronomically stable liquid agricultural composition comprising a diazotrophic bacterium, the method comprising the steps of.

a) providing a diazotrophic bacterium;

b) selecting for inclusion in the composition a cellular density of the diazotrophic bacterium that provides an acceptable rate of decay of the bacterium;

c) selecting a buffering agent for inclusion in the composition;

d) selecting a microbial stabilizer for inclusion in the composition; and e) selecting a physical stabilizer for inclusion in the composition, wherein the composition is stable at room temperature for a period of more than 30 days, and wherein the stability of the composition is greater than the composition absent one or more of the buffering agent, microbial stabilizer, an physical stabilizer.

100. A method for improving the stability of a liquid agricultural composition comprising a diazotrophic bacterium, the method comprising the steps of a) providing a diazotrophic bacterium;

b) selecting for inclusion in the composition a cellular density of the diazotrophic bacterium that provides an acceptable rate of decay of the bacterium;

c) selecting a buffering agent for inclusion in the composition;

d) selecting a microbial stabilizer for inclusion in the composition; and e) selecting a physical stabilizer for inclusion in the composition, wherein the composition has a room temperature shelf life of at least 30 days.

101. The method of embodiment 99 or 100, wherein step (b) comprises generating a titration curve to determine cellular density versus decay rate of the diazotrophic bacterium and selecting a cellular density that provides an acceptable decay rate.

102. The method of any one of embodiments 99-101, wherein steps (c)-(e) can be performed in any order.

103. The method of any one of embodiments 99-102, wherein any subset of steps (c)-(e) can be performed serially or in parallel.

104. The method of any one of embodiments 99-103, wherein step (c) comprises selecting a buffering agent that improves microbial stability when included in the agricultural composition, either in the presence or absence of the microbial and/or physical stabilizer.

105. The method of any one of embodiments 99-104, wherein step (c) comprises comparing two or more buffering agents and selecting the buffering agent that provides greater improvement to the microbial stability when included in the agricultural composition, either in the presence or absence of the microbial and/or physical stabilizer.

106. The method of any one of embodiments 99-105, wherein step (d) comprises selecting a microbial stabilizer that improves microbial stability when included in the agricultural composition, either in the presence or absence of the buffering agent and/or physical stabilizer 107. The method of any one of embodiments 99-106, wherein step (d) comprises comparing two or more microbial stabilizers and selecting the microbial stabilizer that provides greater improvement to the microbial stability when included in the agricultural composition, either in the presence or absence of the buffering agent and/or physical stabilizer.

108. The method of any one of embodiments 99-107, wherein step (e) comprises selecting a physical stabilizer that improves microbial stability when included in the agricultural composition, either in the presence or absence of the buffering agent and/or microbial stabilizer.

109. The method of any one of embodiments 99-108, wherein step (e) comprises comparing two or more physical stabilizers and selecting the physical stabilizer that provides greater improvement to the microbial stability when included in the agricultural composition, either in the presence or absence of the buffering agent and/or microbial stabilizer.

110. The method of any one of embodiments 99-109, wherein the selections of the microbial stabilizer and the physical stabilizer in steps (d) and (e) are performed simultaneously.

111. The method of any one of embodiments 99-110, wherein the method increases the shelf life of the liquid agricultural composition by a factor of at least 2, at least 3, or at least 4.

112. The method of any one of embodiments 99-111, wherein any one of steps (b)-(e) alone provides less improvement to the microbial stability of the composition than all of the steps together.

113. The method of any one of embodiments 99-112, wherein the composition is for application to agricultural plant tissues or the environs thereof.

114. The method of any one of embodiments 99-113, wherein the method decreases the accumulation of toxic byproducts in the composition over the course of its shelf life.

115. The method of any one of embodiments 99-114, wherein the method decreases the accumulation of ammonia in the composition over the course of its shelf life.

116. The method of any one of embodiments 99-115, wherein the method decreases the accumulation of ammonia in the composition by at least two-fold over the course of its shelf life as compared to an agricultural composition absent the microbial stabilizer and buffering agent.

117. The method of any one of embodiments 99-116, wherein the composition at the end of its' shelf life has a colonization potential approximately equal to the colonization potential of the composition when freshly formulated.

118. The method of any one of embodiments 99-117, wherein the microbial stability of the composition is greater than the microbial stability of the composition absent one or more of the buffering agent, microbial stabilizer, and physical stabilizer.

119. The method of any one of embodiments 99-118, wherein the composition has a shelf life of at least two months, at least three months, at least four months, or at least five months.

120. The method of any one of embodiments 99-119, wherein the composition has a shelf life of at least three months.

121. The method of any one of embodiments 99-120, wherein the log loss of CFU/mL over the shelf life of the composition is less than 0.2.

122. The method of any one of embodiments 99-121, wherein the cellular density of the bacterium minimizes the rate of decay over the shelf life of the composition.

123. The method of any one of embodiments 99-122, wherein the cellular density of the bacterium provides a reduced, but not minimized rate of decay.

124. The method of any one of embodiments 99-123, wherein the cellular density of the bacterium provides a rate of decay of less than 1.0 log loss of CFU/mL over 30 days in the agricultural composition absent the buffering agent, microbial stabilizer, and physical stabilizer.

125. The method of any one of embodiments 99-124, wherein the bacterium is present at a cellular density of about 3E9-6E9 CFU/mL.

126. The method of any one of embodiments 99-125, wherein the buffering agent maintains the pH of the composition over the shelf life of the composition.

127. The method of any one of embodiments 99-126, wherein the buffering agent maintains the pH of the composition at about pH 6-8 over the shelf life of the composition.

128. The method of any one of embodiments 99-127, wherein the buffering agent maintains the pH of the composition at about pH 6.5 over the shelf life of the composition.

129. The method of any one of embodiments 99-128, wherein the buffering agent is selected from the list consisting of phosphate buffered saline (PBS); modified, high buffering capacity PBS; 3-Morpholinopropane-1-sulfonic acid (MOPS); and 2-[4-(2-hydroxyethyl)piperazin-1-yl]ethanesulfonic acid (HEPES).

130. The method of any one of embodiments 99-129, wherein the buffering agent is modified, high buffering capacity PBS.

131. The method of any one of embodiments 99-130, wherein the microbial stabilizer slows the doubling rate of the diazotrophic bacterium.

132. The method of any one of embodiments 99-131, wherein the microbial stabilizer slows the toxin accumulation rate within the composition.

133. The method of any one of embodiments 99-132, wherein the microbial stabilizer is a monosaccharide, disaccharide, polysaccharide, pentose, hexose, oligosaccharide, oligofructose, sugar alcohol, amino acid, protein or protein hydrolysate, or polymer.

134. The method of any one of embodiments 99-133, wherein the microbial stabilizer is a monosaccharide or a disaccharide selected from the list consisting of glucose, fructose, trehalose, sucrose, lactose, melibiose, and lactulose.

135. The method of any one of embodiments 99-134, wherein the microbial stabilizer is fructose or trehalose.

136. The method of any one of embodiments 99-135, wherein the microbial stabilizer is fructose.

137. The method of any one of embodiments 99-136, wherein the microbial stabilizer is fructose and is selected for inclusion in the composition at a concentration of about 0.5-2.5% w/v.

138. The method of any one of embodiments 99-137, wherein the microbial stabilizer is fructose and is selected for inclusion in the composition at a concentration of about 1.3% w/v.

139. The method of any one of embodiments 99-138, wherein the physical stabilizer decreases the local density of the diazotrophic bacterium within the composition.

140. The method of any one of embodiments 99-139, wherein the physical stabilizer is a polysaccharide, protein or protein hydrolysate, polymer, or a natural gum or its derivative.

141. The method of any one of embodiments 99-140, wherein the physical stabilizer is a polysaccharide.

142. The method of any one of embodiments 99-141, wherein the physical stabilizer is a polysaccharide selected from the list consisting of maltodextrin, polyethylene glycol (PEG), xanthan gum, pectin, alginates, microcrystalline cellulose, and dextran.

143. The method of any one of embodiments 99-142, wherein the physical stabilizer is xanthan gum.

144. The method of any one of embodiments 99-143, wherein the physical stabilizer is xanthan gum and is selected for inclusion in the composition at a concentration of about 0.001-0.2% w/v.

145. The method of any one of embodiments 99-144, wherein the physical stabilizer is xanthan gum and is selected for inclusion in the composition at a concentration of about 0.1% w/v.

146. The method of any one of embodiments 99-145, wherein the bacterium is a gram-negative bacterium.

147. The method of any one of embodiments 99-146, wherein the bacterium is of a genus selected from the group consisting of: *Acetobacter, Achromobacter, Aerobacter, Anabaena, Azoarcus, Azomonas, Azorhizobium, Azospirillum, Azotobacter, Beijernickia, Bradyrhizobium, Burkholderia, Citrobacter, Derxia, Enterobacter, Herbaspirillum, Klebsiella, Kluyvera, Kosakonia, Mesorhizobium, Metakosakonia, Paraburkholderia, Nostoc, Rahnella, Rhizobium, Rhodobacter, Rhodopseudomonas, Rhodospirillum, Serratia Sinorhizobium, Spirillum, Trichodesmium*, and *Xanthomonas.*

148. The method of any one of embodiments 99-147, wherein the bacterium is of a species selected from the group consisting of: *Achromobacter marplatensis, Achromobacter spiritinus, Azospirillum lipoferum, Enterobacter sacchari, Herbaspirillum aquaticum, Klebsiella variicola, Kluyvera intermedia, Kosakonia pseudosacchari, Kosakonia sacchari, Metakosakonia intestini, Paraburkholderia tropica, Rahnella aquatilis*, and combinations thereof.

149. The method of any one of embodiments 99-148, wherein the bacterium is a gram-positive bacterium.

150. The method of any one of embodiments 99-149, wherein the bacterium is of a genus selected from the group consisting of: *Arthrobacter, Agromyces, Bacillus, Clostridium, Corynebacterium, Frankia, Heliobacillus, Heliobacterium, Heliophilum, Heliorestis Methanobacterium, Microbacterium, Micrococcus, Micromonospora, Mycobacterium, Paenibacillus, Propionibacterium*, and *Streptomyces.*

151. The method of any one of embodiments 99-150, wherein the bacterium is of a species selected from the group consisting of: *Bacillus amyloliquefaciens, Bacillus macerans, Bacillus pumilus, Bacillus thuringiensis, Clostridium acetobutylicum, Corynebacterium autitrophicum Methanobacterium formicicum, Methanobacterium omelionski, Microbacterium murale, Mycobacterium flavum, Paenibacillus polymyxa, Paenibacillus riograndensis, Propionibacterium acidipropio, Propionibacterium freudenreichii, Streptococcus lactis, Streptomyces griseus*, and combinations thereof.

152. The method of any one of embodiments 99-151, wherein the bacterium is of the genus *Klebsiella.*

153. The method of any one of embodiments 99-152, wherein the bacterium is of the species *Klebsiella variicola.*

154. The method of any one of embodiments 99-153, wherein the bacterium is of the strain *Klebsiella variicola* NCMA 201712002.

155. The method of any one of embodiments 99-154, wherein the bacterium is of the genus *Kosakonia.*

156. The method of any one of embodiments 99-155, wherein the bacterium is of the species *Kosakonia sacchari.*

157. The method of any one of embodiments 99-156, wherein the bacterium is of the strain *Kosakonia sacchari* PTA-126743.

158. The method of any one of embodiments 99-157, wherein the bacterium is endophytic, epiphytic, or rhizospheric.

159. The method of any one of embodiments 99-158, wherein the bacterium is a wild type bacterium.

160. The method of any one of embodiments 99-159, wherein the bacterium is an engineered bacterium.

161. The method of any one of embodiments 99-160, wherein the bacterium is a transgenic bacterium.

162. The method of any one of embodiments 99-161, wherein the bacterium is an intragenic bacterium.

163. The method of any one of embodiments 99-162, wherein the bacterium is a remodeled bacterium.

164. The method of any one of embodiments 99-163, wherein the bacterium comprises a non-intergeneric genomic modification.

165. The method of any one of embodiments 99-164, wherein the bacterium is an engineered bacterium capable of fixing atmospheric nitrogen in the presence of exogenous nitrogen.

166. The method of any one of embodiments 99-165, wherein the bacterium is an engineered bacterium comprising at least one genetic variation introduced into at least one gene, or non-coding polynucleotide, of the nitrogen fixation or assimilation genetic regulatory network.

167. The method of any one of embodiments 99-166, wherein the bacterium is an engineered bacterium comprising an introduced control sequence operably linked to at least one gene of the nitrogen fixation or assimilation genetic regulatory network.

168. The method of any one of embodiments 99-167, wherein the bacterium is an engineered bacterium comprising a heterologous promoter operably linked to at least one gene of the nitrogen fixation or assimilation genetic regulatory network.

169. The method of any one of embodiments 99-168, wherein the bacterium is an engineered bacterium comprising at least one genetic variation selected from the group consisting of: nifA, nifL, ntrB, ntrC, polynucleotide encoding glutamine synthetase, glnA, glnB, glnK, drat, amtB, polynucleotide encoding glutaminase, glnD, glnE, nifJ, nifH, nifD, nifK, nifY, nifE, nifN, nifU, nifS, nifV, nifW, nifZ, nifM, nifF, nifB, nifQ, a gene associated with biosynthesis of a nitrogenase enzyme, and combinations thereof.

170. The method of any one of embodiments 99-169, wherein the bacterium is an engineered bacterium comprising at least one genetic variation introduced into at least one gene, or non-coding polynucleotide, of the nitrogen fixation or assimilation genetic regulatory network that results in one or more of: increased expression or activity of NifA or glutaminase; decreased expression or activity of NifL, NtrB, glutamine synthetase, GlnB, GlnK, DraT, AmtB; decreased adenylyl-removing activity of GlnE; or decreased expression or uridylyl-removing activity of GlnD.

171. The method of any one of embodiments 99-170, wherein the bacterium is an engineered bacterium comprising a mutated nifL gene that has been altered to comprise a heterologous promoter inserted into said nifL gene.

172. The method of any one of embodiments 99-171, wherein the bacterium is an engineered bacterium comprising a mutated glnE gene that results in a truncated GlnE protein lacking an adenylyl-removing (AR) domain.

173. The method of any one of embodiments 99-172, wherein the bacterium is an engineered bacterium comprising a mutated glnD gene that results in the lack of expression of said glnD gene.

174. The method of any one of embodiments 99-173, wherein the bacterium is an engineered bacterium comprising a mutated amtB gene that results in the lack of expression of said amtB gene.

175. The method of any one of embodiments 99-174, wherein the bacterium is an engineered bacterium comprising at least one of: a mutated nifL gene that has been altered to comprise a heterologous promoter inserted into said nifL gene; a mutated glnE gene that results in a truncated GlnE protein lacking an adenylyl-removing (AR) domain; a mutated amtB gene that results in the lack of expression of said amtB gene; a mutated glnD gene that results in the lack of expression of said glnD gene; and combinations thereof.

176. The method of any one of embodiments 99-175, wherein the bacterium is an engineered bacterium comprising at least one genetic variation introduced into genes involved in a pathway selected from the group consisting of: exopolysaccharide production, endo-polygalaturonase production, trehalose production, and glutamine conversion.

177. The method of any one of embodiments 99-176, wherein the bacterium is an engineered bacterium comprising at least one genetic variation introduced into genes selected from the group consisting of: bcsii, bcsiii, yjbE, fhaB, pehA, otsB, treZ, glsA2, and combinations thereof.

178. The method of any one of embodiments 99-177, wherein the bacterium is selected from Table 1, or a variant, mutant, or derivative thereof.

179. The method of any one of embodiments 99-178, wherein the bacterium comprises a nucleic acid sequence that shares at least about 90%, 95%, or 99% sequence identity to a nucleic acid sequence selected from SEQ ID NOs: 1-223.

180. The method of any one of embodiments 99-179, wherein the bacterium comprises a nucleic acid sequence selected from SEQ ID NOs: 1-223.

181. The method of any one of embodiments 99-180, wherein the bacterium is a non-intergeneric remodeled bacterium.

What is claimed is:

1. An agronomically stable liquid agricultural composition, comprising:

a) diazotrophic bacteria;

b) a buffering agent;

c) a microbial stabilizer; and d) a physical stabilizer, wherein the composition has a room temperature shelf life of at least 30 days, and wherein the bacteria are present at a cellular density that provides a decay rate of less than 1.0 log loss of colony forming units (CFU) of viable bacterium per mL over 30 days.

2. The composition of claim 1, wherein the composition has a microbial stability that is greater than the microbial stability of the composition absent one or more of the buffering agent, microbial stabilizer, and physical stabilizer.

3. The composition of claim 1, wherein the log loss of CFU/mL over the shelf life of the composition is less than 0.2.

4. The composition of claim 1, wherein the buffering agent maintains the pH of the composition at about pH 6-8 over the shelf life of the composition.

5. The composition of claim 1, wherein the buffering agent is selected from the list consisting of phosphate buffered saline (PBS); modified, high buffering capacity PBS; 3-Morpholinopropane-1-sulfonic acid (MOPS); and 2-[4-(2-hydroxyethyl)piperazin-1-yl]ethanesulfonic acid (HEPES).

6. The composition of claim 1, wherein the microbial stabilizer is a monosaccharide, a disaccharide, a polysaccharide, a pentose, a hexose, an oligosaccharide, oligofructose, a sugar alcohol, an amino acid, a protein or protein hydrolysate, or a polymer.

7. The composition of claim 1, wherein the microbial stabilizer is fructose and is present in the composition at a concentration of about 0.5-2.5% w/v.

8. The composition of claim 1, wherein the physical stabilizer is a polysaccharide, protein or protein hydrolysate, polymer, or a natural gum or its derivative.

9. The composition of claim 1, wherein the physical stabilizer is xanthan gum and is present in the composition at a concentration of about 0.001-0.2% w/v.

10. The composition of claim 1, wherein the bacteria is of a genus selected from the group consisting of: *Acetobacter, Achromobacter, Aerobacter, Anabaena, Arthrobacter, Agromyces, Azoarcus, Azomonas, Azorhizobium, Azospirillum, Azotobacter, Bacillus, Beijernickia, Bradyrhizobium, Burkholderia, Citrobacter, Clostridium, Corynebacterium, Derxia, Enterobacter, Frankia, Heliobacillus, Heliobacterium, Heliophilum, Heliorestis, Herbaspirillum, Klebsiella, Kluyvera, Kosakonia, Mesorhizobium, Metakosakonia, Methanobacterium, Microbacterium, Micrococcus, Micromonospora, Mycobacterium, Paenibacillus, Paraburkholderia, Propionibacterium, Nostoc, Rahnella, Rhizobium, Rhodobacter, Rhodopseudomonas, Rhodospirillum, Serratia Sinorhizobium, Spirillum, Streptomyces, Trichodesmium*, and *Xanthomonas.*

11. The composition of claim 1, wherein the bacteria is of a species selected from the group consisting of: *Achromobacter marplatensis, Achromobacter spiritinus, Azospirillum lipoferum, Enterobacter sacchari, Herbaspirillum aquaticum, Klebsiella variicola, Kluyvera intermedia, Kosakonia pseudosacchari, Kosakonia sacchari, Metakosakonia intestini, Paraburkholderia tropica, Rahnella aquatilis, Bacillus amyloliquefaciens, Bacillus macerans, Bacillus pumilus, Bacillus thuringiensis, Clostridium acetobutylicum, Corynebacterium autitrophicum Methanobacterium formicicum, Methanobacterium omelionski, Microbacterium murale, Mycobacterium flavum, Paenibacillus polymyxa, Paenibacillus riograndensis, Propionibacterium acidipropio, Propionibacterium freudenreichii, Streptococcus lactis, Streptomyces griseus*, and combinations thereof.

12. The composition of claim 1, wherein the bacteria is strain *Klebsiella variicola* NCMA 201712002 or *Kosakonia sacchari* PTA-126743.

13. The composition of claim 1, wherein the bacteria comprise an engineered bacterium capable of fixing atmospheric nitrogen in the presence of exogenous nitrogen.

14. The composition of claim 13, wherein the engineered bacterium comprises a heterologous promoter operably linked to at least one gene of a nitrogen fixation or assimilation genetic regulatory network.

15. The composition of claim 1, wherein the bacteria is selected from *Kosakonia sacchari* NCMA 201701001, Rahnella *aquatilis* NCMA 201701003*, Kosakonia sacchari* NCMA 201701002*, Kosakonia sacchari* NCMA 201708004*, Kosakonia sacchari* NCMA 201708003*, Kosakonia sacchari* NCMA 201708002*, Klebsiella variicola* NCMA 201708001*, Klebsiella variicola* NCMA 201712001*, Klebsiella variicola* NCMA 201712002*, Kosakonia sacchari* PTA-126575*, Kosakonia sacchari* PTA-126576*, Klebsiella variicola* PTA-126577*, Klebsiella variicola* PTA-126578*, Klebsiella variicola* PTA-126579*, Klebsiella variicola* PTA-126580*, Paenibacillus polymyxa* PTA-126581*, Paraburkholderia tropica* PTA-126582*, Herbaspirillum aquaticum* PTA-126583*, Metakosakonia*

*intestine* PTA-126584, *Metakosakonia intestine* PTA-126585, *Metakosakonia intestine* PTA-126586, *Metakosakonia intestine* PTA-126587, *Metakosakonia intestine* PTA-126588, *Klebsiella variicola* PTA-126740, *Kosakonia sacchari* PTA-126743, and mutants thereof.

16. The composition of claim 1, wherein the bacteria comprise a nucleic acid sequence selected from SEQ ID NOs: 1-223, or a sequence that shares at least about 90%, 95%, or 99% sequence identity to a nucleic acid sequence selected from SEQ ID NOs: 1-223.

17. An agronomically stable liquid agricultural composition with a room temperature shelf life of at least 3 months, comprising:

a) diazotrophic bacteria present at a cellular density that provides a decay rate of less than 0.2 log loss of colony forming units of viable bacterium per mL over the shelf life of at least 3 months;

b) a buffering agent that maintains the pH of the composition around pH 6.7 over the shelf life of the composition;

c) a microbial stabilizer that slows the doubling rate of the diazotrophic bacteria; and d) a physical stabilizer that decreases the local density of the diazotrophic bacteria within the composition, wherein the stability of the composition is greater than, and the presence of toxic byproducts is less than, the composition absent one or more of the buffering agent, microbial stabilizer, and physical stabilizer.

18. A method of increasing agricultural plant crop yield comprising applying the composition of claim 1 to an agricultural plant tissue or an environ thereof prior to, during, or immediately following planting, thereby increasing the crop yield of the agricultural plant once planted.

19. A method of providing fixed atmospheric nitrogen to a cereal plant, comprising applying the composition of claim 1 to a cereal plant tissue or an environ thereof.

20. A method of providing fixed atmospheric nitrogen to a corn plant that eliminates the need for addition of in-season exogenous nitrogen application, comprising applying the composition of claim 1 to a corn plant tissue or an environ thereof.

21. The method of claim 18, wherein the composition comprises engineered bacteria, and wherein the engineered bacteria colonize a root surface of said agricultural plant and supplies the plant with fixed nitrogen, and wherein the engineered bacteria produce in an aggregate at least about 15 pounds of fixed nitrogen per acre over a course of at least about 10 days to about 60 days.

22. The method of claim 18, wherein the agricultural plant is corn, rice, wheat, barley, sorghum, millet, oats, or rye.

23. A method of preparing an agronomically stable liquid agricultural composition comprising diazotrophic bacteria, the method comprising the steps of:

a) providing diazotrophic bacteria;

b) selecting for inclusion in the composition a cellular density of the diazotrophic bacteria that provides a decay rate of less than 1.0 log loss of colony forming units of viable bacterium per mL over 30 days;

c) selecting a buffering agent for inclusion in the composition;

d) selecting a microbial stabilizer for inclusion in the composition; and e) selecting a physical stabilizer for inclusion in the composition, wherein the composition is stable at room temperature for a period of more than 30 days, and wherein the stability of the composition is greater than the composition absent one or more of the buffering agent, microbial stabilizer, an physical stabilizer.

* * * * *